US007291495B2

(12) United States Patent
Bejanin et al.

(10) Patent No.: US 7,291,495 B2
(45) Date of Patent: Nov. 6, 2007

(54) β-SECRETASE VARIANT

(75) Inventors: Stephane Bejanin, Paris (FR); Hiroaki Tanaka, Antony (FR)

(73) Assignee: Serono Genetics Institute S.A., Evry (FR)

( * ) Notice: Subject to any disclaimer, the term of this patent is extended or adjusted under 35 U.S.C. 154(b) by 326 days.

(21) Appl. No.: 10/838,854

(22) Filed: May 3, 2004

(65) Prior Publication Data

US 2005/0026182 A1 Feb. 3, 2005

Related U.S. Application Data

(62) Division of application No. 10/000,489, filed on Nov. 14, 2001, now Pat. No. 6,794,363, which is a division of application No. 09/924,340, filed on Aug. 6, 2001, now Pat. No. 7,074,901.

(60) Provisional application No. 60/305,456, filed on Jul. 13, 2001, provisional application No. 60/302,277, filed on Jun. 29, 2001, provisional application No. 60/298,698, filed on Jun. 15, 2001, provisional application No. 60/293,574, filed on May 25, 2001.

(30) Foreign Application Priority Data

Aug. 6, 2001 (WO) ....................... PCT/IB01/01715

(51) Int. Cl.

| | |
|---|---|
| ***C12N 9/64*** | (2006.01) |
| ***C12N 15/63*** | (2006.01) |
| ***C12N 1/20*** | (2006.01) |
| ***C12N 15/00*** | (2006.01) |
| ***C12N 1/15*** | (2006.01) |
| ***C12P 21/00*** | (2006.01) |

(52) U.S. Cl. ................ 435/226; 435/320.1; 435/252.3; 435/252.33; 435/325; 435/254.1; 435/70.1; 435/71.1

(58) Field of Classification Search ..................... None
See application file for complete search history.

(56) References Cited

U.S. PATENT DOCUMENTS

| | | | |
|---|---|---|---|
| 5,744,346 A | 4/1998 | Chrysler et al. | |
| 5,942,400 A | 8/1999 | Anderson et al. | |
| 6,184,241 B1 | 2/2001 | Baures | |
| 6,221,645 B1 | 4/2001 | Chrysler et al. | |
| 2006/0009633 A9* | 1/2006 | Dumas Milne Edwards et al. | 536/23.5 |

FOREIGN PATENT DOCUMENTS

| | | | |
|---|---|---|---|
| EP | 0 855 444 A2 | | 7/1998 |
| WO | WO99/31236 | A2 | 6/1999 |
| WO | WO 00/17369 | A2 | 3/2000 |
| WO | WO 00/47618 | A2 | 8/2000 |
| WO | WO 00/58479 | A1 | 10/2000 |
| WO | WO 01/00663 | A2 | 1/2001 |
| WO | WO 01/00665 | A2 | 1/2001 |

OTHER PUBLICATIONS

Galye et al, Identification of regions in interleukin-1 alpha important for activity. J Biol Chem. Oct. 15, 1993;268(29):22105-11.*
Whisstock et al, Prediction of protein function from protein sequence and structure. Q Rev Biophys. Aug. 2003;36(3):307-40. Review.*
Published_Applications_NA_Main database SEQ ID No. 125 from US20060009633, priority to U.S. Appl. No. 09/215,435, filed Dec. 17, 1998 Edwards et al. Alignment with SEQ ID No. 23.*
Pending_Patents_NA_Main database SEQ ID No. 66 from U.S. Appl. No. 09/215,435, filed Dec. 17, 1998 Edwards et al. Alignment with SEQ ID No. 23.*
Sinha et al, Purification and cloning of amyloid precursor protein beta-secretase from human brain. Nature. Dec. 2, 1999;402(6761):537-40.*
NCBI Accession No. AAF18982 from Sinha et al, Nature. Dec. 2, 1999;402(6761):537-40. Alignment with SEQ ID No. 24.*
Hong et al, Flap position of free memapsin 2 (beta-secretase), a model for flap opening in aspartic protease catalysis. Biochemistry. Apr. 27, 2004;43(16):4689-95.*
Capell, A. et al. "Maturation and Pro-peptide Cleavage of B-Secretase", The Journal of Biological Chemistry, Oct. 6, 2000, pp. 30849-30954, vol. 275, No. 40.
Shi, X. et al. "The Pro Domain of B-Secretase Does Not Confer Strict Zymogen-like Properties but Does Assist Proper Folding of the Protease Domain", The Journal of Biological Chemistry, Mar. 30, 2001, pp. 10366-10373, vol. 276, No. 13.
Marcinkeviciene et al. "Mechanism of Inhibition of Beta-Site APP Cleaving Enzyme (BACE) By a Statine-Based Peptide", JBC Paper in Press, Apr. 16, 2001.
Nixon, Ralph, "A Protease Activation Cascade' in the Pathogenesis of Alzheimer's Disease", Annals New York Academy of Sciences, 2000, pp. 117-131, Center for Dementia Research, Nathan Kline Institute, New York, US.
Benjannet, S. et al. "Post-translation Processing of B-Secretase (B-Amyloid-converting Enzyme) and its Ectodomain Shedding", The Journal of Biological Chemistry, Apr. 6, 2001, pp. 10879-10887, vol. 276, No. 14.
Hussain, I. et al. "Prodomain Processing of ASP1 (BACE2) Is Autocatalytic", JBC Papers in Press, Apr. 20, 2001 as Manscript M101069200.
Haniu, M. et al. "Characterization of Alzheimer's B-Secretase Protein BACE-A Pepsin Family Member with Unusual Properties", The Journal of Biological Chemistry, Jul. 14, 2000, pp. 21099-21106, vol. 275, No. 28.
Walter, J. et al. "Phosphorylation Regulates Intracellular Trafficking of B-Secretase", The Journal of Biological Chemistry, May 4, 2001, pp. 14634-14641, vol. 276, No. 18.

(Continued)

*Primary Examiner*—Sheridan L. Swope
(74) *Attorney, Agent, or Firm*—Saliwanchik, Lloyd & Saliwanchik

(57) ABSTRACT

The invention provides polynucleotides and polypeptides encoding an isolated amyloid inhibitor protein (APIP) and compositions thereof. The polypeptides of the subject invention can be used to inhibit the catabolism or sequential cleavage of amyloid beta precursor protein (APP) by sequential cleavage of APP by beta secretase and gamma secretase.

48 Claims, 4 Drawing Sheets

OTHER PUBLICATIONS

Bodendorf, U. et al. "A Splice Variant of B-Secretase Deficient in the Amyloidogenic Processing of the Amyloid Precursor Protein", The Journal of Biological Chemistry, Apr. 13, 2001, pp. 12019-12023, vol. 276, No. 15.

Nunan, J. et al. "Regulation of APP Cleavage by a-, B- and y-secretases", FEBS Letters, 2000, pp. 6-10, vol. 483, 0014-5793/00.

Vassar, R. et al. "*Homo sapiens* Beta-Site APP-Cleaving Enzyme (BACE), mRNA", Science, 1999, pp. 735-741, vol. 286, No. 5440, Accession No. NM_012104.

Sinha, S. et al. "*Homo sapiens* Beta-Secretase mRNA, Complete Cds", Nature, 1999, pp. 534-540, vol. 402, No. 671, Accession No. AF201468.

Vassar, R. et al. "Beta-Secretase Cleavage of Alzheimer's Amyloid Prescursor Protein by the Transmembrane Aspartic Protease BACE", Science, 1999, pp. 735-741, vol. 286, Accession No. P56817.

Vassar, R. et al. "Beta-Secretase Cleavage of Alzheimer's Amyloid Prescursor Protein by the Transmembrane Aspartic Protease BACE", Science, 1999, pp. 735-741, vol. 286, N. 5440, Accession No. AF190725.

Sinha et al. "Purification and Cloning of Amyloid Percursor Protein Beta-secretase from Human Brain", Nature, Dec. 2, 1999, pp. 537-540, vol. 402, No. 6761.

Genbank Accession No. XM_006430, "*Homo sapiens* Beta-site APP-cleavage Enzyme (BACE), mRNA", NCBI Annotation Project, Apr. 17, 2001, National Center for Biotechnology Information.

Genbank Accession No. AF338816, Michel, B. et al. "*Homo sapiens* Beta-site APP cleaving Enzyme Type B mRNA, Complete Cds", Jan. 19, 2001, Max Planck Institute of Molecular Cell Biology and Genetics.

Genbank Accession No. AB050438, Tanahashi, H. "*Homo sapiens* BACE mRNA for Beta-site APP Cleaving Enzyme I-432, Complete Cds", National Institute of Neuroscience, Division of Demyelinating Disease and Aging, Oct. 21, 2000.

Genbank Accession No. AF338817, Zacchetti, D. et al. "*Homo sapiens* Beta-site APP Cleaving Enzyme Type C mRNA, Complete Cds", San Raffaele Scientific Institute, Jan. 19, 2001.

Genbank Accession No. AB050437, Tanahashi, H. "*Homo sapiens* BACE mRNA for Beta-Site APP Cleaving Enzyme I-457, Complete Cds", National Institute of Neuroscience, Division of Demyelinating Disease and Aging, Oct. 21, 2000.

Genbank Accession No. AB050436, Tanahashi, H. "*Homo sapiens* BACE mRNA for Beta-Site APP Cleaving Enzyme I-476, Complete Cds", National Institute of Neuroscience, Division of Demyelinating Disease and Aging, Oct. 21, 2000.

* cited by examiner

β-SECRETASE VARIANT

RELATED APPLICATIONS

The present application is a divisional of U.S. patent application Ser. No. 10/000,489, filed Nov. 14, 2001, now U.S. Pat. No. 6,794,363, which claims the benefit of International Patent Application No. PCT/IB01/01715, filed Aug. 6, 2001 under 35 U.S.C. § 119 and is a divisional of U.S. patent application Ser. No. 09/924,340, filed Aug. 6, 2001, now U.S. Pat. No. 7,074,901, which claims the benefit of U.S. Provisional Application Ser. No. 60/305,456, filed Jul. 13, 2001, abandoned; U.S. Provisional Application Ser. No. 60/302,277, filed Jun. 29, 2001, abandoned; U.S. Provisional Application Ser. No. 60/298,698, filed Jun. 15, 2001, abandoned; and U.S. Provisional Application Ser. No. 60/293,574, filed May 25, 2001, abandoned, the disclosures of which are incorporated herein by reference in their entireties.

The Sequence Listing for this application is on duplicate compact discs labeled "Copy 1" and "Copy 2." Copy 1 and Copy 2 each contain only one file named "G-091US10DIV-Subst-Seq-List3.txt" which was created on Apr. 2, 2007, and is 402 KB. The entire contents of each of the computer discs are incorporated herein by reference in their entireties.

FIELD OF THE INVENTION

The present invention is directed to GENSET polypeptides, fragments thereof, and the regulatory regions located in the 5'- and 3'-ends of the genes encoding the polypeptides. The invention also concerns polypeptides encoded by GENSET polynucleotides and fragments thereof. The present invention also relates to recombinant vectors including the polynucleotides of the present invention, particularly recombinant vectors comprising a GENSET gene regulatory region or a sequence encoding a GENSET polypeptide, and to host cells containing the polynucleotides of the invention, as well as to methods of making such vectors and host cells. The present invention further relates to the use of these recombinant vectors and host cells in the production of the polypeptides of the invention. The invention further relates to antibodies that specifically bind to the polypeptides of the invention and to methods for producing such antibodies and fragments thereof. The invention also provides for methods of detecting the presence of the polynucleotides and polypeptides of the present invention in a sample, methods of diagnosis and screening of abnormal GENSET polypeptide expression and/or biological activity, methods of screening compounds for their ability to modulate the activity or expression of the GENSET polypeptides, and uses of such compounds.

BACKGROUND OF THE INVENTION cDNAs encoding secreted proteins or fragments thereof represent a particularly valuable source of therapeutic agents. Thus, there is a need for the identification and characterization of secreted proteins and the nucleic acids encoding them.

In addition to being therapeutically useful themselves, secretory proteins include short peptides, called signal peptides, at their amino termini which direct their secretion. These signal peptides are encoded by the signal sequences located at the 5' ends of the coding sequences of genes encoding secreted proteins. Because these signal peptides will direct the extracellular secretion of any protein to which they are operably linked, the signal sequences may be exploited to direct the efficient secretion of any protein by operably linking the signal sequences to a gene encoding the protein for which secretion is desired. In addition, fragments of the signal peptides called membrane-translocating sequences may also be used to direct the intracellular import of a peptide or protein of interest. This may prove beneficial in gene therapy strategies in which it is desired to deliver a particular gene product to cells other than the cells in which it is produced. Signal sequences encoding signal peptides also find application in simplifying protein purification techniques. In such applications, the extracellular secretion of the desired protein greatly facilitates purification by reducing the number of undesired proteins from which the desired protein must be selected. Thus, there exists a need to identify and characterize the 5' fragments of the genes for secretory proteins which encode signal peptides.

Sequences coding for secreted proteins may also find application as therapeutics or diagnostics. In particular, such sequences may be used to determine whether an individual is likely to express a detectable phenotype, such as a disease, as a consequence of a mutation in the coding sequence for a secreted protein. In instances where the individual is at risk of suffering from a disease or other undesirable phenotype as a result of a mutation in such a coding sequence, the undesirable phenotype may be corrected by introducing a normal coding sequence using gene therapy. Alternatively, if the undesirable phenotype results from overexpression of the protein encoded by the coding sequence, expression of the protein may be reduced using antisense or triple helix based strategies.

The secreted human polypeptides encoded by the coding sequences may also be used as therapeutics by administering them directly to an individual having a condition, such as a disease, resulting from a mutation in the sequence encoding the polypeptide. In such an instance, the condition can be cured or ameliorated by administering the polypeptide to the individual.

In addition, the secreted human polypeptides or fragments thereof may be used to, generate antibodies useful in determining the tissue type or species of origin of a biological sample. The antibodies may also be used to determine the cellular localization of the secreted human polypeptides or the cellular localization of polypeptides which have been fused to the human polypeptides. In addition, the antibodies may also be used in immunoaffinity chromatography techniques to isolate, purify, or enrich the human polypeptide or a target polypeptide which has been fused to the human polypeptide.

SUMMARY OF THE INVENTION

The present invention provides a purified or isolated polynucleotide comprising, consisting of, or consisting essentially of a nucleotide sequence selected from the group consisting of: (a) the sequences of the odd SEQ ID NOs:1-111; (b) the sequences of clone inserts of the deposited clone pool; (c) the coding sequences of the odd SEQ ID NOs:1-111; (d) the coding sequences of the clone inserts of the deposited clone pool; (e) the sequences encoding one of the polypeptides of the even SEQ ID NOs:2-112; (f) the sequences encoding one of the polypeptides encoded by the clone inserts of the deposited clone pool; (g) the genomic sequences coding for the GENSET polypeptides; (h) the 5' transcriptional regulatory regions of GENSET genes; (i) the 3' transcriptional regulatory regions of GENSET genes; (j) the polynucleotides comprising the nucleotide sequence of any combination of (g)-(i); (k) the variant polynucleotides of any of the polynucleotides of (a)-(j); (l) the polynucleotides comprising a nucleotide sequence of (a)-(k), wherein the polynucleotide is single stranded, double stranded, or a portion is single stranded and a portion is double stranded; (m) the polynucleotides comprising a nucleotide sequence complementary to any of the single stranded polynucleotides of (l). The invention further provides for fragments of the nucleic acids and polypeptides of (a)-(m) described above.

Further embodiments of the invention include purified or isolated polynucleotides that comprise, consist of, or consist essentially of a nucleotide sequence at least 70% identical, more, preferably at least 75%, and even more preferably at least 80%, 85%, 90%, 95%, 96%, 97%, 98%, or 99% identical, to any of the nucleotide sequences in (a)-(m) above, e.g. over a region of contiguous nucleotides at least about any one integer between 10 and the last integer representing the last integer representing the last nucleotide of a specified sequence of the sequence listing, or a polynucleotide which hybridizes under stringent hybridization conditions to a polynucleotide of the present invention including (a) through (m) above.

The present invention also relates to recombinant vectors, which include the purified or isolated polynucleotides of the present invention, and to host cells recombinant for the polynucleotides of the present invention, as well as to methods of making such vectors and host cells. The present invention further relates to the use of these recombinant vectors and recombinant host cells in the production of GENSET polypeptides. The present invention further relates to a polynucleotide of the present invention operably linked to a regulatory sequence including promoters, enhancers, etc.

The invention further provides a purified or isolated polypeptide comprising, consisting of, or consisting essentially of an amino acid sequence selected from the group consisting of: (a) the full length polypeptides of even SEQ ID NOs:2-112; (b) the full length polypeptides encoded by the clone inserts of the deposited clone pool; (c) the epitope-bearing fragments of the polypeptides of even SEQ ID NOs:2-112; (d) the epitope-bearing fragments of the polypeptides encoded by the clone-inserts contained in the deposited clone pool; (e) the domains of the polypeptides of even SEQ ID NOs:2-112; (f) the domains of the polypeptides encoded by the clone inserts contained in the deposited clone pool; (g) the signal peptides of the polypeptides of even SEQ ID NOs:2-112 or encoded by the human cDNAs of the deposited clone pool; (h) the mature polypeptides of even SEQ ID Nos:2-112 or encoded by the human cDNAs of the deposited clone pool; and (i) the allelic variant polypeptides of any of the polypeptides of (a)-(h). The invention further provides for fragments of the polypeptides of (a)-(i) above, such as those having biological activity or comprising biologically functional domain(s).

The present invention further includes polypeptides with an amino acid sequence with at least 70% similarity, and more preferably at least 75%, 80%, 85%, 90%, 95%, 96%, 97%, 98%, or 99% similarity to those polypeptides described in (a)-(i), or fragments thereof, as well as polypeptides having an amino acid sequence at least 70% identical, more preferably at least 75% identical, and still more preferably 80%, 85%, 90%, 95%, 96%, 97%, 98%, or 99% identical to those polypeptides described in (a)-(i), or fragments thereof, e.g. over a region of amino acids at least any one integer between 6 and the last integer representing the last amino acid of a specified polypeptide sequence of the sequence listing. The invention further relates to methods of making the polypeptides of the present invention.

The present invention further relates to transgenic plants or animals, wherein said transgenic plant or animal is transgenic for a polynucleotide of the present invention and expresses a polypeptide of the present invention.

The invention further relates to antibodies that specifically bind to GENSET polypeptides of the present invention and fragments thereof as well as to methods for producing such antibodies and fragments thereof.

The invention also provides kits, uses and methods for detecting GENSET gene expression and/or biological activity in a biological sample. One such method involves assaying for the expression of a GENSET polynucleotide in a biological sample using the polymerase chain reaction (PCR) to amplify and detect GENSET polynucleotides or Southern and Northern blot hybridization to detect GENSET genomic DNA, cDNA or mRNA. Alternatively, a method of detecting GENSET gene expression in a test sample can be accomplished using a compound which binds to a GENSET polypeptide of the present invention or a portion of a GENSET polypeptide.

The present invention also relates to diagnostic methods and uses of GENSET polynucleotides and polypeptides for identifying individuals or non-human animals having elevated or reduced levels of GENSET gene products, which individuals are likely to benefit from therapies to suppress or enhance GENSET gene expression, respectively, and to methods of identifying individuals or non-human animals at increased risk for developing, or at present having, certain diseases/disorders associated with GENSET polypeptide expression or biological activity.

The present invention also relates to kits, uses and methods of screening compounds for their ability to modulate (e.g. increase or inhibit) the activity or expression of GENSET polypeptides including compounds that interact with GENSET gene regulatory sequences and compounds that interact directly or indirectly with a GENSET polypeptide. Uses of such compounds are also within the scope of the present invention.

The present invention also relates to pharmaceutical or physiologically acceptable compositions comprising, an active agent, the polypeptides, polynucleotides or antibodies of the present invention, as well as, typically, a physiologically acceptable carrier.

The present invention also relates to computer systems containing cDNA codes and polypeptide codes of sequences of the invention and to computer-related methods of comparing sequences, identifying homology or features using GENSET polypeptides or GENSET polynucleotide sequences of the invention.

In another aspect, the present invention provides an isolated polynucleotide, the polynucleotide comprising a nucleic acid sequence encoding a polypeptide of the present invention including the polypeptide of (a) through (i) above.

In another aspect, the present invention provides a non-human transgenic animal comprising the host cell.

In another aspect, the present invention provides a method of making a GENSET polypeptide, the method comprising a) providing a population of host cells comprising a herein-described polynucleotide and b) culturing the population of host cells under conditions conducive to the production of the polypeptide within said host cells.

In one embodiment, the method further comprises purifying the polypeptide from the population of host cells.

In another aspect, the present invention provides a method of making a GENSET polypeptide, the method comprising a) providing a population of cells comprising a polynucleotide encoding a herein-described polypeptide; b) culturing the population of cells under conditions conducive to the production of the polypeptide within the cells; and c) purifying the polypeptide from the population of cells.

In another aspect, the present invention provides a biologically active polypeptide encoded by any of the herein-described polynucleotides.

In one embodiment, the polypeptide is selectively recognized by an antibody raised against an antigenic polypeptide, or an antigenic fragment thereof, the antigenic polypeptide comprising any one of the sequences shown as even SEQ ID NOs:2-112 or any one of the sequences of polypeptides encoded by the human cDNAs of the deposited clone pool.

In another aspect, the present invention provides an antibody that specifically binds to any of the herein-described polypeptides and methods of binding antibody to said polypeptide.

In another aspect, the present invention provides a method of determining whether a GENSET gene is expressed within a mammal, the method comprising the steps of: a) providing a biological sample from said mammal; b) contacting said biological sample with either of: (i) a polynucleotide that hybridizes under stringent conditions to any of the herein-described polynucleotides; or (ii) a polypeptide that specifically binds to any of the herein-described polypeptides; and c) detecting the presence or absence of hybridization between the polynucleotide and an RNA species within the sample, or the presence or absence of binding of the polypeptide to a protein within the sample; wherein a detection of the hybridization or of the binding indicates that the GENSET gene is expressed within the mammal.

In one embodiment, the polynucleotide is a primer, and the hybridization is detected by detecting the presence of an amplification product comprising the sequence of the primer. In another embodiment, the polypeptide is an antibody.

In another aspect, the present invention provides a method of determining whether a mammal has an elevated or reduced level of GENSET gene expression, the method comprising the steps of: a) providing a biological sample from the mammal; and b) comparing the amount of any of the herein-described polypeptides, or of an RNA species encoding the polypeptide, within the biological sample with a level detected in or expected from a control sample; wherein an increased amount of the polypeptide or the RNA species within the biological sample compared to the level detected in or expected from the control sample indicates that the mammal has an elevated level of the GENSET gene expression, and wherein a decreased amount of the polypeptide or the RNA species within the biological sample compared to the level detected in or expected from the control sample indicates that the mammal has a reduced level of the GENSET gene expression.

In another aspect, the present invention provides a method of identifying a candidate modulator of a GENSET polypeptide, the method comprising: a) contacting any of the herein-described polypeptides with a test compound; and b) determining whether the compound specifically binds to the polypeptide; wherein a detection that the compound specifically binds to the polypeptide indicates or inhibits or activates of a specified biological activity that the compound is a candidate modulator of the GENSET polypeptide.

BRIEF DESCRIPTION OF TABLES

Figure 1:
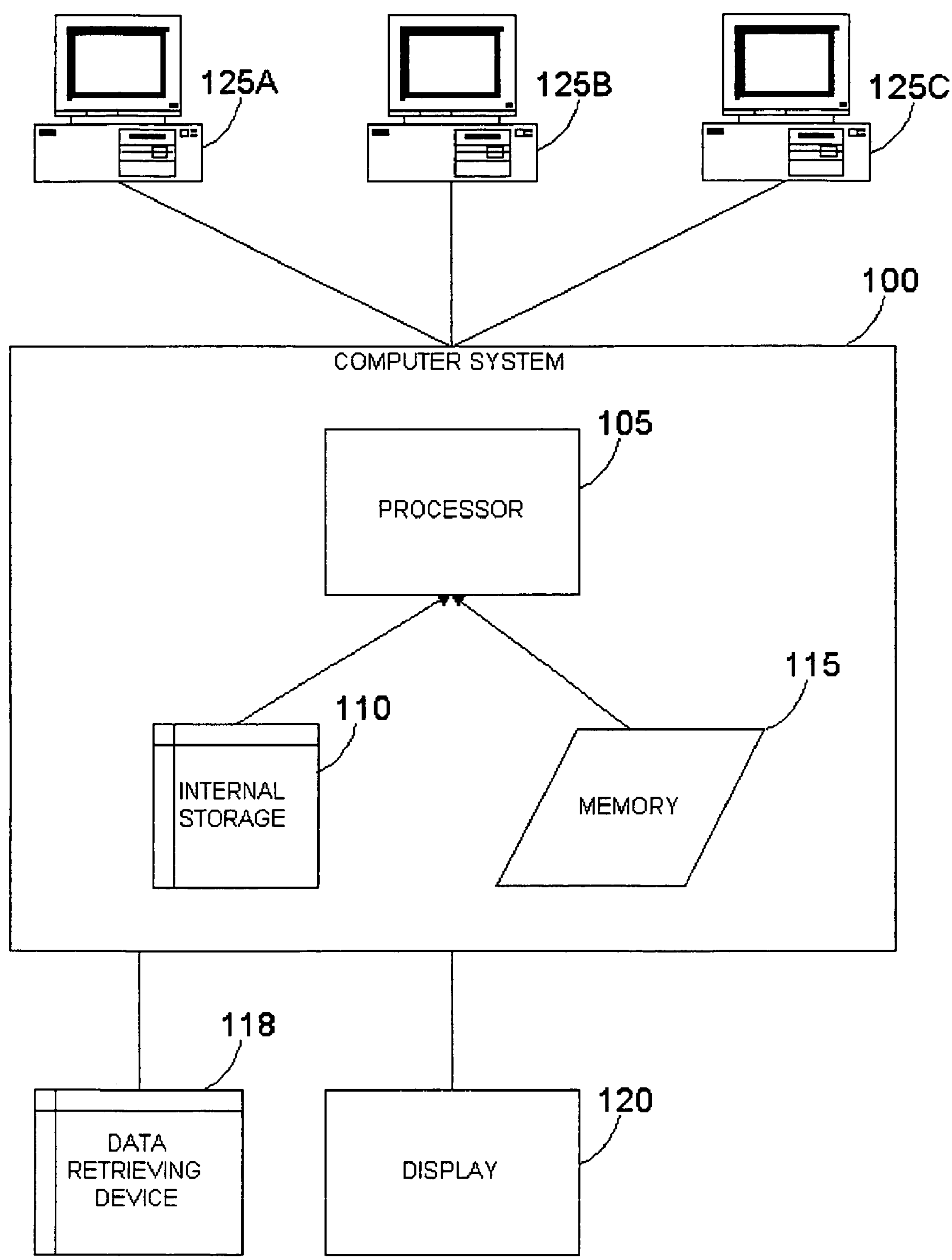
FIG. 1 is a block diagram of an exemplary computer system.

Table I provides the Applicants' internal designation number (Clone ID_Clone Name) which corresponds to each sequence identification number (SEQ ID NO.) of the Sequence Listing, and indicates whether the sequence is a nucleic acid sequence (DNA) or a polypeptide sequence (PRT). Further provided is information regarding the name of the corresponding nucleic acid or polypeptide sequence, and information regarding the deposit of biological material. It should be appreciated that biological materials have been deposited with reference to their corresponding Clone ID, Clone Name, or both Clone ID_Clone Name.

Table II provides the positions of the nucleotides of the corresponding SEQ ID NOs. of the Sequence Listing which comprise the open reading frame (ORF), signal peptide, mature peptide, polyadenylation signal, and the polyA tail of the polynucleotides of the invention.

Table III provides the positions of the amino acid of the corresponding SEQ ID NOs. of the Sequence Listing which comprise the positions of immunogenic epitopes of the polypeptides of the invention, which are useful in antibody generation as described in Example 1.

Table IV provides the positions of the nucleotides comprising preferentially included or excluded fragments of the corresponding SEQ ID NOs. of the Sequence Listing.

BRIEF DESCRIPTION OF SEQUENCES

Sequences are presented in the accompanying Sequence Listing.

Odd SEQ ID NOs:1-111 are the nucleotide sequences of cDNAs, with open reading frames as indicated. When appropriate, the potential polyadenylation site and polyadenylation signal are also indicated.

Even SEQ ID NOs:2-112 are the amino acid sequences of proteins encoded by the cDNAs of odd SEQ ID NOs:1-111.

In accordance with the regulations relating to Sequence Listings, the following codes have been used in the Sequence Listing to describes nucleotide sequences. The code "r" in the sequences indicates that the nucleotide may be a guanine or an adenine. The code "y" in the sequences indicates that the nucleotide may be a thymine or a cytosine. The code "m" in the sequences indicates that the nucleotide may be an adenine or a cytosine. The code "k" in the sequences indicates that the nucleotide may be a guanine or a thymine. The code "s" in the sequences indicates that the nucleotide may be a guanine or a cytosine. The code "w" in the sequences indicates that the nucleotide may be an adenine or an thymine. In addition, all instances of the symbol "n" in the nucleic acid sequences mean that the nucleotide can be adenine, guanine, cytosine or thymine.

In some instances, the polypeptide sequences in the Sequence Listing contain the symbol "Xaa." These "Xaa" symbols indicate either (1) a residue which cannot be identified because of nucleotide sequence ambiguity or (2) a stop codon in the determined sequence where applicants believe one should not exist (if the sequence were determined more accurately). In some instances, several possible identities of the unknown amino acids may be suggested by the genetic code.

In the case of secreted proteins, it should be noted that, in accordance with the regulations governing Sequence Listings, in the appended Sequence Listing the encoded protein (i.e. the protein containing the signal peptide and the mature protein or fragment thereof) extends from an amino acid residue having a negative number through a positively numbered amino acid residue. Thus, the first amino acid of the mature protein resulting from cleavage of the signal peptide is designated as amino acid number 1, and the first amino, acid of the signal peptide is designated with the appropriate negative number.

In the case that a polynucleotide or polypeptide sequence described in the specification for SEQ ID NOs:1-112 is in conflict with the corresponding sequence provided in the Sequence listing, the sequences provided in the Sequence listing controls.

It should be appreciated the polynucleotide and polypeptide sequences of SEQ ID NO:1-112 of the Sequence Listing are hereby incorporated by reference in their entireties.

DETAILED DESCRIPTION OF THE INVENTION AND PREFERRED EMBODIMENTS

Definitions.

Before describing the invention in greater detail, the following definitions are set forth to illustrate and define the meaning and scope of the terms used to describe the invention herein.

The term "GENSET gene," when used herein, encompasses genomic, mRNA and cDNA sequences encoding a GENSET polypeptide, including the 5' and 3' untranslated regions of said sequences.

The term "GENSET polypeptide biological activity" or "GENSET biological activity" is intended for polypeptides exhibiting any activity similar, but not necessarily identical, to an activity of a GENSET polypeptide of the invention. The GENSET polypeptide biological activity of a given polypeptide may be assessed using any suitable biological assay, a number of which are known to those skilled in the art. In contrast, the term "biological activity" refers to any activity that any polypeptide may have.

The term "corresponding mRNA" refers to mRNA which was or can be a template for cDNA synthesis for producing a cDNA of the present invention.

The term "corresponding genomic DNA" refers to genomic DNA which encodes an mRNA of interest, e.g. corresponding to a cDNA of the invention, which genomic DNA includes the sequence of one of the strands of the mRNA, in which thymidine residues in the sequence of the genomic DNA (or cDNA) are replaced by uracil residues in the mRNA.

The term "deposited clone pool" is used herein to refer to the pool of clones entitled cDNA-11-2000 deposited with the ATCC on Nov. 27, 2000, or cDNA-8-2000, deposited with the ATCC on Sep. 15, 2000.

The term "heterologous", when used herein, is intended to designate any polynucleotide or polypeptide other than a GENSET polynucleotide or GENSET polypeptide of the invention, respectively.

"Providing" with respect to, e.g. a biological sample, population of cells, etc. indicates that the sample, population of cells, etc. is somehow used in a method or procedure. Significantly, "providing" a biological sample or population of cells does not require that the sample or cells are specifically isolated or obtained for the purposes of the invention, but can instead refer, for example, to the use of a biological sample obtained by another individual, for another purpose.

An "amplification product" refers to a product of any amplification reaction, e.g. PCR, RT-PCR, LCR, etc.

A "modulator" of a protein or other compound refers to any agent that has a functional effect on the protein, including physical binding to the protein, alterations of the quantity or quality of expression of the protein, altering any measurable or detectable activity, property, or behavior of the protein, or in any way interacts with the protein or compound.

"A test compound" can be any molecule that is evaluated for its ability to modulate a protein or other compound.

An antibody or other compound that specifically binds to a polypeptide or polynucleotide of the invention is also said to "selectively recognize" the polypeptide or polynucleotide.

The term "isolated" with respect to a molecule requires that the molecule be removed from its original environment (e.g., the natural environment if it is naturally occurring). For example, a naturally-occurring polynucleotide or polypeptide present in a living animal is not isolated, but the same polynucleotide or DNA or polypeptide, separated from some or all of the coexisting materials in the natural system, is isolated. Such polynucleotide could be part of a vector and/or such polynucleotide or polypeptide could be part of a composition, and still be isolated in that the vector or composition is not part of its natural environment. For example, a naturally-occurring polynucleotide present in a living animal is not isolated, but the same polynucleotide, separated from some or all of the coexisting materials in the natural system, is isolated. Specifically excluded from the definition of "isolated" are: naturally-occurring chromosomes (such as chromosome spreads), artificial chromosome libraries, genomic libraries, and cDNA libraries that exist either as an in vitro nucleic acid preparation or as a transfected/transformed host cell preparation, wherein the host cells are either an in vitro heterogeneous preparation or plated as a heterogeneous population of single colonies. Also specifically excluded are the above libraries wherein a specified polynucleotide makes up less than 5% (may also be specified as 10%, 25%, 50%, or 75%) of the number of nucleic acid inserts in the vector molecules. Further specifically excluded are whole cell genomic DNA or whole cell RNA preparations (including said whole cell preparations which are mechanically sheared or enzymatically digested). Further specifically excluded are the above whole cell preparations as either an in vitro preparation or as a heterogeneous mixture separated by electrophoresis (including blot transfers of the same) wherein the polynucleotide of the invention has not further been separated from the heterologous polynucleotides in the electrophoresis medium (e.g., further separating by excising a single band from a heterogeneous band population in an agarose gel or nylon blot).

The term "purified" does not require absolute purity; rather, it is intended as a relative definition. Purification of starting material or natural material to at least one order of magnitude, preferably two or three orders, and more preferably four or five orders of magnitude is expressly contemplated.

The term "purified" is further used herein to describe a polypeptide or polynucleotide of the invention which has been separated from other compounds including, but not limited to, polypeptides or polynucleotides, carbohydrates, lipids, etc. The term "purified" may be used to specify the separation of monomeric polypeptides of the invention from oligomeric forms such as homo- or hetero-dimers, trimers, etc. The term "purified" may also be used to specify the separation of covalently closed (i.e. circular) polynucleotides from linear polynucleotides. A substantially pure polypeptide or polynucleotide typically comprises about 50%, preferably 60 to 90% weight/weight of a polypeptide or polynucleotide sample, respectively, more usually about 95%, and preferably is over about 99% pure but, may be specified as any integer of percent between 50 and 100. Polypeptide and polynucleotide purity, or homogeneity, is indicated by a number of means well known in the art, such as agarose or polyacrylamide gel electrophoresis of a sample, followed by visualizing a single band upon staining the gel. For certain purposes higher resolution can be provided by using HPLC or other means well known in the art. As an alternative embodiment, purification of the polypeptides and polynucleotides of the present invention may be expressed as "at least" a percent purity relative to heterologous polypeptides and polynucleotides (DNA, RNA or both). As a preferred embodiment, the polypeptides and polynucleotides of the present invention are at least; 10%, 20%, 30%, 40%, 50%, 60%, 70%, 80%, 90%, 95%, 96%, 96%, 98%, 99%, or 100% pure relative to heterologous polypeptides and polynucleotides, respectively. As a further preferred embodiment the polypeptides and polynucleotides have a purity ranging from any number, to the thousandth position, between 90% and 100% (e.g., a polypeptide or polynucleotide at least 99.995% pure) relative to either heterologous polypeptides or polynucleotides, respectively, or as a weight/weight ratio relative to all compounds and molecules other than those existing in the carrier. Each number representing a percent purity, to the thousandth position, may be claimed as individual species of purity.

As used interchangeably herein, the terms "nucleic acid molecule(s)", "oligonucleotide(s)", and "polynucleotide(s)" include RNA or DNA (either single or double stranded, coding, complementary or antisense), or RNA/DNA hybrid sequences of more than one nucleotide in either single chain or duplex form (although each of the above species may be particularly specified). The term "nucleotide" is used herein as an adjective to describe molecules comprising RNA, DNA, or RNA/DNA hybrid sequences of any length in single-stranded or duplex form. More precisely, the expression "nucleotide sequence" encompasses the nucleic material itself and is thus not restricted to the sequence information (i.e. the succession of letters chosen among the four base letters) that biochemically characterizes a specific DNA or RNA molecule. The term "nucleotide" is also used herein as a noun to refer to individual nucleotides or varieties of nucleotides, meaning a molecule, or individual unit in a larger nucleic acid molecule, comprising a purine or pyrimidine, a ribose or deoxyribose sugar moiety, and a phosphate group, or phosphodiester linkage in the case of nucleotides within an oligonucleotide or polynucleotide. The term "nucleotide" is also used herein to encompass "modified nucleotides" which comprise at least one modification such as (a) an alternative linking group, (b) an analogous form of purine, (c) an analogous form of pyrimidine, or (d) an analogous sugar. For examples of analogous linking groups, purine, pyrimidines, and sugars, see, for example, PCT publication No. WO 95/04064, which disclosure is hereby incorporated by reference in its entirety. Preferred modifications of the present invention include, but are not limited to, 5-fluorouracil, 5-bromouracil, 5-chlorouracil, 5-iodouracil, hypoxanthine, xantine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N-6-isopentenyladenine, uracil-5-oxyacetic acid (v) ybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid, 5-methyl-2-thiouracil, 3-(3-amino-3-N-2-carboxypropyl) uracil, and 2,6-diaminopurine. The polynucleotide sequences of the invention may be prepared by any known method, including synthetic, recombinant, ex vivo generation, or a combination thereof, as well as utilizing any purification methods known in the art. Methylenemethylimino linked oligonucleosides as well as mixed backbone compounds having, may be prepared as described in U.S. Pat. Nos. 5,378,825; 5,386,023; 5,489,677; 5,602,240; and 5,610,289, which disclosures are hereby incorporated by reference in their entireties. Formacetal and thioformacetal linked oligonucleosides may be prepared as described in U.S. Pat. Nos. 5,264,562 and 5,264,564, which disclosures are hereby incorporated by reference in their entireties. Ethylene oxide linked oligonucleosides may be prepared as described in U.S. Pat. No. 5,223,618, which disclosure is hereby incorporated by reference in its entirety. Phosphinate oligonucleotides may be prepared as described in U.S. Pat. No. 5,508,270, which disclosure is hereby incorporated by reference in its entirety. Alkyl phosphonate oligonucleotides may be prepared as described in U.S. Pat. No. 4,469,863, which disclosure is hereby incorporated by reference in its entirety. 3'-Deoxy-3'-methylene phosphonate oligonucleotides may be prepared as described in U.S. Pat. Nos. 5,610,289 or 5,625,050 which disclosures are hereby incorporated by reference in their entireties. Phosphoramidite oligonucleotides may be prepared as described in U.S. Pat. No. 5,256,775 or U.S. Pat. No. 5,366,878 which disclosures are hereby incorporated by reference in their entireties. Alkylphosphonothioate oligonucleotides may be prepared as described in published PCT applications WO 94/17093 and WO 94/02499 which disclosures are hereby incorporated by reference in their entireties. 3'-Deoxy-3'-amino phosphoramidate oligonucleotides may be prepared as described in U.S. Pat. No. 5,476,925, which disclosure is hereby incorporated by reference in its entirety. Phosphotriester oligonucleotides may be prepared as described in U.S. Pat. No. 5,023,243, which disclosure is hereby incorporated by reference in its entirety. Borano phosphate oligonucleotides may be prepared as described in U.S. Pat. Nos. 5,130,302 and 5,177,198 which disclosures are hereby incorporated by reference in their entireties.

The term "upstream" is used herein to refer to a location which is toward the 5' end of the polynucleotide from a specific reference point.

The terms "base paired" and "Watson & Crick base paired" are used interchangeably herein to refer to nucleotides which can be hydrogen bonded to one another by virtue of their sequence identities in a manner like that found in double-helical DNA with thymine or uracil residues linked to adenine residues by two hydrogen bonds and cytosine and guanine residues linked by three hydrogen bonds (see Stryer, (1995) Biochemistry, 4th edition, which disclosure is hereby incorporated by reference in its entirety).

The terms "complementary" or "complement thereof" are used herein to refer to the sequences of polynucleotides which is capable of forming Watson & Crick base pairing with another specified polynucleotide throughout the entirety of the complementary region. For the purpose of the present invention, a first polynucleotide is deemed to be complementary to a second polynucleotide when each base in the first polynucleotide is paired with its complementary base. Complementary bases are, generally, A and T (or A and U), or C and G. "Complement" is used herein as a synonym from "complementary polynucleotide", "complementary nucleic, acid" and "complementary nucleotide sequence". These terms are applied to pairs of polynucleotides based solely upon their sequences and not any particular set of conditions under which the two polynucleotides would actually bind. Unless otherwise stated, all complementary polynucleotides are fully complementary on the whole length of the considered polynucleotide.

The terms "polypeptide" and "protein", used interchangeably herein, refer to a polymer of amino acids without regard to the length of the polymer; thus, peptides, oligopeptides, and proteins are included within the definition of polypeptide. This term also does not specify, or exclude chemical or post-expression modifications of the polypeptides of the invention, although chemical or post-expression modifications of these polypeptides may be included or excluded as specific embodiments. Therefore, for example, modifications to polypeptides that include the covalent attachment of glycosyl groups, acetyl groups, phosphate groups, lipid groups and the like are expressly encompassed by the term polypeptide. Further, polypeptides with these modifications may be specified as individual species to be included or excluded from the present invention. The natural or other chemical modifications, such as those listed in examples above can occur anywhere in a polypeptide, including the peptide backbone, the amino acid side-chains and the amino or carboxyl termini. It will be appreciated that the same type of modification maybe present in the same or varying degrees at several sites in a given polypeptide. Also, a given polypeptide may contain many types of modifications. Polypeptides may be branched, for example, as a result of ubiquitination, and they may be cyclic, with or without branching. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristoylation, oxidation, pegylation, proteolytic processing, phosphorylation, prenylation, racemization, selenoylation, sulfation, transfer-RNA mediated addition of amino acids to proteins such as arginylation, and ubiquitination. [See, for instance, Creighton, (1993), Posttranslational Covalent Modification of Proteins, W.H. Freeman and Company, New York B. C. Johnson, Ed., Academic Press, New York 1-12; Seifter, et al., (1990). Meth Enzymol 182:626-646; Rattan et al., (1992). Ann NY Acad Sci 663:48-62]. Also included within the definition are polypeptides which contain one or more analogs of an amino acid (including, for example, non-naturally occurring amino acids, amino acids which only occur naturally in an unrelated biological system, modified amino acids from mammalian systems, etc.), polypeptides with substituted linkages, as well as other modifications known in the art, both naturally occurring and non-naturally occurring.

As used herein, the terms "recombinant polynucleotide" and "polynucleotide construct" are used interchangeably to refer to linear or circular, purified or isolated polynucleotides that have been artificially designed and which comprise at least two nucleotide sequences that are not found as contiguous nucleotide sequences in their initial natural environment. In particular, these terms mean that the polynucleotide or cDNA is adjacent to "backbone" nucleic acid to which it is not adjacent in its natural environment. Additionally, to be "enriched" the cDNAs will represent 5% or more of the number of nucleic acid inserts in a population of nucleic acid backbone molecules. Backbone molecules according to the present invention include nucleic acids such as expression vectors, self-replicating nucleic acids, viruses, integrating nucleic acids, and other vectors or nucleic acids used to maintain or manipulate a nucleic acid insert of interest. Preferably, the enriched cDNAs represent 15% or more of the number of nucleic acid inserts in the population of recombinant backbone molecules. More preferably, the enriched cDNAs represent 50% or more of the number of nucleic acid inserts in the population of recombinant backbone molecules. In a highly preferred embodiment, the enriched cDNAs represent 90% or more (including any number between 90 and 100%, to the thousandth position, e.g., 99.5%) of the number of nucleic acid inserts in the population of recombinant backbone molecules.

The term "recombinant polypeptide" is used herein to refer to polypeptides that have been artificially designed and which comprise at least two polypeptide sequences that are not found as contiguous polypeptide sequences in their initial natural environment, or to refer to polypeptides which have been expressed from a recombinant polynucleotide.

As used herein, the term "operably linked" refers to a linkage of polynucleotide elements in a functional relationship. A sequence which is "operably linked" to a regulatory sequence such as a promoter means that said regulatory element is in the correct location and orientation in relation to the nucleic acid to control RNA polymerase initiation and expression of the nucleic acid of interest. For instance, a promoter or enhancer, is operably linked to a coding sequence if it affects the transcription of the coding sequence.

The term "domain" refers to an amino acid fragment with specific biological properties. This term encompasses all known structural and linear biological motifs. Examples of such motifs include but are not limited to leucine zippers, helix-turn-helix motifs, glycosylation sites, ubiquitination sites, alpha helices, and beta sheets, signal peptides which direct the secretion of proteins, sites for post-translational modification, enzymatic active sites, substrate binding sites, and enzymatic cleavage sites.

Although each of these terms has a distinct meaning, the terms "comprising", "consisting of" and "consisting essentially of" may be interchanged for one another throughout the instant application. The term "having" has the same meaning as "comprising" and may be replaced with either the term "consisting of" or "consisting essentially of".

Unless otherwise specified in the application, nucleotides and amino acids of polynucleotides and polypeptides, respectively, of the present invention are contiguous and not interrupted by heterologous sequences.

The term "neoplastic cells" as used herein refers to cells that result from abnormal new growth. A neoplastic cell further includes transformed cells, cancer cells including blood cancers and solid tumors (benign and malignant).

As used herein, the term "tumor" refers to an abnormal mass or population of cells that result from excessive cell division, whether malignant or benign, and all pre-cancerous and cancerous cells and tissues. A "tumor" is further defined as two or more, neoplastic cells.

"Malignant tumors" are distinguished from benign growths or tumors in that, in addition to uncontrolled cellular proliferation, they will invade surrounding tissues and may additionally metastasize.

The term "transformed cells," "malignant cells" or "cancer" are interchangeable and refer to cells that have undergone malignant transformation, but may also include lymphocyte cells that have undergone blast transformation. Malignant transformation is a conversion of normal cells to malignant cells. Transformed cells have a greater ability to cause tumors when injected into animals. Transformation can be recognized by changes in growth characteristics, particularly in requirements for macromolecular growth factors, and often also by changes in morphology. Transformed cells usually proliferate without requiring adhesion to a substratum and usually lack cell to cell inhibition and pile up after forming a monolayer in cell culture.

The term "neoplastic disease" as used herein refers to a condition characterized by uncontrolled, abnormal growth of cells. Neoplastic diseases include cancer. Examples of cancer include but are not limited to, carcinoma, lymphoma, blastoma, sarcoma, and leukemia. More particular examples of such cancers include breast cancer, prostate cancer, colon cancer, squamous cell cancer, small-cell lung cancer, non-small cell lung cancer, ovarian cancer, cervical cancer, gastrointestinal cancer, pancreatic cancer, glioblastoma, liver cancer, bladder cancer, hepatoma, colorectal cancer, uterine cervical cancer, endometrial carcinoma, salivary gland carcinoma, kidney cancer, vulval cancer, thyroid cancer, hepatic carcinoma, skin cancer, melanoma, brain cancer, ovarian cancer, neuroblastoma, myeloma, various types of head and neck cancer, acute lymphoblastic leukemia, acute myeloid leukemia, Ewing sarcoma and peripheral neuroepithelioma. All of the possible cancers listed herein are included in, or may be excluded from, the present invention as individual species.

As used herein, the term "carcinoma" refers to a new growth that arises from epithelium, found in skin or, more commonly, the lining of body organs (adenocarcinoma), for example: breast, prostate, lung, stomach or bowel. Carcinomas include bladder carcinoma, hepatocarcinoma, hepatoblastoma, rhabdomyosarcoma, ovarian carcinoma, cervical carcinoma, lung carcinoma, breast carcinoma, colorectal carcinoma, uterine cervical cancer carcinoma, endometrioid carcinoma, paraganglioma, squamous cell carcinoma in head and neck, esophageal carcinoma, thyroid carcinoma, astrocytoma, neuroblastoma and neuroepithelioma. All of the possible carcinomas listed herein are included in, or may be excluded from, the present invention as individual species.

The term "immortalized cells" as used herein refers to cells reproduce indefinitely. The cells escape from the normal limitation on growth of a finite number of division cycles. The term does not include malignant cells.

The term "normal cells" as used herein refers to cells that have a limitation on growth, i.e. a finite number of division cycles (the Hayflick limit); therefore, is a nontumorigenic cell. Normal cell include primary cells, which is a cell or cell line taken directly from a living organism which is not immortalized.

The term "cell cycle" as used herein refers to the cyclic biochemical and structural events occurring during growth and division of cells. The stages of the cell cycle include $G_0$ (Gap 0; rest phase), G1 (Gap 1), S phase (DNA synthesis), G2 (Gap 2) and M phase (mitosis).

The term "cell growth" as used herein refers to an increase in the size of a population of cells.

The term "cell division" as used herein refers to mitosis, i.e., the process of cell reproduction.

The term "proliferation" as used herein means growth and division of cells. "Actively proliferating" means cells that are actively growing and dividing.

The term "inhibiting cellular proliferation" as used herein refers to slowing and/or preventing the growth and division of cells. Cells may further be specified as being arrested in a particular cell cycle stage: G1 (Gap 1), S phase (DNA synthesis), G2 (Gap 2) or M phase (mitosis).

The term "preferentially inhibiting cellular proliferation" as used herein refers to slowing and/or preventing the growth and division of cells as compared to normal cells.

The term "metastasis" refers to the transfer of disease (e.g., cancer) from one organ and/or tissue to another not directly connected with it. As used herein, metastasis refers to neoplastic cell growth in an unregulated fashion and spread to distal tissues and organs of the body.

The term "inhibiting metastasis" refers to slowing and/or preventing metastasis or the spread of neoplastic cells to a site remote from the primary growth area.

The term "invasion" as used herein refers to the spread of cancerous cells to surrounding tissues.

The term "inhibiting invasion" refers to slowing and/or preventing the spread of cancerous cells to surrounding tissues.

The term "apoptosis" as used herein refers to programmed cell death as signaled by the nuclei in normally functioning human and animal cells when age or state of cell health and condition dictates. "Apoptosis" is an active process requiring metabolic activity by the dying cell, often characterized by cleavage of the DNA into fragments that give a so called laddering pattern on gels. Cells that die by apoptosis do not usually elicit the inflammatory responses that are associated with necrosis, though the reasons are not clear. Cancerous cells, however, are unable to experience, or have a reduction in, the normal cell transduction or apoptosis-driven natural cell death process. Morphologically, apoptosis is characterized by loss of contact with neighboring cells, concentration of cytoplasm, endonuclease activity-associated chromatin condensation and pyknosis, and segmentation of the nucleus, among others.

The term "necrosis" as used herein refers to the sum of the morphological changes indicative of cell death and caused by the progressive degradative action of enzymes, it may affect groups of cells or part of a structure or an organ. Morphologically, necrosis is characterized by marked swelling of mitochondria, swelling of cytoplasm and nuclear alteration, followed by cell destruction and autolysis. It occurs passively or incidentally.

The term "inducing apoptosis" refers to increasing the number of cells that undergo apoptosis, or the rate by which cells undergo apoptosis, in a given cell population. Preferably the increase is at least 1.25, 1.5, 2, 5, 10, 50, 100, 500 or 1000 fold increase as compared to normal, untreated or negative control cells.

The term "inhibiting apoptosis" refers to any decrease in the number of cells which undergo apoptosis relative to an untreated control. Preferably, the decrease is at least 1.25, 1.5, 2, 5, 10, 50, 100, 500 or 1000 fold decrease as compared to normal, untreated or negative control cells.

An "effective amount" of a composition disclosed herein or an agonist thereof, in reference to "inhibiting the cellular proliferation" of a neoplastic cell, is an amount capable of inhibiting, to some extent, the growth of target cells. The term further includes an amount capable of invoking a growth inhibitory, cytostatic and/or cytotoxic effect and/or apoptosis and/or necrosis of the target cells. An "effective amount" of a polypeptide of the present invention or an agonist thereof for purposes of inhibiting neoplastic cell growth may be determined empirically and in a routine manner using methods well known in the art.

A "therapeutically effective amount", in reference to the treatment of neoplastic disease or neoplastic cells, refers to an amount capable of invoking one or more of the following effects: (1) inhibition, to some extent, of tumor growth, including, (i) slowing down and (ii) complete growth arrest; (2) reduction in the number of tumor cells; (3) maintaining tumor size; (4) reduction in tumor size; (5) inhibition, including (i) reduction, (ii) slowing down or (iii) complete prevention, of tumor cell infiltration into peripheral organs; (6) inhibition, including (i) reduction, (ii) slowing down or (iii) complete prevention, of metastasis; (7) enhancement of anti-tumor immune response, which may result in (i) maintaining tumor size, (ii) reducing tumor size, (iii) slowing the growth of a tumor, (iv) reducing, slowing or preventing invasion or (v) reducing, slowing or preventing metastasis; and/or (8) relief, to some extent, of one or more symptoms associated with the disorder. A "therapeutically effective amount" of a polypeptide of the present invention or an agonist thereof for purposes of treatment of tumor may be determined empirically and in a routine manner.

A "growth inhibitory amount" of a Polypeptide of the present invention or an agonist thereof is an amount capable of inhibiting the growth of a cell, especially a malignant tumor cell, e.g., cancer cell, either in vitro or in vivo. A "growth inhibitory amount" of a polypeptide of the present invention or an agonist thereof for purposes of inhibiting neoplastic cell growth may be determined empirically and in a routine manner using methods well known in the art.

A "cytotoxic amount" of a polypeptide of the present invention or an agonist thereof is an amount capable of causing the destruction of a cell, especially tumor, e.g., cancer cell, either in vitro or in vivo. A "cytotoxic amount" of a polypeptide of the present invention or an agonist thereof for purposes of inhibiting neoplastic cell growth may be determined empirically and in a routine manner using methods well known in the art.

The terms "killing" or "inducing cytotoxicity" as used herein refer to inducing cell death by either apoptosis and/or necrosis, whereby embodiments of the invention include only apoptosis, only necrosis and both apoptosis and necrosis.

The term "cytotoxic agent" as used herein refers to a substance that inhibits or prevents the function of cells, for example by inhibiting progression of the cell cycle, and/or causes cell death. The term is intended to include radioactive isotopes, chemotherapeutic agents, and toxins such as enzymatically active toxins of bacterial, fungal, plant or animal origin, or fragments thereof.

The term "preventing" as used herein refers to administering a compound prior to the onset of clinical symptoms of a disease or condition so as to prevent a physical manifestation of the disease or condition. Alternatively, the term "preventing" can also be used to signify the reduction, or severity, of clinical symptoms associated with a disease or condition.

"Suppression" involves administration of drug prior to the clinical appearance of disease.

The term "treating" as used herein refers to administering a compound after the onset of clinical symptoms.

In human and veterinary medicine, we use the term "prophylaxis" as distinct from "treatment" to encompass "preventing" and "suppressing". Herein, "protection" includes "prophylaxis". Protection need not be absolute to be useful.

The term "in need of treatment" as used herein refers to a judgment made by a caregiver (e.g. physician, nurse, nurse practitioner, etc in the case of humans; veterinarian in the case of animals, including non-human mammals) that an individual or animal requires or will benefit from treatment. This judgment is made based on a variety of factors that are in the realm of a caregiver's expertise, but that include the knowledge that the individual or animal is ill, or will be ill, as the result of a condition that is treatable by the compounds of the invention.

The term "perceives a need for treatment" refers to a sub-clinical determination that an individual desires treatment. The term "perceives a need for treatment" in other embodiments can refer to the decision that an owner of an animal makes for treatment of the animal.

The term "individual" or "patient" as used herein refers to any animal, including mammals, preferably mice, rats, other rodents, rabbits, dogs, cats, swine, cattle, sheep, horses, or primates, and most preferably humans. The term may specify male or female or both, or exclude male or female.

As used herein, the term "non-human animal" refers to any non-human animal, including insects, birds, rodents and more usually mammals. Preferred non-human animals include: primates; farm animals such as swine, goats, sheep, donkeys, cattle, horses, chickens, rabbits; and rodents, preferably rats or mice. As used herein, the term "animal" is used to refer to any species in the animal kingdom, preferably vertebrates, including birds and fish, and more preferable a mammal. Both the terms "animal" and "mammal" expressly embrace human subjects unless preceded with the term "non-human".

As used herein, the terms "physiologically acceptable," "pharmaceutically acceptable," and "pharmaceutical" are interchangeable.

Identity between Nucleic Acids or Polypeptides

The terms "percentage of sequence identity" and "percentage homology" are used interchangeably herein to refer to comparisons among polynucleotides and polypeptides, and are determined by comparing two optimally aligned sequences over a comparison window, wherein the portion of the polynucleotide or polypeptide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity. Identity is evaluated using any of the variety of sequence comparison algorithms and programs known in the art. Such algorithms and programs include, but are by no means limited to, TBLASTN, BLASTP, FASTA, TFASTA, CLUSTALW, FASTDB [Pearson and Lipman, (1988), Proc. Natl. Acad. Sci. USA 85(8):2444-2448; Altschul et al., (1990), J. Mol. Biol. 215(3):403-410; Thompson et al. (1994), Nucleic Acids. Res. 22(2):4673-4680; Higgins et al., (1996), Meth. Enzymol. 266:383-402; Altschul et al., (1993), Nature Genetics 3:266-272; Brutlag et al. (1990) Comp. App. Biosci. 6:237-24], the disclosures of which are incorporated by reference in their entireties.

In a particularly preferred embodiment, protein and nucleic acid sequence identities are evaluated using the Basic Local Alignment Search Tool ("BLAST") which is well known in the art [e.g., Karlin and Altschul, (1990), Proc. Natl. Acad. Sci. USA 87:2267-2268; Altschul et al., (1997), Nuc. Acids Res. 25:3389-3402] the disclosures of which are incorporated by reference in their entireties. In particular, five specific BLAST programs are used to perform the following task:

(1) LASTP and BLAST3 compare an amino acid query sequence against a protein sequence database;

(2) BLASTN compares a nucleotide query sequence against a nucleotide sequence database;

(3) LASTX compares the six-frame conceptual translation products of a query nucleotide sequence (both strands) against a protein sequence database;

(4) BLASTN compares a query protein sequence against a nucleotide sequence database translated in all six reading frames (both strands); and (5) BLASTX compares the six-frame translations of a nucleotide query sequence against the six-frame translations of a nucleotide sequence database.

The BLAST programs identify homologous sequences by identifying similar segments, which are referred to herein as "high-scoring segment pairs," between a query amino or nucleic acid sequence and a test sequence which is preferably obtained from a protein or nucleic acid sequence database. High-scoring segment pairs are preferably identified (i.e., aligned) by means of a scoring matrix, many of which are known in the art. Preferably, the scoring matrix used is the BLOSUM62 matrix [Gonnet et al., (1992), Science 256:1443-1445; Henikoff and Henikoff, (1993), Proteins 17:49-61, the disclosures of which are incorporated by reference in their entireties]. Less preferably, the PAM or PAM250 matrices may also be used [see, e.g., Schwartz and Dayhoff, (1978), eds., Matrices for Detecting Distance Relationships: Atlas of Protein Sequence and Structure, Washington: National Biomedical Research Foundation, the disclosure of which is incorporated by reference in its entirety]. The BLAST programs evaluate the statistical significance of all high-scoring segment pairs identified, and preferably selects those segments which satisfy a user-specified threshold of significance, such as a user-specified percent homology. Preferably, the statistical significance of a high-scoring segment pair is evaluated using the statistical significance formula of Karlin (see, e.g., Karlin and Altschul, 1990), the disclosure of which is incorporated by reference in its entirety. The BLAST programs may be used with the default parameters or with modified parameters provided by the user.

Another preferred method for determining the best overall match between a query nucleotide sequence (a sequence of the present invention) and a subject sequence, also referred to as a global sequence alignment, can be determined using the FASTDB computer program based on the algorithm of Brutlag et al. (1990), the disclosure of which is incorporated by reference in its entirety. In a sequence alignment the query and subject sequences are both DNA sequences. An RNA sequence can be compared by first converting U's to T's. The result of said global sequence alignment is in percent identity. Preferred parameters used in a FASTDB alignment of DNA sequences to calculate percent identity are: Matrix=Unitary, k-tuple=4, Mismatch Penalty=1, Joining Penalty=30, Randomization Group Length=0, Cutoff Score=1, Gap Penalty=5, Gap Size Penalty=0.05, Window Size=500 or the length of the subject nucleotide sequence, whichever is shorter. If the subject sequence is shorter than the query sequence because of 5' or 3' deletions, not because of internal deletions, a manual correction must be made to the results. This is because the FASTDB program does not account for 5' and 3' truncations of the subject sequence when calculating percent identity. For subject sequences truncated at the 5' or 3' ends, relative to the query sequence, the percent identity is corrected by calculating the number of bases of the query sequence that are 5' and 3' of the subject sequence, which are not matched/aligned, as a percent of the total bases of the query sequence. Whether a nucleotide is matched/aligned is determined by results of the FASTDB sequence alignment. This percentage is then subtracted from the percent identity, calculated by the above FASTDB program using 10, the specified parameters, to arrive at a final percent identity score. This corrected score is what is used for the purposes of the present invention. Only nucleotides outside the 5' and 3' nucleotides of the subject sequence, as displayed by the FASTDB alignment, which are not matched/aligned with the query sequence, are calculated for the purposes of manually adjusting the percent identity score. For example, a 90 nucleotide subject sequence is aligned to a 100 nucleotide query sequence to determine percent identity. The deletions occur at the 5' end of the subject sequence and therefore, the FASTDB alignment does not show a matched/alignment of the first 10 nucleotides at 5' end.

The 10 unpaired nucleotides represent 10% of the sequence (number of nucleotides at the 5' and 3' ends not matched/total number of nucleotides in the query sequence) so 10% is subtracted from the percent identity score calculated by the FASTDB program. If the remaining 90 nucleotides were perfectly matched the final percent identity would be 90%. In another example, a 90 nucleotide subject sequence is compared with a 100 nucleotide query sequence. This time the deletions are internal deletions so that there are no nucleotides on the 5' or 3' of the subject sequence which are not matched/aligned with the query. In this case the percent identity calculated by FASTDB is not manually corrected. Once again, only nucleotides 5' and 3' of the subject sequence which are not matched/aligned with the query sequence are manually corrected. No other manual corrections are made for the purposes of the present invention.

Another preferred method for determining the best overall match between a query amino acid sequence (a sequence of the present invention) and a subject sequence, also referred to as a global sequence alignment, can be determined using the FASTDB computer program based on the algorithm of Brutlag et al. (1990). In a sequence alignment the query and subject sequences are both amino acid sequences. The result of said global sequence alignment is in percent identity. Preferred parameters used in a FASTDB amino acid alignment are: Matrix=PAM 0, k-tuple=2, Mismatch Penalty=1, Joining Penalty=20, Randomization Group Length=0, Cutoff Score=1, Window Size=sequence length, Gap Penalty=5, Gap Size Penalty=0.05, Window Size=500 or the length of the subject amino acid sequence, whichever is shorter. If the subject sequence is shorter than the query sequence due to N- or C-terminal deletions, not because of internal deletions, the results, in percent identity, must be manually corrected. This is because the FASTDB program does not account for N- and C-terminal truncations of the subject sequence when calculating global percent identity. For subject sequences truncated at the N- and C-termini, relative to the query sequence, the percent identity is corrected by calculating the number of residues of the query sequence that are N- and C-terminal of the subject sequence, which are not matched/aligned with a corresponding subject residue, as a percent of the total bases of the query sequence. Whether a residue is matched/aligned is determined by results of the FASTDB sequence alignment. This percentage is then subtracted from the percent identity, calculated by the above FASTDB program using the specified parameters, to arrive at a final percent identity score. This final percent identity score is what is used for the purposes of the present invention. Only residues to the N- and C-termini of the subject sequence, which are not matched/aligned with the query sequence, are considered for the purposes of manually adjusting the percent identity score. That is, only query amino acid residues outside the farthest N- and C-terminal residues of the subject sequence. For example, a 90 amino acid residue subject sequence is aligned with a 100-residue query sequence to determine percent identity. The deletion occurs at the N-terminus of the subject sequence and therefore, the FASTDB alignment does not match/align with the first residues at the N-terminus. The 10 unpaired residues represent 10% of the sequence (number of residues at the N- and C-termini not matched/total number of residues in the query sequence) so 10% is subtracted from the percent identity score calculated by the FASTDB program. If the remaining 90 residues were perfectly matched the final percent identity would be 90%. In another example, a 90-residue subject sequence is compared with a 100-residue query sequence. This time the deletions are internal so there are no residues at the N- or C-termini of the subject sequence, which are not matched/aligned with the query. In this case the percent identity calculated by FASTDB is not manually corrected. Once again, only residue positions outside the N- and C-terminal ends of the subject sequence, as displayed in the FASTDB alignment, which are not matched/aligned with the query sequence are manually corrected. No other manual corrections are made for the purposes of the present invention.

The term "percentage of sequence similarity" refers to comparisons between polypeptide sequences and is determined by comparing two optimally aligned sequences over a comparison window, wherein the portion of the polypeptide sequence in the comparison window may comprise additions or deletions (i.e., gaps) as compared to the reference sequence (which does not comprise additions or deletions) for optimal alignment of the two sequences. The percentage is calculated by determining the number of positions at which an identical or equivalent amino acid residue occurs in both sequences to yield the number of matched positions, dividing the number of matched positions by the total number of positions in the window of comparison and multiplying the result by 100 to yield the percentage of sequence similarity. Similarity is evaluated using any of the variety of sequence comparison algorithms and programs known in the art, including those described above in this section. Equivalent amino acid residues are defined herein in the "Mutated polypeptides" section.

Polynucleotides of the Invention

The present invention concerns GENSET genomic and cDNA sequences. The present invention encompasses GENSET genes, polynucleotides comprising GENSET genomic and cDNA sequences, as well as fragments and variants thereof. These polynucleotides may be purified, isolated, or recombinant.

Also encompassed by the present invention are allelic variants, orthologs, splice variants, and/or species homologues of the GENSET genes. Procedures known in the art can be used to obtain full-length genes and cDNAs, allelic variants, splice variants, full-length coding portions, orthologs, and/or species homologues of genes and cDNAs corresponding to a nucleotide sequence selected from the group consisting of sequences of odd SEQ ID NOs:1-111 and sequences of clone inserts of the deposited clone pool, using information from the sequences disclosed herein or the clone pool deposited with the ATCC. For example, allelic variants, orthologs and/or species homologues may be isolated and identified by making suitable probes or primers from the sequences provided herein and screening a suitable nucleic acid source for allelic variants and/or the desired homologue using any technique known to those skilled in the art including those described into the section entitled "To find similar sequences".

In a specific embodiment, the polynucleotides of the invention are at least 15, 30, 50, 100, 125, 500, or 1000 continuous nucleotides. In another embodiment, the polynucleotides are less than or equal to 300 kb, 200 kb, 100 kb, 50 kb, 10 kb, 7.5 kb, 5 kb, 2.5 kb, 2 kb, 1.5 kb, or 1 kb in length. In a further embodiment, polynucleotides of the invention comprise a portion of the coding sequences, as disclosed herein, but do not comprise all or a portion of any intron. In another embodiment, the polynucleotides comprising coding sequences do not contain coding sequences of a genomic flanking gene (i.e., 5' or 3' to the gene of interest in the genome). In other embodiments, the polynucleotides of the invention do not contain the coding sequence of more than 1000, 500, 250, 100, 75, 50, 25, 20, 15, 10, 5, 4, 3, 2, or 1 naturally occurring genomic flanking gene(s).

Deposited Clone Pool of the Invention

Expression of GENSET genes has been shown to lead to the production of at least one mRNA species per GENSET gene, which cDNA sequence is set forth in the appended Sequence Listing as odd SEQ ID NOs:1-111. The cDNAs corresponding to these GENSET mRNA species were cloned either in the vector pBluescriptII $SK^-$ (Stratagene) or in a vector called pPT. Cells containing the cloned cDNAs of the present invention are maintained in permanent deposit by the inventors at Genset, S.A., 24 Rue Royale, 75008 Paris, France. Table I provides Genset's internal designation number assigned to each SEQ ID NO., and indicates whether the sequence is a nucleic acid sequence (DNA) or a protein (PRT) sequence. Each cDNA can be removed from the Bluescript vector in which it was inserted by performing a NotI Pst I double digestion, or from the pPT vector by performing a MunI HindIII double digestion, to produce the appropriate fragment for each clone, provided the cDNA sequence does not contain any of the corresponding restriction sites within its sequence. Alternatively, other restriction enzymes of the multicloning site of the vector may be used to recover the desired insert as indicated by the manufacturer.

Pools of cells containing GENSET genes as described in the Sequence Listing, from which the cells containing a particular polynucleotide is obtainable, were or will be also deposited with the American Tissue Culture Collection (ATCC), 10801 University. Boulevard, Manassas, Va. 20110-2209, United States. Each cDNA clone has been transfected into separate bacterial cells (*E-coli*) for these composite deposits.

Bacterial cells containing a particular clone can be obtained from the composite deposit as follows:

An oligonucleotide probe or probes should be designed to the sequence that is known for that particular clone. This sequence can be derived from the sequences provided herein, or from a combination of those sequences. The design of the oligonucleotide probe should preferably follow these parameters:

(a) it should be designed to an area of the sequence which has the fewest ambiguous bases ("N's"), if any;

(b) preferably, the probe is designed to have a Tm of approximately 80 degrees Celsius (assuming 2 degrees for each A or T and 4 degrees for each G or C). However, probes having melting temperatures between 40 degrees Celsius and 80 degrees Celsius may also be used provided that specificity is not lost.

The oligonucleotide should preferably be labeled with gamma[$^{32}$P]ATP (specific activity 6000 Ci/mmole), and T4 polynucleotide kinase using commonly employed techniques for labeling oligonucleotides. Other labeling techniques can also be used. Unincorporated label should preferably be removed by gel filtration chromatography or other established methods. The amount of radioactivity incorporated into the probe should be quantified by measurement in a scintillation counter. Preferably, specific activity of the resulting probe should be approximately $4\times10^6$ dpm/pmole.

The bacterial culture containing the pool of full-length clones should preferably be thawed and 100 ul of the stock used to inoculate a sterile culture flask containing 25 ml of sterile L-broth containing ampicillin at 100 ug/ml. The culture should preferably be grown to saturation at 37 degrees Celsius, and the saturated culture should preferably be diluted in fresh L-broth. Aliquots of these dilutions should preferably be plated to determine the dilution and volume which will yield approximately 5000 distinct and well-separated colonies on solid bacteriological media containing L-broth containing ampicillin at 100 ug/ml and agar at 1.5% in a 150 mm petri dish when grown overnight at 37 degrees Celsius. Other known methods of obtaining distinct, well-separated colonies can also be employed.

Standard colony hybridization procedures should then be used to transfer the colonies to nitrocellulose filters and lyse, denature and bake them.

The filter is then preferably incubated at 65 degrees Celsius for 1 hour with gentle agitation in 6×SSC (20× stock is 175.3 g NaCl/liter, 88.2 g Na citrate/liter, adjusted to pH 7.0 with NaOH) containing 0.5% SDS, 100 pg/ml of yeast RNA, and 10 mM EDTA (approximately 10 ml per 150 mm filter). Preferably, the probe is then added to the hybridization mix at a concentration greater than or equal to $1\times10^6$ dpm/ml. The filter is then preferably incubated at 65 degrees Celsius with gentle agitation overnight. The filter is then preferably washed in 500 ml of 2×SSC/0.1% SDS at room temperature with gentle shaking for 15 minutes. A third wash with 0.1×SSC/0.5% SDS at 65 degrees Celsius for 30 minutes to 1 hour is optional. The filter is then preferably dried and subjected to autoradiography for sufficient time to visualize the positives on the X-ray film. Other known hybridization methods can also be employed.

The positive colonies are picked, grown in culture, and plasmid DNA isolated using standard procedures. The clones can then be verified by restriction analysis, hybridization analysis, or DNA sequencing. The plasmid DNA obtained using these procedures may then be manipulated using standard cloning techniques familiar to those skilled in the art.

Alternatively, to recover cDNA inserts from the pool of bacteria, a PCR can be performed on plasmid DNA isolated using standard procedures and primers designed at both ends of the cDNA insertion, including primers designed in the multicloning site of the vector. If a specific cDNA of interest is to be recovered, primers may be designed in order to be specific for the 5' end and the 3' end of this cDNA using sequence information available from the appended sequence listing. The PCR product which corresponds to the cDNA of interest can then be manipulated using standard cloning techniques familiar to those skilled in the art.

Therefore, an object of the invention is an isolated, purified, or recombinant polynucleotide comprising a nucleotide sequence selected from the group consisting of human cDNA inserts of the deposited clone pool. Moreover, preferred polynucleotides of the invention include purified, isolated, or recombinant GENSET cDNAs consisting of, consisting essentially of, or comprising a nucleotide sequence selected from the group consisting of human cDNA inserts of the, deposited clone pool.

cDNA Sequences of the Invention

Another object of the invention is a purified, isolated, or recombinant polynucleotide comprising a nucleotide sequence selected from the group consisting of the polynucleotide sequences of the appended Sequence Listing, the sequences of human cDNA clone inserts of the deposited clone pool, complementary sequences thereto, and fragments thereof. Moreover, preferred polynucleotides of the invention include purified, isolated, or recombinant GENSET cDNAs consisting of, consisting essentially of, or comprising a sequence selected from the group consisting of the polynucleotide sequences of the Sequence Listing and the sequences of clone inserts of the deposited clone pool.

Structural parameters of each of the cDNAs of the present invention are presented in the appended Sequence Listing. Accordingly, the coding sequence (CDS) or open reading frame (ORF) of each cDNA of the invention refers to the nucleotide sequence beginning with the first nucleotide of the start codon and ending with the last nucleotide of the stop codon. Similarly, the 5' untranslated region (or 5'UTR) of each cDNA of the invention refers to the nucleotide sequence starting at nucleotide 1 and ending at the nucleotide immediately 5' to the first nucleotide of the start codon. The 3' untranslated region (or 3'UTR) of each cDNA of the invention refers to the nucleotide sequence starting at the nucleotide immediately 3' to the last nucleotide of the stop codon and ending at the last nucleotide of the cDNA.

Untranslated Regions

In addition, the invention concerns a purified, isolated, and recombinant nucleic acid comprising a nucleotide sequence selected from the group consisting of the 5'UTRs of the polynucleotide sequences of the appended Sequence Listing, those of human cDNA clone inserts of the deposited clone pool, sequences complementary thereto, and allelic variants thereof. The invention also concerns a purified, isolated, and/or recombinant nucleic acid comprising a nucleotide sequence selected from the group consisting of the 3'UTRs of the polynucleotide sequences of the appended Sequence Listing, those of human cDNA clone inserts of the deposited clone pool, sequences complementary thereto, and allelic variants thereof.

These polynucleotides may be used to detect the presence of GENSET mRNA species in a biological sample using either hybridization or RT-PCR techniques well known to those skilled in the art.

In addition, these polynucleotides may be used as regulatory molecules able to affect the processing and maturation of any polynucleotide including them (either a GENSET polynucleotide or an heterologous polynucleotide), preferably the localization, stability and/or translation of said polynucleotide including them [for a review on UTRs see Decker and Parker, (1995) Curr. Opin. Cell. Biol. 7(3):368-92, Derrigo et al., (2000) Int. J. Mol. Med. 5(2):111-23]. In particular, 3'UTRs may be used in order to control the stability of heterologous mRNAs in recombinant vectors using any methods known to those skilled in the art including Makrides (1999) Protein Expr Purif 1999 Nov; 17(2): 183-202), U.S. Pat. Nos. 5,925,564; 5,807,707 and 5,756, 264, which disclosures are hereby incorporated by reference in their entireties.

Coding Sequences

Another object of the invention is an isolated, purified or recombinant polynucleotide comprising the coding sequence of a sequence selected from the group consisting of the polynucleotide sequences of the appended Sequence Listing, those of human cDNA clone inserts of the deposited clone pool and variants thereof.

A further object of the invention is an isolated, purified, or recombinant polynucleotide encoding a polypeptide of the present invention.

It will be appreciated that should the extent of the coding sequence, differ from that indicated in the appended sequence listing as a result of a sequencing error, reverse transcription or amplification error, mRNA splicing, post-translational modification of the encoded protein, enzymatic cleavage of the encoded protein, or other biological factors, one skilled in the art would be readily able to identify the extent of the coding sequences in the polynucleotide sequences of the Sequence Listing, those of the human cDNA inserts of the deposited clone pool, and allelic variants thereof. Accordingly, the scope of any claims herein relating to nucleic acids containing the coding sequence of one of the polynucleotide sequences of the Sequence Listing and those of the cDNA inserts of the deposited clone pool is not to be construed as excluding any readily identifiable variations from or equivalents to the coding sequences described in the appended sequence listing. Equivalents include any alterations in a nucleotide coding sequence that does not result in an amino acid change, or that results in a conservative amino acid substitution, as defined below, in the polypeptide encoded by the nucleotide sequence. Similarly, should the extent of the polypeptides differ from those indicated in the appended Sequence Listing as a result of any of the preceding factors, the scope of claims relating to polypeptides comprising the amino acid sequence of the polypeptide sequences of the appended Sequence Listing is not to be construed as excluding any readily identifiable variations from or equivalents to the sequences described in the appended sequence listing.

The above disclosed polynucleotides that contain the coding sequence of the GENSET genes may be expressed in a desired host cell or a desired host organism, when this polynucleotide is placed under the control of suitable expression signals. The expression signals may be either the expression signals contained in the regulatory regions in the GENSET genes of the invention or, in contrast, the signals may be exogenous regulatory nucleic sequences. Such a polynucleotide, when placed under the suitable expression signals, may also be inserted in a vector for its expression and/or amplification.

Further included in the present invention are polynucleotides encoding the polypeptides of the present invention that are fused in frame to the coding sequences for additional heterologous amino acid sequences. Also included in the present invention are nucleic acids encoding polypeptides of the present invention together with additional, non-coding sequences, including, but not limited to, non-coding 5' and 3' sequences, vector sequence, sequences used for purification, probing, or priming. For example, heterologous sequences include transcribed, untranslated sequences that may play a role in transcription and mRNA processing, such as ribosome binding and stability of mRNA. The heterologous sequences may alternatively comprise additional coding sequences that provide additional functionalities. Thus, a nucleotide sequence encoding a polypeptide may be fused to a tag sequence, such as a sequence encoding a peptide that facilitates purification or detection of the fused polypeptide. In certain preferred embodiments of this aspect of the invention, the tag amino acid sequence is a hexa-histidine peptide, such as the tag provided in a pQE vector (QIAGEN), or in any of a number of additional, commercially available vectors. For instance, hexa-histidine provides for the convenient purification of the fusion protein (see, Gentz et al., 1989, Proc Natl Acad Sci USA Feb; 86(3):821-4, the disclosure of which is incorporated by reference in its entirety). The "HA" tag is another peptide useful for purification which corresponds to an epitope derived from the influenza hemagglutinin protein (see, Wilson, et al., 1984, Cell Jul; 37(3):767-78, the disclosure of which is incorporated by reference in its entirety). As discussed below, other such fusion proteins include a GENSET polypeptide fused to Fc at the N- or C-terminus.

Regulatory Sequences of the Invention

As mentioned, the genomic sequence of GENSET genes contain regulatory sequences in the non-coding 5'-flanking region and possibly in the non-coding 3'-flanking region that border the GENSET polypeptide coding regions containing the exons of these genes.

Polynucleotides derived from GENSET polynucleotide 5' and 3' regulatory regions are useful in order to detect the presence of at least a copy of a genomic nucleotide sequence of the GENSET gene or a fragment thereof in a test sample.

Preferred Regulatory Sequences

Polynucleotides carrying the regulatory elements located at the 5' end and at the 3' end of GENSET polypeptide coding regions may be advantageously used to control, e.g., the transcriptional and translational activity of a heterologous polynucleotide of interest.

Thus, the present invention also concerns a purified or isolated nucleic acid comprising a polynucleotide which is selected from the group consisting of the 5' and 3' GENSET polynucleotide regulatory regions, sequences complementary thereto, regulatory active fragments and variants thereof.

Another object of the invention consists of purified, isolated or recombinant nucleic acids comprising a polynucleotide that hybridizes, under the stringent hybridization conditions defined herein, with a polynucleotide of the present invention.

Preferred fragments of 5' and 3' regulatory regions are any one integer between 20 and 20,000 nucleotides in length.

For the purpose of the invention, a nucleic acid or polynucleotide is "functional" as a "regulatory region" for expressing a recombinant polypeptide or a recombinant polynucleotide if said regulatory polynucleotide contains nucleotide sequences which contain transcriptional and translational regulatory information, and such sequences are "operably linked" to nucleotide sequences which encode the desired polypeptide or the desired polynucleotide. The regulatory polynucleotides of the invention may be prepared using methods known in the art.

The regulatory polynucleotides according to the invention may be part of a recombinant expression vector that may be used to express a coding sequence in a desired host cell or host organism.

Preferred 5'-regulatory polynucleotides of the invention include 5'-UTRs of GENSET cDNAs, or regulatory active fragments or variants thereof.

Preferred 3'-regulatory polynucleotide of the invention include 3'-UTRs of GENSET cDNAs, or regulatory active fragments or variants thereof.

A further object of the invention consists of a purified or isolated nucleic acid comprising:

a) polynucleotide comprising a 5' regulatory nucleotide sequence selected from the group consisting of:
   (i) a nucleotide sequence comprising a polynucleotide of a GENSET polynucleotide 5' regulatory region or a complementary sequence thereto;
   (ii) a nucleotide sequence comprising a polynucleotide having at least 95% of nucleotide identity with the nucleotide sequence of a GENSET polynucleotide 5' regulatory region or a complementary sequence thereto;
   (iii) a nucleotide sequence comprising a polynucleotide that hybridizes under stringent hybridization conditions with the nucleotide sequence of a GENSET polynucleotide 5' regulatory region or a complementary sequence thereto; and
   (iv) a regulatory active fragment or variant of the polynucleotides in (i), (ii) and (iii);

b) a nucleic acid molecule encoding a desired polypeptide or a nucleic acid molecule of interest, wherein said nucleic acid molecule is operably linked to the polynucleotide defined in (a); and c) optionally, a polynucleotide comprising a 3'-regulatory polynucleotide, preferably a 3'-regulatory polynucleotide of a GENSET gene.

In a specific embodiment, the nucleic acid defined above includes the 5'-UTR of a GENSET cDNA, or a regulatory active fragment or variant thereof.

The regulatory polynucleotide of the 3' regulatory region, or its regulatory active fragments or variants, is advantageously operably linked at the 3'-end of the nucleic acid molecule encoding the desired polypeptide or nucleic acid molecule of interest.

The desired polypeptide encoded by the above-described nucleic acid may be of various nature or origin, encompassing proteins of prokaryotic viral or eukaryotic origin. Among the polypeptides expressed under the control of a GENSET polynucleotide regulatory region include bacterial, fungal or viral antigens. Also encompassed are eukaryotic proteins such as intracellular proteins, such as "house keeping" proteins, membrane-bound proteins, such as mitochondrial membrane-bound proteins and cell surface receptors, and secreted proteins such as endogenous mediators such as cytokines. The desired polypeptide may be a heterologous polypeptide or a GENSET polypeptide, especially a protein with an amino acid sequence selected from the group consisting of the polypeptide sequences of the Sequence Listing, those encoded by the cDNA inserts of the deposited clone pool, fragments and variants thereof.

The desired nucleic acids encoded by the above-described polynucleotides, usually an RNA molecule, may be complementary to a desired coding polynucleotide, for example to a GENSET coding sequence, and thus useful as an antisense polynucleotide. Such a polynucleotide may be included in a recombinant expression vector in order to express the desired polypeptide or the desired nucleic acid in host cell or in a host organism. Suitable recombinant vectors that contain a polynucleotide such as described herein are disclosed elsewhere in the specification.

Polynucleotide Variants

The invention also relates to variants of the polynucleotides described herein and fragments thereof. "Variants" of polynucleotides, as the term is used herein, are polynucleotides that differ from a reference polynucleotide. Generally, differences are limited so that the nucleotide sequences of the reference and the variant are closely similar overall and, in many regions, identical. The present invention encompasses both allelic variants and degenerate variants.

Allelic Variant

A variant of a polynucleotide may be a naturally occurring variant such as a naturally occurring allelic variant, or it may be a variant that is not known to occur naturally. By an "allelic variant" is intended one of several alternate forms of a gene occupying a given locus on a chromosome of an organism [see Lewin, (1989), Proc. Natl. Acad. Sci. USA 86:9832-9835], the disclosure of which is incorporated by reference in its entirety. Diploid organisms may be homozygous or heterozygous for an allelic form. Non-naturally occurring variants of the polynucleotide may be made by art-known mutagenesis techniques, including those applied to polynucleotides, cells or organisms. See, for example, Table III, which provides sets of related cDNAs of the invention, e.g. sets of sequences representing allelic variants of a single gene.

Degenerate Variant

In addition to the isolated polynucleotides of the present invention, and fragments thereof, the invention further includes polynucleotides which comprise a sequence substantially different from those described above but which, due to the degeneracy of the genetic code, still encode a GENSET polypeptide of the present invention. These polynucleotide variants are referred to as "degenerate variants" throughout the instant application. That is, all possible polynucleotide sequences that encode the GENSET polypeptides of the present invention are contemplated. This includes the genetic code and species-specific codon preferences known in the art.

Nucleotide changes present in a variant polynucleotide may be silent, which means that they do not alter the amino acids encoded by the polynucleotide. However, nucleotide changes may also result in amino acid substitutions, additions, deletions, fusions and truncations in the polypeptide encoded by the, reference sequence. The substitutions, deletions or additions may involve one or more nucleotides. The variants may be altered in coding or non-coding regions or both. Alterations in the coding regions may produce conservative or non-conservative amino acid substitutions, deletions or additions. In the context of the present invention, preferred embodiments are those in which the polynucleotide variants encode polypeptides which retain substantially the same biological properties or activities as the GENSET protein. More preferred polynucleotide variants are those containing conservative substitutions.

Similar Polynucleotides

Other embodiments of the present invention provide a purified, isolated or recombinant polynucleotide which is at least 80%, 85%, 90%, 95%, 96%, 97%, 98% or 99% identical to a polynucleotide of the present invention. The above polynucleotides are included regardless of whether they encode a polypeptide having a GENSET biological activity. This is because even where a particular nucleic acid molecule does not encode a polypeptide having activity, one of skill in the art would still know how to use the nucleic acid molecule, for instance, as a hybridization probe or primer. Uses of the nucleic acid molecules of the present invention that do not encode a polypeptide having GENSET activity include, inter alia, isolating a GENSET gene or allelic variants thereof from a DNA library, and detecting GENSET mRNA expression in biological samples suspected of containing GENSET mRNA or DNA, e.g., by Northern Blot or PCR analysis.

The present invention is further directed to polynucleotides having sequences at least 50% 60%, 70%, 80%, 90%, 95%, 96%, 97%, 98% or 99% identity to a polynucleotide, where said polynucleotides do, in fact, encode a polypeptide having a GENSET biological activity. Of course, due to the degeneracy of the genetic code, one of ordinary skill in the art will immediately recognize that a large number of the polynucleotides at least 50%, 60%, 70%, 80%, 90%, 95%, 96%, 97%, 98%, or 99% identical to a polynucleotide selected from the group consisting of polynucleotide sequences of the Sequence Listing and those of human cDNA clone inserts of the deposited clone pool will encode a polypeptide having biological activity. By a polynucleotide having a nucleotide sequence at least, for example, 95% "identical" to a reference nucleotide sequence of the present invention, it is intended that the nucleotide sequence of the polynucleotide is identical to the reference sequence except that the polynucleotide sequence may include up to five point mutations per each 100 nucleotides of the reference nucleotide sequence encoding the GENSET polypeptide. In other words, to obtain a polynucleotide having a nucleotide sequence at least 95% identical to a reference nucleotide sequence, up to 5% of the nucleotides in the reference sequence may be deleted, inserted, or substituted with another nucleotide. The query sequence may be any polynucleotide of the present invention.

Hybridizing Polynucleotides

In another aspect, the invention provides an isolated or purified nucleic acid molecule comprising a polynucleotide which hybridizes under stringent hybridization conditions to any polynucleotide of the present. Such hybridizing polynucleotides may be of at least any one integer between 10 and 10,000 nucleotides in length.

Of course, a polynucleotide which hybridizes only to polyA+ sequences (such as any 3' terminal polyA+ tract of a cDNA shown in the sequence listing), or to a 5' complementary stretch of T (or U) residues, would not be included in the definition of "polynucleotide," since such a polynucleotide would hybridize to any nucleic acid molecule containing a poly(A) stretch or the complement thereof (e.g., practically any double-stranded cDNA clone generated using oligo dT as a primer).

Complementary Polynucleotides

The invention further provides isolated nucleic acid molecules having a nucleotide sequence fully complementary to any polynucleotide of the invention.

Polynucleotide Fragments

The present invention is further directed to portions or fragments of the polynucleotides of the present invention. Uses for the polynucleotide fragments of the present invention include probes, primers, molecular weight markers and for expressing the polypeptide fragments of the present invention. Fragments include portions of polynucleotides selected from the group consisting of a) polynucleotide sequences of the Sequence Listing, b) genomic GENSET sequences, c) polynucleotides encoding a polypeptide of the present invention, d) sequences of human cDNA clone inserts of the deposited clone pool, and e) polynucleotides encoding the polypeptides encoded by the human cDNA clone inserts of the deposited clone pool. Particularly included in the present invention is a purified or isolated polynucleotide comprising at least 8 consecutive bases of a polynucleotide of the present invention. In one aspect of this embodiment, the polynucleotide comprises at least 10, 12, 15, 18, 20, 25, 28, 30, 35, 40, 50, 75, 100, 150, 200, 300, 400, 500, 800, 1000, 1500, or 2000 consecutive nucleotides of a polynucleotide of the present invention.

In addition to the above preferred polynucleotide sizes, further preferred sub-genuses of polynucleotides comprise at least X nucleotides, wherein "X" is defined as any integer between 8 and the integer representing the 3' most nucleotide position as set forth in the sequence listing or elsewhere herein. Further included as preferred polynucleotides of the present invention are polynucleotide fragments at least X nucleotides in length, as described above, that are further specified in terms of their 5' and 3' position. The 5' and 3' positions are represented by the position numbers set forth in the appended sequence listing wherein the 5' most nucleotide is 1 and the 3' most nucleotide is the last nucleotide for a particular. SEQ ID No. For allelic, degenerate and other variants, position 1 is defined as the 5' most nucleotide of the ORF, i.e., the nucleotide "A" of the start codon with the remaining nucleotides numbered consecutively. Therefore, every combination of a 5' and 3' nucleotide position that a polynucleotide fragment of the present invention, at least 8 contiguous nucleotides in length, could occupy on a polynucleotide of the invention is included in the invention as an individual species. The polynucleotide fragments specified by 5' and 3' positions can be immediately envisaged and are therefore not individually listed solely for the purpose of not unnecessarily lengthening the specification.

It is noted that the above species of polynucleotide fragments of the present invention may alternatively be described by the formula "a to b"; where "a" equals the 5' most nucleotide position and "b" equals the 3' most nucleotide position of the polynucleotide; and further where "a" equals an integer between 1 and the number of nucleotides of the polynucleotide sequence of the present invention minus 8, and where "b" equals an integer between 9 and the number of nucleotides of the polynucleotide sequence of the present invention; and where "a" is an integer smaller then "b" by at least 8.

The present invention also provides for the exclusion of any species of polynucleotide fragments of the present invention specified by 5' and 3' positions or sub-genuses of polynucleotides specified by size in nucleotides as described above. Any number of fragments specified by 5' and 3' positions or by size in nucleotides, as described above, may be excluded. Preferred excluded fragments include those having substantial homology to repeated sequences including Alu, L1, THE and MER repeats, SSTR sequences or satellite, micro-satellite, and telomeric repeats.

Other preferred fragments of the invention are polynucleotides comprising polynucleotide sequences encoding domains of polypeptides. Such fragments may be used to obtain other polynucleotides encoding polypeptides having similar domains using hybridization or RT-PCR techniques. Alternatively, these fragments may be used to express a polypeptide domain which may have a specific biological property.

Another object of the invention is an isolated, purified or recombinant polynucleotide encoding a polypeptide consisting of, consisting essentially of, or comprising a contiguous span of at least (any integer between 5 and 1,000 consecutive amino acids in length more preferably at least) 5, 6, 8, 10, 12, 15, 20, 25, 30, 35, 40, 50, 60, 75, 100, 150 or 200 consecutive amino. The present invention further encompasses any combination of the polynucleotide fragments listed in this section.

Oligonucleotide Primers and Probes

The present invention also encompasses fragments of GENSET polynucleotides for use as primers and probes. Polynucleotides derived from the GENSET genomic and cDNA sequences are useful in order to detect the presence of at least a copy of a GENSET polynucleotide or fragment, complement, or variant thereof in a test sample.

Structural Definition

Any polynucleotide of the invention may be used as a primer or probe. Particularly preferred probes and primers of the invention include isolated, purified, or recombinant polynucleotides comprising a contiguous span of at least 12, 15, 18, 20, 25, 30, 35, 40, 50, 60, 70, 80, 90, 100, 150, 200, 500, or 1000 nucleotides of a polynucleotide of the present invention.

For amplification purposes, pairs of primers with approximately the same. Tm are preferable. Primers may be designed using methods known in the art. Amplification techniques that can be used in the context of the present invention include, but are not limited to, the ligase chain reaction (LCR) described in EP-A-320 308, WO 9320227 and EP-A-439 182, the polymerase chain reaction (PCR, RT-PCR) and techniques such as the nucleic acid sequence based amplification (NASBA) described in Guatelli et al., (1990) Proc. Natl. Acad. Sci. USA 35:273-286 and in Compton (1991) Nature 350(6313):91-92, Q-beta amplification as described in European Patent Application No 4544610, strand displacement amplification as described in Walker, et al. (1996), Clin. Chem. 42:9-13 and EPA 684315 and, target mediated amplification as described in PCT Publication WO 9322461, the disclosures of which are incorporated by reference in their entireties.

The probes of the present invention are useful for a number of purposes. They can notably be used in Southern hybridization to genomic DNA. The probes can also be used to detect PCR amplification products. They may also be used to detect mismatches in the GENSET gene or mRNA using other techniques. They may also be used to in situ hybridization. Any of the polynucleotides, primers and probes of the present invention can be conveniently immobilized on a solid support. The solid support is not critical and can be selected by one skilled in the art. Thus, latex particles, microparticles, magnetic beads, non-magnetic beads (including polystyrene beads), membranes (including nitrocellulose strips), plastic tubes, walls of microtiter wells, glass or silicon chips, sheep (or other suitable animal's) red blood cells and DURACYTES are all suitable examples. Suitable methods for immobilizing nucleic acids on solid phases include ionic, hydrophobic, covalent interactions and the like. A solid support, as used herein, refers to any material which is insoluble, or can be made insoluble by a subsequent reaction. The solid support can be chosen for its intrinsic ability to attract and immobilize the capture reagent. Alternatively, the solid phase can retain an additional receptor which has the ability to attract and immobilize the capture reagent. The additional receptor can include a charged substance that is oppositely charged with respect to the capture reagent itself or to a charged substance conjugated to the capture reagent. As yet another alternative, the receptor molecule can be any specific binding member which is immobilized upon (attached to) the solid support and which has the ability to immobilize the capture reagent through a specific binding reaction. The receptor molecule enables the indirect binding of the capture reagent to a solid support material before the performance of the assay or during the performance of the assay. The solid phase thus can be a plastic, derivatized plastic, magnetic or non-magnetic metal, glass or silicon surface of a test tube, microtiter well, sheet, bead, microparticle, chip, sheep (or other suitable animal's) red blood cells, DURACYTES and other configurations known to those of ordinary skill in the art. The polynucleotides of the invention can be attached to or immobilized on a solid support individually or in groups of at least 2, 5, 8, 10, 12, 15, 20, or 25 distinct polynucleotides of the invention to a single solid support. In addition, polynucleotides other than those of the invention may be attached to the same solid support as one or more polynucleotides of the invention.

Oligonucleotide Array

A substrate, comprising a plurality of oligonucleotide primers or probes of the invention may be used either for detecting or amplifying targeted sequences in GENSET genes, may be used for detecting mutations in the coding or in the non-coding sequences of GENSET genes, and may also be used to determine GENSET gene expression in different contexts such as in different tissues, at different stages of a process (embryo development, disease treatment), and in patients versus healthy individuals as described elsewhere in the application.

As used herein, the term "array" means a one dimensional, two dimensional, or multidimensional arrangement of nucleic acids of sufficient length to permit specific detection of gene expression. For example, the array may contain a plurality of nucleic acids derived from genes whose expression levels are to be assessed. The array may include a GENSET genomic DNA, a GENSET cDNA, sequences complementary thereto or fragments thereof. Preferably, the fragments are at least 12, 15, 18, 20, 25, 30, 35, 40 or 50 nucleotides in length. More preferably, the fragments are at least 100 nucleotides in length. Even more preferably, the fragments are more than 100 nucleotides in length. In some embodiments the fragments may be more than 500 nucleotides in length.

Any polynucleotide provided herein may be attached in overlapping areas or at random locations on the solid support. Alternatively the polynucleotides of the invention may be attached in an ordered array wherein each polynucleotide is attached to a distinct region of the solid support which does not overlap with the attachment site of any other polynucleotide. Preferably, such an ordered array of polynucleotides is designed to be "addressable" where the distinct locations are recorded and can be accessed as part of an assay procedure. Addressable polynucleotide arrays typically comprise a plurality of different oligonucleotide probes that are coupled to a surface of a substrate in different known locations. The knowledge of the precise location of each polynucleotides location makes these "addressable" arrays particularly useful in hybridization assays. Any addressable array technology known in the art can be employed with the polynucleotides of the invention. One particular embodiment of these polynucleotide arrays is known as the GENECHIPS, and has been generally described in U.S. Pat. No. 5,143,854; PCT publications WO 90/15070 and 92/10092, which disclosures are hereby incorporated by reference in their entireties. These arrays may generally be produced using methods known in the art, e.g., Fodor et al., (1991) Science 251:767-777, which disclosure is hereby incorporated by reference in its entirety. The immobilization of arrays of oligonucleotides on solid supports has been rendered possible by the development of a technology generally identified as "Very Large Scale Immobilized Polymer Synthesis" (VLSIPS) in which, typically, probes are immobilized in a high density array on a solid surface of a chip. Examples of VLSIPS technologies are provided in U.S. Pat. Nos. 5,143,854; and 5,412,087 and in PCT Publications WO 90/15070, WO 92/10092 and WO 95/11995, which disclosures are hereby incorporated by reference in their entireties. In designing strategies aimed at providing arrays of nucleotides immobilized on solid supports, further presentation strategies known in the art may be used, such as those disclosed in PCT Publications WO 94/12305, WO 94/11530, WO 97/29212 and WO 97/31256, the disclosures of which are incorporated herein by reference in their entireties.

Consequently, the invention concerns an array of nucleic acid molecules comprising at least one polynucleotide of the invention. Preferably, the invention concerns an array of nucleic acids comprising at least two polynucleotides of the invention, particularly probes or primers as described herein. Preferably, the invention concerns an array of nucleic acids comprising at least five polynucleotides of the invention, particularly probes or primers as described herein.

Methods of Making the Polynucleotides of the Invention

The present invention also comprises methods of making the polynucleotides of the invention. Polynucleotides of the invention may be synthesized either enzymatically using techniques well known to those skilled in the art including amplification or hybridization-based methods as described herein, or chemically.

A variety of chemical methods of synthesizing nucleic acids are known to those skilled in the art. In many of these methods, synthesis is conducted on a solid support. Alternatively, polynucleotides may be prepared as described in U.S. Pat. No. 5,049,656, which disclosure is hereby incorporated by reference in its entirety. In some embodiments, several polynucleotides prepared as described above are ligated together to generate longer polynucleotides having a desired sequence.

Polypeptides of the Invention

The term "GENSET polypeptides" is used herein to, embrace all of the proteins and polypeptides of the present invention. The present invention encompasses GENSET polypeptides, including recombinant, isolated or purified GENSET polypeptides consisting of: (a) the full length polypeptides of even SEQ ID NOs:2-112; (b) the full length polypeptides encoded by the clone inserts of the deposited clone pool; (c) the epitope-bearing fragments of the polypeptides of even SEQ ID NOs:2-112; (d) the epitope-bearing fragments of the polypeptides encoded by the clone inserts contained in the deposited clone pool; (e) the domains of the polypeptides of even SEQ ID NOs:2-112; (f) the domains of the polypeptides encoded by the clone inserts contained in the deposited clone pool; (g) the signal peptides of the polypeptides of even SEQ ID NOs:2-112 or encoded by the human cDNAs of the deposited clone pool; (h) the mature polypeptides of even SEQ ID Nos:2-112 or encoded by the human cDNAs of the deposited clone pool; and (i) the allelic variant polypeptides of any of the polypeptides of (a)-(f). Other objects of the invention are polypeptides encoded by the polynucleotides of the invention as well as fusion polypeptides comprising such polypeptides.

Polypeptide Variants

The present invention further provides for GENSET polypeptides encoded by allelic and splice variants, orthologs, and/or species homologues. Procedures known in the art can be used to obtain, allelic variants, splice variants, orthologs, and/or species homologues of polynucleotides encoding polypeptides of the Sequence Listing and polypeptides encoded by the clone inserts of the deposited clone pool, using information from the sequences disclosed herein or the clones deposited with the ATCC.

The polypeptides of the present invention also include polypeptides having an amino acid sequence at least 50% identical, more preferably at least 60% identical, and still more preferably 70%, 80%, 90%, 95%, 96%, 97%, 98% or 99% identical to a polypeptide of the present invention. By a polypeptide having an amino acid sequence at least, for example, 95% "identical" to a query amino acid sequence of the present invention, it is intended that the amino acid sequence of the subject polypeptide is identical to the query sequence except that the subject polypeptide sequence may include up to five amino acid alterations per each 100 amino acids of the query amino acid sequence. In other words, to obtain a polypeptide having an amino acid sequence at least 95% identical to a query amino acid sequence, up to 5% (5 of 100) of the amino acid residues in the subject sequence may be inserted, deleted, (indels) or substituted with another amino acid.

Further polypeptides of the present invention include polypeptides which have at least 90% similarity, more preferably at least 95% similarity, and still more preferably at least 96%, 97%, 98% or 99% similarity to those described above. By a polypeptide having an amino acid sequence at least, for example, 95% "similar" to a query amino acid sequence of the present invention, it is intended that the amino acid sequence of the subject polypeptide is similar (i.e contains identical or equivalent amino acid residues) to the query sequence except that the subject polypeptide sequence may include up to five amino acid alterations per each 100 amino acids of the query amino acid sequence. In other words, to obtain a polypeptide having an amino acid sequence at least 95% similar to a query amino acid sequence, up to 5% (5 of 100) of the amino acid residues in the subject sequence may be inserted, deleted, (indels) or substituted with another non-equivalent amino acid.

These alterations of the reference sequence may occur at the amino or carboxy terminal positions of the reference amino acid sequence or anywhere between those terminal positions, interspersed either individually among residues in the reference sequence or in one or more contiguous groups within the reference sequence. The query sequence may be an entire amino acid sequence selected from the group consisting of polypeptide sequences of the Sequence Listing and those encoded by the clone inserts of the deposited clone pool or any fragment specified as described herein.

The variant polypeptides described herein are included in the present invention regardless of whether they have their normal biological activity. This is because even where a particular polypeptide molecule does not have biological activity, one of skill in the art would still know how to use the polypeptide, for instance, as a vaccine or to generate antibodies. Other uses of the polypeptides of the present invention that do not have GENSET biological activity include, inter alia, as epitope tags, in epitope mapping, and as molecular weight markers on SDS-PAGE gels or on molecular sieve gel filtration columns using methods known to those of skill in the art. As described below, the polypeptides of the present invention can also be used to raise polyclonal and monoclonal antibodies, which are useful in assays for detecting GENSET protein expression or as agonists and antagonists capable of enhancing or inhibiting GENSET protein function. Further, such polypeptides can be used in the yeast two-hybrid system to "capture" GENSET protein binding proteins, which are also candidate agonists and antagonists according to the present invention (see, e.g., Fields and Song, (1989), Nature, 340: 245-246, which disclosure is hereby incorporated by reference in its entirety).

Preparation of the Polypeptides of the Invention

The polypeptides of the present invention can be prepared in any suitable manner known in the art. Such polypeptides include isolated naturally occuring polypeptides, recombinantly produced polypeptides, synthetically produced polypeptides, or polypeptides produced by a combination of these methods. The polypeptides of the present invention are preferably provided in an isolated form, and may be partially or preferably substantially purified. Consequently, the present invention also comprises methods of making the polypeptides of the invention.

Isolation

From Natural Sources

The GENSET proteins of the invention may be isolated from natural sources, including bodily fluids, tissues and cells, whether directly isolated or cultured cells, of humans or non-human animals. Methods for extracting and purifying natural proteins are known in the art, and include the use of detergents or chaotropic agents to disrupt particles followed by differential extraction and separation of the polypeptides by ion exchange chromatography, affinity chromatography, sedimentation according to density, and gel electrophoresis. See, for example, "Methods in Enzymology, Academic. Press, 1993" for a variety of methods for purifying proteins, which disclosure is hereby incorporated by reference in its entirety. Polypeptides of the invention also can be purified from natural sources using antibodies directed against the polypeptides of the invention, such as those described herein, in methods which are well known in the art of protein purification.

From Recombinant Sources

Preferably, the GENSET polypeptides of the invention are recombinantly produced using routine expression methods known in the art. The polynucleotide encoding the desired polypeptide is operably linked to a promoter into an expression vector suitable for any convenient host. Both eukaryotic and prokaryotic host systems are used in forming recombinant polypeptides. The polypeptide is then isolated from lysed cells or from the culture medium and purified to the extent needed for its intended use.

Any polynucleotide of the present invention may be used to express GENSET polypeptides. The nucleic acid encoding the GENSET polypeptide to be expressed is operably linked to a promoter in an expression vector using conventional cloning technology. The GENSET insert in the expression vector may comprise the full coding sequence for the GENSET protein or a portion thereof.

Consequently, a further embodiment of the present invention is a method of making a polypeptide of the present invention, said method comprising the steps of:

a) obtaining a cDNA comprising a sequence selected from the group consisting of:
   i) the polynucleotide sequences of the Sequence Listing,
   ii) the sequences of human cDNA clone inserts of the deposited clone pool,
   iii) polynucleotide sequences encoding one of the polypeptides of the Sequence Listing, and
   iv) sequences of polynucleotides encoding polypeptide which is encoded by one of the clone insert of the deposited clone pool;
b) inserting said cDNA in an expression vector such that the cDNA is operably linked to a promoter; and
c) introducing said expression vector into a host cell whereby said host cell produces said polypeptide.

In one aspect of this embodiment, the method further comprises the step of isolating the polypeptide. Another embodiment of the present invention is a polypeptide obtainable by the method described in the preceding paragraph. The expression vector is any of the mammalian, yeast, insect or bacterial expression systems known in the art. Commercially available vectors and expression systems are available from a variety of suppliers including Genetics Institute (Cambridge, Mass.), Stratagene (La Jolla, Calif.), Promega (Madison, Wis.), and Invitrogen (San Diego, Calif.). If desired, to enhance expression and facilitate proper protein folding, the codon context and codon pairing of the sequence is optimized for the particular expression organism in which the expression vector is introduced, as explained in U.S. Pat. No. 5,082,767, which disclosure is hereby incorporated by reference in its entirety.

In one embodiment, the entire coding sequence of a GENSET cDNA and the 3'UTR through the poly A signal of the cDNA is operably linked to a promoter in the expression vector. Alternatively, if the nucleic acid encoding a portion of the GENSET protein lacks a methionine to serve as the initiation site, an initiating methionine can be introduced next to the first codon of the nucleic acid using conventional techniques. Similarly, if the insert from the GENSET cDNA lacks a poly A signal, this sequence can be added to the construct by, for example, splicing out the Poly A signal from pSG5 (Stratagene) using BglI and SalI restriction endonuclease enzymes and incorporating it into the mammalian expression vector pXT1 (Stratagene), pXT1 contains the LTRs and a portion of the gag gene from Moloney Murine Leukemia Virus. The position of the LTRs in the construct allows efficient stable transfection. The vector includes the Herpes Simplex Thymidine Kinase promoter and the selectable neomycin gene.

In another embodiment, it is often advantageous to add to the recombinant polynucleotide additional nucleotide sequence which codes for secretory or leader sequences, pro-sequences, sequences which aid in purification, such as multiple histidine residues, or an additional sequence for stability during recombinant production.

Transfection of a GENSET expression vector into mouse NTH 3T3 cells is but one embodiment of introducing polynucleotides into host cells. Introduction of a polynucleotide encoding a polypeptide into a host cell can be effected by calcium phosphate transfection, DEAE-dextran mediated transfection, cationic lipid-mediated transfection, electroporation, transduction, infection, or other methods. Such methods are described in many standard laboratory, manuals, such as Davis et al., (1986) Basic Methods in Molecular Biology; ed., Elsevier Press, NY, which disclosure is hereby incorporated by reference in its entirety. It is specifically contemplated that the polypeptides of the present invention may in fact be expressed by a host cell lacking a recombinant vector or naturally produced by a cell.

Alternatively, the GENSET polypeptide to be expressed may also be a product of transgenic animals, i.e., as a component of the milk of transgenic cows, goats, pigs or sheep which are characterized by somatic or germ cells containing a nucleotide sequence encoding the protein of interest.

A polypeptide of this invention can be recovered and purified from recombinant cell cultures by well-known methods including differential extraction, ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. See, for example, "Methods in Enzymology", supra for a variety of methods for purifying proteins. Most preferably, high performance liquid chromatography ("HPLC") is employed for purification. A recombinantly produced version of a GENSET polypeptide can be substantially purified using techniques described herein or otherwise known in the art, such as, for example, by the one-step method described in Smith and Johnson (1988) Gene. 67(1): 31-40, which disclosure is hereby incorporated by reference in its entirety. Polypeptides of the invention also can be purified from recombinant sources using antibodies directed against the polypeptides of the invention, such as those described herein, in methods which are well known in the art of protein purification.

Preferably, the recombinantly expressed GENSET polypeptide is purified using standard immunochromatography techniques such as the one described in the section entitled "Immunoaffinity Chromatography". In such procedures, a solution containing the protein of interest, such as the culture medium or a cell extract, is applied to a column having antibodies against the protein attached to the chromatography matrix. The recombinant protein is allowed to bind the immunochromatography column. Thereafter, the column is washed to remove non-specifically bound proteins. The specifically bound secreted protein is then released from the column and recovered using standard techniques.

Depending upon the host employed in a recombinant production procedure, the polypeptides of the present invention may be glycosylated or may be non-glycosylated. In addition, polypeptides of the invention may also include an initial modified methionine residue, in some cases as a result of host-mediated processes. Thus, it is well known in the art that the N-terminal methionine encoded by the translation initiation codon generally is removed with high efficiency from any protein after translation in all eukaryotic cells. While the N-terminal methionine on most proteins also is efficiently removed in most prokaryotes, for some proteins, this prokaryotic removal process is inefficient, depending on the nature of the amino acid to which the N-terminal methionine is covalently linked. Thus, specifically included as an aspect of the invention are polypeptides of the present invention lacking the amino terminal methionine.

From Chemical Synthesis

In addition, polypeptides of the invention, especially short protein fragments, can be chemically synthesized using techniques known in the art [See, e.g., Creighton (1983), Proteins: Structures and Molecular Principles, W.H. Freeman & Co. 2nd Ed., T. E., New York; and Hunkapiller et al, (1984) Nature. 310(5973):105-11], which disclosures are hereby incorporated by reference in their entireties. For example, a polypeptide corresponding to a fragment of a polypeptide sequence of the invention can be synthesized by use of a peptide synthesizer. Alternatively, the methods described in U.S. Pat. No. 5,049,656, which disclosure is hereby incorporated by reference in its entirety, may be used.

Furthermore, if desired, nonclassical amino acids or chemical amino acid analogs can be introduced as a substitution or addition into the polypeptide sequence. Non-classical amino acids include, but are not limited to, to the D-isomers of the common amino acids, 2,4-diaminobutyric acid, a-amino isobutyric acid, 4-aminobutyric acid, Abu, 2-amino butyric acid, g-Abu, e-Ahx, 6-amino hexanoic acid, Aib, 2-amino isobutyric acid, 3-amino propionic acid, omithine, norleucine, norvaline, hydroxyproline, sarcosine, citrulline, homocitrulline, cysteic acid, t-butylglycine, t-butylalanine, phenylglycine, cyclohexylalanine, b-alanine, fluoroamino acids, designer amino acids such as b-methyl amino acids, Ca-methyl amino acids, Na-methyl amino acids, and amino acid analogs in general. Furthermore, the amino acid can be D (dextrorotary) or L (levorotary).

Modifications

The invention encompasses polypeptides which are differentially modified during or after translation, e.g., by glycosylation, acetylation, phosphorylation, amidation, derivatization by known protecting/blocking groups, proteolytic cleavage, linkage to an antibody molecule or other cellular ligand, etc. Any of numerous chemical modifications may be carried out by known techniques, including, but not limited to, specific chemical cleavage by cyanogen bromide, trypsin, chymotrypsin, papain, V8 protease, NaBH4; acetylation, formylation, oxidation, reduction; metabolic synthesis in the presence of tunicamycin; etc.

Additional post-translational modifications encompassed by the invention include, for example, e.g., N-linked or O-linked carbohydrate chains, processing of N-terminal or C-terminal ends), attachment of chemical moieties to the amino acid backbone, chemical modifications of N-linked or O-linked carbohydrate chains, and addition or deletion of an N-terminal methionine residue as a result of prokaryotic host cell expression. The polypeptides may also be modified with a detectable label, such as an enzymatic, fluorescent, isotopic or affinity label to allow for detection and isolation of the protein.

Also provided by the invention are chemically modified derivatives of the polypeptides of the invention which may provide additional advantages such as increased solubility, stability and circulating time of the polypeptide, or decreased immunogenicity. See. U.S. Pat. No. 4,179,337. The chemical moieties for derivatization may be selected. See, U.S. Pat. No. 4,179,337 which disclosure is hereby incorporated by reference in its entirety. The chemical moieties for derivatization may be selected from water soluble polymers such as polyethylene glycol, ethylene glycol/propylene glycol copolymers, carboxymethylcellulose, dextran, polyvinyl alcohol and the like. The polypeptides may be modified at random positions within the molecule, or at predetermined positions within the molecule and may include one, two, three, or more attached chemical moieties.

The polymer may be of any molecular weight, and may be branched or unbranched. For polyethylene glycol, the preferred molecular weight is between about 1 kDa and about 100 kDa (the term "about" indicating that in preparations of polyethylene glycol, some molecules will weigh more, some less, than the stated molecular weight) for ease in handling and manufacturing. Other sizes may be used, depending on the desired therapeutic profile (e.g., the duration of sustained release desired, the effects, if any on biological activity, the ease in handling, the degree or lack of antigenicity and other known effects of the polyethylene glycol to a therapeutic protein or analog).

The polyethylene glycol molecules (or other chemical moieties) should be attached to the protein with consideration of effects on functional or antigenic domains of the protein. There are a number of attachment methods available to those skilled in the art, e.g., EP 0 401 384, (coupling PEG to G-CSF), and Malik et al., (1992), Exp. Hematol. 20:1028-1035 (reporting pegylation of GM-CSF using tresyl chloride), which disclosures are hereby incorporated by reference in their entireties. For example, polyethylene glycol may be covalently bound through amino acid residues via a reactive group, such as, a free amino or carboxyl group. Reactive groups are those to which an activated polyethylene glycol molecule may be bound. The amino acid residues having a free amino group may include lysine residues and the N-terminal amino acid residues; those having a free carboxyl group may include aspartic acid residues glutamic acid residues and the C-terminal amino acid residue. Sulfhydryl groups may also be used as a reactive group for attaching the polyethylene glycol molecules. Preferred for therapeutic purposes is attachment at an amino group, such as attachment at the N-terminus or lysine group.

One may specifically desire proteins chemically modified at the N-terminus. Using polyethylene glycol as an illustration of the present composition, one may select from a variety of polyethylene glycol molecules (by molecular weight, branching, etc.), the proportion of polyethylene glycol molecules to protein (polypeptide) molecules in the reaction mix, the type of pegylation reaction to be performed, and the method of obtaining the selected N-terminally pegylated protein. The method of obtaining the N-terminally pegylated preparation (i.e., separating this moiety from other monopegylated moieties if necessary), may be by purification of the N-terminally pegylated material from a population of pegylated protein molecules. Selective proteins chemically modified at the N-terminus modification may be accomplished by reductive alkylation, which exploits differential reactivity of different types of primary amino groups (lysine versus the N-terminal) available for derivatization in a particular protein. Under the appropriate reaction conditions, substantially selective derivatization of the protein at the N-terminus with a carbonyl group containing polymer is achieved.

Multimerization

The polypeptides of the invention may be in monomers or multimers (i.e., dimers, trimers, tetramers and higher multimers). Accordingly, the present invention relates to monomers and multimers of the polypeptides of the invention, their preparation, and compositions containing them. In specific embodiments, the polypeptides of the invention are monomers, dimers, trimers or tetramers. In additional embodiments, the multimers of the invention are at least dimers, at least trimers, or at least tetramers.

Multimers encompassed by the invention may be homomers or heteromers. As used herein, the term "homomer", refers to a multimer containing only polypeptides corresponding to the amino acid sequences of the Sequence Listing or encoded by the human cDNA clone inserts of the deposited clone pool (including fragments, variants, splice variants, and fusion proteins, corresponding to these polypeptides as described herein). These homomers may contain polypeptides having identical or different amino acid sequences. In a specific embodiment, a homomer of the invention is a multimer containing only polypeptides having an identical amino acid sequence. In another specific embodiment, a homomer of the invention is a multimer containing polypeptides having different amino acid sequences. In specific embodiments, the multimer of the invention is a homodimer (e.g., containing polypeptides having identical or different amino acid sequences) or a homotrimer (e.g., containing polypeptides having identical and/or different amino acid sequences). In additional embodiments, the homomenc multimer of the invention is at least a homodimer, at least a homotrimer, or at least a homotetramer.

As used herein, the term "heteromer" refers to a multimer containing one or more heterologous polypeptides (i.e, polypeptides of different proteins) in addition to the polypeptides of the invention. In a specific embodiment, the multimer of the invention is a heterodimer, a heterotrimer, or a heterotetramer. In additional embodiments, the heteromeric multimer of the invention is at least a heterodimer, at least a heterotrimer, or at least a heterotetramer.

Multimers of the invention may be the result of hydrophobic, hydrophilic, ionic and/or covalent associations and/or may be indirectly linked, by for example, liposome formation. Thus, in one embodiment, multimers of the invention, such as, for example, homodimers or homotrimers are formed when polypeptides of the invention contact one another in solution. In another embodiment, heteromultimers of the invention, such as, for example, heterotrimers or heterotetramers, are formed when polypeptides of the invention contact antibodies to the polypeptides of the invention (including antibodies to the heterologous polypeptide sequence in a fusion protein of the invention) in solution. In other embodiments, multimers of the invention are formed by covalent associations with and/or between the polypeptides of the, invention. Such covalent associations may involve one or more amino acid residues contained in the polypeptide sequence (e.g., that recited in the sequence listing, or contained in the polypeptide encoded by a deposited clone). In one instance, the covalent associations are cross-linking between cysteine residues located within the polypeptide sequences, which interact in the native (i.e., naturally occurring) polypeptide. In another instance, the covalent associations are the consequence of chemical or recombinant manipulation. Alternatively, such covalent associations may involve one or more amino acid residues contained in the heterologous polypeptide sequence in a fusion protein of the invention.

In one example, covalent associations are between the heterologous sequence contained in a fusion protein of the invention (see, e.g., U.S. Pat. No. 5,478,925, which disclosure is hereby incorporated by reference in its entirety). In a specific example, the covalent associations are between the heterologous sequence contained in an Fc fusion protein of the invention (as described herein). In another specific example, covalent associations of fusion proteins of the invention are between heterologous polypeptide sequence from another protein that is capable of forming covalently associated multimers, such as for example, osteoprotegerin (see, e.g., International Publication No: WO 98/49305, the contents of which are herein incorporated by reference in its entirety). In another embodiment, two or more polypeptides of the invention are joined through peptide linkers. Examples include those peptide linkers described in U.S. Pat. No. 5,073,627 (hereby incorporated by reference). Proteins comprising multiple polypeptides of the invention separated by peptide linkers may be produced using conventional recombinant DNA technology.

Another method for preparing multimer polypeptides of the invention involves the use of polypeptides of the invention fused to a leucine zipper or isoleucine zipper polypeptide sequence. Leucine zipper and isoleucine zipper domains are polypeptides that promote multimerization of the proteins in which they are found. Leucine zippers were originally identified in several DNA-binding proteins, and have since been found in a variety of different proteins. [Landschulz et al., (1988), Science. 240:1759]. Among the known leucine zippers are naturally occurring peptides and derivatives thereof that dimerize or trimerize. Examples of leucine zipper domains suitable for producing soluble multimeric proteins of the invention are those described in PCT application WO 94/10308, hereby incorporated by reference. Recombinant fusion proteins comprising a polypeptide of the invention fused to a polypeptide sequence that dimerizes or trimerizes in solution are expressed in suitable host cells, and the resulting soluble multimeric fusion protein is recovered from the culture supernatant using techniques known in the art.

Trimeric polypeptides of the invention may offer the advantage of enhanced biological activity. Preferred leucine zipper moieties and isoleucine moieties are those that preferentially form trimers. One example is a leucine zipper derived from lung surfactant protein D (SPD), as described in Hoppe et al., (1994), FEBS Letters. 344:191 and in U.S. patent application Ser. No. 08/446,922, which disclosure is hereby incorporated by reference in its entirety. Other peptides derived from naturally occurring trimeric proteins may be employed in preparing trimeric polypeptides of the invention. In another example, proteins of the invention are associated by interactions between FLAG polypeptide sequence contained in fusion proteins of the invention containing FLAG polypeptide sequence. In a further embodiment, associations proteins of the invention are associated by interactions between heterologous polypeptide sequence contained in FLAG fusion proteins of the invention and anti FLAG antibody.

The multimers of the invention may be generated using chemical techniques known in the art. For example, polypeptides desired to be contained in the multimers of the invention may be chemically cross-linked using linker molecules and linker molecule length optimization techniques known in the art (see, e.g., U.S. Pat. No. 5,478,925, which is herein incorporated by reference in its entirety). Additionally, multimers of the invention may be generated using techniques known in the art to form one or more inter-molecule cross-links between the cysteine residues located within the sequence of the polypeptides desired to be contained in the multimer. (see, e.g., U.S. Pat. No. 5,478, 925, which is herein incorporated by reference in its entirety). Further, polypeptides of the invention may be routinely modified by the addition of cysteine or biotin to the C terminus or N-terminus of the polypeptide and techniques known in the art may be applied to generate multimers containing one or more of these modified polypeptides (see, e.g., U.S. Pat. No. 5,478,925, which is herein incorporated by reference in its entirety). Additionally, other techniques known in the art may be applied to generate liposomes containing the polypeptide components desired to be contained in the multimer of the invention (see, e.g., U.S. Pat. No. 5,478,925, which is herein incorporated by reference in its entirety).

Alternatively, multimers of the invention may be generated using genetic engineering techniques known in the art. In one embodiment, polypeptides contained in multimers of the invention are produced recombinantly using fusion protein technology described herein or otherwise known in the art (see, e.g., U.S. Pat. No. 5,478,925, which is herein incorporated by reference in its entirety). In a specific embodiment, polynucleotides coding for a homodimer of the invention are generated by ligating a polynucleotide sequence encoding a polypeptide of the invention to a sequence encoding a linker polypeptide and then further to a synthetic polynucleotide encoding the translated product of the polypeptide in the reverse orientation from the original C-terminus to the N-terminus (lacking the leader sequence) (see, e.g., U.S. Pat. No. 5,478,925, which is herein incorporated by reference in its entirety). In another embodiment, recombinant techniques described herein or otherwise known in the art are applied to generate recombinant polypeptides of the invention which contain a transmembrane domain (or hydrophobic or signal peptide) and which can be incorporated by membrane reconstitution techniques into liposomes (see, e.g., U.S. Pat. No. 5,478,925, which is herein incorporated by reference in its entirety).

Mutated Polypeptides

To improve or alter the characteristics of GENSET polypeptides of the present invention, protein engineering may be employed. Recombinant DNA technology known to those skilled in the art can be used to create novel mutant proteins or muteins including single or multiple amino acid substitutions, deletions, additions, or fusion proteins. Such modified polypeptides can show, e.g., increased/decreased biological activity or increased/decreased stability. In addition, they may be purified in higher yields and show better solubility than the corresponding natural polypeptide, at least under certain purification and storage conditions. Further, the polypeptides of the present invention may be produced as multimers including dimers, trimers and tetramers. Multimerization may be facilitated by linkers or recombinantly though heterologous polypeptides such as Fc regions.

N- and C-Terminal Deletions

It is known in the art that one or more amino acids may be deleted from the N-terminus or C-terminus without substantial loss of biological function. [See, e.g., Ron et al., (1993), Biol Chem., 268:2984-2988.] Accordingly, the present invention provides polypeptides having one or more residues deleted from the amino terminus. Similarly, many examples of biologically functional C-terminal deletion mutants are known (see, e.g., Dobeli, et al. 1988). Accordingly, the present invention provides polypeptides having one or more residues deleted from the carboxy terminus. The invention also provides polypeptides having one or more amino acids deleted from both the amino and the carboxyl termini as described below.

Other Mutations

Other mutants in addition to N- and C-terminal deletion forms of the protein discussed above are included in the present invention. Thus, the invention further includes variations of the GENSET polypeptides which show substantial GENSET polypeptide activity. Such mutants include deletions, insertions, inversions, repeats, and substitutions selected according to general rules known in the art so as to have little effect on activity.

There are two main approaches for studying the tolerance of an amino acid sequence to change [see, Bowie et al., (1994), *Science*. 247:1306-1310, which disclosure is hereby incorporated by reference in its entirety]. The first method relies on the process of evolution, in which mutations are either accepted or rejected by natural selection. The second approach uses genetic engineering to introduce amino acid changes at specific positions of a cloned gene and selections or screens to identify sequences that maintain functionality. These studies have revealed that proteins are surprisingly tolerant of amino acid substitutions.

Typically seen as conservative substitutions are the replacements, one for another, among the aliphatic amino acids. Ala, Val, Leu and Phe; interchange of the hydroxyl residues Ser and Thr, exchange of the acidic residues Asp and Glu, substitution between the amide residues Asn and Gln, exchange of the basic residues Lys and Arg and replacements among the aromatic residues Phe, Tyr. Thus, the polypeptide of the present invention may be, for example: (i) one in which one or more of the amino acid residues are substituted with a conserved or non-conserved amino acid residue (preferably a conserved amino acid residue) and such substituted amino acid residue may or may not be one encoded by the genetic code; or (ii) one in which one or more of the amino acid residues includes a substituent group; or (iii) one in which the GENSET polypeptide is fused with another compound, such as a compound to increase the half-life of the polypeptide (for example, polyethylene glycol); or (iv) one in which the additional amino acids are fused to the above form of the polypeptide, such as an IgG Fc fusion region peptide or leader or secretory sequence or a sequence which is employed for purification of the above form of the polypeptide or a pro-protein sequence.

Thus, the GENSET polypeptides of the present invention may include one or more amino acid substitutions, deletions, or additions, either from natural mutations or human manipulation. As indicated, changes are preferably of a minor nature, such as conservative amino acid substitutions that do not significantly affect the folding or activity of the protein. The following groups of amino acids represent equivalent changes: (1) Ala, Pro, Gly, Glu, Asp, Gln, Asn, Ser, Thr; (2) Cys, Ser, Tyr, Thr; (3) Val, Ile, Leu, Met, Ala, Phe; (4) Lys, Arg, His; (5) Phe, Tyr, Trp, His.

Furthermore, GENSET polypeptides of the present invention may include one or more amino acid substitutions that mimic modified amino acids. An example of this type of substitution includes replacing amino acids that are capable of being phosphorylated (e.g., serine, threonine, or tyrosine) with a negatively charged amino acid that resembles the negative charge of the phosphorylated amino acid (e.g., aspartic acid or glutamic acid). Also included is substitution of amino acids that are capable of being modified by hydrophobic groups (e.g., arginine) with amino acids carrying bulky hydrophobic side chains, such as tryptophan or phenylalanine. Therefore, a specific embodiment of the invention includes GENSET polypeptides that include one or more amino acid substitutions that mimic modified amino acids at positions where amino acids that are capable of being modified are normally positioned. Further included are GENSET polypeptides where any subset of modifiable amino acids are substituted. For example, a GENSET polypeptide that includes three serine residues may be substituted at any one, any two, or all three of said serines. Furthermore, any GENSET polypeptide amino acid capable of being modified may be excluded from substitution with a modification-mimicking amino acid.

A specific embodiment of a modified GENSET peptide molecule of interest according to the present invention, includes, but is not limited to, a peptide molecule which is resistant to proteolysis, is a peptide in which the —CONH— peptide bond is modified and replaced by a (CH2NH) reduced bond, a (NHCO) retro inverso bond, a (CH2—O) methylene-oxy bond, a (CH2—S) thiomethylene bond, a (CH2CH2) carba bond, a (CO—CH2) cetomethylene bond, a (CHOH—CH2) hydroxyethylene bond); a (N—N) bound, a E-alcene bond or also a —CH═CH— bond. The invention also encompasses a human GENSET polypeptide or a fragment or a variant thereof in which at least one peptide bond has been modified as described above.

Amino acids in the GENSET proteins of the present invention that are essential for function can be identified by methods known in the art, such as site-directed mutagenesis or alanine-scanning mutagenesis [see, e.g., Cunningham et al. (1989), Science 244:1081-1085, which disclosure is hereby incorporated by reference in its entirety]. Of special interest are substitutions of charged amino acids with other charged or neutral amino acids which may produce proteins with highly desirable improved characteristics, such as less aggregation. Aggregation may not only reduce activity but also be problematic when preparing pharmaceutical formulations, because aggregates can be immunogenic. [See, eg., Pinckard et al., (1967), Clin. Exp. Immunol 2:331-340; Robbins et al., (1987), Diabetes. 36:838-845; and Cleland et al., (1993), Crit. Rev. Therapeutic Drug Carrier Systems. 10:307-377.]

A further embodiment of the invention relates to a polypeptide which comprises the amino acid sequence of a GENSET polypeptide having an amino acid sequence which contains at least any one integer from 1 to 50 of conservative amino acid substitutions. Further included are polypeptides that contain not more than 40 conservative amino acid substitutions, not more than 30 conservative amino acid substitutions, and not more than 20 conservative amino acid substitutions. Also provided are polypeptides which comprise the amino acid sequence of a GENSET polypeptide, having at least one, but not more than 10, 9, 8, 7, 6, 5, 4, 3, 2 or 1 conservative amino acid substitutions. Further provided are conservative amino acid substitutions at any appropriate position or combination of appropriate positions whereby all possible species are included as embodiments of the present invention. Each conservative substitution or combination of substitutions may also be excluded.

Polypeptide Fragments

Structural Definition

The present invention is further directed to fragments of the polypeptides of the present invention. More specifically, the present invention embodies purified, isolated, and recombinant polypeptides comprising at least any one integer between 6 and 1000 (or the length of the polypeptides amino acid residues minus 1 if the length is less than 1000) of consecutive amino acid residues. Preferably, the fragments are at least 6, preferably at least 8 to 10, more preferably 12, 15, 20, 25, 30, 35, 40, 50, 60, 75, 100, 125, 150, 175, 200, 225, 250, 275, or 300 consecutive amino acids of a polypeptide of the present invention.

In addition to the above polypeptide fragments, further preferred sub-genuses of polypeptides comprise at least X amino acids, wherein "X" is defined as any integer between 6 and the integer representing the C-terminal amino acid of the polypeptide of the present invention including the polypeptide sequences of the sequence listing below. Further included are species of polypeptide fragments at least 6 amino acids in length, as described above, that are further specified in terms of their N-terminal and C-terminal positions. However, included in the present invention as individual species are all polypeptide fragments, at least 6 amino acids in length, as described above, and may be particularly specified by a N-terminal and C-terminal position. That is, every combination of a N-terminal and C-terminal position that a fragment at least 6 contiguous amino acid residues in length could occupy, on any given amino acid sequence of the sequence listing or of the present invention is included in the present invention Further preferred polypeptide fragments comprising amino acids of the sequences of the EVEN numbered SEQ ID NOs of the Sequence listing, and polynucleotides encoding the same, are selected from the group consisting of amino acids consecutively numbered from 1-6, 1-7, 1-8, 1-9, 1-10, 1-11, 1-12, 1-13, 1-14, 1-15, 1-16, 1-17, 1-18, 1-19, 1-20, 1-21, 1-22, 1-23, 1-24, 1-25, 1-26, 1-27, 1-28, 1-29, 1-30, 1-31, 1-32, 1-33, 1-34, 1-35, 1-36, 1-37, 1-38, 1-39, 1-40, 1-41, 1-42, 1-43, 1-44, 1-45, 1-46, 1-47, 1-48, 1-49, 1-50, 1-51, 1-52, 1-53, 1-54, 1-55, 1-56, 1-57, 1-58, 1-59, 1-60, 1-61, 1-62, 1-63, 1-64, 1-65, 1-66, 1-67, 1-68, 1-69, 1-70, 1-71, 1-72, 1-73, 1-74, 1-75, 1-76, 1-77, 1-78, 1-79, 1-80, 1-81, 1-82, 1-83, 1-84, 1-85, 1-86, 1-87, 1-88, 1-89, 1-90, 1-91, 1-92, 1-93, 1-94, 1-95, 1-96, 1-97, 1-98, 1-99, 1-100, 1-101, 1-102, 1-103, 1-104, 1-105, 1-106, 1-107, 1-108, 1-109, 1-110, 1-111, 1-112, 1-113, 1-114, 1-115, 1-116, 1-117, 1-118, 1-119, 1-120, 1-121, 1-122, 1-123, 1-124, 1-125, 1-126, 1-127, 1-128, 1-129, 1-130, 1-131, 1-132, 1-133, 1-134, 1-135, 1-136, 1-137, 1-138, 1-139, 1-140, 1-141, 1-142, 1-143, 1-144, 1-145, 1-146, 1-147, 1-148, 1-149, 1-150, 1-151, 1-152, 1-153, 1-154, 1-155, 1-156, 1-157, 1-158, 1-159, 1-160, 1-161, 1-162, 1-163, 1-164, 1-165, 1-166, 1-167, 1-168, 1-169, 1-170, 1-171, 1-172, 1-173, 1-174, 1-175, 1-176, 1-177, 1-178, 1-179, 1-180, 1-181, 1-182, 1-183, 1-184, 1-185, 1-186, 1-187, 1-188, 1-189, 1-190, 1-191, 1-192, 1-193, 1-194, 1-195, 1-196, 1-197, 1-198, 1-199, 1-200, 1-201, 1-202, 1-203, 1-204, 1-205, 1-206, 1-207, 1-208, 1-209, 1-210, 1-211, 1-212, 1-213, 1-214, 1-215, 1-216, 1-217, 1-218, 1-219, 1-220, 1-221, 1-222, 1-223, 1-224, 1-225, 1-226, 1-227, 1-228, 1-229, 1-230, 1-231, 1-232, 1-233, 1-234, 1-235, 1-236, 1-237, 1-238, 1-239, 1-240, 1-241, 1-242, 1-243, 1-244, 1-245, 1-246, 1-247, 1-248, 1-249, 1-250, 1-251, 1-252, 1-253, 1-254, 1-255, 1-256, 1-257, 1-258, 1-259, 1-260, 1-261, 1-262, 1-263, 1-264, 1-265, 1-266, 1-267, 1-268, 1-269, 1-270, 1-271, 1-272, 1-273, 1-274, 1-275, 1-276, 1-277, 1-278, 1-279, 1-280, 1-281, 1-282, 1-283, 1-284, 1-285, 1-286, 1-287, 1-288, 1-289, 1-290, 1-291, 1-292, 1-293, 1-294, 1-295, 1-296, 1-297, 1-298, 1-299, 1-300, 1-301, 1-302, 1-303, 1-304, 1-305, 1-306, 1-307, 1-308, 1-309, 1-310, 1-311, 1-312, 1-313, 1-314, 1-315, 1-316, 1-317, 1-318, 1-319, 1-320, 1-321, 1-322, 1-323, 1-324, 1-325, 1-326, 1-327, 1-328, 1-329, 1-330, 1-331, 1-332, 1-333, 1-334, 1-335, 1-336, 1-337, 1-338, 1-339, 1-340, 1-341, 1-342, 1-343, 1-344, 1-345, 1-346, 1-347, 1-348, 1-349, 1-350, 1-351, 1-352, 1-353, 1-354, 1-355, 1-356, 1-357, 1-358, 1-359, 1-360, 1-361, 1-362, 1-363, 1-364, 1-365, 1-366, 1-367, 1-368, 1-369, 1-370, 1-371, 1-372, 1-373, 1-374, 1-375, 1-376, 1-377, 1-378, 1-379, 1-380, 1-381, 1-382, 1-383, 1-384, 1-385, 1-386, 1-387, 1-388, 1-389, 1-390, 1-391, 1-392, 1-393, 1-394, 1-395, 1-396, 1-397, 1-398, 1-399, 1-400, 1-401, 1-402, 1-403, 1-404, 1-405, 1-406, 1-407, 1-408, 1-409, 1-410, 1-411, 1-412, 1-413, 1-414, 1-415, 1-416, 1-417, 1-418, 1-419, 1-420, 1-421, 1-422, 1-423, 1-424, 1-425, 1-426, 1-427, 1-428, 1-429, 1-430, 1-431, 1-432, 1-433, 1-434, 1-435, 1-436, 1-437, 1-438, 1-439, 1-440, 1-441, 1-442, 1-443, 1-444, 1-445, 1-446, 1-447, 1-448, 1-449, 1-450, 1-451, 1-452, 1-453, 1-454, 1-455, 1-456, 1-457, 1-458, 1-459, 1-460, 1-461, 1-462, 1-463, 1-464, 1-465, 1-466, 1-467, 1-468, 1-469, 1-470, 1-471, 1-472, 1-473, 1-474, 1-475, 1-476, 1-477, 1-478, 1-479, 1-480, 1-481, 1-482, 1-483, 1-484, 1-485, 1-486, 1-487, 1-488, 1-489, 1-490, 1-491, 1-492, 1-493, 1-494, 1-495, 1-496, 1-497, 1-498, 1-499, 1-500, 1-501, 1-502, 1-503, 1-504, 1-505, 1-506, 1-507, 1-508, 1-509, 1-510, 1-511, 1-512, 1-513, 1-514, 1-515, 1-516, 1-517, 1-518, 1-519, 1-520, 1-521, 1-522, 1-523, 1-524, 1-525, 1-526, 1-527, 1-528, 1-529, 1-530, 1-531, 1-532, 1-533, 1-534, 1-535, 1-536, 1-537, 1-538, 1-539, 1-540, 1-541, 1-542, 1-543, 1-544, 1-545, 1-546, 1-547, 1-548, 1-549, 1-550, 1-551, 1-552, 1-553, 1-554, 1-555, 1-556, 1-557, 1-558, 1-559, 1-560, 1-561, 1-562, 1-563, 1-564, 1-565, 1-566, 1-567, 1-568, 1-569, 1-570, 1-571, 1-572, 1-573, 1-574, 1-575, 1-576, 1-577, 1-578, 1-579, 1-580, 1-581, 1-582, 1-583, 1-584, 1-585, 1-586, 1-587, 1-588, 1-589, 1-590, 1-591, 1-592, 1-593, 1-594, 1-595, 1-596, 1-597, 1-598, 1-599, 1-600, 1-601, 1-602, 1-603, 1-604, 1-605, 1-606, 1-607, 1-608, 1-609, 1-610, 1-611, 1-612, 1-613, 1-614, 1-615, 1-616, 1-617, 1-618, 1-619, 1-620, 1-621, 1-622, 1-623, 1-624, 1-625, 1-626, 1-627, 1-628, 1-629, 1-630, 1-631, 1-632, 1-633, 1-634, 1-635, 1-636, 1-637, 1-638, 1-639, 1-640, 1-641, 1-642, 1-643, 1-644, 1-645, 1-646, 1-647, 1-648, 1-649, 1-650, 1-651, 1-652, 1-653, 1-654, 1-655, 1-656, 1-657, 1-658, 1-659, 1-660, 1-661, 1-662, 1-663, 1-664, 1-665, 1-666, 1-667, 1-668, 1-669, 1-670, 1-671, 1-672, 1-673, 1-674, 1-675, 1-676, 1-677, 1-678, 1-679, 1-680, 1-681, 1-682, 1-683, 1-684, 1-685, 1-686, 1-687, 1-688, 1-689, 1-690, 1-691, 1-692, 1-693, 1-694, 1-695, 1-696, 1-697, 1-698, 1-699, 1-700, 1-701, 1-702, 1-703, 1-704, 1-705, 1-706, 1-707, 1-708, 1-709, 1-710, 1-711, 1-712, 1-713, 1-714, 1-715, 1-716, 1-717, 1-718, 1-719, 1-720, 1-721, 1-722, 1-723, 1-724, 1-725, 1-726, 1-727, 1-728, 1-729, 1-730, 1-731, 1-732, 1-733, 1-734, 1-735, 1-736, 1-737, 1-738, 1-739, 1-740, 1-741, 1-742, 1-743, 1-744, 1-745, 1-746, 1-747, 1-748, 1-749, 1-750, 1-751, 1-752, 1-753, 1-754, 1-755, 1-756, 1-757, 1-758, 1-759, 1-760, 1-761, 1-762, 1-763, 1-764, 1-765, 1-766, 1-767, 1-768, 1-769, 1-770, 1-771, 1-772, 1-773, 1-774, 1-775, 1-776, 1-777, 1-778, 1-779, 1-780, 1-781, 1-782, 1-783, 1-784, 1-785, 1-786, 1-787, 2-787, 3-787, 4-787, 5-787, 6-787, 7-787, 8-787, 9-787, 10-787, 11-787, 12-787, 13-787, 14-787, 15-787, 16-787, 17-787, 18-787, 19-787, 20-787, 21-787, 22-787, 23-787, 24-787, 25-787, 26-787, 27-787, 28-787, 29-787, 30-787, 31-787, 32-787, 33-787, 34-787, 35-787, 36-787, 37-787, 38-787, 39-787, 40-787, 41-787, 42-787, 43-787, 44-787, 45-787, 46-787, 47-787, 48-787, 49-787, 50-787, 51-787, 52-787, 53-787, 54-787, 55-787, 56-787, 57-787, 58-787, 59-787, 60-787, 61-787, 62-787, 63-787, 64-787, 65-787, 66-787, 67-787, 68-787, 69-787, 70-787, 71-787, 72-787, 73-787, 74-787, 75-787, 76-787, 77-787, 78-787, 79-787, 80-787, 81-787, 82-787, 83-787, 84-787, 85-787, 86-787, 87-787, 88-787, 89-787, 90-787, 91-787, 92-787, 93-787, 94-787, 95-787, 96-787, 97-787, 98-787, 99-787, 100-787, 101-787, 102-787, 103-787, 104-787, 105-787, 106-787, 107-787, 108-787, 109-787, 110-787, 111-787, 112-787, 113-787, 114-787, 115-787, 116-787, 117-787, 118-787, 119-787, 120-787, 121-787, 122-787, 123-787, 124-787, 125-787, 126-787, 127-787, 128-787, 129-787, 130-787, 131-787, 132-787, 133-787, 134-787, 135-787, 136-787, 137-787, 138-787, 139-787, 140-787, 141-787, 142-787, 143-787, 144-787, 145-787, 146-787, 147-787, 148-787, 149-787, 150-787, 151-787, 152-787, 153-787, 154-787, 155-787, 156-787, 157-787, 158-787, 159-787, 160-787, 161-787, 162-787, 163-787, 164-787, 165-787, 166-787, 167-787, 168-787, 169-787, 170-787, 171-787, 172-787, 173-787, 174-787, 175-787, 176-787, 177-787, 178-787, 179-787, 180-787, 181-787, 182-787, 183-787, 184-787, 185-787, 186-787, 187-787, 188-787, 189-787, 190-787, 191-787, 192-787, 193-787, 194-787, 195-787, 196-787, 197-787, 198-787, 199-787, 200-787, 201-787, 202-787, 203-787, 204-787, 205-787, 206-787, 207-787, 208-787, 209-787, 210-787, 211-787, 212-787, 213-787, 214-787, 215-787, 216-787, 217-787, 218-787, 219-787, 220-787, 221-787, 222-787, 223-787, 224-787, 225-787, 226-787, 227-787, 228-787, 229-787, 230-787, 231-787, 232-787, 233-787, 234-787, 235-787, 236-787, 237-787, 238-787, 239-787, 240-787, 241-787, 242-787, 243-787, 244-787, 245-787, 246-787, 247-787, 248-787, 249-787, 250-787, 251-787, 252-787, 253-787, 254-787, 255-787, 256-787, 257-787, 258-787, 259-787, 260-787, 261-787, 262-787, 263-787, 264-787, 265-787, 266-787, 267-787, 268-787, 269-787, 270-787, 271-787, 272-787, 273-787, 274-787, 275-787, 276-787, 277-787, 278-787, 279-787, 280-787, 281-787, 282-787, 283-787, 284-787, 285-787, 286-787, 287-787, 288-787, 289-787, 290-787, 291-787, 292-787, 293-787, 294-787, 295-787, 296-787, 297-787, 298-787, 299-787, 300-787, 301-787, 302-787, 303-787, 304-787, 305-787, 306-787, 307-787, 308-787, 309-787, 310-787, 311-787, 312-787, 313-787, 314-787, 315-787, 316-787, 317-787, 318-787, 319-787, 320-787, 321-787, 322-787, 323-787, 324-787, 325-787, 326-787, 327-787, 328-787, 329-787, 330-787, 331-787, 332-787, 333-787, 334-787, 335-787, 336-787, 337-787, 338-787, 339-787, 340-787, 341-787, 342-787, 343-787, 344-787, 345-787, 346-787, 347-787, 348-787, 349-787, 350-787, 351-787, 352-787, 353-787, 354-787, 355-787, 356-787, 357-787, 358-787, 359-787, 360-787, 361-787, 362-787, 363-787, 364-787, 365-787, 366-787, 367-787, 368-787, 369-787, 370-787, 371-787, 372-787, 373-787, 374-787, 375-787, 376-787, 377-787, 378-787, 379-787, 380-787, 381-787, 382-787, 383-787, 384-787, 385-787, 386-787, 387-787, 388-787, 389-787, 390-787, 391-787, 392-787, 393-787, 394-787, 395-787, 396-787, 397-787, 398-787, 399-787, 400-787, 401-787, 402-787, 403-787, 404-787, 405-787, 406-787, 407-787, 408-787, 409-787, 410-787, 411-787, 412-787, 413-787, 414-787, 415-787, 416-787, 417-787, 418-787, 419-787, 420-787, 421-787, 422-787, 423-787, 424-787, 425-787, 426-787, 427-787, 428-787, 429-787, 430-787, 431-787, 432-787, 433-787, 434-787, 435-787, 436-787, 437-787, 438-787, 439-787, 440-787, 441-787, 442-787, 443-787, 444-787, 445-787, 446-787, 447-787, 448-787, 449-787, 450-787, 451-787, 452-787, 453-787, 454-787, 455-787, 456-787, 457-787, 458-787, 459-787, 460-787, 461-787, 462-787, 463-787, 464-787, 465-787, 466-787, 467-787, 468-787, 469-787, 470-787, 471-787, 472-787, 473-787, 474-787, 475-787, 476-787, 477-787, 478-787, 479-787, 480-787, 481-787, 482-787, 483-787, 484-787, 485-787, 486-787, 487-787, 488-787, 489-787, 490-787, 491-787, 492-787, 493-787, 494-787, 495-787, 496-787, 497-787, 498-787, 499-787, 500-787, 501-787, 502-787, 503-787, 504-787, 505-787, 506-787, 507-787, 508-787, 509-787, 510-787, 511-787, 512-787, 513-787, 514-787, 515-787, 516-787, 517-787, 518-787, 519-787, 520-787, 521-787, 522-787, 523-787, 524-787, 525-787, 526-787, 527-787, 528-787, 529-787, 530-787, 531-787, 532-787, 533-787, 534-787, 535-787, 536-787, 537-787, 538-787, 539-787, 540-787, 541-787, 542-787, 543-787, 544-787, 545-787, 546-787, 547-787, 548-787, 549-787, 550-787, 551-787, 552-787, 553-787, 554-787, 555-787, 556-787, 557-787, 558-787, 559-787, 560-787, 561-787, 562-787, 563-787, 564-787, 565-787, 566-787, 567-787, 568-787, 569-787, 570-787, 571-787, 572-787, 573-787, 574-787, 575-787, 576-787, 577-787, 578-787, 579-787, 580-787, 581-787, 582-787, 583-787, 584-787, 585-787, 586-787, 587-787, 588-787, 589-787, 590-787, 591-787, 592-787, 593-787, 594-787, 595-787, 596-787, 597-787, 598-787, 599-787, 600-787, 601-787, 602-787, 603-787, 604-787, 605-787, 606-787, 607-787, 608-787, 609-787, 610-787, 611-787, 612-787, 613-787, 614-787, 615-787, 616-787, 617-787, 618-787, 619-787, 620-787, 621-787, 622-787, 623-787, 624-787, 625-787, 626-787, 627-787, 628-787, 629-787, 630-787, 631-787, 632-787, 633-787, 634-787, 635-787, 636-787, 637-787, 638-787, 639-787, 640-787, 641-787, 642-787, 643-787, 644-787, 645-787, 646-787, 647-787, 648-787, 649-787, 650-787, 651-787, 652-787, 653-787, 654-787, 655-787, 656-787, 657-787, 658-787, 659-787, 660-787, 661-787, 662-787, 663-787, 664-787, 665-787, 666-787, 667-787, 668-787, 669-787, 670-787, 671-787, 672-787, 673-787, 674-787, 675-787, 676-787, 677-787, 678-787, 679-787, 680-787, 681-787, 682-787, 683-787, 684-787, 685-787, 686-787, 687-787, 688-787, 689-787, 690-787, 691-787, 692-787, 693-787, 694-787, 695-787, 696-787, 697-787, 698-787, 699-787, 700-787, 701-787, 702-787, 703-787, 704-787, 705-787, 706-787, 707-787, 708-787, 709-787, 710-787, 711-787, 712-787, 713-787, 714-787, 715-787, 716-787, 717-787, 718-787, 719-787, 720-787, 721-787, 722-787, 723-787, 724-787, 725-787, 726-787, 727-787, 728-787, 729-787, 730-787, 731-787, 732-787, 733-787, 734-787, 735-787, 736-787, 737-787, 738-787, 739-787, 740-787, 741-787, 742-787, 743-787, 744-787, 745-787, 746-787, 747-787, 748-787, 749-787, 750-787, 751-787, 752-787, 753-787, 754-787, 755-787, 756-787, 757-787, 758-787, 759-787, 760-787, 761-787, 762-787, 763-787, 764-787, 765-787, 766-787, 767-787, 768-787, 769-787, 770-787, 771-787, 772-787, 773-787, 774-787, 775-787, 776-787, 777-787, 778-787, 779-787, 780-787, 781-787, 782-787, 2-786, 3-785, 4-784, 5-783, 6-782, 7-781, 8-780, 9-779, 10-778, 11-777, 12-776, 13-775, 14-774, 15-773, 16-772, 17-771, 18-770, 19-769, 20-768, 21-767, 22-766, 23-765, 24-764, 25-763, 26-762, 27-761, 28-760, 29-759, 30-758, 31-757, 32-756, 33-755, 34-754, 35-753, 36-752, 37-751, 38-750, 39-749, 40-748, 41-747, 42-746, 43-745, 44-744, 45-743, 46-742, 47-741, 48-740, 49-739, 50-738, 51-737, 52-736, 53-735, 54-734, 55-733, 56-732, 57-731, 58-730, 59-729, 60-728, 61-727, 62-726, 63-725, 64-724, 65-723, 66-722, 67-721, 68-720, 69-719, 70-718, 71-717, 72-716, 73-715, 74-714, 75-713, 76-712, 77-711, 78-710, 79-709, 80-708, 81-707, 82-706, 83-705, 84-704, 85-703, 86-702, 87-701, 88-700, 89-699, 90-698, 91-697, 92-696, 93-695, 94-694, 95-693, 96-692, 97-691, 98-690, 99-689, 100-688, 101-687, 102-686, 103-685, 104-684, 105-683, 106-682, 107-681, 108-680, 109-679, 110-678, 111-677, 112-676, 113-675, 114-674, 115-673, 116-672, 117-671, 118-670, 119-669, 120-668, 121-667, 122-666, 123-665, 124-664, 125-663, 126-662, 127-661, 128-660, 129-659, 130-658, 131-657, 132-656, 133-655, 134-654, 135-653, 136-652, 137-651, 138-650, 139-649, 140-648, 141-647, 142-646, 143-645, 144-644, 145-643, 146-642, 147-641, 148-640, 149-639, 150-638, 151-637, 152-636, 153-635, 154-634, 155-633, 156-632, 157-631, 158-630, 159-629, 160-628, 161-627, 162-626, 163-625, 164-624, 165-623, 166-622, 167-621, 168-620, 169-619, 170-618, 171-617, 172-616, 173-615, 174-614, 175-613, 176-612, 177-611, 178-610, 179-609, 180-608, 181-607, 182-606, 183-605, 184-604, 185-603, 186-602, 187-601, 188-600, 189-599, 190-598, 191-597, 192-596, 193-595, 194-594, 195-593, 196-592, 197-591, 198-590, 199-589, 200-588, 201-587, 202-586, 203-585, 204-584, 205-583, 206-582, 207-581, 208-580, 209-579, 210-578, 211-577, 212-576, 213-575, 214-574, 215-573, 216-572, 217-571, 218-570, 219-569, 220-568, 221-567, 222-566, 223-565, 224-564, 225-563, 226-562, 227-561, 228-560, 229-559, 230-558, 231-557, 232-556, 233-555, 234-554, 235-553, 236-552, 237-551, 238-550, 239-549, 240-548, 241-547, 242-546, 243-545, 244-544, 245-543, 246-542, 247-541, 248-540, 249-539, 250-538, 251-537, 252-536, 253-535, 254-534, 255-533, 256-532, 257-531, 258-530, 259-529, 260-528, 261-527, 262-526, 263-525, 264-524, 265-523, 266-522, 267-521, 268-520, 269-519, 270-518, 271-517, 272-516, 273-515, 274-514, 275-513, 276-512, 277-511, 278-510, 279-509, 280-508, 281-507, 282-506, 283-505, 284-504, 285-503, 286-502, 287-501, 288-500, 289-499, 290-498, 291-497, 292-496, 293-495, 294-494, 295-493, 296-492, 297-491, 298-490, 299-489, 300-488, 301-487, 302-486, 303-485, 304-484, 305-483, 306-482, 307-481, 308-480, 309-479, 310-478, 311-477, 312-476, 313-475, 314-474, 315-473, 316-472, 317-471, 318-470, 319-469, 320-468, 321-467, 322-466, 323-465, 324-464, 325-463, 326-462, 327-461, 328-460, 329-459, 330-458, 331-457, 332-456, 333-455, 334-454, 335-453, 336-452, 337-451, 338-450, 339-449, 340-448, 341-447, 342-446, 343-445, 344-444, 345-443, 346-442, 347-441, 348-440, 349-439, 350-438, 351-437, 352-436, 353-435, 354-434, 355-433, 356-432, 357-431, 358-430, 359-429, 360-428, 361-427, 362-426, 363-425, 364-424, 365-423, 366-422, 367-421, 368-420, 369-419, 370-418, 371-417, 372-416, 373-415, 374-414, 375-413, 376-412, 377-411, 378-410, 379-409, 380-408, 381-407, 382-406, 383-405, 384-404, 385-403, 386-402, 387-401, 388-400, 389-399, 390-398, and 391-397, wherein the numbering of amino acids comprising any one fragment is consistent with the polypeptide sequence of any one EVEN numbered SEQ ID of the Sequence listing.

Further preferred polypeptide fragments of the EVEN numbered SEQ ID NOs of the Sequence listing, and polynucleotides encoding the same, are selected from the group consisting of fragments comprising any 50 consecutive amino acids numbered from 1-50, 2-51, 3-52, 4-53, 5-54, 6-55, 7-56, 8-57, 9-58, 10-59, 11-60, 12-61, 13-62, 14-63, 15-64, 16-65, 17-66, 18-67, 19-68, 20-69, 21-70, 22-71, 23-72, 24-73, 25-74, 26-75, 27-76, 28-77, 29-78, 30-79, 31-80, 32-81, 33-82, 34-83, 35-84, 36-85, 37-86, 38-87, 39-88, 40-89, 41-90, 42-91, 43-92, 44-93, 45-94, 46-95, 47-96, 48-97, 49-98, 50-99, 51-100, 52-101, 53-102, 54-103, 55-104, 56-105, 57-106, 58-107, 59-108, 60-109, 61-110, 62-111, 63-112, 64-113, 65-114, 66-115, 67-116, 68-117, 69-118, 70-119, 71-120, 72-121, 73-122, 74-123, 75-124, 76-125, 77-126, 78-127, 79-128, 80-129, 81-130, 82-131, 83-132, 84-133, 85-134, 86-135, 87-136, 88-137, 89-138, 90-139, 91-140, 92-141, 93-142, 94-143, 95-144, 96-145, 97-146, 98-147, 99-148, 100-149, 101-150, 102-151, 103-152, 104-153, 105-154, 106-155, 107-156, 108-157, 109-158, 110-159, 111-160, 112-161, 113-162, 114-163, 115-164, 116-165, 117-166, 118-167, 119-168, 120-169, 121-170, 122-171, 123-172, 124-173, 125-174, 126-175, 127-176, 128-177, 129-178, 130-179, 131-180, 132-181, 133-182, 134-183, 135-184, 136-185, 137-186, 138-187, 139-188, 140-189, 141-190, 142-191, 143-192, 144-193, 145-194, 146-195, 147-196, 148-197, 149-198, 150-199, 151-200, 152-201, 153-202, 154-203, 155-204, 156-205, 157-206, 158-207, 159-208, 160-209, 161-210, 162-211, 163-212, 164-213, 165-214, 166-215, 167-216, 168-217, 169-218, 170-219, 171-220, 172-221, 173-222, 174-223, 175-224, 176-225, 177-226, 178-227, 179-228, 180-229, 181-230, 182-231, 183-232, 184-233, 185-234, 186-235, 187-236, 188-237, 189-238, 190-239, 191-240, 192-241, 193-242, 194-243, 195-244, 196-245, 197-246, 198-247, 199-248, 200-249, 201-250, 202-251, 203-252, 204-253, 205-254, 206-255, 207-256, 208-257, 209-258, 210-259, 211-260, 212-261, 213-262, 214-263, 215-264, 216-265, 217-266, 218-267, 219-268, 220-269, 221-270, 222-271, 223-272, 224-273, 225-274, 226-275, 227-276, 228-277, 229-278, 230-279, 231-280, 232-281, 233-282, 234-283, 235-284, 236-285, 237-286, 238-287, 239-288, 240-289, 241-290, 242-291, 243-292, 244-293, 245-294, 246-295, 247-296, 248-297, 249-298, 250-299, 251-300, 252-301, 253-302, 254-303, 255-304, 256-305, 257-306, 258-307, 259-308, 260-309, 261-310, 262-311, 263-312, 264-313, 265-314, 266-315, 267-316, 268-317, 269-318, 270-319, 271-320, 272-321, 273-322, 274-323, 275-324, 276-325, 277-326, 278-327, 279-328, 280-329, 281-330, 282-331, 283-332, 284-333, 285-334, 286-335, 287-336, 288-337, 289-338, 290-339, 291-340, 292-341, 293-342, 294-343, 295-344, 296-345, 297-346, 298-347, 299-348, 300-349, 301-350, 302-351, 303-352, 304-353, 305-354, 306-355, 307-356, 308-357, 309-358, 310-359, 311-360, 312-361, 313-362, 314-363, 315-364, 316-365, 317-366, 318-367, 319-368, 320-369, 321-370, 322-371, 323-372, 324-373, 325-374, 326-375, 327-376, 328-377, 329-378, 330-379, 331-380, 332-381, 333-382, 334-383, 335-384, 336-385, 337-386, 338-387, 339-388, 340-389, 341-390, 342-391, 343-392, 344-393, 345-394, 346-395, 347-396, 348-397, 349-398, 350-399, 351-400, 352-401, 353-402, 354-403, 355-404, 356-405, 357-406, 358-407, 359-408, 360-409, 361-410, 362-411, 363-412, 364-413, 365-414, 366-415, 367-416, 368-417, 369-418, 370-419, 371-420, 372-421, 373-422, 374-423, 375-424, 376-425, 377-426, 378-427, 379-428, 380-429, 381-430, 382-431, 383-432, 384-433, 385-434, 386-435, 387-436, 388-437, 389-438, 390-439, 391-440, 392-441, 393-442, 394-443, 395-444, 396-445, 397-446, 398-447, 399-448, 400-449, 401-450, 402-451, 403-452, 404-453, 405-454, 406-455, 407-456, 408-457, 409-458, 410-459, 411-460, 412-461, 413-462, 414-463, 415-464, 416-465, 417-466, 418-467, 419-468, 420-469, 421-470, 422-471, 423-472, 424-473, 425-474, 426-475, 427-476, 428-477, 429-478, 430-479, 431-480, 432-481, 433-482, 434-483, 435-484, 436-485, 437-486, 438-487, 439-488, 440-489, 441-490, 442-491, 443-492, 444-493, 445-494, 446-495, 447-496, 448-497, 449-498, 450-

499, 451-500, 452-501, 453-502, 454-503, 455-504, 456-505, 457-506, 458-507, 459-508, 460-509, 461-510, 462-511, 463-512, 464-513, 465-514, 466-515, 467-516, 468-517, 469-518, 470-519, 471-520, 472-521, 473-522, 474-523, 475-524, 476-525, 477-526, 478-527, 479-528, 480-529, 481-530, 482-531, 483-532, 484-533, 485-534, 486-535, 487-536, 488-537, 489-538, 490-539, 491-540, 492-541, 493-542, 494-543, 495-544, 496-545, 497-546, 498-547, 499-548, 500-549, 501-550, 502-551, 503-552, 504-553, 505-554, 506-555, 507-556, 508-557, 509-558, 510-559, 511-560, 512-561, 513-562, 514-563, 515-564, 516-565, 517-566, 518-567, 519-568, 520-569, 521-570, 522-571, 523-572, 524-573, 525-574, 526-575, 527-576, 528-577, 529-578, 530-579, 531-580, 532-581, 533-582, 534-583, 535-584, 536-585, 537-586, 538-587, 539-588, 540-589, 541-590, 542-591, 543-592, 544-593, 545-594, 546-595, 547-596, 548-597, 549-598, 550-599, 551-600, 552-601, 553-602, 554-603, 555-604, 556-605, 557-606, 558-607, 559-608, 560-609, 561-610, 562-611, 563-612, 564-613, 565-614, 566-615, 567-616, 568-617, 569-618, 570-619, 571-620, 572-621, 573-622, 574-623, 575-624, 576-625, 577-626, 578-627, 579-628, 580-629, 581-630, 582-631, 583-632, 584-633, 585-634, 586-635, 587-636, 588-637, 589-638, 590-639, 591-640, 592-641, 593-642, 594-643, 595-644, 596-645, 597-646, 598-647, 599-648, 600-649, 601-650, 602-651, 603-652, 604-653, 605-654, 606-655, 607-656, 608-657, 609-658, 610-659, 611-660, 612-661, 613-662, 614-663, 615-664, 616-665, 617-666, 618-667, 619-668, 620-669, 621-670, 622-671, 623-672, 624-673, 625-674, 626-675, 627-676, 628-677, 629-678, 630-679, 631-680, 632-681, 633-682, 634-683, 635-684, 636-685, 637-686, 638-687, 639-688, 640-689, 641-690, 642-691, 643-692, 644-693, 645-694, 646-695, 647-696, 648-697, 649-698, 650-699, 651-700, 652-701, 653-702, 654-703, 655-704, 656-705, 657-706, 658-707, 659-708, 660-709, 661-710, 662-711, 663-712, 664-713, 665-714, 666-715, 667-716, 668-717, 669-718, 670-719, 671-720, 672-721, 673-722, 674-723, 675-724, 676-725, 677-726, 678-727, 679-728, 680-729, 681-730, 682-731, 683-732, 684-733, 685-734, 686-735, 687-736, 688-737, 689-738, 690-739, 691-740, 692-741, 693-742, 694-743, 695-744, 696-745, 697-746, 698-747, 699-748, 700-749, 701-750, 702-751, 703-752, 704-753, 705-754, 706-755, 707-756, 708-757, 709-758, 710-759, 711-760, 712-761, 713-762, 714-763, 715-764, 716-765, 717-766, 718-767, 719-768, 720-769, 721-770, 722-771, 723-772, 724-773, 725-774, 726-775, 727-776, 728-777, 729-778, 730-779, 731-780, 732-781, 733-782, 734-783, 735-784, 736-785, 737-786, and 738-787, wherein the numbering of amino acids comprising any one fragment is consistent with the polypeptide sequence of any one EVEN numbered SEQ ID of the Sequence listing.

Further preferred polypeptide fragments of the EVEN numbered SEQ ID NOs of the Sequence listing, and polynucleotides encoding the same, are selected from the group consisting of fragments comprising any 100 consecutive amino acids numbered from 1-100, 2-101, 3-102, 4-103, 5-104, 6-105, 7-106, 8-107, 9-108, 10-109, 11-110, 12-111, 13-112, 14-113, 15-114, 16-115, 17-116, 18-117, 19-118, 20-119, 21-120, 22-121, 23-122, 24-123, 25-124, 26-125, 27-126, 28-127, 29-128, 30-129, 31-130, 32-131, 33-132, 34-133, 35-134, 36-135, 37-136, 38-137, 39-138, 40-139, 41-140, 42-141, 43-142, 44-143, 45-144, 46-145, 47-146, 48-147, 49-148, 50-149, 51-150, 52-151, 53-152, 54-153, 55-154, 56-155, 57-156, 58-157, 59-158, 60-159, 61-160, 62-161, 63-162, 64-163, 65-164, 66-165, 67-166, 68-167, 69-168, 70-169, 71-170, 72-171, 73-172, 74-173, 75-174, 76-175, 77-176, 78-177, 79-178, 80-179, 81-180, 82-181, 83-182, 84-183, 85-184, 86-185, 87-186, 88-187, 89-188, 90-189, 91-190, 92-191, 93-192, 94-193, 95-194, 96-195, 97-196, 98-197, 99-198, 100-199, 101-200, 102-201, 103-202, 104-203, 105-204, 106-205, 107-206, 108-207, 109-208, 110-209, 111-210, 112-211, 113-212, 114-213, 115-214, 116-215, 117-216, 118-217, 119-218, 120-219, 121-220, 122-221, 123-222, 124-223, 125-224, 126-225, 127-226, 128-227, 129-228, 130-229, 131-230, 132-231, 133-232, 134-233, 135-234, 136-235, 137-236, 138-237, 139-238, 140-239, 141-240, 142-241, 143-242, 144-243, 145-244, 146-245, 147-246, 148-247, 149-248, 150-249, 151-250, 152-251, 153-252, 154-253, 155-254, 156-255, 157-256, 158-257, 159-258, 160-259, 161-260, 162-261, 163-262, 164-263, 165-264, 166-265, 167-266, 168-267, 169-268, 170-269, 171-270, 172-271, 173-272, 174-273, 175-274, 176-275, 177-276, 178-277, 179-278, 180-279, 181-280, 182-281, 183-282, 184-283, 185-284, 186-285, 187-286, 188-287, 189-288, 190-289, 191-290, 192-291, 193-292, 194-293, 195-294, 196-295, 197-296, 198-297, 199-298, 200-299, 201-300, 202-301, 203-302, 204-303, 205-304, 206-305, 207-306, 208-307, 209-308, 210-309, 211-310, 212-311, 213-312, 214-313, 215-314, 216-315, 217-316, 218-317, 219-318, 220-319, 221-320, 222-321, 223-322, 224-323, 225-324, 226-325, 227-326, 228-327, 229-328, 230-329, 231-330, 232-331, 233-332, 234-333, 235-334, 236-335, 237-336, 238-337, 239-338, 240-339, 241-340, 242-341, 243-342, 244-343, 245-344, 246-345, 247-346, 248-347, 249-348, 250-349, 251-350, 252-351, 253-352, 254-353, 255-354, 256-355, 257-356, 258-357, 259-358, 260-359, 261-360, 262-361, 263-362, 264-363, 265-364, 266-365, 267-366, 268-367, 269-368, 270-369, 271-370, 272-371, 273-372, 274-373, 275-374, 276-375, 277-376, 278-377, 279-378, 280-379, 281-380, 282-381, 283-382, 284-383, 285-384, 286-385, 287-386, 288-387, 289-388, 290-389, 291-390, 292-391, 293-392, 294-393, 295-394, 296-395, 297-396, 298-397, 299-398, 300-399, 301-400, 302-401, 303-402, 304-403, 305-404, 306-405, 307-406, 308-407, 309-408, 310-409, 311-410, 312-411, 313-412, 314-413, 315-414, 316-415, 317-416, 318-417, 319-418, 320-419, 321-420, 322-421, 323-422, 324-423, 325-424, 326-425, 327-426, 328-427, 329-428, 330-429, 331-430, 332-431, 333-432, 334-433, 335-434, 336-435, 337-436, 338-437, 339-438, 340-439, 341-440, 342-441, 343-442, 344-443, 345-444, 346-445, 347-446, 348-447, 349-448, 350-449, 351-450, 352-451, 353-452, 354-453, 355-454, 356-455, 357-456, 358-457, 359-458, 360-459, 361-460, 362-461, 363-462, 364-463, 365-464, 366-465, 367-466, 368-467, 369-468, 370-469, 371-470, 372-471, 373-472, 374-473, 375-474, 376-475, 377-476, 378-477, 379-478, 380-479, 381-480, 382-481, 383-482, 384-483, 385-484, 386-485, 387-486, 388-487, 389-488, 390-489, 391-490, 392-491, 393-492, 394-493, 395-494, 396-495, 397-496, 398-497, 399-498, 400-499, 401-500, 402-501, 403-502, 404-503, 405-504, 406-505, 407-506, 408-507, 409-508, 410-509, 411-510, 412-511, 413-512, 414-513, 415-514, 416-515, 417-516, 418-517, 419-518, 420-519, 421-520, 422-521, 423-522, 424-523, 425-524, 426-525, 427-526, 428-527, 429-528, 430-529, 431-530, 432-531, 433-532, 434-533, 435-534, 436-535, 437-536, 438-537, 439-538, 440-539, 441-540, 442-541, 443-542, 444-543, 445-544, 446-545, 447-546, 448-547, 449-548, 450-549, 451-550, 452-551, 453-552, 454-553, 455-554, 456-555, 457-556, 458-557, 459-558, 460-559, 461-560, 462-561, 463-562, 464-563, 465-564, 466-565, 467-566, 468-567, 469-568, 470-569, 471-570, 472-571, 473-572, 474-573, 475-574, 476-575, 477-576, 478-577, 479-578, 480-579, 481-

580, 482-581, 483-582, 484-583, 485-584, 486-585, 487-586, 488-587, 489-588, 490-589, 491-590, 492-591, 493-592, 494-593, 495-594, 496-595, 497-596, 498-597, 499-598, 500-599, 501-600, 502-601, 503-602, 504-603, 505-604, 506-605, 507-606, 508-607, 509-608, 510-609, 511-610, 512-611, 513-612, 514-613, 515-614, 516-615, 517-616, 518-617, 519-618, 520-619, 521-620, 522-621, 523-622, 524-623, 525-624, 526-625, 527-626, 528-627, 529-628, 530-629, 531-630, 532-631, 533-632, 534-633, 535-634, 536-635, 537-636, 538-637, 539-638, 540-639, 541-640, 542-641, 543-642, 544-643, 545-644, 546-645, 547-646, 548-647, 549-648, 550-649, 551-650, 552-651, 553-652, 554-653, 555-654, 556-655, 557-656, 558-657, 559-658, 560-659, 561-660, 562-661, 563-662, 564-663, 565-664, 566-665, 567-666, 568-667, 569-668, 570-669, 571-670, 572-671, 573-672, 574-673, 575-674, 576-675, 577-676, 578-677, 579-678, 580-679, 581-680, 582-681, 583-682, 584-683, 585-684, 586-685, 587-686, 588-687, 589-688, 590-689, 591-690, 592-691, 593-692, 594-693, 595-694, 596-695, 597-696, 598-697, 599-698, 600-699, 601-700, 602-701, 603-702, 604-703, 605-704, 606-705, 607-706, 608-707, 609-708, 610-709, 611-710, 612-711, 613-712, 614-713, 615-714, 616-715, 617-716, 618-717, 619-718, 620-719, 621-720, 622-721, 623-722, 624-723, 625-724, 626-725, 627-726, 628-727, 629-728, 630-729, 631-730, 632-731, 633-732, 634-733, 635-734, 636-735, 637-736, 638-737, 639-738, 640-739, 641-740, 642-741, 643-742, 644-743, 645-744, 646-745, 647-746, 648-747, 649-748, 650-749, 651-750, 652-751, 653-752, 654-753, 655-754, 656-755, 657-756, 658-757, 659-758, 660-759, 661-760, 662-761, 663-762, 664-763, 665-764, 666-765, 667-766, 668-767, 669-768, 670-769, 671-770, 672-771, 673-772, 674-773, 675-774, 676-775, 677-776, 678-777, 679-778, 680-779, 681-780, 682-781, 683-782, 684-783, 685-784, 686-785, 687-786, and 688-787, wherein the numbering of amino acids comprising any one fragment is consistent with the polypeptide sequence of any one EVEN numbered SEQ ID of the Sequence listing.

These specific embodiments, and other polypeptide and polynucleotide fragment embodiments described herein may be modified as being "at least", "equal to", "equal to or less than", "less than", "at least ______ but not greater than ______" or "from ______ to ______" a specified size or specified N-terminal and/or C-terminal positions. It is noted that all ranges used to describe any embodiment of the present invention are inclusive unless specifically set forth otherwise.

The present invention also provides for the exclusion of any individual fragment specified by N-terminal and C-terminal positions or of any fragment specified by size in amino acid residues as described above. In addition, any number of fragments specified by N-terminal and C-terminal positions or by size in amino acid residues as described above may be excluded as individual species. Further, any number of fragments specified by N-terminal and C-terminal positions or by size in amino acid residues as described above may make up a polypeptide fragment in any combination and may optionally include non-GENSET and GENSET-Related polypeptide sequences as well.

The above polypeptide fragments of the present invention can be immediately envisaged using the above description and are therefore not individually listed solely for the purpose of not unnecessarily lengthening the specification. Moreover, the above fragments need not have a GENSET biological activity, although polypeptides having these activities are preferred embodiments of the invention, since they would be useful, for example, in immunoassays, in epitope mapping, epitope tagging, as vaccines, and as molecular weight markers. The above fragments may also be used to generate antibodies to a particular portion of the polypeptide. These antibodies can then be used in immunoassays well known in the art to distinguish between human and non-human cells and tissues or to determine whether cells or tissues in a biological sample are or are not of the same type which express the polypeptides of the present invention.

It is noted that the above species of polypeptide fragments of the present invention may alternatively be described by the formula "a to b"; where "a" equals the N-terminal most amino acid position and "b" equals the C-terminal most amino acid position of the polynucleotide; and further where "a" equals an integer between 1 and the number of amino acids of the polypeptide sequence of the present invention minus 6, and where "b" equals an integer between 7 and the number of amino acids of the polypeptide sequence of the present invention; and where "a" is an integer smaller then "b" by at least 6.

The present invention also provides for the exclusion of any species of polypeptide fragments of the present invention specified by 5' and 3' positions or sub-genuses of polypeptides specified by size in amino acids as described above. Any number of fragments specified by 5' and 3' positions or by size in amino acids, as described above, may be excluded.

Functional Definition

Domains

Preferred polynucleotide fragments of the invention comprise domains of polypeptides of the invention. Such domains may eventually comprise linear or structural motifs and signatures including, but not limited to, leucine zippers, helix-turn-helix motifs, post-translational modification sites such as glycosylation sites, ubiquitination sites, alpha helices, and beta sheets, signal sequences encoding signal peptides which direct the secretion of the encoded proteins, sequences implicated in transcription regulation such as homeoboxes, acidic stretches, enzymatic active sites, substrate binding sites, and enzymatic cleavage sites. Such domains may present a particular biological activity such as DNA or RNA-binding, secretion of proteins, transcription regulation, enzymatic activity, substrate binding activity, etc.

In a preferred embodiment, domains comprise a number of amino acids that is any integer between 6 and 1000. Domains may be synthesized using any methods known to those skilled in the art, including those disclosed herein. Methods for determining the amino acids which make up a domain with a particular biological activity include mutagenesis studies and assays to determine the biological activity to be tested.

Alternatively, the polypeptides of the invention may be scanned for motifs, domains and/or signatures in databases using any computer method known to those skilled in the art. Searchable databases include Prosite [Hoffman et al., (1999) Nucl. Acids Res. 27:215-219; Bucher and Bairoch (1994) Proceedings 2nd International Conference on Intelligent Systems for Molecular Biology. Altman et al, Eds., pp 53-61, AAAIPress, Menlo Park], Pfam [Sonnhammer, et al., (1997) Proteins. 28(3):405-20; Henikoff et al., (2000) Electrophoresis 21(9):1700-6; Bateman et al., (2000) Nucleic Acids Res. 28(1):263-6], Blocks [Henikoff et al., (2000) Nucleic Acids Res. 28(1):228-30], Print [Attwood et al., (1996) Nucleic Acids Res. 24(1):182-8], Prodom [Sonnhammer and Kahn, (1994) Protein Sci. 3(3):482-92; Corpet et al.

(2000) Nucleic Acids Res. 28(1):267-9], Sbase [Pongor et al. (1993) Protein Eng. 6(4):391-5; Murvai et al., (2000) Nucleic Acids Res. 28(1):260-2], Smart [Schultz et al. (1998) Proc Natl Acad Sci USA 95, 5857-5864], Dali/FSSP [Hohm and Sander (1996) Nucleic Acids Res. 24(1):206-9, Hohm and Sander (1997) Nucleic Acids Res. 25(1):231-4 and Holm and Sander (1999) Nucleic Acids Res. 27(1):244-7], HSSP [Sander and Schneider (1991) Proteins. 9(1):56-68.], CATH [Orengo et al., (1997) Structure. 5(8):1093-108; Pearl et al., (2000) Biochem Soc Trans. 28(2):269-75], SCOP [Murzin et al., (1995) J. Mol. Biol. 247(4):536-40; Lo Conte et al., (2000) Nucleic Acids Res. 28(1):257-9], COG [Tatusov et al. (1997), Science, 278, 631:637 and Tatusov et al. (2000), Nucleic Acids Res. 28(1):33-6], specific family databases and derivatives thereof [Nevill-Manning et al., (1998) Proc. Natl. Acad. Sci. USA. 95, 5865-5871; Yona, et al, (1999), Proteins. 37(3):360-78; Attwood et al., (2000) Nucleic Acids Res. 28(1):225-7], each of which disclosures are hereby incorporated by reference in their entireties. For a review on available databases, see issue 1 of volume 28 of Nucleic Acid Research (2000), which disclosure is hereby incorporated by reference in its entirety.

Epitopes and Antibody Fusions:

A preferred embodiment of the present invention is directed to epitope-bearing polypeptides and epitope-bearing polypeptide fragments. These epitopes may be "antigenic epitopes" or both an "antigenic epitope" and an "immunogenic epitope". An "immunogenic epitope" is defined as a part of a protein that elicits an antibody response in vivo when the polypeptide is the immunogen. On the other hand, a region of polypeptide to which an antibody binds is defined as an "antigenic determinant" or "antigenic epitope." The number of immunogenic epitopes of a protein generally is less than the number of antigenic epitopes [see, e.g., Geysen et al., (1984), Proc. Natl. Acad. Sci. U.S.A. 81:3998-4002, which disclosure is hereby incorporated by reference in its entirety]. It is particularly noted that although a particular epitope may not be immunogenic, it is nonetheless useful since antibodies can be made to both immunogenic and antigenic epitopes. When the antigen is a polypeptide, it is customary to classify epitopes as being linear (i.e., composed of a contiguous sequence of amino acids repeated along the polypeptide chain), or nonlinear (i.e., composed of amino acids brought into proximity as a result of the folding of the polypeptide chain). Nonlinear epitopes are also called "conformational" because they arise through the folding of the polypeptide chain into a particular conformation, i.e., a distinctive 3-D shape.

An epitope can comprise as few as 3 amino acids in a spatial conformation, which is unique to the epitope. Generally an epitope consists of at least 6 such amino acids, and more often at least 8-10 such amino acids. In preferred embodiment, antigenic epitopes comprise a number of amino acids that is any integer between 3 and 50. Fragments which function as epitopes may be produced by any conventional means [see, e.g., Houghten (1985), Proc. Natl. Acad. Sci. USA 82:5131-5135], also further described in U.S. Pat. No. 4,631,21, which disclosures are hereby incorporated by reference in their entireties. Methods for determining the amino acids which make up an epitope include x-ray crystallography, 2-dimensional nuclear magnetic resonance, and epitope mapping, e.g., the Pepscan method described by Geysen, et al. (1984); PCT Publication No. WO 84/03564; and PCT Publication No. WO 84/03506, which disclosures are hereby incorporated by reference in their entireties. Nonlinear epitopes are determined by methods such as protein footprinting (U.S. Pat. No. 5,691,448, which disclosure is hereby incorporated by reference in its entirety). Another example is the algorithm of Jameson and Wolf, (1988), Comp. Appl. Biosci. 4:181-186 (said reference incorporated by reference in its entirety). The Jameson-Wolf antigenic analysis, for example, may be performed using the computer program PROTEAN, using default parameters (Version 4.0 Windows, DNASTAR, Inc., 1228 South Park Street Madison, Wis.

All fragments of the polypeptides of the present invention, at least 6 amino acids residues in length, are included in the present invention as being useful as antigenic linear epitopes. Amino acid residues comprising other immunogenic epitopes may be determined by Jameson-Wolf analysis, by other similar algorithms, or by in vivo testing for an antigenic response using the methods described herein or those known in the art. Immunogenic epitopes predicted by algorithm analysis describe only amino acid residues comprising linear epitopes predicted to have the highest degree of immunogenicity. Polypeptides of the present invention that are not specifically described as immunogenic are not considered non-antigenic as they may be antigenic in vivo. Alternatively, the polypeptides are most likely antigenic in vitro using methods such as phage display.

Preferably, the epitope-containing polypeptide comprises a contiguous span of at least 6, preferably at least 8 to 10, more preferably 12, 15, 20, 25, 30, 35, 40, 50, 60, 75, 100, 125, 150, 175, 200, 225, 250, 275, or 300 amino acids of a polypeptide of the present invention.

Nonlinear epitopes comprise more than one noncontiguous polypeptide sequence of at least one amino acid each. Such epitopes result from noncontiguous polypeptides brought into proximity by secondary, tertiary, or quaternary structural features. Therefore, the present invention encompasses isolated, purified, or recombinant polypeptides and fragments thereof which comprise a nonlinear epitope. Preferred polypeptides providing nonlinear epitopes are formed by a contiguous surface of natively folded protein and are thus at least 10 amino acids in length, further preferably 12, 15, 20, 25, 30, 35, 40, 50, 60, 75, 100, 125, 150, 175, 200, 225, 250, 275, or 300 amino acids of a polypeptide of the present invention, to the extent that a contiguous span of these lengths is consistent with the lengths of said selected sequence. Further preferred polypeptides comprise full-length polypeptide sequences selected from the group consisting of the polypeptide sequences of the Sequence Listing. Additionally, nonlinear epitopes may be formed by synthetic peptides that mimic an antigenic site or contiguous surface normally presented on a protein in the native conformation. Therefore, preferred polypeptides providing nonlinear epitopes may be formed by synthetic proteins that comprise a combination of at least 5, 6, 7, 8, 9, 10, 12, 15, 20, 25, 30, 35, 40, 50, 60, 75, 100, 125, 150, 175, 200, 225, 250, 275, or 300 amino acids.

The epitope-bearing fragments of the present invention preferably comprise 6 to 50 amino acids (i.e any integer between 6 and 50, inclusive) of a polypeptide of the present invention. Also, included in the present invention are antigenic fragments between the integers of 6 and the full length GENSET sequence of the sequence listing. All combinations of sequences between the integers of 6 and the full-length sequence of a GENSET polypeptide are included. The epitope-bearing fragments may be specified by either the number of contiguous amino acid residues (as a sub-genus) or by specific N-terminal and C-terminal positions (as species) as described above for the polypeptide fragments of the present invention. Any number of epitope-bearing fragments of the present invention may also be excluded in the same manner.

Antigenic epitopes are useful, for example, to raise antibodies, including monoclonal antibodies that specifically bind the epitope (see, Wilson et al., 1984; and Sutcliffe et al., (1983), Science. 219:660-666, which disclosures are hereby incorporated by reference in their entireties). The antibodies are then used in various techniques such as diagnostic and tissue/cell identification techniques, as described herein, and in purification methods such as immunoaffinity chromatography Similarly, immunogenic epitopes can be used to induce antibodies according to methods well known in the art (see, Sutcliffe et al., supra; Wilson et al., supra; Chow et al., (1985), Proc. Natl. Acad. Sci. USA. 82:910-914; and Bittle et al., (1985), Virol. 66:2347-2354, which disclosures are hereby incorporated by reference in their entireties). A preferred immunogenic epitope includes the natural GENSET protein. The immunogenic epitopes may be presented together with a carrier protein, such as an albumin, to an animal system (such as rabbit or mouse) or, if it is long enough (at least about 25 amino acids), without a carrier. However, immunogenic epitopes comprising as few as 8 to 10 amino acids have been shown to be sufficient to raise antibodies capable of binding to, at the very least, linear epitopes in a denatured polypeptide (e.g., in Western blotting.).

Epitope-bearing polypeptides of the present invention are used to induce antibodies according to methods well known in the art including, but not limited to, in vivo immunization, in vitro immunization, and phage display methods (see, e.g., Sutcliffe, et al., supra; Wilson, et al., supra, and Bittle, et al., supra). If in vivo immunization is used, animals may be immunized with free peptide; however, anti-peptide antibody titer may be boosted by coupling of the peptide to a macromolecular carrier, such as keyhole limpet hemacyanin (KLH) or tetanus toxoid. For instance, peptides containing cysteine residues may be coupled to a carrier using a linker such as -maleimidobenzoyl-N-hydroxysuccinimide ester (MBS), while other peptides may be coupled to carriers using a more general linking agent such as glutaraldehyde. Animals such as rabbits, rats and mice are immunized with either free or carrier-coupled peptides, for instance, by intraperitoneal and/or intradermal injection of emulsions containing about 100 μgs of peptide or carrier protein and Freund's adjuvant. Several booster injections may be needed, for instance, at intervals of about two weeks, to provide a useful titer of anti-peptide antibody, which can be detected, for example, by ELISA assay using free peptide adsorbed to a solid surface. The titer of anti-peptide antibodies in serum from an immunized animal may be increased by selection of anti-peptide antibodies, for instance, by adsorption to the peptide on a solid support and elution of the selected antibodies according to methods well known in the art.

As one of skill in the art will appreciate, and discussed above, the polypeptides of the present invention comprising an immunogenic or antigenic epitope can be fused to heterologous polypeptide sequences. For example, the polypeptides of the present invention may be fused with the constant domain of immunoglobulins (IgA, IgE, IgG, IgM), or portions thereof (CH1, CH2, CH3, any combination thereof including both entire domains and portions thereof) resulting in chimeric polypeptides. These fusion proteins facilitate purification, and show an increased half-life in vivo. This has been shown, e.g., for chimeric proteins consisting of the first two domains of the human CD4-polypeptide and various domains of the constant regions of the heavy or light chains of mammalian immunoglobulins [see, e.g., EPA 0,394,827; and Traunecker et al., (1988), Nature. 331:84-86, which disclosures are hereby incorporated by reference in their entireties]. Fusion proteins that have a disulfide-linked dimeric structure due to the IgG portion can also be more efficient in binding and neutralizing other molecules than monomeric polypeptides or fragments thereof alone [see, e.g., Fountoulakis et al., (1995) Biochem. 270:3958-3964, which disclosure is hereby incorporated by reference in its entirety]. Nucleic acids encoding the above epitopes can also be recombined with a gene of interest as an epitope tag to aid in detection and purification of the expressed polypeptide.

Additional fusion proteins of the invention may be generated through the techniques of gene-shuffling, motif-shuffling, exon-shuffling, or codon-shuffling (collectively referred to as "DNA shuffling"). DNA shuffling may be employed to modulate the activities of polypeptides of the present invention thereby effectively generating agonists and antagonists of the polypeptides. See, for example, U.S. Pat. Nos.: 5,605,793; 5,811,238; 5,834,252; 5,837,458; and Patten, et al. (1997), Curr Opinion Biotechnol. 8:724-733; Harayama (1998), Trends Biotechnol. 16(2): 76-82; Hansson et al., (1999), J. Mol. Biol. 287:265-276; and Lorenzo and Blasco (1998) Biotechniques. 24(2):308-313. (Each of these documents are hereby incorporated by reference). In one embodiment, one or more components, motifs, sections, parts, domains, fragments, etc., of coding polynucleotides of the invention, or the polypeptides encoded thereby may be recombined with one or more components, motifs, sections, parts, domains, fragments, etc. of one or more heterologous molecules.

The present invention further encompasses any combination of the polypeptide fragments listed in this section.

Antibodies

Definitions

The present invention further relates to antibodies and T-cell antigen receptors (TCR), which specifically bind the polypeptides, and more specifically, the epitopes of the polypeptides of the present invention. The antibodies of the present invention include IgG (including IgG1, IgG2, IgG3, and IgG4), IgA (including IgA1 and IgA2), IgD, IgE, or IgM, and IgY. The term "antibody" (Ab) refers to a polypeptide or group of polypeptides which are comprised of at least one binding domain, where a binding domain is formed from the folding of variable domains of an antibody molecule to form three-dimensional binding spaces with an internal surface shape and charge distribution complementary to the features of an antigenic determinant of an antigen, which allows an immunological reaction with the antigen. As used herein, the term "antibody" is meant to include whole antibodies, including single-chain whole antibodies, and antigen binding fragments thereof. In a preferred embodiment the antibodies are human antigen binding antibody fragments of the present invention include, but are not limited to, Fab, Fab' F(ab)2 and F(ab')2, Fd, single-chain Fvs (scFv), single-chain antibodies, disulfide-linked Fvs (sdFv) and fragments comprising either a $V_L$ or $V_H$ domain. The antibodies may be from any animal origin including birds and mammals. Preferably, the antibodies are human, murine, rabbit, goat, guinea pig, camel, horse, or chicken.

Antigen-binding antibody fragments, including single-chain antibodies, may comprise the variable region(s) alone or in combination with the entire or partial of the following:

hinge region, CH1, CH2, and CH3 domains. Also included in the invention are any combinations of variable region(s) and hinge region, CH1, CH2, and CH3 domains. The present invention further includes chimeric, humanized, and human monoclonal and polyclonal antibodies, which specifically bind the polypeptides of the present invention. The present invention further includes antibodies that are anti-idiotypic to the antibodies of the present invention.

The antibodies of the present invention may be monospecific, bispecific, and trispecific or have greater multispecificity. Multispecific antibodies may be specific for different epitopes of a polypeptide of the present invention or may be specific for both a polypeptide of the present invention as well as for heterologous compositions, such as a heterologous polypeptide or solid support material. See, e.g., WO 93/17715; WO 92/08802; WO 91/00360; WO 92/05793; Tutt, et al., (1991), J. Immunol. 147:60-69; U.S. Pat. Nos. 5,573,920, 4,474,893, 5,601,819, 4,714,681, 4,925,648; Kostelny et al., (1992), J. Immunol. 148:1547-1553, which disclosures are hereby incorporated by reference in their entireties.

Antibodies of the present invention may be described or specified in terms of the epitope(s) or epitope-bearing portion(s) of a polypeptide of the present invention, which are recognized or specifically bound by the antibody. The antibodies may specifically bind a complete protein encoded by a nucleic acid of the present invention, or a fragment thereof. Therefore, the epitope(s) or epitope bearing polypeptide portion(s) may be specified as described herein, e.g., by N-terminal and C-terminal positions, by size in contiguous amino acid residues, or otherwise described herein (including the sequence listing). Antibodies which specifically bind any epitope or polypeptide of the present invention may also be excluded as individual species. Therefore, the present invention includes antibodies that specifically bind specified polypeptides of the present invention, and allows for the exclusion of the same.

Thus, another embodiment of the present invention is a purified or isolated antibody capable of specifically binding to a polypeptide of the present invention. In one aspect of this embodiment, the antibody is capable of binding to a linear epitope-containing polypeptide comprising at least 6 consecutive amino acids, preferably at least 8 to 10 consecutive amino acids, more preferably at least 12, 15, 20, 25, 30, 40, 50, or 100 consecutive amino acids of a polypeptides of the present invention. In another aspect of this embodiment, the antibody is capable of binding to a nonlinear epitope-containing polypeptide comprising 10 amino acids in length, further preferably 12, 15, 20, 25, 30, 35, 40, 50, 60, 75, or 100 amino acids, further preferably, a contiguous surface of the native conformation of a polypeptide of the present application. Additionally, the antibody is capable of binding a nonlinear epitope presented by a synthetic peptide designed to mimic a contiguous surface of the native conformation of a polypeptide of a sequence selected from the group consisting of GENSET polypeptides. Antibodies that bind linear epitopes may be used in combination with antibodies that bind nonlinear epitopes for instance, in assays that detect proper protein folding.

Antibodies of the present invention may also be described or specified in terms of their cross-reactivity. Antibodies that do not specifically bind any other analog, ortholog, or homologue of the polypeptides of the present invention are included. Antibodies that do not bind polypeptides with less than 95%, less than 90%, less than 85%, less than 80%, less than 75%, less than 70%, less than 65%, less than 60%, less than 55%, and less than 50% identity. (as calculated using methods known in the art and described herein, e.g., using FASTDB and the parameters set forth herein) to a polypeptide of the present invention are also included in the present invention. Further included in the present invention are antibodies, which only bind polypeptides encoded by polynucleotides, which hybridize to a polynucleotide of the present invention under stringent hybridization conditions (as described herein). Antibodies of the present invention may also be described or specified in terms of their binding affinity. Preferred binding affinities include those with a dissociation constant or Kd less than $5\times10^{-6}$M, $10^{-6}$M, $5\times10^{-7}$M, $10^{-7}$M, $5\times10^{-8}$M, $10^{-8}$M, $5\times10^{-9}$M, $10^{-9}$M, $5\times10^{-10}$M, $10^{-10}$M, $5\times10^{-11}$M, $10^{-11}$M, $5\times10^{-12}$M, $10^{-12}$M, $5\times10^{-13}$M, $10^{-13}$M, $5\times10^{14}$M, $10^{-14}$M, $5\times10^{-15}$M, and $10^{-15}$M.

The invention also concerns a purified or isolated antibody capable of specifically binding to a mutated GENSET protein or to a fragment or variant thereof comprising an epitope of the mutated GENSET protein.

Preparation of Antibodies

The antibodies of the present invention may be prepared by any suitable method known in the art. Some of these methods are described in more detail in the example entitled "Example 1: Preparation of Antibody Compositions to the GENSET protein". For example, a polypeptide of the present invention or an antigenic fragment thereof can be administered to an animal in order to induce the production of sera containing "polyclonal antibodies". As used herein, the term "monoclonal antibody" is not limited to antibodies produced through hybridoma technology but it rather refers to an antibody that is derived from a single clone, including eukaryotic, prokaryotic, or phage clone, and not the method by which it is produced. Monoclonal antibodies can be prepared using a wide variety of techniques known in the art including the use of hybridoma, recombinant, and phage display technology.

Hybridoma techniques include those known in the art [see, e.g., Harlow and Lane, (1988) Antibodies A Laboratory Manual. Cold Spring Harbor Laboratory pp 53-242; Hammerling (1981), Monoclonal Antibodies and T-Cell Hybridomas, Elsevier, N.Y. 563-681; said references incorporated by reference in their entireties]. Fab and F(ab')2 fragments may be produced, for example, from hybridoma-produced antibodies by proteolytic cleavage, using enzymes such as papain (to produce Fab fragments) or pepsin (to produce F(ab')2 fragments).

Alternatively, antibodies of the present invention can be produced through the application of recombinant DNA technology or through synthetic chemistry using methods known in the art. For example, the antibodies of the present invention can be prepared using various phage display methods known in the art. In phage display methods, functional antibody domains are displayed on the surface of a phage particle, which carries polynucleotide sequences encoding them. Phage with a desired binding property are selected from a repertoire or combinatorial antibody library (e.g. human or murine) by selecting directly with antigen, typically antigen bound or captured to a solid surface or bead. Phage used in these methods are typically filamentous phage including fd and M13 with Fab, Fv or disulfide stabilized Fv antibody domains recombinantly fused to either the phage gene III or gene VIII protein. Examples of phage display methods that can be used to make the antibodies of the present invention include those disclosed in Brinkman et al., (1995) J. Immunol Methods, 182:41-50; Ames et al., (1995), J. Immunol. Meth., 184:177-186.;

Kettleborough et al., (1994), Eur. L Immunol. 24:952-958; Persic et al., (1997), Gene, 1879-81; Burton et al. (1994), Adv. Immunol., 57:191-280; PCT/GB91/01134; WO 90/02809; WO 91/10737; WO 92/01047; WO 92/18619; WO 93/11236; WO 95/15982; WO 95/20401; and U.S. Pat. Nos. 5,698,426, 5,223,409, 5,403,484, 5,580,717, 5,427,908, 5,750,753, 5,821,047, 5,571,698, 5,427,908, 5,516,637, 5,780,225, 5,658,727 and 5,733,743 (said references incorporated by reference in their entireties).

As described in the above references, after phage selection, the antibody coding regions from the phage can be isolated and used to generate whole antibodies, including human antibodies, or any other desired antigen binding fragment, and expressed in any desired host including mammalian cells, insect cells, plant cells, yeast, and bacteria. For example, techniques to recombinantly produce Fab, Fab' F(ab)2 and F(ab')2 fragments can also be employed using methods known in the art such as those disclosed in WO 92/22324; Mullinax et al., (1992), BioTechniques. 12(6): 864-869; and Sawai et al., (1995), AJRI 34:26-34; and Better et al., (1988) *Science*. 240:1041-1043 (said references incorporated by reference in their entireties).

Examples of techniques which can be used to produce single-chain Fvs and antibodies include those described in U.S. Pat. Nos. 4,946,778 and 5,258,498; Huston et al., (1991), Meth. Enymol. 203:46-88; Shu, et al., (1993), Proc. Natl. Acad. Sci. U.S.A. 90:7995-7999; and Skerra, et al., (1988), Science 240:1038-1040, which disclosures are hereby incorporated by reference in their entireties. For some uses, including in vivo use of antibodies in humans and in vitro detection assays, it may be preferable to use chimeric, humanized, or human antibodies. Methods for producing chimeric antibodies are known in the art. See e.g., Morrison, (1985); Oi et al., (1986), BioTechniques 4:214; Gillies et al., (1989), J. Immunol Methods. 125:191-202; and U.S. Pat. No. 5,807,715, which disclosures are hereby incorporated by reference in their entireties. Antibodies can be humanized using a variety of techniques including CDR-grafting (EP 0 239 400; WO 91/09967; U.S. Pat. Nos. 5,530,101; and 5,585,089), veneering or resurfacing [EP 0 592 106; EP 0 519 596; Padlan (1991), Molec. Immunol. 28(4/5):489-498; Studnicka et al., (1994), Protein Engineering. 7(6):805-814; Roguska et al., (1994), Proc. Natl. Acad. Sci. U.S.A. 91:969-973], and chain shuffling (U.S. Pat. No. 5,565,332), which disclosures are hereby incorporated by reference in their entireties. Human antibodies can be made by a variety of methods known in the art including phage display methods described above. See also, U.S. Pat. Nos. 4,444,887, 4,716,111, 5,545,806, and 5,814,318; WO 98/46645; WO 98/50433; WO 98/24893; WO 96/34096; WO 96/33735; and WO 91/10741 (said references incorporated by reference in their entireties).

Further included in the present invention are antibodies recombinantly fused or chemically conjugated (including both covalent and non-covalent conjugations) to a polypeptide of the present invention. The antibodies may be specific for antigens other than polypeptides of the present invention. For example, antibodies of the present invention may be recombinantly fused or conjugated to molecules useful as labels in detection assays and effector molecules such as heterologous polypeptides, drugs, or toxins. See, e.g., WO 92/08495; WO 91/14438; WO 89/12624; U.S. Pat. No. 5,314,995; and EP 0 396 387, which disclosures are hereby incorporated by reference in their entireties. Fused antibodies may also be used to target the polypeptides of the present invention to particular cell types, either in vitro or in vivo, by fusing or conjugating the polypeptides of the present invention to antibodies specific for particular cell surface receptors. Antibodies fused or conjugated to the polypeptides of the present invention may also be used in vitro immunoassays and purification methods using methods known in the art [see e.g., Harbor, et al. supra; WO 93/21232; EP 0 439 095; Naramura et al., (1994), Immunol. Lett. 39:91-99; U.S. Pat. No. 5,474,981; Gillies et al., (1992), Proc Natl. Acad Sci USA 89:1428-1432; Fell et al., (1991), J. Immunol. 146:2446-2452; said references incorporated by reference in their entireties].

The present invention further includes compositions comprising the polypeptides of the present invention fused or conjugated to antibody domains other than the variable regions. For example, the polypeptides of the present invention may be fused or conjugated to an antibody Fc region, or portion thereof. The antibody portion fused to a polypeptide of the present invention may comprise the hinge region, CH1 domain, CH2 domain, and CH3 domain or any combination of whole domains or portions thereof. The polypeptides of the present invention may be fused or conjugated to the above antibody portions to increase the in vivo half-life of the polypeptides or for use in immunoassays using methods known in the art. The polypeptides may also be fused or conjugated to the above antibody portions to form multimers. For example, Fc portions fused to the polypeptides of the present invention can form dimers through disulfide bonding between the Fc portions. Higher multimeric forms can be made by fusing the polypeptides to portions of IgA and IgM. Methods for fusing or conjugating the polypeptides of the present invention to antibody portions are known in the art. See e.g, U.S. Pat. Nos. 5,336,603, 5,622,929, 5,359,046, 5,349,053, 5,447,851, 5,112,946; EP 0 307 434, EP 0 367 166; WO 96/04388, WO 91/06570; Ashkenazi et al., (1991), Proc. Natl. Acad. Sci. USA 88:10535-10539; Zheng, X. X., et al. (1995), J. Immunol. 154:5590-5600; and Vil, et al. (1992), Proc Natl Acad Sci US 89:11337-11341 (said references incorporated by reference in their entireties).

Non-human animals or mammals, whether wild-type or transgenic, which express a different species of GENSET than the one to which antibody binding is desired, and animals which do not express GENSET (i.e a GENSET knock out animal as described herein) are particularly useful for preparing antibodies. GENSET knock out animals will recognize all or most of the exposed regions of a GENSET protein as foreign antigens, and therefore produce antibodies with a wider array of GENSET epitopes. Moreover, smaller polypeptides with only 10 to 30 amino acids may be useful in obtaining specific binding to any one of the GENSET proteins. In addition, the humoral immune system of animals which produce a species of GENSET that resembles the antigenic sequence will preferentially recognize the differences between the animal's native GENSET species and the antigen sequence, and produce antibodies to these unique sites in the antigen sequence. Such a technique will be particularly useful in obtaining antibodies that specifically bind to any one of the GENSET proteins.

A preferred embodiment of the invention is a method of specifically binding an antibody or antibody fragment to a GENSET polypeptide. This method comprises the step of contacting a GENSET polypeptide-specific antibody or fragment thereof with a GENSET polypeptide under antibody-binding conditions. Further included is a method of specifically binding an antibody or antibody fragment to an epitope, domain, or fragment of a GENSET polypeptide.

This method may be used to, for example, detect, purify, or modify the activity of GENSET polypeptides, as discussed herein.

Antibodies of the invention can be used to assay protein levels in a test sample or biological sample using methods known to those of skill in the art. Antibody-based methods useful for detecting protein include immunoassays, such as the enzyme linked immunosorbent assay (ELISA) and radioimmunoassay (RIA). Suitable antibody assay labels are known in the art and include enzyme labels, such as glucose oxidase, horseradish peroxidase, and alkaline phosphatase; radioisotopes, such as iodine. (125I, 121I), carbon (14C), sulfur (35S), tritium (3H), indium (121In), and technetium (99Tc); luminescent labels, such luminol, isolumino, theromatic acridinium ester, imidazole, acridinium salt, oxalate ester, luciferin, luciferase, and aequorin; and fluorescent labels, such as fluorescein isothiocyanate, rhodamine, phycoerythrin, phycocyanin, allophycocyanin, o-phthaldehyde, and fluorescamine.

Uses of Polynucleotides

Uses of Polynucleotides as Reagents

The polynucleotides of the present invention may be used as reagents in isolation procedures, diagnostic assays, and forensic procedures. For example, sequences from the GENSET polynucleotides of the invention may be detectably labeled and used as probes to isolate other sequences capable of hybridizing to them. In addition, sequences from the GENSET polynucleotides of the invention may be used to design PCR primers to be used in isolation, diagnostic, or forensic procedures.

To Find Corresponding Genomic DNA Sequences

The GENSET cDNAs of the invention may also be used to clone sequences located upstream of the cDNAs of the invention on the corresponding genomic DNA. Such upstream sequences may be capable of regulating gene expression, including promoter sequences, enhancer sequences, and other upstream sequences which influence transcription or translation levels. Once identified and cloned, these upstream regulatory sequences may be used in expression vectors designed to direct the expression of an inserted gene in a desired spatial, temporal, developmental, or quantitative, fashion.

Use of cDNAS or Fragments Thereof to Clone Upstream Sequences from Genomic DNA Sequences derived from polynucleotides of the inventions may be used to isolate the promoters of the corresponding genes using chromosome walking techniques. In one chromosome walking technique, the GENOMEWALKER kit available from Clontech is used according to the manufacturer's instructions.

Identification of Promoters in Cloned Upstream Sequences

Once the upstream genomic sequences have been cloned and sequenced, prospective promoters and transcription start sites within the upstream sequences may be identified by comparing the sequences upstream of the polynucleotides of the inventions with databases containing known transcription start sites, transcription factor binding sites, or promoter sequences.

In addition, promoters in the upstream sequences may be identified using promoter reporter vectors as follows. The expression of the reporter gene will be detected when placed under the control of regulatory active polynucleotide fragments or variants of the GENSET promoter region located upstream of the first exon of the GENSET gene. Suitable promoter reporter vectors, into which the GENSET promoter sequences may be cloned include pSEAP-Basic, pSEAP-Enhancer, pβgal-Basic, pβgal-Enhancer, or pEGFP-1 Promoter Reporter vectors available from Clontech, or pGL2-basic or pGL3-basic promoterless luciferase reporter gene vector from Promega. Briefly, each of these promoter reporter vectors include multiple cloning sites positioned upstream of a reporter gene encoding a readily assayable protein such as secreted alkaline phosphatase, luciferase, beta-galactosidase, or green fluorescent protein. The sequences upstream the GENSET coding region are inserted into the cloning sites upstream of the reporter gene in both orientations and introduced into an appropriate host cell. The level of reporter protein is assayed and compared to the level obtained from a vector which lacks an insert in the cloning site. The presence of an elevated expression level in the vector containing the insert with respect to the control vector indicates the presence of a promoter in the insert. If necessary, the upstream sequences can be cloned into vectors which contain an enhancer for increasing transcription levels from weak promoter sequences. A significant level of expression above that observed with the vector lacking an insert indicates that a promoter sequence is present in the inserted upstream sequence. Promoter sequence within the upstream genomic DNA may be further defined by site directed mutagenesis, linker scanning analysis, or other techniques familiar to those skilled in the art.

The strength and the specificity of the promoter of each GENSET gene can be assessed through the expression levels of a detectable polynucleotide operably linked to the GENSET promoter in different types of cells and tissues. The detectable polynucleotide may be either a polynucleotide that specifically hybridizes with a predefined oligonucleotide probe, or a polynucleotide encoding a detectable protein, including a GENSET polypeptide or a fragment or a variant thereof. This type of assay is well known to those skilled in the art and is described in U.S. Pat. No. 5,502,176; and U.S. Pat. No. 5,266,488; the disclosures of which are incorporated by reference herein in their entirety. Some of the methods are discussed in more detail elsewhere in the application.

The promoters and other regulatory sequences located upstream of the polynucleotides of the inventions may be used to design expression vectors capable of directing the expression of an inserted gene in a desired spatial, temporal, developmental, or quantitative manner. A promoter capable of directing the desired spatial, temporal, developmental, and quantitative patterns may be selected using the results of the expression analysis described herein. For example, if a promoter which confers a high level of expression in muscle is desired, the promoter sequence upstream of a polynucleotide of the invention derived from an mRNA which is expressed at a high level in muscle may be used in the expression vector.

To Find Similar Sequences

Polynucleotides of the invention may be used to isolate and/or purify nucleic acids similar thereto using any methods well known to those skilled in the art including the techniques based on hybridization or on amplification described in this section. These methods may be used to obtain the genomic DNAs which encode the mRNAs from which the GENSET cDNAs are derived, mRNAs corresponding to GENSET cDNAs, or nucleic acids which are homologous to GENSET cDNAs or fragments thereof, such as variants, species homologues or orthologs.

Hybridization-Based Methods

Techniques for identifying cDNA clones in a cDNA library which hybridize to a given probe sequence are disclosed in Sambrook et al., (1989) Molecular Cloning: A Laboratory Manual. (2ed., Cold Spring Harbor Laboratory, Cold Spring Harbor, N.Y.), and in Hames and Higgins (1985) Nucleic Acid Hybridization: A Practical Approach (Hames and Higgins Ed., IRL Press, Oxford), the disclosures of which are incorporated herein by reference in their entireties. The same techniques may be used to isolate genomic DNAs.

A probe comprising at least 10 consecutive nucleotides from a GENSET cDNA or fragment thereof is labeled with a detectable label such as a radioisotope or a fluorescent molecule.

Techniques for labeling the probe are well known and include phosphorylation with polynucleotide kinase, nick translation, in vitro transcription, and non radioactive techniques. The cDNAs or genomic DNAs in the library are transferred to a nitrocellulose or nylon filter and denatured. After blocking of nonspecific sites, the filter is incubated with the labeled probe for an amount of time sufficient to allow binding of the probe to cDNAs or genomic DNAs containing a sequence capable of hybridizing thereto.

By varying the stringency of the hybridization conditions used to identify cDNAs or genomic DNAs which hybridize to the detectable probe, cDNAs or genomic DNAs having different levels of identity to the probe can be identified and isolated as described below.

Stringent Conditions

"Stringent hybridization conditions" are defined as conditions in which only nucleic acids having a high level of identity to the probe are able to hybridize to said probe. These conditions may be calculated as follows:

For probes between 14 and 70 nucleotides in length the melting temperature (Tm) is calculated using the formula: Tm=81.5+16.6(log (Na+))+0.41(fraction G+C)-(600/N) where N is the length of the probe.

If the hybridization is carried out in a solution containing formamide, the melting temperature may be calculated using the equation: Tm=81.5+16.6(log (Na+))+0.41(fraction G+C)-(0.63% formamide)-(600/N) where N is the length of the probe.

Prehybridization may be carried out in 6×SSC, 5× Denhardt's reagent, 0.5% SDS, 100 μg denatured fragmented salmon sperm DNA or 6×SSC, 5× Denhardt's reagent, 0.5% SDS, 100 μg denatured fragmented salmon sperm DNA, 50% formamide. The formulas for SSC and Denhardt's solutions are listed in Sambrook et al., 1986.

Hybridization is conducted by adding the detectable probe to the prehybridization solutions listed above. Where the probe comprises double stranded DNA, it is denatured before addition to the hybridization solution. The filter is contacted with the hybridization solution for a sufficient period of time to allow the probe to hybridize to nucleic acids containing sequences complementary thereto or homologous thereto. For probes over 200 nucleotides in length, the hybridization may be carried out at 15-25° C. below the Tm. For shorter probes, such as oligonucleotide probes, the hybridization may be conducted at 15-25° C. below the Tm. Preferably, for hybridizations in 6×SSC, the hybridization is conducted at approximately 68° C. Preferably, for hybridizations in 50% formamide containing solutions, the hybridization is conducted at approximately 42° C.

Following hybridization, the filter is washed in 2×SSC, 0.1% SDS at room temperature for 15 minutes. The filter is then washed with 0.1×SSC, 0.5% SDS at room temperature for 30 minutes to 1 hour. Thereafter, the solution is washed at the hybridization temperature in 0.1×SSC, 0.5% SDS. A final wash is conducted in 0.1×SSC at room temperature.

Nucleic acids which have hybridized to the probe are identified by autoradiography or other conventional techniques.

Low and Moderate Conditions

Changes in the stringency of hybridization and signal detection are primarily accomplished through the manipulation of formamide concentration (lower percentages of formamide result in lowered stringency); salt conditions, or temperature. The above procedure may thus be modified to identify nucleic acids having decreasing levels of identity to the probe sequence. For example, the hybridization temperature may be decreased in increments of 5° C. from 68° C. to 420° C. in a hybridization buffer having a sodium concentration of approximately 1M. Following hybridization, the filter may be washed with 2×SSC, 0.5% SDS at the temperature of hybridization. These conditions are considered to be "moderate" conditions above 50° C. and "low" conditions below 50° C. Alternatively, the hybridization may be carried out in buffers, such as 6×SSC, containing formamide at a temperature of 42° C. In this case, the concentration of formamide in the hybridization buffer may be reduced in 5% increments from 50% to 0% to identify clones having decreasing levels of identity to the probe. Following hybridization, the filter may be washed with 6×SSC, 0.5% SDS at 50° C. These conditions are considered to be "moderate" conditions above 25% formamide and "low" conditions below 25% formamide, cDNAs or genomic DNAs which have hybridized to the probe are identified by autoradiography or other conventional techniques.

Note that variations in the above conditions may be accomplished through the inclusion and/or substitution of alternate blocking reagents used to suppress background in hybridization experiments. Typical blocking reagents include Denhardt's reagent, BLOTTO, heparin, denatured salmon sperm DNA, and commercially available proprietary formulations. The inclusion of specific blocking reagents may require modification of the hybridization conditions described above, due to problems with compatibility.

Consequently, the present invention encompasses methods of isolating nucleic acids similar to the polynucleotides of the invention, comprising the steps of:

a) contacting a collection of cDNA or genomic DNA molecules with a detectable probe comprising at least 12, 15, 18, 20, 23, 25, 28, 30, 35, 40 or 50 consecutive nucleotides of a polynucleotide of the present invention under stringent, moderate or low conditions which permit said probe to hybridize to at least a cDNA or genomic DNA molecule in said collection;

b) identifying said cDNA or genomic DNA molecule which hybridizes to said detectable probe; and c) isolating said cDNA or genomic DNA Molecule which hybridized to said probe.

PCR-Based Methods

In addition to the above described methods, other protocols are available to obtain homologous cDNAs using GENSET cDNA of the present invention or fragment thereof as outlined in the following paragraphs.

cDNAs may be prepared by obtaining mRNA from the tissue, cell, or organism of interest using mRNA preparation procedures utilizing polyA selection procedures or other techniques known to those skilled in the art. A first primer capable of hybridizing to the polyA tail of the mRNA is hybridized to the mRNA and a reverse transcription reaction is performed to generate a first cDNA strand.

The term "capable of hybridizing to the polyA tail of said mRNA" refers to and embraces all primers containing stretches of thymidine residues, so-called oligo(dT) primers, that hybridize to the 3' end of eukaryotic poly(A)+ mRNAs to prime the synthesis of a first cDNA strand. Techniques for generating said oligo (dT) primers and hybridizing them to mRNA to subsequently prime the reverse transcription of said hybridized mRNA to generate a first cDNA strand are well known to those skilled in the art and are described in Current Protocols in Molecular Biology, John Wiley and Sons, Inc. 1997 and Sambrook, et al., 1989. Preferably, said oligo (dT) primers are present in a large excess in order to allow the hybridization of all mRNA 3' ends to at least one oligo (dT) molecule. The priming and reverse transcription steps are preferably performed between 37° C. and 55° C. depending on the type of reverse transcriptase used. Preferred oligo(dT) primers for priming reverse transcription of mRNAs are oligonucleotides containing a stretch of thymidine residues of sufficient length to hybridize specifically to the polyA tail of mRNAs, preferably of 12 to 18 thymidine residues in length. More preferably, such oligo(T) primers comprise an additional sequence upstream of the poly(dT) stretch in order to allow the addition of a given sequence to the 5' end of all first cDNA strands which may then be used to facilitate subsequent manipulation of the cDNA. Preferably, this added sequence is 8 to 60 residues in length. For instance, the addition of a restriction site in 5' of cDNAs facilitates subcloning of the obtained cDNA. Alternatively, such an added 5' end may also be used to design primers of PCR to specifically amplify cDNA clones of interest.

The first cDNA strand is then hybridized to a second primer. Any appropriate polynucleotide fragment of the invention may be used. This second primer contains at least 10 consecutive nucleotides of a polynucleotide of the invention. Preferably, the primer comprises at least 10, 12, 15, 17, 18, 20, 23, 25, or 28 consecutive nucleotides of a polynucleotide of the invention. In some embodiments, the primer comprises more than 30 nucleotides of a polynucleotide of the invention. If it is desired to obtain cDNAs containing the full protein coding sequence, including the authentic translation initiation site, the second primer used contains sequences located upstream of the translation initiation site. The second primer is extended to generate a second cDNA strand complementary to the first cDNA strand. Alternatively, RT-PCR may be performed as described above using primers from both ends of the cDNA to be obtained.

The double stranded cDNAs made using the methods described above are isolated and cloned. The cDNAs may be cloned into vectors such as plasmids or viral vectors capable of replicating in an appropriate host cell. For example, the host cell may be a bacterial, mammalian, avian, or insect cell.

Techniques for isolating mRNA, reverse transcribing a primer hybridized to mRNA to generate a first cDNA strand, extending a primer to make a second cDNA strand complementary to the first cDNA strand, isolating the double stranded cDNA and cloning the double stranded cDNA are well known to those skilled in the art and are described in *Current Protocols in Molecular Biology*, John Wiley & Sons, Inc. 1997 and Sambrook, et al., 1989.

Consequently, the present invention encompasses methods of making cDNAs. In a first embodiment, the method of making a cDNA comprises the steps of:

a) contacting a collection of mRNA molecules from human cells with a primer comprising at least 12, 15, 18, 20, 23, 25, 28, 30, 35, 40, or 50 consecutive nucleotides of a sequence selected from the group consisting of the polynucleotide sequences complementary to the polynucleotide sequences of the Sequence Listing and those complementary to a human cDNA clone insert of the deposited clone pool;
b) hybridizing said primer to an mRNA in said collection;
c) reverse transcribing said hybridized primer to make a first cDNA strand from said mRNA;
d) making a second cDNA strand complementary to said first cDNA strand; and
e) isolating the resulting cDNA comprising said first cDNA strand and said second cDNA strand.

Another embodiment of the present invention is a purified cDNA obtainable by the method of the preceding paragraph. In one aspect of this embodiment, the cDNA encodes at least a portion of a human polypeptide.

In a second embodiment, the method of making a cDNA comprises the steps of:

a) contacting a collection of mRNA molecules from human cells with a first primer capable of hybridizing to the polyA tail of said mRNA;
b) hybridizing said first primer to said polyA tail;
c) reverse transcribing said mRNA to make a first cDNA strand;
d) making a second cDNA strand complementary to said first cDNA strand using at least one primer comprising at least 12, 15, 18, 20, 23, 25, 28, 30, 35, 40, or 50 consecutive nucleotides of a sequence selected from the group consisting of polynucleotide sequences of the Sequence Listing and those of human cDNA clone inserts of the deposited clone pool; and
e) isolating the resulting cDNA comprising said first cDNA strand and said second cDNA strand.

In another aspect of this method the second cDNA strand is made by:

a) contacting said first cDNA strand with a second primer comprising at least 12, 15, 18, 20, 23, 25, 28, 30, 35, 40, or 50 consecutive nucleotides of a sequence selected from the group consisting of polynucleotide sequences of the Sequence Listing and those of human cDNA clone inserts of the deposited clone pool, and a third primer which sequence is fully included within the sequence of said first primer;
b) performing a first polytmerase chain reaction with said second and third primers to generate a first PCR product;
c) contacting said first PCR product with a fourth primer, comprising at least 12, 15, 18, 20, 23, 25, 28, 30, 35, 40, or 50 consecutive nucleotides of said sequence selected from the, group consisting of polynucleotide sequences of the Sequence Listing and those of human cDNA clone inserts of the deposited clone pool, and a fifth primer, which sequence is fully included within the sequence of said third primer, wherein said fourth and fifth hybridize to sequences within said first PCR product; and
d) performing a second polymerase chain reaction, thereby generating a second PCR product.

Alternatively, the second cDNA strand may be made by contacting said first cDNA strand with a second primer comprising at least 12, 15, 18, 20, 23, 25, 28, 30, 35, 40, or 50 consecutive nucleotides of a sequence selected from the group consisting of polynucleotide sequences of the Sequence Listing and human cDNA clone inserts of the deposited clone pool, and a third primer which sequence is fully included within the sequence of said first primer and performing a polymerase chain reaction with said second and third primers to generate said second cDNA strand.

Alternatively, the second cDNA strand may be made by:

a) contacting said first cDNA strand with a second primer comprising at least 12, 15, 18, 20, 23, 25, 28, 30, 35, 40, or 50 consecutive nucleotides of a sequence selected from the group consisting of polynucleotide sequences of the Sequence Listing and human cDNA clone inserts of the deposited clone pool;

b) hybridizing said second primer to said first strand cDNA; and c) extending said hybridized second primer to generate said second cDNA strand.

Another embodiment of the present invention is a purified cDNA obtainable by a method of making a cDNA of the invention. In one aspect of this embodiment, said cDNA encodes at least a portion of a human polypeptide Other Protocols Alternatively, other procedures may be used for obtaining homologous cDNAs. In one approach, cDNAs are prepared from mRNA and cloned into double stranded phagemids as follows. The cDNA library in the double stranded phagemids is then rendered single stranded by treatment with an endonuclease, such as the Gene II product of the phage F1 and an exonuclease [Chang et al., (1993) Gene 127:95-8, which disclosure is hereby incorporated by reference in its entirety]. A biotinylated oligonucleotide comprising the sequence of a fragment of a known GENSET cDNA, genomic DNA or fragment thereof is hybridized to the single stranded phagemids. Preferably, the fragment comprises at least 10, 12, 15, 17, 18, 20, 23, 25, or 28 consecutive nucleotides of a polynucleotide of the present invention.

Hybrids between the biotinylated oligonucleotide and phagemids are isolated by incubating the hybrids with streptavidin coated paramagnetic beads and retrieving the beads with a magnet [Fry et al., (1992) Biotechniques, 13: 124-131, which disclosure is hereby incorporated by reference in its entirety]. Thereafter, the resulting phagemids are released from the beads and converted into double stranded DNA using a primer specific for the GENSET cDNA or fragment used to design the biotinylated oligonucleotide. Alternatively, protocols such as the Gene Trapper kit (Gibco BRL), which disclosure is which disclosure is hereby incorporated by reference in its entirety, may be used. The resulting double stranded DNA is transformed into bacteria. Homologous cDNAs to the GENSET cDNA or fragment thereof sequence are identified by colony PCR or colony hybridization.

As a Chromosome Marker

GENSET polynucleotides may be mapped to their chromosomal locations using any methods or techniques known to those skilled in the art including radiation hybrid (RH) mapping, PCR-based mapping and Fluorescence in situ hybridization (FISH) mapping described below.

Radiation Hybrid Mapping

Radiation hybrid (RH) mapping is a somatic cell genetic approach that can be used for high resolution mapping of the human genome. [See, e.g., Benham et al. (1989) *Genomics* 4:509-517 and Cox et al., (1990) Science 250:245-250; and Schuler et al., (1996). Science 274:540-546], which disclosure is hereby incorporated by reference in its entirety.]

Mapping of cDNAs to Human Chromosomes Using PCR Techniques

GENSET cDNAs and genomic DNAs may be assigned to human chromosomes using PCR based methodologies. In such approaches, oligonucleotide primer pairs are designed from the cDNA sequence to minimize the chance of amplifying through an intron. Preferably, the oligonucleotide primers are 18-23 bp in length and are designed for PCR amplification. The creation of PCR primers from known sequences is well known to those with skill in the art. For a review of PCR technology see Erlich (1992), which disclosure is hereby incorporated by reference in its entirety.

PCR is used to screen a series of somatic cell hybrid cell lines containing defined sets of human chromosomes for the presence of a given cDNA or genomic DNA. DNA is isolated from the somatic hybrids and used as starting templates for PCR reactions using the primer pairs from the GENSET cDNAs or genomic DNAs. Only those somatic cell hybrids with chromosomes containing the human gene corresponding to the GENSET cDNA or genomic DNA will yield an amplified fragment. The GENSET cDNAs or genomic DNAs are assigned to a chromosome by analysis of the segregation pattern of PCR products from the somatic hybrid DNA templates. The single human chromosome present in all cell hybrids that give rise to an amplified fragment is the chromosome containing that GENSET cDNA or genomic DNA. For a review of techniques and analysis of results from somatic cell gene mapping experiments, see Ledbetter et al., (1990) Genomics 6:475-481, which disclosure is hereby incorporated by reference in its entirety.

Mapping of cDNAs to Chromosomes Using Fluorescence in situ Hybridization

Fluorescence in situ hybridization (FISH) allows the GENSET cDNA or genomic DNA to be mapped to a particular location on a given chromosome. The chromosomes to be used for fluorescence in situ hybridization techniques may be obtained from a variety of sources including cell cultures, tissues, or whole blood.

In a preferred embodiment, chromosomal localization of a GENSET cDNA or genomic DNA is obtained by FISH as described by Cherif et al., (1990), "Simultaneous Localization of Cosmids and Chromosome R-Banding by Fluorescence Microscopy: Application to Regional Mapping of Human Chromosome 11", Proc. Natl. Acad. Sci. U.S.A., 87:6639-6643, which disclosure is hereby incorporated by reference in its entirety. For chromosomal localization, fluorescent R-bands are obtained as previously described (Cherif, et al., 1990, supra).

Use of cDNAs to Construct or Expand Chromosome Maps

Once the GENSET cDNAs or genomic DNAs have been assigned to particular chromosomes using any technique known to those skilled in the art those skilled in the art, particularly those described herein, they may be utilized to construct a high resolution map of the chromosomes on which they are located or to identify the chromosomes in a sample.

Chromosome mapping involves assigning a given unique sequence to a particular chromosome as described above. Once the unique sequence has been mapped to a given chromosome, it is ordered relative to other unique sequences located on the same chromosome. One approach to chromosome mapping utilizes a series of yeast artificial chromosomes (YACs) bearing several thousand long inserts derived from the chromosomes of the organism from which the GENSET cDNAs or genomic DNAs are obtained. This approach is described in Nagaraja et al., (1997) "X chromosome map at 75-kb STS resolution, revealing extremes of recombination and GC content", Genome Res. 1997 Mar;7 (3):210-22, which disclosure is hereby incorporated by reference in its entirety.

Identification of Genes Associated with Hereditary Diseases or Drug Response

This example illustrates an approach useful for the association of GENSET cDNAs or genomic DNAs with particular phenotypic characteristics. In this example, a particular GENSET cDNA or genomic DNA is used as a test probe to associate that GENSET cDNA or genomic DNA with a particular phenotypic characteristic.

GENSET cDNAs or genomic DNAs are mapped to a particular location on a human chromosome using techniques such as those described herein or other techniques known in the art. A search of Mendelian Inheritance in Man (V. McKusick, Mendelian Inheritance in Man; available on line through Johns Hopkins University Welch Medical Library) reveals the region of the human chromosome which contains the GENSET cDNA or genomic DNA to be a very gene rich region containing several known genes and several diseases or phenotypes for which genes have not been identified. The gene corresponding to this GENSET cDNA or genomic DNA thus becomes an immediate candidate for each of these genetic diseases.

Cells from patients with these diseases or phenotypes are isolated and expanded in culture. PCR primers from the GENSET cDNA or genomic DNA are used to screen genomic DNA, mRNA or cDNA obtained from the patients. GENSET cDNAs or genomic DNAs that are not amplified in the patients can be positively associated with a particular disease by further analysis. Alternatively, the PCR analysis may yield fragments of different lengths when the samples are derived from an individual having the phenotype associated with the disease than when the sample is derived from a healthy individual, indicating that the gene containing the cDNA may be responsible for the genetic disease.

Uses of Polynucleotides in Recombinant Vectors

The present invention also relates to recombinant vectors including the isolated polynucleotides of the present invention, and to host cells recombinant for a polynucleotide of the invention, such as the above vectors, as well as to methods of making such vectors and host cells and for using them for production of GENSET polypeptides by recombinant techniques.

Recombinant Vectors

The term "vector" is used herein to designate either a circular or a linear DNA or RNA molecule, which is either double-stranded or single-stranded, and which comprise at least one polynucleotide of interest that is sought to be transferred in a cell host or in a unicellular or multicellular host organism. The present invention encompasses a family of recombinant vectors that comprise a regulatory polynucleotide and/or a coding polynucleotide derived from either the GENSET genomic sequence or the cDNA sequence. Generally, a recombinant vector of the invention may comprise any of the polynucleotides described herein, including regulatory sequences, coding sequences and polynucleotide constructs, as well as any GENSET primer or probe as defined herein.

In a first preferred embodiment, a recombinant vector of the invention is used to amplify the inserted polynucleotide derived from a GENSET genomic sequence or a GENSET cDNA, for example any cDNA selected from the group consisting of polynucleotide sequences of the Sequence Listing, those of human cDNA clone inserts of the deposited clone pool, variants and fragments thereof in a suitable cell host, this polynucleotide being amplified at every time that the recombinant vector replicates.

A second preferred embodiment of the recombinant vectors according to the invention comprises expression vectors comprising either a regulatory polynucleotide or a coding nucleic acid of the invention, or both. Within certain embodiments, expression vectors are employed to express a GENSET polypeptide which can be then purified and, for example be used in ligand screening assays or as an immunogen in order to raise specific antibodies directed against the GENSET protein. In other embodiments, the expression vectors are used for constructing transgenic animals and also for gene therapy. Expression requires that appropriate signals are provided in the vectors, said signals including various regulatory elements, such as enhancers/promoters from both viral and mammalian sources that drive expression of the genes of interest in host cells. Dominant drug selection markers for establishing permanent, stable cell clones expressing the products are generally included in the expression vectors of the invention, as they are elements that link expression of the drug selection markers to expression of the polypeptide.

More particularly, the present invention relates to expression vectors which include nucleic acids encoding a GENSET protein, preferably a GENSET protein with an amino acid sequence selected from the group consisting of polypeptide sequences of the Sequence Listing, those encoded by the human cDNA clone inserts of the deposited clone pool, variants and fragments thereof. The polynucleotides of the present invention may be used to express an encoded protein in a host organism to produce a beneficial effect. In such procedures, the encoded protein may be transiently expressed in the host organism or stably expressed in the host organism. The encoded protein may have any of the activities described herein. The encoded protein may be a protein which the host organism lacks or, alternatively, the encoded protein may augment the existing levels of the protein in the host organism.

Some of the elements which can be found in the vectors of the present invention are described in further detail in the following sections.

General Features of the Expression Vectors of the Invention

A recombinant vector according to the invention comprises, but is not limited to, a YAC (Yeast Artificial Chromosome), a BAC (Bacterial Artificial Chromosome), a phage, a phagemid, a cosmid, a plasmid or even a linear DNA molecule which may comprise a chromosomal, non-chromosomal, semi-synthetic and synthetic DNA. Such a recombinant vector can comprise a transcriptional unit comprising an assembly of:

(1) a genetic element or elements having a regulatory role in gene expression, for example promoters or enhancers. Enhancers are cis-acting elements of DNA, usually from about 10 to 300 bp in length that act on the promoter to increase the transcription.

(2) a structural or coding sequence which is transcribed into mRNA and eventually translated into a polypeptide, said structural or coding sequence being operably linked to the regulatory elements described in (1); and (3) appropriate transcription initiation and termination sequences. Structural units intended for use in yeast or eukaryotic expression systems preferably include a leader sequence enabling extracellular secretion of translated protein by a host cell. Alternatively, when a recombinant protein is expressed without a leader or transport sequence, it may include a N-terminal residue. This residue may or may not be subsequently cleaved from the expressed recombinant protein to provide a final product.

Generally, recombinant expression vectors will include origins of replication, selectable markers permitting transformation of the host cell, and a promoter derived from a highly expressed gene to direct transcription of a downstream structural sequence. The heterologous structural sequence is assembled in appropriate phase with translation initiation and termination sequences, and preferably a leader sequence capable of directing secretion of the translated protein into the periplasmic space or the extracellular medium. In a specific embodiment wherein the vector is adapted for transfecting and expressing desired sequences in mammalian host cells, preferred vectors will comprise an origin of replication in the desired host, a suitable promoter and enhancer, and also any necessary ribosome binding sites, polyadenylation signals, splice donor and acceptor sites, transcriptional termination sequences, and 5'-flanking non-transcribed sequences. DNA sequences derived from the SV40 viral genome, for example SV40 origin, early promoter, enhancer, splice and polyadenylation signals may be used to provide the required non-transcribed genetic elements.

The in vivo expression of a GENSET polypeptide of the present invention may be useful in order to correct a genetic defect related to the expression of the native gene in a host organism, for the treatment or prevention of any disease or condition that can be treated or prevented by increasing the level of GENSET polypeptide expression, or to the production of a biologically inactive GENSET protein. Consequently, the present invention also comprises recombinant expression vectors mainly designed for the in vivo production of a GENSET polypeptide the present invention by the introduction of the appropriate genetic material in the organism or the patient to be treated. This genetic material may be introduced in vitro in a cell that has been previously extracted from the organism, the modified cell being subsequently reintroduced in the said organism, directly in vivo into the appropriate tissue.

Regulatory Elements

The suitable promoter regions used in the expression vectors according to the present invention are chosen taking into account the cell host in which the heterologous gene has to be expressed.

A suitable promoter may be heterologous with respect to the nucleic acid for which it controls the expression or alternatively can be endogenous to the native polynucleotide containing the coding sequence to be expressed. Additionally, the promoter is generally heterologous with respect to the recombinant vector sequences within which the construct promoter/coding sequence has been inserted. Promoter regions can be selected from any desired gene using, for example, CAT (chloramphenicol transferase) vectors and more preferably pKK232-8 and pCM7 vectors.

Preferred bacterial promoters are the LacI, LacZ, the T3 or T7 bacteriophage RNA polymerase promoters, the gpt, lambda PR, PL and trp promoters (EP 0036776), the polyhedrin promoter, or the p10 protein promoter from baculovirus (Kit Novagen) [Smith et al., (1983). Mol. Cell. Biol. 3:2156-2165; O'Reilly et al. (1992), "Baculovirus Expression Vectors: A Laboratory Manual", W.H. Freeman and Co., New York; which disclosures are hereby incorporated by reference in their entireties], the lambda PR promoter or also the trc promoter.

Eukaryotic promoters include CMV immediate early, HSV thymidine kinase, early and late SV40, LTRs from retrovirus, and mouse metallothionein-L. Selection of a convenient vector and promoter is well within the level of ordinary skill in the art.

Other Regulatory Elements

Where a cDNA insert is employed, one will typically desire to include a polyadenylation signal to effect proper polyadenylation of the gene transcript. Also contemplated as an element of the expression cassette is a terminator. These elements can serve to enhance message levels and to minimize read through from the cassette into other sequences.

Selectable Markers

Selectable markers confer an identifiable change to the cell permitting easy identification of cells containing the expression construct. The selectable marker genes for selection of transformed host cells are preferably dihydrofolate reductase or neomycin resistance for eukaryotic cell culture, TRP1 for *S. cerevisiae* or tetracycline, rifampicin or ampicillin resistance in *E. Coli*, or levan saccharase for mycobacteria, this latter marker being a negative selection marker.

Preferred Vectors

Bacterial Vectors

As a representative but non-limiting example, useful expression vectors for bacterial use can comprise a selectable marker and a bacterial origin of replication derived from commercially available plasmids comprising genetic elements of pBR322 (ATCC 37017). Such commercial vectors include, for example, pKK223-3 (Pharmacia, Uppsala, Sweden), and pGEM1 (Promega Biotec, Madison, Wis., USA). Large numbers of other suitable vectors are known to those of skill in the art, and commercially available, such as the following bacterial vectors: pQE70, pQE60, pQE-9 (Qiagen), pbs, pD10, phagescript, psiX174, pbluescript SK, pbsks, pNH8A, pNH16A, pNH18A, pNH46A (Stratagene); ptrc99a, pKK223-3, pKK233-3, pDR540, pRIT5 (Pharmacia); pWLNEO, pSV2CAT, pOG44, pXT1, pSG (Stratagene); pSVK3, pBPV, pMSG, pSVL (Pharmacia); pQE-30 (QIAexpress).

Bacteriophage Vectors

The P1 bacteriophage vector may contain large inserts ranging from about 80 to about 100 kb. The construction of P1 bacteriophage vectors such as p158 or p158/neo8 are notably described by Sternberg (1992) Trends Genet. 8:1-16, and Sternberg (1994) Mamm. Genome. 5:397-404, which disclosure is hereby incorporated by reference in its entirety. Recombinant P1 clones comprising GENSET nucleotide sequences may be designed for inserting large polynucleotides of more than 40 kb [see, Linton et al., (1993) J. Clin. Invest. 92:3029-3037], which disclosure is hereby incorporated by reference in its entirety. To generate P1 DNA for transgenic experiments, a preferred protocol is the protocol described by McCormick et al., (1994) Genet. Anal. Tech. Appl. 11:158-164, which disclosure is hereby incorporated by reference in its entirety. Briefly, *E. coli* (preferably strain NS3529) harboring the P1 plasmid are grown overnight in a suitable broth medium containing 25 μg/ml of kanamycin. The P1 DNA is prepared from the *E. coli* by alkaline lysis using the Qiagen Plasmid Maxi kit (Qiagen, Chatsworth, Calif., USA), according to the manufacturer's instructions. The P1 DNA is purified from the bacterial lysate on two Qiagen-tip 500 columns, using the washing and elution buffers contained in the kit. A phenol/chloroform extraction is then performed before precipitating the DNA with 70% ethanol. After solubilizing the DNA in TE (10 mM Tris-HCl, pH 7.4, 1 mM EDTA), the concentration of the DNA is assessed by spectrophotometry.

When the goal is to express a P1 clone comprising GENSET polypeptide-encoding nucleotide sequences in a transgenic animal, typically in transgenic mice, it is desirable to remove vector sequences from the P1DNA fragment, for example by cleaving the P1DNA at rare-cutting sites within the P1 polylinker (SfiI, NotI or SalI). The P1 insert is then purified from vector sequences on a pulsed-field agarose gel, using methods similar to those originally reported for the isolation of DNA from YACs [see, e.g., Schedl et al., (1993a), Nature, 362: 258-261; Peterson et al., (1993), Proc. Natl. Acad. Sci. USA, 90:7593-7597], which disclosures are hereby incorporated by reference in their entireties. At this stage, the resulting purified insert DNA can be concentrated, if necessary, on a Millipore Ultrafree-MC Filter Unit (Millipore, Bedford, Mass., USA —30,000 molecular weight limit) and then dialyzed against microinjection buffer. (10 mM Tris-HCl, pH 7.4; 250 μM EDTA) containing 100 mM NaCl, 30 μM spermine, 70 μM spermidine on a microdyalisis membrane (type VS, 0.025 μM from Millipore). The intactness of the purified P1 DNA insert is assessed by electrophoresis on 1% agarose (Sea Kem GTG; FMC Bioproducts) pulse-field gel and staining with ethidium bromide.

Viral Vectors

In one specific embodiment, the vector is derived from an adenovirus. Preferred adenovirus vectors according to the invention are those described by Feldman and Steg, (1996), Medecine/Sciences, 12:47-55, or Ohno et al., (1994) Science. 265:781-784, which disclosures are hereby incorporated by reference in their entireties. Another preferred recombinant adenovirus according to this specific embodiment of the present invention is the human adenovirus type 2 or 5 (Ad 2 or Ad 5) or an adenovirus of animal origin (French patent application No. FR-93.05954, which disclosure is hereby incorporated by reference in its entirety). Further included in the present invention are ademo-associated virus vectors.

Retrovirus vectors and adeno-associated virus vectors are generally understood to be the recombinant gene delivery systems of choice for the transfer of exogenous polynucleotides in vivo, particularly to mammals, including humans. Particularly preferred retroviruses for the preparation or construction of retroviral in vitro or in vitro gene delivery vehicles of the present invention include retroviruses selected from the group consisting of Mink-Cell Focus Inducing Virus, Murine Sarcoma Virus, Reticuloendotheliosis virus and Rous Sarcoma virus. Particularly preferred Murine Leukemia Viruses include the 4070A and the 1504A viruses, Abelson (ATCC No VR-999), Friend (ATCC No VR-245), Gross (ATCC No VR-590), Rauscher (ATCC No VR-998) and Moloney Murine Leukemia Virus (ATCC No VR-190; PCT Application No WO 94/24298). Particularly preferred Rous Sarcoma Viruses include Bryan high titer (ATCC Nos. VR-334, VR-657, VR-726, VR-659 and VR-728). Other preferred retroviral vectors are those described in Roth et al., (1996) Nature Medicine, 2(9):985-991, PCT Application No WO 93/25234, PCT Application No WO 94/06920, Roux et al. (1989), Proc. Natl. Acad. Sci. U.S.A. 86:9079-9083, Julan et al. (1992), J. Gen. Virol. 73:3251-3255, and Neda et al. (1991), J. Biol. Chem. 266:14143-14146, which disclosures are hereby incorporated by reference in their entireties.

BAC Vectors

The bacterial artificial chromosome (BAC) cloning system [Shizuya et al. (1992), Proc. Natl. Acad. Sci. U.S.A. 89:8794-8797], which disclosure is hereby incorporated by reference in its entirety, has been developed to stably maintain large fragments of genomic DNA (100-300 kb) in *E. coli*. A preferred BAG vector comprises a pBeloBAC11 vector that has been described by Kim U-J. et al. (1996), Genomics 34:213-218, which disclosure is hereby incorporated by reference in its entirety. BAG libraries are prepared with this vector using size-selected genomic DNA that has been partially digested using enzymes that permit ligation into either the Bam HI or HindII sites in the vector. Flanking these cloning sites are T7 and SP6 RNA polymerase transcription initiation sites that can be used to generate end probes by either. RNA transcription or PCR methods. After the construction of a BAC library in *E. coli*, BAC DNA is purified from the host cell as a supercoiled circle. Converting these circular molecules into a linear form precedes both size determination and introduction of the BACs into recipient cells. The cloning site is flanked by two NotI sites, permitting cloned segments to be excised from the vector by NotI digestion. Alternatively, the DNA insert contained in the pBeloBAC11 vector may be linearized by treatment of the BAC vector with the commercially available enzyme lambda terminase that leads to the cleavage at the unique cosN site, but this cleavage method results in a full length BAC clone containing both the insert DNA and the BAC sequences.

Baculovirus

Another specific suitable host vector system is the pVL1392/1393 baculovirus transfer vector (Pharmingen) that is used to transfect the SF9 cell line (ATCC No. CRL 1711) which is derived from *Spodoptera frugiperda*. Other suitable vectors for the expression of the GENSET polypeptide of the present invention in a baculovirus expression system include those described by Chai et al. (1993), Biotechnol. Appl. Biochem. 18:259-273; Vlasak, et al. (1983), Eur. J. Biochem. 135:123-126, and Lenhard et al., (1996) Gene. 169:187-190, which disclosures are hereby incorporated by reference in their entireties.

Delivery of the Recombinant Vectors

To effect expression of the polynucleotides and polynucleotide constructs of the invention, the constructs must be delivered into a cell. This delivery may be accomplished in vitro, as in laboratory procedures for transforming cell lines, or in vivo or ex vivo, as in the treatment of certain diseases states.

One mechanism is viral infection where the expression construct is encapsulated in an infectious viral particle. The expression construct, preferably a recombinant viral vector as discussed herein, may transduce packaging cells through any means known in the art such as electroporation, liposomes, and CaPO4 precipitation. The packaging cell generates infectious viral particles that include a polynucleotide encoding a polypeptide of the present invention. Such viral particles then may be employed to transduce eukaryotic cells in vitro, ex vivo or in vivo. The transduced eukaryotic cells will express a polypeptide of the present invention. Preferably, the viruses used in the present invention are rendered replication deficient by deletion of one or more of all or a portion of the following genes: E1a, E1b, E3, E4, E2a, or L1 through L5. (U.S. Pat. No. 6,228,844, which disclosure is hereby incorporated by reference in its entirety). Viral delivery is discussed in more detail herein (see also, U.S. Pat. No. 5,968,821, which disclosure is hereby incorporated by reference in its entirety).

Retrovirus vectors and adeno-associated virus vectors are generally understood to be the recombinant gene delivery system of choice for the transfer of exogenous genes in vivo, particularly into humans. These vectors provide efficient delivery of genes into cells, and the transferred nucleic acids are stably integrated into the chromosomal DNA of the host. A major prerequisite for the use of retroviruses is to ensure the safety of their use, particularly with regard to the possibility of the spread of wild-type virus in the cell population. The development of specialized cell lines (termed "packaging cells") which produce only replication-defective retroviruses has increased the utility of retroviruses for gene therapy, and defective retroviruses are well characterized for use in gene transfer for gene therapy purposes (for a review see Miller, A. D. (1990) Blood 76:271). Thus, recombinant retrovirus can be constructed in which part of the retroviral coding sequence (gag, pol, env) has been replaced by nucleic acid encoding one of the subject CCR-proteins, rendering the retrovirus replication defective. The replication defective retrovirus is then packaged into virions which can be used to infect a target cell through the use of a helper virus by standard techniques.

Protocols for producing recombinant retroviruses and for infecting cells in vitro or in vivo with such viruses can be found in Current Protocols in Molecular Biology, Ausubel, F. M. et al. (eds.) Greene Publishing Associates, (1989), Sections 9.10-9.14 and other standard laboratory manuals. Examples of suitable retroviruses include pLJ, pZIP, pWE and pEM which are well known to those skilled in the art. Examples of suitable packaging virus lines for preparing both ecotropic and amphotropic retroviral systems include .psi.Crip, .psi.Cre, .psi.2 and .psi.Am. Retroviruses have been used to introduce a variety of genes into many different cell types, including neural cells, epithelial cells, endothelial cells, lymphocytes, myoblasts, hepatocytes, bone marrow cells, in vitro and/or in vivo (see for example Eglitis, et al. (1985) Science 230:1395-1398; Danos and Mulligan (1988) Proc. Natl. Acad. Sci. USA 85:6460-6464; Wilson, et al. (1988) Proc. Natl. Acad. Sci. USA 85:3014-3018; Armentano, et al. (1990) Proc. Natl. Acad. Sci. USA 87:6141-6145; Huber, et al. (1991) Proc. Natl. Acad. Sci. USA 88:8039-8043; Ferry, et al. (1991) Proc. Natl. Acad. Sci. USA 88:8377-8381; Chowdhury, et al. (1991) Science 254:1802-1805; van Beusechern, et al. (1992) Proc. Natl. Acad. Sci. USA 89:7640-7644; Kay, et al. (1992) Human Gene Therapy 3:641-647; Dai, et al. (1992) Proc. Natl. Acad. Sci. USA 89:10892-10895; Hwu, et al. (1993) J. Immunol. 150:4104-4115; U.S. Pat. No. 4,868,116; U.S. Pat. No. 4,980,286; PCT Application WO 89/07136; PCT Application WO 89/02468; PCT Application WO 89/05345; and PCT Application WO 92/07573).

Furthermore, it has been shown that it is possible to limit the infection spectrum of retroviruses and consequently of retroviral-based vectors, by modifying the viral packaging proteins on the surface of the viral particle (see, for example PCT publications WO93/25234, WO94/06920, and WO94/11524). For instance, strategies for the modification of the infection spectrum of retroviral vectors include: coupling antibodies specific for cell surface antigens to the viral env protein (Roux, et al. (1989) PNAS 86:9079-9083; Julan, et al. (1992) J. Gen Virol 73:3251-3255; and Goud, et al. (1983) Virology 163:251-254); or coupling cell surface ligands to the viral env proteins (Neda, et al. (1991) J Biol Chem 266:14143-14146). Coupling can be in the form of the chemical cross-linking with a protein or other variety (e.g. lactose to convert the env protein to an asialoglycoprotein), as well as by generating fusion proteins (e.g. single-chain antibody/env fusion proteins). This technique, while useful to limit or otherwise direct the infection to certain tissue types, and can also be used to convert an ecotropic vector in to an amphotropic vector.

Moreover, use of retroviral gene delivery can be further enhanced by the use of tissue- or cell-specific transcriptional regulatory sequences that control expression of the desired gene.

Another viral gene delivery system useful in the present invention utilizes adenovirus-derived vectors. The genome of an adenovirus can be manipulated such that it encodes a gene product of interest, but is inactivate in terms of its ability to replicate in a normal lytic viral life cycle (see, for example, Berkner, et al. (1988) BioTechniques 6:616; Rosenfeld, et al. (1991) Science 252:431-434; and Rosenfeld, et al. (1992) Cell 68:143-155). Suitable adenoviral vectors derived from the adenovirus strain Ad type 5 d1324 or other strains of adenovirus (e.g., Ad2, Ad3, Ad7 etc.) are well known to those skilled in the art. Recombinant adenoviruses can be advantageous in certain circumstances in that they are not capable of infecting nondividing cells and can be used to infect a wide variety of cell types, including airway epithelium (Rosenfeld, et al. (1992) cited supra), endothelial cells (Lemarchand et al. (1992) Proc. Natl. Sci. USA 89:6482-6486), hepatocytes (Herz and Gerard (1993) Proc. Natl. Acad. Sci. USA 90:2812-2816) and muscle cells (Quantin, et al. (1992) Proc. Natl. Acad. Sci. USA 89:2581-2584). Furthermore, the virus particle is relatively stable and amenable to purification and concentration, and as above, can be modified so as to affect the spectrum of infectivity. Additionally, introduced adenoviral polynucleotides (and foreign polynucleotides contained therein) is not integrated into the genome of a host cell but remains episomal, thereby avoiding potential problems that can occur as a result of insertional mutagenesis in situations where introduced DNA becomes integrated into the host genome (e.g., retroviral DNA). Moreover, the carrying capacity of the adenoviral genome for foreign DNA is large (up to 8 kilobases) relative to other gene delivery vectors (Haj-Ahmand and Graham (1986) J. Virol. 57:267) Most replication-defective adenoviral vectors currently in use and therefore favored by the present invention are deleted for all or parts of the viral E1 and E3 genes but retain as much as 80% of the adenoviral genetic material (see, e.g., Jones, et al. (1979) Cell 16:683; Berkner, et al., supra; and Graham, et al. in Methods in Molecular Biology, E. J. Murray, Ed. (Humana, Clifton, N.J., 1991) vol. 7. pp. 109-127). Expression of desired polynucleotides can be under control of, for example, the E1A promoter, the major late promoter (MLP) and associated leader sequences, the E3 promoter, or exogenously added promoter sequences.

Yet another viral vector system useful for delivery of polynucleotides is the adeno-associated virus (AAV). Adeno-associated virus is a naturally occurring defective virus that requires another virus, such as an adenovirus or a herpes virus, as a helper virus for efficient replication and a productive life cycle. (For a review see Muzyczka, et al., Curr. Topics in Micro. and Immunol. (1992) 158:97-129). It is also one of the few viruses that may integrate its nucleic acids into non-dividing cells, and exhibits a high frequency of stable integration (see for example Flotte et al., (1992) Am. J. Respir. Cell Mol. Biol. 7:349-356; Am. J. Respir.

Cell. Mol. Biol. 7:349-356; Samulski et al. (1989) J. Virol. 63:3822-3828; and McLaughlin et al. (1989) J. Virol. 62:1963-1973). Vectors containing as little as 300 base pairs of AAV can be packaged and can integrate. Space for exogenous DNA is limited to about 4.5 kb. An AAV vector such as that described in Tratschin, et al. (1985) Mol. Cell. Biol. 5:3251-3260 can be used to introduce DNA into cells. A variety of nucleic acids have been introduced into different cell types using AAV vectors (see for example Hermonat, et al. (1984) Proc. Natl. Acad. Sci. USA 81:6466-6470; Tratschin, et al. (1985) Mol. Cell. Biol. 4:2072-2081; Wondisford, et al. (1988) Mol. Endocrinol. 2:32-39; Tratschin, et al. (1984) J. Virol. 51:611-619; and Flotte, et al. (1993) J. Biol. Chem. 268:3781-3790).

Other viral vector systems that may have application in gene therapy have been derived from herpes virus, vaccinia virus, and several RNA viruses. In particular, herpes virus vectors may provide a unique strategy for persistence of inserted gene expression in cells of the central nervous system and ocular tissue (Pepose, et al. (1994) Invest Ophthalmol Vis Sci 35:2662-2666).

Several non-viral methods for the transfer of polynucleotides into cultured mammalian cells are also contemplated by the present invention, and include, without being limited to, calcium phosphate precipitation [Graham et al., (1973) Virol. 52:456-457; Chen et al. (1987) Mol. Cell. Biol. 7:2745-2752]; DEAE-dextran [Gopal (1985) Mol. Cell. Biol., 5:1188-1190]; electroporation [Tur-Kaspa et al. (1986) Mol. Cell. Biol. 6:716-718; Potter et al., (1984) Proc. Natl. Acad. Sci. U.S.A. 81(22):7161-7165]; direct microinjection (Harland et al., (1985) J. Cell. Biol. 101:1094-1095); DNA-loaded liposomes [Nicolau et al., (1982) Biochim. Biophys. Acta. 721:185-190; Fraley et al., (1979) Proc. Natl. Acad. Sci. USA. 76:3348-3352]; and receptor-mediated transfection. [Wu and Wu (1987), J. Biol. Chem. 262:4429-4432; and Wu and Wu (1988), Biochemistry 27:887-892], which disclosures are hereby incorporated by reference in their entireties. Some of these techniques may be successfully adapted for in vivo or ex vivo use, as discussed herein.

Once the expression polynucleotide has been delivered into the cell, it may be stably integrated into the genome of the recipient cell. This integration may be in the cognate location and orientation via homologous recombination (gene replacement) or it may be integrated in a random, non-specific location (gene augmentation). In yet further embodiments, the nucleic acid may be stably maintained in the cell as a separate, episormal segment of DNA. Such nucleic acid segments or "episomes" encode sequences sufficient to permit maintenance and replication independent of or in synchronization with the host cell cycle.

One specific embodiment for a method for delivering a protein or peptide to the interior of a cell of a vertebrate in vivo comprises the step of introducing a preparation comprising a physiologically acceptable carrier and a naked polynucleotide operatively coding for the polypeptide of interest into the interstitial space of a tissue comprising the cell, whereby the naked polynucleotide is taken up into the interior of the cell and has a physiological effect. This is particularly applicable for transfer in vitro but it may be applied to in vivo as well.

Compositions for use in vitro and in vivo comprising a "naked" polynucleotide are described in PCT application No. WO 90/11092 (Vical Inc.) and also in PCT application No. WO. 95/11307 (Institut Pasteur, INSERM, Universitè d'Ottawa) as well as in the articles of Tascon et al. (1996), Nature Medicine. 2(8):888-892 and of Huygen et al., (1996) Nature Medicine. 2(8):893-898, which disclosures are hereby incorporated by reference in their entireties.

In still another embodiment of the invention, the transfer of a naked polynucleotide of the invention, including a polynucleotide construct of the invention, into cells may be accomplished with particle bombardment (biolistic), said particles being DNA-coated microprojectiles accelerated to a high velocity allowing them to pierce cell membranes and enter cells without killing them, such as described by Klein et al., (1987) Nature 327:70-73, which disclosure is hereby incorporated by reference in its entirety. Liposomal preparations for use in the present invention include cationic (positively charged), anionic (negatively charged) and neutral preparations. However, cationic liposomes are particularly preferred because a tight charge complex can be formed between the cationic liposome and the polyanionic nucleic acid. Cationic liposomes have been shown to mediate intracellular delivery of plasmid DNA (Felgner, et al., Proc. Nat. Acad. Sci. USA (1987) 84:7413-7416, which is herein incorporated by reference); mRNA (Malone, et al., Proc. Natl. Acad. Sci. USA (1989) 86:6077-6081, which is herein incorporated by reference); and purified transcription factors (Debs et al., J. Biol. Chem. (1990) 265:10189-10192, which is herein incorporated by reference), in functional form.

Cationic liposomes are readily available. For example, N[1-2, 3-dioleyloxy)propyl]-N,N,N-triethylammonium (DOTMA) liposomes are particularly useful and are available under the trademark Lipofectin, from GIBCO BRL, Grand Island, N.Y. (See, also, Feigner, et al., Proc. Nad Acad. Sci. USA (1987) 84:7413-7416, which is herein incorporated by reference). Other commercially available liposomes include transfectace (DDAB/DOPE) and DOTAP/DOPE (Boehringer).

Similarly, anionic and neutral liposomes are readily available, such as from AvantiPolar Lipids (Birmingham, Ala.), or can be easily prepared using readily available materials. Such materials include phosphatidyl, choline, cholesterol, phosphatidyl ethanolamine, dioleoylphosphatidyl choline (DOPC), dioleoylphosphatidyl glycerol (DOPG), dioleoylphoshatidyl ethanolamine (DOPE), among others. These materials can also be mixed with the DOTMA and DOTAP starting materials in appropriate ratios. Methods for making liposomes using these materials are well known in the art.

For example, commercially dioleoylphosphatidyl choline (DOPC), dioleoylphosphatidyl glycerol (DOPG), and dioleoylphosphatidyl ethanolamine (DOPE) can be used in various combinations to make conventional liposomes, with or without the addition of cholesterol. The liposomes can comprise multilamellar vesicles (MLVs), small unilamellar vesicles (SUVs), or large unilamellar vesicles (LUVs), with SUVs being preferred. The various liposome-nucleic acid complexes are prepared using methods well known in the art (Straubinger, et al., Methods of Immunology (1983), 101: 512-527, which is herein incorporated by reference). For example, MLVs containing nucleic acid can be prepared by depositing a thin film of phospholipid on the walls of a glass tube and subsequently hydrating with a solution of the material to be encapsulated (U.S. Pat. No. 5,965,421, which disclosure is hereby incorporated by reference).

Generally, the ratio of DNA to liposomes will be from about 10:1 to about 1:10. Preferably, the ratio will be from about 5:1 to about 1:5. More preferably, the ratio will be about 3:1 to about 1:3. Still more preferably, the ratio will be about 1:1. Additionally, liposomes may be targeted to specific cell types by embedding a targeting moiety such as a member of a receptor-receptor ligand pair into the lipid envelope of the vesicle. Useful targeting moieties specifically bind cell surface ligands, for example, CD48 or the SCF receptor on mast cells. Thus, anti-CD48 antibodies or SCF ligand are examples of useful mast cell-targeting moieties (U.S. Pat. No. 6,177,433, U.S. Pat. No. 6,110,490, and PCT No. WO9704748, which disclosures are hereby incorporated by reference in their entireties).

In a further embodiment, the polynucleotide of the invention may be entrapped in a liposome [Ghosh and Bacchawat, (1991), Targeting of liposomes to hepatocytes, IN: Liver Diseases, Targeted diagnosis and therapy using specific receptors and ligands. Eds., Marcel Dekeker, New York, pp. 87-104; Wong, et al. (1980), Gene. 10:87-94; Nicolau et al, (1987), Meth. Enzymol., 149:157-76, which disclosures are hereby incorporated by reference in their entireties].

In a specific embodiment, the invention provides a composition for the in vivo production of the GENSET polypeptides described herein. It comprises a naked polynucleotide operatively coding for this polypeptide, in solution in a physiologically acceptable carrier, and suitable for introduction into a tissue to cause cells of the tissue to express the said protein or polypeptide.

The amount of vector to be injected to the desired host organism varies according to the site of injection. As an indicative dose, it will be injected between 0.1 and 100 μg of the vector in an animal body, preferably a mammal body, for example a mouse body.

In another embodiment of the vector according to the invention, it may be introduced in vitro in a host cell, preferably in a host cell previously harvested from the animal to be treated and more preferably a somatic cell such as a muscle cell. In a subsequent step, the cell that has been transformed with the vector coding for the desired GENSET polypeptide or the desired fragment thereof is reintroduced into the animal body in order to deliver the recombinant protein within the body either locally or systemically.

Secretion Vectors

Some of the GENSET cDNAs or genomic DNAs of the invention may also be used to construct secretion vectors capable of directing the secretion of the proteins encoded by genes inserted in the vectors. Such secretion vectors may facilitate the purification or enrichment of the proteins encoded by genes inserted therein by reducing the number of background proteins from which the desired protein must be purified or enriched. Exemplary secretion vectors are described below.

The secretion vectors of the present invention include a promoter capable of directing gene expression in the host cell, tissue, or organism of interest. Such promoters include the Rous Sarcoma Virus promoter, the SV40 promoter, the human cytomegalovirus promoter; and other promoters familiar to those skilled in the art.

A signal sequence from a polynucleotide of the invention and signal sequences of clone inserts of the deposited clone pool is operably linked to the promoter such that the mRNA transcribed from the promoter will direct the translation of the signal peptide. The host cell, tissue, or organism may be any cell, tissue, or organism which recognizes the signal peptide encoded by the signal sequence in the GENSET cDNA or genomic DNA. Suitable hosts include mammalian cells, tissues or organisms, avian cells, tissues, or organisms, insect cells, tissues or organisms, or yeast.

In addition, the secretion vector contains cloning sites for inserting genes encoding the proteins which are to be secreted. The cloning sites facilitate the cloning of the insert gene in frame with the signal sequence such that a fusion protein in which the signal peptide is fused to the protein encoded by the inserted gene is expressed from the mRNA transcribed from the promoter. The signal peptide directs the extracellular secretion of the fusion protein.

The secretion vector may be DNA or RNA and may integrate into the chromosome of the host, be stably maintained as an extrachromosomal replicon in the host, be an artificial chromosome, or be transiently present in the host. Preferably, the secretion vector is maintained in multiple copies in each host cell. As used herein, multiple copies means at least 2, 5, 10, 20, 25, 50 or more than 50 copies per cell. In some embodiments, the multiple copies are maintained extrachromosomally. In other embodiments, the multiple copies result from amplification of a chromosomal sequence.

Many nucleic acid backbones suitable for use as secretion vectors are known to those skilled in the art, including retroviral vectors, SV40 vectors, Bovine Papilloma Virus vectors, yeast integrating plasmids, yeast episomal plasmids, yeast artificial chromosomes, human artificial chromosomes, P element vectors, baculovirus vectors, or bacterial plasmids capable of being transiently introduced into the host.

The secretion vector may also contain a polyA signal such that the polyA signal is located downstream of the gene inserted into the secretion vector.

After the gene encoding the protein for which secretion is desired is inserted into the secretion vector, the secretion vector is introduced into the host cell, tissue, or organism using calcium phosphate precipitation, DEAE-Dextran, electroporation, liposome-mediated transfection, viral particles or as naked DNA. The protein encoded by the inserted gene is then purified or enriched from the supernatant using conventional techniques such as ammonium sulfate precipitation, immunoprecipitation, immunochromatography, size exclusion chromatography, ion exchange chromatography, and HPLC. Alternatively, the secreted protein may be in a sufficiently enriched or pure state in the supernatant or growth media of the host to permit it to be used for its intended purpose without further enrichment.

The signal sequences may also be inserted into vectors designed for gene therapy. In such vectors, the signal sequence is operably linked to a promoter such that mRNA transcribed from the promoter encodes the signal peptide. A cloning site is located downstream of the signal sequence such that a gene encoding a protein whose secretion is desired may readily be inserted into the vector and fused to the signal sequence. The vector is introduced into an appropriate host cell. The protein expressed from the promoter is secreted extracellularly, thereby producing a therapeutic effect.

Cell Hosts

Another object of the invention comprises a host cell that has been transformed or transfected with one of the polynucleotides described herein, and in particular a polynucleotide either comprising a GENSET polypeptide-encoding polynucleotide regulatory sequence or the polynucleotide coding for a GENSET polypeptide. Also included are host cells that are transformed (prokaryotic cells), transfected (eukaryotic cells), or transduced with a recombinant vector such as one of those described above. However, the cell hosts of the present invention can comprise any of the polynucleotides of the present invention. Preferred host cells used as recipients for the expression vectors of the invention are the following:

a) Prokaryotic host cells: *Escherichia coli* strains (I.E.DH5-α strain), *Bacillus subtilis, Salmonella typhimurium*, and strains from species like *Pseudomonas, Streptomyces* and *Staphylococcus*.

b) Eukaryotic host cells: HeLa cells (ATCC No.CCL2; No.CCL2.1; No.CCL2.2), Cv 1 cells (ATCC No.CCL70), COS cells (ATCC No.CRL1650; No.CRL1651), Sf-9 cells (ATCC No.CRL1711), C127 cells (ATCC No. CRL-1804), 3T3 (ATCC No. CRL-6361), CHO (ATCC No. CCL-61), human kidney 293. (ATCC No. 45504; No. CRL-1573) and BHK (ECACC No. 84100501; No. 84111301).

The present invention also encompasses primary, secondary, and imnmortalized homologously recombinant host cells of vertebrate origin, preferably mammalian origin and particularly human origin, that have been engineered to: a) insert exogenous (heterologous) polynucleotides into the endogenous chromosomal DNA of a targeted gene, b) delete endogenous chromosomal DNA, and/or c) replace endogenous chromosomal DNA with exogenous polynucleotides. Insertions, deletions, and/or replacements of polynucleotide sequences may be to the coding sequences of the targeted gene and/or to regulatory regions, such as promoter and enhancer sequences, operably associated with the targeted gene.

In addition to encompassing host cells containing the vector constructs discussed herein, the invention also encompasses primary, secondary, and imnmortalized host cells of vertebrate origin, particularly mammalian origin, that have been engineered to delete or replace endogenous genetic material (e.g., coding sequence), and/or to include genetic material (e.g., heterologous polynucleotide sequences) that is operably associated with the polynucleotides of the invention, and which activates, alters, and/or amplifies endogenous polynucleotides. For example, techniques known in the art may be used to operably associate heterologous control regions (e.g., promoter and/or enhancer) and endogenous polynucleotide sequences via homologous recombination, see, e.g., U.S. Pat. No. 5,641,670, issued Jun. 24, 1997; International Publication No. WO 96/29411, published Sep. 26, 1996; International Publication No. WO 94/12650, published Aug. 4, 1994; Koller, et al., (1989); and Zijlstra, et al. (1989) (the disclosures of each of which are incorporated by reference in their entireties).

The present invention further relates to a method of making a homologously recombinant host cell in vitro or in vivo, wherein the expression of a targeted gene not normally expressed in the cell is altered. Preferably the alteration causes expression of the targeted gene under normal growth conditions or under conditions suitable for producing the polypeptide encoded by the targeted gene. The method comprises the steps of: (a) transfecting the cell in vitro or in vivo with a polynucleotide construct, said polynucleotide construct comprising; (i) a targeting sequence; (ii) a regulatory sequence and/or a coding sequence; and (iii) an unpaired splice donor site, if necessary, thereby producing a transfected cell; and (b) maintaining the transfected cell in vitro or in vivo under conditions appropriate for homologous recombination.

The present invention further relates to a method of altering the expression of a targeted gene in a cell in vitro or in vivo wherein the gene is not normally expressed in the cell, comprising the steps of: (a) transfecting the cell in vitro or in vivo with a polynucleotide construct, said polynucleotide construct comprising: (i) a targeting sequence; (ii) a regulatory, sequence and/or a coding sequence; and (iii) an unpaired splice donor site, if necessary, thereby producing a transfected cell; and (b) maintaining the transfected cell in vitro or in vivo under conditions appropriate for homologous recombination, thereby producing a homologously recombinant cell; and (c) maintaining the homologously recombinant cell in vitro or in vivo under conditions appropriate for expression of the gene.

The present invention further relates to a method of making a polypeptide of the present invention by altering the expression of a targeted endogenous gene in a cell in vitro or in vivo wherein the gene is not normally expressed in the cell, comprising the steps of: a) transfecting the cell in vitro with a polynucleotide construct, said polynucleotide construct comprising: (i) a targeting sequence; (ii) a regulatory sequence and/or a coding sequence; and (iii) an unpaired splice donor site, if necessary, thereby producing a transfected cell; (b) maintaining the transfected cell in vitro or in vivo under conditions appropriate for homologous recombination, thereby producing a homologously recombinant cell; and c) maintaining the homologously recombinant cell in vitro or in vivo under conditions appropriate for expression of the gene thereby making the polypeptide.

The present invention further relates to a polynucleotide construct which alters the expression of a targeted gene in a cell type in which the gene is not normally expressed. This occurs when the polynucleotide construct is inserted into the chromosomal DNA of the target cell, wherein said polynucleotide construct comprises: a) a targeting sequence; b) a regulatory sequence and/or coding sequence; and c) an unpaired splice-donor site, if necessary. Further included are a polynucleotide construct, as described above, wherein said polynucleotide construct further comprises a polynucleotide which encodes a polypeptide and is in-frame with the targeted endogenous gene after homologous recombination with chromosomal DNA.

The compositions may be produced, and methods performed, by techniques known in the art, such as those described in U.S. Pat. Nos. 6,054,288; 6,048,729; 6,048,724; 6,048,524; 5,994,127; 5,968,502; 5,965,125; 5,869,239; 5,817,789; 5,783,385; 5,733,761; 5,641,670; 5,580,734; International Publication NOs: WO96/29411, WO 94/12650; and scientific articles described by Koller, et al., (1994). (The disclosures of each of which are incorporated by reference in their entireties).

GENSET gene expression in mammalian cells, preferably human cells, may be rendered defective, or alternatively may be altered by replacing endogenous GENSET polypeptide-encoding genes in the genome of an animal cell by a GENSET polypeptide-encoding polynucleotide according to the invention. These genetic alterations may be generated by homologous recombination using previously described specific polynucleotide constructs.

Mammal zygotes, such as murine zygotes may be used as cell hosts. For example, murine zygotes may undergo microinjection with a purified DNA molecule of interest.

Any one of the polynucleotides of the invention, including the polypeptide constructs described herein, may be introduced in an embryonic stem (ES) cell line, preferably a mouse ES cell line. ES cell lines are derived from pluripotent, uncommitted cells of the inner cell mass of preimplantation blastocysts. Preferred ES cell lines are the following: ES-E14TG2a (ATCC No. CRL-1821), ES-D3 (ATCC No. CRL-1934 and No. CRL-11632), YS001 (ATCC No. CRL-11776), 36.5 (ATCC No. CRL-11116). ES cells are maintained in an uncommitted state by culture in the presence of growth-inhibited feeder cells which provide the appropriate signals to preserve this embryonic phenotype and serve as a matrix for ES cell adherence. Preferred feeder cells are primary embryonic fibroblasts that are established from tissue of day 13- day 14 embryos of virtually any mouse strain, that are maintained in culture, such as described by Abbondanzo et al., (1993), Meth. Enzymol., Academic Press, New York, pp 803-823 and are growth-inhibited by irradiation, such as described by Robertson, (1987), Embryo-derived stem cell lines; In: E. J. Robertson Ed. Teratocarcinomas and embryonic stem cells: a practical approach. IRL Press, Oxford, pp. 71, or by the presence of an inhibitory concentration of LIF, such as described by Pease and William, (1990), Exp. Cell. Res. 190: 209-211, which disclosures are hereby incorporated by reference in their entireties.

The constructs in the host cells can be used in a conventional manner to produce the gene product encoded by the recombinant sequence.

Transgenic Animals

The terms "transgenic animals" or "host animals" are used herein to designate animals that have their genome genetically and artificially manipulated so as to include one of the nucleic acids according to the invention. The cells affected may be somactic, germ cells, or both. Preferred animals are non-human mammals and include those belonging to a genus selected from *Mus* (e.g mice), *Rattus* (e.g. rats) and *Oryctogalus* (e.g. rabbits) which have their genome artificially and genetically altered by the insertion of a nucleic acid according to the invention. In one embodiment, the invention encompasses non-human host mammals and animals comprising a recombinant vector of the invention or a GENSET gene disrupted by homologous recombination with a knock out vector.

The transgenic animals of the invention all include within a plurality of their cells a cloned recombinant or synthetic DNA sequence, more specifically one of the purified or isolated nucleic acids comprising a GENSET polypeptide coding sequence, a GENSET polynucleotide regulatory sequence, a polynucleotide construct, or a DNA sequence encoding an antisense polynucleotide such as described in the present specification.

Generally, a transgenic animal according the present invention comprises any of the polynucleotides, the recombinant vectors and the cell hosts described in the present invention. In a first preferred embodiment, these transgenic animals may be good experimental models in order to study the diverse pathologies related to the dysregulation of the expression of a given GENSET gene, in particular the transgenic animals containing within their genome one or several copies of an inserted polynucleotide encoding a native GENSET polypeptide, or alternatively a mutant GENSET polypeptide.

In a second preferred embodiment, these transgenic animals may express a desired polypeptide of interest under the control of the regulatory polynucleotides of the GENSET gene, leading to high yields in the synthesis of this protein of interest, and eventually to tissue specific expression of the protein of interest.

The design of the transgenic animals of the invention may be made according to the conventional techniques well known from the one skilled in the art. For more details regarding the production of transgenic animals, and specifically transgenic mice, it may be referred to U.S. Pat. No. 4,873,191, issued Oct. 10, 1989; U.S. Pat. No. 5,464,764 issued Nov. 7, 1995; and U.S. Pat. No. 5,789,215, issued Aug. 4, 1998; these documents being herein incorporated by reference to disclose methods producing transgenic mice.

Transgenic animals of the present invention are produced by the application of procedures which result in an animal with a genome that has incorporated exogenous genetic material. The procedure involves obtaining the genetic material which encodes either a GENSET polypeptide coding sequence, a GENSET polynucleotide regulatory sequence, or a DNA sequence encoding a GENSET polynucleotide antisense sequence, or a portion thereof, such as described in the present specification. A recombinant polynucleotide of the invention is inserted into an embryonic or ES stem cell line. [See, e.g, Thomas, et al. (1987), Cell. 51:503-512, which disclosure is hereby incorporated by reference in its entirety.] An illustrative positive-negative selection procedure that may be used according to the invention is described by Mansour et al., (1988) Nature. 336:348-352, which disclosure is hereby incorporated by reference in its entirety.

The positive cells are then isolated, cloned and injected into 3.5 days old blastocysts from mice, such as described by Bradley (1987) [Production and analysis of chimaeric mice In: E. J. Robertson (Ed.), Teratocarcinomas and embryonic stem cells: A practical approach. IRL Press, Oxford, pp. 113)], which disclosure is hereby incorporated by reference in its entirety. The blastocysts are then inserted into a female host animal and allowed to grow to term. Alternatively, the positive ES cells are brought into contact with embryos at the 2.5 days old 8-16 cell stage (morulae) such as described by Wood, et al. (1993), Proc. Natl. Acad. Sci. USA, 90: 4582-4585, or by Nagy et al., (1993), Proc. Natl. Acad. Sci. USA 90:8424-8428, which disclosures are hereby incorporated by reference in their entireties, the ES cells being internalized to colonize extensively the blastocyst including the cells which will give rise to the germ line.

The offspring of the female host are tested to determine which animals are transgenic e.g include the inserted exogenous DNA sequence and which ones are wild type.

Thus, the present invention also concerns a transgenic animal containing a nucleic acid, a recombinant expression vector or a recombinant host cell according to the invention.

In another embodiment, transgenic animals are produced by microinjecting polynucleotides ares microinjected into a fertilized oocyte. Methods for culturing fertilized oocytes to the pre-implantation stage are described, e.g., by Gordon, et al. ((1984) Methods in Enzymology, 101, 414); Hogan, et al. [(1986) in Manipulating the mouse embryo, A Laboratory Manual. Cold Spring Harbor Laboratory Press, Cold Spring Harbor, N.Y. (for the mouse embryo)]; Hammer, et al. [(1985) Nature, 315, 680 (for rabbit and porcine embryos)]; Gandolfi, et al. [(1987) J. Reprod. Fert. 81, 23-28]; Rexroad, et al. [(1988) J. Anim. Sci. 66, 947-953) (for ovine embryos)]; and Eyestone, et al. [(1989) J. Reprod. Fert. 85, 715-720]; Camous et al. [(1984) J. Reprod. Fert. 72, 779-785]; and Heyman, et al. [(1987) Theriogenology 27, 5968 (for bovine embryos)]; the disclosures of each of which are incorporated herein in their entireties. Pre-implantation embryos are then transferred to an appropriate female by standard methods to permit the birth of a transgenic or chimeric animal, depending upon the stage of development when the transgene is introduced.

Any of a number of methods known in the art can be used to detect the presence of a transgene in a pre-implantation embryo.

In a particularly preferred embodiment of the present invention, transgenic mammals are generated that secrete recombinant GENSET polypeptides in their milk. As the mammary gland is a highly efficient protein-producing organ, such methods can be used to produce protein concentrations in the gram per liter range, and often significantly more. Preferably, expression in the mammary gland is accomplished by operably linking the polynucleotide encoding the GENSET polypeptide to a mammary gland specific promoter and, optionally, other regulatory elements. Suitable promoters and other elements include, but are not limited to, those derived from mammalian short and long WAP, alpha, beta, and kappa, casein, alpha and beta lactoglobulin, beta-CN 5' genes, as well as the mouse mammary tumor virus (MMTV) promoter. Such promoters and other elements may be derived from any mammal, including, but not limited to, cows, goats, sheep, pigs, mice, rabbits, and guinea pigs. Promoter and other regulatory sequences, vectors, and other relevant teachings are provided, e.g., by Clark (1998) J Mammary Gland Biol Neoplasia 3:337-50; Jost, et al. (1999) Nat. Biotechnol 17:160-4; U.S. Pat. Nos. 5,994, 616; 6,140,552; 6,013,857; Sohn, et al. (1999) DNA Cell Biol. 18:845-52; Kim, et al. (1999) J. Biochem. (Japan) 126:320-5; Soulier, et al. (1999) Euro. J. Biochem.260:533-9; Zhang, et al. (1997) Chin. J. Biotech. 13:271-6; Rijnkels, et al. (1998) Transgen. Res. 7:5-14; Korhonen, et al. (1997) Euro. J. Biochem. 245:482-9; Uusi-Oukari, et al. (1997) Transgen. Res. 6:75-84; Hitchin, et al. (1996) Prot. Expr. Purif. 7:247-52; Platenburg, et al. (1994) Transgen. Res. 3:99-108; Heng-Cherl, et al. (1993) Animal Biotech. 4:89-107; and Christa, et al. (2000) Euro. J. Biochem. 267:1665-71; the entire disclosure of each of which is herein incorporated by reference.

In another embodiment, the polypeptides of the invention can be produced in milk by introducing polynucleotides encoding the polypeptides into somatic cells of the mammary gland in vivo, e.g. mammary secreting epithelial cells. For example, plasmid DNA can be infused through the nipple canal, e.g. in association with DEAE-dextran (see, e.g., Hens, et al. (2000) Biochim. Biophys. Acta 1523:161-171), in association with a ligand that can lead to receptor-mediated endocytosis of the construct (see, e.g., Sobolev, et al. (1998) 273:7928-33), or in a viral vector such as a retroviral vector, e.g. the Gibbon ape leukemia virus (see, e.g., Archer, et al. (1994) PNAS 91:6840-6844). In any of these embodiments, the polynucleotide may be operably linked to a mammary gland specific promoter, as described above, or, alternatively, any strongly expressing promoter such as CMV or MoMLV LTR.

The suitability of any vector, promoter, regulatory element, etc. for use in the present invention can be assessed beforehand by transfecting cells such as mammary epithelial cells, e.g. MacT cells (bovine mammary epithelial cells) or GME cells (goat mammary epithelial cells), in vitro and assessing the efficiency of transfection and expression of the transgene in the cells.

In a preferred embodiment, a retroviral vector such as Gibbon ape leukemia viral vector is used, as described in Archer, et al. ((1994) PNAS 91:6840-6844). As retroviral infection typically requires cell division, cell division in the mammary glands can be stimulated in conjunction with the administration of the vector, e.g. using a factor such as estrodiol benzoate, progesterone, reserpine, or dexamethasone. Further, retroviral and other methods of infection can be facilitated using accessory compounds such as polybrene. Alternatively, an adenoviral or adeno-associated viral vector may be used to infect non-dividing cells as discussed herein.

In any of the herein-described methods for obtaining GENSET polypeptides from milk, the quantity of milk obtained, and thus the quantity of GENSET polypeptides produced, can be enhanced using any standard method of lacation induction, e.g. using hexestrol, estrogen, and/or progesterone.

The polynucleotides used in such embodiments can either encode a full-length GENSET protein or a GENSET fragment. Typically, the encoded polypeptide will include a signal sequence to ensure the secretion of the protein into the milk.

Recombinant Cell Lines Derived From the Transgenic Animals of the Invention:

A further object of the invention comprises recombinant host cells obtained from a transgenic animal described herein. In one embodiment the invention encompasses cells derived from non-human host mammals and animals comprising a recombinant vector of the invention or a GENSET gene disrupted by homologous recombination with a knock out vector. Recombinant cell lines may be established in vitro from cells obtained from any tissue of a transgenic animal according to the invention, for example by transfection of primary cell cultures with vectors expressing oncgenes such as SV40 large T antigen, as described by Chou, (1989), Mol. Endocrinol. 3:1511-1514, and Shay et al., (1991), Biochem. Biophys. Acta, 1072: 1-7, which disclosures are hereby incorporated by reference in their entireties.

Uses of Polypeptides of the Invention

Protein of SEQ ID NO:24 (Internal designation Clone 47-14-1-C3-CL0_5)

The cDNA of clone 47-14-1-C3-CL0_5 (SEQ ID NO:23) encodes the protein of SEQ ID NO:24, comprising the amino acid sequence: MVPFIYLQAHFTLCSG-WSSTYRDLRKGVYVPYTQGKWEGELGT-DLVSIPHGPNVTVRANI AAITESDKFFINGSNWEGIL-GLAYAEIARPDDSPEPFFDSLVKQTHVP-NLFSLQLCGAGFPL NQSEVLASVGGSMIIGGIDH-SLYTGSLWYTPIRREWYYEVIIVRVE-INGQDLKMDCKEYNY DKSIVDSGTTNLRLPKKVFEAAVKSI-KAASSTEKFPDGFWLGEQLVCWQAGTTPWNIFPVI SLYLMGEVTNQSFRITILPQQYLRPVED-VATSQDDCYKFAISQSSTGTVMGAVIMEGFYVV FDRARKRIGFAVSACHVHDEFRTAAVEG-PFVTLDMEDCGYNIPQTDESTLMTIAYVMAAI CALFMLPLCLMVCQWRCLRCLRQQHD-DFADDISLLK. Accordingly, it will be appreciated that all characteristics and uses of polypeptides of SEQ ID NO:24 described throughout the present application also pertain to the polypeptides encoded by the nucleic acids included in Clone 47-14-1-C3-CL0_5. In addition, it will be appreciated that all characteristics and uses of the polynucleotides of SEQ ID NO:23 described throughout the present application also pertain to the nucleic acids included in Clone 47-14-1-C3-CL0_5. A preferred embodiment of the invention is directed toward the compositions of SEQ ID NO:23, SEQ ID NO:24, and Clone 47-14-1-C3-CL0_5.

```
SPEPFFDSLVKQTHVPNLFSLQLCGAGFPLNQSEVLASVGGSMIIGGIDHSLYTGSLWYTPI (SEQ ID NO: 229)
RREWYYEVIIVRVEINGQDLKMDCKEYNYDKSIVDSGTTNLRLPKKVFEAAVKSIKAAS
STEKFPDGFWLGEQLVCWQAGTTPWNIFPVISLYLMGEVTNQSFRITILPQQYLRPV
EDVATSQDDCYKFAISQSSTGTVMGAVIMEGFYVVFDRARKRIGFAVSACHVHDEFR
TAAVEGPFVTLDMEDCGYNIPQTDESTLMTIAY;
DLKMDCKEYNYDKSIVDSGTTNLRLPKKVFEAAVKSIKAASSTEKFPDGFWLGEQLVCWQ (SEQ ID NO: 230)
and
AITESDKFFINGSNWEGILGLAYAEIARPDDSPEPFFDSLVKQTHVPNLFSLQLCGAGFPLN (SEQ ID NO: 231)
QSEVLASVGGSMIIGGIDHSLYTGSLWYTPIRREWYYEVIIVRVEINGQDLKMDCKEYNYD
KSIVDSGTTNLRLPKKVFEAAVKSIKAASSTEKFPDGFWLGEQLVCWQAGTTPWNIFPVIS
LYLMGEVTNQSFRITILPQQYLRPVEDVATSQDDCYKFAISQSSTGTVMGAVIMEGFYVVF
DRARKRIGFAVSACH.
```

Also preferred are polypeptide fragments having biological activity as described herein and the polynucleotides encoding the fragments.

The protein of SEQ ID NO:24 encodes amyloid processing inhibitor protein (APIP). APIP is expressed in mammalian tissues, particularly in neuronal cells, and is an incomplete aspartyl protease which is able to bind substrate but lacks catalytic activity. Examples of compounds which interact with APIP include, but are not limited to, amyloid beta precursor protein, amyloid precursor like protein-1, amyloid precursor like protein-2, Protease nexin-2, Antitrypsin protein, Kunitz protease inhibitors and amyloid like proteins.

Amyloid beta precursor protein (APP) can be processed by several types of proteases to yield fragments that are soluble or insoluble (Nunan and Small, FEBS Lett (2000) 483(1):6-10, which disclosures are hereby incorporated by reference in their entirety). Sequential cleavage of APP by beta secretase and gamma secretase yields a secreted and insoluble fibrillar amyloid protein, known as beta amyloid, which is the major component of extracellular amyloid plaques. Deposition of beta amyloid proteins form intraneuronal neurofibrillary tangles, amyloid plaques and vascular amyloid deposits characteristic of both Alzheimer's Disease and aged Down's Syndrome. Defects in processing APP can also lead to cerebral hemorrhage. Polypeptides of SEQ ID NO:24 and fragments thereof, bind to APP and other amyloid like proteins, and reduce the rate of processing of these proteins.

In a number of embodiments, APIP is used to bind to and/or inhibit any of a number of substrates in a biological sample. For example, one preferred embodiment is directed to a method of contacting compositions comprising APIP with APP. Further preferred is a method of contacting compositions comprising APIP with amyloid precursor like protein-1. (APLP1). Still further preferred is a method of contacting compositions comprising APIP with amyloid precursor like protein-2 (APLP2). Such methods are useful, e.g. to inhibit the activity of the substrate such as APP, APLP1, or APLP2, or to label the substrate, e.g. by labeling APIP and using it to specifically bind to and thus allow the visualization of the substrate or a cell or tissue expressing the substrate.

Another embodiment is directed at a method for reducing catabolism of extracellular secreted amyloid beta precursor protein (APP) which comprises contacting a mammalian cell with APIP. Preferably the said mammalian cell produces APP. The mammalian cell is preferably a neuronal cell. The mammal is preferably a rodent, canine, or primate.

Another embodiment is directed at a method for reducing catabolism of extracellular secreted APLP1 which comprises contacting a mammalian cell with APIP. Preferably the said mammalian cell produces APLP1. The mammalian cell is preferably a neuronal cell. The mammal is preferably a rodent, canine, or primate.

Another embodiment is directed at a method for reducing catabolism of extracellular secreted APLP2 which comprises contacting a mammalian cell with APIP. Preferably the said mammalian cell produces APLP2. The mammalian cell is preferably a neuronal cell. The mammal is preferably a rodent, canine, or primate.

Amyloid plaques in the brain contribute to disruption of neuronal conductivity which leads to disturbances in behavior, perception, memory and mood. Another preferred embodiment of the invention is directed to a method of preventing or alleviate mood disorders by contacting compositions comprising APIP neuronal cells. Further preferred is a method to prevent or alleviate schizophrenia by contacting compositions comprising APIP with neuronal cells. Still further preferred is a method to prevent or alleviate Alzheimer's disease by contacting compositions comprising APIP with neuronal cells.

Amyloidosis also occurs in the pancreas and may contribute to the development of glucose intolerance, insulin insufficiency, or diabetes. A preferred embodiment is directed to a method of preventing of alleviating glucose intolerance by contacting compositions comprising APIP with pancreatic cells. Further preferred is a method to prevent or alleviate insulin insufficiency by contacting compositions comprising APIP with pancreatic cells. Still further preferred is a method to prevent or alleviate diabetes by contacting compositions comprising APIP with pancreatic cells.

It should be appreciated that preferred compositions of the invention to be used in methods of the invention described for clone 47-14-1-C3-CL0_5 of SEQ ID NO:23 include polypeptides of SEQ ID NO:24 (APIP), and fragments thereof, and compositions comprising the polypeptides of SEQ ID NO:24, and fragments thereof.

Protein of SEQ ID NO:28 (Internal Designation Clone 117401_106-006-4-0-B11-F)

The cDNA of clone 117401_106-006-4-0-B11-F (SEQ ID NO:27) encodes the protein of SEQ ID NO:28. Accordingly, it will be appreciated that all characteristics and uses of polypeptides of SEQ ID NO:28 described throughout the present application also pertain to the polypeptides encoded by the nucleic acids included in Clone 117401_106-006-4-0-B11-F. In addition, it will be appreciated that all characteristics and uses of the polynucleotides of SEQ ID NO:27 described throughout the present application also pertain to the nucleic acids included in Clone 117401_106-006-4-0B11-F. Also preferred are polypeptide fragments having a biological activity as described herein and the polynucleotides encoding the fragments. The gene for the protein of SEQ ID NO:28 is located on chromosome 8.

The protein of SEQ ID NO:28 is referred to herein as Frangiopogen. Frangiopogen is highly expressed in human fetal liver and lung. It stimulates liver regeneration, has mitogenic activity and is actively involved in embryonic development. Frangiopogen is involved in complex regulatory processes including cell proliferation and angiogenesis.

In a preferred embodiment of the invention, Frangiopogen is used in tissue treatment compositions to promote wound healing, preferably after injury, such as ischemia, or after surgery, including general surgery, ear-, nose- and throat surgery, tissue transplantation, dermal or dental or artificial joint transplants, or plastic surgery. Further preferred are uses for Frangiopogen in tissue treatment compositions for tissue regeneration.

Preferred tissue treatment compositions of the present invention include physiologically acceptable formulations comprising the protein of SEQ ID NO:28. Further preferred are physiologically acceptable formulations comprising the protein of SEQ ID NO:28 in combination with an additional compound such as any or all of the compounds selected from the group consisting of fibrin, fibrinogen, thrombin, factor XII, calcium chloride, a plasminogen activator, a plasmin inhibitor (such as aprotin), a growth factor, and a polysaccharide such as hyaluronic acid.

Still further preferred are formulations comprising the protein of SEQ ID NO:28 alone or in compositions, e.g. as described in U.S. Pat. Nos. 6,083,902 and 5,631,011, herein incorporated by reference in their entireties.

In further embodiments, the tissue treatment compositions of the invention are used in methods of treating injuries comprising the step of contacting a wound or injured tissue with a healing or regenerative effective amount (an amount that would increase the rate or progression of healing or regeneration as compared to the same wound or injured tissue not treated with a composition of the present invention) of a Frangiopogen polypeptide. Further embodiments include use of the tissue treatment compositions of the invention for topical application to a site of injury. (e.g. as defined as a site in which the integument is damaged in such a way as to expose the. dermis), following an accident or following surgery comprising the step of contacting the injured tissue with a healing or regenerative effective amount of a Frangiopogen polypeptide. In still further embodiments, the tissue treatment compositions of the invention, alone or in combination with chondrocytes such as embryonic chondrocytes, are used in methods to treat joint cartilage and bone defect repair.

The present invention provides for methods of stimulating proliferation of endothelial cells comprising the step of contacting endothelial cells with a proliferative effective amount of a Frangiopogen polypeptide of the present invention. Preferably the endothelial cells are vascular endothelial cells, arterial or venous. Further preferably, the method results in angiogenesis or the process of vascularzation of a tissue involving the development of new capillary blood vessels. Preferably, angiogenesis occurs in a mammal, more preferably the mammal is a dog, cat, horse, cow, pig or human.

In addition, the present invention provides for an antibody that specifically binds a Frangiopogen polypeptide of the present invention. The antibody, may be monoclonal or polyclonal. The invention also provides for a method of inhibiting the growth of endothelial cells. comprising the step of contacting a biological sample comprising endothelial cells with a growth inhibiting effective amount of an anti-Frangiopogen antibody. Preferably, the endothelial cells are vascular endothelial cells, arterial or venous. Further preferably, the methods results in the inhibition of angiogenesis or blood vessel growth. Further preferably, the inhibition of angiogenesis occurs in a mammal, more preferably the mammal is a dog, cat, horse, cow, pig or human.

Alternatively, the invention provides for a Frangiopogen polypeptide-cytotoxic agent conjugate, whereby the cytotoxic agent is covalently or noncovalently, recombinantly or nonrecombinantly, attached or conjugated to a Frangiopogen polypeptide using cytotoxic agents and methods well known in the art. The invention also provides for a method of inhibiting the growth of endothelial cells comprising the step of contacting a biological sample comprising endothelial cells or an individual with a growth inhibiting or endothelial cell killing effective amount of a Frangiopogen-cytotoxic agent conjugate. Preferably, the endothelial cells are vascular endothelial cells. Further preferably, the methods results in the inhibition of angiogenesis or blood vessel growth. Further preferably, the inhibition of angiogenesis occurs in a mammal, more preferably the mammal is a dog, cat, horse, cow, pig or human. To examine whether a particular anti-Frangiopogen antibody or a Frangiopogen-cytotoxic agent conjugate is useful to disrupt vascular growth or angiogenesis, models well known in the art may be sued, e.g., the chick chorioallantoic membrane assay.

```
MRLRAQVRLLETRVKQQQVKIKQLLQENEVQFLDKGDENTVVDLGSKRQYADCSEIFN     (SEQ ID NO: 28)

DGYKLSGFYKIKPLQSPAEFSVYCDMSDGGGWTVIQRRSDGSENFNRGWKDYENGFGX

FVQKHGEYWLGNKNLHFLTTQEDYTLKIDLADFEKNSRYAQYKNFKVGDEKNFYELNI

GEYSGTAGDSLAGNFHPEVQWWASHQRMKFSTWDRDHDNYEGNCAEEDQSGWWFN

RCHXANLNGVYYSGPYTAKTDNGIVWYTWHGWWYSLKSVVMKIRPNDFIPNVI;
```

-continued a polypeptide comprising the amino acid sequence of:
MAKVFSFILVTTALIMGREISALEDCAQEQMRLRAQVRLLETRVKQQQVKIKQLLQENE (SEQ ID NO: 113)

VQFLDKGDEDTVVDLGSKRQYADCSEIFNDGYKLSGFYKIKPLQSPAEFSVYCDMSDGG

GWTVIQRRSDGSENFNRGWKDYENGFGNFVQKHGEYWLGNKNLHFLTTQEDYTLKIDL

ADFEKNSRYAQYKNFKVGDEKNFYELNIGEYSGTAGDSLAGNFHPEVQWWASHQRMK

FSTWDRDHDNYEGNCAEEDQSGWWFNRCHSANLNGVYYSGPYTAKTDNGIVWYTWH

GWWYSLKSVVMKIRPNDFIPNYI;

a polypeptide comprising the amino acid sequence of:
SPISNCEITITDPGKFYNSNSVFSRGNMAKVFSFILVTTALXMGREISALEDCAQEQMRLR (SEQ ID NO: 114)

AQVRLLETRVKQQQVKIKQLLQENEVQFLDKGDENTVVDLGSKRQYADCSEIFNDGYK

LSGFYKIKPLQSPAEFSVYCDMSDGGGWTVIQRRSDGSENFNRGWDYENGFGNFVQKH

GEYWLGNKNLHFLTTQEDYTLKIDLADFEKNSRYAQYKNFKVGDEKNFYELNIGEYSGT

AGDSLAGNFHPEVQWWASHQRMK FSTWDRDHDNYEGNCAEEDQSGWWFNRCHSA

NLNGVYYSGPYTAKTDNGIVWYTWHGWWY SLKSVVMKIR PNDFIPNVI;

a polypeptide comprising the amino acid sequence of:
MAKVFSFILVTTALIMGREISALEDCAQEQMRLRAQVRLLETRVKQQQVKIKQLLQENE (SEQ ID NO: 115)

VAQFLDKGDENTVVDLGSKRQYADCSEIFNDGYKLSGFYKIKPLQSPAEFSVYCDMSDGG

GWTVIQRRSDGSENFNRGWKDYENGFGNFVQKHGEYWLGNKNLHFLTTQEDYTLKIDL

ADFEKNSRYAQYKNFKVGDEKNFYELNIGEYSGTAGDSLAGNFHPEVQWWASHQRMK

FSTWDRDHDNYEGNCAEEDQSGWWFNRCHSANLNGVYYSGPYTAKTDNGIVWYTWH

GWWYSLKSVVMKIRPNDFIPNVI;

and a polypeptide comprising the amino acid sequence of:
MKLANWYWLSSAVLATYGFLVVANNETEEIKDERAKDVCPVRLESRGKCEEAGECPYQ (SEQ ID NO: 227)

VSLPPLTIQLPKQFSRIEEVFKEVQNLKEIVNSLKKSCQDCKLQADDNGDPGRNGLLLPST

GAPGEVGDNRVRELESEVNKLSSELKNAKEEINVLHGRLEKLNLVNMNNIENYVDSKVA

NLTFVVNSLDGKCSKCPSQEQIQSRPVQHLIYKDCSDYYAIGKRSSETYRVTPDPKNSSFE

VYCDMETMGGGWTVLQARLDGSTNFTRTWQDYKAGFGNLRREFWLGNDKIHLLTKSK

EMILRIDLEDFNGVELYALYDQFYVANEFLKYRLHVGNYNGTAGDALRFNKHYNHDLK

FFTTPDKDNDRYPSGNCGLYYSSGWWFDACLSANLNGKYYHQKYRGVRNGIFWGTWP

GVSEAHPGGYKSSFKEAKMMIRPKHFKP.

Proteins of SEQ ID NO:10 (Internal Designation Clone 147103__106-024-1-0-H6-F), SEQ ID NO:12 (Internal designation Clone 224168__116-096-3-0G11-F), SEQ ID NO:16 (Internal designation Clone 225432__116-083-3-0-C6-F), and SEQ ID NO:14 (Internal designation Clone 243303__116-118-4-0-A3-F)

The polynucleotides of SEQ ID NOs:9, 11, 13 and 15 and the polypeptides of SEQ ID NOs:10, 12, 14, and 16, respectively, encode the soluble Low density lipoprotein receptor- Related Protein- 10 (sLRP 10)

MSASCCLSWCPAKAKSKCGPTFFPCAS-GIHCIIGRFRCNGFEDCPDGSDEENCTANPLLCS TARYHCKNGLCIDKSFICDGQNNCQDNS-DEESCESSQAIFPQITVS (SEQ ID NO:116). Preferred polynucleotides and polypeptides of the invention comprise the nucleic acid sequences of SEQ ID NOs:9, 11, 13, and 15 and amino acid sequences of SEQ ID NOs:10, 12, 14, and 16. It will be appreciated that all characteristics and uses of the polynucleotides of SEQ ID NOs:9, 11, 13, and 15 and polypeptides of SEQ ID NOs:10, 12, 14, and 16 described throughout the present application also pertain to the human cDNAs of Clones 147103__106-024-1-0-H6-F, 224168__116-096-3-0-G11-F, 243303__116-1 18-4-0-A3-F, and 225432__116-083-3-C6-F, and the polypeptides encoded thereby. Preferred compositions of the invention include polynucleotides and polypeptides of Clones 147103__106-024-1-0-H6-F, 224168116-096-3-0-G11-F, 243303__116-118-4-0-A3-F, and 225432116-083-3-0-C6-F; SEQ ID NOs: 9, 11, 13, and 15; SEQ ID NOs:10, 12, 14, and 16. Also preferred are polypeptide fragments having a biological activity as described herein and the polynucleotides encoding the fragments.

sLRP10 is a non-membrane, soluble member of the Low Density Lipoprotein Receptor (LDLR) family. This family is characterized by the presence of a number of conserved, cysteine-rich LDLR domains. This domain folds to form a defined ligand-binding structure. Most members of the LDLR family are transmembrane proteins that function in clathrin-mediated endocytosis of various ligands. These ligands are usually then destroyed by lysosomal degradation. However, shorter, secreted family members have been described (U.S. Pat. No. 5,496,926 and Quinn, K. et al., Exp. Cell Res. 251:43341(1999) which disclosures are hereby incorporated by reference in their entirety). The LDLR family of proteins is capable of binding a variety of protein and lipoprotein ligands. Furthermore, certain viruses target the LDLR domain to gain entry to cells expressing LDLR family members. LDLR proteins are expressed on a variety of cell types including hepatocytes, neurons, fibroblasts, epithelial, adipose, muscle, and pancreatic cells.

High levels of Low Density. Lipoprotein (LDL), Very. Low Density Lipoprotein (VLDL), chylomicrons, and Apolipoprotein E (ApoE) are associated with atherosclerosis and other cholesterol-associated disorders. These molecules are subjects of intense study in the medical field. As a preferred embodiment, sLRP10 is used to bind LDL, VLDL, chylomicrons, and ApoE. While many members of the LDLR family, such as LDLR andalpha-2-macroglobulin receptor, are very large (>400 kD) membrane spanning proteins, sLRP10 is relatively small and not membrane associated. Thus, sLRP10 is an easily purified polypeptide that can be used for binding LDLR domain ligands. As a part of this embodiment, sLRP 10 polypeptide is covalently or non-covalently attached to a solid matrix and allowed to bind LDL, VLDL, chylomicrons, or. ApoE in solution using techniques well known in the art. Once bound, these proteins can be purified using the following steps: i) wash the solid matrix to get rid of contaminants, ii) elute the protein of interest using more stringent conditions, e.g., increasing salt concentration.

Additional aspects of this embodiment include methods of detecting and quantifying LDL, VLDL, chylomicrons, or ApoE. bound to sLRP10 using techniques common in the art (e.g., Western blotting, ELISA, or use of a labeled secondary detection method) comprising the steps of obtaining a biological sample suspected of containing LDL, VLDL, chylomicrons, or ApoE; contacting said sample with an LDL, VLDL, chylomicrons, or ApoE binding sLRP10 polypeptide of the present invention under conditions suitable for binding of sLRP10 to LDL, VLDL, or ApoE; detecting the presence or absence of LDL, VLDL, or ApoE by detecting the presence or absence of sLRP10 bound to LDL, VLDL, or ApoE. This embodiment is useful, for example, as a diagnostic tool for detecting plasma levels of these proteins.

In another embodiment of the invention, the sLRP10 polypeptide is used to bind LDL, VLDL, chylomicrons, and ApoE in vivo and remove these molecules from the bloodstream. In this embodiment, the sLRP10 polypeptide may further be expressed as a fusion protein with a polypeptide signal specifying excretion from the body. The invention is delivered to individuals at risk of atherosclerosis or arterial lipoprotein deposits of LDL, VLDL, chylomicrons, or ApoE as determined by common medical techniques including those described in U.S. Pat. No. 5,652,224, incorporated herein by reference in its entirety, and comprising the steps of i) determining the familial predisposition of the individual for these disorders, ii) obtaining a biological sample from the individual, and iii) subjecting that sample to analysis for lipoprotein content Delivery includes administering an appropriate amount of sLRP10 polypeptide to the bloodstream of the diagnosed individual, e.g., by injection.

ApoE is also associated with the, pathogenesis of diabetes. Abnormally high levels of ApoE are linked to amyloid plaques and destruction of pancreatic P-cells. Furthermore, ApoE has antioxidant activity (Miyata and Smith, Nature Genet. 14:55-61. (1996) which disclosures are hereby incorporated by reference in their entirety) and oxidative damage destroys P-cells in type 1 diabetes (Bach J., Endocrin. Rev. 15:516-542 (1994) and PCT application WO9846743, incorporated herein by reference in its entirety). This embodiment of the invention could further be delivered to patients suffering from or at risk of diabetes to reduce levels of pancreatic. ApoE. In this embodiment, the sLRP10 polypeptide may further be expressed as a fusion protein with a polypeptide signal specifying excretion from the body. An appropriate dosage of sLRP10 may be delivered specifically to the bloodstream, by injection for example, or to pancreatic cells using methods known in the art including those described in U.S. Pat. No. 5,652,224, incorporated herein by reference in its entirety. These include steps comprising i) construction of a recombinant viral vector comprising the DNA of, or corresponding to, a portion of the genome of an adenovirus, which portion is capable of infecting a pancreatic cell, operatively linked to the nucleotide sequence of the invention and the regulatory sequences directing its expression; ii) delivery of an effective amount of the recombinant adenoviral vector to an individual at risk for diabetes.

The polypeptide sLRP10 invention can bind ApoE as well as the amyloid precursor protein (APP), both of which are associated with the pathogenesis of Alzheimer's disease (Kounnas, M. Z., et al., Cell 82:331-40. (1995) which disclosures are hereby incorporated by reference in their. entirety). As a further embodiment of the invention, sLRP10 polypeptide is used to bind these proteins in neuronal cell populations to allow study of Alzheimer's pathogenesis. In particular, the invention is directly added to a population of neurons to block ApoE activity and study the formation of amyloid plaques.

sLRP10 is also able to, bind the protooncogene Wnt-1. (Tamai, K., et al., Nature 407:530-35 (2000) which disclosures are hereby incorporated by reference in their entirety); Wnt-1 usually functions as a soluble growth factor that binds to Frizzled receptors but Wnt-1 has also been associated with transformation of cells (van Ooyen, A., Cell 39:233-40 (1984) which disclosures are hereby incorporated by reference in their entirety). Additionally, Wnt-1 has been associated with schizophrenia (Shackleford, G., et al., Neuron 11:865-75. (1993) which disclosures are hereby incorporated by reference in their entirety), making this protein of particular interest to the biomedical community. Another embodiment of the sLRP10 polypeptide invention provides a method to study Wnt-1 and its effects using techniques common to the art. This embodiment provides a method of purifying Wnt-1 protein from a biological solution using steps comprising:

i) attaching sLRP10, to a solid matrix; ii) applying a solution containing Wnt-1; iii) allowing Wnt-1 to bind to sLRP10; iv) washing and eluting Wnt-1. Purifying Wnt-1 is useful for a number of applications, for example to use purified Wnt-1 as a growth factor to administer to cells, to, generate antibodies against Wnt-1, and others. Additionally, this embodiment of the sLRP10 polypeptide is used to bind Wnt-1 in solution and prevent its association with Frizzled receptors, thereby preventing molecular signaling events leading to cell growth, proliferation, and/or transformation.

sLRP10 binds to viruses comprising the Rous sarcoma, Flaviviridae (including hepatitis C), and Rhinovirus (including those responsible for the "common cold") families (Bates, P., et al., Cell 93:1043-51 (1993), Agnello, V., et al., PNAS 96:12766-71 (1999), Hofer, F., et al., PNAS 91:1839-42 (1994) which disclosures are hereby incorporated by reference in their entirety). As a preferred embodiment of the invention, the sLRP10 polypeptide is used to bind viruses in solution. This embodiment can be used to detect and quantify virus by techniques common to the art (e.g., fluorescent labeling of sLRP 10) comprising steps of obtaining a biological sample suspected of containing virus from at least one of the Rous sarcoma, Flaviviridae, or Rhinovirus families; contacting said sample with labeled or otherwise detectable sLRP10 polypeptide; and detecting and quantifying virus by visualizing the labeled sLRP10.

Membrane spanning LDLR family members are targeted by viruses of the Rous sarcoma, Flaviviridae, and Rhinovirus families for entry into cells. However, as sLRP10 is not associated with the cellular membrane, it acts to block viral binding to LDLR proteins on the cells that express these receptors, thereby preventing infection of those cells. As a preferred embodiment of the invention, the sLRP10 protein is used to bind virus and prevent infection of LDLR family-expressing cells using methods known in the art including U.S. Pat. No. 5,496,926, incorporated herein by reference in its entirety. This embodiment may be carried out by steps comprising:

i) adding the sLPR10 polypeptide directly to cells, e.g. cells that express an LDLR family receptor, that may be exposed to a viral sample and ii) preventing the infection of said cells by viruses of the Rous sarcoma, Flaviviridae, and Rhinovirus families.

Protein of SEQ ED NO:20 (Internal Designation Clone 158523_106-036-2-0-A3-F)

The cDNA of Clone 158523_106-030-2-0-A3-F (SEQ ID NO:19) encodes the OsteoAngioRemodeling (OAR) protein comprising the amino acid sequence MRAWIFFLLCLAGRALAAPQQEALPDETEVVEETVAEVTEVSVGANPVQVEVGEFDDG AEETEEEVVAENPCQNHHCKHGKVCELDENNTPMCVCQDPTSCPAPIGEFEKVCSNDNKTFDSSCHFFATKCTLEGTKKGHKLHLDYIGPCKYIPPCLDSELTEFPLRMRDWLKNVLVTLYERDEDNNLLTEKQKLRVKKIIIENEKRLEAGDHPVELLARDCQAVSARKAKIKSEM (SEQ ID NO:20). Accordingly, it will be appreciated that all characteristics and uses of the polypeptides of SEQ ID NO:20 described throughout the present application also pertain to the polypeptides encoded by the nucleic acids included in Clone 158523_106-030-2-0-A3-F. In addition, it will be appreciated that all characteristics and uses of the polynucleotides of SEQ ID NO: 19 described throughout the present application also pertain to the nucleic acids included in Clone 158523_106-030-2-0-A3-F. A preferred embodiment of the invention is directed toward the compositions comprising SEQ ID NO:19, SEQ ID NO:20, or Clone 158523_106-030-2-0-A3-F. Also preferred are polypeptide fragments having a biological activity as described herein and the polynucleotides encoding the fragments. Another preferred embodiment of the invention is directed toward compositions comprising polypeptide fragments of at least six amino acids within SEQ ID NO:20: LLARDCQAVSARK (SEQ ID NO:117), including those having a biological activity described herein, and the corresponding polynucleotides. Preferred polypeptides of the present invention include polypeptide fragments of SEQ ID NO:20 comprising KKIHENEKRLEAGDHPVELLARDCQAVSARKAKIKSEM (SEQ ID NO:118) and the corresponding polynucleotides. Further preferred polypeptides of the present invention include polypeptide fragments of SEQ ID NO:20 comprising DYIGPCKYIPPCLDSELTEFPLRMRDWLKNVLVTLYERDEDNNLLTEKQKLRVKKIHENE KRLEAGDHPVELLARDCQAVSARKAKJKSEM (SEQ ID NO:119) and the corresponding polynucleotides. Polypeptide fragments of SEQ ID NO:20 having a biological activity of those described herein and polynucleotides encoding the same are also included in the invention. Biological activities include increasing bone density when contacted with osteoblasts, tissue remodeling, and wound healing.

The polypeptides of the OsteoAngioRemodeling (OAR) protein of SEQ ID NO:20 encode a carboxy-terminal variant of the human Osteonectin (also SPARC/BM40) protein. OAR is encoded by the polynucleotides of SEQ ID NO:19 and represents an alternative splice variant of the full-length Osteonectin cDNA. This splice variant is characterized by the presence of an alternative carboxy-terminal 15 amino acids starting at residue 219 of the 303-amino acid Osteonectin protein.

OAR, like Osteonectin, is a non-collagenous, extracellular matrix-associated protein. Expression is found in a number of cell types that include osteoblasts, platelets, and vascular, epithelia, and is upregulated in sites of proliferation and extracellular matrix (ECM) remodeling. OAR is a modular protein whose domains mediate structure and protein-protein interactions. OAR lacks domain IV of full-length Osteonectin, which contains one of two EF-hand motifs. OAR binds molecules such as collagen, PDGF, and FGF. Collagen type binding specificity is in part determined by differential N-glycosylation of amino acids 71 and 99. This level of regulation is tissue-specific, so that OAR from the bone binds collagens. I, III, and V, yolk sac-derived OAR binds only III and V, and platelet-derived OAR does not bind collagen at all. Furthermore, binding decreases in low pH conditions. OAR plays a role in regulating cell mobility, proliferation, bone and tissue remodeling, and metalloproteinase production. OAR is involved in osteoporosis, osteoarthritis, atherosclerosis, angiogenesis, obesity, and metastatic tumors.

OAR is associated with increased bone density and remodeling. OAR is also associated with metalloproteinase production, which is vital for bone remodeling. As a preferred embodiment, the OAR polypeptide of the invention is used to increase the activity of osteoblasts using methods common to the art, for example, by adding a osteoblast-stimulating amount of OAR to increase bone production to a culture of osteoblastic cells. This embodiment is applied to increase the productivity of osteoblasts for purposes comprising study or replacement therapy. As a further embodiment, OAR is used in methods of bone remodeling such as those described in Gerber, H., et al. (1999) Nat. Med. 5:623-8, which disclosures are hereby incorporated by reference in their entirety. For example, OAR is used in a method to promote osteoblast differentiation and bone remodeling by inducing metalloproteinase or osteocalcin production by contacting OAR with osteoblastic cells in culture. Furthermore, OAR is used in a method to promote in vivo osteoblast differentiation by contacting OAR with an area of potential bone growth, for instance, in the growth plate of the femur or in the hip which is often the site, of fracture. An effective amount of OAR is delivered to the site by injection or other methods common to the art and effectiveness determined using any suitable method such as X-rays, or methods described in Delany, A., et al. (2000) J. Clin. Invest. 105:915-23, which disclosure is hereby incorporated by reference in its entirety.

Cells derived from certain tissues adhere to specific collagens. OAR binds collagen types I, II, and V which are found, for example, in epithelia and bone tissue. This allows OAR to act as an anti-adhesion factor by inhibiting normal interaction of collagen in the ECM to cell surface adhesion molecules. This activity is associated with cell migration and differentiation. Furthermore, OAR is associated with increased metalloproteinase expression, which leads to ECM degradation and tissue remodeling. Thus, a preferred embodiment of the invention is directed to a method of using OAR in tissue remodeling, whereby contacting OAR with osteoblasts to inhibit binding of collagen to cells allows tissue remodeling. Further preferred is a method to use OAR in wound healing (e.g., from surgical damage or chronic conditions such as diabetic ulcers), tissue grafts, necrotic or hypoxic tissue in ECM environments comprising collagen types I, III, and V that bind OAR. A method to treat these conditions includes steps comprising: i) identifying the ECM of the tissue in need of repair as one that binds OAR using methods common in the art (e.g., applying fluorescently-labeled OAR to an ECM sample and visualizing by microscopy); ii) localizing an effective amount of OAR to the wound area either directly or by injection; iii) allowing ECM remodeling to occur as OAR inhibits cell adhesion.

Osteonectin binds to VEGF, which regulates blood vessel formation. This interaction prevents VEGF binding to its receptor. The OAR polypeptide lacks a VEGF-binding domain while it retains its ability to bind the ECM and affect remodeling (Kupprion, C., et al. (1998) J. Biol. Chem. 273:29635-40 which disclosure is hereby incorporated by reference in its entirety). In a preferred embodiment of the invention, OAR polypeptide is used to replace Osteonectin in conditions that require VEGF activity in addition to the ECM interactions that mediate wound healing and tissue remodeling. This is accomplished in steps comprising: i) obtaining a cell or tissue sample in culture that contains at least VEGF and VEGF-responsive cells; ii) adding OAR to the culture in an amount effective for ECM binding, iii) allowing OAR to enable ECM remodeling as well as VEGF signaling to aid in angiogenesis and tissue healing. In addition, expression of Osteonectin may be inhibited by introducing IL-1 to the affected area and as described in Nakamura, S., et al. (1996) Arthritis Rheum 39:539-51, which disclosure is hereby incorporated by reference in its entirety. As a further embodiment, the invention is applied to the growth and healing of necrotic or hypoxic tissue, tissue grafts, and bone-associated tissue. The OAR polypeptide is delivered to these tissues using methods common to the art such as injection or use of OAR polypeptide fused to a targeting molecule specific for the tissue of interest.

In the extreme, decreased "contact inhibition" from the ECM to the cell surface is linked to tumor formation and metastasis. As OAR inhibits contact of cells to specific types of collagen in the ECM, OAR is involved in metastasis of a number of tumor cell types including breast and prostate carcinomas. In a preferred embodiment of the invention, the OAR polypeptide is used to develop inhibitors of its collagen-binding activity to prevent ECM invasion. This invasion includes the proliferation of cells into inappropriate tissues, such as that observed in rheumatoid arthritis and cancers including breast and prostate carcinomas. Inhibitors of OAR are comprised of antibodies raised against the carboxy-terminal 15 amino acids of the OAR polypeptide and small molecules that interfere with OAR collagen binding activity. OAR binding to ECM environments is determined using methods common to the art such as applying fluorescently-labeled OAR to a tissue sample and visualizing by microscopy. Effectiveness of OAR inhibitors is determined using the aforementioned method or by observing cell invasion of the ECM as described by Kato, Y., et al. (1998-99). Invasion Metastasis 18:105-147, which disclosure is hereby incorporated by reference in its entirety. An example use of this embodiment would include methods comprising the steps: i) purifying the OAR inhibitor such as an antibody using methods common in the art (e.g.—affinity chromatography); ii) determining a site of inappropriate ECM invasion using methods common to the art such as tissue imaging, X-ray, or palpation, ii) localizing an effective amount of OAR inhibitor to the site to allow cell surface-collagen interactions and prevent FCM invasion. Localization of the OAR inhibitor is effected using methods common in the art such as injection. Further included in the invention is a method for delivering the OAR polypeptide fused to a targeting molecule specific for the tissue of interest.

OAR binds to growth factors including PDGF, which can induce cell migration and proliferation, and inhibits binding of the growth factor to its receptor under certain conditions. As a preferred embodiment of the invention, the OAR polypeptide is used to inhibit signaling through growth factor receptors such as the PDGF receptor. This embodiment is useful in preventing inappropriate growth of PDGF-responsive cells, such as dermal fibroblasts (e.g., in the case of hypertrophic scars) and platelets (e.g., in cases of malignant lyrnphomas). This embodiment is carried out, for instance to reduce the volume of a hypertrophic scar, by identifying a region with excess scar tissue using methods described by Nedelec, B., et al. (2000). J. Burn Care Rehabil. 21:205-12, which disclosure is hereby incorporated by reference in its entirety; administering an effective amount of OAR to the scar directly or by injection; and monitoring the scar using aforementioned method or others common to the art.

Protein of SEQ ID NO:30 (Internal Designation Clone 133431_105-092-4-0-G11-F)

The cDNA of clone 133431_105-092-4-0-G11-F (SEQ ID NO:29) encodes a variant of the ALEX-1 protein with the amino acid sequence MGRTREAGCVAAGVVIGAGACYCVYRLAWGRDENEKIWDEDEESTDTSXJGVETVKGAKTNAGAGSGAKLQGDSEVKPEVSLGLEDCPGVKEKAHSGSHSGGGLEAKAKAFNTLKEQASAKAGKGARVGTISGNRTLAPSLPCPGGRGGGCHPTRSGSRAGGRASGKSKGKARSKSTRAPATTWPVRRGKFNFYKIDDILSAPDLQKVLNILERTNDPFIQEVALVILGNNAAYSF NQNAIRELGGVPIIAKK (SEQ ID NO:30). It will be appreciated that all characteristics and uses of polypeptides of SEQ ID NO:30 described throughout the present application also pertain to the polypeptides encoded by the nucleic acids included in Clone 133431_105-092-4-0-G11-F. In addition, it will be appreciated that all characteristics and uses of the polynucleotides of SEQ ID NO:29 described throughout the present application also pertain to the nucleic acids included in Clone 133431_105-092-4-0-G11-F. A preferred embodiment of the invention is directed toward the compositions of SEQ ID NO:29, SEQ ID NO:30, and Clone 133431_105-092-4-0-G11-F. Also preferred are polypeptide fragments having a biological activity as described herein and the polynucleotides encoding the fragments. The gene of SEQ ID NO:29 is located on the X-chromosome. It encodes a new armadillo repeat protein with a death effector domain and is involved in cell-cell adhesion, cell signaling and apostolic processes and is hereby referred to as Armapoptin.

Armapoptin promotes cell growth and differentiation during embryonic development. It is part of multi-protein complexes, which mediate cell-cell adhesion, anchorage to the actin cytoskeleton with adjacent cells, and a signal in response to cell adhesion to initiate cell polarity and the formation of epithelia. Armapoptin complexes, which include E-Catherine and different Catherine-binding proteins including β-catenin can also be associated with a tumor suppressor protein such as Adenomatous *Polyposis Coli* (APC), which is mutated in hereditary colon cancer. Cell-cell adhesion in normal differentiation processes and malignant proliferation is mediated by the armadillo domain serving as a scaffold for the assembly of multi-protein complexes.

The N-terminal region of Armapoptin contains a death effector domain (DED) comprising residues RLAWGRDENEKIWDEDEES. Death effector domains are involved in caspase-dependent apostolic processes. Armapoptin is expressed in most tissues, but is not expressed or significantly underexpressed in breast carcinoma biopsies of patients as well as in epithelial based-tumor cell lines including ovarian carcinoma, cervix adenocarcinoma cells, lung carcinomas, and immortalized endothelial cell lines such as t-HUE2.

In an embodiment, Armapoptin polynucleotides are used in a method of gene therapies to restore cell-cell adhesion and to promote caspase-dependent apoptosis, preferably in epithelial cell-based tumors including breast carcinoma, ovarian carcinoma, lung carcinoma, non-small cell lung carcinoma (NSCLC), and squamous cell carcinoma of head and neck (SCCHN). Preferred compositions of Armapoptin to be used in methods of gene therapy, further referred to as "gene therapy compositions of Armapoptin" are compositions comprising the full-length DNA, SEQ ID NO:29, or fragments thereof, encoding a polypeptide or fragments thereof, including the sequences

```
aatcctagtcttcgtttggtccggttgcactcttcctatagcccagagggc
gagagggcctgtggcctgggggaaggaggacgaggttctgcctggatccca
gcaggacgctgtgccatttgggaacaaaggaatagtctgcctggaatccct
gcagatcttggggccggaggccagtccaacccttggagcaggaagaaacgc
aaagttgtcaagaaccaagtcgagctgcctcagagccggcccgcagtagct
gcagactccgcccgcgacgtgtgcgcgcttctctgggccagagcgagcctg
ttttgtgctcgggttaagagatttgtcccagctataccgcgtggccgctgg
tgtggttatcggggctggtgcctgctactgtgtatacagactggcttgggg
aagagacgagaacgagaaaatctgggacgaagacgaggagtctacggacac
ctcakagattggggttgagactgtgaaaggagctaaaactaacgctggggc
agggtctggggccaaacttcagggtgattcagaggtcaagcctgaggtgag
tttgggactcgaggattgtccgggtgtaaaagagaaggcccattcaggatc
ccacagcggaggtggcctagaggccaaggccaaggcccttttcaacacgct
gaaggaacaggcaagtgcaaaggcaggcaaaggggctagggtgggtaccat
ctctgggaacaggacccttgcaccgagtttaccctgcccaggaggcagggg
tggaggctgccaccccaccaggagtggatctagggccgggggcagggcaag
```

-continued

```
tggaaaatccaagggaaaggcccgaagtaagagcaccagggctccagctac
aacatggcctgtccggagaggcaagttcaactttccttataaaattgatga
tattctgagtgctcccgacctccaaaaggtcctcaacatcctggagcgaac
aaatgatccttttattcaagaagtagccttggtcactctgggtaacaatgc
agcatattcatttaaccagaatgccatacgtgaattgggtggtgtcccaat
tattgcaaaaaaaaaaaaaaa (SEQ ID NO:120),
```

or

```
tctgagtacc agctccccac tgccctgagg gcgggccggc
ctgcggcgga gggaaaaagg aagaggagaa ggaaattgtc
ccgaatccct gcagtgggtc caagcctctc ccgggtggcc
agtctttctg taggttgcgg cacaacgcca ggcaaaagaa
gaggaaggaa tttaatccta atcggtggag gtcgatttga
gggtctgctg tagcaggtgg ctccgcttga agcgagggag
gaagtttcct ccgatcagta gagattggaa agattgttgg
gagtggcaca ccactaggga aaagaagaag gggcgaactg
cttgtcttga ggaggtcaac cccacaatc agctcttgtg
gccttgaagt ggctgaagac gatcaccctc cacaggcttg
agcccagtcc cacagccttc ctcccccagc ctgagtgact
actctattcc ttggtccctg ctattgtcgg ggacgattgc
atgggctacg ccaggaaagt aggctgggtg accgcaggcc
tggtgattgg ggctggcgcc tgctattgca tttatagact
gactagggga agaaaacaga acaaggaaaa aatggctgag
ggtggatctg gggatgtgga tgatgctggg gactgttctg
gggccaggta taatgactgg tctgatgatg atgatgacag
caatgagagc aagagtatag tatggtaccc accttgggct
cggattggga ctgaagctgg aaccagagct agggccaggg
caagggccag ggctacccgg gcacgtcggg ctgtccagaa
acgggcttcc cccaattcag atgataccgt tttgtcccct
caagagctac aaaaggttct ttgcttggtt gagatgtctg
aaaagcctta tattcttgaa gcagctttaa ttgctctggg
taacaatgct gcttatgcat ttaacagaga tattattcgt
gatctgggtg gtctcccaat tgtcgcaaag attctcaata
ctcgggatcc catagttaag gaaaaggctt taattgtcct
gaataacttg agtgtgaatg ctgaaaatca gcgcaggctt
aaagtataca tgaatcaagt gtgtgatgac acaatcactt
ctcgcttgaa ctcatctgtg cagcttgctg gactgagatt
gcttacaaat atgactgtta ctaatgagta tcagcacatg
cttgctaatt ccatttctga ctttttcgt ttattttcag
cgggaaatga agaaaccaaa cttcaggttc tgaaactcct
tttgaatttg gctgaaaatc cagccatgac tagggaactg
```

-continued

```
ctcagggccc aagtaccatc ttcactgggc tccctcttta
ataagaaaga gaacaaagaa gttattctta aacttctggt
catatttgag aacataaatg ataatttcaa atgggaagaa
aatgaaccta ctcagaatca attcggtgaa ggttcacttt
ttttcttttt aaaagaattt caagtgtgtg ctgataaggt
tctgggaata gaaagtcacc atgatttttt ggtgaaagta
aaagttggaa aattcatggc caaacttgct gaacatatgt
tcccaaagag ccaggaataa caccttgatt ttgtaattta
gaagcaacac acattgtaaa ctattcattt tctccacctt
gtttatatgg taaaggaatc ctttcagctg ccagttttga
ataatgaata tcatattgta tcatcaatgc tgatatttaa
ctgagttggt ctttaggttt aagatggata aatgaatatc
actacttgtt ctgaaaacat gtttgttgct ttttatctcg
ctgcctagat tgaaatattt tgctatttct tctgcataag
tgacagtgaa ccaattcatc atgagtaagc tcccttctgt
cattttcatt gatttaattt gtgtatcatc aataaaattg
tatgttaatg ctggaaggga aaaaaaaaaa aaaaaaaaaa
aaaaaaaaaa aaaaaaaaaa aaaaa (SEQ ID NO:121).
```

Further preferred are compositions comprising PCR-based subcloning of the gene therapy compositions of Armapoptin into plasmid vectors such as pCMVβ or pSVβ, tissue-specific promoter-containing plasmids such as the MUC1 promoter, which allows epithelial cell specific expression and is up-regulated during malignancy, and the P450arom promoter II for breast carcinomas employing liposomal delivery systems by methods described in Patel, U.S. Pat. No. 6,225,090, 2001, Thierry, U.S. Pat. No. 6,110,490, 2000; Wolff, et al., U.S. Pat. No. 6,228,844, 2001, Graham, et al., Int. J. Cancer. 92:382-387, 2001, Zhou, et al, Cancer Res. 61:2328-2334, 2001, which disclosures are hereby incorporated in their entireties. Further preferred are compositions comprising polynucleotides of the invention cloned into adenoviral vectors (Beach, et al., U.S. Pat. No. 5,968,821, 1999, and U.S. Pat. No. 6,211,334, 2001; Mehtali, et al., U.S. Pat. No. 6,204,060, 2001), and MoMLV-based retroviralvectors for gene delivery into dividing cells, i.e tumor tissues according to methods described by Holt, et al., U.S. Pat. No. 6,177,410, 2001, which disclosures are hereby incorporated in their entirety.

Methods to deliver preferred compositions of Armapoptin polynucleotides and fragments thereof, comprise local injection of preferred compositions of the invention into tumor tissue or surrounding vessels, or ex vivo therapy. Further methods comprise tumor tissue specific targeting of Armapoptin polynucleotides or fragments thereof in a plasmid via antibodies or other ligands, which recognize tumor-specific receptors. These ligands will be covalently linked to polycations such as poly-L-lysine or liposomes, and complexed with preferred gene therapy compositions of Armapoptin. Preferred tumor cell types to be used in methods of gene therapy include breast carcinoma, cervix adenocarcinoma, ovarian carcinoma, lung carcinoma, and squamous cell carcinoma of head and neck derived from mammalian cells including rodent and human. Assessment of therapeutic efficacies will include tumor regression following delivery of preferred gene therapy compositions of Armapoptin as monitored by measurement of tumor circumference. Apoptosis will be measured by morphological assessments including retraction of cytoplasmic extension, cell rounding and detachment, and via Mu assays, which measure mitochondrial function for viability, cell death and caspase activity, and DNA fragmentation analysis as described by Noteborn, et al. U.S. Pat. No. 5,981,502, 1999; Boone, et al., J. Biol. Chem. 275:37596-37603, 2000; Shibata, et al., Cancer Gene Therapy. 8:23-35, 2001;Lacour, et al., Cancer Research 61:1645-1651, 2001), which disclosures are hereby incorporated by reference in their entireties.

Further embodiments include putative death effector domains for therapeutic use in caspase-dependent cell death including incubation of carcinoma cells with compositions comprising polypeptides of preferred sequences comprising RLAWGRDENEKIWDEDEES (SEQ ID NO:122) and FADD (SEQ ID NO:226) DED-related domains as described in Eberstadt, et al., Nature. 392:941-945, 1998, and Hackam, et al., J. Biol. Chem. 275:41299-41308, 2000, which disclosures are hereby incorporated by reference in their entireties, with the consensus sequence SSYRVLLLLISEELDSEELEVLLFLCNDDIPKRKLEIKTALDLFSALEEQGLLSEDNLSLLAELL YRLRRLDLLRRLFG (SEQ ID NO:123).

Further, these DED domain-encoding sequences will be subdloned into expression vectors and used for cell transfections and apoptosis studies as described above.

In another embodiment, Armapoptin polypeptides or fragments thereof will be used as immunotherapeutics by covalent or noncovalent linkage to a cell-specific (e.g. tumor cell-specific) antibody, or to a ligand which is recognized by a tumor cell-specific receptor and internalized. Receptors which are abundantly expressed on tumor cells but not on intact, quiescent tissues to be employed in the present invention include H11. [(C-antigen); Dan, et al., U.S. Pat. No. 6,207,153, 2001], tyrosine growth factor receptors including erbB-2 (HER-2-neu). (Suzuki, et al., Biochim Biophys Acta. 1525:191-196, 2001; Kumar, et al., Sernin Oncol. 27:84-91, 2000; Lango, et al., Current Opin Oncol. 13:168-175, 2001), the folate receptor. (Ward, Current Opin Mol Ther. 2:182-187, 2000), human epidermal growth factor receptor (Schlessinger, et al., U.S. Pat. No. 6,217,866, 2001), and endoglin on endothelial cells for tumor vascular targeting (Seon, U.S. Pat. No. 6,200,566, 2001), which disclosures are hereby incorporated by reference in their entirety.

The death effector domain causes neuronal cell death in Huntington's disease (Hackam, et al., J. Biol. Chem. 275: 41299-41308, 2000, which disclosures are hereby incorporated by reference in their entirety) by stronger association with the mutant, glutamine rich protein, which causes the disease as opposed to wild-type huntingtin in healthy individuals. Another embodiment uses Armapoptin and ALEX-1, partial sequences thereof including the death effector domain RLAWGRDENEKIWDEDEES, and the death effector domain of the huntingtin-interacting protein (HIP-1), conserved among related sequences with the consensus peptide SSYRVLLLLISEELDSEELEVLLFLCNDDIPKRKLEIKTALDLFSALEEQGLLSEDNLSLLAE LLYRLRRLDLLRRLFG (SEQ ID NO: 123) for competitive binding studies with wild-type huntingtin and the disease-causing mutant. By contacting polypeptides of the invention with wt-and mt- (glutamine-rich) huntingtin, peptide-protein interactions will be analyzed by biophysical methods and validated using the following steps as described in Scalley, et al., Biochemistry. 38:15927-15935, 1999; Chaillan-Lluntington et al., J. Biol. Chem. 275:5874-5879, 2000; Lohner et al., Biochim Biophys Acta. 1462: 141-156, 1999; Eberstadt, et at., Nature 392:941-945, 1998, which disclosures are hereby incorporated in their entireties.

Structural transitions in the denatured state ensemble, fluorescence energy transfer, and determination of peptide conformation and structural characteristics using circular dichroism Isothermal titration calorimetry, fluorescence binding assays, and differential scanning calorimetry to determine comparative $K_d$ values, and strength of interactions.

Structure determination of polypeptidelhuntingtin complexes by NMR and X-ray crystallography. Co-incubation of cell lines like 293 T cells with protein-peptide complexes, and co-transfection of cells with wt- and mt-huntingtin-encoding plasmids and cloned oligonucleotides for cytotoxicity assays as well known in the art.

Another embodiment includes the method to use armadillo repeats of armapoptin, including NFPYKIDDILSAPDLQKVLNILERTNDPFIQEVALVTLGNNAA(SEQ ID NO:124), and YSFNQNAIRELGGVPIIAKLIKTKDPIIREKTYNALNNLSV(SEO ID NO:125) as single repeats, and naturally occurring tandem array repeats NFPYKIDDILSAPDLQKVLNILERTNDPFIQEVALVTLGNNAAYSFNQNAIRELGGVPIIAK LIKTKDPIIREKTYNALNNLSV (SEQ ID NO:126) for the restoration of cell-cell adhesion in treatment or prevention of cancer or other diseases or disorders where restoration of cell-cell adhesion is sought, wherein said method includes contacting cells in need of cell-cell adhesion with either monomers or concatamerized forms, either recombinantly or nonrecombinantly, such as dimmers, trimers, or longer repeats, in a cell-cell adhesion restorative amount of an Armapoptin polypeptide of the present invention.

Protein of SEQ ID NO:26 (Internal designation Clone 545542_182-1-2-0-D12-F)

The cDNA of clone 545542_182-1-2-0-D12-F (SEQ ID NO:25) encodes the 251 amino acid human Fibroblast Growth Factor-22 protein (FGF-22) comprising the amino acid sequence:

MLGARLRLWVCALGSVCSMSVLRAYPNASPLLGSSWGGLIHIYTATARNSYHLQIHKNG HVDGAPHQTIYSALMIRSEDAGFVVITGVMSRRYLCMDFRGNLFGSHYFDPENCRFQHQT LENGYDVYHSPQYHFLVSLGRAKRFLPGMNPPPYSQFLSRRNEIPLIHHFNTPIPRRHTRSA EDDSERDPLNVLKPRARMTPAPASCSQELPSAEDNSPMASDPLGVVRGGRVNTHAGGTGP EGCRPFAKFI (SEQ ID NO:26). Accordingly, it will be appreciated that all characteristics and uses of the polypeptides of SEQ ID NO:26 described throughout the present application also pertain to the polypeptides encoded by the nucleic acids included in Clone 545542_182-1-2-0-D12-F. In addition, it will be appreciated that all characteristics and uses of the polynucleotides of SEQ ID NO:25 described throughout the present application also pertain to the nucleic acids included in Clone 545542_182-1-2-0-D12-F. A preferred embodiment of the invention is directed toward the compositions of SEQ ID NO:25, SEQ ID NO:26, and Clone 545542_182-1-2-0-D12-F. Also preferred are polypeptide fragments having a biological activity as described herein and the polynucleotides encoding the fragments.

FGFs exert their biological effects through interaction with cognate single transmembrane, heparin-binding, fibroblast growth factor receptors (FGFR) with intrinsic kinase activity, designated fibroblast growth factor receptor 1 (FGFR-1), fibroblast growth factor receptor 2 (FGFR-2), fibroblast growth factor receptor 3 (FGFR-3) and fibroblast growth factor receptor 4 (FGFR-4). Physiologically, FGFs bind heparin sulfate proteoglycans which are sulfated glycosaminoglycans covalently bound to core protein. The ability to bind heparin-like moieties includes FGFs within the more encompassing Heparin Binding Growth Factor (HBGF). superfamily of peptide growth factors. Additionally, FGFs bind the cysteine-rich FGF-R(CFR), an integral single transmembrane protein in a mutually exclusive manner with respect to the other. FGFRs.

FGF-22 exibits a pattern of temporal and spatial expression in the embryonic and adult organism most pronounced in the brain, including but not limited to the ventrolateral thalamic nucleus and thalamus. FGF-22 is directly associated with the inherited disorder. Autosomal Dominant Hypophosphatemic Rickets (ADHR), represented by missense mutations in FGF-22 polypeptide residues ARG176GLN and ARG179TRP of SEQ ID 26, respectively, resulting from FGF-22 nucleotide transitions at position G527A and C535T, respectively of SEQ ID 25.

Included as an embodiment of the present invention is a method of elevating serum phosphate levels to within physiologically acceptable concentrations comprising the step of contacting kidney tissue or cells, in vitro or in vivo, with an effective amount of a FGF-22 polypeptide. The polypeptide of the present invention may be employed in combination with a suitable physiologically acceptable carrier to comprise a physiologically acceptable composition for administration. Such compositions comprise a therapeutically effective amount of the FGF-22 polypeptide and a physiologically acceptable carrier or excipient. Such a carrier includes but is not limited to saline, buffered saline, dextrose, water, glycerol, ethanol, and combinations thereof. The formulation should suit the mode of administration. Preferably, the kidney cells are nephron renal tubules and associated vascular components (collectively designated the glomerular capsule). capable of altering tubular reabsorption, and/or distal or collecting tubules. Preferably, the kidney tissue or cell is contacted by administering a FGF-22 polypeptide to an individual. As used herein, the term "individual" includes members of the animal kingdom including but not limited to human beings. Preferably, the FGF-22 polypeptide is administered parenterally, more preferably intraperitoneal.

Further included in the present invention is a method of attenuating osteomalacia or tumor-induced osteomalacia comprising contacting osseous tissue (osteocytes, osteoblasts, osteoclasts) with an osteomalacia inhibiting effective amount of a FGF-22 polypeptide. The polypeptide of the present invention may be employed in combination with a suitable physiologically acceptable carrier to comprise a physiologically acceptable composition for administration. Such compositions comprise a therapeutically effective amount of the FGF-22 polypeptide and a physiologically acceptable carrier or excipient. Such a carrier includes but is not limited to saline, buffered saline, dextrose, water, glycerol, ethanol, and combinations thereof. The formulation should suit the mode of administration. Preferably, the osseus tissue or cell is contacted by administering a FGF-22 polypeptide to an individual. Preferably, the FGF-22 polypeptide is administered parenterally, more preferably intraperitoneal.

In another embodiment of the present invention is a method of attenuating osteopenia comprising contacting osseus tissue (osteocytes, osteoblasts, osteoclasts) with an osteopenia inhibiting effective amount of a FGF-22 polypeptide. The polypeptide of the present invention may be employed in combination with a suitable physiologically acceptable carrier to comprise a physiologically acceptable composition for administration. Such compositions comprise a therapeutically effective amount of the FGF-22 polypeptide and a physiologically acceptablely acceptable carrier or excipient. Such a carrier includes but is not limited to saline, buffered saline, dextrose, water, glycerol, ethanol, and combinations thereof. The formulation should suit the mode of administration. Preferably, the osseous tissue is contacted by administering a FGF-22 polypeptide to an individual. Preferably, the FGF-22 polypeptide is administered parenterally, more preferably intraperitoneal.

In another embodiment of the present invention is a method of attenuating osseous bone matrix deposition, including defects associated with congenital malformations, osteogenesis imperfecta (types I-IV), osteoporosis (type I and/or type II), rickets, fracture remodeling, surgical repair and restoration, and associated with deficiencies in osteoid mineralization or deposition, comprising contacting osseous tissue (osteocytes, osteoblasts, osteoclasts) with a osteoid deposition or osteoid mineralization stimulating effective amount of a FGF-22 polypeptide. The polypeptide of the present invention may be employed in combination with a suitable physiologically acceptable carrier to comprise a physiologically acceptable composition for administration. Such compositions comprise a therapeutically effective amount of the FGF-22 polypeptide and a physiologically acceptablely acceptable carrier or excipient. Such a carrier includes but is not limited to saline, buffered saline, dextrose, water, glycerol, ethanol, and combinations thereof. The formulation should suit the mode of administration. Preferably, the osseous tissue is contacted by administering a FGF-22 polypeptide to an individual. Preferably, the FGF-22 polypeptide is administered parenterally, more preferably intraperitoneal.

In another embodiment of the present invention is a method of attenuating bone resorption or jaw atropy associated with dental abscess (eriapical or periodontal) formation or progression, congenital or derived edentulous conditions, or consequent to elective dental extraction, comprising contacting oral cavity osseous tissue (ostebcytes, osteoblasts, osteoclasts) of the mandible or maxilla, preferably located adjacent to the sulcular groove region, with an effective amount of an FGF-22 polypeptide. The polypeptide of the present invention may be employed in combination with a suitable physiologically acceptable carrier to comprise a physiologically acceptable composition for administration Such compositions comprise a therapeutically effective amount of the FGF-22 polypeptide and a physiologically acceptable carrier or excipient. Such a carrier includes but is not limited to saline, buffered saline, dextrose, water, glycerol, ethanol, and combinations thereof. The formulation should suit the mode of administration. Preferably, the osseous tissue is contacted by administering a FGF-22 polypeptide to an individual. Preferably, the FGF-22 polypeptide is administered parenterally, by any convenient manner, typically by syringe or catheter at the location of targeted osteosynthesis. In a further embodiment of this invention is a method of facilitating osseointegration of dental implant prostheses comprising contacting oral cavity osseous tissue (osteocytes, osteoblasts, osteoclasts) of the maxilla and/or mandible as well as osseous tissue i.e autogeneic or allogeneic bone graft, or dental biornaterial matrix i.e coral or hydroxyapatite, incorporated within the dental implant device, or bioabsorbable cement in peri-implant region with an effective amount of an FGF-22 polypeptide. Following tooth extraction, implant osteotomies were prepared and FGF-22 polypeptide included with a bioabsorbable cement placed circumferentially within the osteotomies. Implant prostheses were placed into the prepared sites including the FGF-22 dental cement (Meraw et al., (J Periodontol 71: 8-13, 2000)). Preferably, the osseous tissue is contacted by administering a FGF-22 polypeptide to an individual. The polypeptide of the present invention may be employed in combination with a suitable physiologically acceptable carrier to comprise a physiologically acceptable composition for administration. Such compositions comprise a therapeutically effective amount of the FGF-22 polypeptide and a physiologically acceptable carrier or excipient. Such a carrier includes but is not limited to saline, buffered saline, dextrose, water, glycerol, ethanol, and combinations thereof. The formulation should suit the mode of administration. Preferably, the FGF-22 polypeptide is administered parenterally, by any convenient manner, typically by syringe or catheter at the location of targeted osteosynthesis. FGF-22 polypeptide is alternatively or additionally administered directly associated with the biodegradable matrix of the dental implant using methods of Illi U.S. Pat. No. 6,214,008; PCT WO98/46289), Gayer and Comfort (U.S. Pat. No. 6,214,049), and/or associated with the bioabsorbable cement using the methods of Meraw, et al. (J Periodontol 71: 8-13, 2000), which disclosures are hereby incorporated by reference in their entireties.

A further embodiment of the current invention is a method of facilitating osteosynthesis of bone to acetablular erosion or osteonecrosis of the femoral head in advance of orthopedic osseointegration of hip joint implant prostheses for hip arthroplasty comprising contacting implant localized osseous tissue (osteocytes, osteoblasts, osteoclasts) of the hip joint, preferably the acetabular region and/or femoral head, with a stimulating effective amount of a FGF-22 polypeptide. The polypeptide of the present invention may be employed in combination with a suitable physiologically acceptable carrier to comprise a physiologically acceptable composition for administration. Such compositions comprise a therapeutically effective amount of the FGF-22 polypeptide and a physiologically acceptable carrier or excipient. Such a carrier includes but is not limited to saline, buffered saline, dextrose, water, glycerol, ethanol, and combinations thereof. The formulation should suit the mode of administration. Preferably, the osseous tissue is contacted by administering a FGF-22 polypeptide to an individual. Preferably, the FGF-22 polypeptide is administered parenterally, preferably intraperitoneal, or by any convenient manner, or by syringe or catheter at the location of targeted osteosynthesis. FGF-22 polypeptide is additionally administered by incorporation with the biodegradable matrix of the prosthetic joint implant.

An additional embodiment of this invention is a method of facilitating osteosynthesis of bone to attenuate articular surface erosion or osteonecrosis of the femur and/or tibia and/or patella in advance of orthopedic osseointegration of knee joint implant prostheses forknee joint arthroplasty, or osteochondral fracture repair, or the placement of orthopedic pins or screws, comprising contacting implant localized osseous tissue. (osteocytes, osteoblasts, osteoclasts) of the knee joint, preferably the articular surfaces, with a stimulating effective amount of a FGF-22 polypeptide. The polypeptide of the present invention may be employed in combination with a suitable physiologically acceptable, carrier to comprise a physiologically acceptable composition for administration. Such compositions comprise a therapeutically effective amount of the FGF-22 polypeptide and a physiologically acceptable carrier or excipient. Such a carrier includes but is not limited to saline, buffered saline, dextrose, water, glycerol, ethanol, and combinations thereof. The formulation should suit the mode of administration. Preferably, the osseous tissue is contacted by administering a FGF-22 polypeptide to an individual. Preferably, the FGF-22 polypeptide is administered parenterally, preferably intraperitoneal, or by any convenient manner, typically by syringe or catheter at the location of targeted osteosynthesis. FGF-22 polypeptide, is additionally administered by incorporation with the biodegradable matrix of the prosthetic joint implant. FGF-22 is a potent inducer of epithelial cell proliferation. Therefore, another embodiment of this invention is a method of stimulating epithelial cell proliferation or increasing epithelial cell viability by contacting said cells, in vitro or in vivo, with a proliferative stimulating or viability increasing effective amount of a FGF-22 polypeptide. More specifically a method of promoting wound repair or tissue healing, such as resultant from burn, ulcer (e.g., venous ulcers in diabetics), aging, post-operative damage, disease, or other insult, by stimulating epithelial cell proliferation or increasing epithelial cell viability by contacting said cells or tissue, in vitro or in vivo, with a proliferation stimulating or viability increasing effective amount of a FGF-22 polypeptide. The polypeptide of the present invention may be employed in combination with a suitable physiologically acceptable carrier to comprise a physiologically acceptable composition for administration. Such compositions comprise a therapeutically effective amount of the FGF-22 polypeptide and a physiologically acceptable, carrier or excipient. Such a carrier includes but is not limited to saline, buffered saline, dextrose, water, glycerol, ethanol, and combinations thereof. The formulation should suit the mode of administration. Preferably, the epithelial tissue is contacted by administering a FGF-22 polypeptide to an individual. Preferably, the FGF-22 polypeptide is administered parenterally, preferably intraperitoneal, or by any convenient manner, typically by syringe or catheter directly at the location of targeted epithelial proliferation.

FGF-22 is a potent regulator of connective tissue proliferation, including embryonic mesechymal cells, fibrobastic cells of areolar, collagenous and elastic connective tissue, chondrocytes of cartilage and osteocytes of bone. Therefore, another embodiment of this invention is a method of stimulating fibroblast cell proliferation or increasing fibroblast cell viability by contacting said cells, in vitro or in vivo, with a proliferative stimulating or viability increasing effective amount of a FGF-22 polypeptide. A further specified embodiment of the present invention is a method of promoting wound repair or tissue healing, in vitro and in vivo, such as resultant from burn, ulcer, aging, post-operative damage such as tendon and ligament repair. (Chan, et al., Acta Orthop. Scand 71: 513-518, 2000; Kuroda, et al., Knee Surg Sports Traumatol Arthrosc 8: 120-126, 2000), disease, or other insult, by stimulating connective tissue cell proliferation or increasing connective tissue cell viability by contacting said cells, in vitro or in vivo, with a proliferation stimulating or viability increasing effective amount of a FGF-22 polypeptide. The polypeptide of the present invention may be employed in combination with a suitable physiologically acceptable carrier to comprise a physiologically acceptable composition for administration. Such compositions comprise a therapeutically effective amount of the FGF-22 polypeptide and a physiologically acceptablely acceptable carrier or excipient. Such a carrier includes but is not limited to saline, buffered saline, dextrose, water, glycerol, ethanol, and combinations thereof. The formulation should suit the mode of administration. Preferably the cells. are located in tendons, ligaments, and synovial membranes. More specifically the cells would be fibroblasts present in loose, dense, collagenous and elastic connective tissues of the tendons and/or ligaments and/or synoviocytes within synovial membranes and contacted using the methods of Chan, et al. (Acta Orthop Scand 71: 513-518, 2000) and Kuroda, et al. (Knee. Surg Sports Traumatol Arthrosc 8: 120-126, 2000), which disclosures are hereby incorporated by reference in their entirety. More preferably the fibroblasts would be induced to actively synthesize dense connective tissue and/or collagen. Preferably, the connective tissue is contacted by administering a FGF-22 polypeptide to an individual. Preferably, the FGF-22 polypeptide is administered parenterally, more preferably intraperitoneal.

A further specified embodiment of the present invention is a method of promoting cartilage (hyaline cartilage, fibrocartilage, elastic cartilage) wound repair or tissue healing, in vitro and in vivo, such as resultant from aging, post-operative damage, disease, or other insult, by stimulating cartilage tissue cell proliferation or increasing cartilage tissue cell viability by contacting said cells, in vitro or in vivo, with a proliferation stimulating or viability increasing effective amount of a FGF-22 polypeptide. The polypeptide of the present invention may be employed in combination with a suitable, physiologically acceptable carrier to comprise a physiologically acceptable composition for administration. Such compositions comprise a therapeutically effective amount of the FGF-22 polypeptide and a physiologically acceptable carrier or excipient. Such a carrier includes but is not limited to saline, buffered saline, dextrose, water, glycerol, ethanol, and combinations thereof. The formulation should suit the mode of administration. Preferably the cells are located within joints and/or articular surfaces involved in interstitial/endogenous growth and/or appositional/exogenous growth, ends of long bones. (articular cartilage), ends of ribs (costal cartilage), intervertebral disks, symphysis of pubis, menisci of knee, nasal septum, larynx, pharynx, trachea, bronchi, epiglottis, sternum, Eustachian tubes, and of the external (pinna), middle, and inner ear. More specifically the cells would be ground substance (collagenous or elastic fibers, glycosaminoglycans, chondroitin sulfate matrix) remodeling cells (chondrocytes, chondroblasts, chondroclasts) present in cartilagenous connective tissues and contacted using the methods of Toolan, et al. (J Biomed Mater Res 31: 273-280, 1996), Shida, et al. (J Orthop Res 14: 265-272, 1996), and/or Chan, et al. (Clin Orthop 342: 239-247, 1997), which disclosures are hereby incorporated by reference in their entirety. More preferably the cartilage cells (chondrocytes, chondroblasts) would be induced to actively synthesize ground substance. Preferably, the connective tissue is contacted by administering a FGF-22 polypeptide to an individual. Preferably, the FGF-22 polypeptide is administered parenterally, preferably intraperitoneal, or by any convenient manner, or by syringe or catheter at the location of targeted cartilage connective tissue biosynthesis (Chan et al., Clin Orthop 342: 239-247, 1997).

A further specified embodiment of the present invention is a method of promoting osseous. (compact bone, spongy, bone) wound repair or tissue healing, in vitro and in vivo, such as resultant from aging, post-operative damage, disease, or other insult, by stimulating osseous connective tissue cell (osteoblast progenitor stromal stem cell, osteocyte, osteoblast, osteoclast) proliferation or increasing osseus connective tissue cell viability by contacting said cells, in vitro or in vivo, with a proliferation stimulating or viability increasing effective amount of a FGF-22 polypeptide. The polypeptide of the present invention may be employed in combination with a suitable physiologically acceptable carrier to comprise a physiologically acceptable composition for administration. Such compositions comprise a therapeutically effective amount of the FGF-22 polypeptide and a physiologically acceptable carrier or excipient. Such a carrier, includes but is not limited to saline, buffered saline, dextrose, water, glycerol, ethanol, and combinations thereof. The formulation should suit the mode of administration. Preferably the cells (osteoblast progenitor stromal stem cell, osteocytes, osteoblast) would be induced to actively synthesize intestitial matrix substance containing mineral salts such as calcium phosphate and calcium carbonate as well as collagenous fibers. The osseous tissue cells would be contacted using the methods of Mathijssen, et al. (J Craniofac Genet Dev Biol 20: 127-136, 2000), Reiff, et al. (J Trauma 50: 433-438, 2001) and/or Mackenzie, et al. (Plast Reconstr. Surg 107: 989-996, 2001). In response to FGF-22 treatment, radiomorphometric. (percentage of radiopacity of defect) and histomorphometric (square millimeters of new bone formation) methods would be used to derive quantitative outcome data bone formation). Preferably, the osseus connective tissue is contacted by administering a FGF-22 polypeptide to an individual. Preferably, the FGF-22, polypeptide is administered parenterally, preferably intraperitoneal, or by any convenient manner, or by syringe or catheter at the location of targeted osteosynthesis (Radomsky, et al., Clin Orthop 355. Suppl: S283-S293, 1998), or by directed intraosseous injection using the methods of (Nakamura, et al., J Orthop Res 15: 307-313, 1996; Nakamura et al., Int Orthop 22: 49-54, 1998).

FGF-22 is expressed in the ventrolateral thalamic nucleus of the CNS, a region associated with paralysis agitans, or Parkinson's Disease. Surgical intervention using thalamatomy for Parkinson's disease involves introduction of lesions in the ventrolateral thalamus to relieve tremor and improve rigidity. Therefore, a further embodiment of this invention is a method of attenuating Parkinson's Disease associated tremors, or unrelated benign essential tremors, by contacting ventrolateral thalamic tissue comprising the steps of contacting said cells with an effective amount of a FGF-22 polypeptide. Another aspect of the present invention relates to a method for enhancing and/or stimulating and/or maintaining and/or regenerating the formation and/or survival of neurons in vitro or in the central nervous system of a mammal which comprises contacting neurons or neural progenitor cells, e.g., in vitro or by administering to said mammal, an effective amount of FGF-22 for a time and under conditions sufficient to effect an increase in and/or to maintain the number of neurons in the central nervous system. Preferably the cells and/or tissue is located within the thalamic region of the CNS. More preferably the cells and/or tissue are of the thalamic ventral nuclei. The polypeptide of the present invention may be employed in combination with a suitable physiologically acceptable carrier to comprise a physiologically acceptable composition for administration. Such compositions comprise a therapeutically effective amount of the FGF-22 polypeptide and a physiologically acceptable carrier or excipient. Such a carrier includes but is not limited to saline, buffered saline, dextrose, water, glycerol, ethanol, and combinations thereof. The formulation should suit the mode of administration. Preferably, the CNS tissue is contacted by administering a FGF-22 polypeptide to an individual., Preferably, the FGF-22 polypeptide is administered parenterally, with the route of administration intraperitoneal, intramuscular, or by intravenous injection, or using gene therapy, although additional routes are possible such as infusion, drip, intracerebral injection (Mufson, et al., Prog Neurabiol 57: 451-484, 1999) and/or implants (Shults, et al., Brain Res 883: 192-204, 2000; Tomqvist, et al., Exp Neurol 164: 130-138, 2000) and as described in U.S. Pat. No. 6,179,826, which disclosures are hereby incorporated by reference in their entireties. FGF-22 may also be, administered directly to the brain. In an additional embodiment of this invention, FGF-22 may also be employed to stimulate neuronal growth and to treat and prevent neuronal damage associated with stroke or which occurs in certain neuronal disorders or neurodegenerative conditions such as Alzheimer's and AIDS-related complex.

The Adeno Associated Virus (AAV) utilizes the human FGFR-1 as a co-receptor for infection in mammalian cells (Qing, et al., Nat Med 5: 71-77, 1999, which disclosures are hereby incorporated by reference in their entirety) as well as the ubiquitously expressed heparan sulfate proteoglycans on cell surfaces. Similarly, adenoviral vectors are effectively targeted for the treatment of systemic and local disease using the ability of FGF family polypeptides to bind their cognate FGFR's with high affinity. (Sosnowski, et al., Curr. Opin Mol Ther 1: 573-579, 1999, which disclosures are hereby incorporated by reference in their entirety). As a further embodiment of this invention is a method of retargeting a FGF-22 polypeptide or chimeric polypeptide encoded as part of an adenoviral or AAV delivery system to cells expressing cognate FGFR complexes using the methods of Hoganson, et al., (Mol Ther 3: 105-112, 2001) and Qing, et al. (Nat Med 5: 71-77, 1999), which disclosures are hereby incorporated by reference in their entirety. Preferably the FGF-22 polypeptide is expressed, in part or in whole, with the viral delivery system as a bifunctional conjugate consisting of a blocking anti-adenoviral knob. Fab fragment linked to FGF-22 using the methods of Goldman, et al. (Cancer. Res 57:1447-51, 1997) and Doukas, et al. (FASEB. J 13:1459-66, 1999). Preferably the, FGFR complex is the FGFR-1 polypeptide or FGFR-1 polypeptide ligand binding moiety Protein of SEQ ID NO:18 (Internal designation Clone 229633_253-2-5-2-A11-F)

The cDNA of Clone 229633_253-2-5-2-A11-F (SEQ ID NO:17) encodes the STAM-SAPper (STAMSAP) protein comprising the amino acid sequence: MDRALQVLQSIDPTDSKPDSQDLLDLEDICQQMGPMIDEKLEEIDRKHSELSELNVKVLEALELYNKLVNEAPVYSVYSKLHPPAHYPPASSGVPMQTYPVQSHGGNYMGQSIHQVTVAQSYSLGPDQIGPLRSLPPNVNSSVTAQPAQTSYLSTGQDTVSNPTYMNQNSNLQSATGTTAYTQQMGMSVDNSSYONTTSNLPQLAGFPVTVPAHPVAQQHTNYHQQPLL (SEQ ID NO:18). Accordingly, it will be appreciated that all characteristics and uses of the polypeptides of SEQ ID NO:18 described throughout the present application also pertain to the polypeptides encoded by the nucleic acids included in Clone 229633_253-2-5-2-A11-F. In addition, it will be appreciated that all characteristics and uses of the polynucleotides of SEQ ID NO: 17 described throughout the present application also pertain to the nucleic acids included in Clone 229633_253-2-5-2-A11-F. A preferred embodiment of the invention is directed toward the compositions comprising SEQ ID NO:17, SEQ ID NO:18, and Clone 229633_253-2-5-2-A11-F. Another preferred embodiment of the invention is directed toward compositions comprising polynucleotide fragments of at least eighteen contiguous nucleotides selected from:

gagcaagacgtggtgatgccaattggtggaaaggagaaaatcac (SEQ ID NO:127), preferably those polynucleotides that encode for polypeptides having a biological activity described herein.

Further preferred polynucleotides of the present invention include nucleic acids comprising:

gaagcggmgsggtctagggagccgcggc-cgcgggtcacccggcgggtagcagt-tgctgagtgtcagctagacagcagcgactagggct cgggcgccggcgagatgc-ctttgttcaccgccaaccccttcgagcaagacgtggtgatgccaattggtggaaag-gagaaaatcac (SEQ ID NO:128 preferably those that encode for polypeptides having a biological activity described herein. Further preferred polynucleotides of the present invention include nucleic acids of SEQ ID NO:17 comprising gaagcggmgsggtctagggagccgcg-gcrzgcgggtcacccggcgggtagcagt-tgctgagtgtcagctagacagcagcgactagggct cgggcgccggcgagatgc-ctttgttcaccgccaaccccttcgagcaagacgtggtgatgccaattggtggaaa ggagaaaatcacagagg aataggacttttcccatccaattttg-taacaactaatttaaacatagagact-gaggcagcggctgtggacaaattgaatgtaattgatgatgatgt ggaggaaat-taagaaatcagagcctgagcctgtttatatagatgaggataagatggatagagccc-tgcaggtacttcagagtatagatccaac agattcaaaaccagactcccaagac-cttttggatttagaagatatctgccaaca (SEQ ID NO:129) preferably those that encode for polypeptides of having a biological activity described herein Polypeptides of the invention having a biological activity of x %, where x is any integer between 1 and 100 of those described herein and polynucleotides encoding the same are also included in the invention. Polypeptides of the invention with biological activity are defined as polypeptides that can be phosphorylated by a tyrosine kinase such as a Janus kinase (Jak).

STAMSAP protein results from a splice event within the Signal Transducing Adaptor Molecule (STAM)-2 transcript. This splice variant contacts or recombines nucleotide 152 of STAM-2 with nucleotide 817. The resulting STAMSAP splice variant encodes the carboxy-terminal 228 amino acids of the 525-amino acid STAM-2 protein. STAM-2 contains three well-characterized domains. The, first is an SH3 domain spanning amino acids 212-266 that is not shared with STAMSAP. This SH3 domain binds the downstream effector of STAM-2, AMSH, which activates proto-oncogenic transcription factors comprising c-myc and AP-1, and results in responses that include cell proliferation (Tanaka, N., et al. (1999). J. Biol. Chem. 274:19129-35 which disclosure is hereby incorporated by reference in its entirety). An Immunoreceptor Tyrosine-based Activation Motif (ITAM) spanning amino acids 359-387 of STAM-2 and a carboxy-terminal tyrosine-rich domain are shared with STAMSAP (Endo, K., et al. (2000) FEBS Let. 477:55-61 and Pandey, A., et al. (2000). J. Biol. Chem. 275:38633-9 which disclosures are hereby incorporated by reference in their entireties).

STAMSAP is phosphorylated on tyrosine residues within the ITAM and carboxy-terminal domains by Jak molecules comprising Jak2 and Jak3. Jak2 and Jak3 phosphorylate STAMSAP in response to ligand binding of cell surface receptors comprising IL-2R, IL-3R, IL-4R, IL-7R, Platlet Derived Factor Receptor (PDGFR), Epidermal Growth Factor Receptor (EGFR), and Granulocyte Macrophage Colony Stimulating Factor Receptor(GM-CSFR). Jak activation and subsequent gene expression is associated with proliferation and cancers comprising breast and colon carcinomas and B cell lymphomas (Yamauchi, T., et al. (2000) J. Biol. Chem. 275:33937-44; Kaulsay, K., (2000) Endocrinology 141:1571-84; U.S. Pat. No. 6,177,433 which disclosures are hereby incorporated by reference in their entireties). Jak is often hyperactivated due to abnormally high expression of upstream receptors or their ligands in cancer cells. For example, higher than normal levels of PDGF are indicative of advanced stages of breast cancer (Seymour, L., et al. (1993) Breast Cancer Res. Treat. 26:247-52 which disclosure is hereby incorporated by reference in its entirety). EGFR is overexpressed in a variety of tumors including cervical cancer. (Mathur, R., et al. (2000) Am. J. Reprod. Immunol. 44:114-20 which disclosure is hereby incorporated by reference in its entirety). Furthermore, Jak3 is activated in stimulated mast cells, causing degranulation and subsequent allergic reactions (U.S. Pat. No. 6,177,433 which disclosure is hereby incorporated by reference in its entirety).

STAMSAP does not have a downstream effector and therefore acts as a dominant negative inhibitor of Jak signaling. In a preferred embodiment of the invention, the STAMSAP polypeptide is used to inhibit cell proliferation, cell survival, or viral replication downstream of Jak signaling. This embodiment is accomplished by methods comprising the step of delivering STAMSAP to cells responsive to activated Jak, for example, MOLT-4 cells expressing IL-2R (ATCC number. CRL-1582). Methods for delivering STAMSAP to, Jak-resposive cells include contacting said cells with STAMSAP polynucleotides or polypeptides by methods common to the art as discussed in the following paragraph. Further included in this embodiment is a polynucleotide comprising polynucleotides encoding a STAMSAP polypeptide with biological activity operably linked to an expression control element such as a promotor. Said polynucleotide is delivered to Jak-responsive cells by methods common to the art such as electroporation or transfection of naked polynucleotides. In addition, genes activated by Jak signaling may be monitored or assayed using methods common to the art, for example, reporter gene assays such as luciferase or beta-galactosidase. This embodiment is applied to, for example, inhibiting Jak-dependent cell responses in vitro.

Another preferred embodiment of the invention is directed towards methods to use STAMSAP to inhibit Jak-induced cell proliferation. In particular, this embodiment is directed toward inhibiting proliferation of cells resulting from activation of any upstream effector of Jak, such as a growth factor. Preferred upstream effector molecules include but are not limited to: PDGFR, EGFR, IL-2R, IL-3R, IL4R, IL-7R, and GM-CSFR. STAMSAP is used in this method comprising the step of introducing a STAMSAP polypeptide or a polynucleotide comprising polynucleotides encoding said polypeptide operably linked to an expression control element into cells activated by Jak or any upstream effector of Jak (e.g., cervical cancer cells stimulated with EGF). Preferred control elements express an amount of STAMSAP effective to inhibit proliferation of cells to which the invention is delivered. Alternative preferred control elements comprise cell- or tissue-specific enhancer elements, for example, the lyn enhancer for B cells, or c-myc or AP-1 sites for proliferating cells. Said polypeptides or polynucleotides are introduced into, said cells using methods common to, the art, including but not limited to lipid vesicles or viral transduction, as described in any one of the list: U.S. Pat. No. 5,616,565, U.S. Pat. No. 6,110,490, U.S. Pat. No.

6,204,060, or WO9704748 which disclosures are hereby incorporated by reference in their entireties. For example, polynucleotides are delivered to said cells by: i) compressing a polynucleotide expression unit, preferably an expression unit containing polynucleotides encoding biologically active STAMSAP polypeptide, into a lipid vesicle derived from any of the following list: viral envelopes, liposomes, micelles, and modified versions of these, as described in U.S. Pat. No. 6,110,490 or P.C.T.904748, which disclosures are hereby incorporated by reference in their entireties; ii) optionally targeting the lipid vesicle to, specific cells, for example, by embedding a member of a receptor-receptor ligand pair into the lipid envelope (e.g., CD40 ligand for targeting to B cells); iii) contacting the targeted vesicle with specific cells by methods common to the art such as injection or inhalant (U.S. Pat. No. 6,110,490, P.C.T 9704748, and U.S. Pat. No. 6,034,062 which disclosures are hereby incorporated by reference in their entireties). An example of delivering polypeptides to said cells comprises the steps: i) packaging a biologically active STAMSAP polypeptide into a lipid vesicle; ii) targeting the lipid vesicle to specific cells, for example, by including a member of a receptor-receptor ligand pair in the lipid envelope; iii) embedding a fusogenic component such as a peptide in the lipid envelope to promote delivery of encapsulated polypeptides to target cells; and iv) contacting the targeted vesicle with specific cells by injection or inhalant (P.C.T. 9704748 and U.S. Pat. No. 6,034,062 which disclosures are hereby incorporated by reference in their entireties).

In another preferred embodiment, STAMSAP is used to inhibit Jak3 in cells that induce an inflammatory response, such as mast cells, eosinophils, T cells, and B cells. This embodiment includes a method to deliver a biologically active STAMSAP polypeptide or a polynucleotide comprising polynucleotides encoding said polypeptide operably linked to an expression control element to individuals displaying the effects of an inflammatory response. (e.g., allergic rhinitis (hay fever), allergic urticaria (hives), angioedema, allergic asthma, or anaphylaxis). Preferred methods of delivery include but are not limited to a method comprising the steps: i) packaging of said polynucleotide into a lipid vesicle as described in U.S. Pat. No. 6,110,490, U.S. Pat. No. 5,616,565, and P.C.T. 9704748 which disclosures are hereby incorporated by reference in their entireties, and ii) delivering the vesicle to cells that induce an allergic response, such as mast cells, so that STAMSAP polypeptide is contacted with the relevant intracellular site. Preferred control elements direct expression of an amount of STAMSAP effective to inhibit an inflammatory response. Further preferred control elements for use in this embodiment include promoters of cell-specific genes such as CD48 in mast cells. The lipid vesicle is derived from any of the following list: viral envelopes, liposomes, micelles, and modified versions of these. Targeting of vesicles to specific cell types, as referred to in step. (ii), is effected by embedding a targeting moiety such as a member of a receptor-receptor ligand pair into the lipid envelope of the vesicle. Useful targeting moieties specifically bind cell surface ligands, such as CD48 or the SCF receptor on mast cells. Thus, anti-CD48 antibodies or SCF ligand are examples of useful mast cell-targeting moieties. In addition, the antibodies B43 and TXU are useful for B and T cells, respectively. Vectors and targeting are further described in U.S. Pat. No. 6,177,433, U.S. Pat. No. 6,110,490, and P.C.T. 9704748, which disclosures are hereby incorporated by reference in their entireties. The invention is delivered to the appropriate site by methods common to the art such as injection or inhalant as described in U.S. Pat. No. 6,177,433 and U.S. Pat. No. 6,034,062, which disclosures are hereby incorporated by reference in their entireties.

Protein of SEQ ID NO:22 (Internal designation Clone 589198_184-11-1-0-E4-F)

The cDNA of Clone 589198_184-11-1-0-E4-F (SEQ ID NO:21) encodes the Corneal Osteo-Vascular. Inducing (COVI) protein comprising the amino acid sequence: MKTLQSTLLLLLLVPLIKPAPPTQQD-SRIIYDYGTDNFEESIFSQDYEDKYLDGKNIKEKET VIIPNEKSLQLQKDEAITPLPPKKEN-DEMPTCLLCVCLSGSVYCEEVDIDAVPPLPKESAYL YARFNKIKKLTAKDFADIPNLRRLDFT-GNLIEDIEDGTFSKLSLLEELSLAENXLLKLPVLPP KLTLFNAKYNKIKSRGI-KANAFKKLNNLTFLYLDHNALESVPLN-LPESLRVIHLQFNNIASI TDDTFCKANDTSYIRDRIEE-IXLEGNPIVLGKHPNSFICLKRLPIGSYF (SEQ ID NO:22).

Accordingly, it will be appreciated that all characteristics and uses of the polypeptides of SEQ ID NO:22 described throughout the present application also pertain to the polypeptides encoded by the nucleic acids included in Clone 589198_184-11-1-0-E4-F. In addition, it will be appreciated that all characteristics and uses of the polynucleotides of SEQ ID NO:21 described throughout the present application also pertain to the nucleic acids included in Clone 589198_184-11-1-0-E4-F. A preferred embodiment of the invention is directed toward the compositions of SEQ ID NO:21, SEQ ID NO:22, and Clone 589198_184-11-1-0-E4-F. Further included in the invention are polypeptide fragments at least seven amino acids in length of SEQ ID NO:22 and those having a biological activity of those described herein and polynucleotides encoding the same. Biological activities include but are not limited to increasing bone density when contacted with osteogenic cells and remodeling of vascular tissue.

The COVI polypeptide is a unique splice, variant of the mimecan (also called osteoglycin and osteoinductive factor) gene (Kukita, A., et al. (1990) Proc. Natl. Acad. Sci. 87:3023-6, Funderburgh, J., et al. (1997) J. Biol. Chem. 272:28089-95, and Tasheva, E., et al. (1999) J. Biol. Chem. 274:18693-701 which disclosures are hereby incorporated by reference in their entireties). The 1997 base pair COVI transcript begins in exon 3 of full-length mimecan and encodes a 298 amino acid protein.

The COVI polypeptide is a secreted protein associated with the extracellular matrix (ECM) that promotes growth and remodeling of bone. In a preferred embodiment of the invention, COVI polypeptide is used in a method to promote bone growth by contacting a bone growth-stimulating effective amount of COVI polypeptide with cells. Preferred cells are those that normally produce bone tissue, including but not limited to osteoblasts, osteocytes, and their precursors. This method is useful to facilitate bone growth in cases including but not limited to bone loss, atrophy, or malformation due to injury, congenital or chronic conditions, surgery, or disease. Examples include but are not limited to osteopenia, osteoporosis, rickets, malignant melanoma-induced bone degradation, and bone fissures or fractures due to injury, elective surgery (e.g., plastic surgery), reconstructive surgery, and dental procedures or surgeries. COVI polypeptides are delivered in a physiologically acceptable solution, for example, pH-buffered saline, viscous solutions such as those including glycerol or dextrose, or in solutions that include other components to support bone growth. Preferred bone growth components comprise bone fragments, ground bone, and matrix materials including calcium sulfate, hydroxyapatite, ultrahigh molecular weight polyethylene (UHMWPE), and proteins such as collagen. COVI polypeptides in physiologically acceptable solution are delivered locally or systemically (as the case dictates) by methods including but not limited to injection, catheter delivery, or direct implantation (U.S. Pat. No. 6,034,062 which disclosures are hereby incorporated by reference in their entirety).

A further embodiment of the invention is a method of contacting a bone growth-stimulating amount of COVI polypeptide with cells to facilitate integration of bone, for example, for purposes of bone transplantation in cases of dental implants, orthopedic prosthesis, or other surgical procedures. Preferred cells are those present in bone tissue, including but not limited to osteoblasts, osteocytes, and their precursors. COVI polypeptides are delivered in a physiologically acceptable solution, for example, pH-buffered saline, viscous solutions such as those including glycerol or dextrose, or in solutions that include other components to support bone growth. Preferred bone growth components comprise bone fragments, ground bone, and matrix materials including calcium sulfate, hydroxyapatite, UHMWPE, and proteins such as collagen. COVI polypeptides in physiologically acceptable solution are delivered to the site of desired bone integration by methods comprising injection or direct addition to the integrated tissue (U.S. Pat. No. 6,034,062, which disclosure is hereby incorporated by reference in its entirety).

A further embodiment of this invention is a method of contacting a growth-stimulating amount of COVI polypeptide with cells to facilitate bone growth for example, for purposes of transplantation. Preferred cells include bone cells. Further preferred cells include but are not limited to human osteoblast cells, for example the cell lines MG63 or C2C12 or osteoblasts purified directly from bone, or their progenitors, such as those purified from bone marrow stroma or mesenchymal stem cells. Preferred culture conditions are common to the art and can include but are not limited to other factors to, promote bone formation, for example bone or composite matrices to direct shaping, ascorbic acid, beta-glycerophosphate, dexamethasone, calcium salts, and collagen [Dean, D., et al. (2001) J. Orthop. Res. 19:179-86 and Buttery, L., et al. (2001) Tissue Eng. 7:89-99, which disclosures are hereby incorporated by reference in their entireties]. A preferred method comprises the steps: contacting COVI polypeptide directly with cells in culture; harvesting mineralized bone formation; and surgically implanting newly formed bone into desired location (U.S. Pat. No. 4,950,296, U.S. Pat. No. 5,385,566, and U.S. Pat. No. 6,200,324, which disclosures are hereby incorporated by reference in their entireties). Another preferred method comprises the steps: delivering polynucleotides to cells in culture; delivering cells to sites of desired bone growth (for example, to the site of a fracture or to an osteopenic bone). Preferred polynucleotides comprise polynucleotides encoding COVI polypeptide operably linked to an expression control unit (e.g., a promoter) that will deliver a bone growth-stimulating amount of COVI expression (for example, high, constitutive expression from the CMV promoter or regulated expression from a tetracycline-repressible promoter, both of which are readily commercially available). Said polynucleotides are delivered to cells in vitro or in situ by methods common to the art such as electroporation, calcium phosphate transfection, or adenoviral tnansduction [Maniatis, T., et al. Molecular, Cloning A Laboratory Manual, Cold Spring Harbor Laboratory. (1982) and Cheng, S., et al. (2001) Calcif. Tissue Int. 68:87-94, which disclosures are hereby incorporated by reference in their entireties]. Cells are introduced to a site of desired bone growth in vitro, in situ, or in vivo by methods comprising injection, introduction through a catheter, or surgical implantation of a cell-containing stent, for example, on an osteopenic bone (U.S. Pat. No. 6,034,062 and U.S Pat. No. 6,206,914, which disclosures are hereby incorporated by reference in their entireties).

COVI is associated with vascular, smooth muscle cells (VSMC) in the ECM. The COVI splice variant has enhanced ability to promote vascular matrix remodeling, i.e., formation of new vessels (e.g., during development or tissue expansion), and healing of damaged vessels such as those resulting from injury, incision, burns, disease, cardiac infarction, ulcers, diabetic ulcers, and chronic conditions such as atherosclerosis. A preferred embodiment of the invention is a method to promote vascular remodeling by contacting a vascular remodeling-stimulating amount of COVI polypeptide with cells. Preferred cells include but are not limited to VSMC, vascular epithelial cells, and fibroblasts. Further preferred cells include but are not limited to human VSMC, vascular epithelial cells, and fibroblasts in intact tissue (i.e., in a milieu of ECM proteins such as collagen). COVI polypeptides are delivered to cells in physiologically acceptable solution, for example, pH-buffered saline or viscous solutions such as those including glycerol or dextrose. Said solution may be applied topically to surface wound tissue in the treatment of ulcers, lesions, injuries, diabetic ulcers, burns, trauma, stasis ulcers, periodontal conditions, lacerations, and other conditions. In addition, intraperitoneal wound tissue such as that resulting from invasive surgery may be treated with a physiologically acceptable solution comprising COVI polypeptides to accelerate vascular remodeling. For example, the surgical plane may be coated with said solution prior to closing the surgical site facilitate internal capillary perfusion and healing. In addition, the rate of localized healing may be increased by the subdermal administration of said solution by methods common to the art such as injection (U.S. Pat. No. 6,096,709, which disclosure is hereby incorporated by reference in its entirety).

Timely vascular remodeling is an urgent factor in the case of cardiac infarction to prevent enlargement of the organ. A further preferred embodiment of the invention is a method of contacting a vascular remodeling-stimulating amount of COVI polypeptide with cells. The method comprises the step of contacting COVI polypeptides with cells by implantation of a COVI polypeptide-releasing stent, for example surgically or via catheter (U.S. Pat. No. 5,500,013 and U.S. Pat. No. 5,449,382, which disclosures are hereby incorporated by reference in their entireties). Preferred cells include but are not limited to those found in cardiac tissue damaged as a result of infarction or within vessels for treating various problems such as atherosclerosis, stenonses, strictures, or aneurysms to reinforce collapsing, partially occluded, or weakened sections.

A further preferred embodiment of the invention is a method to promote vascular remodeling by delivering polynucleotides encoding COVI polypeptides to cells. This method is directed toward purposes such as transplantation of cells expressing COVI polypeptides. Preferred cells include but are not limited to VSMC, vascular epithelial cells, and fibroblasts. Further preferred cells include but are not limited to human VSMC, vascular epithelial cells, and fibroblasts, preferably in intact tissue (i.e., in a milieu of ECM proteins such as collagen). Preferred polynucleotides comprise polynucleotides encoding COVI polypeptides operably linked to an expression control unit (e.g., a promoter) that will deliver a vascular remodeling-stimulating amount of COVI expression (for example, high, constitutive expression from the CMV promoter or regulated expression from a tetracycline-repressible promoter, both of which are readily commercially available). Said polynucleotides are delivered to, cells in vitro or in situ by methods common to the art such as electroporation, calcium phosphate transfection, or adenoviral transduction [Maniatis, T., et al., Molecular. Cloning A Laboratory. Manual, Cold Spring Harbor Laboratory (1982) and Cheng, S., et al. (2001) Calcif. Tissue Int. 68:87-94, which disclosures are hereby incorporated by reference in their entireties]. Further included in the method is a step of delivering said cells to a desired site of vascular remodeling (including but not limited to wounds, incisions, injuries, ulcers, and diseased or otherwise hypovascular lesions) by methods common to the art such as injection or catheter delivery of cell suspensions or surgical implantation of intact tissue endoscopically or invasively (U.S. Pat. No. 5,669,925 and U.S. Pat. No. 5,683,345, which disclosures are hereby incorporated by reference in their entireties).

COVI polypeptide is also present as a highly modified keratan sulfate proteoglycan (KSPG) in the cornea. KSPG's are associated with ECM proteins in the cornea and function to maintain corneal shape and opacity. In a further embodiment of the invention, a cornea-maintaining effective amount of COVI polypeptide is used in a method for maintaining a desired shape (e.g., following laser surgery or non-invasive orthokeratological procedures) or opacity of corneal tissues (e.g., at the onset of cataract formation). This method comprises the step of contacting COVI polypeptides with the ECM of the cornea in a physiologically acceptable solution. A preferred physiologically acceptably solution includes pH-buffered saline. Preferred method of contact is by an eye-drop mechanism (P.C.T. 00119386, which disclosure is hereby incorporated by reference in its entirety).

Protein of SEQ ED NO:4 (Internal designation Clone 1000848582_181-40-4-0-A11-F)

The cDNA of clone 1000848582_181-40-4-0-A11-F (SEQ ID NO:3) encodes the protein of SEQ ID NO:4 comprising the amino acid sequence MELALRRSPVPRWLLLLPLLLGLNAGA-VIDWPTEEGKEVWDYVTVRKDAYMFWWLYY ATNSCKNFSELPLVMWLQGGPGGSSTGF-GNFEEIGPLDSDLKPRKTTWLQAASLLFVDN PVGT-GFSYVNGSGAYAKDLAMVASDMMVLLKT-FFSCHKEFQTVPFYIFSESYGGKMAA GIGLELYKAIQRGTIKCNFAGVALGD-SWISPVDSVLSWGPYLYSMSLLEDKGLAEVSKVA EQVLNAVNKGLYREATELWGKAEMI-IEQVKRGNTQRLACLAFSGGYRAHGWCCQTWS LH (SEQ ID NO:4). Accordingly it will be appreciated that all characteristics and uses of polypeptides of SEQ ID NO:4 described throughout the present application also pertain to the polypeptides encoded by the nucleic acids included in Clone 1000848582_181-40-4-0-A11-F. In addition, it will be appreciated that all characteristics and uses of the polynucleotides of SEQ ID NO:3 described throughout the present application also pertain to the nucleic acids included in Clone 1000848582_181-40-4-0-A11-F. A preferred embodiment of the invention is directed toward the compositions of SEQ ID NO:3, SEQ ID NO:4, and Clone 1000848582_181-40-4-0-A11-F. Also preferred are polypeptide fragments having a biological activity as described herein and the polynucleotides encoding the fragments.

The protein of SEQ ID NO:4 encodes a novel serine carboxypeptidase designated here serine carboxypeptidase hx (SCPhx). SCPhx has a unique C-terminal sequence of 31 amino acids comprising KRGNTQRLACLAFSGGYRAH-GWCLQTWSLH. This unique sequence within SCPhx contributes the histidine of the catalytic triad. SCPhx cleaves the peptide bond between the penultimate and C-terminal amino acid residues of its protein or peptide substrate and, in so doing, can either activate or inactivate the biological function of the substrate.

A preferred embodiment of the invention is directed to compositions comprising the amino acid sequence of SEQ ID NO:4 (SCPhx) or fragments thereof.

Further preferred is a method to use the serine carboxypeptidase activity of compositions comprising SCPhx polypeptide for biosynthetic procedures. Further preferred is an application of said method wherein a recombinant polypeptide engineered with a protective but inactivating C-terminal amino acid is activated through removal of this amino acid by SCPhx.

Further preferred is a method to use the serine carboxypeptidase activity of compositions comprising SCPhx polypeptide for analytical procedures. Further preferred is an application of said method wherein the requirement for the C-terminal amino acid for the function of a given protein is determined through removal of the amino acid by SCPhx.

The serine carboxypeptidase activity of SCPhx confers on SCPhx antifibrinolytic activity. In a further embodiment, compositions of the invention comprised of SCPhx are used in methods wherein the antifibrinolytic activity of SCPhx is used to promote wound healing. In further preferred embodiment, the composition is used in methods of stabilizing blood clots at sites where there is a breach in the vasculature by contacting a wound or injured tissue with a regenerative-effective amount of compositions of the invention.

In a further embodiment of the invention, SCPhx is used in a method for antibody-directed enzyme prodrug therapy (ADEPT). In said method, in vivo localization of SCPhx serine carboxypeptidase activity is effected through conjugation of SCPhx to specific antibody. Injection of SCPhx-antibody conjugate in conjunction with prodrug (drug-alpha-peptide)(Shi, P. T., et al., Yao Xue Bao 32:106-9 (1997) which disclosure is hereby incorporated by reference in its entirety) results in localized activation of the drug.

In said method for ADEPT, a preferred embodiment of the invention is directed to compositions comprising SCPhx conjugated to tumor-reactive antibody [Napier, M. P., et al., Clin. Cancer Res. 6:765-72(2000) which disclosure is hereby incorporated by reference in its entirety]. In further preferred embodiment, SCPhx is conjugated to antibody reactive with carcinoembryonic antigen (CEA) and is used in conjunction with methotrexate prodrug for the treatment of colorectal carcinoma.

In a further preferred embodiment, the present invention provides for an antibody that binds SCPhx with or without neutralization of SCPhx serine carboxypeptidase activity. The antibody may be monoclonal or polyclonal. Preferred compositions comprise the SCPhx antibody.

SCPhx serine carboxypeptidase activity expressed by breast cancer cells can activate autocrine neuropeptide growth factors concomitantly expressed by the tumor cells. In further embodiment of the invention, neutralizing anti-SCPhx antibody is used by intravenous injection to suppress tumor growth by blocking the activation of autocrine growth factors by SCPhx constitutively expressed by the tumor. In further preferred embodiment, said method is used for the treatment of breast cancer. In further preferred embodiment, said method is used for the treatment of cancer of the salivary gland.

SCPhx serine carboxypeptidase activity can process beta-amyloid precursor protein and generate beta-amyloid. In further embodiment of the invention, neutralizing anti-SCPhx antibody is used by injection in Alzheimer's disease to block processing of beta-amyloid precursor protein and generation of beta-amyloid.

Daily administration of a very low dose of the polypeptide gAcrp30 to mice consuming a high-fat/sucrose diet causes profound and sustainable weight reduction without affecting food intake (Fruebis, J., et al., Proc. Natl. Acad. Sci. USA 98:2005-10 (2001) which disclosure is hereby incorporated by reference in its entirety). Said activity of gAcrp30 is abrogated by SCPhx serine carboxypeptidase activity. In a preferred embodiment of the invention, compositions comprising said neutralizing SCPhx antibody are used in methods to block in vivo, inactivation of polypeptide function by SCPhx serine carboxypeptidase activity. In further preferred embodiment, compositions comprising said neutralizing SCPhx antibody are used in methods to treat obesity in humans by intravenous injection concomitant with human gAcrp30. In further preferred embodiment, compositions comprising said neutralizing SCPhx antibody are, used in methods to treat obesity in other mammals by intravenous injection concomitant with mammal or human gAcrp30.

The invention further relates to a method of screening for test compounds that bind and/or inhibit SCPhx serine carboxypeptidase activity above comprising the steps of contacting an SCPhx polypeptide with said test compound and detecting or measuring whether said test compound binds said SCPhx polypeptide. Alternatively, the method comprises the steps of contacting an SCPhx polypeptide with substrate of said SCPhx polypeptide in the presence of test compound and detecting or measuring the release of the C-terminal amino acid from said SCPhx substrate, wherein a difference in the amount of said release relative to the amount of release in the absence of the test compound modulates, preferably inhibits, the serine carboxypeptidase activity of SCPhx.

Protein of SEQ ID NO:8 (Internal designation Clone 1000770704_208-27-3-0-G6F)

The cDNA of clone 1000770704_208-27-3-0-G6-F (SEQ ID NO:7) encodes the protein of SEQ ID NO:8 comprising the amino acid sequence MRLPAQLLGLLMLWVSGSSGDIVMTQS-PLFLPVTPGEPASISCRSSQSLLHVQGSNYLDW YHQKPGQSPQLLIYLGSNRASGVPDRF-SGSGSGTDFTLKISRVEAEDVGVYYCMQALQT PFTF-GPGTRVDIKRTVAAPSVFIFPPSD-EQLKSGTASVVCLLNNFYPREAKVQWKVDNAL QSGNSQESVTEQDSKDSTYSLSSTLTL-SKADYEKHKVYACEVTHQGLSSPVTKSFNRGE C (SEQ ID NO:8). Accordingly it will be appreciated that all characteristics and uses of polypeptides of SEQ ID NO:8 described throughout the present application also pertain to the polypeptides encoded by the nucleic acids included in Clone 1000770704_208-27-3-0-G6-F. In addition, it will be appreciated that all characteristics and uses of the polynucleotides of SEQ ID NO:7 described throughout the present application also pertain to the nucleic acids included in Clone 1000770704_208-27-3-0-G6-F. A preferred embodiment of the invention is directed toward the compositions of SEQ ID NO:7, SEQ ID NO:8, and Clone 1000770704_208-27-3-0-G6-F. Also preferred are polypeptide fragments having a biological activity as described herein and the polynucleotides encoding the fragments.

The protein of SEQ ID NO:8 encodes the polypeptide CalX, which binds parathyroid hormone related protein (PTHrP), a hormone involved in bone metabolism.

PTHrP was initially discovered as a tumor-derived systemic factor that causes humoral hypercalcemia of malignancy (HHM). PTHrP is now known to play a major role in HHM. It has been identified as the major causative agent in tumors that were previously thought to cause hypercalcemia through skeletal metastatic involvement. Hypercalcemia is the most common life-threatening metabolic disorder associated with neoplastic diseases, occurring in an estimated 10% to 20% of all persons with cancer. That PTHrP is not just a bystander but is the cause of the hypercalcemia is indicated by the observation that in animals with hypercalcemia caused by xenografts of human tumors, the infusion of neutralizing antibodies to PTHrP reverses the hypercalcemia.

CalX binds to and neutralizes the activity of PTHrp, including the induction of HHM. A preferred embodiment of the invention is directed to comprising the amino acid sequence of SEQ ID NO:8(CalX). Further included in the invention are fragments of full-length CalX having a biological activity described herein as well as the polynucleotides encoding these fragments.

In a preferred embodiment, compositions of the invention are used in methods to neutralize PTHrP, wherein compositions comprising CalX are contacted with and thereby block PTHrP activity. A further embodiment is directed toward a method to use compositions of CalX to suppress HHM. In further preferred embodiment, CalX is used to suppress HHM associated with breast cancer, pancreatic adenocarcinoma, prostate cancer, squamous cell carcinoma of lung, renal cell carcinoma, ovarian carcinoma, and T cell leukemia/lymphoma.

It is believed that PTHrP plays a role in the pathophysiology associated with osteoarthritis. In further preferred embodiment, CalX is used in a method to suppress bone resorption within an affected joint, preferably in the synovium of a joint capsule. Said methods comprise contacting CalX compositions with the synodal fluid of the joint capsule. Preferred delivery of CalX includes injection or transdermal contact at the site of the joint.

It is believed that PTHRrP plays a role in the pathophysiology associated with rheumatoid arthritis. In further preferred embodiment, CalX is used in a method to decrease inflammation within an affected joint, preferably in the synovium of a joint capsule. In further preferred embodiment, CalX is used in a method to decrease bone resorption within an affected joint, preferably in the synovium of a joint capsule. Said methods comprise contacting CalX compositions with the synodal fluid of the joint capsule. Preferred delivery of CalX includes injection or transdermal contact at the site of the joint.

Protein of SEQ ID NO:6 (Internal designation Clone 1000839315_220-26-1-0-F3-F)

The cDNA of clone 1000839315_220-26-1-0-F3-F (SEQ ID NO:5) encodes the protein of SEQ ID NO:6 comprising the amino acid sequence:

MRLPAQLLGLLMLWVSGSSGDIVMTQS-PLFLPVTPGEPASISCRSSQSLLHVQGSNYLDW YHQKPGQSPQLLIYLGSNRASGVPDRF-

SGSGSGTDFTLKISRVEAEDVGVYYCMQALQT PFTF-GPGTRVDIKRTVAAPSVFIFPPSD-EQLKSGTASVVCLLNNFYPREAKVQWKVDNAL QSGNSQESVTEQDSKDSTYSLSSTLTL-SKADYEKHKVYACEVTHQGLSSPVTKSFNRGE C (SEQ ID NO:8). Accordingly it will be appreciated that all characteristics and uses of polypeptides of SEQ ID NO:6 described throughout the present application also pertain to the polypeptides encoded by the nucleic acids included in Clone 1000839315__220-26-l-0-F3-F. In addition, it will be appreciated that all characteristics and uses of the polynucleotides of SEQ ID NO:5 described throughout the present application also pertain to the nucleic acids included in Clone 1000839315__220-26-1-0-F3-F. A preferred embodiment of the invention is directed toward the compositions of SEQ ID NO:5, SEQ ID NO:6, and Clone 1000839315__ 220-26-l-0-F3-F. Also preferred are polypeptide fragments having a biological activity as described herein and the polynucleotides encoding the fragments.

The protein of SEQ ID NO:6 encodes Chimerin, a chimeric polypeptide encoded by an exon derived from the histatin 1 gene spliced downstream onto an exon derived from the linked statherin gene. Specifically, an exon encoding the N-terminal amino acids of both histatin 1 and Chimerin (MKFFVFALVLALMISMISADSHEKRHH-GYRRKFHEKHHS (SEQ ID NO: 131)) is spliced onto a statherin-derived exon that encodes the novel C-terminal amino acids of Chimerin (YHITLLPLFEES SKSNANEKHYNLLYTLCFRILAFSIVT(SEQ ID NO:132)) but in contradistinction entirely 3' -untranslated nucleotide sequence in statherin mRNA.

Chimerin is a low molecular weight, histidine-rich salivary polypeptide. Chimerin functions as part of the nonimmune host defence, system in the oral cavity.

Chimerin possesses broad spectrum antifungal activity, including that against the pathogenic yeast *Candida alibcans*, with minimal cytotoxicity towards normal host cells, suggesting its high potential as a novel anti-fungal therapeutic agent. Chimerin also possesses anti-bacterial activity, including that against *Streptococcus mutans* strains and the periodontopatheogenic *Porphyromonas gingivalis*. A great benefit of Chimerin is that to date no resistant fungal strains have been demonstrated and moreover, that Chimerin can be hydrolyzed in a natural way in the digestive tract. Therefore, Chimerin might be applied for long term use, intermitting the application of antibiotics.

A preferred embodiment of the invention is directed to compositions comprising the amino acid sequence of SEQ NO:6 (Chimerin) MKFFVFALVLALMISADSHEKRHH-GYRRKFHEKHHSYHITLLPLFEESSKSNANEKH YNLLYTLCFRILAFSIVT (SEQ ID NO:6)

Further included in the invention are fragments of the full-length Chimerin polypeptide having a biological activity described herein as well as the polynucleotides encoding these fragments. Preferred fragments with biological activity include the amino acid sequence comprising Further preferred is a method to use formulations comprising Chimerin in a physiologically compatible solution as further described in U.S. Pat. No. 4,725,576 ("Fungicidal polypeptide compositions containing L-histidine and methods for use therefore") and incorporated by reference in its entirety, including but not limited to the incorporation of Chimerin into a mouthwash.

Further preferred is a method to use compositions comprising Chimerin as agents with which to treat a fungal or bacterial infection as further described in U.S. Pat. No. 5,912,230 ("Anti-fungal and anti-bacterial histatin-based peptides") and incorporated by reference in its entirety. The said method is comprised of contacting said fungi and bacteria with an effective amount of Chimerin polypeptide of the present invention. Said method for treating a fungal or bacterial infection of claim is applicable when said fungal or bacterial infection is selected from the group consisting of: (a) an infection of the oral cavity; (b) an infection of the vagina; (c) an infection of the urethra; (d) an infection of the ear; (e) an infection of the skin; (f) a respiratory infection; (g) a mucosal infection; (h) an ophthalmic infection; and (i) systemic infection.

Further preferred is a method to use compositions comprising Chimerin as described as agents with which to prevent recurring fungal or bacterial infection in patients including, but not limited to, those from the group consisting of: AIDS, patients; diabetics; and xerostomia patients, including patients with Sjogren's syndrome and those patients whose salivary gland function has been compromised as a result of radiation therapy.

Further preferred is a method to use compositions comprising Chimerin for treating a fungal or bacterial infection wherein the fungus or bacterium is selected from the group consisting of: (a) *Candida albicans*; (b) *Actinomyces actinomycetemcomitans*; (c) *Actinomyces viscosus*; (d) *Bacteroides forsythus*; (e) *Bacteriodes fragilis*; (f) *Bacteriodes gracilis*; (g) *Bacteriodes ureolyticus*; (h) *Campylobacter concisus*; (i) *Campylobacter rectus*; (j) *Campylobacter showae*; (k) *Campylobacter sputorum*; (l) *Capnocytophaga gingivalis*; (m) *Capnocytophaga ochracea*; (n) *Capnocytophaga sputigena*; (o) *Clostridium histolyticum*; (p) Eikenella corrodens; (q) *Eubacterium* nodatum; (r) *Fusobacterium nucleatum*; (s) *Fusobacterium periodonticum*; (t) *Peptostreptococcus micros*; (u) *Porphyromonas endodontalis*; (v) *Porphyromonas gingivalis*; (w) *Prevotella intermedia*; (x) *Prevotella nigrescens*; (y) *Propionibacterium acnes*; (z) *Pseudomonas aeruginosa*; (aa) *Selenomonas noxia*; (bb). *Staphylococcus aureus*; (cc) *Streptococcus constellatus*; (dd) *Streptococcus gordonii*; (ee) *Streptococcus intermedius*; (ff) *Streptococcus mutans*; (gg). *Streptococcus oralis*; (hh) *Streptococcus pneumonia*; (ii) *Streptococcus sanguis*; (kk) *Treponema denticola*; (ll) *Treponema pectinovorum*; (mm) *Treponema socranskii*; (nn) *Veillonella parvula*; and (oo) *Wolinella succinogenes*.

```
DSHEKRHHGYRRKFHEKHHSYHITLLPLFEESSKSNANEKHYNLLYTLCFRILAFSIVT (SEQ ID NO: 133)

or

DSHEKRHHGYRR                                                (SEQ ID NO: 134)

or

KFHEKHHSYHITLLPLFEESSKSNANEKHYNLLYTLCFRILAFSIVT.            (SEQ ID NO: 135)
```

The compositions and methods for treatment of fungal and bacterial infections discussed above are not limited to use in humans, but can have veterinary applications as well.

In a further preferred embodiment, the present invention provides for an antibody that specifically binds Chimerin. The invention further relates to a method of screening for antibodies that specifically bind Chimerin comprising the steps of contacting the unique C-terminal 39 amino acids of Chimerin (YHITLLPLFEESSKSNANEKHYNLLYTL-CFRILAFSIVT(SEQ ID NO:132)) with said test antibody and detecting or measuring whether said test antibody binds said Chimerin polypeptide. Further preferred is a method to use compositions comprising this antibody in diagnostic assays to measure Chimerin concentration in bodily fluids, including saliva.

Further preferred is a method to use compositions comprising this antibody to specifically purify Chimerin from bodily fluids, including saliva, or from recombinant sources utilizing compositions comprising the nucleotide sequence of SEQ NO:5 (Chimerin) or fragments thereof.

Protein of SEQ ID NO:2 (Internal designation Clone 223583_114-044-2-0-E11-F)

The cDNA of clone 223583_114-044-2-0-E11-F (SEQ ID NO:1) encodes the protein of SEQ ID NO:2 comprising the amino acid sequence:

MAACQLLLEITTFLRETFS-CLPRPRTEPLVASTDHTKMPSQME-HAMETMMFTFHKFAGD KGYLTKEDLRVLMEKEF-PGFLENQKDPLAVDKIMKDLDQCRDGKVGFQSFFS-LIAGLTIA CNDYFVVHMKQKGKK (SEQ ID NO:2). Accordingly it will be appreciated that all characteristics and uses of polypeptides of SEQ ID NO:2 described throughout the present application also pertain to the polypeptides encoded by the nucleic acids included in Clone 223583_114-044-2-0-E11-F. In addition, it will be appreciated that all characteristics and uses of the polynucleotides of SEQ ID NO:1 described throughout the present application also pertain to the nucleic acids included in Clone 223583_114-044-2-0-E11-F. A preferred embodiment of the invention is directed toward the compositions of SEQ ID NO:1, SEQ ID NO:2, and Clone 223583_114-044-2-0-E11-F. Also preferred are polypeptide fragments having a biological activity as described herein and the polynucleotides encoding the fragments.

The protein of SEQ ID NO:2 encodes S-100A10 Related Protein (S-100A10rP), which is a splice variant of S-100A. Specifically, the protein of SEQ ID NO:2 encodes the S-100A10 polypeptide preceded by a unique sequence of 37 amino acids at the amino terminus comprising MAACQLL-LEITTFLRETFSCLPRPRTEP LV ASTDHTK (SEQ ID NO:136).

The protein of SEQ ID NO:2 encodes S-100A10 Related Protein (S-100A10rP), which is a splice variant of S-100A. Specifically, the protein of SEQ ID NO:2 encodes the S-100A10 polypeptide preceded by a unique sequence of 37 amino acids at the amino terminus comprising MAACQLL-LEITIFLRETFSCLPRPRTEP LVASTDHTK.

Dimeric S-100A10 can associate with dimeric annexin II to form a heterotetramer. As a component of this heterotetramer, S-100A10 can mediate a number of activities at the cell surface (Kassam G., et al., Biochemistry 37:16958-66 (1998), Mai, J., et al., J. Biol. Chem. 275:12806-12 (2000) which disclosures are hereby incorporated by reference in their entirety). S-100A10rP antagonizes these activities.

Heterotetrameric annexin II at the cell surface promotes the generation of plasmin, a serine protease with broad substrate specificity, through its association with both plasminogen and tissue plasminogen activator. The promotion of plasmin generation by annexin II plays a role in:

(i) control of hemostasis and coagulation, (ii) macrophage migration and matrix remodeling, (iii) neuronal cell differentiation, (iv) tumor cell invasion and metastasis, and (v) cardiovascular development and angiogenesis.

A preferred embodiment of the invention is directed to compositions comprising the amino acid sequence of SEQ NO:2 (S-100ArP). Further preferred embodiment of the invention is directed to compositions comprising either monomeric or dimeric S-100A10rP. Further included in the invention are fragments of the length S-100A10rP polypeptide having a biological activity described herein as well as the polynucleotides encoding these fragments.

Further preferred is a method to use compositions comprising S-100ArP to suppress plasmin generation and thereby decrease inflammation at sites of chronic inflammation, preferably in the synovium of a joint capsule. Said methods comprise contacting S-100A10rP compositions with the synodal fluid of the joint capsule. Preferred delivery of S-100A10rP includes injection or transdermal contact at the site of the joint.

Preferred is a method to use compositions comprising S-100ArP to suppress tumor cell metastasis. Further preferred is an embodiment of the method directed to the use of compositions of S-100A10rP to suppress tumor cell metastasis facilitated by the binding of the cysteine protease cathepsin B. to cell surface hetertetrameric annexin II. Said method is comprised of contacting said tumor cells with an effective dose of S-100A10rP by injection. Further preferred is an embodiment of the method directed to the use of S-100A10rP to suppress the metastasis of breast cancer. Further preferred is an embodiment of the method directed to the use of S-100A10rP to suppress the metastasis of glioma.

Preferred is a method to use compositions comprising S-100ArP to suppress inflammation associated with wound healing. Further preferred are compositions comprised S-100ArP used in methods of treatment comprised of contacting a wound or injured tissue with an ameliorative effective amount by injection or transdermal contact at the site of the wound.

Acute promyelocytic leukemia (APL) is characterized by hyperfinbrinolysis due to heterotetrameric annexin II promoted plasmin generation and a consequential disseminated intravascular coagulation. In a preferred embodiment of the invention, S-100A10rP is used to suppress this hyperfibrinolysis. Said method is comprised of contacting APL cells with an effective amount of S-100A10rP by injection.

A preferred embodiment of the invention is to use compositions comprising S-100A10rP. in a method to suppress angiogenesis associated with the growth of solid tumors. Further preferred is a method to use compositions comprising S-100A10rP to suppress angiogenesis associated with breast cancer, prostate cancer, pancreatic, adenocarcinoma, colorectal cancer, renal cell carcinoma, squamous cell carcinoma of the lung, and T cell lymphoma. Preferred delivery includes contacting the tumor with an effective amount of S-100A10rP by intravenous injection.

A preferred embodiment of the invention is to use compositions comprising S-100A10rP in a method to suppress angiogenesis associated with chronic inflammation. Further preferred is a method to use compositions comprising S-100A10rP to suppress angiogenesis associated with rheumatoid arthritis and thereby decrease, inflammation, preferably in the synovium of a joint capsule. Said methods comprise contacting S-100A10rP compositions with the synodal fluid of the joint capsule.

In a further preferred embodiment, the present invention provides for an antibody that specifically binds an S100A10rP polypeptide of the present invention in a method of neutralizing S-100A10rP function and thereby up-regulating the functional activity of extracellular heterotetrameric annexin II. Further preferred is a method to use compositions comprising this antibody to promote angiogenesis in ischemic heart tissue. Preferred delivery, includes contacting the heart tissue, with an effective amount of anti-S-100A10rP antibody by intravenous injection. Further preferred is a method to use compositions comprising anti-S-100A10rP antibody to promote neuritogenesis in ischemnic brain tissue. Preferred delivery includes contacting the neural tissue with an effective amount of anti-S-100A10rP antibody by local injection or transdermal contact.

Protein of SEQ ID NO:32 (Internal designation clone 477709_174-8-2-0-C10-F)

The cDNA of Clone 477709_174-8-2-0-C10-F (SEQ ID NO:31) encodes the protein of SEQ ID NO:32 comprising the amino acid sequence:

MAWRGWAQRGWGCGQAWGASVGGRS-CEELTAVLTPPQLLGRRYNFFIQQKCGFRKAP RKVE-PRRSDPGTSGEAYKRSALIPPVEETV-FYPSPYPIRSLIKPLFFTVGFTGCAFGSAAIW QYESLKSRVQSYFDGIKADWLDSIR-PQKEGDFRKEINKWWNNLSDGQRTVTGIIAANVL VFCLWRVPSLQRTMIRYFTSNPASKV-LCSPMLLSTFSHFSLFHMAANMYVLWSFSSSIVN ILGQEQFMAVYLSAGVISNFVSYVGK-VATGRYGPSLGAALKAIIAMDTAGMILGWKFFD HAAHLGGALFGIWYVTYGHELIWKNRE-PLVKIWHEIRTNGPKKGGGSK (SEQ ID NO:32). Accordingly, it will be appreciated that all characteristics and uses of polypeptides of SEQ ID NO:32 described throughout the present application also pertain to the polypeptides encoded by the nucleic acids included in Clone 477709_174-8-2-0-C10-F. In addition, it will be appreciated that all characteristics and uses of the polynucleotides of SEQ ID NO:31 described throughout the present application also pertain to the nucleic acids included in Clone 477709_174-8-2-0-C10-F. A preferred embodiment of the invention is directed toward the compositions of SEQ ID NO:31, SEQ ID NO:32, and Clone 477709_174-8-2-0-C10-F. Also preferred are polypeptide fragments having a biological activity as described herein and the polynucleotides encoding the fragments.

The protein of SEQ ID NO:32 encodes Pretactilin, a splice variant of the protein of EMBL entry Q9H300. The corresponding locus located on chromosome 3 possesses at least 2 known variants described in entries AAH03653 and Q9H300 in EMBL. The closest known sequence, both at the nucleotide and amino acid levels, is Q9H300. Q9H300 is split into 10 exons, of which the protein of the invention is missing exon 8, while in AAH03653, it is exon 6 that is absent.

Pretactilin is a polypeptide that interacts with the carboxyl-terminus of presenilin-1 and presenilin-2. Pretactilin harbours six putative transmembrane domains and belongs to the family of transmembrane rhomboid like proteins that have been isolated from various organisrms, ranging from bacteria, plants, invertebrates to humans. The first isolated member of this family, the *Drosophila melanogaster* Rhomboid protein, is a seven transmembrane domain protein that has been implicated in Epidermal Growth Factor Receptor (EGFR) signaling, which as in mammals controls many aspects of growth and development. Genetic evidence indicates that Rhomboid controls the activation by proteolysis of the transmembrane EGFR ligand, Spitz, a TGFα-like molecule presents at the surface of neighboring cells, to generate an active diffusible form of the ligand.

The rhomboid domain of the Pretactilin extends from amino acid positions 186 to 323, and includes the predicted transmembrane domain region. It has been recently proposed by Pellegrini et al., 2001,J. Alzheimers Dis. 3 (2) which disclosure is hereby incorporated by reference in its entirety, that the members of the Rhomboid superfamily possess a metal-dependent protease activity.

The familial Alzheimer disease gene products, presenilin-1 and presenilin-2, are multipass membrane proteins consisting of 6-8 spanning regions that undergo endoproteolytic processing within their large hydrophilic loop at their carboxyl terminus. Immunolocalization studies have demonstrated that these ubiquitously expressed molecules, primarily located to the, endoplasmic. reticulum and the golgi apparatus, are also found on nuclear and plasma membranes. The presenilin proteins have been reported to be functionally involved in amyloid precursor protein processing, notch receptor signalling, and programmed cell death, or apoptosis.

Alzheimer's Disease (AD) is a devastating neurodegenerative disorder characterized by progressive memory and cognition impairment associated with an increase secretion and deposition of a 4 kDa beta amyloid peptide (A beta) in extracellular senile plaques in the brain. In both healthy and AD patients, A beta is derived by proteolytic cleavage from the single transmembrane amyloid precursor protein (APP) by various proteinases that have been called APP secretases. Alpha secretases cleave. APP within the amyloid sequences, whereas other proteases called beta- and gamma-secretases cleave on the N- and C-terminal ends, respectively. While a transmembrane aspartyl protease, BACE, has been identified as beta-secretase and several proteases may be alpha-secretases (ADAM-10, TACE, PC7), the nature of the gamma-secretase(s) remains elusive. Recently, a number of studies have suggested that the presenilins themselves, missense mutations in which cause the most aggressive forms of familial AD with increased production of A beta, could be the long sought gamma-secretases which release A-beta.

The presenilins family of proteins has also been shown to interact with the Notch signalling pathway by forming stable complexes with Notch and being required for its proper cleavage at the cell surface. Notch is a single transmembrane domain cell surface receptor that mediates many cell fate decisions during development in both vertebrates and invertebrates. Notch is synthesized as a large precursor that is cleaved in the trans-golgi network lumen to generate two fragments that form a heterodimeric receptor at the cell surface. Following ligand receptor binding, the C-terminal transmembrane-intracellular fragment of Notch is cleaved within its transmembrane domain by an as yet unidentified protease. This ligand-activated cleavage releases the Notch intracellular domain from the membrane, allowing it to translocate to the nucleus where it affects the transcriptional activity of target genes through interactions with proteins that include members of the CSL family.

In addition to their roles in APP processing and Notch receptor signaling, extensive evidence suggests that presenilins are also involved in programmed cell death. Overexpression of Presenilin-2 increases apoptosis induced by a number of apostolic stimuli, whereas mutations in the presenilin genes as found in Familial Azheimer's Disease cases generate molecules with constitutive pro-apostolic activity. Complementary studies have demonstrated that depletion of PS2 protein levels by antisense RNA protects cells against apoptosis induced by a number of cell-death-inducing apostolic stimuli. At the molecular level, it has been observed recently that the carboxyl-termini of presenilin-1 and presenilin-2 interact with Bcl-XL protein, an anti-apostolic member of the Bcl-2 family, providing an additional link between these proteins and the apostolic pathway.

By virtue of its being either a transmembrane protease or a transmembrane protease cofactor, Pretactilin interacts physically with presenilins to form active complexes in the membranes that are involved in APP metabolism, Notch signalling and programmed cell death via specific, protein processing. Specifically, Pretactilin contributes to the proteolytic processing of a number of protein substrates including APP and Notch.

In one embodiment of the present invention, Pretactilin can be used in a protease cocktail in order to digest proteins, preferentially transmembrane proteins, from a biological sample. Use of a protease cocktail could be of particular interest either to quickly purify. DNA from crude cellular extracts or to remove transmembrane and membrane-associated proteins in isolated membranes preparation in order to prepare protein-free membranes vesicles useful for protein reconstitution and functional assays in vitro. In a preferred embodiment, Pretactilin is added to a protease cocktail in combination with one or more presenilin proteins.

In another embodiment, Pretactilin can be used as a transmembrane marker that would be useful during protein purification methods for monitoring the recovery of transmembrane proteins from a biological sample or from cells grown in vitro. In such methods, the proteins can be detected in any of a number of ways. For example, Pretactilin can be labeled and added to the sample or the cells prior to the purification step. Alternatively, Pretactilin can be recombinantly fused to a detectable protein such as GFP and expressed in the organism from which the sample will be taken, or in the cells, prior to purification. In addition, Pretactilin can be detected throughout the purification steps using a monoclonal or polyclonal antibody that specifically recognizes Pretactilin.

The present invention also provides new methods to purify wild type and mutant presenilin proteins, preferentially human presenilins, consisting in using Pretactilin or fragments thereof to co-immunopurify presenilins from cellular extracts. Methods to co-immunopurify proteins are well known to those skilled in the art. For example, presenilins can be co-immunopurified by affinity column chromatography or by immobilisation on sepharose-beads with monoclonal or a polyclonal antibody that specifically binds. Pretactilin. Such purified wild type and mutant presenilins would then be of particular interest to generate presenilin antibodies that could be used for the treatment of Alzheimer's disease. In addition, the purified presenilin polypeptides could subsequently be used for the diagnosis of Alzheimer's disease as described below.

In a further embodiment, the present invention is used in a diagnostic method for detecting Alzheimer's disease in an individual comprising the steps of:

(a) co-immunopurifying presenilins with Pretactilin from a biological sample, (b) adding the corresponding purified polypeptides to membranes vesicles containing a reconstituted presenilins substrate, preferentially the, Notch protein, as well as, optionally, a reconstituted Pretactilin, (c) quantifying protease activity of these membrane vesicles compared to reconstituted positive and negative controls (e.g., identical membrane vesicles where wild type and mutant presenilins have been incorporated, respectively), by proteolytic fragment detection and quantification.

In another embodiment, the present invention provides new methods to identify other proteins that interact physically with presenilins and/or Pretactilin. In a preferred method, Pretactilin is used to co-immunopurify presenilin complexes from cellular extracts, preferentially from brain cellular extracts, then disrupting the isolated complexes in order to release its components and identifying the associated proteins, for example by microsequencing followed by gene cloning and characterisation. Alternatively, Pretactilin can be used as bait in two-hybrid experiments in yeast for the screening of interacting polypeptides. Because such interacting proteins would likely be also involved in the modulation of A beta peptide production, their characterisation would certainly lead to the identification of new genes whose mutations cause or predispose to Alzheimer's disease. They would also provide useful novel targets for gene and drug therapies of the disease.

In a further embodiment, Pretactilin can be used in a method to locate presenilins in subcellular compartments of a cell, preferentially neuronal cells, comprising the steps of contacting an isolated sample of cells with labeled Pretactilin and detecting the labeling in those cells. Methods used for labeling proteins are well known in the art, any of which can be used in the present invention.

Pretactilin also provides a method to restore normal APP processing in mutant cells producing increased level of A beta peptide by reducing the level or the activity of the present protein in the cells. This can be achieved using techniques well known in the art, for example using antibodies, antisense molecules, ribozymes, or administrating to said mutant cells small molecule inhibitors of Pretactilin.

The present invention also provides an in vitro system useful to screen for inhibitors of A beta production that could be of particular interest either for the prevention or the treatment of Alzheimer's disease, consisting in transfecting cultured cells in vitro, preferentially brain cells, more preferentially neuronal cells, with a nucleotide sequence encoding Pretactilin placed under the control of a strong constitutive promoter sequence in order to achieve high expression level of Pretactilin in those cells, applying to the cells the substance to be tested, measuring the amount of A beta peptide produced by these cells compared to control transfected cells.

In another embodiment, Pretactilin can be used to modulate apoptosis of cells. For example, the level of Pretactilin can be increased in cells, preferentially in tumor cells, in vitro or in vivo, thereby inducing apoptosis. The level or the activity of Pretactilin can be increased in any of a number of ways, including by administering purified Pretactilin to the cells, transfecting the cells with a polynucleotide encoding Pretactilin, or administering a compound to the cells that causes an increase in the activity or expression of Pretactilin. Alternatively, apoptosis can be inhibited by decreasing the level or the activity of Pretactilin in cells, for example using antibodies, antisense molecules, ribozymes, or small molecule inhibitors of Pretactilin. In a preferred embodiment, Pretactilin is used to inhibit apoptosis of neuronal cells in patients suffering of neurodegenerative diseases, preferentially, Alzheimer's disease.

In another embodiment, the present invention provides a transgenic non-human animal, preferentially a mammal, more preferentially a rodent, producing high level of A beta peptide due to overproduction of Pretactilin. Such trangenic animal would provide a useful in vivo model to study the onset of Alzheimer's disease and more particularly to investigate the role of A beta peptide deposits in the etiology of the disease. It would also be of considerable interest for the screening of compounds that inhibit A beta peptide secretion or accumulation. Such transgenic animal can be obtained by any of the current methods used to generate transgenic animals that are well known for those skilled in the art, for example in the mouse, using DNA microinjection into fertilized eggs or transfection of embryonic stem cells. High over-expression of Pretactilin can be achieved by placing the nucleotide sequence encoding Pretactilin under the control of a strong promoter sequence. The promoter sequence can be derived from a gene having a broad expression in the animal or from a gene whose, expression is restricted to the brain. Preferentially, a regulatable promoter sequence is used in order to control temporally the expression of the transgene once introduced into the animal.

In another embodiment, the level or the activity of Pretactilin can be modulated to provide a treatment for Alzheimer's disease in a patient. Indeed as A beta peptide deposition is an early and invariant event in Alzheimer's disease, it is believed that a treatment that affects A beta production will be useful in the treatment of the disease. Accordingly, reducing level or activity of Pretactilin in mutant cells would thereby diminish A beta production. This could be achieved by any of the well known strategies used for therapy in vivo, for example using antisens molecules, antibody or small molecule inhibitors of Pretactilin.

Protein of SEQ ID NO 34: (Internal designation 145606_106-023-2-0-B3-F):

The cDNA of clone (SEQ ID NO:33) encodes the human MS4A5 protein, comprising the sequence:

MDSSTAHSPVFLVFPPEITASEYESTEL-SATTFSTQSPLQKLFARKMKILGTIQILFGIMTFSF GVIFLFTLLKPYPRFPFIFLSGYPFWGS-VLFINSGAFLIAVKRKTTETLIILSRIMNFLSALGAI AGIILLTFGFILDQNYICGYSHQNSQCK-AVTVLFLGILITLNTFSIIELFISLPFSILGCHSEDCD CEQCC (SEQ ID NO:34) Accordingly, it will be appreciated that all characteristics and uses of polypeptides of SEQ ID NO:34 described throughout the present application also pertain to the polypeptides encoded by the nucleic acids included in clone 145606_106-023-2-0-B3-F. In addition, it will be appreciated that all characteristics and uses of the polynucleotides of SEQ ID NO:33 described throughout the present application also pertain to the nucleic acids included in clone 145606_106-023-2-0-B3-F. A preferred embodiment of the invention is directed toward the compositions of SEQ ID NO:33, SEQ ID NO:34, and Clone 145606106-023-2-0-B3-F. Also preferred are polypeptide fragments having a biological activity as described herein and the polynucleotides encoding the fragments.

The cDNA of SEQ ID NO:33 comprising 5 exons encodes the 200 amino-acid MS4A5 protein (STR Q9H3V2), which belongs to the MS4A protein family (membrane-spanning four-domains, subfamily A). Four members of MS4A family in human (MS4A4-7) and in mouse (MS4A8-11) have been described (Ishibashi K. et al, Gene (2001), 264: 87-83), which disclosure is hereby incorporated by reference in its entirety). As with the other members of the CD20/Fc(sigma) RI(beta)/HTm4 superfamily, all MS4A proteins are highly hydrophobic, with four transmembrane domains (but are distinct from tetraspanin family members which also have four transmembrane domains). The cDNA of SEQ ID NO:33 encoding the protein of SEQ ID NO:34 possesses a conserved sequence around the initiating methionine (ATC ATG G), and a consensus protein kinase A (PKA) phosphorylation site (KRKTT) at the intracellular loop between the second and third transmembrane domains. In contrast with other members of MS4A family, which are mostly expressed in lymphoid tissues, MS4A5 is expressed in testis, pancreas, and at low levels in the heart and brain. The gene of MS4A5 is located on human chromosome 11, specifically at position 11q12, the same chromosome as the CD20, Fc(sigma)RI (beta) and HTm4 genes. MS4A5 is a novel transmembrane protein that acts alone or in combination with other proteins as an ion channel, e.g. a ligand-gated calcium channel. MS4A5 is involved in a number of cellular functions in non-lymphoid cells, for example intracellular signaling, regulating intracellular calcium concentrations, exocrine functions, and endocrine functions.

In one embodiment, the protein of the invention or fragment thereof provides a method to detect cells specifically expressing the present protein, using for example flow cytometry technology or classical in situ detection techniques which are well known in the art. Such methods are useful, e.g. to specifically detect cells of the testis, pancreas, heart, or brain, as the present protein is highly expressed in these cell types. Such methods are also useful to detect cells over- or under-expressing the present protein, and is thus useful for diagnosing diseases or conditions resulting from or associated with an increase or decrease in expression or activity of the protein. This method includes the steps of contacting a biological sample obtained from an individual suspected of suffering from the disease or condition, or at risk of developing the disease or condition, with a compound capable of selectively binding the present protein or nucleic acids, e.g. an antibody directed against the present protein or a polynucleotide probe directed against the present cDNA. Following this binding step, the method further comprises detecting the presence or absence of selective binding between the compound and the cells or proteins within the sample. In preferred embodiments, the compound is labeled, and the sample comprises cells derived from the testis, pancreas, heart, or brain.

In another embodiment, the protein of the invention or fragment thereof can be used to modulate the proliferation of cells. For example, the level or activity of the present protein can be increased in cells to increase the rate or extent of proliferation of the cells. In one such embodiment, the proliferation of cells in a biological sample is increased by contacting the biological sample with an amount of the present protein sufficient to increase the rate or extent of proliferation of one or more cells within the sample, or with a compound that increases the activity or expression of the present protein within one or more cells of the sample. Such methods can be performed either in vitro or in vivo and, preferably, the cells comprise pancreatic, testicular, heart or brain cells. The level of the present protein can be increased in cells in any of a number of ways, including by administering purified protein to the cells, transfecting the cells with a polynucleotide encoding the protein, or administering a compound to the cells that causes an increase in the activity or expression of the protein. Alternatively, proliferation of cells can be inhibited by decreasing the level of the present protein in cells, for example using antisense molecules, or more specifically inhibit the activity of the present protein using direct or indirect inhibitor molecules or antagonistic antibodies directed against the present protein.

In a further embodiment, the protein of the invention or fragment thereof can be used to modulate cellular calcium concentration and thereby modulate calcium-dependant signaling. Calcium transport can be modulated, for example, by contacting a biological sample with an amount of the present protein sufficient to increase calcium transport of one or more cells within the sample, or with a compound that increases the activity or expression of the present protein within one or more cells of the sample. Such methods can be used either in vitro or in vivo and preferably, but not limited to, the methods are performed on cells comprising pancreatic, testicular, heart or brain cells. The level of the present protein can be increased in cells in any of a number of ways, including by administering purified protein to the cells, transfecting the cells with a polynucleotide encoding the protein, or administering a compound to the cells that causes an increase in the activity or expression of the protein. Alternatively, the activity of the present protein can be inhibited by decreasing the level of the present protein in cells, for example using antisense molecules, by using direct or indirect inhibitor molecules or antagonistic antibodies of the present protein, or by expressing in the cells an inactive form of the protein that acts in a dominant negative fashion to inhibit the normal calcium signalling in the cells carried out by other members of the MS4A family.

The present invention also provides animal models generated by modulating the expression or activity of the, present protein in one or more tissues of the animal. Such animals represent an in vivo assay method for testing candidate molecules potentially useful for the treatment of various pathophysiological aspects of diseases associated with abnormal calcium homeostasis and/or cell growth or any function specifically related to the activity of the present protein. These animals can be generated with any method of increasing or decreasing the expression of the present protein.

In another embodiment, since calcium is an universal intracellular messenger, controlling a diverse range of cellular processes such as gene transcription, cell proliferation, and more specifically muscle contraction, synaptic function, secretion of insulin in pancreatic islets of Langerhans, and many others, the present protein or fragment thereof provides a method of treating different pathological states arising from or associated with destabilization of calcium homeostasis in many organs (brain, kidney, parathyroid gland, pancreas, bone, intestine). In addition, any of these processes can be enhanced or inhibited in cells or in patients, even when the protein is at normal levels in the cells or in the cells of the patient, by causing a decrease or increase in the normal level of the protein in the cells. For any of the herein-described methods, the activity of the present protein can be increased or inhibited in any of a large number of ways, for example by using polyclonal or monoclonal antibodies, or any other compound having qualitative biological activity in common with a full-length antibody, that specifically binds to the present protein and exerts stimulatory or inhibitory effects on functions involving the present protein.

Any compound interacting with the present protein and thereby promoting or interfering with its activities can also be used as a method of treating any of the pathologies described above. Such compounds can be identified, e.g., using interaction-screening approaches such as, but not limited to, co-immunoprecipitation, two-hybrid methods. Further, compounds can be screened for the ability to modulate the activity of the present protein by providing a cell expressing the present protein, or providing lipid bilayers reconstituted with the present protein, and detecting the ability of a compound to modulate the activity of the present protein in the cell or in the bilayer. Such activity can be detected in any of a large number of ways, including but not limited to detecting calcium flux or calcium signalling in the cells or membranes, e.g. as manifest in the activity of downstream members of the signal transduction pathway. The present invention also provides an in vitro method to identify any compound able to promote or interfere with some or all activities of the present protein, the method comprising the steps of contacting the present protein with a test compound and detecting the ability of the compound to bind to or modulate the activity of the protein. Also in this embodiment, the present protein or any effective compound identified by this way of investigation useful for the treatment of disorders described above can be used in combination with other drugs or compounds.

As it has been shown that multiple loci on chromosome 11q 13 are relevant to atopic asthma (Adra CN et al, Clin. Genet. (1999) June; 55(6):431-437), the present invention also provides a novel candidate gene for this condition. Accordingly, the present invention provides methods for the diagnosis of atopic asthma, the method comprising determining the identity of one or more nucleotides of the present nucleic acids in one or more cells of an individual suspected of having the condition, or at risk of developing the condition, and determining if the cell or cell contains a nucleotide within the present nucleic acid sequence indicative of the condition, or of an elevated risk of developing the condition. The identity of such nucleotides can be determined in any of a number of ways, for example using any standard sequencing or genotyping method, many of which are well known in the art.

Protein of SEQ ID NO:36 (Internal designation Clone 1000769575_208-22-1-0-B2-F)

The cDNA of Clone 1000769575_208-22-1-0-B2-F (SEQ ID NO:35) encodes the protein of SEQ ID NO:36 comprising the amino acid sequence MGMSSLKLLKYVLFFFNLLFWICGC-CILGFGIYLLIHNNFGVLFFINLPSLTLGNVFVIVGSII MVVAFLGCMGSIKENKCLLMSFFILLLI-ILLAEVTLAILLFVAKGLTDSIHRYHSDNSTKAA WDSIQSFLQCCGINGTSDWTSGPPAS-CPSDRKVEGCYAKARLWFHSNFFIRGPY (SEQ ID NO:136). Accordingly it will be appreciated that all characteristics and uses of polypeptides of SEQ ID NO:36 described throughout the present application also pertain to the polypeptides encoded by the nucleic acids included in Clone 1000769575_208-22-1-0-B2-F. In addition, it will be appreciated that all characteristics and uses of the polynucleotides of SEQ ID NO:35 described throughout the present application also pertain to the nucleic acids included in Clone 1000769575_208-22-l-0-B2-F. A preferred embodiment of the invention is directed toward the compositions of SEQ ID NO:35, SEQ ID NO:36, and Clone 1000769575_208-22-l-0-B2-F. Also preferred are polypeptide fragments having a biological activity as described herein and the polynucleotides encoding the fragments.

The protein of SEQ. ID NO:36 encodes Antaginin, a complex splice variant of CD53 with novel function. In Antaginin, splicing of exon 4 onto exon 5 results in a deletion of 9 amino acids (4 from exon 4, 5 from exon 5) and a correspondingly unique junctional sequence. In addition, splicing of exon 7 onto normally 3'-untranslated nucleotide sequence within exon 8 results in a deletion of 14 amino acids from exon 7, as well as the deletion of the carboxy-terminal 23 amino acids of CD53 and its replacement with a unique carboxy-terminal sequence of 6 amino acids in Antaginin.

CD53, restricted in expression to leukocytes, is a member of the tetraspaninin superfamily CD53 is an integral membrane protein characterized by four transmembrane domains (TM1-TM4), forming a small and a large extracellular loop(EC1 and EC2, respectively), with short intracellular amino and carboxyl tails. EC1 and EC2 of CD53 comprise the amino acid sequences 37-54 and 107-181, respectively (numbered from the initiating methionine of CD53). TM1-TM4 of CD53 comprise the amino acid sequences 11-36, 55-69, 81-106, and 182-206, respectively (numbered from the initiating methionine of CD53) (Rost, B. et al., Prot. Sci. 5:1704-18, (1996) which disclosure is hereby incorporated by reference in its entirety).

CD53 facilitates the assembly of modular signalling complexes at the cell surface. Specifically, CD53 acts as an adaptor to functionally link an extracellular ligand-binding domain (such as that of beta 1 integrin) to an intracellular domain involved in signal transduction (such as that of protein kinase C) (Zhang, XA et al., J. Biol. Chem. (2001) which disclosure is hereby incorporated by reference in its entirety). Beta 1 integrin has been shown to associate with CD53 through EC2. Moreover, through its interaction with other tetraspaninins, CD53 is incorporated into a higher order tetraspaninin web exisiting at the cell surface. CD53 displays numerous properties that indicate its physiological importance in cell adhesion, motility, activation (including the delivery of a co-stimulatory signal to for CD3/T. cell receptor-mediated T cell activation), and proliferation (Boucheix, C. et al. Expert Reviews in Molecular. Medicine (2001) which disclosure is hereby incorporated by reference in its entirety).

Antaginin is characterized by a highly perturbed EC2 loop and a highly divergent TM4 transmembrane domain. The EC2/TM4 region of Antaginin comprises amino acids 107-179 (numbered from the initiating methionine of Antagmnin). In addition, Antaginin is characterized by an extracelluar perturbation of the amino acid sequence at the junction of exons 4 and 5(amino acids 124/125, numbered from the initiating methionine of Antaginin). (Rost, B. et al., Prot. Sci. 5:1704-18, (1996) which disclosure is hereby incorporated by reference in its entirety). Antaginin antagonizes CD53-facilitated assembly of functional modular signalling complexes at the cell surface.

In a preferred embodiment, the present invention provides for an antibody that specifically binds Anataginin of the present invention. Further preferred is a method for making such antibody wherein a mouse is immunized with a syngeneic cell line transfected with Antaginin. Monoclonal antibodies derived from said mouse are screened for binding to the Antaginin-transfected cell line but not to the identical cell line transfected with human CD53. Antibody specificity is further established through amino acid sequence analysis of immunoprecipitated material. Further preferred is a method for making said antibody wherein said antibody binds to EC1 or the sequence carboxyl-terminal (EC2/TM4 region) of Antaginin. EC1 and the EC2/TM4 region of Antaginin comprise the amino acid sequences 37-54 and 107-179, respectively (numbered from the initiating methionine of Antaginin). Further preferred is a method for making said antibody wherein said antibody binds to the EC2/TM4 region of Antaginin. Methods of generating said monoclonal antibody and of establishing its specificity are well known to those skilled in the art.

In a preferred embodiment, the present invention provides for a method of contacting said antibody and specifically binding it with Antaginin. Further preferred is a method for using said antibody diagnostically to determine the basis for an impaired immune response. Further preferred is a method of using said antibody diagnostically in a flow cytometric analysis of Antaginin expression by leukocytes in a pathological context. Further preferred is a method of using said antibody diagnostically in a flow cytometric analysis of Antaginin expression by leukocytes in the context of viral infection wherein the virus is selected from, but not restricted to, the group consisting of: (a) Cytomegalovirus; (b) Human immunodeficiency virus; (c) Human herpes virus 6 (HHV 6); (d) Hepatitis C virus; and (e) Hepatitis D virus.

Further preferred is a method of using said antibody diagnostically in a flow cytometric analysis of Antaginin expression by normal leukocytes in the leukemic patient to determine the basis for an impaired anti-tumor immune response wherein the leukemia is selected from, but not restricted to, the group consisting of: (a) B cell acute lymphoblastic leukemia (B-ALL); (b) Chronic lymphocytic leukemia (CLL); (c) T cell acute lymphoblastic leukemia (T-ALL); (d) Multiple myeloma; and (e) Acute myeloid leukemia (AML).

Further preferred is a method of using said antibody diagnostically in a flow cytometric analysis of Antaginin expression by normal leukocytes in the cancer patient to determine the basis for an impaired anti-tumor immune response wherein the cancer is selected from, but not restricted to, the group consisting of: (a) Melanoma; (b) Breast carcinoma; (c) Lung carcinoma; (d) Colon carcinoma; (e) Hodgkin's lymphoma; (f) Non-Hodgkin's lymphoma; (g) Prostatic carcinoma; (h) Pancreatic carcinoma; (i) Uterine carcinoma; (j) Ovarian carcinoma; (k) Testicular carcinoma; (l) Renal carcinoma; (m) Hepatic carcinoma; and (n) Lung non-small-cell carcinoma.

The threshold for leukocyte activation can be regulated by cytokine. In a further embodiment, the present invention provides for the use of said Antaginin antibody in in vitro analysis of cytokine regulation of Antaginin expression by leukocytes. Further preferred is a method of using said antibody in a flow cytoinetric analysis of said regulation by cytokine wherein the cytokine is selected from, but not restricted to, the group consisting of: (a) Interferon gamma; (b) Interleukin 17; (c) Interleukin 4; (d) Interleukin 10; (e) Interleukin 13; (f) Interleukin 15; (g) Interleukin 1; (h) Interleukin 6; (i) Monocyte chemotactic protein 1 (MCP-1); (j) Interleukin 8; and (k) Tumor necrosis factor alpha.

Further preferred is a method of contacting said antibody with Antaginin and thereby sterically inhibiting the capacity of Antaginin to antagonize the CD53-facilitated assembly of functional modular signalling complexes at the cell surface. In so doing, said Antaginin antibody up-regulates CD53-mediated leukocyte activation. Preferred compositions comprise the Antaginin antibody or fragments or derivatives thereof. Preferred route of administration is intravenous injection.

In a further, embodiment of the invention, said Antaginin antibody is incorporated as an adjuvant in vaccine preparations in a method to up-regulate the elicited immune response. In said method, said Antaginin antibody facilitates the CD53-mediated leukocyte activation contributing to establishment of specific immunity. Said Antaginin antibody up-regulates CD53-mediated leukocyte activation by sterically inhibiting the capacity of Antaginin to antagonize the CD53-facilitated assembly of functional modular signaling complexes at the cell surface. Further preferred is a method to use said antibody in a vaccine targeting a viral infection wherein the virus is selected from, but not restricted to, the group consisting of: (a) Human immunodeficiency virus; (b) Human herpes virus 6 (HHV 6); (c) Hepatitis C virus; (d) Hepatitis D virus; (e) Hepatitis E virus; (f) *Cytomegalovirus*; (g) Respiratory syncytial virus; (h) Herpes simplex virus type I; (i) Herpes simplex virus type II; (j) Influenza virus; (k) *Parvovirus*; (l) Coxsachie virus; (m) Echovinis; (n) Epstein-Barr virus; (o) Dengue virus; (p) Lassa fever virus; and (q) Ebola virus.

Further preferred is a method to use said Antaginin antibody in a vaccine targeting a protozoan infection wherein the protozoa is selected from, but not restricted to, the group consisting of: (a) *Entamoeba histolytica*; (b): *Cryptosporidium parvum*; (c) *Plasmodium falciparum*; (d) *Trypanosoma*; (e) *Leishmania*; (f) *Trichomonas vaginalis*; and (g) *Acanthamoeba.*

Viruses can suppress the immune response as a means of evading immune surveillance. In a further embodiment of the invention, said Antaginin antibody is used in a method of up-regulating the immune response against an ongoing viral infection. In said method, said Antaginin antibody facilitates the CD53-mediated leukocyte activation contributing to the anti-viral immune response. Said Antaginin antibody up-regulates CD53-mediated leukocyte activation by sterically inhibiting the capacity of Antaginin to antagonize the CD53-facilitated assembly of functional modular signaling complexes at the cell surface. Further preferred is a method of up-regulating the immune response against an ongoing viral infection wherein the virus is selected from, but not restricted to, the group consisting of: (a) Human immunodeficiency virus; (b) Human herpes virus 6 (HHV 6); (c) Hepatitis B. virus; (d) Hepatitis C virus; (e) Hepatitis D virus; (f) Cytomegalovirus; (g) Respiratory syncytial virus; (h) Influenza virus; (i) Herpes simplex virus type I; 6). Herpes simlex virus type II; (k) Epstein Barr virus; (l) *Varicella zoster* virus; (m) Morbillivirus; (n) Parmyxovirus; (O). Papilloma virus; (p) Adenovirus; (q) Dengue virus; (r) Lassa fever virus; (s) Coxsachie virus; (t) Echovirus; and (u) Ebola virus.

Bacteria can suppress the immune response as a means of evading immune surveillance. In a further embodiment of the invention, said Antaginin antibody is used in a method of up-regulating the immune response against an ongoing bacterial infection. In said method, said Antaginin antibody facilitates the CD53-mediated leukocyte activation contributing to the anti-bacterial immune response. Said Antaginin antibody up-regulates CD53-mediated leukocyte activation by sterically inhibiting the capacity of Antaginin to antagonize the CD53-facilitated assembly of functional modular signaling complexes at the cell surface. Further preferred is a method of up-regulating the immune response against an ongoing bacterial infection wherein the bacteria is selected from, but not restricted to, the group consisting of: (a) *Mycobacterium avium* complex; (b) *Pneumocystis carinii*; (c) Acne vulgaris; (d) *Legionella pneumophilia*; (e) *Yersinia pestis*; (f) *Ureaplasma urealyticum*; (g) *Chlamydia pneumoniae*; (h) *Helicobacter pylori*; (i) *Treponema pallidum*; (j) *Neisseria gonorrhoeae*; (k) *Salmonella typhimurium*; (l) *Vibrio cholera*; (m) *Clostridium difficile*; (n) Bacillary dysentery; (o) Pencillin resistant *Pneumococcus*; (p) *Burkholderia mallei*; (q) *Mycobacterium leprae*; (r) *Mycobacterium* haemophilum; (s) *Mycobacterium kansasii*; (t) *Haemophilus influenzae*; and (u) *Bacillus anthracis.*

Protozoa can suppress the immune response, as a means of evading immune surveillance. In a further embodiment of the invention, said Antaginin antibody is used in a method of up-regulating the immune response against an ongoing protozoan infection. In said method, said Antaginin antibody facilitates the CD53-mediated leukocyte activation contributing to the anti-protozoan immune response. Said Antaginin antibody up-regulates CD53-mediated leukocyte activation by sterically inhibiting the capacity of Antaginin to antagonize the CD53-facilitated assembly of functional modular signaling complexes at the cell surface. Further preferred is a method of up-regulating the immune response against an ongoing protozoan infection wherein the protozoa is selected from, but not restricted to, the group consisting of. (a) Entamoeba histolytica; (b) *Cryptosporidium parvurm* (c) *Giardia lamblia*; (d) *Toxoplasma gondii*; (e) *Isospora belli*; (f) *Encephalitozoon cuniculi*; (g) *Enterocytozoon bieneusi*; (h) *Plasmodium falciparum*; (i) *Trypanosoma*; (j) *Leishmania*; (k) *Trichomonas vaginalis*; and (1) *Acanthwnoeba.*

In a further embodiment of the invention, said Antaginin antibody is used in a method of up-regulating the immune response against an ongoing fungal infection wherein the fungus is selected from, but not restricted to, the group consisting of: (a) *Cryptococcal meningitis*; (b) *Histoplasma capstulatum*; (c) *Coccidiodes immitis*; and (d) *Candida albicans.*

Tumors can suppress the immune response as a means of evading immune surveillance. In a further embodiment of the invention, said Antaginin antibody is used in a method of up-regulating the immune response against a tumor. In said method, said Antaginin antibody facilitates the CD53-mediated leukocyte activation contributing to the anti-tumor immune response. Said Antaginin antibody up-regulates CD53-mediated leukocyte activation by sterically inhibiting the capacity of Antaginin to antagonize the CD53-facilitated assembly of functional modular signaling complexes at the cell surface. Further preferred is a method of up-regulating the immune response against a tumor wherein the tumor is selected from, but not restricted to, the group consisting of: (a) Melanoma; (b) Breast carcinoma; (c) Lung carcinoma; (d) Colon carcinoma; (e) Hodgkin's lymphoma; (f) Non-Hodgkin's lymphoma; (g) Prostatic carcinoma; (h) Pancreatic carcinoma; (i) Uterine carcinoma; (j) Ovarian carcinoma; (k) Testicular carcinoma; (l) Renal carcinoma; (m) Hepatic carcinoma; and (n) Lung non-small-cell carcinoma.

In a further embodiment of the invention, said Antaginin antibody is incorporated as an adjuvant in therapeutic anti-tumor vaccines wherein the tumor is selected from, but not restricted to, the group consisting of: (a) Melanoma; (b) Breast carcinoma; (c) Lung carcinoma; (d) Colon carcinoma; (e) Hodgkin's lymphoma; (f)Non-Hodgkin's lymphoma; (g) Prostatic carcinoma; (h) Pancreatic carcinoma; (i) Uterine carcinoma; ( ). Ovarian carcinoma; (k) Testicular carcinoma; (l) Renal carcinoma; (m) Hepatic carcinoma; and (n) Lung non-small-cell carcinoma.

Intracellular (macrophage) pathogens can be eliminated either through macrophage activation or through lysis of infected macrophages by, cytolytic T lymphocytes (Chun et al., J. Exp. Med. 193:1213 (2001) which disclosure is hereby incorporated by reference in its entirety).

In a further embodiment of the invention, said Antaginin antibody is used in a method to eliminate intracellular pathogens by facilitating macrophage activation or cytolytic T lymphocyte generation wherein the pathogen is selected from, but not restricted to, the group of intracellular. (macrophage). pathogens consisting of: (a) *Histoplasma capsu-*

*latum*; (b) *Mycobacterium tuberculosis*; (c) *Salmonella typhimurim*; (d) *Chlamydia trachomatis*; and (e) *Pneumocystis carinii*.

There have been several examples of tetraspanins playing a role in the viral life cycle. Anti-tetraspanin antibodies inhibit syncytium formation and/or virus production. This was observed for the tetraspanins CD81 and CD82 with human T4hymphotropic virus 1, and for the tetraspanin CD9 with the feline immunodeficiency virus and the canine distemper virus. It is also believed that the tetraspanin CD81 also plays a role in the aetiopathogenesis of hepatitis C virus (Boucheix, C. et al. (2001) which disclosure is hereby incorporated by reference in its entirety). In a further embodiment of the invention, said Antaginin antibody is used in a method of blocking viral infection when Antaginin is used as a virus receptor. Further preferred is the use of said Antaginin antibody in a method of blocking said viral infection when Antaginin used as said virus receptor and is expressed by a leukocyte type selected from, but not restricted to, the group of leukocyte types consisting of: (a) T lymphocyte; (b) B lymphocyte; (c)NK lymphocyte; (d) Monocyte; (e) Macrophage; (f) Neutrophil; and (g) Dendritic cell.

In a further preferred embodiment, the present invention provides for a method of screening test compounds for the ability to bind Antaginin and either inhibit or promote the capacity of Antaginin to interfere with CD53 function. Further preferred is a method of screening said test compounds for the ability to bind Antaginin and either inhibit or promote the capacity of Antaginin to interfere with CD53 function as it relates its facilitation of signal transduction through beta 1 integrin (Zhang, X A et al., J. Biol. Chem. (2001) which disclosure is hereby incorporated by reference in its entirety). Further preferred is a method of screening said test compounds for the ability to bind Antaginin and either inhibit or promote the capacity of Antaginin to interfere with the CD53-facilitated association of protein kinase C with beta 1 integrin. Further preferred is a method of screening said test compounds for the ability to bind Antaginin and either inhibit or promote the association of protein kinase C. with beta 1 integrin in a beta 1 (alpha3beta1, alpha4beta1, or alpha6beta1)-expressing cell line transfected with CD53 and Antaginin but not in the identical cell line transfected with CD53 alone. Methods of screening said test compounds and for characterizing their effect on CD53-facilitated association of protein kinase C with beta 1 integrin are well known to those skilled in the art.

Preferred formulation of said compound is that selected from, but not restricted to, formulations compatible with the routes of delivery selected from the group: (a) Oral; (b) Transdermal; (c) Injection; (d) Buccal; and (d) Aerosol.

Compounds found to bind Antaginin and to inhibit the capacity of Antaginin to interfere with CD53 function, thereby effectively up-regulating CD53 activity, are used in methods analogous to those described above for Antaginin antibody.

Compounds found to bind Antaginin and to promote the capacity of Antaginin to interfere with CD53 function effectively down-regulate CD53 activity. Such compounds have application to chronic inflammatory autoimmune disease and to other disorders of immune dysregulation. Such compounds down-regulate CD53-mediated leukocyte activation by promoting the capacity of Antaginin to antagonize the CD53-facilitated assembly of functional modular signaling complexes at the cell surface. In a further embodiment of the invention, said compound is used in a method of contacting Antaginin to down-regulate a dysregulated immune response and thereby treat the associated immune disorder wherein said immune disorder is selected from, but not restricted to, the group: (a) Rheumatoid arthritis; (b) Inflammatory bowel disease; (c) Insulin dependent diabetes mellitus (Type 1 diabetes); (d) Multiple sclerosis; (e) Systemic lupus erythematosus; (f) Psoriasis; (g) Allergic asthma; (h) Allergic rhinitis (hayfever); and (i) Graft versus host disease. In a further embodiment of the invention, said test compound having the ability to promote the capacity of Antaginin to interfere with CD53 function is used in a method to suppress acute inflammation. Said test compounds down-regulate CD53-mediated leukocyte activation by promoting the capacity of Antaginin to antagonize the CD53-facilitated assembly of functional modular signalling complexes at the cell surface. Further preferred is a method to use said test compound to suppress inflammation associated with wound healing. Further preferred are compositions comprised of said test compound used in methods of contacting a wound or injured tissue with an ameliorative effective amount by injection or transdermal contact at the site of the wound.

Protein of SEQ ID NO:38 (Internal designation Clone 146994_106-023-4-0-C9-F)

The cDNA of Clone 146994_106-023-4-0-C9-F (SEQ ID NO:37) encodes the protein of SEQ. ID NO:38 comprising the amino acid sequence:

MSPGQPMTFPPEALWVTVGLSV-CLIALLVALAFVCWRKIKQSCEEENA-GAEDQDGEGEGS KTALQPLKHSDSKEDDGQEIA. Accordingly it will be appreciated that all characteristics and uses of polypeptides of SEQ ID NO:38 described throughout the present application also pertain to the polypeptides encoded by the nucleic acids included in Clone 146994_106-0-234-0-C9-F. In addition, it will be appreciated that all characteristics and uses of the polynucleotides of SEQ ID NO: 37 described throughout the present application also pertain to the nucleic acids included in Clone 146994_106-023-4-0-C9-F. A preferred embodiment of the invention is directed toward the compositions of SEQ ID NO:37, SEQ ID NO:38, and Clone 146994_106-0-234-0-C9-F. Also preferred are polypeptide fragments having a biological activity as described herein and the polynucleotides encoding the fragments.

The protein of SEQ ID NO:38 encodes Beferin. Beferin is a novel splice variant of two recently described members of the B lymphocyte activation antigen B7. (BLAA) family, B7-H3 and Blaa. Beferin has novel function as described below.

B7-H3 was identified as a human B7-like molecule with T lymphocyte costimulatory activity. (Chapoval, AI et al., Nature Immunology 2:269-74 (2001) which disclosure is hereby incorporated by reference in its entirety). B7-H3 has the structure:

[Signal peptide]-[IgV-like domain 1]-[IgC-like domain 2]-[transmembrane region]-[cytoplasmic tail].

Blaa (NCBI Accession No. AX097550) was identified as a human B7like molecule, as described in Patent Application WO 00118204A1 ("Polynucleotides encoding members of the human B lymphocyte activation antigen B7 family and polypeptides encoded thereby") and incorporated by reference in its entirety. Blaa has the structure:

[Signal peptide]-[IgV-Iike domain 1]-[IgC-like domain l]-[IgV-like domain 2]-[IgC-like domain 2]–[transmembrane region]–[cytoplasmic tail]

Blaa (NCBI Accession No. AX047070) was independently identified as a protein with beta-secretase (betaamyloid-converting enzyme) activity, as described in Patent Application WO00068266A1 ("Amyloid precursor protein protease and related nucleic acid compositions"). and incorporated by reference in its entirety. The amino acid sequence of AX947070 is identical to that of AX097550.

IgV-like domain 1 is highly similar, but not identical, to the amino acid sequence of IgV-like domain 2. IgC-like domain 1 is highly similar, but not identical, to the amino acid sequence of IgC-like domain 2.

In the case of Beferin, a novel 5' exon is spliced directly onto the exons encoding the transmembrane region and cytoplasmic tail. This results in the deletion of the IgV-like and IgC-like extracellular domains. The short extracellular tail of Beferin is comprised of approximately seven amino acids shared with B7-H3 and Blaa preceded by three novel (not found in either. B7-H3 or Blaa) N-terminal amino acids encoded by the novel 5' exon (underlined here): MSPGQP-MTFP.

Costimulation, in addition to T cell receptor engagement, is required for optimal activation of T cells. The most extensively studied costimulatory molecules are members of the B lymphocyte activation antigen B7 family, of which there are presently five. Each B7 family member binds to one or more counter-receptor on the T cell, of which there are presently four. B7-H 3 is highly expressed in many human tissues including heart, liver, placenta, prostate, testis, uterus, pancreas, small intestine, and colon. Low expression of B7-H3 was also found in brain, skeletal muscle, kidney, and lung. B7-H3 is not detectable in peripheral blood mononuclear cells, although it can be induced on dendritic cells and monocytes by inflammatory cytokines. Several tumor lines also express B7-H3, including those derived from melanoma, cervical adenocarcinoma, chronic myelogenous leukemia, lung carcinoma, and colorectal adenocarcinoma. B7-H3 costimulates proliferation of both $CD4^{+}$and $CD8^{+}$ T cells, enhances the induction of cytotoxic T lymphocytes (CTL), and selectively stimulates proinflammatory cytokine interferon gamma (IFNgamra) production in the presence of T cell receptor signaling. B7-H3 exists as non-covalent oligomers on the antigen-presenting cell, and this is important for high-avidity binding of B7-H3 to its counter-receptor in its role as T cell costimulator.

In non-neuronal tissue, Blaa cleaves the 751 amino acid isoform of amyloid beta protein precursor (APP751) at the cell surface by virtue of its beta-secretase activity to generate a soluble fragment identical to the serine protease inhibitor protease nexin 2 (PN2). PN2 and its Kunitz protease inhibitory domain have been shown to be inhibitors of coagulation factor VIIa (FVIIa) and factor VIIa-tissue factor complex (FVIIa-TF)(Mahdi, F et al., Thromb. Res. 99:267-76 (2000). which disclosure is hereby incorporated by reference in its entirety) initiators of the extrinsic coagulation cascade. TF expression and its engagement of the extrinsic coagulation pathway by ovarian cancer cells has been shown to play role in metastasis of the cancer (Fischer, EG et al., J. Clin. Invest. 104:1213-21 (1999) which disclosure is hereby incorporated by reference in its entirety). Factor Xa (FXa) generated by FVIIa-TF has been shown to lead to pro-inflamnmatory activation of vascular endothelial cells through its cleavage of protease-activated receptor 2 (PAR2) (Camerer, E et al., Proc. Natl. Acad. Sci. USA 97:5255-60 (2000) which disclosure is hereby incorporated by reference in its entirety). FXa can also elicit a pro-inflammatory cellular response by cleavage of protease-activated receptor 1 (PAR1). (Kravchenko, R M Blood 97:3109-16 (2001) which disclosure is hereby incorporated by reference in its entirety).

Beferin interferes with B7-H3 co-stimulation of *T lymphocytes* through its non-productive incorporation into B7-H3 oligomers at the cell surface. One function of Beferin therefore is to negatively regulate T lymphocyte co-stimulation. In a pathological context, Beferin up-regulation facilitates evasion of immune surveillance by pathogens and tumor cells.

Beferin interferes with Blaa generation of PN2 through its non-productive interactions with APP751. A second functional consequence of Beferin expression is therefore up-regulated engagement of the extrinsic coagulation coagulation pathway, including the generation of FXa. In a pathological context, Beferin up-regulation facilitates hypercoagulability, and cancer metastasis.

In a preferred embodiment, the present invention provides for an antibody that specifically binds Beferin of the present invention. Further preferred is a method for making such antibody wherein a mouse is irnunumized with a syngeneic cell line transfected with Beferin. Monoclonal antibodies derived from said mouse are screened for binding to the Beferin-transfected cell line but not to the identical cell line transfected with human B7-H3 or Blaa. Antibody specificity is further established through amino acid sequence analysis of inumunoprecipitated material. Further preferred is a method for making said antibody wherein said antibody specifically binds all or in part to the extracellular amino terminus of Beferin. The extracellular amino terminus of Beferin is comprises the amino acid sequence 1-10 (numbered from the initiating methiorine of Beferin). Methods of generating said monoclonal antibodv and of establishing its specificity are well known to those skilled in the art.

In a preferred embodiment, the present invention provides for a method of contacting said antibody and specifically binding it with Beferin. Further preferred is a method for using said antibody diagnostically to determine the basis for an impaired immune response or for hypercoagulability. Further preferred is a method of using said antibody diagnostically in a flow cytometric analysis of Beferin expression by leukocytes in a pathological context. Further preferred is a method of using said antibody diagnostically in an immunohistochemical analysis of Beferin expression by tissue in a pathological context. Methods of carrying out immunohistochemical or flow cytometric analysis are well known to those skilled in the art.

Further preferred is a method of using said antibody diagnostically in a flow cytometric analysis of Beferin expression by normal leukocytes and leukemia cells in the leukemic patient to determine the basis either for an impaired anti-tumor immune response or for hypercoagulability wherein the leukemia is selected from, but not restricted to, the group consisting of: (a) B cell acute lymphoblastic leukemia (B-ALL); (b) Chronic lymphocytic leukemia (CLL); (c) T cell acute lymphoblastic leukemia (T-ALL); (d) Multiple myeloma; and (f) Acute myeloid leukemia (AML).

Further preferred is a method of using said antibody diagnostically in a flow cytometric analysis of Beferin expression by leukocytes in a patient with viral infection to determine the basis either for an impaired anti-viral immune response or for hypercoagulability wherein the virus is selected from, but not restricted to, the group consisting of: (a) *Cytomegalovirus*; (b) Human herpes virus 6(HV 6); (c) Human immunodeficiency virus; (d) Hepatitis C virus; and (e) Hepatitis D virus.

Further preferred is a method of using said antibody diagnostically in an immunohistochemical analysis of Beferin expression by tissue to determine the basis for hypercoagulability wherein said tissue is.selected from, but not restricted to, the group consisting of: (a) Heart; (b) Liver; (c) Placenta; (d) Prostate; (e) Testis; (f) Uterus; (g) Pancreas; (h) Small intestine; (i) Colon; (j) Kidney; and (k) Lung.

Further preferred is a method of using said antibody diagnostically in an immunohistochemical analysis of Beferin expression by tumor cells to determine the basis either for an impaired anti-tumor immune response or for hypercoagulability wherein the tumor cell is selected from, but not restricted to, the group consisting of: (a) Melanoma; (b) Breast carcinoma; (c) Lung carcinoma; (d) Colon carcinoma; (e) Hodgkin's lymphoma; (f) Non-Hodgkin's lymphoma; (g) Prostatic carcinoma; (h) Pancreatic carcinoma; (i) Uterine carcinoma; (o) Ovarian carcinoma; (k) Testicular carcinoma; (l). Renal carcinoma; (m) Hepatic carcinoma; and (n) Lung non-small-cell carcinoma.

The efficiency of T lymphocyte co-stimulation, as well as coagulability status, can be regulated by cytokine. In a further embodiment, the present invention provides for the use of said Beferin antibody in in vitro analysis of cytokine regulation of Beferin expression by normal leukocytes. Further preferred is a method of using said antibody in a flow cytometric analysis of said regulation by cytokine wherein the cytokine is selected from, but not restricted to, the group, consisting of: (a) Interferon gamma; (b) Interleukin 17; (c) Interleukin 4; (d) Interleukin 10; (e) Interleukin 13; (f) Interleukin 15; (g) Interleukin 1; (h) Interleukin 6; (i) Monocyte chemotactic protein 1 (MCP-1); (j) Vascular endothelial growth factor (VEGF); (k) Transforming growth factor beta; (l) Interleukin 8; and (m) Tumor necrosis factor alpha.

In a further embodiment, the present invention provides for the use of said Beferin antibody in in vitro analysis of cytokine regulation of Beferin expression by non-leukocytic cell lines. Further preferred is a method of using said antibody in a flow cytometric analysis of said regulation by cytokine wherein the cytokine is selected from, but not restricted to, the group consisting of: (a) Interferon gamma; (b) Interleukin 17; (c) Interleukin 4; (d) Interleukin 10; (e) Interleukin 13; (f) Interleukin 15; (g) Interleukin 1; (h) Interleukin 6; (i) Monocyte chemotactic protein 1; (MCP-1); (j) Vascular endothelial growth factor (VEGF); (k) Transforming growth factor beta; (l) Interleukin 8; and (m) Tumor necrosis factor alpha.

Further preferred is a method of contacting and specifically binding said antibody with Beferin and thereby sterically inhibiting the non-productive incorporation of Beferin into B7-H3 oligomers at the cell surface. In so doing, said Beferin antibody up-regulates. B7-H3-mediated T lymphocyte co-stimulation. Further preferred is a method of contacting and specifically binding said antibody with Beferin and thereby sterically interfering with the non-productive interaction of Beferin with APP751, thereby un-regulating Blaa-mediated beta secretase cleavage of APP751 to generate PN2. As PN2 is an inhibitor of the extrinsic coagulation pathway at the level of FVIIa-TF, this in turn down-regulates coagulability status. Preferred compositions comprise the Beferin antibody or fragments or derivatives thereof. Preferred route of administration is intravenous injection.

In a further embodiment of the invention, said Beferin antibody is incorporated as an adjuvant in vaccine preparations in a method to up-regulate the elicited immune response. In said method, said Beferin antibody facilitates the B7-H3-mediated T lymphocyte co-stimulation contributing to establishment of specific immunity. Said Beferin antibody up-regulates B7-H3-mediated T lymphocyte co-stimulation by sterically inhibiting the non-productive incorporation of Beferin into B7-H3 oligomers at the cell surface. Further preferred is a method to use said antibody in a vaccine targeting a viral infection wherein the virus is selected from, but not restricted to, the group consisting of: (a) Human immunodeficiency virus; (b) Human herpes virus 6(HHV 6); (c) Hepatitis C virus; (d) Hepatitis D virus; (e) Hepatitis E virus; (f) Cytomegalovirus; (g) Respiratory syncytial virus; (h) Herpes simplex virus type I; (i) Herpes simplex virus type, II; (j) Influenza virus; (k) Parvovirus; (m) Coxsachie virus; (n) Echovirus; (o) Epstein-Barr virus; (p) Dengue virus; (q) Lassa fever virus; and (r) Ebola virus.

Further preferred is a method to use said Beferin antibody in a vaccine targeting a protozoan infection wherein the protozoa is selected from, but not restricted to, the group consisting of: (a) *Entamoeba histolytica*; (b) *Cryptosporidium parvum*; (c) *Plasmodiumn falciparurm*; (d) *Trypanosoma*; (e) *Leishmania*; (f) *Trichomonas vaginalis*; and (g) *Acanthamoeba*.

Viruses can suppress the inmmune response as a means of evading immune surveillance. In a further embodiment of the invention, said Beferin antibody is used in a method of up-regulating the immune response against an ongoing viral infection. In said method, said Beferin antibody facilitates the B7-H3-mediated T lymphocyte co-stimulation contributing to the anti-viral immune response. Said Beferin antibody up-regulates B7-H3-mediated T lymphocyte co-stimulation by sterically inhibiting the non-productive incorporation of Beferin into B7-H3 oligomers at the cell surface. Further preferred is a method of up-regulating the immune response against an ongoing viral infection wherein the virus is selected from, but not restricted to, the group consisting of: (a) Human immunodeficiency virus; (b) Human herpes virus 6 (HHV 6); (c) Hepatitis B virus; (d) Hepatitis C virus; (e) Hepatitis D virus; (f) Cytomegalovirus; (g) Respiratory syncytial virus; (h) Influenza virus; (i) Herpes simplex virus type I; (j). Herpes simlex virus type II; (k) Epstein Barr virus; (l) *Varicella zoster* virus; (m) Morbillivirus; (n) Parmyxovirus; (o) Papilloma virus; (p) Adenovirus; (q) Dengue virus; (r) Lassa fever virus; (s) Coxsachie virus; (t) Echovirus; and (u) Ebola virus.

Bacteria can suppress the immune response as a means of evading immune surveillance.

In a further embodiment of the invention, said Beferin antibody is used in a method of up-regulating the immune response against an ongoing bacterial infection. In said method, said Beferin antibody facilitates the B7-H3-mediated T lymphocyte co-stimulation contributing to the antibacterial immune response. Said Beferin antibody up-regulates B7-H3-mediated T lymphocyte co-stimulation by sterically inhibiting the non-productive incorporation of Beferin into B7-H3 oligomers at the cell surface. Further preferred is a method of up-regulating the immune response against an ongoing bacterial infection wherein the bacteria is selected from, but not restricted to, the group consisting of: (a) *Mycobacterium avium* complex; (b) *Pneumocystis carinii*; (c) *Acne vulgaris*; (d) *Legionella pneumophilia*; (e) *Yersinia pestis*; (f) *Ureaplasma urealyticum*; (g) *Chlarnydia pneumoniae*; (h) *Helicobacter pylori*; (i) *Treponema pallidum*; (j) *Neisseria gonorrhoeae*; (k) *Salmonella typhimuriurn*; (l) *Vibrio cholera*; (m) *Clostridium difficile*; (n) *Bacillary dysentary*; (o) Pencillin resistant *Pneumococcus*; (p) *Burkholderia mallei*; (q) *Mycobacterium leprae*; (r) *Mycobacterium* haemophilurn; (s) *Mycobacterium kansasii*; (t) *Haemophilus influenzae*; and (u) *Bacillus anthracis*.

Protozoa can suppress the immune response as a means of evading immune surveillance. In a further embodiment of the invention, said Beferin antibody is used in a method of up-regulating the immune response against an ongoing protozoan infection. In said method, said Beferin antibody facilitates the B7-H3-mediated T lymphocyte co-stimulation contributing to the anti-protozoan immune response. Said Beferin antibody up-regulates. B7-H3-mediated T lymphocyte co-stimulation by sterically inhibiting the non-productive incorporation of Beferin into B7-H3 oligomers at the cell surface. Further preferred is a method of up-regulating the immune response against an ongoing protozoan infection wherein the protozoa is selected from, but not restricted to, the, group consisting of: (a) *Entamoeba histolytica*; (b) *Cryptosporidium parvum* (c) *Giardia lamblia*; (d) *Toxoplasma gondii*; (e) *Isospora belli*; (f) *Encephalitozoon cuniculi*; (g) *Enterocytozoon bieneusi*; (h) *Plasmoditrm falciparum*; (i) *Trypanosoma*; (j) *Leishmania*; (k) *Trichomonas vaginalis*; and (l) Acanthamoeba.

In a further embodiment of the invention, said Beferin antibody is used in a method of up-regulating the immune response against an ongoing fungal infection wherein the fungus is selected from, but not restricted to, the group consisting of: (a) *Cryptococcal meningitis*; (b) *Histoplasma capstulatum*; (c) Coccidiodes immitis; and (d) *Candida albicans.*

Tumors can suppress the immune response as a means of evading immune surveillance. In a further embodiment of the invention, said Beferin antibody is used in a method of up-regulating the immune response against a tumor. In said method, said Beferin antibody facilitates the B7-H3-mediated T lymphocyte co-stimulation contributing to the anti-tumor immune response. Said Beferin antibody up-regulates B7-H3-mediated T lymphocyte co-stimulation by sterically inhibiting the non-productive incorporation of Beferin into B7-H3 oligomers at the cell surface. Further preferred is a method of up-regulating the immune response against a tumor wherein the tumor is selected from, but not restricted to, the group, consisting of: (a) Melanoma; (b) Breast carcinoma; (c) Lung carcinoma; (d) Colon carcinoma; (e) Prostatic carcinoma; (f) Hodgkin's lymphoma; (g) Non-Hodgkin's lymphoma; (h) Pancreatic carcinoma; (i) Uterine carcinoma; (j) Ovarian carcinoma; (k). Testicular carcinoma; (l). Renal carcinoma; (m) Hepatic carcinoma; and (n) Lung non-small-cell carcinoma.

In a further embodiment of the invention, said Beferin antibody is incorporated as an adjuvant in therapeutic anti-tumor vaccines wherein the tumor is selected from, but not restricted to, the group consisting of: (a) Melanoma; (b) Breast carcinoma; (c) Lung carcinoma; (d) Colon carcinoma; (e) Prostatic carcinoma; (f) Pancreatic carcinoma; (g) Uterine carcinoma; (h) Ovarian carcinoma; (i) Testicular carcinoma; (j) Renal carcinoma; (k) Hepatic carcinoma; and (l) Lung non-small-cell carcinoma.

Intracellular. (macrophage) pathogens can be eliminated either through macrophage activation or through lysis of infected macrophages by cytolytic T lymphocytes' (Chun et al., J. Exp. Med. 193:1213 (2001) which disclosure is hereby incorporated by reference, in its entirety). Ligation of B7 family members expressed on the macrophage can lead to macrophage activation [Hirokawa, M Immunol. Lett. 50:95-8 (1996), which disclosure is hereby incorporated by reference in its entirety]. In a further embodiment of the invention, said Beferin antibody is used in a method to eliminate intracellular pathogens by facilitating macrophage activation or cytolytic T lymphocyte generation wherein the pathogen is selected from, but not restricted to, the group of intracellular (macrophage) pathogens consisting of: (a) *Histoplasma capsulatum*; (b) *Mycobacterium tuberculosis*; (c) *Salinonella typhimurium*; (d) *Chlamydia trachomatis*; and (e) *Pneumocystis carinii.*

Tumors can engage the extrinsic coagulation pathway through TF expression as a means of facilitating metastasis. In a further embodiment of the invention, said Beferin antibody is used in a method of down-regulating said tumor engagement of the extrinsic coagulation pathway. In said method, said Beferin antibody facilitates Blaa-mediated beta secretase cleavage of APP751 to generate PN2, which is an inhibitor of the extrinsic coagulation pathway at the level of FVIIa-TF. Said Beferin antibody facilitates. Blaa-mediated generation of PN2 by sterically interfering with the non-productive interaction of Beferin with APP751. Further preferred is a method of down-regulating tumor engagement of the extrinsic coagulation pathway wherein the tumor is selected from, but not restricted to, the group consisting of: (a) Melanoma; (b) Breast carcinoma; (c) Lung carcinoma; (d) Colon carcinoma; (e) Prostatic carcinoma; (f) Hodgkin's lymphoma; (g) Non-Hodgkin's lymphoma; (h) Pancreatic carcinoma; (i) Uterine carcinoma; (j) Ovarian carcinoma; (k) Testicular carcinoma; (l) Renal carcinoma; (m) Hepatic carcinoma; and (n) Lung non-small-cell carcinoma.

In a further preferred embodiment, the present invention provides for a method of screening test compounds for the ability to bind Beferin and either inhibit orpromote the capacity of Beferin to interfere with B7-H3 function. Further preferred is a method of screening said test compounds for the ability to bind Beferin and either inhibit or promote the capacity of Beferin to interfere with B7-H3-mediated T lymphocyte co-stimulation. Further preferred is a method of screening said test compounds for the ability to bind Beferin and either inhibit or promote the capacity of Beferin to interfere B7-H3-mediated T lymphocyte co-stimulation. Further preferred is a method of screening said test compounds for the ability to bind Beferin and either inhibit or promote B7-H3-mediated T lymphocyte co-stimulation when the antigen-presenting cell is transfected with B7-H3 and Beferin but not when the identical cell is transfected with B7-H3 alone. Methods of screening said test compounds and for characterizing their effect on B7-H3-mediated T lymphocyte co-stimulation are well known to those skilled in the art.

Preferred formulation of said compound is that selected from, but not restricted to, formulations compatible with the routes of delivery selected from the group: (a) Oral; (b) Transdermal; (c) Injection; (d) Buccal; and (e) Aerosol.

Compounds found to bind Beferin and to inhibit the capacity of Beferin to interfere with B7-H3 function, thereby effectively up-regulating B7-H3 activity, are used ii methods analogous to those described above for Beferin antibody.

Compounds found to, bind Beferin and to promote the capacity of Beferin to interfere with B7-H3-mediated T lymphocyte co-stimulation effectively down-regulate B7-H3 activity. Such compounds have application to chronic: inflammatory autoimmune disease and to other disorders of immune dysregulation. Such compounds down-regulate B7-H3-mediated T lymphocyte co-stimulation by promoting the non-productive incorporation of Beferin into B7-H3 oligomers at the cell surface. In a further embodiment of the invention, said compound is used in a method of contacting Beferin to down-regulate a dysregulated immune response and thereby treat the associated immune disorder wherein said immune disorder is selected from, but not restricted to, the group: (a) Rheumatoid arthritis; (b) Inflammatory bowel disease; (c) Insulin dependent diabetes mellitus (Type 1 diabetes); (d) Multiple sclerosis; (e) Systemic lupus erythematosus; (f) Psoriasis; (g) Allergic asthma; (h) Allergic rhinitis (hayfever); and (i) Graft versus host disease.

In a further preferred embodiment, the present invention provides for a method of screening test compounds for the ability to bind Beferin and inhibit the capacity of Beferin to interfere with Blaa function. Further preferred is a method of screening said test compounds for the ability to bind Beferin and up-regulate Blaa-mediated PN2 generation through APP751 cleavage, thereby down-regulating engagement of the extrinsic coagulation pathway by virtue of PN2 being an inhibitor of said pathway. Further preferred is a method of screening said test compounds for the ability to bind Beferin and up-regulate Blaa-mediated PN2 generation by interfering with the non-productive interaction of Beferin with APP751. Further preferred is a method of screening said test compounds for the ability to bind Beferin and up-regulate PN2 release from an APP751-expressing cell transfected with Beferin and Blaa but not from the identical cell line transfected with Blaa alone. Methods of screening said test compounds and for measuring the amount PN2 released into the culture medium are well known to those skilled in the art.

Said compounds found to bind Beferin and to, effect said down-regulation of the extrinsic coagulation pathway are used in methods in methods analogous to those described above for Beferin antibody.

Protein of SEQ ID NO:40 (Internal Designation Clone 1000838788_228-28-4-0-F7-F)

The cDNA of Clone 1000838788_228-284-0-F7-F (SEQ ID NO:39) encodes the Reductase Protein (RP):

MVSGRFYLSCLLLGSLGSMCILFTIYWM-QYWRGGFAWNGSIYMFNWHPVLMVAGMVVF YGGASLVYRLPQSWVGPKLPWKLL-HAALHLMAFVLTVVGLVAVFTFHNHGRTANLYSL HSWLGITTVFLFGCQWFLGFAVFLLP-WASMWLRSLLKPIHVFFGAAILSLSIASVISGINEK LFFSLKNTTRPYHSLPSEAVFANSTGM-LVVAFGLLVLYILLASSWKRPEPGILTDRQLLLQL RPGSRPFPVTYVSVTGRQPYKSW (SEQ ID NO:40). Accordingly, it will be appreciated that all characteristics and uses of the polypeptides of SEQ ID NO:40 described throughout the present application also pertain to the polypeptides encoded by the nucleic acids included in Clone 1000838788_228-28-4-0-F7-F. In addition, it will be appreciated that all characteristics and uses of the polynucleotides of SEQ ID NO:39 descried throughout the present application also pertain to the nucleic acids included in Clone 1000838788_228-284-0-F7-F. A preferred embodiment of the invention is directed toward the compositions of SEQ ID NO:39, SEQ ID NO:40, and Clone 1000838788_228-28-4-0-F7-F. Also preferred are polypeptide fragments having a biological activity described herein and the polynucleotides encoding the fragments.

RP is a novel member of the cytochrome b561 family of transmembrane electron transfer proteins. RP supplies reducing equivalents by catalyzing the transfer of electrons across a membrane from a donor to an electron acceptor. This process depends on the interaction of histidine residues within the protein and transition metals (usually iron). Also required are cofactors to act as electron donors and acceptors. Examples of electron donors include but are not limited to ascorbic acid, NADH, NADPH, flavins, and reducing polypeptides. Electron acceptors include but are not limited to semidehydroascorbic acid, NAD+, NADP+, oxidized flavin species, and electron-accepting polypeptide complexes. Therefore, RP requires membrane association, a transition metal cofactor, and electron donor/acceptor cofactors for activity. These "required components of RP activity" will be referred to hereafter as such.

Preferred embodiments of the invention include: (1) a composition comprising an RP polypeptide sequence of SEQ ID NO:40; (2) a composition comprising an RP polypeptide fragment having biological activity; (3) a composition comprising a polynucleotide sequence of SEQ ID NO:39 encoding an RP polypeptide; (4) a composition comprising a polynucleotide sequence encoding an RP polypeptide fragment having biological activity.

A method of reducing oxidized species of iron comprising the step of: contacting an RP polypeptide or polynucleotide construct comprising polynucleotides encoding an RP polypeptide with iron and a cell. Preferably, ferric iron is reduced to ferrous iron. Preferably, the cell is involved in iron-uptake. Further preferably, the cell is derived from duodenal or small intestinal epithelium. Further preferably, the cell is a brush border, enterocyte.

A method of reducing monooxygenases comprising the step of: contacting an RP polypeptide or polynucleotide construct comprising polynucleotides encoding an RP polypeptide with a monooxygenase enzyme and a cell. Preferably, the monooxygenase is peptidylglycine alpha-amidiating monooxygenase (PAM). Also preferred is the monooxygenase dopamine beta-hydroxylase (DBH). Preferably, the cell is an endocrine cell. Further preferably, the cell is a neuroendocrine cell.

A method of screening for molecules that.bind and/or inhibit the ability of RP polypeptides to transfer electrons comprising the steps: (1) contacting an RP polypeptide with a test molecule; (2) detecting test molecule binding to said RP polypeptide; and (3) detecting test molecule inhibiting of RP polypeptide biological activity. Preferably, a test molecule is immobilized on a semi-solid matrix.

Also preferred is a test molecule immobilized on a solid matrix. Preferably, a test molecule binding to RP polypeptide is detected using fluorescently-labelled RP antibody. Preferably, RP biological activity is detected using a common redox assay. Further preferably, RP biological activity is detected using an NMT reduction assay. Also further preferred is RP biological activity detected using an NBT reduction assay.

A method of inhibiting RP polypeptide-dependent electron transfer comprising the step in contacting an RP polypeptide with an RP polypeptide inhibitor.

RP polypeptides are capable of transferring electrons to iron species, for example, reducing ferric (III) iron to ferrous (II) iron. Non-heme associated Fe (III) is highly insoluble in the body, while reduced Fe (II) is more readily absorbed. Thus, a method for reducing Fe (III) to Fe (II) is a highly desirable treatment for disorders such as hemolytic diseases (e.g., sickle cell anemia), hemoglobinopathies, low iron absorption, rheumatoid arthritis, hypoxia, anemias associated with pregnancy, end-stage renal failure, cancer chemotherapy, and AIDS (particularly in subjects who are being treated with zidovudine (AZT)), and chronic anemia. Furthermore, increased iron uptake enables rapid weight gain desired in livestock. In a preferred embodiment of the invention, an iron-reducing effective amount of RP polypeptides or a polynucleotide construct comprising polynucleotides encoding said polypeptide are used in a method to reduce oxidized species of iron. This method comprises the step of contacting a RP polypeptide or polynucleotide construct with required components of RP activity, iron, and cells. Preferred cells are those involved in iron-uptake. Further preferred cells are those of the duodenum and small intestinal epithelium such as brush border enterocytes [for review, see Siddiqi, S., et al. (2001) Curr. Opin. Gastroenterol. 17:110-7, which disclosure is hereby incorporated by reference in its entirety].

RP is expressed in neuroendocrine tissues where it is localized to secretory vesicles. RP supplies reducing ability (i.e., electrons) to monooxygenase enzymes, which play a role in biosynthesis and processing of catecholamines (e.g., dopamine and norepinephrine) and peptide hormones (e.g., neuropeptides, gonadotropins, somatotropins, thyrotropins, corticotropins, and lactotropins such as vasopressin, oxytocin, and insulin). In a preferred embodiment of the invention, a reducing effective amount of RP polypeptides or polynucleotides encoding said polypeptides are used in a method to reduce monooxygenases, thereby increasing the activity of these enzymes. This method comprises the step of contacting a RP polypeptide or polynucleotide construct with required components of RP activity, monooxygenase enzymes, and cells. Preferred monooxygenase enzymes include but are not limited to peptidylglycine alpha-amidating monooxygenase (PAM) and dopamine beta-hydroxylase (DBH). Preferred cells are those that express endogenous monooxygenases, such as cells of the adrenal medulla, pituitary gland, and other neural and endocrine tissues.

Delivery of RP polypeptide or a polynucleotide construct comprising polynucleotides encoding RP polypeptide to cells is accomplished by methods common to the art such as transfection, electroporation, or microinjection. Additional methods of contacting said polynucleotide construct with cells include but are not limited to: lipid vesicle delivery (including micelles, viral envelope components, lipsomes, and modified versions of these) as discussed in U.S. Pat. Nos. 6,110,490, 5,019,369, and P.C.T. 9704748, which disclosures are hereby incorporated by reference in their entireties; viral transduction (including attenuated lentiviral and adenoviral systems) as discussed in U.S. Pat. No. 6,204,060, which disclosure is hereby incorporated by reference in its entirety; and delivery of naked polynucleotides (preferably to cells of the gastrointestinal tract) as discussed in U.S. Pat. No. 6,225,290, which disclosure is hereby incorporated by reference in its entirety.

An example method of delivery comprises steps: i) compressing a polynucleotide, construct, preferably comprising the polynucleotides encoding RP polypeptide operably linked to, an expression control element (e.g., a CMV promoter to direct constitutive expression), into a lipid vesicle derived from any of the following list: viral envelopes, liposomes, micelles, gangliosides and modified versions of these, preferably GM-1 ganglioside and phosphatidylserine, as described in U.S. Pat. Nos. 6,180,603, 6,110,490 or P.C.T. 9704748, which disclosures are hereby incorporated by reference in their entireties; ii) targeting the lipid vesicle to specific cells, for example, by embedding a targeting moiety into the lipid envelope. (e.g., growth hormone secretagogue for pituitary localization); iii) contacting the targeted vesicle with specific cells by methods common to the art such as injection or inhalant (U.S. Pat. No. 6,110,490, P.C.T. 9704748, and U.S. Pat. No. 6,180,603, which disclosures are hereby incorporated by reference in their entireties).

In an additional example of delivery, a polynucleotide construct comprising polynucleotides encoding the RP polypeptide operably linked to an expression control element (e.g., a CMV promoter to direct constitutive expression or a brush border-specific promoter such as the sucrase promoter) is delivered orally (e.g., in a physiologically-acceptable liquid, slurry, syrup, paste, powder, pill, or capsule form) to increase iron absorption by brush border enterocytes in the duodenum. Said naked polynucleotide construct may be modified to specifically target certain cells of the intestine, for example, by adding an oligosaccharide modification specific for brush border cell lectins (e.g., wheat germ agglut). Said naked polynucleotide construct may further provide for site-specific integration into the genome of the target intestinal cell. For example, said construct can be modified such that polynucleotides encoding RP polypeptide and an operably linked promoter to are flanked by the position-specific integration markers of *Saccharomyces cerevisiae* Ty3 (U.S. Pat. No. 5,292,662, which disclosures are hereby incorporated by reference in their entirety).

Further included in the present invention are methods of inhibiting the above RP activities using an inhibitor of RP. Thus, a preferred embodiment of the present invention is a method of inhibiting RP polypeptide-dependent electron transfer (including reduction of ferric iron to ferrous iron and reduction of monooxygenase enzymes) by contacting RP polypeptides with RP polypeptide inhibitors. A further embodiment of the invention is a method of screening for compounds that bind and/or inhibit the ability of RP polypeptides to transfer electrons. This method comprises the steps of: i) contacting an RP polypeptide with a test compound; and ii) detecting whether said test compound binds and/or inhibits RP polypeptide reducing activity. Detection of RP polypeptide binding is accomplished by methods common to the art (e.g., by immobilizating said test compound on a solid or semi-solid matrix and detecting RP polypeptides by fluorescently-labelled RP antibody). Inhibition of RP polypeptide reducing activity is measured using common assays to detect redox and electron transfer activity, such as MTT reduction (Chakrabarti, R., et al. (2000). J. Cell Biochem. 18:133-8, which disclosure is hereby incorporated by reference in its entirety) or NBT reduction [Meerhof, L. and Roos, D. (1986).J. Leukoc.Biol.39:699-711, which disclosure is hereby incorporated by reference in its entirety].

Protein of SEQ ID NO:42 (Internal Designation Clone 1000943975_160-213-2-0-A5-F)

The cDNA of Clone 1000943975_160-213-2-0-A5-F (SEQ ID NO:41) encodes the Small Secreted Serine Protease Inhibitor (SSSPI) comprising the amino acid sequence:

MPACRLGPLAAALLLSLLLFGFTLVSGT-GAEKTGVCPELQADQNCTQECVSDSECADNLK CCSAGCATFCSLPNDKEGSCPKEG-SCPQVNINFPQLGLCRDQCQVD-SQCPGQMKCCRNGCGKVSC VTPNF (SEQ ID NO:42). Accordingly, it will be appreciated that all characteristics and uses of the polypeptides of SEQ ID NO:42 described throughout the present application also pertain to the polypeptides encoded by the nucleic acids included in Clone 1000943975_160-213-2-0-A5-F. In addition, it will be appreciated that all characteristics and uses of the polynucleotides of SEQ ID NO:41 described throughout the present application also pertain to the nucleic acids included in Clone 1000943975_160-213-2-0-A5-F. A preferred embodiment of the invention is directed toward the compositions of SEQ ID NO:41, SEQ ID NO:42, and Clone 1000943975_160-213-2-0-A 5-F. Also preferred are polypeptide fragments having a biological activity as described herein and the polynucleotides encoding said fragments.

The Small Secreted Serine Protease Inhibitor (SSSPI) includes two WAP. (whey acidic protein)/four-disulfide core domains, which are commonly found in serine protease inhibitors. SSSPI is extremely stable due to the presence of extensive intramolecular disulfide bonds. The biological activity of SSSPI is to inhibit protein degradation by serine proteases determined, for instance, by tracking protein degradation by methods common to the art (e.g., Coomassie Blue stain). Furthermore, SSSPI activity is associated with retarding growth in tissues that include smooth muscle, colon, ovarian, and mammary tissues.

In a preferred embodiment of the invention, SSSPI polypeptides or fragments thereof are used to screen libraries of compounds for formation of binding complexes between SSSPI polypeptide and the agentbeing tested. The fragment employed in such screening may be free in solution, affixed to, a solid support, borne on a cell surface, or located intracellularly. The formation of binding complexes is measured by methods known in the art (e.g., fluorescent labeling or green fluorescent protein tagging of the test agent, SSSPI polypeptides, or antibodies against either). A preferred method for screening provides for high throughput screening of compounds having suitable binding affinity to SSSPI polypeptide. An example of this method comprises the steps: i) synthesizing large numbers of different small test compounds onto a solid substrate, such as plastic pins; ii) reacting test compounds with SSSPI polypeptides and washed; iii) detecting bound SSSPI polypeptides by methods known in the art. Alternatively, SSSPI polypeptides are coated directly onto plates or immobilized using non-neutralizing antibodies and used in the aforementioned screening techniques. This method is applied, for example, to detecting protease levels in a test solution or to screening for molecules that interact with SSSPI as discussed in the following embodiment. In another embodiment of the invention, binding complexes of SSSPI polypeptide and the aforementioned test agents are used in a method to screen for compounds that inhibit interaction of SSSPI polypeptide with serine protease substrates. This method comprises the steps: i) allowing SSSPI polypeptide-test agent binding complex to form; ii) adding SSSPI substrate (such as elastase); iii) measuring SSSPI binding to substrate directly or indirectly by methods common in the art (e.g., fluorescent labeling of the substrate molecule or of an antibody against said substrate). This method is applied, for example, to screening for molecules that inhibit SSSPI biological activity.

In a preferred embodiment of the invention, a method of inhibiting protein degradation with a biologically active SSSPI polypeptide or a polynucleotide construct comprising polynucleotides encoding said polypeptide is provided. This method comprises the step of contacting a protein degradation-inhibiting effective amount of SSSPI polypeptide with proteins in a solution of appropriate pH and salt concentration to allow SSSPI biological activity (e.g., buffered saline). In an additional embodiment, SSSPI polypeptide is combined with other protease inhibitors and used in a method to inhibit protein degradation. This method comprises the steps: combining a protein degradation-inhibiting effective amount of SSSPI polypeptide with effective amounts of other protease inhibitors to form a protease inhibitor cocktail and contacting said cocktail with proteins in a solution of appropriate pH and salt concentration to, allow SSSPI biological activity. Preferred protease inhibitors are of a different specificity than SSSPI to maximize the protease-inhibiting effectiveness of the cocktail, such as Kunitz-, trypsin inhibitor-like cystine-rich domain (TIL)-, thyroglobulin-, Kazal-, and netrin (NTR)- type protease inhibitors.

Biologically acceptable salts of the SSSPI polypeptide also fall within the scope of the invention. The term "biologically acceptable salts" as used herein means an inorganic acid addition salt such as hydrochloride, sulfate, and phosphate, or an organic acid addition salt such as acetate, maleate, fumarate, tartrate, and citrate. Examples of biologically acceptable metal salts are alkali metal salts such as sodium salt and potassium salt, alkaline earth metal salts such as magnesium salt and calcium salt, aluminum salt, and zinc salt. Examples of biologically acceptable organic amine addition salts are salts with morpholine and piperidine. Examples of biologically acceptable amino acid addition salts are salts with lysine, glycine, and phenylalanine.

Compounds provided herein can be formulated into "physiologically acceptable compositions" by admixture with physiologically acceptable nontoxic excipients and carriers. Such compositions may be prepared for use in parenteral administration, particularly in the form of liquid solutions or suspensions; oral administration, particularly in the form of tablets or capsules; intranasally, particularly in the form of powders, nasal drops, or aerosols; dermally, via, for example, transdermal patches; or prepared in other suitable fashions for these and other forms of administration as will be apparent to those skilled in the art.

Common excipients include, for example, sterile water or saline, polyalkylene glycols such as polyethylene glycol, oils of vegetable origin, and hydrogenated naphthalenes. Further excipient formulations include but are not limited to lactose, polyoxyethylene-9-lauryl ether, glycocholate, deoxycholate, salicylate, citric acid, oily or gel-like solutions and lipophilic emulsions. Potentially useful parenteral delivery systems for these active compounds include ethylene-vinyl acetate copolymer particles, osmotic pumps, implantable infusion systems, and liposomes. The invention can be employed as the sole active agent or can be used in combination with other active ingredients which could facilitate inhibition of serine proteases.

Protease activity is associated with tumor formation by mechanisms that include proteolytic processing of growth factors (e.g., insulin-like growth factor, fibroblast growth factor (FGF), epidermal growth factor (EGF), heparin-binding epidermal growth factor-like growth factor, tumor necrosis factor (TNF)-alpha, and transforming growth factor (TGF)-beta). Indeed, SSSPI is capable of inhibiting proliferation of prostate carcinoma cells and pulmonary artery smooth muscle by preventing proteolytic processing of insulin-like growth factor II and FGF, respectively. In a preferred embodiment of the invention, a protein degradation-inhibiting effective amount of SSSPI polypeptide is contacted with cells to inhibit proteolytic processing and degradation of proteins. Preferred cells are those expressing growth factors that require proteolytic processing to promote proliferation, such as those listed above. Examples of preferred cells include those from the lung, gastrointestinal tract, liver, skin, mammary gland, pancreas, ovary, prostate gland, and vascular smooth muscle and epithelia. This method comprises the step of contacting a physiologically acceptable composition of SSSPI polypeptide with cells. Delivery of said composition to cells is accomplished as discussed above, as determined appropriate by one skilled in the art.

An additional embodiment of the invention provides a method of introducing a polynucleotide construct comprising polynucleotides encoding SSSPI polypeptides to cells to inhibit proteolytic, processing and degradation of proteins. Preferred cells are those expressing growth-factors that require proteblytic processing to promote proliferation (e.g., insulin-like growth factor, FGF, EGF, heparin-binding epidermal growth factor-like growth factor, TNF-alpha, and TGF-beta) or cells that contact said cells. Examples of preferred cells include those from the lung, gastrointestinal tract, liver, skin, mammary gland, pancreas, ovary, prostate gland, and vascular smooth muscle and epithelia. Preferred polynucleotide constructs comprise polynucleotides encoding SSSPI polypeptide operably linked to an expression control element such as a promoter. Preferred expression control elements direct expression of SSSPI polypeptide in amount effective to inhibit protein degradation. Examples include the CMV promoter for constitutive expression or a tissue-specific promoter, such as the human glandular kallikrein-2 promoter for expression in androgen receptor-positive prostate cancer cells. A physiologically acceptable composition comprising the polynucleotide construct is introduced to cells using methods common to the art such as electroporation or transfection. Additional delivery methods of said physiologically acceptable composition include but are not limited to: lipid vesicle delivery (including micelles, viral envelope components, lipsomes, and modified versions of these) as discussed in U.S. Pat. Nos. 6,110,490, 5,019, 369, and P.C.T. 9704748, which disclosures are hereby incorporated by reference in their entireties; viral transduction (including attenuated lentiviral and adenoviral systems) as discussed in U.S. Pat. No. 6,204,060, which disclosure is hereby incorporated by reference in its entirety; and delivery of a physiologically acceptable composition comprising naked polynucleotides (for example, to cells of the gastrointestinal tract) as discussed in U.S. Pat. No. 6,225,290, which disclosure is hereby incorporated by reference in its entirety.

SSSPI is capable of inhibiting serine proteases implicated in degenerative disorders including but not limited to thrombin, human leukocyte elastase, pancreatic elastase, trypsin, chymase, and cathepsin G. Thrombin is produced in the blood coagulation cascade and is implicated disorders such as thrombophlebitis, thrombosis, other bleeding disorders, and asthma Human leukocyte elastase is implicated in tissue degenerative disorders such as rheumatoid arthritis, osteoarthritis, atherosclerosis, bronchitis, cystic fibrosis, and emphysema. Pancreatic elastase and trypsin are implicated soft tissue degradation, particularly in cases of pancreatitis. Chymase, an enzyme important in angiotensin synthesis, is implicated in disorders such as hypertension, myocardial infarction, and coronary heart disease. Cathepsin G is implicated in abnormal connective tissue degradation, particularly in the lung. In the extreme, serine proteases including but not limited to those mentioned above, kallikrein, and prostate specific antigen (PSA) are involved in tumor formation through proteolytic remodeling of extracellular matrix (ECM) proteins. This proteolytic remodeling may result in disruption of the integrity, of tissue epithelial lining and basement membranes and result in metastasis. In a preferred embodiment of the invention, a protein degradation-inhibiting effective amount of SSSPI polypeptides are applied to cells to inhibit protein degradation and resulting tissue or ECM degeneration. This method comprises the step of contacting a physiologically acceptable composition comprising SSSPI polypetdses with cells. Preferred cells include those diagnosed or at risk of degenerative disorders as a result of serine protease activity, such as those lung, gastrointestinal tract, liver, skin, mammary gland, pancreas, ovary, prostate gland, bone and cartilage, and vascular smooth muscle and epithelia. Further preferred cells include those diagnosed or at risk of tumor invasion as a result of serine protease activity such as those involved in formation of epithelial linings, basement membranes, and ECM (e.g., epithelial cells and fibroblasts). Delivery of said composition to cells is accomplished as discussed above, as determined appropriate by one skilled in the art.

In a further embodiment of the invention, SSSPI polypeptides or fragments thereof are used in a method to detect serine proteases. This method is directed toward diagnosis of the aforementioned disorders and diseases. An example of this method comprises the steps of contacting SSSPI polypeptides with a biological fluids (e.g., cell culture media, blood, serum, cell suspensions or samples) suspected of containing serine proteases, washing, and detecting serine protease-SSSPI complexes. Detection of said complexes is accomplished by methods common to the art such as competition with a fluorescently-labeled neutralizing antibody.

Protein of SEQ ID NO:44 (Internal Designation Clone 147441_106-025-2-0-C1-F)

The cDNA of Clone 147441_106-025-2-0-C11-F (SEQ ID NO:43) encodes the CarboxyPeptidase Inhibitor-1 (CPI-1):

MQGRPGGTRPGPSPVDRRTLLVFSFI-LAAALGQMNFTGDQVLRVLAKDEKQLSLLGDLE GLKPQKVDFWRGPARPVDMRVPFSELKD (SEQ ID NO:44). Accordingly, it will be appreciated that all characteristics and uses of the polypeptides of SEQ ID NO:44 described throughout the present application also pertain to the polypeptides encoded by the nucleic acids included in Clone 147441_106-025-2-0-C11-F. In addition, it will be appreciated that all characteristics and uses of the polynucleotides of SEQ ID NO:43 described throughout the present application also pertain to the nucleic acids included in Clone 147441_106-025-2-0-C11-F. A preferred embodiment of the invention is directed toward the compositions of SEQ ID NO:43, SEQ ID NO:44, and Clone 147441_106-025-2-0-C11-F. Also preferred are polypeptide fragments having a biological activity as described herein and the polynucleotides encoding the fragments.

CPI-1 is a 91 amino acid protein that is highly homologous to the amino-terminal "prepro" region of preprocarboxypeptidase. The "pre" region represents a signal peptide while the "pro" region inhibits carboxypeptidase enzyme activity by binding to the active site of the enzyme before being proteolytically removed. Proteolytic cleavage of procarboxypeptidase results in formation of mature, active carboxypeptidase. Proteolytic processing of procarboxypeptidase (e.g., by trypsin) relies on the carboxy-terminus of the "pro" region, which is absent in CPI-1. CPI-1 therefore acts as a small, independent inhibitor of carboxypeptidase activity that is not recognized by carboxypeptidase-specific proteases. Carboxypeptidases comprise a family of proteins that function in many physiological processes. These proteins remove a wide range of carboxyl-terminal amino acids, and in doing so are able to, activate, inactivate, and modulate enzyme and peptide hormone activity, as well as participate in peptide degradation and amino acid absorption. Active forms of mammalian carboxypeptidases may be secreted or located in lysosomes where they regulate intracellular protein processing, degradation and turnover. The "biological activity" of CPI-1 polypeptide is defined as the ability to inhibit carboxypeptidase activity.

Carboxypeptidase activity may be measured by methods common to the art, such as incubation of a test sample with a radiolabeled Bolton-Hunter reagent-coupled peptide substrate (Normant, E., et al. (1995) Proc. Natl. Acad. Sci. 92:12225-9). "Carboxypeptidase" is used herein to refer to any member of the carboxypeptidase family.

Preferred embodiments of the present invention include: (1) a composition, comprising a CPI-1 polypeptide sequence of SEQ ID NO:44; (2) a composition, comprising a CPI-1 polypeptide fragment having a carboxypeptidase-inhibiting biological activity; (3) a composition, comprising a polynucleotide sequence of SEQ ID NO:43 encoding a CPI-1 polypeptide; (4) a composition, comprising a polynucleotide sequence encoding a carboxypeptidase-inhibiting biologically active CPI-1 polypeptide fragment.

A method of inhibiting carboxypeptidase-mediated anti-fibrinolytic activity, comprising the step of: contacting an effective amount of a CPI-1 polypeptide or biologically active fragment thereof with carboxypeptidase in the bloodstream of an individual. Further preferably, CPI-1 polypeptide is delivered to a human.

A method of preventing or inhibiting the progression of carboxypeptidase-mediated pancreatitis, comprising the step of: contacting a CPI-1 polypeptide or biologically active fragment thereof with a pancreatic cell.

A method of preventing or inhibiting the progression of carboxypeptidase-mediated pancreatic cancer, comprising the step of: contacting a CPI-1 polypeptide or biologically active fragment thereof with a pancreatic cell.

A method of preventing or inhibiting the progression of carboxypeptidase-mediated lung cancer, comprising the step of: contacting a CPI-1 polypeptide or biologically active fragment thereof with a lung cell.

A method of preventing or inhibiting the progression of carboxypeptidase-mediated ovarian cancer, comprising the step of: contacting a CPI-1 polypeptide or biologically active fragment thereof with an ovarian cell.

A method of preventing or inhibiting the progression of carboxypeptidase-mediated larynx cancer, comprising the step of: contacting a CPI-1 polypeptide or biologically active fragment thereof with a larynx cell.

A method of preventing or inhibiting the progression of carboxypeptidase-mediated uterine cancer, comprising the step of: contacting a CPI-1 polypeptide or biologically active fragment thereof with a uterine cell.

A method of preventing or inhibiting the progression of carboxypeptidase-mediated hepatic cancer, comprising the step of: contacting a CPI-1 polypeptide or biologically active fragment thereof with a hepatic cell.

A method of binding an antibody or antibody fragment to a CPI-1 polypeptide comprising the step of: contacting said antibody or antibody fragment with a biological sample.

A method of using an antibody or antibody fragment that specifically binds CPI-1 polypeptides or fragments thereof in a detection assay comprising the steps of: contacting said antibody or antibody fragment with a biological sample; and detecting antibody or antibody fragment binding to said sample.

A further preferred method comprises the additional step of: contacting a second antibody, or antibody fragment, that does not bind CPI-1 polypeptides or fragments thereof with said biological sample.

Further preferably, the first and/or second antibodies or antibody fragments are, modified with detectable molecular tags.

Further preferably, the biological sample is a blood sample or a tissue sample.

Further preferably, the detection assay is used for purposes of diagnosis.

A method of using an antibody or antibody fragment that binds CPI-1 polypeptides or fragments thereof to inhibit CPI-1 biological activity and facilitate carboxypeptidase activity, comprising the step of: contacting said antibody or antibody fragment with CPI-1 polypeptides or biologically active fragments thereof.

The coagulation and fibrinolytic pathways are balanced to produce blood clotting and clot degradation, respectively, at appropriate times. Carboxypeptidase activity is anti-fibrinolytic, i.e., carboxypeptidase abrogates clot degradation, most likely by inhibiting plasminogen activation. In a preferred embodiment of the invention, a carboxypeptidase-inhibiting effective amount of a CPI-1 polypeptide, fragment thereof, or a polynucleotide encoding said polypeptide is used to inhibit carboxypeptidase-mediated blood clot formation and retention. This method may be directed toward facilitating anti-coagulant activity as desired in cases such as immobilization, thrombophilia, hereditary thrombophilia, stroke, myocardial infarction, coronary artery disease, malignant conditions, during and after surgical procedures, and in cases of increased risk of blood clots associated with medications. Preferably, this method is directed toward treatment of these conditions in a human. This method comprises the step of contacting a CPI-1 polypeptide or a biologically active fragment thereof with carboxypeptidase by administering a CPI-1 polypeptide to and individual. A preferred method of delivering CPI-1 polypeptides or biologically active fragments thereof to an individual includes direct, intravenous injection of said polypeptides or fragments in a physiologically acceptable solution (e.g., pH-buffered isotonic saline solutions, pH-buffered isotonic saline solutions modified by addition of viscous elements such as glycerol).

An additional preferred method of delivering CPI-1 polypeptides or fragments to an individual comprises the step of introducing a polynucleotide construct comprising polynucleotides encoding CPI-1 polypeptides or biologically active fragments thereof into a cell. Preferred cells are those lining the bloodstream, such as vascular endothelial cells, vascular smooth muscle cells, and fibroblasts. Additional preferred cells are those that travel through the bloodstream, such as hematopoetic cells and their precursors, lymphocytes, macrophages, eosinophils, neutrophils, and red blood cells. Preferred polynucleotide constructs comprise an expression control element operably linked to polynucleotides encoding a CPI-1 polypeptide or biologically active fragment thereof. Examples of commercially available expression control units include but are not limited to a CMV promoter for constitutive expression or a tetracycline-repressible promoter for regulated expression. Said polynucleotide construct is delivered to the cell by methods determined appropriate for the cell type. Delivery to cells that travel through the bloodstream may be accomplished by methods common to the art such as transfection or electroporation. Cells carrying the polynucleotide construct are then introduced to the bloodstream by, for instance, injection. Delivery to cells that line the bloodstream may be accomplished by methods including but not limited to lipid vesicles or viral transduction, as described in any one of the list: U.S. Pat. Nos. 5,616,565, 6,110,490, 6,204,060, and P.C.T. 9704748 which disclosures are hereby incorporated by reference in their entireties. Lipid vesicles may be derived from elements including but not limited to: viral envelopes, liposomes, micelles, and modified versions of these, as described in U.S. Pat. No. 6,110,490 or P.C.T. 9704748, which disclosures are hereby incorporated by reference in their entireties. Lipid vesicles or viruses may further be targeted to specific cells, for example, by embedding a member of a receptor-receptor ligand pair into the lipid envelope (e.g., VEGF/VEGFR for targeting to vascular endothelial cells).

While carboxypeptidase activity is required for normal protein processing in the pancreas, higher than normal levels of activity lead to pancreatitis, or destruction and inflammation of the pancreas. Pancreatitis often leads to pancreatic cancer. Carboxypeptidase is active in the extracellular space of the pancreas as well as in vacuolar compartments such as lysosomes. In a preferred embodiment of the invention, a carboxypeptidase-inhibiting effective amount of CPI-1 polypeptides, biologically active fragments thereof, or polynucleotides encoding said polypeptides are used to prevent or inhibit progression of pancreatitis or pancreatic cancer. This method comprises the step of contacting a physiologically acceptable solution comprising a CPI-1 polypeptide or biologically active fragment thereof with a pancreatic cell. Said polypeptides may be delivered, for example, by implanting a CPI-1 polypeptide-releasing stent surgically or via catheter. (U.S. Pat. No. 5,500,013 and U.S. Pat. No. 5,449,382, which disclosures are hereby incorporated by reference in their entireties). Polypeptides may further be delivered by direct injection (catheter or syringe) into the pancreatic organ. A further preferred method of delivering CPI-1 polypeptides or biologically active fragments thereof includes introducing a polynucleotide construct comprising polynucleotides encoding said polypeptides into a pancreatic cell. This method has the advantage of contacting CPI-1 polypeptides with intracellular compartments of carbokypeptidase activity. Said polynucleotide construct may further include an expression control element operably linked to polynucleotides encoding CPI-1 polypeptides or biologically active fragments thereof. Said polynucleotide construct may be delivered to a pancreatic cell by methods including but not limited to lipid vesicles or viral transduction, as described in any one of the list: U.S. Pat. Nos. 5,616,565, 6,110,490, 6,204,060, and P.C.T.9704748 which disclosures are hereby incorporated by reference in their entireties. Lipid vesicles may be derived from elements including but not limited to the following list: viral envelopes, liposomes, micelles, and modified versions of these, as described in U.S. Pat. No. 6,110,490 or P.C.T. 9704748, which disclosures are hereby incorporated by reference in their entireties. Lipid vesicles or viruses may further be targeted to specific cells, for example, by embedding a member of a receptor-receptor ligand pair into the lipid envelope.

Aside from pancreatic cancer, higher than normal levels of carboxypeptidase activity are found in cancers that include: lung, ovary, larynx, uterus, liver, stomach, and breast cancers. Carboxypeptidase activity leads to an increase in inflammatory cytokines, such as Tumor Necrosis Factor (TNF)-alpha. Therefore, carboxypeptidase-mediated tumorigenesis results from inflammation and destruction in a number of tissue types. As a preferred embodiment of the invention, a carboxypeptidase-inhibiting effective amount of CPI-1 polypeptides, biologically active fragments thereof, or polynucleotides encoding said polypeptides are used to prevent or inhibit progression of cancers. Preferred cancers include those listed above. This method comprises the step of contacting a physiologically acceptable solution comprising a CPI-1 polypeptide or biologically active fragment thereof with a cell. Preferred cells include those of the lung, ovary, larynx, uterus, liver, stomach, and breast. Further preferred cells are those at risk of or displaying cancerous or precancerous pathology as is commonly determined by those skilled in the art (e.g., loss of contact inhibition, abnormal cell size or shape). CPI-1 polypeptides, biologically active fragments thereof, or polynucleotides encoding said polypeptides are delivered to a specific cell by methods common to the art such as those discussed herein.

In an additional embodiment of the invention, CPI-1 polypeptides or fragments thereof are used to generate antibodies (or antibody fragments) that specifically bind to CPI-1 polypeptides or fragments thereof (detAbs for "detection antibodies") and/or inhibit the biological activity of CPI-1 polypeptides or fragments thereof (inhAbs for "inhibitory antibodies"). Antibodies may be polyclonal or monoclonal and may be generated by any method known to one skilled in the art.

In a preferred embodiment of the invention, antibodies or antibody fragments that specifically bind and inhibit CPI-1 biological activity. (inhAbs) are used to facilitate carboxypeptidase activity. This method may be directed toward increasing carboxypeptidase-mediated anti-fibrinolytic activity for example, to prevent or treat bleeding disorders. This method may alternatively be directed toward increasing carboxypeptidase-mediated uptake of low density lipoprotein (LDL) particles by macrophages for example, to prevent or treat high blood pressure or atherosclerosis. This method comprises the step of contacting inhAbs with CPI-1. A preferred method of contact includes injection of a physiologically acceptable solution comprising inhAbs to the bloodstream of an individual at risk of or suffering from a bleeding disorder or high LDL levels.

In a further preferred embodiment of the invention, antibodies or antibody fragments that bind CPI-1 polypeptides or fragments thereof (detAbs) are used in assays to bind and/or detect CPI-1 polypeptides or fragments thereof. This method may be directed toward in vitro uses such as purification of CPI-1 or carboxypeptidase polypeptides for drug development. An example of this method comprises the steps of: immobilizing a detAb on a solid or semi-solid matrix (e.g., sepharose); and exposing said immobilized detAb with a biological solution comprising proteins, preferably CPI-1 polypeptides or fragments thereof. This method may further be directed toward diagnosis of pancreatitis, pancreatic cancer, LDL-mediated disorders, and clotting disorders such as hemophilia, thrombophilia, hereditary thrombophilia, stroke, myocardial infarction, coronary artery disease, malignant conditions, and blood clots. This method comprises the steps of: contacting a detAb, preferably a detectably-labeled detAb. (e.g., conjugated to a fluorescent tag), with a biological sample, preferably a tissue or blood sample; and detecting detAb binding to said sample. A further step of contacting a second antibody or antibody fragment that does not bind CPI-1 polypeptides or fragments thereof may be added to determine the specific nature of the protein detected by the first antibody or antibody fragment. The second antibody or antibody fragment is preferably labeled with a detectable molecular tag such as a fluorescent molecule. Further preferably, a different molecular tag than that used by the first antibody or antibody fragment is used with the second antibody or antibody fragment.

Protein of SEQ ID No:46 (Internal Designation Clone 124610_113-003-3-0-$H_5$F)

The polypeptides of SEQ ID NO:46 are encoded by the polynucleotides of SEQ ID NO:45 of Clone 124610_113-003-3-0-H5-F. It will be appreciated that all characteristics and uses of the polynucleotides of SEQ ID NO:45 and polypeptides of SEQ ID NO:46, described throughout the present application also pertain to the human cDNA of Clone 124610_113-003-3-0-H5-F and the polypeptides encoded thereby. The gene of SEQ ID NO:45 is located on chromosome 17, encodes a human retinoic acid-inducible regulator of growth arrest and differentiation and is hereby referred to as RET-A-MODULIN comprising the polypeptide.

MTPSEGARAGTGRELEMLDSLLALGGLV-LLRDSXXWEGXSLLKALVKKSALCGE QVHILGCEV-SEEEFREGFDSDINNRLVYHDFFRDPLN-WSKTEEAFPGGPLGALRAMCKRT DPVPVTIALDSLSWLLLRLPCTTLCQVL-HAVSHQDSCPGDSSSVGKVSVLGLLHEELHGPG PVGALSSLAQTEVTLGGTMGQASA-HILCRRPRQRPTDQTQWFSILPDFSLDLQEGPSVESQ PYSDPHIPPVSKNAKARTRKCSLVSGH-GRENKSCRGWGWGQGF. A preferred embodiment of the invention is directed toward the compositions of SEQ ID NO:45, SEQ ID NO:46, and Clone 124610_113-003-3-0-H5-F. Also preferred are polypeptide fragments having a biological activity as described herein and the polynucleotides encoding the fragments.

A preferred embodiment of the invention is directed towards using compositions comprising RET-A-MODULIN and other preferred compositions in a method for inhibiting neoplastic cell growth, killing neoplastic cells and treating cancer. More particularly, the invention concerns methods and compositions to inhibit cellular proliferation of neoplastic cells, induce cytotoxicity in neoplastic cells and kill neoplastic cells (e.g., carcinomas, melanoma, and lymphoid tumors such as acute myelocytic leukemia (AML)), wherein said methods comprises contacting cells with a proliferation-inhibiting amount of RET-A-MODULIN or other sequences of the invention. The method of suppressing neoplastic cell growth comprises the effects selected from the group consisting of: (a) inhibiting cell growth or proliferation; (b) killing said neoplastic cells; (c) inducing apoptosis in said neoplastic cells; (d) inducing necrosis in said neoplastic cells; (e) preventing or inhibiting neoplastic cell invasion; and (f) preventing or inhibiting neoplastic cell metastasis. In a preferred embodiment, the neoplastic are cancerous or from a tumor. In another aspect of the invention, said neoplastic cells is selected from the group consisting of bladder carcinoma, hepatocellular carcinoma, hepatoblastoma, rhabdomyosarcoma, ovarian carcinoma, cervical carcinoma, lung carcinoma, breast carcinoma, squamous cell carcinoma in head and neck, esophageal carcinoma, thyroid carcinoma, astrocytoma, ganglioblastoma, neuroblastoma, lymphoma, myeloma, sarcoma and neuroepithelioma. In yet another aspect of the invention, said neoplastic cells are malignant or benign. Further included in the invention are the following protein sequences:

```
MLDSLLALGGLVLLRDSVEWEGRSLLKALVKKSALCGEQVHILGCEVSEEEFREGFDSDI      (SEQ ID NO: 137)
NNRLVYHDFFRDPLNWSKTEEAFPGGPLGALRAMCKRTDPVPVTIALDSLSWLLLRLPC
TTLCQVLHAVSHQDSCPGDSSSVGKVSVLGLLHEELHGPGPVGALSSLAQTEVTLGGTM
GQASAHILCRRPRQRPTDQTQWFSILPDFSLDLQEGPSVESQPYSDPHIPPVDPTTHLTFNL
HLSKKEREARDSLILPFQFSSEKQQALLRPRPGQATSHIFYEPDAYYDLDQEDPDDDLDI,

MLDSLLAIGGLVLLRDSVEWEGRSLLKALIKKSALRGEQVHVLGCEVSEEEFREGFDSDV      (SEQ ID NO: 138)
NSRLVYHDLFRDPLNWSKPGEAVPEGPLKALRSMCKRTDHGSVTIALDSLSWLLCHIPC
VTLCQALHALSQQNGDPGDNSLVEQVHVLGLLHEELHGPGSMGALNTLAHTEVTLSGK
VDQTSASILCRRPQQRATYQTWWFSVLPDFSLTLHEGLPLRSELHPDHHTTQVDPTAHLT
FNLHLSKKEREARDSLTLPFQFSSEKQKALLHPVPSRTTGRIFYEPDAFDDVDQEDPDDD
LDI,

SLLKALIKKSALRGEQVHVLGCEVSEEEFREGFDSDVNSRLVYHDLFRDPLNWSKPGEA       (SEQ ID NO: 139)
VPEGPLKALRSMCKRTDHGSVTIALDSLSWLLCHIPCVTLCQALHALSQQNGDPGDNSL
VEQVRVLGLLHEELHGPGSMGALNTLAHTEVTLSGKVDQTSASILCRRPQQRATYQTW
WFSVLPDFSLTLHEGLPLRSELHPDHHTTQVDPTAHLTFNLHLSKKEREARDSLTLPFQFS
SEKQKALLHPVPSRTTGHIFYEPDAFDDVDPEDPDDDLDI,

MLDSLLAIGGLVLLRDSVEWEGRSLLKALIKKSALRGEQVHVLGCEVSEEEFREGFDSDV      (SEQ ID NO: 138)
NSRLVYHDLFRDPLNWSKPGEAVPEGPLKALRSMCKRTDHGSVTIALDSLSWLLCHIPC
VTLCQALHALSQQNGDPGDNSLVEQVHVLGLLHEELHGPGSMGALNTLAHTEVTLSGK
VDQTSASILCRRPQQRATYQTWWFSVLPDFSLTLHEGLPLRSELHPDHHTTQVDPTAHLT
FNLHLSKKEREARDSLTLPFQFSSEKQKALLHPVPSRTTGRIFYEPDAFDDVDQEDPDDD
LDI, and

MGTPGEGLGRCSHALIRGVPESLASGEGAGAGLPALDLAKAQREHGVLGGKLRQRLGL        (SEQ ID NO: 140)
QLLELPPEESLPLGPLLGDTAVIQGDTALITRPWSPARRPEVDGVRKALQDLGLRIVEMG
DENATLDGTDVLFTGREFFVGLSKWTNHRGAEIVADTFRDFAVSTVPVSGSSHLRGLCG
```

-continued

MGGPRTVVAGSSEAAQKAVRAMAALTDHPYASLTLPDDAASDCLFLRPGLPGATPFLL

HRGGSAEAL.

LVKKSALCGEQVHIL (SEQ ID NO: 141), LVKRHRLATMPPMV (SEQ ID NO: 142),

LGWLCLLLLPIPLI (SEQ ID NO: 143), LHSDSGISVDSQSL (SEQ ID NO: 144),

LPAGDRLTGIPSHI (SEQ ID NO: 145), LLLPLVLRALLVDV (SEQ ID NO: 146),

LQPGPQLYDVMDAV (SEQ ID NO: 147), LDCVRLLLQYDAEI (SEQ ID NO: 148),

LDCVRLLLQYNAEI (SEQ ID NO: 149), LLEQNDLEPGHTEL (SEQ ID NO: 150),

LLEQNDLERGHTGL (SEQ ID NO: 151), MDGPRLLLLLLLGV (SEQ ID NO: 152),

MDRLRLLLLLILGV (SEQ ID NO: 153), LKPENILVDNDFHI (SEQ ID NO: 154),

LKPENILVDRDFHI (SEQ ID NO: 155), LLLPLVLLELLVGI (SEQ ID NO: 156),

LLLSLVLLALLMGI (SEQ ID NO: 157), LLLSLVLLALLMGI (SEQ ID NO: 158),

LWALLILLIPIVLI (SEQ ID NO: 159), LWLLTILVLLIPLV (SEQ ID NO: 160),

LLPLPVRAQLCAHL (SEQ ID NO: 161), WTELARELDFTEEQIH (SEQ ID NO: 162),

WRRLARQLKVSDTKID (SEQ ID NO: 163), WKRLARELKVSEAKMD (SEQ ID NO: 164),

WHQLHGKKEAYDTLIK (SEQ ID NO: 165),

WRQLAGELGYKEDLID (SEQ ID NO: 166), WEPMVLSLGLSQTDIY (SEQ ID NO: 167),

WAELARELQFSVEDIN (SEQ ID NO: 168), WAELARELQFSVEDIN (SEQ ID NO: 169),

WRHLAGELGYQPEHID (SEQ ID NO: 170),

WRHLAGELGYQPEHID (SEQ ID NO: 171), WKNCARKLGFTQSQID (SEQ ID NO: 172),

WKNCARKLGFTESQID (SEQ ID NO: 173), WKEFVRRLGLSDHEID (SEQ ID NO: 174),

WKEFMRFMGLSEHEIE (SEQ ID NO: 175),

WKEFVRRLGLSEHEIE (SEQ ID NO: 176), WKEFMRLLGLSEHEIE (SEQ ID NO: 177),

WKEFVRTLGLREAEIE (SEQ ID NO: 178), VKEFVRKNGMEEAKID (SEQ ID NO: 179),

CWYQSHGKSDAYQDLIK (SEQ ID NO: 180),

WQQLATAVKLYPDQVE (SEQ ID NO: 181).

A preferred embodiments of the invention comprise physiologically acceptable compositions and methods of treating cancer in a patient (such as prostate cancer, skin cancer/melanoma, pancreatic carcinoma, colon cancer, melanoma, ovarian cancer, liver cancer, small cell lung carcinoma, non-small cell lung carcinoma, cervical cancer, breast cancer, bladder cancer, brain canceri neuroblastoma/glioblastoma, leukemia, lymphorna, head and neck cancer, kidney cancer, myeloma and ovarian cancer) characterized by proliferation of neoplastic cells which comprises administering to the patient an amount of a polypeptide of the invention, effective to: (a) selectively induce apoptosis and/or necrosis in such neoplastic cells and thereby inhibit their proliferation; (b) inhibit cell growth and proliferation of the neoplastic cells; (c) inhibit invasion of the neoplastic cells; (d) inhibit metastasis of the neoplastic cells; (e) kill neoplastic cells; (f) preferentially inhibit cell growth and proliferation of the neoplastic cells; and (g) preferentially kill neoplastic cells. RET-A-MODULIN or other proteins of the invention or fragments thereof can be used in combination with one or more of various anticancer agents known as cancer chemotherapeutic agents and/or radiation therapy. The active ingredient compound of the invention which can produce an excellent anticancer effect can thus markedly promote the effect of the other anticancer agent or agents used in combination, to produce a synergistic effect. Therefore, even when the partner anticancer agent or agents are used in doses much smaller than the usual doses, a satisfactory anticancer effect can be obtained, whereby the adverse effects of the partner anticancer agent or agents can be minimized. As such chemotherapeutic agents included but not limited to, for example, 5-fluorouracil (5-FU; Kyowa Hakko. Kogyo), mitomycin C (Kyowa Hakko Kogyo), futraful (FT-207; Taiho Pharmaceutical), endoxan (Shionogi & Co.) and toyomycin (Takeda Chemical Industries). In addition, the apoptosis regulating composition of the present invention may be administered with a vitamin D derivative to further enhance its cytotoxic, characteristics (U.S. Pat. No. 6,087,350). The anti-cancer agents of the present invention may be combined with an anti-oestrogen compound such as tamoxifen or anti-progesterone such as onapristone (see, EP 616812) in dosages known for such molecules.

The pharmaceutically and physiologically acceptable compositions utilized in this invention may be administered by any number of routes including, but not limited to, parenteral, subcutaneous, intracranial, intraorbital, intracapsular, intraspinal, intracisternal, intrapulmonary (inhaled), oral, intravenous, intramuscular, intra-arterial, intramedullary, intrathecal, intraventricular, transderrnal, subcutaneous, intraperitoneal, intranasal, enteral, topical, sublingual, or rectal means. In addition to the active ingredients, these pharmaceutically and physiologically acceptable compositions may contain suitable physiologically acceptable carriers comprising excipients and auxiliaries, which facilitate processing of the active compounds into preparations, which can be used pharmaceutically. Further details on techniques for formulation and administration may be found in the latest edition of Remington's Pharmaceutical Sciences (Maack Publishing Co. Easton, Pa.). Pharmaceutically and physiologically acceptable compositions for oral administration can be formulated using physiologically acceptable carriers well known in the art in dosages suitable for oral administration. Such carriers enable the pharmaceutically and physiologically acceptable compositions to be formulated as tablets, pills, dragees, capsules, liquids, gels, syrups, slurries, suspensions, and the like, for ingestion by the patient Pharmaceutical preparations for oral use can be obtained through a combination of active compounds with solid excipient, sulting mixture is optionally grinding, and processing the mixture of granules, after adding suitable auxiliaries, if desired, to obtain tablets or dragee cores. Suitable excipients are carbohydrate or protein fillers, such as sugars, including lactose, sucrose, mannitol, or sorbitol; starch from corn, wheat, rice, potato, or other plants; cellulose, such as methyl cellulose, hydroxypropylmethyl-cellulose, or sodium carboxymethylcellulose; gums including arabic and tragacanth; and proteins such as gelatin and collagen. If desired, disintegrating or solubilizing agents may be added, such as the cross-linked polyvinyl pyrrolidone, agar, alginic acid, or a salt thereof, such as sodium alginate.

Dragee cores may be used in conjunction with suitable coatings, such as concentrated sugar solutions, which may also contain gum arabic, talc, polyvinylpyrrolidone, carbopol gel, polyethylene glycol, and/or titaniumdioxide, lacquer solutions, and suitable organic solvents or solvent mixtures. Dyestuffs or pigments may be added to the tablets or dragee coatings for product identification or to characterize the quantity of active compound, i.e., dosage.

Pharmaceutical preparations, which can be used orally, include push-fit capsules made of gelatin, as well as soft, sealed capsules made of gelatin and a coating, such as glycerol or sorbitol. Push-fit capsules can contain active ingredients mixed with filler or binders, such as lactose or starches, lubricants, such as talc or magnesium stearate, and, optionally, stabilizers. In soft capsules, the active compounds may be dissolved or suspended in suitable liquids, such as fatty oils, liquid, or liquid polyethylene glycol with or without stabilizers. Pharmaceutical formulations suitable for parenteral administration may be formulated in aqueous solutions, preferably in physiologically compatible buffers such as Hanks solution, Ringer's solution, or physiologically buffered saline. Aqueous injection suspensions may contain substances, which increase the viscosity of the suspension, such as sodium carboxymethylcellulose, sorbitol, or dextran. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Optionally, the suspension may also contain suitable stabilizers or agents, which increase the solubility of the compounds to allow for the preparation of highly, concentrated solutions. For topical or nasal administration, penetrants appropriate, to the particular barrier to be permeated are used in the formulation. Such penetrants are generally known in the art. The pharmaceutically and physiologically acceptable compositions of the present invention may be manufactured in a manner that is known in the art, e.g., by means of conventional mixing, dissolving, granulating, dragee-making, levigating, emulsifying, encapsulating, entrapping, or lyophilizing processes.

The pharmaceutical composition may be provided as a salt and can be formed with many acids, including but not limited to, hydrochloric, sulfuric, acetic, lactic, tartaric, malic, succinic, etc. Salts tend to be more soluble in aqueous or other protonic solvents than are the corresponding free base forms. In other cases, the preferred preparation may be a lyophilized powder which may contain any or all of the following: 1-50 mM histidine, 0.1%-2% sucrose, and 2-7% mannitol, at a pH range of 4.5 to 5.5, that is combined with buffer prior to use. After pharmaceutically and physiologically acceptable compositions have been prepared, they can be placed in an appropriate container and labeled for treatment of an indicated condition. For administration of RET-A-MODULIN, such labeling would include amount, frequency, and method of administration. Pharmaceutically and physiologically acceptable compositions suitable for use in the invention include compositions wherein the active ingredients are contained in an effective amount to achieve the intended purpose. The determination of an effective dose is well within the capability of those skilled in the art. For any compound, the therapeutically effective dose can be estimated initially either in cell culture assays, e.g., of neoplastic cells, or in animal models, usually mice, rabbits, dogs, or pigs. The animal model may also be used to determine the appropriate concentration range and route of administration. Such information can then be used to determine useful doses and routes for administration in humans. Those of ordinary, skill in the art are well able to extrapolate from one model (be it an in vitro, or an in vivo model). A therapeutically effective dose refers to that amount of active ingredient, for example RET-A-MODULIN polypeptides or other proteins of the invention or fragments thereof, which ameliorates the symptoms or condition. Therapeutic efficacy and toxicity may be determined by standard pharmaceutical procedures in cell cultures or experimental animals, e.g., ED50 (the dose therapeutically effective in 50% of the population) and LD50 (the dose lethal to 50% of the population). The dose ratio between therapeutic and toxic effects is the therapeutic index, and it can be expressed as the ratio, LD50/ED50. Pharmaceutically and physiologically acceptable compositions, which exhibit large therapeutic indices, are preferred. The data obtained from cell culture assays and animal studies is used in formulating a range of dosage for human use. The, dosage contained in such compositions is preferably within a range of circulating concentrations that include the ED50 with little or no toxicity. The dosage varies within this range depending upon the dosage form employed, sensitivity of the patient, and the route of administration. The practitioner, in light of factors related to the subject that requires treatment, will determine, the, exact dosage. Dosage and administration are adjusted to provide sufficient levels of the active moiety or to maintain the desired effect.

Factors, which may be taken into account, include the severity of the disease state, general health of the subject, age, weight, and gender of the subject, diet, time and frequency of administration, drug combination(s), reaction sensitivities, and tolerance/response to therapy. Long-acting pharmaceutically and physiologically acceptable compositions maybe administered every 3 to 4 days, every week, or once every two weeks depending on half-life and clearance rate of the particular formulation. Normal dosage amounts may vary from 0.1 to 100,000 micrograms, up to a total dose of about 1 g, depending upon the route of administration. Guidance as to particular dosages and methods of delivery is provided in the literature and generally available to practitioners in the art. Those skilled in the art will employ different formulations for nucleotides than for proteins or their inhibitors. Similarly, delivery of polynucleotides or polypeptides will be specific to particular cells, conditions, locations, etc. For the prevention or treatment of disease, the appropriate dosage of an anti-tumor agent herein will depend on the type of disease to be treated, as defined above, the severity and course of the disease, whether the agent is administered for preventive or therapeutic purposes, previous therapy, the patient's clinical history and response to the agent, and the discretion of the attending physician. The agent is suitably administered to the patient at one time or over a series of treatments. Animal experiments provide reliable guidance for the determination of effective doses for human therapy. Interspecies scaling of effective doses can be performed following the principles laid down by Mordenti, J. and Chappell, W. "The use of interspecies scaling in toxicokinetics" in Toxicokinetics and New Drug Development, Yacobi et al., eds., Pergamon Press, New York 1989, pp. 42-96. For example, depending on the type and severity of the disease, about 1 g/kg to 15 mg/kg (e.g., 0.1-20 mg/kg) of an antitumor agent is an initial candidate, dosage for administration to the patient, whether, for example, by one or more separate administrations, or by continuous infusion. A typical daily dosage might range from about 1 g/kg to 100 g/kg or more, depending on the factors mentioned above. For repeated administrations over several days or longer, depending on the condition, the treatment is sustained until a desired suppression of disease symptoms occurs. However, other dosage regimens may be useful. The progress of this therapy is easily monitored by conventional techniques and assays. Guidance as to particular dosages and methods of delivery is provided in the literature; see, for example, U.S. Pat. Nos. 4,657,760; 5,206,344; or 5,225,212. It is anticipated that different formulations will be effective for different treatment compounds and different disorders, that administration targeting one organ or tissue, for example, may necessitate delivery in a manner different from that to another organ or tissue. Therapies may be designed to utilize RET-A-MODULIN cytotoxic properties. In particular, therapies to enhance RET-A-MODULIN expression or administration of said polypeptides are useful in promoting inhibition or death of cancerous cells. Cytotoxic reagents may include, without limitation, full length or fragment RET-A-MODULIN polypeptides, mRNA, or any compound, which increases RET-A-MODULIN, biological activity.

Another therapeutic approach within the invention involves administration of RET-A-MODULIN therapeutic compositions (polynucleodtide, antibody, small molecule agonist or recombinant RET-A-MODULIN polypeptide), either directly to the site of a desired target cell or tissue (for example, by injection) or to a site where the composition will be further directed to the target cell or tissue, or systemically (for example, by any conventional recombinant protein administration technique). The dosage of RET-A-MODULIN depends on a number of factors, including the size and health of the individual patient, but, generally, between 0.1 mg and 100 mg inclusive is administered per day to an adult in any physiologically acceptable formulation.

In another embodiment, RET-A-MODULIN polypeptides and nucleic acid sequences find diagnostic use in the detection or monitoring of conditions involving aberrant levels of apoptosis. For example, decreased expression of RET-A-MODULIN may be correlated with decreased apoptosis in humans. Accordingly, a decrease or increase in the level of RET-A-MODULIN, production may provide an indication of a deleterious condition. Levels of RET-A-MODULIN, expression may be assayed by any standard technique such as Northern blot analysis and RT-PCR in biopsy specimen.

These embodiments comprise methods for detection of RET-A-MODULIN-mediated proliferation inhibition and apoptosis including in vitro activity tests of RET-A-MODULIN or other proteins of the invention or fragments thereof, further cellular proliferation assays, and cellular apoptosis/necrosis assays. Specific examples of apoptosis assays are also provided in the following references. Assays for apoptosis in lymphocytes are disclosed by Notebom et al., U.S. Pat. No. 5,981,502, 1999, Li et al., "Induction of apoptosis in uninfected lymphocytes by HTV-1 Tat protein", Science 268: 429-431, 1995; Gibellini et al., "Tat-expressing Jurkat cells show an increased resistance to different apostolic stimuli, including acute human immunodeficiency virus-type 1 (HIV-1) infection", Br. J. Haematol. 89: 24-33, 1995; Martin et al., "HIV-1 infection of human CD4$^+$ T cells in vitro. Differential induction of apoptosis in these cells." J. Immunol. 152:330-342, 1994; Terai et al., "Apoptosis as a mechanism of cell death in cultured T lymphoblasts acutely infected with HIV-1", J. Clin Invest. 87: 1710-1715, 1991; Dhein et al., "Autocrine T-cell suicide mediated by APO-1/(Fas/CD95)", Nature 373: 438-441, 1995; Katsikis et al., "Fas antigen stimulation induces marked apoptosis of T lymphocytes in human immunodeficiency virus-infected individuals", J. Exp. Med. 1815:2029-2036, 1995; Westendorp et al., "Sensitization of T cells to CD95-mediated apoptosis by HIV-1 Tat and gp120", Nature 375:497, 1995; DeRossi et al, Virology 198:234-244, 1994. Assays for apoptosis in fibroblasts are disclosed by: Vossbeck et al, "Direct transforming activity of TGF-beta on rat fibroblasts", Int. J. Cancer 61:92-97, 1995; Goruppi et al., "Dissection of c-myc domains involved in S phase induction of NIH3T3 fibroblasts", Oncogene 9:1537-44, 1994; Fernandez et al, "Differential sensitivity of normal and Ha-ras transformed C3H mouse embryo fibroblasts to tumor necrosis factor: induction of bcl-2, c-myc, and manganese superoxide dismutase in resistant cells", Oncogene 9:2009-2017, 1994; Harrington et al., "c-Myc-induced apoptosis in fibroblasts is inhibited by specific cytokines", EMBO J. 13:3286-3295, 1994; Itoh et al., "A novel protein domain required for apoptosis. Mutational analysis of human Fas antigen", J. Biol. Chem. 268:10932-10937, 1993. In vitro cellular proliferation assays comprise cultured cells such as Jurkat, HepG2, K562, or HeLa, which are treated with RET-A-MODULIN or fragments thereof at concentration ranges for example from 0.5 to 25 μg/mL, and percent decrease in cellular proliferation is measured 24, 48, and 72 hours after treatment. Cellular apoptosis is measured using an apoptosis assay kit such as VYBRANT Apoptosis Assay Kit #3 (Molecular Probes). After harvesting and washing, cells are stained with a FITC-labeled anti-RET-A-MODU- LIN antibody and analyzed by FACS according to manufacturer's instructions. Cells will be stained with P1 or DAP1 to detect apostolic nuclei. DNA fragmentation analysis will be performed by cellular DNA extraction and Southern blot analysis using about 1 ug of DNA and hybridized with randomly primed $^{32}$P-labeled chromosomal DNA from said cells, which had not been treated, with RET-A-MODULIN.

These embodiments also comprise the production of RET-A-MODULIN or other proteins of the invention or fragments thereof by subcloning of said nucleotides into an expression vector such as pCMV-neo for transfection assays, Western blot analysis to measure protein expression, and detection of RET-A-MODULIN-induced apoptosis by indirect immunofluorescence and DNA fragmentation analysis. Also included in the invention is the generation of specific antibodies against RET-A-MODULIN or other proteins of the invention or fragments thereof according to methods described in the art, wherein said antibodies can be polyclonal or monoclonal.

RET-A-MODULJN also shares homologies with two phosphorylated matrix proteins with the human cytomegalovirus, a pathogenic herpesvirus causing complications in patients with suppressed cellular immune functions and in prenatal infections (Ruger et al., J Virology 61:446-453, 1987, Koretz et al., N. Engl. J. Med.314:801-805, 1986, Bowden et al., N. Engl. J. Med.314:1006-1010, 1986). A preferred embodiment comprises the use of RET-A-MODULIN and fragments thereof including

GPGPVGALSSLAQTEVTLG, (SEQ ID NO:182)

EGPSVESQPYSD, (SEQ ID NO:183)

EVSEEEFREGFDSDINN, (SEQ ID NO:184)

TTLCQVLHAVSHQDSCPGDSSSVGKVSVLGLLHEELHGPGPVGALS, (SEQ ID NO:185)

GPSVESQPYSD, (SEQ ID NO:186)

CQVLHAVSH, (SEQ ID NO:187)

GKVSVLGLLHEELHGPGPV (SEQ ID NO:188)

for vaccination against Herpesvirus infections, as well as a vaccine preparation against Herpesviruses such as human cytomegalovirus (HCMV) and Kaposi Sarcoma-Associated Herpesvirus/Human Herpesvirus 8, which preparation comprises a RET-A-MODULIN protein or protein part according to the invention and optionally one or more carriers and adjuvants suitable for subunit vaccines. The use of a RET-A-MODULIN protein or protein part as defined above in a process for producing RET-A-MODULIN-specific polyclonal or monoclonal antibodies also falls within the scope of the invention. Vaccination and immunization generally refer to the introduction of a non-virulent agent against which an individual's immune system can initiate an immune response, which will then be available to defend against challenge by a pathogen. The immune system identifies invading "foreign" compositions and agents primarily by identifying proteins and other large molecules that are not normally present in the individual. The foreign protein represents a target against which the immune response is made. A further example is a use of RET-A-MODULIN-specific antibodies according to the invention for passive immunization against Herpesvirus infections, as well as an immunization preparation for passive immunization against Herpesvirus infections, which preparation includes RET-A-MODULIN-specific antibodies according to the invention and optionally one or more carriers and adjuvants suitable for passive immunization preparations.

As regards preparative applications, one example is the use of RET-A-MODULIN-specific antibodies according to the invention in a process for isolating and/or purifying RET-A-MODULIN. Routes of administration include, but are not limited to, intramuscular, intraperitoneal, intradermal, subcutaneous, intravenous, intraarterially, intraocularly and oral as well as transdermally or by inhalation or suppository. Preferred routes of administration include intramuscular, intraperitoneal, intradermal and subcutaneous injection as described by Pachuk et al., U.S. Pat. No. 6,235,888 (2001); see also Noteborn et al., U.S. Pat. No. 6,238,669 (2001),Patel et al., Diagnostic. Molecular Pathology. 10:95-99 (2001), and Aoki and Tosato, Leuk Lymphoma, 41:229-237 (2001), which references are hereby incorporated in their entirety.

Proteins of SEQ ID NO:48 (Internal Designation Clone 1000855165_205-99-1-0-A5-F) and SEQ ID NO:52 (Internal designation Clone 500721700_2044-34-0-H10-F)

The cDNA of clone 1000855165_205-99-1-0-A5-F (SEQ ID:47) encodes the protein of SEQ ID NO:48 comprising the amino acid sequence:

MIYTMKKVHALWASVCLLLNLAPA-PLNADSEEDEEHTIITDTELPPLKLMHSFCAFKADD GPCKAIMKRFFFNIFTRQCEEFIYG-GCEGNQNRFESLEECKKMCTREKPDFCFLEEDPGIC RGYITRYFYNNQTKQCERFKYGGCLGN-MNNFETLEECKNICEDGPNGXQVDNYGTQLN AVNNSLTPQSTKVPSLFEFHGPSWCLT-PADRGLCRANENRFYYNSVIGKCRPFKYSGCG GNENNFTSKQECLRACKKGFIQRISKGG-LIKTKRKRKKQRVKIAYEEIFVKNM (SEQ ID NO:48). Accordingly, it will be appreciated that all characteristics and uses of polypeptides of SEQ ID NO:48 described throughout the present application also pertain to the polypeptides encoded by the nucleic acids included in Clone 1000855165_205-99-1-0-A5-F. In addition, it will be appreciated that all characteristics and uses of the polynucleotides of SEQ ID NO:47 described throughout the present application also pertain to the nucleic acids included in Clone 1000855165_205-99-1-0-A5-F. A preferred embodiment of the invention is directed toward the compositions of SEQ ID NO:47, SEQ ID NO:48, and Clone 1000855165_205-99-1-0-A5-F. Also preferred are polypeptide fragments having a biological activity as described herein and the polynucleotides encoding the fragments.

The cDNA of clone 500721700_204A43-0-H10-F (SEQ. ID: 51) encodes the protein of SEQ ID NO:52 comprising the amino acid sequence:

MIYTMKKVHALWASVCLLLNLAPA-PLNADSEEDEEHTIITDTELPPLKLMHSFCAFKSDD GPCKAIMKRFFFNIFTRQCEEFIYG-GCEGNQNRFESLEECKKMCTREKPDFCFLEEDPGICR GYITRYFYNNQTKQGERFKYGGCLGNMN-NFETLEECKNICEDGPNGXQVDNYGTQLNAV NNSLTPQSTKVPSLFEFHGPSWCLT-PADRGLCRANENRFYYNSVIGKCRPFKYSGCGGNE NNFTSKQECLRACKKGFIQRISKGGLIK-TKRKRKKQRVKIAYEEIFVKNM. Accordingly, it will be appreciated that all characteristics and uses of polypeptides of SEQ ID NO:52 described throughout the present application also pertain to the polypeptides encoded by the nucleic acids included in Clone 500721700_204-43-4-0-H10-F. In addition, it will be appreciated that all characteristics and uses of the polynucleotides of SEQ ID NO:51 described throughout the present application also pertain to the nucleic acids included in Clone 500721700_204-43-4-0-H10-F. A preferred embodiment of the invention is directed toward the compositions of SEQ ID NO:51, SEQ ID NO:52, and Clone 500721700_204-43-4-0-H10-F. Also preferred are polypeptide fragments having a biological activity as described herein and the polynucleotides encoding the fragments.

The protein of SEQ ID NO:48 encodes Tifapix. The protein of SEQ ID NO:52 encodes Tifapinix-A58S. Tifapinix-A58S differs from Tifapinix in having serine at position 58 rather than alanine (A58S) (numbered from the initiating methionine of Tifapinix). It will be appreciated that the specification, composition, and embodiments directed herein to Tifapirtix also are given to be directed as well to Tifapinix-A58S. Furthermore, it will also be appreciated that in said specification, composition, and embodiments directed to any polypeptide of Tifapinix wherein said polypeptide includes alanine at position 58, that said specification, composition, and embodiments given to be directed as well to the corresponding polypeptide of Tifapinix include amino acid serine at position 58.

Tifapinx is a novel splice variant of tissue factor pathway inhibitor (TFPI-1). Tissue factor (TF) initiates the extrinsic coagulation pathway (U.S. Pat. Nos. 5,849,875; 5,106,833; 6,103,499; 5,773,251; 5,994,125, 1999, which disclosures are hereby incorporated by reference in their entirety). TFPI-1 is also known as lipoprotein associated coagulation inhibitor (LACI), so named because of its affinity for plasma lipoprotein.

Tifapinix has novel function as described below.

TFPI-1 is a secreted trivalent Kunitz-type plasma proteinase inhibitor that negatively regulates the initiation of coagulation by producing activated factor X (FXa) feedback inhibition of the catalytic complex of activated factor VII (FVIIa) and TF. The second Kunitz domain of TFPI- 1 binds and inhibits FXa, whereas the first Kunitz domain is responsible for the inhibition of FVIIa in the TF-FVIIa complex. The linker region between Kunitz domains 1 and 2 of TFPI-1 is comprised of 20 amino acids (U.S. Pat. No. 5,849,875 which disclosures is hereby incorporated by reference in its entirety): TRDNANRIIKTTLQQEKPDF (SEQ ID NO:189). The function of the third Kunitz domain is unknown, although there is evidence that it contains a heparin binding site. Heparin binding site(s) have also been mapped carboxyl-terminal to the third Kunitz domain.

TFPI-1 directly inhibits FXa and, in a FXa-dependent fashion, produces feedback inhibition of the TF-FVIIa catalytic complex. TFPI-1 is the major inhibitor of the protease activity of the TF-FVIIa cornplex. The allosteric promotion of TF-FVIIa binding by Kunitz domain 1 on FXa binding to Kunitz domain 2 presumably is carried out at least in part through the linker region between Kunitz domains 1 and 2. The finding that the Kunitz domain 2, which binds. FXa, is required for inhibition of the TF-VIIa complex has led to the proposal that TFPI-1 inhibits. TF-FVIIa by forming a quaternary TF-FVIIa-FXa-TFPI-1 complex. The formation of a quaternary complex can result from either the initial binding of TFPI-1 to FXa, with subsequent binding to the TF-VIIa complex or, alternatively, TFPI-1 could bind directly to a preformed TF-FVIIa-FXa complex. The consequence of the formation of the quaternary complex is that TF can no longer participate in initiating coagulation.

Aside from it role in coagulation, FXa plays a role in inflammation. FXa generated by TF-FVIIa has been shown to lead to pro-inflammatory activation of vascular endothelial cells through its cleavage of protease-activated receptor 2 (PAR2) (Camerer, E et al., Proc. Natl., Acad. Sci. USA 97:5255-60 (2000) which disclosure is, hereby incorporated by reference in its entirety). FXa can also elicit a pro-inflamrmatory, cellular response by cleavage of protease-activated receptor 1 (PAR1) (Kravchenko, R M Blood 97:3109-16 (2001) which disclosure is hereby incorporated by reference in its entirety). HLA-DR-restricted macrophage expression of TF in rheumatoid synovium is believed to play a role in disease pathogenesis in part through generation of FXa (Dialynas DP et al., Arthritis and Rheumatism 41:1515-6 (1998) which disclosure is hereby incorporated by reference in its entirety).

TF is a bifunctional molecule capable of inducing both fibrin deposition and angiogenesis in cancer. Cancer patients are prone to venous thromboembolism, and this hypercoagulability favors tumor growth and metastasis. In human lung cancer, melanoma, and breast cancer, TE and vascular endothelial growth factor (VEGF) co-localize in tumor cells; a close correlation exists between TF and VEGF synthesis in tumor cell lines and with angiogenesis in vivo in a severe, combined immunodeficient mouse model (Rickles, FR et al., Int. J. Hematol. 73:145-50 (2001); Wojtukiewicz M Z et al., Thromb. Haemost. 82:1659-62 (1999);Abdulkadir S A, et al., Hum. Pathol. 31:443-7 (2000); Koomagi R et al., Int. J. Cancer 79:19-22 (1998) which disclosures are hereby incorporated by reference in their entirety).

TF supports metastasis (Mueller BM et al., J. Clin. Invest. 101:1372-8 (1998); Fischer EG et al., J. Clin. Invest. 104: 1213-21 (1999) which disclosures are hereby incorporated by reference in their entirety). Equally important for this process are (a) interactions of the TF cytoplasmic domain, which binds the mobility-enhancing actin-binding protein 280, and (b) formation of a proteolytically active TF-FVlla complex on the tumor cell surface. In primary bladder carcinoma cells, this complex localizes to the invasive edge, in proximity to tumor-infiltrating vessels that stain intensely for TFPI-1. Tumor cell adhesion and migration was shown in vitro to be supported by interaction of TF-FVIIa with TFPI-1 immobilized heparin.

TF antigen has been detected in all cellular elements comprising the atheriosclerotic plaque. The most abundant sources of TF appear to be the macrophages and intimal smooth muscle cells located in the cap surrounding the lipid-rich necrotic core. TF antigen is also present in the medial and endothelial cells overlying the plaque. In addition to its association with vascular cells, TF antigen is also found in the extracellular matrix of the intima and in the necrotic core. This TF may come in contact with circulating blood when the plaque ruptures—the most important precipitant of acute arterial thrombosis (Taubman M B et al., Thrombosis and Haemostasis 82:801-5 (1999) which disclosure is hereby incorporated by reference in its entirety).

Recently it has been shown that TFPI-1 inhibits the proliferation of basic fibroblast growth factor-stimulated endothelial cells. A truncated form of TFPI-1, containing only the first two Kunitz-type proteinase inhibitor domains, has very little antiproliferative activity, suggesting that the carboxyl-terminal region of TFPI-1 is responsible for this activity (Hembrough, T A et al., J., Biol. Chem. 276:12241-8 (2001) which disclosure is hereby incorporated by reference in its entirely). By virtue of this activity, TFPI-1 is an inhibitor of angiogenesis. Anomalous angiogeneisis plays an important role in a number of pathologies, including cancer, proliferative diabetic retinopathy, and rheumatoid arthritis (Folkman, J, Forum (Geneva) 9 (3 Suppl 3):59-62 (1999); Danis, RP et al., Expert Opin. Pharmacother 2:395-407 (2001); Stupack, DG et al., Braz J. Med. Biol. Res. 32:573-81 (1999) which disclosures are hereby incorporated by reference in their entirety).

In the case of Tifapinix, alternative splicing results in the internal deletion of exon 5 comprised of 13 amino acids from the linker region between Kunitz domains 1 and 2 (Girard, T J et al., J. Biol. Chem. 266:5036-41 (1991) which disclosure is hereby incorporated by reference in its entirety). The A58S amino acid substitution that distinguishes Tifapinix-A58S from Tifapinix, as well as from the canonical TFPI-1 amino acid sequence (NCBI Accession No. P10646 which disclosure is hereby incorporated by reference in its entirety), establishes that the alternative splicing of TFPI-1 represented by Tifapinix can occur for more than one allele of TFPI-1, thereby supporting the thesis that the alternative splicing represented by Tifapinix plays a significant and unique role in TFPI-1 biology.

The resultant shortened linker region between Kunitz domains 1 and 2 is comprised of 7 amino acids: TREKPDF. The deletion also results in the generation of a novel amino acid neighborhood around the two, amino acids bracketing the deletion (RE, underlined above). Tifapinix retains the capacity to bind to FXa (Kunitz domain 2), but has lost the capacity to allosterically promote binding of Kunitz domain 1 to TF-FVIIa in response to the FXa binding. As Tifapinix retains the capacity to inhibit FXa, Tifapinix therefore remains both an anti-coagulant and an anti-inflammatory. As the carboxyl terminus of Tifapinix remains intact, Tifapinix retains the capacity to inhibit angiogenesis.

Importantly however and in contradistinction to TFPI-1, by virtue of having lost the capacity to allosterically promote TF-FVIIa-binding by Kunitz domain 1, Tifapinix has lost the capacity to be recruited by TF-FVIIa for promotion of tumor cell metastasis (Mueller. B M et al., J. Clin. Invest. 101:1372-8 (1998); Fischer E G et al., J. Clin. Invest. 104:1213-21 (1999) which disclosures are hereby incorporated by reference in their entirety).

In a preferred embodiment, the present invention provides for an antibody that specifically binds Tifapinix of the present invention. Further preferred is a method for making said antibody wherein said antibody recognizes a non-conformational or conformational epitope of Tifapinix.

Further preferred is a method for making said antibody wherein a mouse is immunized with Tifapinix. Further preferred is a method wherein monoclonal antibodies derived from said mouse are screened for binding to Tifapinix but not to TFPI-1. Further preferred is a method of making said antibody wherein said antibody is directed to the novel linker region sequence of Tifapinix comprised of amino acids 105-111, numbered from the initiating methionine of Tifapinix, or any fragment thereof. Further preferred is a method wherein monoclonal antibodies derived from said mouse are screened by sandwich enzyme-linked immunosorbent assay (ELISA) for binding to Tifapinix but not to TFPI-1. Methods of generating said monoclonal antibody and of establishing its specificity by methods including sandwich ELSA are well known to those skilled in the art.

In a preferred embodiment, the present invention provides for a method of contacting said antibody and specifically binding it with Tifapinix. Further preferred is a method for using said antibody diagnostically to determine the basis either for immune dysfunction or for inflammopathology. In the case of inflammopathology, of which the disease states below are representative, the level of Tifapinix expression is expected to be depressed. In the case of non-inflammatory immune dysregulation, Tifapinix status is more difficult to predict a priori. In either case, Tifapinix status is expected to facilitate diagnosis and, moreover, facilitate stratification of disease states. Furthermore, Tifapinix status may also have prognostic value. Further preferred is a method of using said antibody diagnostically in a sandwich ELISA format to quantitate Tifapirnix in plasma or other bodily fluid, including but not restricted to synodal fluid and cerebrospinal fluid, within a pathological context. Further preferred is a method of using said diagnostic assay to determine the level of Tifapinix in plasma or other bodily fluid of a patient with either dysregulated immune function or inflammopathology wherein the immune dysfunction or inflammopathology is selected from, but not restricted to, the group consisting of: (a) Rheumatoid arthritis; (b) Atheriosclerosis; (c) Inflanunatory bowel disease; (d) Insulin dependent diabetes mellitus (Type 1 diabetes); (e) Systemic lupus erythematosus; (f) Multiple sclerosis; (g) Psoriasis; (h) Allergic asthma; (i) Reperfusion injury; and (o). Stroke.

In further preferred embodiment, the present invention provides for a method of using Tifapinix to treat patients with immune dysfunction or inflammopathology. Preferred compositions comprise Tifapmix. Further preferred compositions comprise Tifapinixu. Preferred formulation of said composition is that formulation compatible with the route of delivery wherein said route of delivery is selected from, but not restricted to, the group: (a) Oral; (b) Transdermal; (c) Injection wherein injection is selected from, but not restricted to, the group consisting of: intravenous, intramuscular, subcutaneous, intra-synodal, and intra-tumoral; (d) Buccal; and (e) Aerosol.

Neovascularization plays a role in the pathogenesis of a number of diseases, including but not restricted to rheumatoid arthritis [Danis RP et al., Expert Opin. Pharmacother. 2:395-407 (2001) which disclosure is hereby incorporated by reference in its entirety].

In a further embodiment of the invention, said composition comprised of Tifapinix is used in a method of treating said patients with immune dysfunction or inflammopathology. Further preferred is a method of treating said patients in a method of ameliorating the symptoms or pathology associated with said immune dysfunction or inflammopathology. Further preferred is a method of treating said patients in a method of ameliorating the symptoms or pathology associated with pathogenetic engagement of the extrinsic coagulation pathway or the promotion of angiogenesis by TF. Further preferred are compositions comprised of Tifapinix used in methods of delivering to said patients an ameliorative effective amount of Tifapinix by said route of delivery. Further preferred is a method of delivering said composition comprising Tifapinix by said route of delivery to patients with immune dysfunction or inflammopathology wherein the, immune dysfunction or inflanmmopathology is selected from, but not restricted to, the group:

(a) Rheumatoid arthritis; (b) Atheriosclerosis; (c) Inflammatory bowel disease; (d) Insulin dependent diabetes mellitus (Typel diabetes); (e) Systemic lupus erythematosus; (f) Psoriasis; (g) Multiple sclerosis; (h) Allergic asthma; (i) Reperfusion injury; and (j). Stroke.

In acute myocardial infarction (ANE), the monocyte TF procoagulant activity is increased and may contribute to the risk for recurrence and other thrombotic events [Ott I et al., Blood 97:3721-6 (2001) which disclosure is hereby incorporated by reference in its entirety]. In a further embodiment of the invention, said composition comprised of Tifapinix is used in a method to treat patients with AMI. Further preferred is a method of delivering by intravenous injection an ameliorative effective amount of Tifapinix in a method to treat patients with AMI.

Studies confirm the important role of TF-mediated coagulation in the smooth muscle proliferation and neointimal thickening that follows vascular injury. [Han X et al., Arterioscler. Thromb. Vasc. Biol. 19:2563-7 (1999); Taubman M B et al., Thrombosis and Haemostasis 82:801-5 (1999) which disclosures are hereby incorporated by reference in their entirety]. In a further embodiment of the invention, said composition comprised of Tifapinix is used in a method to treat patients with neointimal thickening following vascular injury, including but not restricted to that consequential to balloon-induced vascular injury. Further preferred is a method of delivering by intravenous injection an ameliorative effective amount of Tifapinix in a method to treat patients with intimal thickening following vascular injury.

Studies confirm the important role of TF engagement of the extrinsic coagulation pathway in vascular pathology. In a further embodiment of the invention, said composition comprised of Tifapinix is used in a method to treat patients with said TF-associated vascular pathology. Further preferred is a method of delivering by intravenous injection an ameliorative effective amount of Tifapinix in a method to treat patients with said vascular pathology. Further preferred is a method of delivering by intravenous injection an ameliorative effective amount of Tifapinix in a method to treat patients with said vascular pathology wherein said pathology is selected from, but not restricted to, the group consisting of: (a) Disseminated intravascular coagulation (DIC); (b) Hypercoagulability; and (c) Septic shock.

Proliferative diabetic retinopathy (PDR) remains one of the major causes of aquired blindness in developed nations. The hallmark of PDR is neovascularization, abnormal angiogenesis that may ultimately cause severe vitreous cavity bleeding and/or retinal detachment. In a further embodiment of the invention, said composition comprised of Tifapinix is used in a method to treat patients with said PDR.

In a further embodiment of the invention, said composition comprised of Tifapinix is used in a method of anti-angrogenesis or anti-metastasis to treat patients with cancer. Further preferred is a method of treating said patients in a method of ameliorating the symptoms or pathology associated with said cancer. Further preferred are compositions comprised of Tifapinix used in methods of delivering to said patients an ameliorative effective amount of Tifapinix by said route of delivery. Further preferred is a method of delivering Tifapinix by said route of delivery to patients with cancer wherein the cancer is selected from, but not restricted to, the group:

(a) Melanoma; (b) Breast carcinoma; (c) Lung carcinoma; (d) Colon carcinoma; (e) Prostatic carcinoma; (f) Hodgkin's lymphoma; (g) Non-Hodgkin's lymphoma; (h) Pancreatic carcinoma; (i) Uterine carcinoma; (j) Ovarian carcinoma; (k) Testicular carcinoma; (l) Renal carcinoma; (m) Hepatic carcinoma; and (n) Lung non-small-cell carcinoma.

Tifapinix represents a uniquely valuable, reagent with which to address the molecular basis for the allosteric relationship between the initial FXa binding to Kunitz domain 2 and the subsequent TF-FVIa binding to Kunitz domain 1. That is because the lesion is. Tifapinix is small and well-defined: a deletion of 13 contiguous amino acids from the linker region between Kunitz domains 1 and 2. Specifically, the relative importance of linker length and linker amino acid composition can be readily addressed. In further preferred embodiment, therefore, the present invention provides for a method of recombinant DNA manipulation of polynucleotides encoding Tifapinix to identify the critical molecular parameters for said allosteric mechanism. Methods of manipulating nucleic acid sequence, including but not restricted to site-specific mutagenesis, and expression of recombinant protein are well known to those skilled in the art.

The capacity of Tifapinix to specifically inhibit the serine protease activity of FXa makes it a very useful reagent for assessing the role either of FXa serine protease activity or more generally that of the active site of FXa in a number of activities. These activities include but are not necessarily restricted to the group:

Amplification of extrinsic coagulation, as read out in a clotting assay (Dialynas DP et al. Cellular Immunology 177:671-9 (1997) which disclosure is hereby incorporated by reference in its entirety;

Serine proteolytic cleavage of specific substrate; and

Docking with its receptor, EPR-1, expressed on vascular endothelial cells and smooth muscle cells (Nicholson AC et al., J. Biol. Chen. 271:28407-13 (1996) which disclosure is hereby incorporated by reference in its entirety).

Whereas (a) and (b) require the active site of FXa, (c) does not. Tifapinix therefore would be a discriminating reagent with which to assess the involvement of FXa active site in diverse activities. For example, Tifapinix blocks (a) and (b), but does not block (c). In further preferred embodiment, the present invention provides for a method of using Tifapinix to investigate the requirement for FXa active site, and by inference FXa, in an activity manifested by a test sample.

In further preferred embodiment, Tifapinix is used for plasmin binding and inhibition. Any suitable method may be used to test the compounds of this invention (U.S. Pat. No. 6,103,499, 2000). Scatchard (Ann N.Y. Acad Sci (1949) 51:660-669) described a classical method of measuring and analyzing binding, which is applicable to protein binding. This method requires relatively pure protein and the ability to distinguish bound protein from unbound. A second appropriate method of measuring K.sub.D is to measure the inhibitory activity against the enzyme. If the K.sub.D to be measured is in the 1 nM to 1 muM range, this method requires chromogenic or fluorogenic substrates and tens of micrograms to milligrams of relatively pure inhibitor. For the proteins of this invention, having K.sub.D in the range 5 nM to 50 pM, nanograms to micrograms of inhibitor suffice. When using this method, the competition between the, inhibitor and the enzyme substrate can give a measured K.sub.i that is higher than the true K.sub.i. Measurement reported here is not so corrected because the correction would be very small and the any correction would reduce the K.sub.i. Here, we use the measured K.sub.i as a direct measure of KD. Tifapinix has a K.sub.D for plasmin of at most about 5 nM, more preferably at most about 300 pM, and most preferably 100 pM or less. Preferably, the binding is inhibitory so that K.sub.i is the same as K.sub.D. The K.sub.i of QS4 for plasnin is about 2 nM. The K.sub.i of SPI11 for plasmin is about 88 pM.

In another preferred embodiment, Tifapinix is used for pharmnaceutical methods and preparations. The preferred subject of this invention is a mammal. The invention is particularly useful in the treatment of humans, but is suitable for veterinary applications, too. Herein, "protection" includes "prevention", "suppression", and "treatment".

"Prevention" involves administration of drug prior to the induction of disease. "Suppression" involves administration of drug prior to the clinical appearance of disease. "Treatment" involves administration of drug after the appearance of disease. In human and veterinary medicine, it may not be possible to distinguish between "preventing" and "suppressing" since the inductive event(s) may be unknown or latent, or the patient is not ascertained until after the occurrence of the inductive event(s). We use the term "prophylaxis" as distinct from "treatment" to encompass "preventing" and "suppressing". Herein, "protection" includes "prophylaxis". Protection need not by absolute to be useful. Tifapinix or fragments thereof may be administered, by any means, systemically or topically, to protect a subject against a disease or adverse condition. For example, administration of such a composition may be by any parenteral route, by bolus injection or by gradual perfusion. Alternatively, or concurrently, administration may be by the oral route. A suitable regimen comprises administration of an effective amount of the protein, administered as a single dose or as several doses over a period of hours, days, months, or years. The suitable dosage of a protein of this invention may depend on the age, sex, health, and weight of the recipient, kind of concurrent treatment, if any, frequency of treatment, and the desired effect. However, the most preferred dosage can be tailored to the individual subject, as is understood and determinable by one of skill in the art, without undue experimentation by adjustment of the dose in ways known in the art. For methods of preclinical and clinical testing of drugs, including proteins, see, e.g., Berkow et al, eds., The Merck Manual, 15$^{th}$ edition, Merck and Co., Rahway, N.J., 1987; Goodman et al, eds., Goodman and Gilman's The Pharmacological Basis of Therapeutics, 8th edition, Pergamon Press, Inc., Elmsford, N.Y., (1990); Avery's Drug Treatment: Principles and Practice of Clinical Pharmacology and Therapeutics, 3rd edition, ADIS Press, LTD., Williams and Wilkins, Baltimore, Md. (1987), Ebadi, Pharmacology, Little, Brown and Co., Boston, (1985), which references are hereby incorporated in their entirety. In addition to Tifapinix, a pharmaceutical composition may contain pharmaceutically acceptable carriers, excipients, or auxiliaries. See, e.g., Berker, supra, Goodman, supra, Avery, supra and Ebadi, supra.

In yet another preferred embodiment, Tifapinix or fragments thereof are used for in vitro diagnostic methods and reagents. Tifapinix and related sequences may be applied in vitro to any suitable sample that might contain plasmin to measure the plasmin present. The assay must include a Signal Producing System (SPS) providing a detectable signal that depends on the amount of plasmin present. The signal may be detected visually or instrumentally. Possible signals include production of colored, fluorescent, or luminescent products, alteration of the characteristics of absorption or emission of radiation by an assay component or product, and precipitation or agglutination of a component or product. The component of the SPS most intimately associated with the diagnostic reagent is called the "label". A label may be, e.g., a radioisotope, a fluorophore, an enzyme, a co-enzyme, an enzyme substrate, an electron-dense compound, or an agglutinable particle. A radioactive isotope can be detected by use of, for example, a .gamma counter or a scintillation counter or by autoradiography. Isotopes which are particularly useful are $^{3}H$, $^{125}I$, $^{131}I$, $^{35}S$, $^{14}C$, and, preferably, $^{125}I$. It is also possible to label a compound with a fluorescent compound. When the fluorescent-labeled compound is exposed to light of the proper wavelength, its presence can be detected. Among the most commonly used fluorescent labeling compounds are fluorescein isothiocyanate, rhodamine, phycoerythrin, phycocyanin, allophycocyanin, o-phthaldehyde, and fluorescamine. Alternatively, fluorescence-emitting metals, such as $^{125}Eu$ or other anthamide, may be attached to the binding protein using such metal chelating groups as diethylenetriaminepentaacetic acid or ethylenediamine-tetraacetic acid. The proteins also can be detectably labeled by coupling to a chemiluminescent compound, such as luminol, isolumino, theromatic acridinium ester, imidazole, acridinium salt, and oxalate ester. Likewise, a bioluminescent compound, such as luciferin, luciferase and aequorin, may be used to label the binding protein. The presence of a bioluminescent protein is determined by detecting the presence of luminescence. Enzyme labels, such as horseradish peroxidase and alkaline phosphatase, are preferred. There are two basic types of assays: heterogeneous and homogeneous. In heterogeneous assays, binding of the affinity molecule to analyte does not affect the label; thus, to determine the amount of analyte, bound label must be separated from free label. In homogeneous assays, the interaction does affect the activity of the label, and analyte can be measured without separation. Tifapinix, as a plasmin-binding protein may be used diagnostically in the same way that an antiplasmin antibody is used. Thus, depending on the assay format, it may be used to assay plasmin, or, by competitive inhibition, other substances which bind plasmin. The sample will normally be a biological fluid, such as blood, urine, lymph, semen, milk, or cerebrospinal fluid, or a derivative thereof, or a biological tissue, e.g., a tissue section or homogenate. If the sample is a biological fluid or tissue, it may be taken from a human or other mammal, vertebrate or animal, or from a plant. The preferred sample is blood, or a fraction or derivative thereof. In a related embodiment, Tifapinix or fragments thereof is immobilized, and plasmin in the sample is allowed to compete with a known quantity of a labeled or specifically labelable plasmin analogue. The "plasmin analogue" is a molecule capable of competing with plasmin for binding to Tifapinix or fragments thereof. It may be labeled already, or it may be labeled subsequently by specifically binding the label to a moiety differentiating the plasmin analogue from plasmin. The phases are separated, and the labeled plasmin analogue in one phase is quantified. In a "sandwich assay", both an insolubilized plasnin-binding agent (PBA), and a labeled PBA are employed. The plasmin analyte is captured by the insolubilized PBA and is tagged by the labeled PBA, forming a tertiary complex. The reagents may be added to the sample in any order. The PBAs may be the same or different, and only one PBA needs to comprise Tifapinix or fragments thereof according to this invention (the other may be, e.g., an antibody). The amount of labeled PBA in the tertiary complex is directly proportional to the amount of plasmin in the sample. The two, embodiments described above are both heterogeneous assays. A homogeneous assay requires only that the label be affected by the binding of Tifapinix or fragments thereof to plasmin. The plasmin analyte may act as its own label if Tifapinix or fragments thereof are used as a diagnostic reagent A label may be conjugated, directly or indirectly (e.g., through a labeled anti-Tifapinix antibody), covalently (e.g., with SPDP) or noncovalently, to the plasmin-binding protein, to produce a diagnostic reagent. Similarly, the plasmin-binding protein may be conjugated to a solid phase support to form a solid phase ("capture") diagnostic reagent. Suitable supports include glass, polystyrene, polypropylene, polyethylene, dextran, nylon, amylases, and magnetite. The carrier can be soluble to, some extent or insoluble for the purposes of this invention. The support material may have any structure so long as the coupled molecule is capable of binding plasmin.

In yet another preferred embodiment, Tifapinix or fragments thereof are used for in vivo diagnostic uses. Tifapinix or fragments thereof, i.e a Kunitz domain that binds very tightly to plasmin can be used for in vivo imaging. Radiolabeled Tifapinix may be administered to a human or animal subject, typically by injection, e.g., intravenous or arterial other means of administration such as subcutaneous, intramuscular in a quantity sufficient to permit subsequent dynamic and/or static imaging using suitable radio-detecting devices. The dosage is the smallest amount capable of providing a diagnostically effective image, and may be determined by means conventional in the art, using known radio-imaging agents as guides. Typically, the imaging is carried out on the whole body of the subject, or on that portion of the body or organ relevant to the condition or disease under study. The radiolabeled binding protein has accumulated. The amount of radiolabeled binding protein accumulated at a given point in time in relevant target organs can then be quantified. A particularly suitable radio-detecting device is a scintillation camera, such as a. gamma. camera. The detection device in the camera senses and records (and optional digitizes) the radioactive decay. Digitized information can be analyzed in any suitable way, many of which are known in the art. For example, a time-activity analysis can illustrate uptake through clearance of the radiolabeled binding protein by the target organs with time. The radioisotope used should preferably be pharmacologically inert, and the quantities administered should not have substantial physiological effect. The binding protein may be radio-labeled with different isotopes of iodine, for example $^{123}$I, $^{125}$I, or $^{131}$I (see, for example, U.S. Pat. No. 4,609,725). The amount of labeling must be suitably monitored.

In applications to human subjects, it may be desirable to use radioisotopes other than $^{125}$ I for labeling to decrease the total dosimetry exposure of the body and to optimize the detectability of the labeled molecule. Considering ready clinical availability for use in humans, preferred radio-labels include: $^{99m}$Tc, $^{67}$Ga, $^{68}$Ga, $^{90}$Y, $^{111}$In, $^{113m}$In, $^{123}$I, $^{186}$Re, $^{188}$Re, or $^{211}$At. Radiolabeled protein may be prepared by various methods. These include radio-halogenation by the chloramine-T or lactoperoxidase method and subsequent purification by high pressure liquid chromatography, for example, see Gutkowska et al in "Endocrinology and Metabolism Clinics of America 16 (1):183, 1987. Other methods of radiolabeling can be used, such as IODOBEADS Tifapinix or fragments thereof may also be used to purify plasmin from a fluid, e.g., blood. For this purpose, it is preferably immobilized on an insoluble support. Such supports include those also useful in preparing solid phase diagnostic reagents. Proteins can be used as molecular weight markers for reference in the separation or purification of proteins.

These embodiments also relate to isolation, purification and production of antibodies wherein antibodies can be polyclonal or monoclonal as described (U.S. Pat. No. 6,171,587 B1, 2000), hereby enclosed in their entirety.

Another preferred embodiment relates to the use of Tifapinix and Kunitz domains thereof for the inhibition of kallikrein activity. Kallikreins are serine proteases found in both tissues and plasma (see U.S. Pat. No. 5,994,125, 1999, U.S. Pat. No. 6,057,287, 2000) which references are hereby enclosed in their entirety). Plasma kallikrein is involved in contact-activated coagulation, fibrinolysis, hypotension, and inflammation mediated through the activities of factor XII (coagulation), pro-urokinase/plasrninogen (fibrinolysis), and kininogens (hypotension and inflammation). Kallikrein cleavage of kininogens results in the production of highly potent bioactive peptides (kinins), which cause increased vascular permeability, vasodilation, bronchospasm, and pain induction. Thus, kinins mediate life-threatening vascular shock and edema associated with bacteremia (sepsis) or trauma, asthma, and inflarmmatory and neurogenic pain associated with tissue injury, and edema in C1-inhibitor-deficient diseases (hereditary angioedenia). Tifapinix, as a protease inhibitor, and fragments thereof said Kunitz domains, prevent the cleavage of kallikrein and thus the release of said kinins.

Tifapinix may be used for any of the foregoing purposes. Methods for production using eukaryotic and prokaryotic expression systems have been reported previously and are well known in the art (U.S. Pat. No. 6,103,500, 2000; PCT. WO 95/18830). For example, Tifapinix or fragments thereof, whereas preferred fragments comprise said Kunitz domains, preferably Kunitz domain three, may be produced by any conventional technique including (i) nonbiological synthesis by sequential coupling of component amino acids, (ii) production by recombinant DNA techniques in a suitable host cell such as bacterial, insect- or mammalian cells, (iii) removal of undesired sequences from LACI and in coupling of synthetic replacement sequences (U.S. Pat. No. 5,994,125, 1999, hereby incorporated in its entirety).

Protein of SEQ ID NO:50 (Internal Designation Clone 588098_184-11-4-0-H4-F)

The cDNA of Clone 588098_184-11-4-0-H4-F (SEQ ID NO:49) encodes the protein of SEQ ID NO:50 comprising the amino acid sequence MPSSVSWGILLLAGLCCLVPVSLGT-KADTHDEILEGLNFNLTEIPEAQIHEGFQELLRTLN QPDSQLQLTTGNGLFLSEGLKLVD-KFLEDVKKLYHSEAFTVNFGDTEEAKKQINDYVEK GTQGKIVDLVKELDRDTVFALVNY-IFFKGKWERPFEVKDTEEEDFHVDQVTTVKVPMM KRLGMFNIQHCKKLSSWVLLMKYLGNA-TAIFFLPDEGKLQHLENELTHDIITKFLENEDR RSASLHLPKLSITGTYDLKSVLGQLGIT-KVFSNGADLSGVTEEAPLKLSKAVHKAVLTIDE KGTEAAGAMFLEAIPMSIPPEVKFNK-PFVFLMIDXNTKSPLFMGKVVNPTQK (SEQ ID NO:50). Accordingly it will be appreciated that all characteristics and uses of polypeptides of SEQ ID NO:50 described throughout the present application also pertain to the polypeptides encoded by the nucleic acids included in Clone 588098_184-11-4-0-H4-F. In addition, it will be appreciated that all characteristics and uses of the polynucleotides of SEQ ID NO:49 described throughout the present application also pertain to the nucleic acids included in Clone 588098_184-11-4-0-H4-F. A preferred embodiment of the invention is directed toward the compositions of SEQ ID NO:49, SEQ ID NO:50, and Clone 588098_184-11-4-0-H4-F. Also preferred are polypeptide fragments having a biological activity as described herein and the polynucleotides encoding the fragments.

The protein of SEQ ID NO:50 encodes CrypAAT, a splice variant of alpha-1-antitrypsin (antitrypsin) with novel function. In CrypAAT, internal splicing within exon 2 leaves the signal sequence intact but results in an N-terminal deletion of 67 amino acids from the mature protein. This deletion extends from the disordered N-terminus through helix A and into helix B (Stein, PE et al., Nature Structural Biology 2:96-113 (1995) which disclosure is hereby incorporated by reference in its entirety). The Met-Ser active site near the C-terminus is intact.

Antitrypsin is synthesized primarily by hepatocytes and is the most abundant proteinase inhibitor in human plasma. Although it diffuses through all organs, and inhibits a large number of proteases, its primary function is in the lung parenchyma, where it protects alveolar tissue from damage by neutrophil elastase, a serine protease released in the course of an inflammatory response. Elastases are defined by their ability to cleave elastin, the matrix protein that gives tissues the property of elasticity. If left uncontrolled, neutrophil elastase leads to excessive inflammation and progressive emphysema. Individuals with antitrypsin deficiency have at least a 20-fold increase risk of developing emphysema. Antitrypsin is a member of the serpin (sie protease inhibitor) supergene family. The primary function of most of the serpins is the regulation of proteolytic enzymes under both physiological and pathological conditions. On the basis of strong sequence similarities, a number of proteins with no known inhibitory activity have been classified as serpins. For example, thyroxine binding globulin (TBG) and corticosteroid binding globulin (CBG) serve as transporters of lipophilic hormones, and angiotensinogen is a peptide hormone precursor (Janciauskiene, S, Biochimica et Biophysica Acta. 1535:221-35 (2001) which disclosure is hereby incorporated by reference in its entirety).

Serpins are competitive, irreversible inhibitors of serine proteases. Serpins have a common molecular design based on a five-stranded beta-sheet A and the reactive loop arising from it, that presents a peptide sequence to the target proteinase. The function of antitrypsin as a proteinase inhibitor depends on its undergoing conformational change when it binds to neutrophil elastase. This change involves the insertion of the cleaved reactive loop as the $4^{th}$ strand in its beta-sheet A, and deactivates neutrophil elastase by swinging it from the top to the bottom of the antitrypsin molecule (described as a mousetrap action). (Parar, JS et al., Journal of the Royal College of Physicians of London 34:295-300 (2000) which disclosure is hereby incorporated by reference in its entirety). A complex 'shutter' domain is responsible for maintaining the usual, closed state of beta-sheet A (Stein, PE et al., Nature Structural Biology 2:96-113 (1995); Gils, A et al. Thromb. Haemost. 80:531-41 (1998) which disclosures are hereby incorporated by reference in their entirety).

By virtue of conformational perturbation imposed on the protein by the novel splicing event, CrypAAT is without proteinase inhibitory function. CrypAAT retains its susceptibility to cleavage by neutrophil elastase, however. It also retains its susceptibility to cleavage by a number of non-target proteinases, such as gelatinase B (MMP-9). Unlike antitrypsin, therefore, CrypAAT functions as a proteinase substrate. Cleavage of CrypAAT by neutrophil elastase and the non-target proteinases generates a 4 kDa C-terminal fragment of 36 residues, which on cleavage remains non-covalently bound to the cleaved CrypAAT.

CrypAAT plays a number of diverse physiological roles as a proteinase substrate (Janciauskiene, S, Biochimica et Biophysica Acta 1535:221-35 (2001) which disclosure is hereby incorporated by reference in its entirety). Cleaved CrypAAT contributes to: the later phase of polymorphonuclear leukocyte infiltration and is a potent chemoattractant for monocytes. The isolated C-terminal fragment of CrypAAT can associate with extracellular matrix proteins such as collagen and/or laminin-1 and, in so doing, play an important role in protecting these proteins from inappropriate enzyme digestion. The C-terminal fragment of CrypAAT also exerts significant effects on cellular lipid catabolism and proinflammatory activation, by activating peroxisome proliferator-activated receptors (PPARs), transcription factors that recently have been proposed to regulate genes for lipid metabolism and proinflammatory proteins.

CrypAAT has also been implicated in several pathologies, namely atherosclerosis and cancer. The C-terminal cleavage fragment of CrypAAT is a component of atherosclerotic plaque, located specifically in the fibrous cap near the necrotic core. CrypAAT plays a role in atherosclerosis as a protease substrate and a reservoir of physiologically active peptide, degradation products. CrypAAT-positive adenocarcinormas of colon and lung have a worse prognosis than CrypAAT-negative ones. Recent studies provide good experimental evidence that the C-terminal fragment of CrypAAT generated by matrix metalloproteinases (MMws) enhances tumor growth and invasiveness in vivo.

Contrary to previous dogmas, it is now well established that brain cells can produce cytokines and chemokines, and can express adhesion molecules than enable an in situ inflammatory reaction. Brain ischemia and trauma elicit robust inflammation. The accumulation of neutrophils early after brain injury is believed to contribute to the degree of brain tissue loss.

In a preferred embodiment, the present invention provides for an antibody that specifically binds CrypAAT of the present invention. Further preferred is a method for making said antibody wherein said antibody recognizes a non-conformational or conformational epitope of CrypAAT.

Further preferred is a method for making said antibody wherein a mouse is immunized with CrypAAT. Further preferred is a method wherein monoclonal antibodies derived from said mouse are screened for binding to CrypAAT but not to antitrypsin. Further preferred is a method wherein monoclonal antibodies derived from said mouse are screened by enzyme-linked immunosorbent assay (ELISA) for binding to CrypAAT but not to antitrypsin. Further preferred is a method wherein said antibody is screened for the capacity to sterically or allosterically abrogate the protease susceptibility of CrypAAT. Further preferred is a method wherein said antibody is screened for the capacity to sterically or allosterically abrogate the neutrophil elastase or gelatinase susceptibility of CrypAAT. Methods of generating said monoclonal antibody and of establishing its specificity by methods including ELISA are well known to those skilled in the art. Methods of screening said antibody for the capacity to abrogate the protease susceptibility of CrypAAT are well known to those skilled in the art and include, but are not limited to: contacting the antibody with CrypAAT, incubating the antibody-CrypAAT complex with neutrophil elastase or gelatinase, and following proteolytic generation of the 4 kDa carboxyl fragment by denaturing polyacrylamide gel electrophoresis.

In a preferred embodiment, the present invention provides for a method of contacting said antibody and specifically binding it with CrypAAT. Further preferred is a method for using said antibody diagnostically to determine the basis either for immune dysfunction or for inflammopathology. Further preferred is a method of using said antibody diagnostically in a sandwich ELISA format to quantitate CrypAAT in plasma or other bodily fluid, including but not restricted to synodal fluid and cerebrospinal fluid, within a pathological context. Further preferred is a method of using said diagnostic assay to determine the level of CrypAAT in plasma or other bodily fluid of a patient with either dysregulated immune function or inflammopathology wherein the immune dysfunction or inflammopathology is selected from, but not restricted to, the group consisting of: (a) Rheumatoid arthritis; (b) Atheriosclerosis; (c) Inflammatory bowel disease; (d) Insulin dependent diabetes meilitus (Type 1 diabetes); (e) Systemic lupus erythemat-osus; (f), Multiple sclerosis, (g) Psoriasis; (h) Allergic asthma; (i) Acute myocardial infarction; (j) Septic shock; (k) Reperfusion injury; and (l) Stroke.

In further preferred embodiment, the present invention provides for a method of contacting and specifically binding to CrypAAT said antibody having the capacity to, abrogate the, proteolytic susceptibility, including but not restricted to that of neutrophil elastase and gelatinase, of CrypAAT. Further preferred is a method of using said antibody in contact with CrypAAT as a therapeutic for patients with either immune dysfunction or inflammopathology. Preferred compositions comprise said CrypAAT antibody or fragments or derivatives thereof. Preferred formulation of said composition is that compatible with the route of delivery wherein said route of delivery is selected from, but not restricted to, the group: (a) Oral; (b) Transdermal; (c) Injection; (d) Buccal; and (e) Aerosol.

In further preferred embodiment, the present invention provides for a method of contacting and specifically binding to CrypAAT said antibody having the capacity to abrogate the proteolytic susceptibility, including but not restricted to that of neutrophil elastase and gelatinase, susceptibility of CrypAAT. Further preferred is a method for using said CrypAAT antibody to treat patients with immune dysfunction or inflammopathology. Further preferred is a method of treating said patients with said CrypAAT antibody in a method of ameliorating the symptoms or pathology associated with immune dysfunction or inflammopathology. Said CrypAAT antibody ameliorates the symptoms or pathology associated with immune dysfunction or inflammopathology by suppressing proteolytic generation of bioactive fragments of CrypAAT, including but not restricted to, the 4 kDa carboxyl fragment. Further preferred is a method of delivering to said patients an ameliorative effective amount of said CrypAAT antibody. Further preferred is a method of delivering to said patients an ameliorative effective amount of said CrypAAT antibody by injection. Further preferred is a method of delivering to said patients with immune dysfunction or inflammopathology an ameliorative effective amount of said CrypAAT antibody wherein said immune dysfunction or inflammopathology is selected from, but not restricted to, the group: (a) Rheumatoid arthritis; (b) Atheriosclerosis; (c) Inflammatory bowel disease; (d) Insulin dependent diabetes mellitus. (Type 1 diabetes); (e) Systemic lupus erythematosus; (f) Psoriasis; (g) Multiple sclerosis; (h) Allergic asthma; (i) Acute myocardial infarction; (j) Septic shock; (k) Reperfusion injury; and (l) Stroke.

Further preferred is a method of contacting and specifically binding said antibody with CrypAAT in a method of transdermal contact to ameliorate the symptoms or pathology of psoriasis. Further preferred are compositions comprised of said CrypAAT antibody used in methods of contacting the psoriatic lesion with an ameliorative effective, amount of said CrypAAT antibody by injection or transdermal contact at the site of the lesion.

Further preferred is a method of contacting and specifically binding said antibody with CrypAAT in a method to ameliorate the symptoms or pathology of allergic asthma Preferred route of delivery is aerosol. Further preferred are compositions comprised of said CrypAAT antibody used in methods of contacting asthmatic tissue with an ameliorative effective amount of said CrypAAT antibody by aerosol.

Further preferred is a method of contacting and specifically binding said antibody with CrypAAT in a method to ameliorate the symptoms or pathology of allergic rhinitis (hayfever). Preferred route of delivery is aerosol. Further preferred are compositions comprised of said CrypAAT antibody used in methods of contacting inflamed nasal tissue with an ameliorative effective amount of said CrypAAT antibody by aerosol.

In a further embodiment, the present invention provides for said CrypAAT antibody to be used in a method to suppress acute inflammation. Further preferred is a method to use said CrypAAT antibody to suppress inflammation associated with wound healing. Further preferred are, compositions comprised of said antibody used in methods of contacting a wound or injured tissue with an ameliorative effective amount by injection or transdermal contact at the site of the wound.

In further preferred embodiment, the present invention provides for a method of contacting and specifically binding to CrypAAT said antibody having the capacity to abrogate the proteolytic susceptibility, including but not restricted to that of neutrophil elastase and gelatinase, susceptibility of CrypAAT. Further preferred is a method of treating cancer patients with said CrypAAT antibody in a method of ameliorating the symptoms or pathology associated with the cancer. Said CrypAAT antibody ameliorates the symptoms or pathology associated with cancer (including but not restricted to metastasis and invasiveness) by suppressing proteolytic generation of bioactive fragments of CrypAAT, including but not restricted to the 4 kDa carboxyl fragment. Further preferred is a method of delivering to said patients an ameliorative effective amount of said CrypAAT antibody by said route of delivery. Preferred route of delivery is intravenous or intra-tumoral injection. Further preferred is a method of delivering to said patients with cancer an ameliorative effective amount of said CrypAAT antibody wherein said cancer is selected from, but not restricted to, the group: (a) Melanoma; (b) Breast carcinoma; (c) Lung carcinoma; (d) Colon carcinoma; (e) Hodgkin's lymphoma; (f) Non-Hodgkin's lymphoma; (g) Prostatic carcinoma; (h) Pancreatic carcinoma; (i) Uterine carcinoma; (j). Ovarian carcinoma; (k) Testicular carcinoma; (l). Renal carcinoma; (m) Hepatic carcinoma; and (n) Lung non-small-cell carcinoma.

In a further embodiment, the present invention provides for said CrypAAT antibody to be used in a method of preclinical pharmacology in animal models of disease, including but not restricted to those of immune dysfunction, inflammopathology, and cancer.

Further preferred is a method in which said CrypAAT antibody is used in a rodent or primate model of human immune dysfunction or inflammopathology to optimize the therapeutic efficacy of said CrypAAT antibody. Further preferred is a method in which said CrypAAT antibody is used in a rodent or primate model of human immune dysfunction or inflammopathology wherein said immune dysfunction or inflammopathology is selected from but not restricted to the group: (a) Rheumatoid arthritis; Atheriosclerosis, inflammatory bowel disease; Insulin dependent diabetes (Type 1 diabetes); Systemic lupus erythematosus; Psoriasis; Multiple sclerosis; Allergic asthma; Acute myocardial infarction; Septic shock; Reperfusion injury; and Stroke.

Further preferred is a method in which said CrypAAT antibody is used in a mouse model of human cancer to optimize the therapeutic efficacy of said CrypAAT antibody. Further preferred is a method in which said CrypAAT antibody is used in a xenogeneic mouse model of human leukemia. Preferred route of delivering said composition comprised of CrypAAT antibody includes but is not restricted to intravenous injection and implanted pump. Further preferred is a method in which said CrypAAT antibody is used in a xenogeneic mousemodel of human leukemia engrafted with primary leukemia cells obtained from patients (Dialynas, DP et al., Blood 97:3218-25 (2001) which disclosure is hereby incorporated by reference in its entirety) wherein the leukemia is selected from but not restricted to the group: (a) Childhood T lymphocyte acute lymphoblastic leukemia (Pediatric T-ALL); (b) Adult T lymphocyte acute lymphoblastic leukemia (Adult T-ALL); (c) B lymphocyte acute lymphoblastic leukemia (B-ALL); (d) Acute myeloid leukemia (AML); (e) Chronic lymphocytic leukemia (CLL); and (f) Multiple myeloma.

In a further embodiment, the present invention provides for the use of said CrypAAT antibody in a method to abrogate proteolytic generation of the bioactive 4 kDa fragment of CrypAAT in in vitro cell cultures using human serum.Further preferred is a method of contacting and specifically binding said CrypAAT antibody to CrypAAT in culture to block in situ proteolytic generation of the bioactive 4 kDa carboxyl fragment from CrypAAT introduced into culture by human serum. Further preferred is a method of contacting and specifically binding said CrypAAT antibody immobilized on a resin to CrypAAT to deplete CrypAAT from human serum samples by immunoaffinity chromatography.

In a further embodiment, the present invention provides for the screening of test compounds for the capacity to specifically bind to CrypAAT and block the proteolytic generation of the 4 kDa carboxyl fragment by proteases including but not restricted to neutrophil elastase and gelatinase. Further preferred are said test compounds that specifically bind to either a non-conformational or conformational site on CrypAAT. Further preferred are said test compounds that block said proteolytic cleavage of CrypAAT either sterically or allosterically. Further preferred is a method of screening said test compounds for the capacity to block cleavage within the active site of CrypAAT by neutrophil eleastase or non-target proteinase and so generate the 4 kDa carboxyl fragment. Methods of screening said test compound for the capacity to abrogate the protease susceptibility of CrypAAT are well known to those skilled in the art and include, but are not limited to: contacting the test compound with CrypAAT, incubating the test compound-CrypAAT complex with neutrophil elastase or gelatinase, and following proteolytic generation of the 4 kDa carboxyl fragment by denaturing polyacrylamide gel electrophoresis.

Preferred formulations of said compound are those selected from, but not restricted to, formulations amenable to the routes of delivery selected from the group: (a) Oral; (b) Transdermal; (c) Injection; (d) Buccal; and (e) Aerosol.

Compounds found to block the cleavage of CrypAAT within its active site by elastase or non-target proteinase are used in in vivo and in vitro methods analogous to those described above for CrypAAT antibody.

Protein of SEQ ID NO:54 (Internal Designation Clone 789749_182-14-3-0-C12-F)

The cDNA of clone 789749_182-14-3-0-C12-F (SEQ ID NO:53) encodes the protein of SEQ ID NO:54 comprising the amino acid sequence:

MHFCGGTLISPEWVLTAAHCLEKSPRPSSYKVILGA-HQEVNLEPHVQEIEVSRLFLEPTRKDIALLKLSSPAV-ITDKVIPACLPSPNYVVADRTECFITGWGETQGTF-GAGLLKEAQLPVIENKVCNRYEFLNGRVQSTELCA-GHLAGGTDSCQGDSGGPLVCFEKDKYILQGVTS-WGLG CARPNKPGVYVRVSRFVTWIEGVMRNN (SEQ ID NO:50).

Accordingly it will be appreciated that all characteristics and uses of polypeptides of SEQ ID NO:54 described throughout the present application also pertain to the polypeptides encoded by the nucleic acids included in Clone 789749_182-14-3-0-C 12-F. In addition, it will be appreciated that all characteristics and uses of the polynucleotides of SEQ ID NO:53 described throughout the present application also pertain to the nucleic acids included in Clone 789749_182-14-3-0-C12-F. Also preferred are fragments having a biological activity as described therein and the polynucleotides encoding the fragments.

The protein of SEQ ID NO:54 encodes Plasminute, a variant of plasmin resulting from alternative transcription initiation within the plasminogen gene. Plasminute has novel function as described below.

The terminal event in activation of the human fibrinolytic system is generation of the enzyme plasmin, a serine protease possessing a variety of functional properties, the most notable of which is clearance by proteolytic degradation of fibrin deposits. Plasmin is formed upon activation of its zymogen, plasminogen, as a result of cleavage of a single peptide bond. This latter event is catalyzed by serine proteases with narrow specificity, termed plasminogen activators. Urokinase-type plasminogen activator and tissue-type plasminogen activator act directly; streptokinase acts indirectly. In its capacity as a serine protease, plasmin functions to dissolve the fibrin clot. Each of these plasminogen activators is commercially available and is indicated for the treatment of acute vascular diseases such a myocardial infarct, stroke, pulmonary embolism, deep vein thrombosis, peripheral arterial occlusion, and other venous thromboses (U.S. Pat. No. 5,753,486; "Human tissue plasminogen activator;" which disclosure is hereby incorporated by reference in its entirety). Collectively, these diseases account for major health hazards and risks.

In its capacity as a serine protease, plasmin also plays a role in normal processes involving cell migration in tissue remodeling. In this regard, plasmin is believed to function in processes in which cell movement is essential, such as macrophage invasion inflammation, angiogenesis, and keratinocyte accumulation after wound healing. Furthermore, plasmin has also been strongly implicated as an important mediator in pathological processes of cell migration that are involved in tumor cell growth (plasmin can activate growth factors) and invasion of surrounding tissue and, perhaps, metastases. Involvement of plasmin in these latter processes is supported by the ability of plasmin to degrade extracellular matrix proteins directly, such as proteoglycans, fibronectin, laminin, and type IV collagen, and/or be indirectly responsible for the degradation of matrix proteins through activation of metalloprotease zymogens, such as stromolysin and procollagenase. As a result of degradation of the extracellular matrix, cell migration into surrounding areas becomes more facile (Castellino, F J in *Molecular Basis of Thrombosis and Hemostasis*, High, K A & Roberts, H R, editors, New York, pp. 495-515 (1995) which disclosure is hereby incorporated by reference in its entirety).

Plasminogen is synthesized by endothelial cells as an 810-residue single chain glycoprotein, from which is excised a 19-residue signal peptide during secretion. Plasminogen is converted to plasmin as a result of activator-catalyzed cleavage of the Arg561-Val562 peptide bond (numbered from the amino-terminal glutamic acid residue of secreted plasminogen). The resulting plasmin contains a heavy chain, originating from the amino-terminus of plasminogen, doubly disulfide-linked to a light chain. This latter region, containing the carboxy-terminus of plasminogen, is homologous to serine proteases such as trypsin and elastase. The heavy chain of plasmin consists of five repeating triple-disulfide-linked peptide regions, about 80 amino, acid residues in length, termined kringles, that are responsible in part for interactions of plasmin with inhibitors (Castellino, F J et al., Ciba Found. Symp. 212:46-60 (1997). which disclosure is hereby incorporated by reference in its entirety).

The gene for human plasminogen spans about 52.5 kilobases of DNA and consists of 19 exons separated by 18 introns. (Petersen, T E et al., J. Biol. Chem. 265:6104-11 (1990) which disclosure is hereby incorporated by reference in its entirety).

Plasminogens exist in about three different forms in solution, as determined by laser light scattering experiments and NMR. Three truncated forms of plasminogen have been described. Removal of the amino-terminal domain yields a shorter proenzyme (Lys-plasminogen) that is more efficiently activated than the parent (Glu-plasminogen). Further cleavage using the enzyme elastase removes the amino-terminal domain and four kringle domains leaving miniplasninogen. Miniplasminogen is activatable by urokinase to the enzyme miniplasmin with fibrinolytic activity equivalent to that of plasmin. The most striking functional difference of miniplasmin is its relative resistance to inhibition by the primary plasmin inhibitor, alpha-2-antiplasmin, probably reflecting the absence of kringle domain 1, which is thought to facilitate primary interaction of plasmin with the inhibitor (Moroz, L A, Blood, 58:97-104 (1981) which disclosure is hereby incorporated by reference in its entirety).

A functionally active human microplasminogen without kringle structures was produced by incubation of plasminogen with urokinase-free plasmin at alkaline pH. Microplasminogen can be activated by urokinase and streptokinase to catalytically active microplasmin. Microplasmin consists of two polypeptide chains connected by disulfide bonds: one is the intact light chain, and the other is a peptide of 31 residues from the carboxyl-terminal portion of the heavy chain (Shi, G-Y et al., J. Biol. Chem. 263:17071-5 (1988) which disclosure is hereby incorporated by reference in its entirety).

It is significant that the formation of plasminogen fragments such as miniplasminogen-like molecules has been observed under some pathophysiological conditions. Of particular note is a report that synovial fluid in acute inflammatory arthritis (including rheumatoid arthritis), unlike that of acute non-inflammatory arthritis (including osteoarthritis), contains low molecular weight fragments of plasminogen with the properties of miniplasminogen (Moroz, L A et al., Thrombosis Research 43:417-24 (1986) which disclosure is hereby incorporated by reference in its entirety). Whether neutrophil elastase or other mechanisms are responsible for their generation, the presence, in inflamed joints of molecules with properties of miniplasminogen indicates a potential for their participation in inflammatory events where plasmin activity has been implicated, as in the activation of procollagenase to collagenase in rheumatoid synovium, but where the inhibitory activity of alpha-2-antiplasmin has been invoked as an obstacle to such a view. However, the ability of molecules such as miniplasmin to escape such inhibition suggests the possibility that generation of miniplasmin might lead to activation of procollagenase, or destroy joint structural proteins directly.

Plasminute is the product of alternative transcription initiation within the plasminogen gene. Transcription initiates within intron N (at least 1036 nucleotides upstream of exon XV) and proceeds through the remainder of the plasminogen gene (Petersen, TE et al., J. Biol. Chem. 265:6104-11 (1990); NCBI Accession No. AL109933.25 which disclosures are hereby incorporated by reference in their entirety). Splicing occurs normally between transcribed exons XV to XIX. Translation initiates within exon XV and is carried out in the plasminogen open reading frame. Plasminute represents the carboxyl-terminal fragment of plasminogen corresponding to amino acids 585 to 790 (numbered from the amino-terminal glutamic acid residue of secreted plasminogen).

Importantly, Plasminute is a variant of plasmin distinguished by the novel manner in which its protease activity escapes regulation. Plasminute retains the catalytic triad of plasmin (His603, Asp646, Ser741, numbered from the amino-terminal glutamic acid residue of secreted plasminogen). Plasminute manifests constitutive protease activity, circumventing the requirement for proteolytic activation by virtue of its translation initiating downstream of the cleavage site involved in the conversion to plasmin from plasminogen (amino acids 561-562 of secreted plasminogen, numbered from the amino terminal glutamic acid residue) In addition, the protease activity of Plasminute is relatively resistant to inhibition by the primary plasmin inhibitor, alpha-2-antiplasmin, by virtue of its translation initiating downstream of the plasminogen kringle domains.

In a preferred embodiment, the present invention provides for a method of contacting Plasminute with a blood clot in patients with acute vascular disease. The advantage of Plasminute over plasminogen activators is two-fold: 1) it circumvents the necessity to generate plasmin within the patient and therefore is more direct and controllable; and 2) it is not immediately neutralized by excess alpha-2-antiplasmin, as is the case for most of the plasmin generated through exogenously administered activator (U.S. Pat. No. 5,753,486; "Human tissue plasminogen activator;" which disclosure is hereby incorporated by reference in its entirety). Preferred compositions comprise Plasminute. Preferred mode of admistration is intravenous injection.

In further preferred embodiment, the present invention provides for a method of contacting Plasminute with a blood clot in patients with diseases having an etiological basis pointing to either a partial or, in severe cases, total occlusion of a blood vessel by a blood clot—thrombus or thromboembolus. Further preferred is a method of contacting Plasminute with a blood clot in said patients for the purpose of dissolving said clot. Further preferred are compositions comprised of Plasminute used in methods of contacting a blood clot with an ameliorative effective amount in patients with acute vascular disease wherein the acute vascular disease is selected from, but not restricted to, the group consisting of: (a) Myocardial infarct; (b) Stroke; (c) Pulmonary embolism; (d) Deep vein thrombosis; (e) Peripheral arterial occlusion; and (f) Other venous thromboses.

Plasmin plays an important role in wound healing, including recovery from myocardial infarction, skin wounds, and arterial neointima formation. In the course of myocardial infarction, cardiomyocytes die and a process that resembles wound healing in, for instance, skin wounds and requiring plasmin occurs (Creemers E, et al., Am. J. Pathol. 156:1865-73 (2000) which disclosure is hereby incorporated by reference in its entirety). Specifically with respect to skin wounds, plasmin is required for the efficient keratinocyte migration necessary for wound closure (Romer. J et al., Nat.

Med. 2:287-92 (1996) which disclosure is incorporated by reference in its entirety). With respect to arterial neointima formation, plasmin is required for migration of smooth muscle cells into the necrotic center of the induced arterial wall injury. (Carneliet, P. et al., J. Clin. Invest. 99:200-8 (1997) which disclosure is incorporated by reference in its entirety).

In further embodiment, the present invention.provides for compositions comprised of Plasminute used in methods of promoting wound healing. Further preferred are compositions comprised of Plasminute used in methods of contacting said wound with an ameliorative effective amount wherein the wound is selected from, but not restricted to, the group consisting of: (a)Myocardial infarction; (b)Skin wound; and (c)Arterial wall injury.

The compositions and methods for treatment of acute vascular, disease and wound healing discussed above are not limited to use in humans, but can have veterinary applications as well.

Partial digestion of a protein by plasmin is frequently exploited in in vitro biochemical analysis of sad protein (Bewley, T A, Biochemistry 16:209-15 (1977); Nawratil, P et al., J. Biol. Chem. 271:31735-41 (1996); Kost, C et al., Eur. J. Biochem. 236:682-8 (1996); Angelloz-Nicoud, P et al., Growth Hormone and IGF Research 8:71-75 (1998); Itoh, Y et al., J Biochem 128:1017-24 (2000); which disclosures are hereby incorporated by reference in their entirety). For example, partial digestion by plasmin can be useful in assigning function to specific protein domains and in mapping antigenic epitopes onto the protein. Plasminute has utility over plasmin for said biochemical analysis in that: 1) production of Plasminute does not require proteolytic activation of plasminogen; and 2) the smaller size of Plasminute makes it easier to manipulate.

Further preferred are compositions comprised of Plasminute used in methods of in vitro biochemical analysis of protein, including but not restricted to the analysis of protein function and antigenicity. Further preferred are compositions comprised of Plasminute used as part of a kit in methods of in vitro biochemical analysis of protein, including but not restricted to the analysis of protein function and antigenicity.

In a preferred embodiment, the present invention provides for an antibody that specifically binds Plasminute of the present invention. Further preferred is a method of making said antibody wherein said antibody recognizes a non-conformational or conformational epitope of Plasminute. Further preferred is a method of making said antibody wherein said antibody neutralizes the serine protease activity of Plasminute or facilitates the elimination of Plasminute from tissue.

Further preferred is a method wherein a mouse is immunized with Plasminute. Further preferred is a method wherein monoclonal antibodies from said mouse are screened for binding to Plasminute but not to plasmin or plasminogen. Further preferred is a method wherein monoclonal antibodies derived from said mouse are screened by enzyme-linked immunosorbent assay. (ELISA) for binding to Plasminute but not to plasmin or plasminogen. Further preferred is a method wherein monoclonal antibodies from said mouse are screened for binding to Plasminute but not to plasmin, plasminogen, miniplasmin, miniplasminogen, microplasmin, or microplasminogen. Further preferred is a method wherein monoclonal antibodies derived from said mouse are screened by ELISA for binding to Plasminute but not to plasmin, plasminogen, miniplasmin, miniplasminogen, microplasmin, or microplasminogen. Further preferred is a method wherein said antibody is screened for the capacity to sterically or allosterically neutralize the serine protease activity of Plasminute. Further preferred is a method of humanizing said monoclonal antibody. Methods of generating said monoclonal antibody and of establishing specificity by methods including ELISA are well known to those skilled in the art. Methods of screening said antibody to neutralize the serine protease activity of Plasminute are well known to those skilled in the art and include, but are not limited to: contacting the antibody with Plasminute, incubating the antibody-Plasminute complex with a substrate of Plasminute, and following proteolytic activation of the Plasminute substrate. Methods of humanizing said monoclonal antibody are well known to those skilled in the art. The functionality of Plasminute is proinflammatory. Functional fragments of plasminogen at least as small as miniplasminogen have been observed in synovial fluid in acute inflammatory arthritis but not in synovial fluid in acute non-inflammatory arthritis (Moroz, L A et al., Thrombosis Research 43:417-24 (1986) which disclosure is hereby incorporated by reference in its entirety).

In a preferred embodiment, the present invention provides for a method of contacting said antibody and specifically binding it with Plasminute. Further preferred is a method for using said antibody diagnostically to determine the basis for inflammopathology. Further preferred is a method for using said antibody diagnostically in a sandwich ELISA format to determine the level of Plasminute in plasma or other bodily fluid, including but not restricted to synovial fluid and cerebrospinal fluid, within a pathological context. Further preferred is a method for using said antibody in a sandwich ELISA format to determine, the level of Plasminute in plasma or other bodily fluid, including but not restricted to synovial fluid and cerebrospinal fluid, from normal subjects in order to establish a baseline level of Plasminute. Further preferred is a method of using said diagnostic assay to determine the level of Plasminute in plasma or other bodily fluid of a patient with inflammopathology wherein the inflammopathology is selected from, but not restricted to, the group consisting of: (a) Atheriosclerosis; (b) Inflammatory bowel disease; (c) Insuline dependent diabetes mellitus (Type 1 diabetes); (d) Systemic lupus erythematosus; (e) Multiple sclerosis; Psoriasis; (f) Allergic asthma; (g) Septic shock; and (h) Reperfusion injury.

In a preferred embodiment, the present invention provides for a method of contacting said antibody and specifically binding it with Plasminute. Further preferred is a method for using said antibody diagnostically to determine the basis for inflammatory arthritis. Further preferred is a method of using said diagnostic assay to determine the level of Plasminute in synovial fluid of a patient with acute inflammatory arthritis. (a-d below) or acute non-inflammatory arthritis (e-f below). Plasminute level may be additionally useful is distinguishing the former from the latter (Moroz, L A et al., Thrombosis Research 43:417-24 (1986) which disclosure is hereby incorporated by reference in its entirety).

In a preferred embodiment, the present invention provides for a method of contacting said antibody and specifically binding it with Plasminute. Further preferred is a method of using said diagnostic assay in said sandwich ELISA format to determine the level of Plasminute in synovial fluid of a patient with acute inflammatory arthritis or acute non-inflammatory arthritis. Further preferred is a method of using said diagnostic assay to determine the level of Plasminute in synovial fluid of a patient with acute inflammatory arthritis or acute non-inflammatory arthritis wherein the arthritis is selected from, but not restricted to, the group consisting of: (a) Rheumatoid arthritis; (b) Gout; (c) Septic arthritis; (d) Reiter's syndrome; (e) Osteoarritis; and (f) Trauma.

In a preferred embodiment, the present invention provides for a method of contacting said antibody and specifically binding it with Plasminute. Further preferred is a method of using said antibody diagnostically in an immunohistochemistry format to determine the level of Plasminute in affected tissue in a patient presenting with inflammopathology. Further preferred is a method of using said antibody diagnostically in an immunohistochemistry format to determine the, level of Plasminute in affected tissue in a patient presenting with inflammopathology wherein said inflammopathology is selected from, but not restricted to, the group consisting of: (a) Inflammatory arthritis; (b) Atheriosclerosis; (c) Inflammatory bowel disease; (d) Insuline dependent diabetes mellitus (Type 1 diabetes); (e) Systemic lupus erythematosus; (f) Multiple sclerosis; (g) Psoriasis; (h) Allergic asthma; (i) Septic shock; and (j) Reperfusion injury.

The components of the urokinase plasminogen activator system involved in conversion of plasminogen to plasmin are present in significantly higher amounts in malignant tumors than in normal tissue or benign tumors, and said elevated expression is related to poor prognosis for a variety of patients diagnosed with tumors including breast, prostate, lung, or colon cancer (Andreasen, P A et al., Cell. Mol. Life Sci. 57:25-40 (2000) which disclosure is hereby incorporated by reference in its entirety). (discussed in more detail below). The largest data sets correlating urokinase plasnminogen activator level with patient prognosis are available for breast cancer. In the Western world, about one in every ten women will develop breast cancer. In a significant number of these patients, metastatic cells will have spread to the lymph nodes and other tissues by the time their breast tumor is diagnosed. Therefore, following surgery these patients will normally receive some kind of additional therapy aimed at reducing their risk of developing secondary cancer.

Even for those patients whose lymph nodes are free of tumor cells (node negative), it is still important to know whether they are at high or low risk of developing secondary tumors. Measuring the levels of the components of the urokinase plasminogen activator system can assess this risk, high levels indicating a high risk of developing metastases and suggesting that patients should be treated with additional therapy. Just as elevated plasmin generation on engagement of the urolinase plasminogen activator system indicates high risk for metastases, elevated Plasminute expression by the tumor cells indicates high risk for metastases. In a preferred embodiment, the present invention provides for a method of contacting said antibody and specifically binding it with Plasminute. Further preferred is a method of using said antibody diagnostically in an immunohistochemistry format to determine the level of Plasminute in affected tissue in a patient presenting with cancer. Further preferred is a method of using said antibody diagnostically in an immunohistochemistry format to determine the level of Plasminute expressed by tumor cells in a patient presenting with cancer wherein said cancer is selected from, but not restricted to, the group consisting of: (a) Melanoma; (b) Squamous cell carcinoma of the skin; (c) Breast carcinoma; (d) Lung small-cell carcinoma; (e) Colon carcinoma; (f) Hodgkin's lymphoma; (g) Non-Hodgkin's lymphoma; (h): Prostatic carcinoma; (i) Pancreatic carcinoma; (j). Osteosarcoma; (k) Uterine carcinoma; (l). Ovarian carcinoma (m) Chondrosarcoma; (n) Endometrial cancer; (o). Testicular carcinoma; (p) Renal carcinoma; (q) Hepatic carcinoma; (r) Lung non-small-cell carcinoma; (s) T lymphocyte acute lymphoblastic leukemia (T-ALL); (t) B lymphocyte acute lymphoblastic leukemia (B-ALL); (u) Acute myeloid leukemia (AML); (v) Chronic lymphocytic leukemia (CLL); and (w) Multiple myeloma.

Viral hemorrhagic fevers are a group of diseases caused by viruses from four distinct families: filoviruses, arenaviruses, flaviviruses, and bunyaviruses. Virus driven expression of host Plasminute and a consequential hyperfibrinolysis may be contributory to at least some said viral pathologies. Furthermore, measuring Plasminute level may have diagnostic value in distinguishing between viruses in this group or have diagnostic value in distinguishing viruses belonging to this group from viruses not belonging to this group.

In a preferred embodiment, the present invention provides for a method of contacting said antibody and specifically binding it with Plasminute. Further preferred is a method of using said diagnostic assay in sandwich ELISA format to determine the level of Plasminute in plasma or other bodily fluid in a patient suspected of having viral hemorrhagic fever. Further preferred is a method for using said diagnostic assay to determine the level of Plasminute in a patient infected by a virus not belonging to the group causing viral hemorrhagic fever, in order to establish a baseline level of Plasminute level in said other viral infection. Further preferred is a method of using said diagnostic assay to determine the level of Plasminute in plasma or other bodily fluid in patient suspected of having viral hemorrhagic fever when said virus is selected from, but is not restricted to, the group consisting of: (a) Ebola virus; (b) Omsk hemorrhagic fever virus; (c) Junin virus; (d) Marburg virus; (e) Crimean-Congo hemorrhagic fever virus; and (f) Dengue fever virus.

The serine protease activity of Plasminute is relatively resistant to inhibition by the primary plasmin inhibitor, alpha-2-antiplasmin, by virtue of its translation initiating downstream of the plasminogen kringle domains. In in vitro analysis of clinical samples, it is important to prevent artifactual proteolysis of the sample ex vivo, including that by plasmin or a derivative thereof. If the sample contains Plasminute, the current art of using alpha-2-antiplasmin to block said proteolysis would be inadequate. In this context, said antibody directed to Plasminute and neutralizing its serine protease activity would have utility over alpha-2-antiplasmin. In a preferred embodiment, the present invention provides for a method of contacting said antibody and specifically binding it with Plasminute. Further preferred is a method of using said neutralizing anti-Plasminute antibody to block ex vivo proteolysis by Plasminute within clinical samples.

There is precedent for the expression of two alternatively spliced transcripts derived from the same gene and encoding functionally distinct protein isoforms being reciprocally modulated by cytokine. This is the case for monocyte expression of CD86, a T lymphocyte co-stimulator molecule, for example. Interferon gamma down-regulates monocyte expression of the alternatively spliced transcript encoding a truncated and interfering version of CD86 and up-regulates the spliced transcript encoding full-length CD86 (Magistrelli, G et al., Biochem. Biophys. Res. Commun. 280:1211-5 (2001) which disclosure is hereby incorporated by reference in its entirety). It is not unreasonable to expect, therefore, that there may be cytokine modulation of transcription initiation within a gene leading to alternative transcripts encoding functionally distinct protein isoforms, as is the case for the present invention. Identification of said cytokine regulation of alternative transcription initiation within a gene would be expected to have therapeutic value and to lead to a better understanding of disease pathology.

In a preferred embodiment, the present invention provides for a method of contacting said antibody and specifically binding it with Plasminute. Further preferred is a method of using said antibody to characterize cytokine regulation of Plasminute expression by endothelial cells. Further preferred is a method of using said antibody in said sandwich ELISA to characterize cytokine regulation of Plasminute expression by endothelial cells. Further preferred is a method of using said antibody in said sandwich ELISA to characterize cytokine regulation of Plasminute expression by endothelial cells wherein the cytokine is selected from, but not restricted to, the group consisting of: (a) Interferon gamma; (b) Interleukin 17; (c) Interleukin 4; (d) Interleukin 10; (e) Interleukin 13; (f) Interleukin 15; (g) Interleukin 12; (h) Interleukin 18; (i) Interleukin 20; (j) Interleukin 21; (k) Interleukin 1 beta; (l) Interleukin 6; (m) Monocyte chemotactic protein 1. (MCP-1); (n) RANTES; (o) IP-10; (p) Vascular endothelial growth factor (VEGF); (q) Transforming growth factor beta; (r) Interleukin 8; and (s) Tumor necrosis factor alpha.

Methods of characterizing cytokine regulation of Plasminute expression by endothelial cells are well known to those skilled in the art and include, but are not limited to: incubation of endothelial cells with or without cytokine for 24-48 hours, collection of culture supernatant, and determination of Plasminute protein in the culture supernatant by sandwich ELISA.

The transcript encoding Plasminute can be readily distinguished from that encoding plasminogen and its derivatives. Further preferred therefore is a method of directly characterizing cytokine regulation of Plasminute mRNA expression by endothelial cells. Further preferred is a method of using polynucleotide comprising Plasminute to determine the level of Plasminute mRNA in endothelial cells. Further preferred is a method of using polynucleotide comprising Plasminute to determine the level of Plasminute mRNA in endothelial cells that have been incubated in the presence or absence of cytokine for 0, 2, 4, 6, 8, 12, or 24 hours. Further preferred is a method of using a Plasminute cDNA fragment encoding 5'-untranslated sequence derived from intron N as a specific probe in Northern blot analysis of said Plasminute mRNA level. Further preferred is a method of using a primer specified in Plasminute 5'-untranslated sequence derived from intron N. in conjunction with a primer specified in Plasminute 3'-untranslated sequence to specifically determine said Plasminute mRNA level by reverse transcriptase-polymerase chain reaction (RT-PCR). Methods of carrying out Northern blot analysis or RT-PCR on total or poly(A)+ RNA are well known to those in the art.

The functionality of Plasminute is proinflammatory. In this context, it is significant that functional fragments of plasminogen at least as small as miniplasminogen have been observed in synovial fluid in acute inflammatory arthritis but not in synovial fluid in acute non-inflammatory arthritis (Moroz, L A et al., Thrombosis Research 43:417-24 (1986) which disclosure is hereby incorporated by reference in its entirety). Said neutralizing anti-Plasminute antibody would be expected to have therapeutic value in inflammopathologies in which Plasminute plays a role.

In its capacity as a serine protease, plasmin plays a role in normal processes involving cell migration in tissue remodeling. In this regard, plasmin is believed to function in processes in which cell movement is essential, such as macrophage invasion in inflammation and angiogenesis. Involvement of plasmin in these processes is supported by the ability of plasmin to degrade extracellular matrix proteins directly, such as proteoglycans, fibronectin, laminin, and type IV collagen, and/or be indirectly responsible for the degradation of matrix proteins through activation of metaloprotease zynogens, such as stromolysin and procollagenase. As a result of degradation of the extracellular matrix, cell migration into surrounding areas becomes more facile (Castellino, F J in *Molecular Basis of Thrombosis and Hemostasis*, High, K A & Roberts, H R, editors, New York, pp 495-515 (1995) which disclosure is hereby incorporated by reference in its entirety).

Neovascularization plays a role in a number of diseases, including but not limited to rheumatoid arthritis (Danis, RP et al., Expert Opin. Pharmacother. 2:395407 (2001) which disclosure is hereby incorporated by reference in its entirety).

In a further preferred embodiment, the present invention provides for a method of contacting and specifically binding to Plasminute said antibody having the capacity to neutralize the serine protease activity of Plasminute or to facilitate the elimination of Plasminute from tissue. Further preferred is a method of using said antibody in contact with Plasminute as a therapeutic for patients with inflammopathology. Preferred compositions comprise said Plasminute antibody or fragments or derivatives thereof. Preferred formulation of said composition is that compatible with the route of delivery wherein said route of delivery is selected from, but not restricted to the group consisting of: (a) Oral; (b) Transdermal; (c) Injection; (d) Buccal; and (e) Aerosol.

In further preferred embodiment, the present invention provides for a method of contacting and specifically binding to Plasminute said antibody having the capacity to neutralize the serine protease activity of Plasminute or to facilitate the elimination of Plasminute from tissue. Further preferred is a method of using said Plasminute antibody to treat patients with inflammopathology. Further preferred is a method of using said composition comprised of said Plasminute antibody to ameliorate the symptoms or pathology associated with said inflammopathology. Said Plasminute antibody ameliorates the symptoms or pathology associated with said inflammopathology by blocking the proteolytic remodeling of matrix that is directly or indirectly mediated by Plasminute and that facilitates the inflammatory process, including macrophage invasion, or angiogenesis that is associated with the pathology. Further preferred is a method of delivering to patients with said inflammopathology an ameliorative effective amount of said Plasminute antibody wherein said inflammopathology is selected from, but not restricted to, the group consisting of: (a) Rheumatoid arthritis; (b) Atheriosclrosis; (c) Inflammatory bowel disease; (d) Insulin dependent diabetes mellitus (Type 1 diabetes); (e) Systemic lupus erythematosus; (f) Multiple sclerosis; (g) Psoriasis; (h) Allergic asthma; (i) Septic shock; and (j) Reperfusion injury.

Proliferative diabetic retinopathy (PDR) remains one of the major causes of aquired blindness in developed nations. The hallmark of PDR is neovascularization, abnormal angiogenesis that may ultimately cause severe vitreous cavity bleeding and/or retinal detachment. In a further embodiment of the invention, said composition comprised of neutralizing anti-Plasminute antibody is used in a method to treat patients with said PDR.

In its capacity as a serine protease, plasmin plays a role in pathological processes of cell migration that are involved in tumor cell growth and invasion of surrounding tissue and, perhaps, metastases [Andreasen, P A et al., Cell. Mol. Life Sci. 57:25-40 (2000), which disclosure is hereby incorporated by reference in its entirety]. Involvement of plasmin in these processes is supported by the ability of plasmin to degrade extracellular matrix proteins directly, such as proteoglycans, fibronectin, laminin, and type IV collagen, and/or be indirectly responsible for the degradation of matrix proteins through activation of metalloprotease zymogens, such as stromolysin and procollagenase. As a result of degradation of the extracellular matrix, cell migration into surrounding areas becomes more facile (Castellino, F J in *Molecular Basis of Thrombosis, and Hemostasis*, High, K A & Roberts, H P, editors, New. York, pp 495-515 (1995) which disclosure is hereby incorporated by reference in its entirety).

The urokinase plasminogen activator system, and by implication plasmin, is associated with high risk of tumor invasiveness and metastates [Konno, H et al., Jpn. J. Cancer. Res.92:516-23 (2001); Fisher, JL et al., Clin. Cancer Res. 7:1654-60 (2001); Vazquez-Rivera, F et al., Proceedings of the. 11th NCI-EORTC-AACR Symposium, Abstract 294 (2000); Ellrieder, V et al., Annals of Oncology 10, suppl.4, 41-45 (1999); Smolarz, B et al., Med. Sci. Monit. 5:833-7 (1999); Romer, J et al., J. Invest. Dermatol. 116:353-8 (2001); Abe, J et al., Cancer 86:2602-11 (1999); Morii, T et al., Anticancer Res. 20(5A):3031-6 (2000); Tecimer, C et al., Gynecol. Oncol. 80:48-55 (2001); Zheng, Q et al., J. Cancer Res. Clin. Oncol. 126:641-6 (2000); Swiercz, R et al. Oncol. Rep. 8:463-70(2001);Borgfeldt, C et al. Int. J. Cancer 92:497-502 (2001); He, C et al., J. Cancer Res. Clin., Oncol. 127:180-6 (2001); which disclosures are hereby incorporated by reference in their entirety].

In further preferred embodiment, the present invention provides for a method of contacting and specifically binding to Plasminute said antibody having the capacity to neutralize the serine protease activity of Plasminute or to facilitate the elimination of Plasminute from tissue. Further preferred is a method of using said Plasminute antibody to treat patients with cancer. Further preferred is a method of using said composition comprised of said Plasminute antibody to ameliorate the symptoms or pathology associated with said cancer. Said Plasminute antibody ameliorates the symptoms or pathology associated with said cancer by blocking the proteolytic remodeling of matrix that is directly or indirectly mediated by Plasminute and that facilitates the invasive and metastatic processes or angiogenesis that is associated with the pathology. Further preferred is a method of delivering said composition comprised of said Plasminute antibody by intravenous injection. Further preferred is a method of delivering to patients with said cancer an ameliorative effective amount of said Plasminute antibody wherein said cancer is selected from, but not restricted to, the group consisting of: (a) Melanoma; (b) Squamous cell carcinoma of the skin; (c) Breast carcinoma; (d) Lung small-cell carcinoma; (e) Colon carcinoma; (f) Hodgkin's lymphoma; (g) Non-Hodgkin's lymphoma; (h) Prostatic carcinoma; (i) Pancreatic carcinoma; (j) Osteosarcoma; (k) Uterine carcinoma; (m) Ovarian carcinoma; (n) Chondrosarcoma; (o) Endometrial cancer; (p) Testicular carcinoma; (q) Renal carcinoma; (r) Hepatic carcinoma; (s) Lung non-small-cell carcinoma; (t) T lymphocyte acute lymphoblastic leukemia (T-ALL); (u) B. lymphocyte acute lymphoblastic leukemia (B-ALL); (v) Acute myeloid leukemia (AML); (w) Chronic lyrnphocytic leukemia (CLL); and (x) Multiple myeloma.

In a further preferred embodiment, the present invention provides for a method of screening test compounds for the ability to bind Plasminute and specifically neutralize the serine protease activity of Plasminute. Further preferred are said test compounds that bind to either a non-conformational or conformational site on Plasminute. Further preferred are test compounds that neutralize said serine protease activity of Plasminute either sterically or allosterically. Further preferred is a method of screening said test compounds for the capacity to neutralize said serine protease activity of Plasminute. Methods of screening said test compounds for the capacity to neutralize said serine protease activity of Plasminute are well known to those skilled in the art and include, but are not limited to: contacting the test compound with Plasminute, incubating the test compound-Plasminute complex with a substrate of Plasminute, and following proteolytic activation of the Plasminute substrate.

Preferred formulations of said compound are those selected from, but not restricted to, the group consisting of: (a) Oral; (b) Transdermal; (c) Injection; (d) Buccal; and (e) Aerosol.

Said compounds found to bind to and specifically neutralize the serine protease activity of Plasminute are used in methods analogous to those described above for neutralizing anti-Plasminute antibody.

Protein of SEQ ID NO:56 (internal designation Clone 519757_184-4-2-0-F7-F)

The cDNA of clone 519757_184-4-2-0-F7-F (SEQ ID NO:55) encodes the human intracellular signaling protein comprising the amino acid sequence: MLEVSDALGG-PGRVPGATAGMNGVDTSLLCDLLQALTFLTRNEI-LCIHDTFLKLCPPGKY YKEATLTMDQVSSLPALRVN-PFRDRICRVFSHKGMFSFEDVLGMASVFSEQACP-SLKIEYAFRIYDFNENGFIDEEDLQRIILRLLNSDD-MSEDLLMDLTNHVLSESDLDNDNMLSFSEFE HAMAKSPDFMNSFRIHFWGC (SEQ ID NO:55) and shares features with the Calcium and Integrin-Binding (CIB)- and the DNA-dependent kinase interacting (KIP) protein. It will be appreciated that all characteristics and uses of the polynucleotides of SEQ ID NO:55 and polypeptides of SEQ ID NO:56, described throughout the present application also pertain to the human cDNA of clone 519757_184-4-2-0-F7-F and polypeptide fragments encoded thereby. Polypeptide fragments having a biological activity described herein and polynucleotides encoding the same are included in the present invention. Related polypeptide sequences included in the present invention are MGQCLRYQMH WEDLEEYQALTFLTRNEILCIHDTFLKL-CPPGKYYKEATLTMDQVSSLPALRVNPFRDRI CRVF-SHKGMFSFEDVLGMASVFSEQACPSLK-IEYAFRIYDFNENGFIDEEDLQRIILRLL NSDDMSEDLLMDLTNHVLSESDLDNDN-MLSFSEFEHAMAKSPDFMYSFRIRFWGC (SEQ ID NO:228).

The gene of SEQ ID:55 is located on chromosome 2, is ubiquitously expressed, has two EF-hand calcium- and zinc-binding domains, regulates $Ca^{2+}$-dependent dephosphorylation processes such as neuronal transmission, muscle glycogen metabolism, and lymphocyte activation and is hereby referred to as CALSIGN. CALSIGN stimulates signaling processes which lead to platelet aggregation and blood clot formation. It binds to the cytoplasmic domain of integrins and regulates integrin function in physiological processes via the fibrinogen receptor (integrin $\alpha_{IIb}\beta_3$), which is expressed on platelets, and thereby activates integrin for binding to fibrinogen, fibronectin, the von-Willebrand factor, vitronectin, and thrombospondin; it also binds to the interferon 1-receptor and contributes to signal transduction events in platelets, which lead to strong cell-cell adhesion, platelet aggregation, and blood clot formation. CALSIGN also facilitates immune responses via restoration of surface antigen expression and T-cell activation in response to viraland bacterial infections and to endogenous factors. Further characteristics of CALSIGN comprise VDJ-recombination in B-cell maturation and surface antigen expression on mature B-cells [Naik et al., J. Biol. Chem.272:4651-4654, 1997; PCT. WO 98/14471, 1998; Wu and Lieber, Mutat.Res.385:13-20, 1997; PCT WO 98/31796, 1998; Hynes, Cell 69:11-25, 1992; Smyth et al., Blood 81:2827-2843, 1993; U.S. Pat. No. 6,093,565, 2000, which references are hereby incorporated in their entirety].

In a preferred embodiment, CALSIGN or other polypeptides of the invention are used in a method for tissue regeneration and wound healing after injuries. Wounds, in particular those occurring in the skin as second and third degree burns, stasis ulcers, trophic lesions such as decubitus ulcers, severe cuts and abrasions, which are commonly resistant to natural healing processes, may be treated with a composition comprising CALSIGN or other polypeptides included in the invention, or fragments thereof, in a formulation, which might include a growth factor such as platelet derived growth factor (PDGF) or connective tissue growth factor (CTGF), or a wound dressing with aseptic properties such as silver-coated fibers U.S. Pat. No. 6,149,916, 2000; U.S. Pat. No. 6,187,743, 2001; U.S. Pat. No. 6,087,549, 2000), which references are hereby incorporated in their entirety.

The process of wound healing consists of three phases during which the injured tissue is repaired, regenerated, and now tissue is reorganized into a scar. These three phases are classified as: a) an inflammation phase which begins from day 0 to 3 days, b) a cellular, proliferation phase from 3 to 12 days, and c) a remodeling phase from 3 days to about 6 months. In all three phases, antioxidants play a vital role in the healing process. In the inflammation phase, inflammatory cells, mostly neutrophils, enter the site of the wound followed by lymphocytes, monocytes, and later macrophages. The neutrophils that are stimulated begin to release proteases and reactive oxygen species into the surrounding medium with potential adverse effects on both the adjacent tissues and the invading microorganisms. The oxygen species known to be released by the neutrophils are superoxide (O.sub.2.sup.-) through the action of a plasma membrane-bound NADPH oxidase, hydrogen peroxide (H.sub.2 O.sub.2) formed by action of dismutation of O.sub.2.sup.-, and HOCI produced by the action of myeloperoxidase with H.sub.2 O.sub.2.

The proliferative phase consists of laying down new granulation tissue, and the formation of new blood vessels in the injured area. The fibroblasts, endothelial cells, and epithelial cells migrate in the wound site. These fibroblasts produce the collagen that is necessary for wound repair. Ascorbic acid is crucial in the formation of collagen. Several studies have demonstrated that ascorbic acid was capable of overcoming the reduced proliferative capacity of elderly dermal fibroblasts, as well as increasing collagen synthesis in elderly cells by similar degrees as in newborn cells even though the basal levels of collagen synthesis are age dependent A decrease of ascorbic acid at the injury area will decrease the rate of wound healing. In reepithelialization, epithelial cells migrate from the free edges of the tissue across the wound. This event is succeeded by the proliferation of epithelial cells, at the periphery of the wound. Research has also shown that reepithelialization is enhanced by the presence of occlusive wound dressings which maintain a moisture barrer. The final phase of wound healing, which is remodeling, is effected by both the replacement of granulation tissue with collagen and elastin fibers and the devascularization of the granulation tissue. Recent studies have shown that topical application of antioxidants, especially alpha-tocopherol, reduces scarring and normalizes blood coagulation during therapy.

A particularly effective healing treatment for wounds and skin defects such as burns, ulcers and lesions is the application of a medicinal dressing containing as an essential ingredient starch hydrolysate having Dextrose Equivalent of less than about 35. In such wound treatment the starch hydrolysate produces the formation of a film which is intimately adhered to the underlying granulation tissue and which is semi-permeable to gas and fluids and provides an ideal protective cover that will reduce fluid and plasma losses and invasion by pathogenic bacteria. In addition, it appears that the starch hydrolysate provides a topical or local hyperalimentation, that is local nutrition, providing a gradual release of glucose which is particularly effective in nutrition of tissue, both damaged and nascent, which have become relatively isolated from normal blood flow nutrition. The cessation of blood flow to such an ischemic lesion can be developed in a slow and gradual form such as in the case of decubitus ulcers and stasis ulcers, or may take place more acutely such as in thermo-radiation and chemical burns. In the absence of nutrition, the rate of fluid delivery of nutrients decreases bringing a progressive impairment in the viability of cells and tissues. This eventually leads to degeneration and death of the tissue and cells in a condition known as necrosis. Necrosis is generally accompanied by bacterial, fungal and/or viral contamination. As further pointed out in the aforementioned patent, treatment of exudative skin wounds with a starch hydrolysate dressing produces a greatly reduced bacteria count of an infected wound and inhibits infection of an uninfected wound. In addition, application of the starch hydrolysate to a wound or ulcer produces a film or semi-permeable membrane which allows edematous liquid to pass through while proteinaceous material is retained within the body, allowing reduction in the volume of exudate in relatively clean condition.

Compositions which enhance and promote the wound healing process comprise suspensions of CALSIGN, said fibrous protein, collagen, and a polysaccharide such as a glycosaminoglycan, which exhibits chemotaxis for fibroblasts or endothelial cells; the preferred glycosaminoglycans are said to be heparin, heparan sulfate, or alginate; collagen type I, vitamins such as ascorbic acid (vitamin C) and alpha-tocopherol (vitamin E), and particulate starch hydrolysate are applied on wounds to promote the formation and growth of healthy granulation tissue. Wound healing processes will be significantly improved by multilayer laminate "wound dressings" comprising alternate layers of silver or silver-coated fibers and non-metalized fibers, which promote cellular proliferation and comprise antibacterial, antifungal, and analgesic properties (U.S. Pat. No. 6,087,549, 2000). The repair process for even minor breaches or ruptures takes a period of time extending from hours and days to weeks; and in some instances, as in ulceration, the breach or rupture may persist for extended periods of time, i.e., months or even years. At all times, be it brief or extended, the potential for invasion by pathogenic organisms or foreign substances continues until new tissue has been generated to fully close the rupture or breach. Because of the danger of infections, the customary management of wounds includes an initial thorough cleansing of the affected area to remove any contaminants such as dirt, cloth particles, or other debris that may introduce pathogenic materials. Any hopelessly damaged tissues may be debrided and antiseptic materials are applied to make the area as sterile as possible. If considered necessary, sutures may be used to reduce the area of the underlying tissues and thereby limit the amount of tissue exposed to subsequent contamination. The healing process is brought about by complex biological mechanisms generally involving several groups of special cells and proteins. Leukocytes, such as neutrophils and macrophages, crown the wound site and digest foreign pathogens and debris. Such cells also send out chemical signals that marshal fibroblasts in the wound vicinity and ultimately generate connective structures, principally, collagen, which make up a major portion of the new tissues. Endothelial cells generate new blood capillaries that grow into the reconstructed tissue areas where their presence is necessary to supply nutrients to the newly growing tissue cells and remove catabolic products. As the new capillaries grow, the cells on margin of the wound simultaneously multiply and grow inwardly. The fibrous tissue arising from this cell growth eventually fills the wound cavity with a network of interlacing threads of collagen which in due time, arrange themselves in firm bands and form the permanent new tissue.

Said method for promoting wound healing comprises the steps of:

Applying to the wound a composition of a therapeutically effective concentration of CALSIGN or other polypeptides included in the invention in an aqueous suspension with bovine collagen type I and alpha-tocopherol in a mixture with starch hydrolysate of a low dextrose equivalent DE, wherein said composition is chemotactic for fibroblasts and endothelial cells. Said bovine collagen is pre-treated to remove extraneous proteinaceous material by various dissolution, precipitation and filtration techniques to provide pure coulagenous product.

The composition may be combined with a combination of vitamins such as vitamin C and vitamin E, and with a therapeutically effective concentration of a purified connective tissue growth factor (CTGF), and platelet derived growth factor (PDGF).

Said aqueous suspension is applied repeatedly to the wound during the healing to effectively promote the healing process.

Said aqueous suspension may be combined with said multilaminate silver dressing for the treatment of postoperative wounds.

These embodiments also include the production of an antibody against CALSIGN and other polypeptides of the invention, wherein said antibodies can be polyclonal or monoclonal. For the production of recombinant CALSIGN, an expression vector and a corresponding cell system will be used, wherein the expression system can be prokaryotic such as *E. coli*, and eukaryotic such as Baculovirus/insect cells, or mammalian systems as well-known in the art.

Protein of SEQ ID NO:58 (Internal Designation Clone 625004_188-15-4-0-H6-F) The cDNA of clone (SEQ ID NO:57) encodes the protein of SEQ ID NO:58, comprising the sequence:

MGPPGFKGKTGHPGLPGPKGDCGKPGP-PGSTGRPGAEGEPGAMGPQGRPGPPGHVGPP GPPGQPGPAGISAVGLKGDRGATGER-GLAGLPGQPGPPGPQGPPGYGKMGATGMGQQG IPGIPGPPGPMGQPGKAGHCNPSDCF-GAMPMEQQYPPMKTMKGPFG (SEQ ID NO:58).

The cDNA of SEQ ID NO:57 is a novel splice, variant of the human alpha 1 type XVI collagen gene (GB M92642.1) located on chromosome 1, specifically in the p34-35 region. The cDNA clone of SEQ ID NO:57 encodes an open reading flame of 489 nucleotides. Whereas the native form of human alpha 1 type XVI collagen possess 71 exons encoding a 1603 amino-acid protein, the cDNA of SEQ ID NO:57 contains 14 exons and encodes a 163 amino-acid protein of SEQ ID NO:58. The present protein represents the first described variant of the human alpha 1 type XVI collagen, named vCOL16A1. The present protein contains two collagen triple helix repeat domains (positions 11-70 and 73-131).

Collagens represent a large family of structurally related proteins that to date includes more than 20 collagen types. These proteins constitute the major extracellular matrix components of connective tissues and play a dominant role in maintaining the structural integrity of various tissues and also have a number of other important functions. Collagens can be divided into two major classes: the fibril-forming collagens and the non-fibril-forming collagens; the latter class includes a subgroup named the fibril-associated collagens with interrupted triple helices (FACIT). The human alpha 1 type XVI collagen exhibits most of the characteristics of the proteins of the non-fibril-forming collagen class.

In one embodiment, the protein of the invention or fragment thereof provide an in vitro. assay to test the specific activity of various proteases which degrade or denature collagen, such as collagenases and many others. Methods to assess the activity of such proteases include the steps of contacting the protease to be tested with the present protein, and detecting the amount of proteolytic cleavage of the present protein that occurs.

Since collagen fibrils are often heterogenous structures containing more than one collagen type, the present invention provides a method to determine the types of collagen present in a tissue or biological sample. For example, the collagen composition of a diseased tissue can be determined by isolating the present protein under conditions that do not disrupt protein-protein interactions, and determining the identity of proteins associated with the present protein. Such associated proteins can be identified by any standard method including, but not limited to, immunoprecipitation and immuno-affinity columns.

The present invention also provides animal models generated by modulating the expression or activity of the present protein in one or more tissues of the animal. Such animals are useful for a number of purposes, for example because they represent an in vivo assay method for testing candidate molecules potentially useful for the treatment of various pathophysiological aspects of diseases associated with abnormal collagen metabolism specifically related to the activity of the present protein. Study of the phenotype of such models can also allow the identification of additional human equivalent diseases caused by or linked with collagen mutations. These animals can be generated with any method of targeting overexpression or inactivation of the present protein. In one such embodiment, purified forms of the present protein are injected into the joints of an animal, or the protein is recombinantly expressed in the joints, to provoke "collagen induced arthritis" in the joints, a well known model for arthritis. Such models are extremely useful, e.g. in the assesment of candidate therapies and drugs for the treatment of artritis and other inflammatory diseases and conditions.

In other embodiments, the protein of the invention or fragment thereof is used to diagnose diseases or disorders associated with abnormalities of the metabolism of collagen. Examples of such diseases and disorders include, but are not limited to, hereditary nephritis of Alport's type due to a defect in collagen assembly that lead to progressive renal failure, disorders of bone tissue comprising osteoporosis, Paget's disease, disorders of cartilage tissue occurring in arthritis (such as osteo-arthritis and rheumatoid arthritis), disorders of the cardiovascular system prominent in atherosclerosis, hypertension, myocardial infarction and hypertrophy. This method includes the steps of contacting a biological sample obtained from an individual suspected of suffering from the disease or condition, or at risk of developing the disease or condition, with a compound capable of selectively binding the present protein or nucleic acids, e.g. a polyclonal or monoclonal antibody or any immunologically active fragment thereof, a nucleic acid probe, etc., and detecting the level, spatial distribution, or any other detectable property of the present protein in the sample, where a difference in the level, spatial distribution, or other property in the sample relative to in a control sample indicates the presence of the disease or disorder, or of a propensity for developing the disease or disorder.

A further embodiment of the present invention is to provide novel methods and compositions useful for the treatment of diseases and conditions associated with collagen matrix destruction, including for wound treatment, including fractures. Such methods comprise the administration of a therapeutically-effective amount of the present protein to a patient suffering from the disease or condition. Preferably, the protein is administered directly to the site of collagen matrix destruction. The methods and compositions: can also be used in, for example, the restoration of surgically induced wounds, or for the correction of physiological malfunction, for example to control urinary incontinence and more specifically for intrinsic sphincter deficiency. In such methods, the present protein can be administered by peri-urethral injection to reduce lumen aperture. These compositions can comprise the protein of the invention, and, optionally, one or more other types of collagen, collagen derivatives, or any other compound of interest. All of these components may be either obtained from natural sources or produced by recombinant genetic engineering techniques and/or chemical modification.

Since aberrant degradation of collagen is an indication of disorders of connective tissues, another embodiment the present invention is to provide an assay for the monitoring of collagen degradation in vivo. The invention thus includes test kits useful for the quantification in a biological sample of the amount of collagen fragment derived from the degradation of collagen, i.e the degradation of the present protein. The kits comprise at least one immunological binding partner, e.g. a monoclonal or polyclonal antibody specific for a peptide derived from the degradation of the present protein or the intact present protein and coupled to detectable markers. Collagen degradation can be measured effectively in plasma, serum or blood by any suitable method, including immunoassays. Thus, the condition of a subject can be monitored continuously and the quantified amount of collagen fragments measured in the pathological sample can be compared with the amount quantified in a biological sample of a normal individual.

In this embodiment, the application of such assays can be used to monitor the progress of therapy administered to treat these or other conditions. Further, the assays can be used as a measure of toxicity, since the administration of toxic substances often results in tissue degradation. It can also be used during clinical testing of new drugs to assess the impact of these drugs on collagen metabolism. Thus the assays may be applied in any situation wherein the metabolic condition of collagen tissues can be used as an index of the condition, treatment, or effect of substances directly administered to the subject or to which the subject is exposed in the environment.

Also in this embodiment, the present invention provides a method of detecting the presence and/or monitoring the metastatic progress of a malignancy. Indeed, metastatic potential can be influenced both positively and negatively by a variety of cell surface adhesive molecules that act both independently and in concert with connective tissue elements such as collagen, allowing subsequent growth of tumor cells at secondary sites in particular tissues. The invention thus includes test kits useful for quantify the amount of the present protein or any specifically associated collagen type in a biological sample comprising the steps of contacting the biological sample with a specific monoclonal or polyclonal antibody specific for the present protein or any specifically associated collagen type, and coupled to detectable markers. Thus, the condition of a patient can be monitored continuously and the quantified amount of such proteins measured in the pathological sample can be compared with the amount quantified in a biological sample of a normal individual or with the previous analysis of the same patient.

Excessive production and deposition of collagen leads to, fibrosis and thereby impairs the normal functioning of the affected organ and tissues. There are numerous examples of fibrosis, including the formation of scar tissue following a heart attack, which impairs the ability of the heart to pump. Diabetes frequently causes damage/scarring in the kidneys which leads to a progressive loss of kidney function. Even after surgery, scar tissue can form between internal organs causing contracture, pain, and in some cases, infertility. Thus, the present invention provides a method to inhibit collagen accumulation, specifically the accumulation of the present protein, and thereby to avoid delayed healing. The level of the present protein can be inhibited or decreased using any of a number of methods, including using antisense molecules or ribozymes, or alternatively the activity of the present protein can be inhibited using direct or indirect inhibitor molecules or antagonistic antibodies directed against the present protein. The inhibition of the expression or the activity of the present protein is also useful in the treatment of acute fibrosis (in response to various forms of trauma including injuries, infections, surgery, burns, radiation, chemotherapy treatments) or in the treatment of chronic fibrosis of the most commonly affected organs (heart, liver, kidney, lung, eye and skin), e.g. induced by viral infection, diabetes, hypertension or other chronic conditions.

In another embodiment, the invention is useful for preparing cosmetic compositions such as skin creams with anti-wrinkle activity. Cosmetic applications also include the use of the present invention as a dermal implant to increase tissue size by injections of collagenous suspensions following eyebrow uplift, for lip augmentation and to rectify facial defects, frown lines and acne scars. The present protein can be used as an injectible biomaterial as a dermal implant to increase tissue size for cosmetic (wrinkle reduction). The protein of the invention is held to be an ideal biomaterial due to its ability to persist in the body long enough to carry out its specific role without developing a foreign body response that could lead to the premature rejection or overall failure of the biomaterial. These compositions can comprise purified forms of the present protein and, optionally, one or more other types of collagen or collagen derivatives. All of these components may be either obtained from natural sources or produced by recombinant genetic engineering techniques and/or chemical modification.

The present invention can also be used in a variety of applications as a food source. Since the transmission risks of bovine spongiform encephalopathy to humans from various commonly used bovine derived products, such as bovine collagen, are still unclear, there is a need for alternative products to replace bovine derived products. Thus, another advantage of the present invention is derived from the fact that it is a human collagen rather than an animal-derived collagen. It is useful for making a casing for food products that are usually sausages, but the present invention can also be applied to any type of material including animal meat, fish meat, shellfish, and fish eggs, such as salmon roe, cheese, noodles. In addition, the present protein can be used as the binder element instead of caseins, which have been considered in the art to be indispensable for obtaining satisfactory binding strength in bound food. Thus, consumers who are allergic to these proteins can enjoy the bound food prepared containing the present invention without the fear of having an allergic reaction. The use of the present invention is also attractive for pet food, for example dogs or cats, and can be even more so if it is combined with solid products conventionally used in animal nutrition, for example pieces of meat or fish, and/or extruded cereals and/or extruded proteins. In a such embodiment, the present invention can be deliverable as a mixture, including, but not limited to, in a fluidized state, as a mixture in a gel state, in a freeze-dried state, or in a salt-precipitated state.

In another embodiment, the present protein can be used as a biomaterial for tissue engineering, to regenerate or replace damaged tissues. The, present invention thus provides various clinical applications for the generation of tissues or organs unable to repair or regenerate themselves. It can be used, for example, to promote bone regeneration, to repair tendons, ligaments or cartilage, to generate blood vessels or heart valves, to create dental implants, but also in burn injuries, for dermal replacement in chronically unstable scars, after skin loss for hereditary, traumatic or oncological reasons, or for corneal reconstruction (see, e.g. Atala, (2000) J Endourol Feb;14(1):49-57; Schwartnmann (2000) Implant Dent 9(1):63-6; Machens et al. (2000) Cells Tissues Organs 167(2-3):88-94; the disclosures of which are hereby incorporated by reference in their entireties). The present invention is suited to the culturing of three-dimensional mammalian tissues for purposes including transplantation or implantation in vivo, and as the primary component of an extracorporeal organ assist device. Methods are also provided involving stem cells, for example pluripotential cells, which can differentiate into various tissue types (muscle, cartilage, skin, bone, etc) when stimulated by an appropriate environment, e.g. comprising the present protein. For example, stem cells can be expanded in vitro and suspended in collagen gel matrices to form composites. The resulting composites will be implanted in a gap defect as a graft, which after remodeling in vivo, becomes populated with host cells and recapitulates normal functional architecture. In this embodiment, these substitutes can also serve as in vitro models for toxicology testing to better understand the response and healing mechanisms in human tissues.

Protein of SEQ ID NO:60 (internal designation Clone 422353_145-11-3-0E7-F)

The cDNA of SEQ ID NO:59 encodes the protein of SEQ ID NO:60, comprising the sequence:

MCFPKVLSDDMKKLKARMHQAIERFYDK-MQNAESGRGQVMSSLAELEDDFKEGYLET VAAYY-EEQHPELTPLLEKERDGLRCRGNRSPVP-DVEDPATEEPGESFCDKVMRWFQAM LQRLQTWWHGVLAWVKEKV-VALVHAVQALWKQFQSFCCSLSELFMSS-FQSYGAPRGD KEELTPQKCSEPQSSK (SEQ ID NO:60). Accordingly, it will be appreciated that all characteristics and uses of the polypeptide of SEQ ID NO:60 described throughout the present application also pertain to the polypeptide encoded by the nucleic acids included in clone 422353_145-11-3-0E7-F. In addition, it will be appreciated that all characteristics and uses of the nucleic acid of SEQ ID NO:59 described throughout the present application also pertain to the nucleic acids included in clone 422353_145-11-3-0E7-F. A preferred embodiment of the invention is directed toward the compositions of SEQ ID NO:59, SEQ ID NO:60, and Clone 422353_145-11-3-0E7-F. Also preferred are polypeptide fragments having a biological activity as described herein and the polynucleotides encoding the fragments.

The protein of SEQ ID NO:60 (NK5) is a novel splice variant of the human Natural Killer cells protein 4 precursor (NK4) (Genbank accession number M59807). NK5 is a 188-amino-acid-long protein that displays an RGD cell-attachment sequence from positions 170 to 172. An epitope, located from positions 163 to 187, overlaps this RGD motif. NK5 displays a putative trans-membrane domain from positions 148 to 168. Contrarily, in contrast to NK4, NK5 displays no signal peptide. The NK4 cDNA contains 6 exons (Bernot et al., Genomics 50:147-60 (1998)), whereas the NK5 cDNA contains 7 exons. Exons 1 and 2 are identical for NK4 and NK5, and exons 5, 6 and 7 of NK5 are identical to exons 4, 5 and 6 of NK4. Exon 3 of NK5 is shorter than exon 3 of NK4, and exon 4 is unique for NK5.

NKE4 gene expressions is ubiquitous (Bernot et al., Genomics 50:147-60 (1998)). Nevertheless, its expression is greatly increased in mitogen-activated T cells and in IL-2-activated Natural Killer cells (Dahl et al, J. Immun. 148: 597-603 (1992)).

Natural killer (NK) cells and T cells provide anti-infectious, anti-neoplastic, and immunomodulatory function effected by both cytokine production and direct cellular cytotoxicity. In particular, NK cells play a primary role in preventing and removing cancer cells in the body, removing many types of viruses (including herpes and measles) and have been found to be present at low levels in women with endometriosis. Moreover, in addition to these overtly immuno-protective functions, NK cells also mediate a variety of homeostatic functions, particularly in the regulation of haematopoesis and they may have an important role to play in the maintenance and development of placentation. The behaviour of NK and T cells in these various situations is regulated by a large number of distinct receptors that transmit positive and negative signals. Resting NK and T cells express a number of surface molecules which, when stimulated, can activate the cytotoxic mechanism. The balance of these signals determines whether an NK or T cell does nothing or is activated to proliferate, kill or secrete a wide range of cytokines and chemokines. More particularly, IL-2 activates many NK-cell functions, including baseline or "natural" anti-tumor cytotoxicity, antibody-dependent cellular cytotoxicity (ADCC), proliferation, and cytokine production (Trinchieri, Adv. Immunol. 47:187-376 (1989)), and IL-2-activated NK cells display a broader spectrum of reactivity against human and murine tumor target cells. The RGD motif, which is found in a number of proteins, has been shown to play a role in cell adhesion. It was shown that anchorage of NK cells is necessary for full activation (Li et al, J Immunother 20:123-30 (1997)), and that long term-activated NK cells acquire new adhesive properties. This suggests a central role for RGD recognition in the regulation of immune responses.

The expression of the NK5 gene is greatly increased in IL2-activated NK cells and in mitogen mitogen-activated T cells, and thus likely plays an important role in lymphocyte activation. In particular, NK5 is believed to play a role in the new adhesive properties that are acquired by activated lymphocytes. As NK5 does not display a signal peptide, NK5 likely plays a distinct role from NK4 in this process.

An embodiment of the present invention relates to methods of using NK5 or fragment thereof as a marker to selectively detect and/or quantify activated T cells and/or activated NK cells. Any method of detecting the presence, level, or activity of NK5 can be used in such methods. For example, the protein of the invention or fragment thereof may be used to generate specific antibodies using standard methods, and the antibodies can be used to detect the level of the present protein in a NK cell or a T cell, wherein a detection of a higher level of the present protein in the cell compared to a control level representative of a resting T cell or NK cell indicates that the cell is activated. Preferably, the antibodies are either directly or indirectly labeled, and bind more specifically to NK5 than to related proteins such as NK4. Alternatively, the nucleic acid of the invention or fragment thereof may be used to synthesize specific probes using any technique known to those skilled in the art. Such antibodies and/or probes may then be used in assays and diagnostic, kits for the detection and/or quantification of activated T cells and/or activated NK cells in, e.g., bodily fluids, in tissue samples and in mammalian cell cultures.

In a preferred embodiment, such methods of detecting the polypeptides or polynucleotides of the invention, e.g. using specific antibodies and/or probes, can be used to measure the effect of a test compound on T cell and/or NK cell activity in mammalian cell cultures. In another preferred embodiment, such methods can be used to monitor the effects of a treatment aiming to increase or decrease T cell and/or NK cell activity in a patient, or to detect the beginning of a graft rejection reaction in a patient.

Another embodiment of the invention relates to compositions and methods for inhibiting the expression or activity of NK5 in a patient for the treatment or prevention of diseases and disorders caused as a result of T cell and/or NK cell activation. The inhibition and/or reduction of T cell and/or NK cell activation can be achieved using any suitable method, e.g. through the administration of a therapeutically effective amount of an antibody that specifically recognizes NK5 or fragment thereof to a patient. Preferably, the antibody recognizes the epitope overlapping the RGD domain. The antibody can be administered alone or in combination with one or more agent known in the art, e.g. other immunosuppressive agents. Administration of the antibody can be done following any method known in the art, including those described in U.S. Pat. No. 5,817,311, which disclosure is hereby incorporated by reference in its entirety. Other inhibitors of NK5 expression or activity which can be used include, but are not limited to, antisense molecules, ribozymes, dominant negative forms of NK5, and compounds that decrease the activity or expression of NK5 in a cell. Such compounds can be, readily identified, e.g. by screening test agents against T cells or natural killer cells expressing NK5, or capable of expressing NK5, and detecting the ability of the test agents to inhibit natural killer cell or T cell activation, or to diminish the level of NK5 expression. Diseases and disorders caused as a result of T cell and/or NK cell activation include, but are not limited to, allergy and asthma, and the methods can also be used in treatments for preventing and/or inhibiting on-going immune responses. More particularly, such treatments can be used to prevent, or inhibit, or reduce in severity graft rejection, or induce tolerance to graft transplantation. Such transplantation may by way of example include, but not be limited to, transplantation of cells, bone marrow, tissue, solid-organ, bone, etc. Such treatments can also, be used to prevent or reduce in severity graft versus host diseases and autoimmune diseases, which by way of example include but are not limited to rheumatoid arthritis, systemic lupus, multiple sclerosis, insulin-dependent diabetes, hepatitis, rheumatoid arthritis, Graves disease, etc.

Another embodiment of the invention relates to the activation and/or prevention of inactivation of NK and/or T cells, based on compositions and methods containing, e.g., NK5 or fragment thereof, a polynucleotide encoding the protein, or a compound that increases the expression or activity of NK5. Such compounds can be readily identified, e.g. by screening test agents against T cells or natural killer cells expressing NK5, or capable of expressing NK5, and detecting the ability of the test agents to enhance natural killer cell or T cell activation, or to increase the level of NK5 expression. Diseases and disorders that may be treated and/or reduced in severity by T cell and/or NK cell activation include but are not limited to tumors, viral infections, inflammation, or conditions associated with impaired immunity, bacterial infections, hepatic dysfunction, liver regeneration, haematopoesis and maintenance and development of placentation. More particularly, such treatments can be used to treat proliferative disorders (including various forms of cancer such as leukemias, lymphomas, sarcomas, melanomas, adenomas, carcinomas of solid tissue, hypoxic tumors, squamous cell carcinomas, genitourinary cancers, hematopoietic cancers, head and neck cancers, and nervous system cancers, benign lesions such as papillomas, atherosclerosis, angiogenesis), viral infections (in particular HBV, HCV, HIV, hepatitis, measles and herpes viruses infections, as well as other viral-induced infections), and other various immune deficiencies. These immune deficiencies may be genetic (eg., rheumatoid and osteo arthritis and severe combined immunodeficiency (SCID)) or be caused by various bacterial or fungal infections (e.g. infections by *mycobacteria, Leishmania* spp., *malaria* spp. and *candidiasis*). Of course, NK5 may also be useful where a boost to the immune system generally may be desirable, i.e., in radiation therapy or chemotherapy when treating the cancer. NK5 or fragment thereof can be administered alone or in combination with other known agents capable of activating NK and/or T cells, such as methods described in U.S. Pat. No. 6,245,563 and in U.S. Pat. No. 6,197,302, which disclosures are hereby incorporated by reference in their entireties.

Protein of SEQ ID NO:62 (Internal Designation Clone 500715621_204-15-3-0-C6-F)

The cDNA of Clone 500715621_204-15-3-0-C6-F (SEQ ID NO:61) encodes the 202 amino acid long polypeptide of SEQ ID NO:62 comprising the amino acid sequence: MELWGAYLLLCLFSLLTQVTTEPPTQKPKKIVNAKKDVVNTKMFEELKSRLDTLAQEVALLKEQQALQTVCLKGTKVHMKCFLAFTQTKTFHESSEDCISRGGTLSTPQTGSENDALXYEYLRQSVGNEAEIWLGLNDMAAEGTWVDMTGARIAYKNWETEITAQPDGGKTENCAVLSGAANGKWFDKRCRDQLPYICQFGIV (SEQ ID NO:62). Accordingly, it will be appreciated that all characteristics and uses of polypeptides of SEQ ID NO:62 described throughout the present application also pertain to the polypeptides encoded by the nucleic acids included in Clone 500715621_204-15-3-0-C6-F. In addition, it will be appreciated that all characteristics and uses of the polynucleotides of SEQ ID NO:61 described throughout the present application also pertain to the nucleic acids included in Clone 500715621_204-15-3-0-C6-F. A preferred embodiment of the invention is directed toward the compositions of SEQ ID NO:61, SEQ ID NO:62, and Clone 500715621_204-15-3-0-C6-F. Also preferred are polypeptide fragments having a biological activity as described herein and the polynucleotides encoding the fragments.

The protein of SEQ ID NO:62 represents a new variant form of the human tetranactin precursor polypeptide (Swissport entry P05452), harboring an amino acid substitutiion at position 94 which replaces an alanine residue by a serine residue. The protein of SEQ ID NO:62 is a 202 amino acid long polypeptide comprising a 21 amino acid signal peptide followed by a 181 amino acid sequence corresponding to a mature polpeptide of the invention, Plasminogen carrier protein (PLCP).

PLCP is a 68 kilodalton homotrimeric plasminogen-binding protein in plasma. In addition to plasminogen, PLCP bins calcium as well as a number of sulphated polysaccharides including heparin, chondroitin and fucoidan. It also binds Apoliprotein A and fibrin.

In terms of primary and tertiary structure, the protein is related to the family of Ca(2+)— binding C-type lectins, proteins that bind a wide diversity of compounds, including carbohydrates, lipids and proteins.

The protein is encoded by three exons corresponding to three functional domains. Exon 3 (nt367 to nt771 on SEQ ID NO:61) encodes the long-form C-type Lectin domain (aa77 to aa198 on SEQ ID NO:62), also termed the carbohydrate recognition domain (CRD), which is involved in Ca(2+) and plasminogen binding. Exon 2 (nt268 to nt366) encodes an alpha-helix domain that governs the trimerization of PLCP oligomers by assembling into a triple helical coiled-coil structural element. Finally, residues encoded by exoni (nt13 to nt267), but not the CRD, bind heparmn, suggesting a specific role for this domain in sulphated carbohydrate ligand binding (Lorentsen et al. 2000, Biochem. J. 347:83-87 which disclosure is hereby incorporated by reference in its entirety).

PLCP binds plasminogen via its CRD through a specific interaction with the fourth kringle domain of plasminogen, and binding has been reported to facilitate the proteolytic activation of plasminogen to plasmin by the tissue-type plasminogen activator. Because plasminogen activation is involved in a variety of extracellular proteolytic events including fibrinolysis, cell migration, angiogenesis, tumor cell invasion, inflammation, wound healing, and tissue remodeling, PLCP is useful in the modulation of these biological processes.

The present protein is isolated from human blood, but is also found to be deposited in the extracellular matrix of various tissues. In particular, PLCP is deposited in the tumor surrounding stroma of breast, colon, and ovarian tumors and is found to co-localise with plasmin/plasminogen at the invasive front of cutaneous melanoma lesions, whereas little or no PLCP is found in the corresponding normal tissues. Plasma PLCP level is reduced in cancer patients, and PLCP is useful as a prognostic marker for the diagnosis of certain types of cancer.

Preferred PLCP polypeptides for uses in the methods described below include the polypeptides comprising the amino sequence of: EPPTQKPKKIVNAKKDVVNTKMFEELKSRLDTLAQEVALLKEQQALQTVCLKGTKVHM KCFLAFTQTKTFHESSEDCISRGGTLSTPQTGSENDALYEYLRQSVGNEAEIWLGLNDMA AEGTWVDMTGARIAYKNWETEITAQPDGGKTENCAVLSGAANGKWFDKRCRDQLPYI CQFGIV (SEQ ID NO:190);

A polypeptide comprising the amino acid sequence of: VCLKGTKVHMKCFLAFTQTKTFHESSEDCISRGGTLSTPQTGSENDALYEYLRQSVGNE AEIWLGLNDMAAEGTWVDMTGARIAYKNWETEITAQPDGGKTENCAVLSGAANGKWF DKRCRDQLPYICQFGIV (SEQ ID NO:191);

A polypeptide comprising the amino acid sequence of: VHMKCFLAFTQTKTFHESSEDCISRGGTLSTPQTGSENDALYEYLRQSVGNEAEIWLGLN DMAAEGTWVDMTGARIAYKNWETEITAQPDGGKTENCAVLSGAANGKWFDKRCRDQ LPYICQ (SEQ ID NO:192).

In one embodiment, the cDNA of SEQ ID NO:61 bearing a G to T substitution at position 438, which replaces an alanine residue by a serine at position 94 of SEQ ID NO:62, is used for DNA genotype. Indeed genotype this locus could be of interest in DNA fingerprinting for paternity studies or forensic analyses. It could also be used for genetic association studies, especially in pathologies relating to coagulation disorders.

In another embodiment, the polynucleotide sequence of the invention is used in pharmacogenomic applications in order to aid in the choice of the ideal drug (e.g. a coagulation or anticoagulation drug), or dosage of a drug, for the treatment of a condition or disease in a patient. For example, in one embodiment, the invention provides a method of genotype the patient to determine the identity of the nucleotide encoding the amino acid at position 438 of SEQ ID NO:62, and administering to the patient a drug or a dosage of the drug that has been established to, be preferentially efficacious in those with a serine residue at position 438 (e.g. because of preferential binding of the drug to the isoform of the protein with a serine at that position). In another embodiment, the patient is genotyped for the nucleotide encoding amino acid position 438, and a drug is determined to be not desirably administered to the patient, e.g. because side effects are known to be associated with the administration of the drug to individuals with a serine at position 438.

In another embodiment, the present protein is used to copurify plasminogen from a biological sample, preferably from a liver cell extract. This is achieved using any method, a large number of which are known in the art. For example, plasminogen is purified using affinity column chromatography with the protein of SEQ ID NO:62 or by coimmunopurification using a monoclonal or polyclonal antibody that specifically binds the protein of the invention. Purified plasminogen is useful for many purposes, including for the preparation of therapeutic fibrinolytic compositions.

In a further embodiment, the present protein provides a method to purify a protein harboring one or more kringle domains from a cellular extract, the method comprising using a fragment of the present protein retaining an intact CRD domain, preferably fragment restricted to the CRD domain itself, to purify the kringle domain-containing protein, e.g. using a method such as affinity chromatography. Preferably, the, protein to be purified is selected from the group consisting of plasminogen, angiostatin, thrombin, Hepatocyte Growth Factor, Macrophage Stimulating Protein and apolipoprotein a. The protein to be purified using the present method is derived from any source, e.g. protein expressed in vitro using an invertebrate, yeast or bacterial heterologous expression system.

In another embodiment, the present protein provides a method to determine the localization of plasminogen in vivo or ex vivo. In one such method, a tissue section is contacted with a labeled protein of SEQ ID NO:62, and the labeling in the tissue section is detected. Plasminogen can also be detected directly from crude cell or tissue extracts using the protein of the invention. Methods for labeling proteins are well known in the art, any of which is used in the present invention.

In another embodiment, the protein of SEQ ID NO:62 is used to determine circulating levels of plasminogen in the blood of an individual, the method comprising obtaining a blood sample from the individual, using the protein of the invention to copurify plasminogen from the blood sample (e.g. by affinity column chromatography), and measuring the level of plasminogen in the sample using methods well known in the art, for example Elisa, western blot or radioimmunoessay (RMA). Determining plasminogen levels in circulating blood could be of special interest for the monitoring of patients with diseases associated with impaired coagulation or fibrinolysis.

In another embodiment, the present protein is used as a diagnostic or pronostic marker for breast cancer, ovarian cancer, colon or colorectal cancers, the method comprising contacting a blood sample from a patient, preferably a serum sample, with an antibody directed to the present protein, and determining the level of PLCP in the sample compared to, a control level representative of a healthy patient, wherein a lower level of PLCP in the patient sample relative to the control level indicates that the patient has the disease, is at an elevated risk of developing the disease, or has a worse prognosis that a patient with normal levels of the protein. The antibody used is either monoclonal or polyclonal and is labeled directly or indirectly for quantification of immune complexes by methods well known to those skilled in the art.

In another embodiment, the present protein provides a transgenic animal, preferably a mammal, more preferably a rodent, with impaired fibrinolytic activity due to no or reduced expression of the protein of SEQ ID NO:62. Such transgenic animals provide a powerful model in which to, study pathologies associated with defective fibrinolysis, especially fibrosis and thrombosis. In addition, such animal is used to screen candidate molecules for the ability to inhibit coagulation or fibrosis.

Transgenic animals with reduced or eliminated PLCP expresssion or activity is obtained using any of a number of ways, including by PLCP gene knock-out, for example in the mouse, using DNA microinjection into fertilized eggs or transfection of embryonic stem cells. Alternatively, low level expression of the present protein is achieved using antisens methods, e.g., by placing the reverse nucleotide sequence encoding the protein of SEQ ID NO:62 under the control of a strong promoter sequence. Preferably, a regulatable and ubiquitous promoter sequence is used in order to temporally control the expression of the genetic construct once introduced into the animal. Other methods suitable for use in the present methods include the use of ribozymes, antibodies, and dominant negative forms of the present protein.

In another embodiment, the present protein provides a method to increase fibrinolysis in an individual, the method comprising administering to said individual an amount of the present protein sufficient to increase plasminogen activation. The present protein is administered in any of a number of ways, including by intravenous injection. Such methods is used in order to eliminate clots in the prevention or the treatment of cardiovascular diseases including, but not limited to, strokes or pulmonary embolisms.

Protein of SEQ ID NO:64 (Internal Designation Clone 165843_116-008-4-0-G4-F)

The cDNA of Clone 165843_116-008-4-0-G4-F (SEQ ID NO:63) encodes Novel Calpastatin 1 (NC1) protein of SEQ ID NO:64, comprising the amino acid sequence: MTVLEITLAVILTLLGLAILAILLTRWARRKQSEMHISRYSSEQSARLLDYEDGRGSRHAYSTQSERSKRDYTPSTNSLALSRSSIALPQGSMSSIKCLQTTEELPSRTAGAMSKFFFCPLILMCFALLNC. Accordingly, it will be appreciated that all characteristics and uses of the polypeptides of SEQ ID NO:64 described throughout the present application also pertain to the polypeptides encoded by the nucleic acids included in Clone 165843_116-008-4-0-G4-F. In addition, it will be appreciated that all characteristics and uses of the polynucleotides of SEQ ID NO:64 described throughout the present application also pertain to the nucleic acids included in Clone 165843_116-008-4-0-G4-F. A preferred embodiment of the invention is directed toward the compositions of SEQ ID NO:63, 64 and Clone 165843_116-008-4-0-G4-F. Also preferred are polypeptide fragments having a biological activity as described herein and the polynucleotides encoding the fragments.

NC1 is a physiological inhibitor of calpains. Calpains, a group of ubiquitous Ca2+-activated cytosolic proteases, have been implicated in cytoskeletal remodeling events, cellular adhesion, shape change, and mobility involving site-specific regulatory proteolysis of membrane—and actin-associated cytoskeletalproteins and apoptosis [Beckerle et al., Cell 51:569-577, 1987; Yao et al., Am. J. Physiol. 265(pt. 1):C36-46, 1993; and Shuster et al., J. Cell Biol. 128:837-848, 1995; Squier et al., J. Cell Physiol., 178(3): 311-319, 1999]. Calpains have also been implicated in the pathophysiology of cerebral and myocardial ischemia, platelet activation, NF-kB activation, Alzeimer's disease, muscular dystrophy, cataract progression and rheumatoid arthritis. There is considerable interest in inhibitors of calpain, as cellular, adhesion, cytoskeletal remodeling events and cell mobility are linked to numerous pathologies (Wang et al., Trends in Pharm Sci. 15:412-419, 1994; Mehdi, Trends in Biochem. Sci.16:150-153, 1991).In addition, as the calpain/calpastatin system is involved in membrane fusion events for several cell types, and calpain can be detected in human sperm and testes extracts by Western blotting with specific antisera, tCAST rnay modulate calpain in the calcium-mediated acrosome reaction that is required for fertilization (Li S. et al., Biol Reprod, 63(1):172-8, 2000).

NC1 has a unique N-terminal domain (domain L) and four repetitive protease-inhibitor domains (domains I-IV) (Lee WJ et al., J. Biol Chem, 267(12):8437-42, 1992). The protein of SEQ ID NO:64 has calpastatin domains T and II. The T domain targets cytosolic localization and membrane association, whereas domain I exhibits a nuclear localization function.

NC1 plays a role in cytoskeletal remodeling events, cellular adhesion, shape change, and mobility by the site-specific regulatory proteolysis of membrane- and actin-associated cytoskeletal proteins. Preferred polypeptides of the invention are polypeptides comprising the amino acids of SEQ ID NO:64 from positions 1 to 116. Also preferred are fragments of SEQ ID NO:64 having a biological activity as described therein and the polynucleotides encoding the fragments.

One embodiment of the present invention relates to methods of using the protein of the invention or fragment thereof in assays to detect the presence of calpain in a biological sample, such as in bodily fluids, in tissue samples, or in mammalian cell cultures. As NC1 binds calpain (Murachi, Biochemistry int., 18(2):263-294, 1989), the protein of the invention can be used in assays and diagnostic kits to test the presence of calpain using techniques known to those skilled in the art. Preferably, a defined quantity of the protein of the invention or fragment thereof is added to the sample under conditions allowing the formation of a complex between the protein of the invention or fragment thereof and heterologous proteins, and the presence of a complex and/or the free protein of the invention or fragment thereof is assayed and compared to a control. NC1 is useful as a marker of intracellular calpain activation, and can be used for monitoring the involvement of calpain in pathological situations (De Tullio et al., FEBS letter, 475(1):17-21, 2000). Calpain has been implicated in cytoskeletal protein degradation involved in the pathophysiology of ischemia and disorders like Alzheimer's disease (Wronski et al., J. Neural transm., 107(2):145-157, 2000) and Parkinson's disease (Mouatt-Prigent et al., J. Comp. Neurol., 419:175-92, 2000), apoptosis in neural cells of rat with spinal cord injury (SCI) (Ray, Brain res., 867(1-2):80-9, 2000), cell fusibility (Kosower et al., Methods Mol Biol., 144:181-94, 2000) and other physiopathologies. Assays detecting any increased or decreased calpain levels in a cell are thus useful in the diagnosis of any of these diseases or conditions. In addition, a recent study showed that in addition to their proteolytic activities on cytoskeletal proteins and other cellular regulatory proteins, calpain-calpastatin systems can also affect expression levels of genes encoding structural or regulatory proteins (Chen et al., Am. J. Physiol. Cell Physiol, 279:C709-C716, 2000). Thus, the ability to detect NC 1 and calpain levels is also useful for the diagnosis of an even larger number of diseases and conditions.

In another embodiment, the polynucleotides or polypeptides of the invention may be used for the detection of gametes, gametic precursor cells (such as spermatogenic stem cells), or of specific structures within the gametes, using any technique known to those skilled in the art, including those involving the use of specific antibodies and nucleic acid probes. The ability to visualize spermatozoa generally, or the sperm acrosome in particular, has obvious utility for a number of applications, including for the analysis of infertility in patients.

Another embodiment of the present invention relates to a method of inhibiting calpain in a cell, the method comprising administering to the cell an amount of the present protein sufficient to inhibit calpain in the cell. Such methods can be performed in vitro or in vivo. The inhibition of calpain has numerous uses in the treatment or prevention of various diseases and conditions, for example the pathophysiology of cerebral, myocardial, renal ischemia, platelet activation, NF-kB. activation, Alzheimer's disease, Parkinson's disease, muscular dystrophy, cataract progression, cancer cachexia and rheumatoid arthritis. Such an increase can be effected in any of a number of ways, including, but not limited to administering purified protein of the invention directly to the cells, transfecting the cells with a polynucleotide encoding the protein, operably inked to a promoter; and administering to a cell a compound that increases the activity or expression of the protein of the invention. In addition, the expression or activation of the protein of the invention can be inhibited in any of a large number of ways, including using antisense oligonucleotides, antibodies, dominant negative forms of the protein, and using heterologous compounds that decrease the expression or activation of the protein. Such compounds can be readily identified, e.g. by screening candidate compounds and detecting the level of expression or activity of the protein using any standard assay. Other calpain inhibitors are also known which can be used in conjunction with the present protein, or which can be used as controls in the identification of additional inhibitors or activators of calpastatin. Such inhibitors include, but are not limited to, cerebrolysin (Wronski et al., J. Neural TransnL. Suppl., 59:263-272, 2000), E-64-D (Ray et al., Brain Res., 867(1-2):80-9, 2000), and the calpain active site inhibitor. N-acetyl-leucyl-leucyl-norleucinal (Squier et al., J. Cell Physiol., 178(3):311-319, 1999).

In still another embodiment, the protein of SEQ ID:64 or fragment thereof can be used to prevent cells from undergoing apoptosis. Specifically, any method of increasing the level or activity of the present protein in cells can be used to prevent the cells from undergoing apoptosis, in vitro or in vivo. For example, a polynucleotide encoding a protein of SEQ ID NO:64, or any fragment or derivative thereof, can be introduced into cells, e.g. in a vector, wherein the protein is expressed in the cells. Alternatively, a protein of SEQ ID NO:64 itself can be administered to cells, preferably in a formulation that leads to the internalization of the protein by the cells. Also, any compound that increases the expression or activation of the proteins within the cells can be administered. Preventing cells from undergoing apoptosis can be used for any of a large number of purposes, including, but not limited to, to prevent the death of cells being grown in culture, to prevent in a patient the apoptosis associated with any of a number of disorders, or to prevent apoptosis in cells of a patient undergoing a treatment that increases the level of cellular stress, such as chemotherapy. Furthermore, the invention relates to methods and compositions using the protein of the invention or fragment thereof to diagnose, prevent and/or treat disorders characterized by abnormal cell proliferation and/or programmed cell death, including but not limited to cancer, immune deficiency syndromes (including AIDS), type I diabetes, pathogenic infections, cardiovascular and neurological injury, alopecia, aging, degenerative diseases such as Alzheimer's Disease, Parkinson's Disease, Huntington's disease, dystonia, Leber's hereditary optic neuropathy, schizophrenia, and myodegenerative disorders such as "mitochondrial encephalopathy, lactic acidosis, and stroke". (MELAS), and "myoclonic epilepsy ragged red fiber syndrome". (MERRF). For diagnostic purposes, the expression of the protein of the invention can be detected using any method such as Northern blotting, RT-PCR or immunoblotting methods, and compared to the expression in control individuals, wherein an increase or decrease of the level of the present protein compared to the control level indicates the presence of the disease or condition, or of a propensity for the disease or condition. For prevention and/or treatment purposes of disorders in which cell proliferation needs to be reduced and/or apoptosis increased, the expression of protein of the invention may be enhanced using any method, for example administering the purified protein to cells, transfecting the cells with a polynucleotide encoding the protein, or administering to the cells a compound that increases the expression or activity of the protein. For prevention and/or treatment purposes of disorders in which cell proliferation needs to be enhanced and/or apoptosis reduced, inhibition of endogenous expression of the protein of the invention may be achieved using any method, including triple helix and antisense strategies.

In another embodiment, inhibiting the proteins of the invention can be used to induce apoptosis in undesired cells. Such inhibition can be accomplished in any of a number of ways, including, but not limited to, using antibodies, antisense sequences, dominant negative forms of the protein, or small molecule inhibitors of the expression or activity of the proteins. Such induction of apoptosis can be used to eliminate any undesired cells, for example cancer cells, in a patient. Preferably, such inhibitors are targeted specifically to the undesired cells in the patient using standard methods.

In another preferred embodiment, the protein of the invention can be used to modulate and/or characterize fertility, including for the treatment or diagnosis of infertility, and for contraception. As NC1 is involved in the acrosomal reaction which is a required step in fertilization, over- or under-expression or activation of the present protein can be used to disrupt this reaction and thereby inhibit fertility. For example, for contraception, the expression or activation of the protein can be artificially disrupted, for example by increasing the protein level using polynucleotides encoding the protein, using the protein itself, or using activators of protein expression or activity, or by decreasing the protein level using inhibitors such as antisense oligonucleotides, antibodies, dominant negative forms of the protein, and using heterologous compounds that inhibit protein expression or activity. Similarly, the cause of infertility in many patients can be detected by detecting the level of expression of the present protein, where an abnormal level of activity or expression of the protein indicates that a cause of infertility involves the calpain-dependent acrosomal reaction. Such a diagnosis would also point to methods of treating the infertility, e.g. by increasing or decreasing the expression or activation of the present protein in spermatozoa.

In another embodiment, the invention relates to methods and compositions using the protein of the invention or fragment thereof as a marker protein to selectively identify tissues, preferably testis, or to distinguish between two or more possible sources of a tissue sample on the basis of the level of the protein of SEQ ID NO:64 in the sample. For example, the protein of SEQ ID NO:64 or fragments thereof may be used to generate antibodies using any techniques known to those skilled in the art, including those described therein. Such tissue-specific antibodies may then be used to identify tissues of unknown origin, for example, forensic samples, differentiated tumor tissue that has metastasized to foreign bodily sites, or to differentiate different tissue types in a tissue cross-section using immunochemistry. In such methods a tissue sample is contacted with the antibody, which may be detectably labeled, under conditions which facilitate antibody binding. The level of antibody binding to the test sample is measured and compared to the level of binding to control cells from testis or tissues other than testis to determine whether the test sample is from testis. Similar methods can be used to specifically detect cells expressing the protein, as well as to specifically isolate cells expressing the protein or to isolate the protein itself. For example, an antibody against the protein of SEQ ID NO:64 or a fragment thereof may be fixed to a solid support, such as a chromatography matrix. A preparation containing cells expressing the protein of SEQ ID NO:64 is placed in contact with the antibody under conditions which facilitate binding to the antibody. The support is washed and then the protein is released from the support by contacting the support with agents which cause the protein to dissociate from the antibody.

Alternatively, the level of the protein of SEQ ID NO:64 in a test sample may be measured by determining the level of RNA encoding the protein of SEQ ID NO:64 in the test sample. RNA levels may be measured using nucleic acid arrays or using techniques such as in situ hybridization, Northern blots, dot blots or other techniques familiar to those skilled in the art. If desired, an amplification reaction, such as a PCR reaction, may be performed on the nucleic acid sample prior to analysis. The level of RNA in the test sample is compared to RNA levels in control cells from testis or tissues other than testis to determine whether the test sample is from testis. For a number of disorders listed above, particularly of inflammatory processes, expression of the genes encoding the polypeptide of SEQ ID NO:64 at significant higher or lower levels may be routinely detected in certain tissues or cell types (e.g., cancerous and wounded tissues) or bodily fluids (e.g., serum, plasma, synovial fluid, and spinal fluid) or another tissue of cell sample taken from an individual having such a disorder, relative to the standard gene expression level, i.e., the expression level in healthy tissue or bodily fluid from an individual not having the disorder.

In another embodiment, the invention relates to methods for using the protein of the invention or fragments to identify autoantibodies which indicate inflammatory processes and particularly, rheumatoid arthritis (RA), a systemic disease characterized by chronic polyarthritis and joint destruction, and in which high levels of autoantibodies directed against calpastatin have been identified. Accordingly, the present protein may be used to detect the presence and/or the localization of autoantibodies in a cell. In a typical embodiment, the protein of SEQ ID NO:64 is labeled with any detectable moiety including, but are not limited to, a fluorescent label, a radioactive atom, a paramagnetic ion, biotin, a chemiluminescent label or a label which can be detected through a secondary enzymatic or binding step. The invention further provides a method of diagnosing inflammatory processes, e.g. rheumatoid arthritis, and distinguishing such processes from other diseases.

Protein of SEQ ID NO:66 (Internal Designation 335752_157-15-4-0-B11-F)

The cDNA of Clone 335752_157-15-4-0-B 11-F (SEQ ID NO:65) encodes Novel Calpastatin 2 (NC2) protein of SEQ ID NO:66, comprising the amino acid sequence:

MTVLEITLAVILTLLGLAILAILLTR-WARRKQSEMYISRYSSEQSARLLDYEDGRGSRIHIAy STQSERSKRDYTPSTNSLALSRS-SIALPQGSMSSIKCLQTTEEPPSRTAG-AMMQFTAPIPGA TGPIKLSQKTIVQTLGPIVQYPGSN-GRINISQLTSEDLTGAKGRVTSGPQFPNSHHVPENLH GYMNSLSLFSPA (SEQ ID NO:66). Accordingly, it will be appreciated that all characteristics and uses of the polypeptides of SEQ ID NO:66 described throughout the present application also pertain to the polypeptides encoded by the nucleic acids included in Clone 335752_157-15-4-0-B 11-F. In addition, it will be appreciated that all characteristics and uses of the polynucleotides of SEQ ID NO:66 described throughout the present application also pertain to the nucleic acids included in Clone 335752_157-15-4-0-B 11-F. A preferred embodiment of the invention is directed toward the compositions of SEQ ID NO:65, 66 and Clone 335752_157-15-4-0-B 11-F. Also preferred are polypeptide fragments having a biological activity as described herein and the polynucleotides encoding the fragments.

NC2 is a physiological inhibitor of calpains. Calpains, a group of ubiquitous Ca2+-activated cytosolic proteases, have been implicated in cytoskeletal remodeling events, cellular adhesion, shape change, and mobility involving site-specific regulatory proteolysis of membrane-and actin-associated cytoskeletal proteins and apoptosis (Beckerle et al., Cell 51:569-577, 1987; Yao et al., Am. J. Physiol. 265(pt. 1):C36-46, 1993; and Shuster et al., J. Cell Biol. 128:837-848, 1995; Squier et al., J. Cell Physiol., 178(3): 311-319, 1999). Calpains have also been implicated in the pathophysiology of cerebral and myocardial ischemia, platelet activation, NF-kB activation, Alzheimer's disease, muscular dystrophy, cataract progression and rheumatoid arthritis. There is considerable interest in inhibitors of calpain, as cellular adhesion, cytoskeletal remodeling events and cell mobility are linked to numerous pathologies (Wang et al., Trends in Pharm. Sci. 15:412-419, 1994; Mehdi, Trends in BiochenL. Sci. 16:150-153, 1991). In addition, as the calpain/calpastatin system is involved in membrane fusion events for several cell types, and calpain can be detected in human sperm and testes extracts.

NC2 consists of calpastatin domain T and II. The T domain targets cytosolic localization and membrane association, whereas domain I of exhibits a nuclear localization function.

The protein of SEQ ID NO:66 is a novel member of the calpastatin family and, as such, plays a role in cytoskeletal remodeling events, cellular adhesion, shape change, and mobility by the site-specific regulatory proteolysis of membrane- and actin-associated cytoskeletal proteins. Preferred polypeptides of the invention are polypeptides comprising the amino acids of SEQ ID NO:66 from positions. 1 to 116. Also preferred are fragments of SEQ ID NO:66 having a biological activity as described therein and the polynucleotides encoding the fragments.

One embodiment of the present invention relates to methods of using the protein of the invention or fragment thereof in assays to detect the presence of calpain in a biological sample, such as in bodily fluids, in tissue samples, or in mammalian cell cultures. As NC2 binds calpain, the protein of the invention can be used in assays and diagnostic kits to test the presence of calpain using techniques known to those skilled in the art. Preferably, a defined quantity of the protein of the invention or fragment thereof is added to the sample under conditions allowing the formation of a complex between the protein of the invention or fragment thereof and heterologous proteins, and the presence of a complex and/or the free protein of the invention or fragment thereof is assayed and compared to a control. NC2 is useful as a marker of intracellular calpain activation, and can be used for monitoring the involvement of calpain in pathological situations (De Tullio et al., FEBS letter, 475(1):17-21, 2000). Calpain has been implicated in cytoskeletal protein degradation involved in the pathophysiology of ischemia and disorders like Alzheimer's disease (Wronski et al., J.Neural trans., 107(2):145-157, 2000) and Parkinson's disease. (Mouatt-Prigent et al., J. Comp. Neurol.,419:175-92, 2000), apoptosis in neural cells of rat with spinal cord injury. (SCI). (Ray, Brain res., 867(1-2):80-9, 2000), cell fusibility (Kosower et al., Methods. Mol. Biol., 144:181-94, 2000) and other physiopathologies. Assays detecting any increased or decreased calpain levels in a cell are thus useful in the diagnosis of any of these diseases or conditions. In addition to proteolytic activities on cytoskeletal proteins and other cellular regulatory proteins, calpain-NC2 systems can also affect expression levels of genes encoding structural or regulatory proteins. Thus, the ability to detect NC2 and calpain levels is also useful for the diagnosis of an even larger number of diseases and conditions.

In another embodiment, the polynucleotides or polypeptides of the invention may be used for the detection of gametes, gametic precursor cells (such as spermatogenic stem cells), or of specific structures within the gametes, using any technique known to those skilled in the art, including those involving the use of specific antibodies and nucleic acid probes. The ability to visualize spermatozoa generally, or the sperm acrosome in particular, has obvious utility for a number of applications, including for the analysis of infertility in patients.

Another embodiment of the present invention relates to a method of inhibiting calpain in a cell, the method comprising administering to the cell an amount of the present protein sufficient to inhibit calpain in the cell. Such methods can be performed in vitro or in vivo. The inhibition of calpain has numerous uses in the treatment or prevention of various diseases and conditions, for example, the pathophysiology of cerebral, myocardial, renal ischemia, platelet activation, NF-kB activation, Alzheimer's disease, Parkinson's disease, muscular dystrophy, cataract progression, cancer cachexia and rheumatoid arthritis. Such an increase can be effected in any of a number of ways, including, but not limited to administering purified protein of the invention directly to the cells, transfecting the cells with a polynucleotide encoding the protein, operably linked to a promoter; and administering to a cell a compound that increases the activity or expression of the protein of the invention. In addition, the expression or activation of the protein of the invention can be inhibited in any of a large number of ways, including using antisense oligonucleotides, antibodies, dominant negative forms of the protein, and using heterologous compounds that decrease the expression or activation of the protein. Such compounds can be readily identified, e.g. by screening candidate compounds and detecting the level of expression or activity of the protein using any standard assay. Other calpain inhibitors are also known which can be used in conjunction with the present protein, or which can be used as controls in the identification of additional inhibitors or activators of calpastatin. Such inhibitors include, but are not limited to, cerebrolysin (Wronski et al., J. Neural Transm. Suppl., 59:263-272, 2000), E-64-D (Ray et al., Brain Res., 867(1-2): 80-9, 2000), and the calpain active site inhibitor N-acetyl-leucyl-leucyl-norleucinal (Squier et al., J. Cell Physiol., 178(3): 311-319, 1999).

In still another embodiment, the protein of SEQ ID:66 or fragment thereof can be used to prevent cells from undergoing apoptosis. Specifically, any method of increasing the level or activity of the present protein in cells can be used to prevent the cells from undergoing apoptosis, in vitro or in vivo. For example, a polynucleotide encoding a protein of SEQ ID NO:66, or any fragment or derivative thereof, can be introduced into cells, e.g. in a vector, wherein the protein is expressed in the cells. Alternatively, a protein of SEQ ID NO:66 itself can be administered to cells, preferably in a formulation that leads to the internalization of the protein by the cells. Also, any compound that increases the expression or activation of the proteins within the cells can be administered. Preventing cells from undergoing apoptosis can be used for any of a large number of purposes, including, but not limited to, to prevent the death of cells being grown in culture, to prevent in a patient the apoptosis associated with any of a number of disorders, or to prevent apoptosis in cells of a patient undergoing a treatment that increases the level of cellular stress, such as chemotherapy. Furthermore, the invention relates to methods and compositions using the protein of the invention or fragment thereof to diagnose, prevent and/or treat disorders characterized by abnormal cell proliferation and/or programmed cell death, including but not limited to cancer, immune deficiency syndromes (including AIDS), type I diabetes, pathogenic infections, cardiovascular and neurological injury, alopecia, aging, degenerative diseases such as Alzheimer's Disease, Parkinson's Disease, Huntington's disease, dystonia, Leber's hereditary optic neuropathy, schizophrenia, and myodegenerative disorders such as "mitochondrial encephalopathy, lactic acidosis, and stroke"(MELAS), and "myoclonic epilepsy ragged red fiber syndrome" (MERRF). For diagnostic purposes, the expression of the protein of the invention can be detected using any method such as Northern blotting, RT-PCR or immunoblotting methods, and compared to the expression in control individuals, wherein an increase or decrease of the level of the present protein compared to the control level indicates the presence of the disease or condition, or of a propensity for the disease or condition. For prevention and/or treatment purposes of disorders in which cell proliferation needs to be reduced and/or apoptosis increased, the expression of protein of the invention may be enhanced using any method, for example administering the purified protein to cells, transfecting the cells with a polynucleotide encoding the protein, or administering to the cells a compound that increases the expression or activity of the protein. For prevention and/or treatment purposes of disorders in which cell proliferation needs to be enhanced and/or apoptosis reduced, inhibition of endogenous expression of the protein of the invention may be achieved using any method, including triple helix and antisense strategies.

In another embodiment, inhibiting the proteins of the invention can be used to induce apoptosis in undesired cells. Such inhibition can be accomplished in any of a number of ways, including, but not limited to, using antibodies, antisense sequences, dominant negative forms of the protein, or small molecule inhibitors of the expression or activity of the proteins. Such induction of apoptosis can be used to eliminate any undesired cells, for example cancer cells, in a patient. Preferably, such inhibitors are targeted specifically to the undesired cells in the patient using standard methods.

In another preferred embodiment, the protein of the invention can be used to modulate and/or characterize fertility, including for the treatment or diagnosis of infertility, and for contraception. As NC2 is involved in the acrosomal reaction which is a required step in fertilization, over- or under-expression or activation of the present protein can be used to disrupt this reaction and thereby inhibit fertility. For example, for contraception, the expression or activation of the protein can be artificially disrupted, for example by increasing the protein level using polynucleotides encoding the protein, using the protein itself, or using activators of protein expression or activity, or by decreasing the protein level using inhibitors such as antisense oligonucleotides, antibodies, dominant negative forms of the protein, and using heterologous compounds that inhibit protein expression or activity. Similarly, the cause of infertility in many patients can be detected by detecting the level of expression of the present protein, where an abnormal level of activity or expression of the protein indicates that a cause of infertility involves the calpain-dependent acrosomal reaction. Such a diagnosis would also point to methods of treating the infertility, e.g. by increasing or decreasing the expression or activation of the present protein in spermatozoa.

In another embodiment, the invention relates to methods and compositions using the protein of the invention or fragment thereof as a marker protein to selectively identify tissues, preferably testis, or to distinguish between two or more possible sources of a tissue sample on the basis of the, level of the protein of SEQ ID NO:66 in the sample. For example, the protein of SEQ ID NO:66 or fragments thereof may be used to generate antibodies using any techniques known to those skilled in the art, including those described therein. Such tissue-specific antibodies may then be used to identify tissues of unknown origin, for example, forensic samples, differentiated tumor tissue that has metastasized to foreign bodily sites, or to differentiate different tissue types in a tissue cross-section using immunochemistry. In such methods a tissue sample is contacted with the antibody, which may be detectably labeled, under conditions which facilitate antibody binding. The level of antibody binding to the test sample is measured and compared to the level of binding to control cells from testis or tissues other than testis to determine whether the test sample is from testis. Similar methods can be used to specifically detect cells expressing the protein, as well as to specifically isolate cells expressing the protein or to isolate the protein itself. For example, an antibody against the protein of SEQ ID NO:66 or a fragment thereof may be fixed to a solid support, such as a chromatography matrix. A preparation containing cells expressing the protein of SEQ ID NO:66 is placed in contact with the antibody under conditions which facilitate binding to the antibody. The support is washed and then the protein is released from the support by contacting the support with agents which cause the protein to dissociate from the antibody.

Alternatively, the level of the protein of SEQ ID NO:66 in a test sample may be measured by determining the level of RNA encoding the protein of SEQ ID NO:66 in the test sample. RNA levels may be measured using nucleic acid arrays or using techniques such as in situ hybridization, Northern blots, dot blots or other techniques familiar to those skilled in the art. If desired, an amplification reaction, such as a PCR reaction, may be performed on the nucleic acid sample prior to, analysis. The level of RNA in the test sample is compared to RNA levels in control cells from testis or tissues other than testis to determine whether the test sample is from testis. For a number, of disorders listed above, particularly of inflammatory processes, expression of the genes encoding the polypeptide of SEQ ID NO:66 at significant higher or lower levels may be routinely detected in certain tissues or cell types (e.g., cancerous and wounded tissues) or bodily fluids (e.g., serum, plasma, synovial fluid, and spinal fluid) or another tissue of cell sample taken from an individual having such a disorder, relative to the standard gene expression level, i.e., the expression level in healthy tissue or bodily fluid from an individual not having the disorder.

In another embodiment, the invention relates to, methods for using the protein of the invention or fragments to identity autoantibodies which indicate inflammatory processes and particularly, rheumatoid arthritis (RA), a systemic disease characterized by chronic polyarthritis and joint destruction, and in which high levels of autoantibodies directed against calpastatin have been identified. Accordingly, the present protein may be used to detect the presence and/or the localization of autoantibodies in a cell. In a typical embodiment, the protein of SEQ ID NO:66 is labeled with any detectable moiety including, but are not limited to, a fluorescent label, a radioactive atom, a paramagnetic ion, biotin, a chemiluminescent label or a label which can be detected through a secondary enzymatic or binding step. The invention further provides a method of diagnosing inflammatory processes, e.g. rheumatoid arthritis, and distinguishing such processes from other diseases.

Protein of SEQ ID NO:68 (internal designation Clone 646607_181-15-2-0-E2-F)

The cDNA of Clone 646607_181-15-2-0-E2-F (SEQ ID NO:67) encodes Benzodiazepine Receptor 2 (BZRP-R2) protein of SEQ ID NO:68, comprising the amino acid sequence:

MRLQGAIFVLLPHLGPILVWLFTRDHMSGWCEGPR-MLSWCPFYKVLLLVQTAIYSVVGYASYLVWKDL-GGGLGWPLALPLRLYAVQLTISWTVLVLFFTVHNPG-LALLHLLLLYGLVVSTALIWHPNKLAALLLLPYLA-WLTVTSALTYHLWRDSLCPVHQPQPTEKSD (SEQ ID NO:68). Accordingly, it will be appreciated that all characteristics and uses of the polypeptides of SEQ ID NO:68 described throughout the present application also pertain to the polypeptides encoded by the nucleic acids included in Clone 646607__181-15-2-0-E2-F. In addition, it will be appreciated that all characteristics and uses of the polynucleotides of SEQ ID NO:68 described throughout the present application also pertain to the nucleic acids included in Clone 646607__181-15-2-0-E2-F. A preferred embodiment of the invention is directed toward the compositions of SEQ ID NO:67, 68 and Clone 646607__181-15-2-0-E2-F. Also preferred are polypeptide fragments having a biological activity as described herein and the polynucleotides encoding the fragments.

BZRP-R2 is homologous to peripheral benzodiazepine receptor/isoquinoline binding protein (PBR/IBP) of human, bovine and murine origin (Genbank accession numbers MA36035, M64520 and L17306 respectively). The 170-amino-acid protein of SEQ ID NO:68 is similar in size and hydropathicity to known peripheral PBR/IBP benzodiazepine receptors/isoquinoline binding proteins. BZRP-R2 has five transmembrane domains at positions 3-23, 45-65, 82-102, 105-125 and 130-150. Moreover, BZRP-R2 displays a stretch of 11 amino acids (starting with V144 and ending with R154) that corresponds to a recently identified putative cholesterol recognition/interaction alino acid consensus pattern (-L/V-(X)(1-5)-Y-(X)(1-5)-R/K-). [See Li et al, Endocrinology 1998 December; 139 (12): 4991-7].

BZRP-R2 is capable of binding benzodiazepine and imidazopyridine derivatives, but is distinct from the GABA neurotransmitter receptor. BZRP-R2 polypeptides are most abundant in steroidogenic, cells and are found primarily on outer mitochondrial membranes BZRP-R2 is associated with a 34-kDa pore-forming, voltage-dependent anion channel protein located on the outer/inner mitochondrial membrane contact sites. Ligands of BZRP-R2, upon binding to the receptor, simulate steroid synthesis in steroidogenic cells in vitro and in vivo. BZRP-R2 stimulates steroid formation by increasing the rate of cholesterol transfer from the outer to the inner mitochondrial membrane.

In addition to its role in mediating cholesterol movement across membranes, BZRP-R2 has been implicated in several other physiological functions, including cell growth and differentiation, chemotaxis, mitochondrial physiology, porphyrin and heme biosynthesis, immune response, and anion transport. In addition, BZRP-R2 agonists are potent anti-apoptotic compounds.

BZRP-R2 is associated with stress and anxiety disorders. BZRP-R2 plays a role in the regulation of several stress systems such as the HPA axis, the sympathetic nervous system, the renin-angiotensin axis, and the neuroendocrine axis. In these systems, acute stress typically leads to increases in BZRP-R2 density, whereas chronic stress typically leads to decreases in BZRP-R2 density. For example, in Generalized Anxiety Disorder (GAD), Panic Disorder (PD), Generalized Social Phobia (GSP), and Post-Traumatic Stress Disorders (PTSD), BZRP-R2 density is typically decreased. BZRP-R2 is expressed glial cells in the brain. Furthermore, BZRP-2 expression is increased in neurodegenerative disorders and after neurotoxic and traumatic-ischemic brain damage BZRP-R2 expression is decreased in chronic schizophrenics, suggesting that the decreased density of BZRP-R2 in the brain may be involved in the pathophysiology of schizophrenia. However, BZRP-R2 is higher than normal in autopsied brain tissue from PSE patients (Portal-Systemic Encephalopathy patients).

BZRP-R2 increases mitochondrial activity and prevents apoptosis and is therefore implicated in tumor cell proliferation. BZRP-R2 is preferentially expressed in liver and breast cancers. Further, BZRP-R2 is useful as a tool/marker for detection, diagnosis, prognosis and treatment of cancer.

Many ligands have been described that bind to BZRP-R2 with various affinities. Some benzodiazepines, Ro 5-4864 [4-chlorodiazepam], diazepam and structurally related compounds, are potent and selective PBR ligands. Exogenous ligands also include 2-phenylquinoline carboxamides (PK11195 series), imidazo[1, 2-a]pyridine-3-acetamides (Alpidem series), pyridazine, and isoquinilone derivatives. Some endogenous compounds, including porphyrins and diazepam binding inhibitor (DBI), bind to BZRP-R2.

In one embodiment, a preferred polypeptide of the invention comprises the amino acids of SEQ ID NO:68 from position 144 to 154: VTSALTYHLWR. Further preferred fragments of BZRP-R2 comprise the epitope: ALPLRLYAV or fragments thereof. In another embodiment, the subject invention provides a polypeptide comprising the sequence of SEQ ID NO:68. Other preferred polypeptides of the invention include biologically active fragments of SEQ ID NO:68. Biologically active fragments of the protein of BZRP-R2 have any of the biological activities described herein. In another embodiment, the polypeptide of the invention is encoded by clone 646607 215-15-5-0-B11-F.

A preferred embodiment of the invention is a method of screening for compounds that modulate the expression of BZRP-R2. This method comprises the steps of i) contacting a cell with a test compound and ii) comparing the level of BZRP-R2 polypeptides in a cell after exposure to the test compound to that of an untreated control cell. The level of BZRP-R2 polypeptides may be inferred by detecting mRNA for BZRP-R2 by methods common to the art such as Northern blotting or RT-PCR. The level of BZRP-R2 polypeptides may also be detected by antibody-based methods common to the art such as Western blotting or immunofluorescence. Test compounds that increase BZRP-R2 expression are useful as agonists, as discussed herein. Test compounds that decrease BZRP-R2 expression are useful as antagonists, as discussed herein.

Antagonists of BZRP-R2 include agents which decrease the levels of expressed mRNA encoding the protein of SEQ ID NO:68. These include, but are not limited to, RNAi, one or more ribozymes capable of digesting the protein of the invention, or antisense oligonucleotides capable of hybridizing to nRNA encoding BZRP-R2. Antisense oligonucleotides can be administrated as DNA, RNA, as DNA entrapped in proteoliposomes containing viral envelope receptor proteins [Kanoda, Y. et al. (1989) Science 243: 375, which disclosure is hereby incorporated by reference in its entirety] or as part of a vector which can be expressed in the target cell to provide antisense DNA or RNA. Vectors which are expressed in particular cell types are known in the art. Alternatively, the DNA can be injected along with a carrier. A carrier can be a protein such as a cytokine, for example interleukin 2, or polylysine-glycoprotein carriers. Carrier proteins, vectors, and methods of making and using polylysine carrier systems are known in the art. Alternatively, nucleic acid encoding antisense molecules may be coated onto gold beads and introduced into the skin with, for example, a gene gun [Ulmer, J. B. et al. (1993) Science 259:1745, which disclosure is hereby incorporated by reference in its entirety].

A preferred embodiment of the invention is a method of screening for compounds that bind to BZRP-R2 polypeptides. Such compounds are useful for developing agonists and antagonists of BZRP-R2 activity. This method comprises the steps of: i) contacting a BZRP-R2 polypeptide or fragment thereof with a test compound under conditions that allow binding to occur and ii). detecting binding of said test compound. Binding may be detected by any method common to the art such as competition with a labeled antibody specific for BZRP-R2 or by direct labeling of each test substance. In one example of such a method, a polynucleotide encoding a BZRP-R2 polypeptide or a biologically active fragment thereof is transformed into a eukaryotic or prokaryotic host cell. The transformed cells may be viable or fixed. Drugs or compounds which are candidates for binding BZRP-R2 polypeptides are screened against such transformed cells in binding assays well known to those skilled in the art. Alternatively, assays such as those taught in Geysen H. N., WO Application 84/03564, published on Sep. 13, 1984, and incorporated herein by reference in its entirety, may be used to screen for peptide compounds which demonstrate binding affinity for BZRP-R2 polypeptides or fragments thereof. In another embodiment, competitive drug screening assays using neutralizing antibodies specifically compete with a test compound for binding to BZRP-R2 polypeptides or fragments thereof. Preferred test compounds are those included in the benzodiazepine class, such as diazepam (i.e., valium), triazolobenzodiazepine, and adinazolam, as well as modified versions thereof. Further preferred test compounds are in the imidazo pyridine and isoquinilone classes.

A variety of drug screening techniques may be employed. In this aspect of the invention, BZRP-R2 polypeptide or biologically active fragments thereof, may be free in solution, affixed to a solid support, recombinantly expressed on or chemically attached to a cell surface, or located intracellularly. The formation of binding complexes between BZRP-R2 polypepetides or biologically active fragments thereof, and the compound being tested, may then be measured as described.

Another embodiment of the subject invention provides compositions and methods of selectively modulating the activity of the protein of the invention. Modulation of BZRP-R2 allows for the successful prevention, treatment, or management of disorders or biochemical abnormalities associated with BZRP-R2. Agonist compounds are those that increase the amount of BZRP-R2 polypeptides in a cell or increase the biological activity of BZRP-R2. A preferred embodiment of the invention is a method of screening for agonists that bind to BZRP-R2 comprising the steps of: i) screening for test substances that bind to BZRP-R2, as described above and ii) detecting BZRP-R2 biological activity. Preferably, this method is accomplished in an intact cell. Further preferably, the cell is a steroidogenic cell such as a testicular or ovarian cell. Preferably, the biological activity of BZRP-R2 is determined by measuring the concentration of steroid hormones released from the cell before and after exposure to the test substance. Agonists of BZRP-R2 will increase the release of steroid hormones from the cell. Antagonist compounds are those that decrease the amount of BZRP-R2 polypeptides in a cell or decrease the biological activity of BZRP-R2. Another preferred embodiment of the invention is a method of screening for antagonists that bind to BZRP-R2 comprising the steps of: i) screening for test substances that bind to BZRP-R2, as described above and ii) detecting BZRP-R2 biological activity. Preferably, this method is accomplished in an intact cell. Further preferably, the cell is a steroidogenic cell such as a testicular or ovarian cell. Preferably, the biological activity of BZRP-R2 is determined by measuring the concentration of steroid hormones released from the cell before and after exposure to the test substance. Antagonists of BZRP-R2 will decrease the release of steroid hormones from the cell.

Antagonists, able to reduce or inhibit the expression or the activity of the protein of the invention, are useful in the treatment of diseases associated with elevated levels of BZRP-R2, increased cell proliferation or reduced apoptosis, and increased cholesterol transport. Thus, the subject invention provides methods for treating a variety of diseases or disorders, including but not limited to, cancers, especially liver and breast cancer, and portal-systemic encephalopathy. Increased cholesterol transport into the mitochondria of steroidogenic cells results in higher than normal production of steroid hormones such as progesterone, testosterone, and estrogen. Abnormally high levels of steroid hormones lead to disruption of adrenocortical feedback mechanisms and underproduction of trophic hormones from the hypothalamus and pituitary. Inhibition of BZRP-R2 and steroidogenesis may increase levels of trophic hormones such as gonadotropin-releasing hormone.

Alternatively, the subject invention provides a method of treating diseases or disorders associated with decreased levels of BZRP-R2 polypeptides and decreased steroid hormone release with an agonist thereof. Such method comprises the step of contacting a cell with a BZRP-R2 agonist. This method comprises the step of contacting a cell with an agonist of BZRP-R2. Thus, the subject invention provides methods of treating disorders including, but not limited to, schizophrenia, chronic stress, GAD, PD, GSP and PTSD. Other disorders which may be treated by agonists of BZRP-R2 include those associated with decreases in cell proliferation, e.g developmental retardation. Furthermore, because BZRP-R2 is able to transport cholesterol into cells, BZRP-R2 agonists may also be used to increase cholesterol transport into cells. Diseases associated with cholesterol transport deficiencies include lipoidal adrenal hyperplasia, ovarian cysts, abnormal lipid deposits in steroidogenic cells. Disorders that reflect a requirement for cholesterol for myelin and myelination, include Alzheimer's disease, multiple sclerosis, spinal cord injury, and brain development neuropathy. The methods of treating disorders associated with decreased levels of BZRP-R2 may be practiced by introducing agonists which stimulate the expression or the activity of BZRP-R2. Additionally, disorders resulting from defective mitochondrial activity may be treated with an agonist to BZRP-R2. Defective mitochondrial activity may alternatively or additionally result in the generation of highly reactive free radicals that have the potential of damaging cells and tissues. These free radicals may include reactive oxygen species (ROS) such as superoxide, peroxynitrite and hydroxyl radicals, and other reactive species that may be toxic to cells and cause apoptosis. For example, oxygen free radical induced lipid peroxidation is a well-established pathogenic mechanism in central nervous system (CNS) injury such as that found in a number of degenerative diseases, and in ischemia (i.e., stroke). Diseases associated with altered mitochondrial function and apoptosis include: Alzheimer's Disease, diabetes mellitus, Parkinson's Disease, Huntington's disease, dystonia, Leber's hereditary optic neuropathy, schizophrenia, mitochondrial encephalopathy, lactic acidosis, and stroke.

A further preferred embodiment includes a method of inhibiting apoptosis of cells in culture. This method comprises the step of contacting a cell in culture with an agonist to BZRP-R2. Such methods are useful for culturing cells that are notoriously undergo apoptosis, such as primary neurons and lymphocytes.

In one embodiment, the level of BZRP-R2 in a cell may be increased by introducing nucleic acids encoding a BZRP-R2 polypeptide or biologically active fragment thereof into a targeted cell type. Vectors useful in such methods are known to those skilled in the art, as are methods of introducing such nucleic acids into target tissues.

Antibodies or other polypeptides capable of reducing or inhibiting the activity of BZRP-R2 may be provided as in isolated and substantially purified form. Alternatively, antibodies or other polypeptides capable of inhibiting or reducing the activity of BZRP-R2 may be recombinantly expressed in the target cell to provide a modulating effect. In addition, compounds which inhibit or reduce the activity of BZRP-R2 may be incorporated into biodegradable polymers being implanted in the vicinity of where drug delivery is desired. For example, biodegradable polymers may be implanted at the site of a tumor or, alternatively, biodegradable polymers containing antagonists/agonists may be implanted to slowly release the compounds systemically. Biodegradable polymers, and their use, are known to those of skill in the art (see, for example, Brem et al. (1991) J. Neurosurg. 74:441-446, which disclosure is hereby incorporated by reference in its entirety).

In another embodiment, the invention provides methods and compositions for detecting the level of expression of the mRNA encoding the protein of the invention. Quantification of mRNA levels of BZRP-R2 may be useful for the diagnosis or prognosis of diseases associated with an altered expression of the protein of the invention. Assays for the detection and quantification of the mRNA encoding BZRP-R2 are well known in the art (see, for example, Maniatis, Fitsch and Sambrook, Molecular. Cloning; A Laboratory Manual (1982), or Current Protocols in Molecular Biology, Ausubel, F. M. et al. (Eds), Wiley & Sons, Inc., disclosures of which are hereby incorporated by reference in their entireties).

Polynucleotides probes or primers for the detection of BZRP-R2 mRNA can be designed from the cDNA of SEQ ID NO:67. Methods for designing probes and primers are known in the art. In another embodiment, the subject invention provides diagnostic kits for the detection of the mRNA of the protein of the invention in cells. The kit comprises a package having one or more containers of oligonucleotide primers for detection of the protein of the invention in PCR assays or one or more containers of polynucleotide probes for the detection of the mRNA of the protein of the invention by in situ hybridization or Northern analysis. Kits may, optionally, include containers of various reagents used in various hybridization assays. The kit may also, optionally, contain one or more of the following items: polymerization enzymes, buffers, instructions, controls, or detection labels. Kits may also, optionally, include containers of reagents mixed together in suitable proportions for performing the hybridization assay methods in accordance with the invention. Reagent containers preferably contain reagents in unit quantities that obviate measuring steps when performing the subject methods.

In another embodiment, the invention relates to methods and compositions for detecting and quantifying the level of the protein of the invention present in a particular biological sample. These methods are useful for the diagnosis or prognosis of diseases associated with altered levels of the protein of the invention. Diagnostic assays to detect the protein of the invention may comprise a biopsy, in situ assay of cells from organ or tissue sections, or an aspirate of cells from a tumor or normal tissue. In addition, assays may be conducted upon cellular extracts from organs, tissues, cells, urine, or serum or blood or any other body fluid or extract.

Assays for the quantification of BZRP-R2 polypeptides may be performed according to methods well known in the art. Typically, these assays comprise the steps of: contacting the sample with a ligand of the protein of the invention or an antibody (polyclonal or monoclonal) that specifically recognizes the protein of the invention or a fragment thereof and detecting the complex formed between the protein of the invention present in the sample and the ligand or antibody. Fragments of the ligands and antibodies may also be used in the binding assays, provided these fragments are capable of specifically interacting with BZRP-R2 polypeptides. Further, ligands and antibodies which bind to BZRP-R2 may be labeled according to methods known in the art. Labels which are useful in the subject invention include, but are not limited to, enzymes labels, radioisotopic labels, paramagnetic labels, and chemiluminescent labels. Typical techniques are described by Kennedy, J. H., et al. (1976) Clin. Chim. Acta 70:1-31; and Schurs, A. H. et al. (1977) Clin. Chimn. Acta 81:1-40, disclosures of which are hereby incorporated by reference in their entireties.

The subject invention also provides methods and compositions for the identification of metastatic tumor masses. In this aspect of the invention, the polypeptide or antibody that specifically binds a BZRP-R2 polypeptide or fragment thereof may be used as a marker for the identification of the metastatic tumor mass. Metastatic tumors which originated from the breast or liver may overexpress BZRP-R2 polypeptides, whereas newly forming tumors, or those originating from other tissues are not expected to bear BZRP-R2.

Protein of SEQ ID NO:70 (Internal designation Clone 229654_114-049-1-0-F12-F (cFS))

The cDNA of Clone 229654_114-049-1-0F12-F (SEQ ID NO:69) encodes the 787 amino acid long polypeptide called LAP of SEQ ID NO:70 comprising the amino acid sequence:

MFRLWLLLAGLCGLLASRPGFQNSLL-QIVIPEKIQTNTNDSSEIEYEQISYIIPIDEKLYTVH LKQRYFLTDNFMIYLYNQGSMNTYSS-DIQTQCYYQGNIEEYPDSMVTLSTCSGLRGILQF ENVSYGIEPLESAVEFQHVLHKLKNEDN-DIAIFIDRSLKEQPMDDNIFISEKSEPAVPDLFP LYLEMHIVVDKTLYDYWGSDSMIVT-NKVIEIVGLANSMFTQFKVTIVLSSLELWSDENKI STVGEADELLQKFLEWKQSYLNLRPHDI-AYLLIYMDYPRYLGAVFPGTMCITRYSAGVA LYP-KEITLEAFAVIVTQMLALSLGISYDDP-KKCQCSESTCIMNPEVVQSNGVKTFSSCSLR SFQNFISNVGVKCLONKPQMQKKSPK-PVCGNGRLEGNEICDCGTEAQCGPASCCDFRTC VLKDGAKCYKGLCCKDCQILQSGVECRP-KAHPECDIAENCNGSSPECGPDITLINGLSCK NNKFI-CYDGDCHDLDARCESVFGKGSRNAPFA-CYEEIQSQSDRFGNCGRDRNNKYVFCG WRNLICGRLVCTYPTRKPFHQENGD-VIYAFVRDSVCITVDYKLPRTVPDPLAVKNGSQC DIGRVCVNRECVESRIIKASAHVCSQQC-SGHGVCDSRNKCHCSPGYKPPNCQIRSKGFSIF PEEDMGSIMERASGKTENTWLLGFLIAL-PILIVTTAIVLARKQLKNWFAKEEEFPSSESKSE GSTQTYASQSSSEGSTQTY-

AGQTRSESSSQADTSKSKSEDSAEAY-TSRSKSQDSTQTQSS SN (SEQ ID NO:70). Accordingly, it will be appreciated that all characteristics and uses of polypeptides of SEQ ID NO:70 described throughout the present application also pertain to the polypeptides encoded by the nucleic acids included in Clone 229654_114-049-1-0-F 12-F. In addition, it will be appreciated that all characteristics and uses of the polynucleotides of SEQ ID NO:69 described throughout the present application also pertain to the nucleic acids included in Clone 229654_114-049-1-0-F 12-F. A preferred embodiment of the invention is directed toward the compositions of SEQ ID NO:69, SEQ ID NO:70, and Clone 229654_114-049-1-0-F12-F. Also preferred are polypeptide fragments having a biological activity as described herein and the polynucleotides encoding the fragments.

LAP, the protein of SEQ ID NO:70, is a new member of the ADAM (A Disintegrin And Metalloprotease domain) family of proteins. The gene for Clone 229654.cFS is located on chromosome 8 and is expressed in tissues including liver, adipose and testis.

LAP, as an ADAM family member is a membrane-anchored cell surface protein. The members of this family form a large group of cell surface adhesion molecules and proteases whose name describes the two domains that these proteins share with their closest relatives, the PIII class of snake venom metalloproteinases (SVMPs). The ADAM proteases fall with the SVMPS within the adamalysin/reprolysin subfamily of Zinc-dependent metalloproteinases. ADAMs have also been referred to as MDCs (metalloproteinase/disintegrin/cysteine-rich), cellular disintegrins, and metalloproteinase-desintegrins.

These proteins have been isolated from a wide range of organisms ranging from yeast, worm, flies, frogs and mammals. Expression studies have shown that while some ADAMS have wide tissue expression, some have their expression restricted to one tissue.

The ADAM proteins have been shown to function in cell-cell interaction, cell-signaling, and in the processing of the ectodomains of membrane-anchored proteins and have been implicated in diverse biological processes, including sperm-egg binding and fusion, myoblast fusion, protein-ectodomain shedding of cytokines, cytokine receptors, adhesions and other extracellular protein domains. Furthermore, they have been shown to be necessary for proper axonal guidance, neural and wing development in *Drosophila*, vulval development in *Caenorhabditis elegans*, and epithelial maturation and skin and hair development in the mouse.

Structurally, LAP has an N-terminal signal sequence (MFRLWLLLAGLCGLLAS (SEQ ID NO:193)), a pro-domain (HLKQRYFLTDNFMIYLYNQGSMNTYSSDIQ-TQCYYQGNIEEYPDSMVTLSTCSGLRGILQFENVSY-GIEPLESAVEFQHVLHKLKNEDNDIAIFIDRSLKEQP-MDDNIFISEKS(SEQ ID NO: 194)) that has been shown to maintain the enzyme in an inactive state, followed by a metalloprotease domain (LYLEMHIVVDKTLYDYWGS-DSMIVTNKVIEIVGLANSMFTQFKVTIVLSSLELWS-DENKISTVGEADELLQKFLEWKQSYLNLRPHDIAY-LLIYMDYPRYLGAVFPGTMCITRYSAGVALYPKEIT-LEAFAVIVTQMLALSLGISYDDPKKCQCSESTCIM-NPEVVQSNGVKTFSSCSLRSFQNFISNVGVKCLQNKP (SEQ ID NO: 195)) that is important for proteolysis and contains the zinc-binding catalytic site, a disintegrin-like domain (KPVCGNGRLEGNEICDCGTEAQCGPASC-CDFRTCVLKDGAKCYKGLCCKDCQILQSGV ECP-KAHPECDIAENCNGSSPEC (SEQ ID NO: 196)) that has been demonstrated to bind integrins, a cystein-rich region (GLSCKNNKFICYDGDCHDLDARCESVF-GKGSRNAPFACYEEIQSQSDRFGNCGRDRNN KYVFCGWRNLICGRLVCTYPTRKPF-HQENGDVIYAFVRDSVC (SEQ ID NO: 197)) that also have adhesion activity, an EGF-like domain (CDI-GRVCVNRECVESRIIKASAHVCSQQCS-GHGVCDSRNKCHCSPGYKPPNC (SEQ ID NO:198)) important for substrate recognition, a transmembrane domain (TWLLGFLIALPILIVTTAIVL(SEO ID NO: 199)) and a cytoplasmic tail (ARKQLKNWFAKEEEFPSSESK-SEGSTQTYASQSSSEGSTQTYAGQTRSESSSQADTSKS KSEDSAEAYTSRSKSQDSTQTQSSSN (SEQ ID NO:200)) that has been shown in many ADAMs to contain SH3 binding sites and which might be important for cell signaling.

Interestingly, the cytoplasmic C-terminal domain of the LAP protein does not contains any SH3 binding sites but it ends by a 69 amino acid region rich in serine/threonine residues (36% of serine residues;

A polypeptide comprising the amino acid sequence of: KPVCGNGRLEGNEICDCGTEAQCGPASC-CDFRTCVLKDGAKCYKGLCCKDCQILQSGV ECRP-KAHPECDIAENCNGSSPECGPD (SEQ ID NO:206).

A polypeptide comprising the amino acid sequence of: GLSCKNNKFICYDGDCHDLDARCESVF-GKGSRNAPFACYEEIQSQSDRFGNCGRDRNNK YVFCGWRNLICGRLVCTYPTRKPF-HQENGDVIYAFVRDSVC (SEQ ID NO:207).

A polypeptide comprising the amino acid sequence of: PSSESKSEGSTQTYASQSSSEGSTQTY-AGQTRSESSSQADTSKSKSEDSAEAYTSRSKSQD STQTQSSSN (SEQ ID NO:208).

An embodiment of the invention is directed to a method to screen for molecules which block the interaction of LAP with the cell-surface receptors on the oocyte surface comprising the steps of contacting sperm with said molecule to be screen, contacting the sperm with the oocyte, and disrupting sperm-oocyte binding.

A preferred embodiment of the invention is directed to a method of inhibiting sperm-oocyte interaction by blocking the LAP interaction with the oocyte cell surface comprising the steps of contacting sperm with a blocking molecule, as identified in a screen, which inhibits or blocks the LAP-oocyte interaction. Preferred agents include antibodies directed to LAP-disintegrin domain.

LAP is a plasma membrane-anchored protein having adhesion and cell signaling activities in liver cells as well as in adipocytes. More specifically, it is believed that the mature LAP protein interacts, via its extracellular domain, with as yet unidentified integrins and other proteins present at the surface of neighbouring cells, while its cytoplasmic serine-rich domain is involved in signaling events by interacting with cytoplasmic or plasma membrane-associated proteins that interact with serine-rich domains. More over, as serine and threonine residues are both phosphorylatable residues, the signaling activity of the LAP protein is regulated by phosphorylation/dephosphorylation events of specific serine and or threonine residue(s) present on this domain.

In a further embodiment, polyclonal or monoclonal antibodies directed against polypeptides of the invention are, used in methods to reduce or inhibit cell-cell interactions between cells in vitro, preferably liver or adipose cells. A preferred method of reducing or inhibiting cell-cell interactions comprises the steps: i) contacting the cells with a composition comprising an inhibitory-effective amount of an antibody directed against polypeptides of the invention, preferably a monoclonal antibody directed against the disintegrin-like domain or a monoclonal antibody directed against the cysteine-rich domain.

A further embodiment is directed to a method of blocking or inhibiting the interaction of LAP with at least one of its binding-partners comprising the steps: i) contacting cells with a blocking-effective amount of a polypeptide fragment of the invention comprising an extracellular domain of LAP. Preferred extracellular domains to be used in said methods of blocking the interaction of LAP and a binding partner include the disintegrin-like domain of LAP and the cysteine-rich domain of LAP. Preferred synthetic peptides to be used in compositions of said methods have amino acid sequences comprising CRPKAHPECDIAENC or CGNGRLEGNEICDCG, or a combination thereof.

Protein of SEQ ID:72 (Internal Designation Clone 338116_174-1-1-0-B10-F)

The cDNA of Clone 338116_174-1-1-0-B10-F (SEQ ID NO:71) encodes the protein of SEQ ID NO:72, herein referred as Short Histone Deacetylase (SHDAC), comprising the amino acid sequence: MGPHLHLCLCVPDLRSLRVCVSLWSVHHRPHESLAREEALTALGKLLYLLDGMLDGQV NSGIAATPASAAAATLDVAVRRGLSHAAQRLLCVALGQLDRPPDLAHDGRSLWLNIRG KEAAALSMFHVSTPLPVMTGGFLSCILGLVLPLAYGFQPDLVLVALGPGHGLQGPHXAL LAAMLRGLAGGRVLALLEENSTPQLAGILARVLNGEAPPSLGPSSVASPEDVQALMYLR GQLEPQWKMLQCHPHLVA (SEQ ID NO:72), is encoded by the cDNA clone 338116_174-1-1-0-B 10-F (SEQ ID:71). The protein of SEQ ID NQ:72 is a novel variant of histone deacetylase (HDAC). Accordingly, it will be appreciated that all characteristics and uses of the polypeptide of SEQ ID NQ:72 described throughout the present application also pertain to the polypeptide encoded by a nucleic acid included in clone 338116_174-1-1-0-B10-F. In addition, it will be appreciated that all characteristics and uses of the nucleic acid of SEQ ID NO:71 described throughout the present application also pertain to the nucleic acid included in clone 338116_174-1-1-0-B10-F. A preferred embodiment of the invention is directed toward the compositions of SEQ ID NO:71, SEQ ID NO:72, and Clone 338116_174-1-1-0-B10-F. Also preferred are polypeptide fragments having a biological activity as described herein and the polynucleotides encoding the fragments.

The protein of SEQ ID:72 contains one potential transmembrane segment (position 130 to 150), and a signal peptide (position 1: MGPHLHLCLCVPDLRSL (SEQ ID NO:209)). The protein of SEQ ID:72 is highly expressed in placenta and salivary glands.

Histone deacetylase (HDAC) proteins comprise a family of related proteins that act in conjunction with histone acetyl-transferase proteins to modulate chromatin structure and transcriptional activity via changes in the acetylation status of histones. HDACs remove acetyl groups from histones by hydrolysis [Davie, J. R. Curr. Opin. Genet. Dev. 8, 173-178 (1998)], thereby causing local chromatin condensation and decreasing the accessibility of particular DNA regions for RNA polymerase complexes. In fact, transcriptionally active chromatin correlates with histone hyperacetylation [Grundstein M. Nature 389:349-352 (1997)], and it has been suggested that histone acetyltransferases promote transcription while histone deacetylases act as repressors and transcriptional silencer. [Doetzlhofer A. et al., Mol. Cell. Biol. 19:5504-5511(1999)].

Histone deacetylase proteins belong to a superfamily of zinc metalloenzymes with a conserved 380 residue catalytic domain [Finnin, M. S. et al., Nature 401:188-193(1999)]. Histone deacetylases are found in high-molecular-weight complexes associated with adapter proteins like SIN3, RbAp46/48, SAP18, SAP30, and nuclear corepressors like N-CoR, SMRT, and SUN-CoR [Alland, L. et al., Nature 387:49-55 (1997); Heinzel, T. et al., Nature 387:43-48 (1997); Laherty, C. D. et al., Cell 89: 349-356 (1997); Nagy, L. H. et al., Cell 89:373-380 (1997); Zhang, W. et al., EMBO J. 17:3155-3167 (1997); Zhang; Y. et al., Cell 89:357-364 (1997); Knoepfker, P. S. & Eisemnan, R. N. Cell 99:447-450 (1999)].

Histone deacetylases are recruited to specific promoters by mammalian transcriptions factors such as Matix-associated Deacetylase (Mad). [Sommer, A. et al., Curr. Biol. 7 :357-365. (1997)], YY1 [Yang, W. M. Proc. Natl. Acad. Sci. USA 93:12845-12850 (1996)], hormone-dependent nuclear receptor. [Nagy, L. H. et al., Cell 89:373-380 (1997)], MeCP2 [Jones, P. L. et al., Nat. Genet. 19:187-191 (1998)], CBF [Kao, H.Y. P. et al., Genes Dev. 12:2269-2277 (1998)], Retinoblastoma protein (Rb) [Brehm, A., et al., Nature 391:597-601 (1998)], groucho [Chen, G. et al., Genes Dev. 13:2218-2230 (1999)]B-ymphocyte-induced maturation protein [Yu, J. et al., Mol. Cell. Biol. 20:2592-2603 (2000)] and related pocket proteins [Ferreira et al., Proc. Natl. Acad. Sci. USA 95:10493-10498 (1998)] for repression. The recruitment of human histone deacetylases by PZLF (promyelocytic leukaemia zinc finger), PML (promyelocytic leukaemia), and ETO fusion proteins can interfere with differentiation of hematopoietic precursor cells in acute promyelocytic leukemia [Lin, R. J. et al., Nature 311:811-815 (1996); David, G. L. et al., Oncogene 16:25492556 (1998); Grignani, F. S. et al., Nature 391:815-818 (1998); Guidez et al., Blood 91:2634-2642 (1998)].

Several drugs have been identified as acting upon histone acetylation. Some examples are: trichostatin A (TSA), apicidin (antiprotozoal agent), superoylanilide hydroxamic acid (SAHA), cyclic hydroxamic acid-containing peptide (CHAP) 1, FR901228 (a potent antitumor), CBHA (m-carboxycinnamic acid bis-hydroxamide), trapoxin, MS-275 (antitunor), pyroxamide (suberoyl-3-aminopyridineamide hydroxamic), acid and phenyl butyrate. Such drugs cause major alterations in cellular activity, including the induction of cellular differentiation and apoptosis [Medina, V. et al., Cancer Res. 57:3697-3707 (1997); Richon, V. M. et al., Proc. Natl. Acad. Sci. U.S.A. 95:3003-3007 (1998); Sambucetti, L. C. et al., J. Biol. Chem. 274:34940-34947 (1999); Buter, L. M. et al., Clin. Cancer. Res. 7:962-970 (2001); Coffey, D. C. et al., Cancer Res. 61:3591-3594 (2001); Colletti, S. L. et al., Bioorg. Med. Chem. Lett. 11:107-111 (2001); Furumai, R. et al., Proc. Natl. Acad. Sci. USA 98:87-92 (2001); Lee, B. I. et al., Cancer Res. 63:931-934 (2001)].

The protein of SEQ ID NO:72 is a novel splice and polymorphism variant of histone deacetylase and, as such, plays a role in transcription, chromosome stability, cell cycle progression, gene silencing, lymphocyte and muscle differentiation, aging, regulation of neuronal phenotype, DNA replication and the response to DNA damage. Particularly, the protein of the invention may deacetylate substrates, preferably acetylated histones, either directly or indirectly as enzymes cofactors. Preferred polypeptides of the invention are polypeptides comprising the amino acids of SEQ ID NO:72 from positions 29 to 252. Also preferred are fragments of SEQ ID NO:72 having a biological activity as described therein and the polynucleotides encoding the fragments. The deacetylation activity of the protein of the invention or fragment thereof may be assayed using any of a number of methods known to those skilled in the art.

The invention relates to methods and compositions using the protein of SEQ ID NO:72 or fragment thereof to inhibit or modulate cellular transcriptional activity, thereby modulating cellular differentiation. Specifically, as histone deacetylases play a role in inhibiting transcription associated with differentiation, then an increase in the activity or expression of the protein can be used to inhibit differentiation. The ability to inhibit differentiation has a number of uses, for example during the cultivation of undifferentiated pluripotent cells to maintain the cultured cells in an undifferentiated state until the need for a given cell type arises. (in cases of grafts for instance). For example, the histone deacetylase of the invention may be used to arrest a population of non-neoplastic cells grown in vitro in the G1 or G2 phase of the cell cycle. Such synchronization allows, for example, the identification of gene and/or gene products expressed during the G1 or G2 phase of the cell cycle. Such a synchronization of cultured cells may also be useful, for testing the efficacy of a new transfection protocol, where transfection efficiency varies and is dependent upon the particular cell cycle phase of the cell to be transfected. Use of the histone deacetylase of the invention allows the synchronization of a population of cells, thereby adding detection of enhanced transfection efficiency. The level of the protein activity or expression can be increased in any of a number of ways, including by introducing a polynucleotide encoding the protein into cells, by administering the protein itself to cells, or by administering to cells a compound that increases protein activity or expression. Alternatively, the expression or activation of the protein of the invention can be inhibited in any of a large number of ways, including using antisense oligonucleotides, antibodies, dominant negative forms of the protein, and using heterologous compounds that decrease the expression or activation of the protein. Such compounds can be readily identified, e.g. by screening candidate compounds and detecting the level of expression or activity of the protein using any standard assay. The ability to promote differentiation has many uses, including in the treatment or prevention of cancer, as cancer cells are often in a relatively undifferentiated state, and cellular differentiation typically accompanies by growth arrest.

In another embodiment, eukaryotic cells are genetically engineered in order to express the protein of the invention or fragment thereof under specific, conditions in order to prevent and/or treat disorders characterized by abnormal cell proliferation and/or programmed cell death, including but not limited to cancer, immune deficiency syndromes (including AIDS), type I diabetes, pathogenic infections, cardiovascular and neurological injury, alopecia, aging, degenerative diseases such as Alzheimer's Disease, Parkinson's Disease, Huntington's disease, dystonia, Leber's hereditary optic neuropathy, schizophrenia, and myodegenerative disorders such as "mitochondrial encephalopathy, lactic acidosis, and stroke" (MELAS), and "myoclonic epilepsy ragged red fiber syndrome" (MERRF). For example, a vector capable of expressing the protein of SEQ ID NO:72, or biologically active fragments thereof, can be administered to a subject to treat or prevent disorders including, but not limited to, those described above. Alternatively, the vector can encode a variant, or biologically active fragment of the variant protein. Multiple vectors encoding any combination of SEQ ID NO:72, variants, and/or biologically active fragments of SEQ ID NO:72 and/or variants can be administered to a subject.

The invention relates to methods and compositions using the protein of the invention or fragment thereof to deacetylate substrates, alone or in combination with other, substances, for example, but not limited to silence specific target genes. Acetylated substrates used in such methods are preferably acetylated histones and acetyltransferases. For example, the protein of the invention or fragment thereof is added to a sample containing a substrate in conditions allowing deacetylation, and allowed to catalyze the deacetylation of the substrate. In a preferred embodiment, the deacetylation is carried out using a standard assay such as those described in Landry and collaborators [Landry et al., Proc. Natl. Acad. Sci. 97:5807-5811 (2000), the disclosure of which is incorporated by reference in its entirety]. Deacetylated histones obtained by this method may be mixed with purified naked DNA (plasmid preparations for example) in order to reconstitute chromatine-like structures in vitro. Such structures are of great interest in the study of enzymatic factors involved in transcription and replication. Natural transcription factors are unable to enter the condensed chromatin, and the gene function is effectively switched-off. Also, the chromatin condensation constitutes a valuable parameter in the assessment of male fertility, completely independent of conventional sperm parameters [Hammnadeh, M. E., et al., Arch Androl;46(2):99-104 (2001)].

Another embodiment of the present invention relates to composition and methods of using the protein of the invention or fragment thereof to screen for inhibitors and activators of deacetylase activity. Such deacetylase inhibitors are of great potential as new drugs due to their ability to influence transcriptional regulation and to induce apoptosis or differentiation in cancer cells [Marks P. A. et al., Clin. Cancer. Res. 7:759-760 (2001)], and also as antiproliferative reagents involved in antiprotozoal, antifungal, phytotoxic and antiviral applications [Meinke, P. T. & Liberator, P., Curr. Med. Chem. 8:211-235 (2001)]. In one such embodiment, the protein of the invention is contacted in vitro with a fluorescently labeled acetylated substrate as well as a test agent, and the activity of the protein is detected, wherein a difference in the activity of the protein in the presence of the test agent in comparison to the activity in the absence of the test agent indicates that the test agent is a modulator of the protein. Suitable substrates include, e.g., aminocoumarin derivative of an acetylated lysine, which can be quantitated using a reverse-phase HPLC-system with a fluorescence detector [see, e.g., Hoffmann et al., Nucl. Acids Res. 27:2057-2058 (1999); Hoffmann et al., Pharmazie 55:601-606 (2000); the disclosures of each of which are incorporated herein in their entireties].

In another preferred embodiment, the polynucleotides of SEQ ID:71, polypeptides of SEQ ID:72 or antibodies to the polypeptide of the present invention may also be used in screening methods for detecting an abnormally decreased or increased level of polypeptides or mRNA, as well as to detect the effect of added compounds on the production of the present mRNA and polypeptide in cells. Abnormal activity of our protein is associated with accelerated aging syndromes such as Cochayne's syndrome, Ataxia telangiectasia and Werner's syndrome as well as age-associated diseases as well as "early onset" forms of diseases associated with old age such as dementia and Parkinson's disease. Decreased or increased expression can be measured, for example, at the RNA level using any of the methods known in the art for the quantification of polynucleotides, such as nucleic acid amplification methods including PCR and RT-PCR, as well as RNAse protection, Northern blotting and other hybridization methods. Expression can also be detected using assays to determine levels of the present protein, such as ELISA assays. These methods can also be used to discover agents which inhibit or enhance the production of polypeptide in cells or tissues. Examples of potential polypeptide inhibitors include antibodies, oligonucleotides, heterologous proteins, or small molecule inhibitors of the present protein.

Another embodiment of the, invention relates to methods of preparing antibodies that selectively bind to the protein of the invention or fragment thereof. Such antibodies may be used, for example, in co-immunoprecipitation procedures that enrich for chromatin fragments containing binding sites for the protein of the invention. This method may identify genes or regions of the human genome silenced by the deacetylase activity of the protein of the invention and also proteins which interact with the compacted form of the chromatin like RCC1 (regulator of chromosome condensation) [Renault, L. et al., Cell, 105:245-255 (2001)]. For example, in one method, antibodies that selectively bind to HDAC are coupled to protein A or protein G sepharose beads and added to samples containing fragments of native chromatin under conditions amenable to immunoprecipitation, and the DNA fragments co-precipitated with HDAC are extracted and subcloned. These DNA fragments can then be either, sequenced and/or used as probes to screen genomic libraries [Gould et al., Nature. 348:308-312 (1990), the disclosure of which is incorporated herein by reference in its entirety].

In another embodiment, the invention relates to methods and compositions using the protein of the invention or fragment thereof as a marker protein to selectively identify tissues, such as salivary gland or placenta, or to distinguish between two or more possible sources of a tissue sample on the basis of the level of the protein of SEQ ID NO:72 in the sample. For example, the protein of SEQ ID NO:72 or fragments thereof may be used to generate antibodies using any techniques known to those skilled in the art, and the antibodies may then be used to identify tissues of unknown origin, for example, forensic samples, differentiated tumor tissue that has metastasized to foreign bodily sites, or to differentiate different tissue types in a tissue cross-section using immunochemistry. Typically, in such methods a tissue sample is contacted with the antibody, which may be detectably labeled, under conditions which facilitate antibody binding. In one embodiment, the level of antibody binding to the test sample is measured and compared to the level of binding expected from control cells from salivary gland and placenta, or tissues other than salivary gland and placenta, to determine whether the test sample is from salivary gland and placenta. Such methods may also be performed in conjunction with other, independant methods for determining cellular identity. Similar methods can be used to specifically detect cells expressing the protein, as well as to specifically isolate cells expressing the protein or to isolate the protein itself. For example, an antibody against the protein of SEQ ID NO:72 or a fragment thereof may be fixed to a solid support, such as a chromatography matrix. A preparation containing cells expressing the protein of SEQ ID NO:72 is placed in contact with the antibody under conditions which facilitate binding to the antibody. The support is washed and then the protein is released from the support by contacting the support with agents which cause the protein to dissociate from the antibody.

A preferred embodiment of the invention relates to compositions or methods using the protein of SEQ ID NO:72 or fragment thereof to diagnose, treat and/or prevent disorders caused by the expression of genes whose transcription is regulated by the extent of local chromatin condensation. The number of pathologies and conditions that could be treated by the protein of the invention is potentially huge and unlimited. Favored disorders linked to dysregulation of gene transcription such as cancer and other disorders relating to abnormal cellular differentiation, proliferation, or degeneration, including leukemia, lymphomas, prostate hypertrophy, kidney diseases, kidney failures, viral infection especially IRV and viral hepatitis (i.e expression of viral proteins), metabolic diseases such as obesity and a number of inflammatory diseases, for example due to interleukin over-expression. For diagnostic purposes, the expression of the protein of the invention can be investigated using any method, for example Northern blotting, RT-PCR or immunoblotting methods, and compared to the expression in control individuals. For prevention and/or treatment purposes, the expression of the protein of the invention may be enhanced, inhibited, or otherwise altered in a patient using any of a number of methods, including gene therapy methods, or by administering a compound that enhances or inhibits the expression or activity of the protein.

In one embodiment, the present invention provides a method for inhibiting the proliferation of a cell, the method comprising introducing into the cell the protein of the invention, linked to a heterologous protein domain that specifically targets the present protein to a cell-proliferation-regulating gene, wherein the targeting of the present protein to the gene results in local chromatin condensation and an inhibition in the expression of the gene. Cell-fusion proteins containing both the deacetylase activity and the specific DNA binding domain are obtained by methods of molecular biology well known to those skilled in the art. In one embodiment, such fusion proteins are introduced into the cell by transfecting the cell with a polynucleotide encoding the fusion protein, wherein the fusion protein is expressed in the cell. Such polynucleotides, e.g. in the form of expression vectors, which can thus be used, e.g., for gene therapy to treat or prevent cancer, metabolic disorders, aging and any disorder where a gene is over-expressed in association with local chromatin decondensation. Such recombinant cDNA may be introduced, for example, using in any vector, viral or non-viral, and viral vectors can be but not limited to retroviral, adenoviral, and adeno-associated vectors, which have been used in cancer therapy (Alemany et al., Nat. Biotechnol. 18:723-727 (2000)). Another approach is to administer a therapeutic amount of a polypeptide of SEQ ID:72, preferably in combination with a suitable pharmaceutical carrier. Such carriers include, but are not limited to, saline, buffered saline, dextrose, water, glycerol, ethanol and combinations thereof.

In another embodiment, an array of oligonucleotides probes comprising the nucleotide sequence of SEQ ID NO:71 or fragments thereof can be constructed to conduct efficient screening of e.g., genetic, mutations. The microarray can be used to monitor the expression level of large numbers of genes simultaneously and to identify genetic variants, mutations, and polymorphisms. This information may be used to determine gene function, to understand the genetic basis of a disorder, to diagnose a disorder, and to develop and monitor the activities of therapeutic agents (see for example: Chee, M. et al., Science, 274:610-614 (1996)). It has been shown that multiple classical features of cancer cells can be manifested by improper histone deacetylation [for review see Wade, P. A. Hum Mol Genet; 10(7):693-698 (2001)].

Another related embodiment relates to the use of SEQ. ID NO: 72, its complement, or any part thereof to develop antagonists of the protein of the invention and of the HDAC complex. Antagonists or inhibitors of histone deacetylase may indeed be used to suppress gene silencing., Such antagonists and/or inhibitors may be antibodies specific for the protein of the invention that can be used directly as an antagonist, or indirectly as a targeting or delivery mechanism for bringing a pharmaceutical agent to cells or tissue which express the protein of the invention. Other methods to inhibit the expression of the protein of the invention include antisense and triple helix stategies as described herein. Other antagonists or inhibitors of the protein of the invention may be produced using methods which are generally known in the art, including the screening of libraries of pharmaceutical agents to identify those which specifically bind the protein of the invention. The protein of the invention, or fragment thereof, preferably its functional or immunogenic fragments, or oligopeptides related thereto, can be used for screening libraries of compounds in any of a variety of drug screening techniques. The fragment employed in such screening may be free in solution, affixed to a solid support, borne on a cell surface, or located intracellularly. The formation of binding complexes, between the protein of the invention, or fragment thereof, or derivative thereof, and the agent being tested, may be measured. Another technique for drug screening which may be used provides for high throughput screening of compounds having suitable binding affinity to the protein of the invention as described in published PCT application WO84/03564. Abnormal gene silencing causes conditions like, but not limited to, accelerated aging syndromes such as Cochayne's syndrome, Ataxia telangiectasia and Werner's syndrome as well as age-associated diseases as well as "early onset" forms of diseases associated with old age such as dementia and Parkinson's disease.

Protein of SEQ ID:74 (Internal designation Clone 500716683_204-24-2-0D12-F)

The protein of SEQ ID NO:74, herein referred as short Paraplegin, comprising the amino acid sequence: MAVLLLLLLRALRRGPGPGPRPLWGPGPAWSPGFPARPGRGRPYMASRPPGDLAEAGGR ALQSLQLRLLTPTFEGINGLLLKQHLVQNPVRLWQLLGGTFYFNTSRIKQKNKEKDKSK GKAPEEDEGIFI (SEQ ID NO:74), is encoded by the cDNA of clone 500716683_204-24-2-0-D12-F (SEQ ID NO:73). Accordingly, it will be appreciated that all characteristics and uses of the polypeptide of SEQ ID NO:74 described throughout the present application also pertain to the polypeptide encoded by a nucleic acid included in clone 500716683_204-24-2-0-D12-F. In addition, it will be appreciated that all characteristics and uses of the nucleic acid of SEQ ID NO:73 described throughout the present application also pertain to the nucleic acid included in clone 500716683_204-24-2-0-D12-F. A preferred embodiment of the invention is directed toward the compositions of SEQ ID NO:73, SEQ ID NO:74, and Clone 500716683_204-24-2-0-D12-F. Also preferred are polypeptide fragments having a biological activity as described herein and the polynucleotides encoding the fragments.

The protein of SEQ. ID NO:74 is encoded by a nucleic acid of 879 nucleotides with an ORF between nt 9 to 395 yielding a 129 amino acid protein. The protein is a variant of the sequence for human protease and associated protein-15. (PPRG-15) (described in PCT publication WO200009709-A2, the disclosure of which is incorporated herein by reference in its entirety) and of the sequence of the protein associated to hereditary spastic paraplegia (described in PCT publication WO9958556-A2, the disclosure of which is incorporated herein byreference in its entirety). It has a signal peptide spanning 17 amino acid residues at its. N-terminal. The protein of SEQ ID NO:74 is localized in the brain and has a mitochondrial localizing signal peptide.

Moreover, the protein of SEQ ID NO:74 exhibits high homology to the N-terminal of hereditary spastic paraplegia protein sequence (described in PCT publication WO9958556-A2). Hereditary Spastic paraplegia (HSP) is characterized by progressive weakness and spasticity of the lower limbs due to degeneration of corticospinal axons. (Harding, A. E., J. Med. Genet. 18: 436-441(1981); Fink, J. K., et al., Am. J. Hum. Genet. 56:188-192 (1997); Reid, E., J. Med. Genet. 34:499-503, (1997)). This is a genetically heterogeneous group of neurodegenerative disorders. affecting approximately 1 in 10,000 individuals (Filla (1992); Polo et al. (1993)). Patients with HSP typically show leg stiffness and gait disturbance, decreased perception of sharp stimulation, and diminished vibratory sense in the distal lower limbs. Both the age of onset and severity of the symptoms are highly variable even among individuals from the same family (Harding, A. E., J. Med. Genet. 18:436-441(1981); Dürr et al., 1994). Currently, no specific treatment is available to prevent, cure, or delay progression of symptoms of HSP.

In addition to the above-described clinical spectrum, which is typical of the "pure" form of HSP, several patients have been shown to have "complicated" forms of HSP characterized by the presence of additional neurological and non-neurological symptoms such as mental retardation, peripheral neuropathy, amyotrophy, ataxia, retinitis pigmentosa, optic atrophy, deafness, and ichtyosis (Bonneau, D., et al., J. Med. Genet. 30:381-384 (1993); Gigli, G.L., et al., Am. J. Med. Genet. 45:711-716 (1993); Lizcano-Gil, L.A. et al., Am. J. Med. Genet. 68:1-6 (1997); Webb, S., et al., Epilepsia 38:495-499 (1997)). Albeit some of these forms have been found to segregate in families, it is still unclear whether complicated forms of HSP represent distinct genetic entities or variant presentations of pure HSP. However, even in pure forms of HSP (i.e., with clinical features limited to the lower segments), a broader subclinical involvement of the nervous system has been demonstrated [Tedeschi, G. et al., J. Neurol. Sci. 103:55-60 (1991); Durr, A., et al., Neurology 44:1274-1277 (1994)].

Autosomal dominant, autosomal recessive, and X-linked forms of HSP have been described, indicating genetic heterogeneity. [Harding, A. E., J. Med. Genet. 18: 436-441 (1981); Fink, J. K, et al., Am. J. Hum. Genet. 56:188-192 (1997); Reid, E., J. Med. Genet. 34:499-503, (1997)]. Casari and collaborators have identified and characterized a gene associated to hereditary spastic paraplegia, located in the telomere region of chromosome 16q, and the protein deriving, therefrom, named paraplegin [Casari, G., et al. Cell 93:973, 983 (1998)].

It is believed that the protein of SEQ ID NO:74, or fragment thereof is a mitochondrial protein associated to hereditary spastic paraplegia. The protein of the invention or fragment thereof may play a role in the mitochondrial degradation machinery. Preferred polypeptides of the invention are polypeptides comprising the amino acids of SEQ ID NO:74 from positions 1 to 125. Other preferred polypeptides of the invention are fragments of SEQ ID NO:74 having any of the biological activities described herein.

Another embodiment of thee invention relates to compositions and methods using the protein of the invention or fragment thereof to label mitochondria in order to visualize any change in number, topology or morphology of this organelle, for example in association with a mitochondria-related human disorder, such as hereditary spastic paraplegia [Casari, G., et al. Cell 93:973, 983 (1998)], neuroleptic malignant syndrome (NMS) [Kubo et al., Forensic. Sci. Int. 115:155-158 (2001)], the Rett syndrome [Armstrong, Brain Dev. 14 Suppl:S89-98 (1992)], Alpers disease [Chow and Thorbum, Hum. Reprod. 15 Suppl 2:68-78 (2000)]or mitochondrial encephalomyopathies [Handran et al., Neurobiol. Dis. 3:287-298 (1997)]. Casari and collaborators have shown that paraplegin protein localizes to mitochondria by immunofluorescence studies [Casari, G., et al. Cell 93:973, 983 (1998)]. Paraplegin protein exhibits a helical wheel pattern (an amphiphilic structure composed of basic residues, mainly arginine, on one side and a polar residues on the opposite side), of the N-terminal which is highly homolog to the protein of the invention; moreover the high ratio of arginine to lysin among the first 41 amino acids indicates the presence of typical mitochondrial leader sequences [Casari, G., et al. Cell 93:973, 983 (1998)]. For example, the protein may be rendered easily detectable by inserting the cDNA encoding the protein of the invention into a eukaryotic expression vector in frame with a sequence encoding a tag sequence. Eukaryotic cells expressing the tagged protein of the invention may also be used for the in vitro. screening of drugs or genes capable of treating any mitochondria-related disease or conditions. Another example, the protein of the invention or fragment thereof may be used to generate specific antibodies which would in turn allow the visualization of mitochondrial structures by methods well-known to those of skill in the art.

In another embodiment, the protein of the invention may be used to target heterologous compounds (polypeptides or polynucleotides) to the brain and/or the mitochondria. For instance, a chimeric protein composed of the protein of the invention recombinantly or chemically fused to a protein or polynucleotide of therapeutic interest would allow the delivery of the therapeutic protein/polynucleotide specifically to the above-mentioned cellular/tissue targets (mitochondria, brain). Preferred fragments are the putative peptide signal, and/or any other fragments of the protein of the invention that may contain targeting signals for mitochondria). Such heterologous compounds may be used to modulate mitochondrial activities, such as to induce and/or prevent mitochondrial-induced apoptosis or necrosis. For example, these heterologous compounds may be used in the treatment and/or the prevention of disorders due to mitochondrial dysfunction, including, but not limited to, hereditary spastic paraplegia. In addition, heterologous polynucleotides may be used to deliver nucleic acids for mitochondrial gene therapy, i.e to replace a defective mitochondrial gene and/or to inhibit the deleterious expression of a mitochondrial gene.

An antagonist of the protein of SEQ ID NO:74 may be produced using methods which are generally know in the art. In one aspect, the protein of the invention or fragment may be used to synthesize specific antibodies using any techniques known to those skilled in the art including those described therein. In particular, purified short paraplegin may be used to produce antibodies or to screen libraries of pharmaceutical agents to identify those which specifically bind short paraplegin.

In a further embodiment, a pharmaceutical composition comprising a substantially purified protein of SEQ ID NO:74 in conjunction with a suitable pharmaceutical carrier may be administered to a subject to treat or prevent a disorder associated with change of expression or activity of short paraplegin including, but not limited to, those described above. The antibody which specifically binds short paraplegin may be used directly as an antagonist or indirectly as a targeting or delivery mechanism for bringing a pharmaceutical agent to cells or tissues which express short paraplegin.

In another embodiment, antibodies which specifically bind the protein of SEQ ID NO:74 may be used for the diagnosis of disorders characterized by expression of short paraplegin. Truncated forms of paraplegin are, involved in hereditary spastic paraplegia (Casari, G., et al. Cell 93:973, 983 (1998)). Diagnostics assays for short paraplegin include methods which utilize the antibody and a label to detect short paraplegin in human body fluids or in extract of cells or tissues. A variety of protocols for measuring short paraplegin, including ELISA's, RIAs, and FACs, are known in the art and provide a basis for diagnosing the presence of short paraplegin expression.

In another embodiment, the polynucleotide of SEQ ID NO:73 or a fragment may be used for diagnostic purposes in assays that detect the presence of associated disorders, for example but not limited to, hereditary spastic paraplegia. The polynucleotides which may be used include oligonucleotide sequences, complementary RNA and DNA molecules, PNAs. The polynucleotides may be used to detect and quantitate gene expression in biopsied tissues in which expression of short paraplegin may be correlate with disease. The nucleotide sequences encoding short paraplegin may be labeled by standard methods and added to a fluid or tissue sample from a patient under conditions suitable for the formation of hybridization complexes. After a suitable incubation period, the sample is washed and the signal is quantitated and compared with a standard value. If the amount of signal in the patient sample is significantly increased in comparison to a control sample then the presence of increased levels of nucleotide sequences encoding short paraplegin in the sample indicates the presence of associated disorder, particularly but not limited to, hereditary spastic paraplegia. Such assays may also be used to evaluate the efficacy of a particular therapeutic treatment regimen in animal studies, in clinical trials, or to monitor the treatment of an individual patient.

Once the presence of a disorder is established and a treatment protocol is initiated, hybridization assays may be repeated on a regular basis to determine if the level of expression in the patient begins to approximate that which is observed in the normal subject. The results obtained from successive assays may be used to show the efficacy of treatment over a period of time.

In another embodiment, an array of oligonucleotide probes comprising the nucleotide sequence of SEQ ID NO:73 or fragments thereof can be constructed to conduct efficient screening of e.g., genetic mutations. The microarray can be used to monitor the expression level of large numbers of genes simultaneously and to identify genetic variants, mutations, and polymorphisms. This information may be used to determine gene function, to understand the genetic basis of a disorder, to diagnose a disorder, and to develop and monitor the activities of therapeutic agents [see for example: Chee, M. et al., Science, 274:610-614 (1996)]. For example, it has been shown that genetic variants, mutations, and polymorphisms are related to hereditary spastic paraplegia [for review see Casari, G., and Rugarli, E. Curr. Opin. Genetics and Development, 11:336-342 (2001)].

In another preferred embodiment, the protein of the invention or fragment thereof can be used in an enzyme/prodrug strategy to treat a number of pathologies, especially those treated with drugs associated with severe side effects, including, but not limited to, autoimmune diseases and chronic inflammatory diseases such as rheumatoid arthritis, and cancer chemotherapy. These side effects can be mainly explained by the fact that the in vivo selectivity of the drugs used is too low (for example, the inadequate selectivity between tumor and normal cells of most anticancer drugs is well known and their toxicity to normal tissues is dose limiting). In the first phase of one example of such a protocol, a conjugate of the protein of the invention or fragment thereof and an antibody to a tissue specific antigen (for example, tumor specific antigens in the case of cancer chemotherapy) is administered. After a delay to allow residual enzyme conjugate to be cleared from the blood, a relatively non-toxic compound is administered to the patient. This non-toxic compound is a substrate of the protein of the invention, and is converted by the protein into a substantially more toxic compound. Thus, because of the previous, targeted administration of the protein of the invention, when the non-toxic compound is administered, the toxic compound is only produced in the vicinity of the cells targeted by the fusion protein. This two-phase approach has been termed antibody-directed enzyme-prodrug therapy (ADEPT), this approach is, reviewed by Melton et al. [Melton R. et al., J. Natl. Cancer. Inst., 88, p153-165 (1996)]. Alternatively the first phase can be replaced by a gene therapy approach resulting in the de novo synthesis of the protein of the invention or fragment thereof by cells from the targeted tissue, this has been termed gene-dependent enzyme/prodrug therapy (GDEPT). Another advantage of these 2 approaches (ADEPT and GDEPT) is that a single enzyme molecule is capable of activating many prodrug molecules.

Protein of SEQ ID:76 (Internal designation Clone 500760207_205-58-4-0-H6-F)

The protein of SEQ ID NO:76, herein referred as Ketothiolase (KT), comprising the amino acid sequence: MMGVFVVAAKRTPFGAYGGLLKDFTATDLSEFAAKAALSAGKVSPETVDSVIMGNVLQ SSSDAIYLARHVGLRVGIPKETPALTINRLCGSGFQSIVNGCQEICVKEAEVVLCGGTESM SQAPYCVRNVRFGTKLGSDIKLEDSLWVSLTDQHVQLPMAMTAENLAVKHKISREECD KYALQSQQRWKAANDAGYFNDEMAPIEVKTKKGKQTMQVDEHARPQTTLEQLQKLPP VFKKDGTVTAGNASGVADGAGAVIIASEDAVKKHNFTPLARIVGYFVSGCDPSIMGIGP VPAISGALKKAGLSLKDMDLVEVNEAFAPQYLAVERSLDLDISKTNVNGGAIALGHPLG GSGSRITAHLVHELRRRGGKYAVGSACIGGGQGIAVIIQSTA(SEO ID NO:76), is encoded by the cDNA of clone 500760207_205-58-4-0-H6-F (SEQ ID NO:75). Accordingly, it will be appreciated that all characteristics and uses of the polypeptide of SEQ ID NO:76 described throughout the present application also pertain to the polypeptide encoded by the human cDNA of clone 500760207_205-58-4-0-H6-F. In addition, it will be appreciated that all characteristics and uses of the nucleic acid of SEQ ID NO:75 described throughout the present application also pertain to the human cDNA of clone 500760207_205-58-4-0-H6-F. A preferred embodiment of the invention is directed toward the compositions of SEQ ID NO:75, SEQ ID NO:76, and Clone 500760207_205-58-4-0-H6-F. Also preferred are polypeptide fragments having a biological activity as described herein and the polynucleotides encoding the fragments.

The protein of SEQ ID NO:76 encoded by the cDNA of SEQ ID NO:75 is a polymorphism variant of 3-Ketoacyl CoA Thiolase protein (GENPEPT accession number, D16294). Furthermore, a BLAST search with the amino acid sequence of SEQ ID NO:76 indicates that the protein of the invention is homologous to 3-Ketoacyl CoA thiolase of rat (Swissprot accession number P13437) and *Bacillus halodurans* (Genbank accession number AP001514).

The 394 amino acids protein of SEQ ID NO:76 displays 1 candidate membrane-spanning segment, from amino acids 373 to 393. Accordingly, some embodiments of the present invention relate to polypeptides comprising the transmembrane domain. Finally, the protein of the invention displays the 3 thiolase signatures (PS00098, PS00737, PS00099) spanning from positions 85 to 103, positions 339 to 355, and positions 374 to 387, respectively. Accordingly, some embodiments of the present invention relate to polypeptides comprising the thiolase signature.

Living organisms are exposed to a number of different fatty acids and their various derivatives arising either via endogenous synthesis or from exogenous sources. These hydrophobic compounds can play specific metabolic structural or endocrinic functions in the organisms before their elimination, which can be metabolism to $CO_2$ or to more polar lipid metabolites allowing their excretion. Quantitatively, one of the major pathways metabolizing fatty acids is β-oxidation, which is often described as a spiral of four reactions catalyzed by three enzymes.

The three consecutive steps of mitochondrial β-oxidation of fatty acids, including the long-chain 3-hydroxyl-CoA dehydrogenase, are catalyzed by the trifunctional protein: 2-enoyl-CoA hydratase, 3-hydroxyacyl-CoA dehydrogenase and 3-ketoacyl-CoA thiolase. Deficiencies in enzyme activities of the heterocomplex, which contains 4 alpha and 4 beta subunits, causes sudden unexplained infant death, a Reye-like syndrome, cardiomyopathy, or skeletal myopathy.

Defects in the trifunctional protein fall into two groups: patients with an isolated defect in 3-hydroxyacyl-CoA dehydrogenase and those with a deficiency in all three activities and absence of immunoreactive protein (Tyni, J. et al., Acta Paeditr. 88:237-245 (1999)). Patients in the second group have been found to have either deletions in the α-subunit cDNA encoding for 2-enoyl-CoA hydratase and 3-hydroxyacyl-CoA dehydrogenase or point mutations in the β-subunit encoding for 3-ketoacyl-CoA thiolase [Ushikubo, S. et al., Am. J. Hum. Genet. 58:979-988 (1996); Ori, K. F. et al., Hum. Mol Genet. 6:1215-1224 (1997)].

Defects in the trifunctional protein fall into two groups: patients with an isolated defect in 3-hydroxyacyl-CoA dehydrogenase and those with a deficiency in all three activities and absence of immunoreactive protein (Tyni, J. et al., Acta Paeditr. 88:237-245 (1999)). Patients in the second group have been found to have either deletions in the α-subunit cDNA encoding for 2-enoyl-CoA hydratase and 3-hydroxyacyl-CoA deshydrogenase or point mutations in the δ-subunit encoding for 3-ketoacyl-CoA thiolase [Ushikubo, S. etal., Am J; Hum. Genet. 58: 979-988 (1996); Ori, K. F. et al., Hum. Mol Genet. 6: 1215-1224 (1997)].

It is believed that the protein of SEQ ID NO:76 or fragment thereof is an hydrolase, preferably acting on ester bonds, more preferably a thiolester hydrolase, even more preferably an ketoacyl-CoA thiolase which, as such, plays a role in fatty acid metabolism, in cellular vesicle transport and maintenance of the cytoarchitecture, in cellular proteolysis, endocytosis, signal transduction, lysosomal storage, cell proliferation and differentiation, immune and inflammatory response. The enzyme's substrates are compounds preferably containing an ester bond, preferably a thiol ester bond, more preferably an acyl thioester bond. Preferred polypeptides of the invention are polypeptides comprising the amino acids of SEQ ID NO:76 from positions 85 to 103, positions 339 to 355, and positions 374 to 387. Other preferred polypeptides of the invention are fragments of SEQ ID NO:76 having any of the biological activities described herein. The hydrolytic activity of the protein of the invention or fragment thereof may be assayed using any of the assays known to those skilled in the art including those described in U.S. Pat. No. 5,445,942. The ability to bind a cofactor may also be assayed using any techniques well known to those skilled in the art including, for example, the assay for binding NAD described in U.S. Pat. No. 5,986,172.

Another embodiment of the invention relates to compositions and methods using the protein of the invention or fragment thereof to label mitochondria, or more specifically the inner mitochondrial membrane, in order, to visualize any change in number, topology or morphology of this organelle, for example in association with a mitochondria-related human disorder, such as neuroleptic malignant syndrome (NMS) (Kubo et al., Forensic Sci. Int. 115:155-158 (2001)), the Rett syndrome (Armstrong, Brain Dev. 14 Suppl:S89-98 (1992)), Alpers disease (Chow and Thorburn, Hum. Reprod. 15 Suppl 2:68-78 (2000)) or mitochondrial encephalomyopathies (Handran et al., Neurobiol. Dis. 3:287-298 (1997)). For example, the protein may be rendered easily detectable by inserting the cDNA encoding the protein of the invention into a eukaryotic expression vector in frame with a sequence encoding a tag sequence. Eukaryotic cells expressing the tagged protein of the invention may also be used for the in vitro screening of drugs or genes capable of treating any mitochondria-related disease or conditions.

In one embodiment, the invention relates to compositions and methods using the protein of SEQ ID NO:76 or fragment thereof as a marker for tissue types (especially placenta), or to distinguish between two or more possible sources of a tissue sample on the basis of the level of the protein of SEQ ID NO:76 in the sample. For example, the protein of SEQ ID NO:76 or fragments thereof may be used to generate antibodies using any techniques known to those skilled in the art, and the antibodies may then be used to identify tissues of unknown origin, for example, forensic samples, differentiated tumor tissue that has metastasized to, foreign bodily sites, or to differentiate. different tissue types in a tissue cross-section using immunochemistry. Typically, in such methods a tissue sample is contacted with the antibody, which may be detectably labeled, under conditions which facilitate antibody binding. In one embodiment, the level of antibody binding to the test sample is measured and compared to the level of binding expected from control cells from placenta, or tissues other than placenta to determine whether the test sample is from placenta. Such methods may also be performed in conjunction with other, independant methods for determining cellular identity. Similar methods can be used to specifically detect cells expressing the protein, as well as to specifically isolate cells expressing the protein or to isolate the protein itself. For example, an antibody against the protein of SEQ ID NO:76 or a fragment thereof may be fixed to a solid support, such as a chromatography matrix. A preparation containing cells expressing the protein of SEQ ID NO:76 is placed in contact with the antibody under conditions which facilitate binding to the antibody. The support is washed and then the protein is released from the support by contacting the support with agents which cause the protein to dissociate from the antibody.

In another embodiment, the protein of the invention may be used to target heterologous compounds (polypeptides or polynucleotides) to the placenta and/or the cell mitochondria. For instance, a chimeric protein composed of the protein of the invention recombinantly or chemically fused to a protein or polynucleotide of therapeutic interest would allow the delivery of the therapeutic protein/polynucleotide specifically to the above-mentioned cellular/tissue targets (mitochondria, placenta).

Another embodiment of the invention relates to composition and methods using polynucleotide sequences encoding the protein of the invention or fragment thereof to establish transgenic model animals (*D. melanogaster, M. musculus*), by any method familiar to those skilled in the art. By modulating in vivo the expression of the transgene with drugs or modifier genes (activator or suppressor genes), animal models can be developed that mimic human mitochondria-associated disorders such as myopathies or obesity. These animal models would thus allow the identification of potential therapeutic agents for treatment of the disorders. In addition, recombinant cell lines derived from these transgenic animals may be used for similar approaches ex vivo.

In another embodiment, the invention relates to compositions and methods using the proteins of the invention or fragment thereof such as ligands for substrates of interest. In a preferred embodiment, the proteins of the invention or fragment thereof may be used to identify and/or quantify substrates using any techniques known to those skilled in the art. To find substrates, the proteins of the invention, or fragment thereof, or derivative thereof, may be used for screening libraries of compounds in any of a variety of drug screening techniques. The fragment employed in such screening may be free in solution, affixed to a solid support, borne on a cell surface, or located intracellularly. The formation of binding complexes, between the proteins of the invention, or fragment thereof, or derivative thereof, and the agent being tested, may be measured. Antagonists or inhibitors of the proteins of the invention may be produced using methods which are generally known in the art, including the screening of libraries of pharmaceutical agents to identify those which specifically bind the protein of the invention. Another technique for drug screening which may be used provides for high throughput screening of compounds having suitable binding affinity to the proteins of the invention as described in published PCT application WO84/03564.

In another embodiment, the invention relates to methods and compositions for detecting and quantifying the level of the protein of the invention present in a particular biological sample. These methods are useful for the diagnosis or prognosis of diseases associated with an altered levels of the protein of the invention like, but not limited to, deficiency of the hydrogenase activity (LCHAD deficiency). Diagnostic assays to detect the protein of the invention may comprise a biopsy, in situ assay of cells from organ or tissue sections, or an aspirate of cells from a tumor or normal tissue. In addition, assays may be conducted upon cellular extracts from organs, tissues, cells, urine, or serum or blood or any other body fluid or extract.

Assays for the quantification of the KT of SEQ ID NO:76 may be performed according to methods well known in the art. Typically, these assays comprise contacting the sample with a ligand of the protein of the invention or an antibody (polyclonal or monoclonal) which recognizes the protein of the invention or a fragment thereof, and detecting the complex formed between the protein of the invention present in the sample and the ligand or antibody. Fragments of the ligands and antibodiesm may also be used in the binding assays, provided these fragments are capable of specifically interacting with the KT of the subject invention. Further, the ligands and antibodies which bind to the KT of the invention may be labeled according to methods known in the art. Labels which are useful in the subject invention include, but are not limited to, enzymes labels, radioisotopic labels, paramagnetic labels, and chemiluminescent labels. Typical techniques are described by Kennedy, J. H., et al. (1976). *Clin. Chim. Acta* 70:1-31; and Schurs, A. H. et al. (1977). *Clin. Chim. Acta* 81: 140.

In another embodiment, the present invention includes the use of the protein of SEQ ID NO:76, or fragments having a desired biological activity to treat or ameliorate a condition in an individual. For example, the condition may be deficiency of the hydrogenase activity (LCHAD deficiency), hypoglycemia, muscular hypotonia, hyperamonia, mild liver dysfunction, 3-hydroxydicarboxylic acidunia, cardiomyopathy, retinal dystrophy, Bannayan-Riley-Ruvalcaba syndrome, or an abnormality in any of the functions of the hydrogenase activity. In such embodiments, the protein of SEQ ID NO:76, or a fragment thereof, is administered to an individual in whom it is desired to increase or decrease any of the activities of the protein of SEQ ID NO:76. The protein of SEQ ID NO:76 or fragment thereof may be administered directly to the individual or, alternatively, a nucleic acid encoding the protein of SEQ ID NO:76 or a fragment thereof may be administered to the individual. Alternatively, an agent which increases the activity of the protein of SEQ ID NO:76 may be administered to the individual. Such agents may be identified by contacting the protein of SEQ ID NO:76 or a cell or preparation containing the protein of SEQ ID NO:76 with a test agent and assaying whether the test agent increases the activity of the protein. For example, the test agent may be a chemical compound or a polypeptide or peptide. Alternatively, the activity of the protein of SEQ ID NO:76 may be decreased by administering an agent which interferes with such activity to an individual. Agents which interfere with the activity of the protein of SEQ ID NO:76 may be identified by contacting the protein of SEQ ID NO:76 or a cell or preparation containing the protein of SEQ ID NO:76 with a test agent and assaying whether the test agent decreases the activity of the protein. For example, the agent may be a chemical compound, a polypeptide or peptide, an antibody, or a nucleic acid such as an antisense nucleic acid or a triple helix-forming nucleic acid.

In another embodiment, the invention also relates to the use of polynucleotides of SEQ ID. NO:75 as diagnostic reagents. Detection of a mutated form of the gene characterized by the polynucleotide of SEQ ID NO:75 which is associated with a dysfunction will provide a diagnostic tool that can add to, or define, a diagnosis of a disease, or susceptibility to a disease. It has been shown previously that mutations in the beta subunit are responsible for trifunctional protein related diseases like those listed above [Ushikibo, S., et al., Am. J. Hum. Genet. 58:979-988 (1996); Ori, K. F., et al., Hum. Mol Genet. 6:1215-1224 (1997)]. Individuals carrying mutations in the gene may be detected at the DNA level by a variety of techniques known by those skilled in the art. Nucleic acids for diagnosis may be obtained from a subject cells, such as from blood, urine, saliva, tissue biopsy or autopsy material. The genomic. DNA may be used directly for detection or may be amplified enzymatically by using PCR or other amplification techniques prior to analysis.

In another embodiment, an array of oligonucleotide probes comprising the nucleotide sequence of SEQ ID NO:75 or fragments thereof can be constructed to conduct efficient screening of e.g., genetic mutations. The microarray can be used to monitor the expression level of large numbers of genes simultaneously and to identify genetic variants, mutations, and polymorphisms. This information may be used to determine gene function, to understand the genetic basis of a disorder, to diagnose a disorder, and to develop and monitor the activities of therapeutic agents (see for example: Chee, M. et al., Science, 274:610-614 (1996)).

Protein of SEQ ID NO:78 (Internal designation Clone 122421_105-076-4-0H1-F)

The cDNA of clone 122421_105-076-4-0-H1-F (SEQ ID NO:77) encodes the protein of SEQ ID NO:78, comprising the amino acid sequence: MAAALFVLLGFALLGTHGASGAAGTVFTTVEDLGSKILLTCSLNDSATEVTGHRWLKGG VVLKEDALPGQKTEFKVDSDDQWGEYSCVFLPEPMGTANIQLHGPPRVKAVKSSEHINE GETAMLVCKSESVPPVTDWAWYKITDSEDKALMNGSESRFFVSSSQGLSELHIENLNMEADPGQYRCNGTSSKGSDQAIITLRVRSHLAALWPFLGIVAEVLVLVTIIFIYEKRRKPEDVLDDDDAGSAPLKSSGQHQNDKGKNVRQRNSS (SEO ID NO:78). Accordingly, it will be appreciated that all characteristics and uses of the polypeptide of SEQ ID NO:78 described throughout the present application also pertain to the polypeptide encoded by the nucleic acids included in clone 122421_105-076-4-0-H1-F. In addition, it will be appreciated that all characteristics and uses of the nucleic acid of SEQ ID NO:77 described throughout the present application also pertain to the nucleic acids included in clone 122421_105-076-4-0-H1-F. A preferred embodiment of the invention is directed toward the compositions of SEQ ID NO:77, SEQ ID NO:78, and Clone 122421_105-076-4-0-H1-F. Also preferred are polypeptide fragments having a biological activity as described herein and the polynucleotides encoding the fragments.

The protein of SEQ ID NO:78 (BASI2) is a novel polymorphic variant of human basigin. BASI2 displays a signal peptide (MAAALFVLLGFALLGTHG (SEQ ID NO:210)), and two immunoglobulin (Ig) domains (GSKILLTCSLNDSATEVTGHRWLKGGVVLKEDALPGQKTEFKVDSDDQWGEYSCVF (SEQ ID NO:211) and GETAMLVCKSESVPPVTDWAWYKITDSEDKALMNGSESRFFVSSSQGLSELHIENLNMEADGQYRCNGTSS (SEQ ID NO:212)). Furthermore, BASI2 displays three N-glycosylation sites (NDSA (SEQ ID NO:213), NGSE (SEQ ID NO:214), and NGTS (SEQ ID NO:215)). The arginine at position 166 in basigin is changed to leucine in BASI2. Thus, the polymorphic, nonconservative change present in BASI2 is located in the second Ig domain, which is involved in protein-protein interactions. Such a polymorphic change located in the second Ig domain has never been previously reported. Thus, as a novel polymorphic variant of basigin, BASI2 displays similar biological activities as basigin, but displays enhanced kinetic parameters during protein-protein interactions.

BASI2 is a member of the immunoglobulin superfamily, which includes T cell receptors, neural cell adhesion molecules and major histocompatibility complex antigens. BASI2 is a cell surface transmembrane glycoprotein that is broadly distributed, and expressed at particularly high levels on activated gliomas, on tumor cells, on activated T cells and at the retinal pigment epithelium and neonatal blood-brain barrier. BASI2 is involved in cell-cell interactions, and has a multiplicity of biological roles. Notably, BASI2 stimulates the biosynthesis of various matrix metalloproteinases (MMPs), a group of enzymes involved in the degradation of most of the components of the extracellular matrix. In particular, MMP biosynthesis is crucial in tumor secretion and in immune response. BASI2 plays a role in spermatogenesis and fertilization, in neuronal interactions in the central nervous system and in HIV-1 infection.

An embodiment of the present invention relates to methods of using BASI2 or fragment thereof to stimulate the biosynthesis of metalloproteinases. In a preferred embodiment, metalloproteinases produced by such methods can be used in a "cocktail" of proteases that is able to digest a wide range of proteins without knowing any of the proteins. Such protease cocktails are useful in laboratory assays to degrade undesirable proteins in a sample, for example for removing proteins in a DNA preparation or for removing enzymes after any enzymatic reaction. In another preferred embodiment, metalloproteinases produced by such methods can be used for screening and/or assaying metalloproteinases inhibitors. Such metalloproteinase inhibitors are very useful to treat and/or prevent a wide range of diseases associated to metalloproteinase activation. In still another preferred embodiment, metalloproteinases produced by such methods can be used for degradation of connective tissues, for example in food industry. Any method of stimulating metalloproteinases biosynthesis can be used in such methods. For example, fibroblasts can be stimulated as described by Guo et al (J Biol Chem 272:24-7 (1997)), which disclosure is hereby incorporated by reference in its entirety.

An embodiment of the present invention relates to methods of using BASI2 or fragment thereof for the diagnosis of cancers, graft rejections, and graft versus host diseases. In such methods, BASI2 or fragment thereof is used as a marker to detect and/or quantify cells in which BASI2 and/or basigin expression is up-regulated, and in which NiPs are synthetised. Any method of detecting the presence, level or activity of BASI2 and/or basigin can be used in such methods. For example, the protein of the invention or fragment thereof may be used to generate specific antibodies using standard methods. Preferably, the antibodies are either directly or indirectly labeled, and recognize the second Ig domain. In a preferred embodiment, the antibodies bind more specifically to BASI2 than to related proteins such as basigin. Such antibodies can be used for specifically detecting the presence of the BASI2 variant. In another preferred embodiment, the antibodies recognize both basigin and BASI2. Such antibodies can be used for detecting total amount of basigin and BASI2 molecules. Alternatively, the nucleic acid of the invention or fragment thereof may be used to synthesize specific probes using any technique known to those skilled in the art. In such assays and diagnostic kits, the detection of a higher level of BASI2 and/or basigin expression, compared to a control representative of a non-malignant cell coming from a given tissue or bodily fluid, diagnostics the presence of a tumor or the beginning of a graft rejection reaction.

Another embodiment of the present invention relates to compositions and methods for inhibiting the activity or expression of BASI2 in a patient for the treatment or prevention of disorders caused or aggravated as a result of metalloproteinase biosynthesis. The inhibition of BASI2 activity or expression can be achieved using any suitable method, e.g. through administration of a therapeutically effective amount of an antibody that recognizes BASI2 or fragment thereof to a patient. Preferably, the antibodies are either directly or indirectly labeled, and recognize the second Ig domain. In a preferred embodiment, the antibodies bind more specifically to BASI2 than to related proteins such as basigin. Such antibodies can be used for specifically inhibiting the BASI2 variant. In another preferred embodiment, the antibody recognizes both BASI2 and basigin. Such antibodies can be used for inhibiting both isoforms. The antibody can be administrated alone or in combination with one or more agent known in the art, e.g. ABX-CBL antibody described in PCT Patent WO99/45031. Administration of the antibody can be done-following any method known in the art, including that described in PCT Patent WO99/45031, which disclosure is hereby incorporated by reference in its entirety. Other inhibitors of BASI2 expression or activity which can be used include, but are not limited to, antisense molecules, ribozymes, dominant negative forms of BASI2, and compounds that decrease the activity or expression of BASI2 in a cell. Such compounds can be readily identified, e.g. by screening test agents tumor cells over expressing BASI2, and detecting the ability of the test agents to decrease metalloproteinase biosynthesis or to diminish the level of BASI2 expression. Diseases and disorders caused or aggravated as a result of M biosynthesis and that can be treated by administrating an inhibitor of BASI2 and/or basigin include but are limited to cancers, graft rejections and graft versus host diseases.

Still another embodiment relates to compositions and methods for inhibiting the expression or activity of BASI2 in a patient for the treatment or prevention of disorders caused or aggravated as a result of microglial activation. The inhibition of BASI2 activity or expression can be achieved using any of the methods described above. Disorders caused or aggravated as a result of microglial activation include but are not limited to spinal cord contusion, Huntington disease, dementia with Lewy bodies, ischemia, multiple sclerosis, and Alzheimer's disease.

Still another embodiment relates to compositions and methods for inhibiting the interaction between BASI2 and cyclophilin A (CyPA) in a patient, in order to treat or to reduce in severity HIV-infection. Inhibition of the interaction can be achieved using any suitable method, e.g through administration of a therapeutically effective amount of an antibody that recognizes BASI2 or fragment thereof to a patient. Preferably, the antibodies are either directly or indirectly labeled, and recognize the first Ig domain and/or the second Ig domain. Administration of the antibodies can be performed as described above.

Another embodiment of the present invention relates to compositions and methods for enhancing the expression or activity of BASI2 and/or basigin in a patient for the treatment or prevention of disorders caused or aggravated as a result of BASI2 and/or basigin deficiency such as sterility, learning and memory impairments, and retinal angiogenesis. Any method or composition enhancing the expression or activity of BASI2 and/or basigin, containing BASI2 or fragment thereof, a polynucleotide encoding the protein, or a compound that increases the expression or activity of BASI2, can be used. Such compounds can be readily identified, e.g. by screening test agents against non activated glial cells expressing BASI2 and detecting the ability of the test agents to enhance metalloproteinases biosynthesis, or to increase the level of BASI2 expression. The compositions of the invention can be administered directly to the patient using any suitable method, for example by intravenous perfusion or by oral administration. Effective doses of the polypeptides of the present invention are determined according to the relevant techniques.

Protein of SEQ ID NO:80 (Internal designation 99483_105-016-1-0-D7-F)

The cDNA clone 99483_105-016-1-0-D7-F (SEQ ID NO:79) encodes KSPI1, the protein of SEQ ID NO:80, comprising the amino acid sequence:

MLPPPRPAAALALPVLLLLLVVLTPPPT-GARPSPGPDYLRRGWMRILAEGEGCAPCRPEE CAAPRGCLAGRVRDACGCCWECAN-LEGQLCDLDPSAHFYGHCGEQLECRLDTGGDLS RGEVPEPLCACRSQSPLCGSDGHTYSQI-CRLQEAARARPDANLTVAHPGPCESGPQIVSH PYDTWNVTGQDVIFGCEVFAYPMASIE-WRKDGLDIQLPGDDPHISVQFRGGPQRFEVTG WLQIQAVRPSDEGTYRCLGPMPWVKWRPLLA (SEQ ID NO:80). Accordingly, it will be appreciated that all characteristics and uses of the polypeptide of SEQ ID NO:80 described throughout the present application also pertain to the polypeptide encoded by the nucleic acids included in clone 99483_105-016-1-0-D7-F. In addition, it will be appreciated that all characteristics and uses of the nucleic acid of SEQ ID NO:79 described throughout the present application also pertain to the nucleic acids included in clone 99483_105-016-1-0D7-F. A preferred embodiment of the invention is directed toward the compositions of SEQ ID NO:79, SEQ ID NO:80, and Clone 99483_105-016-1-0D7-F. Also preferred are polypeptide fragments having a biological activity as described herein and the polynucleotides encoding the fragments. Preferred KSPI 1 polypeptides for uses in the methods described below include the polypeptides comprising the amino sequence of:

CAPCRPEECAAPRGCLAGRVRDACGC-CWECANLEGQLCDLDPSAHFYGHCGEQ LECRLDTGGDLSRGEVPEPLCACRSQS-PLCGSDGHTYSQICRLQEAARARPDANLTVAHP GPC (SEQ ID NO:216) and the polypeptide comprising the amino acid sequence of: VPEPLCACRSQSPLCGS-DGHTYSQICRLQEAARARPDANLTVAHPGPC (SEQ ID NO:217).

The protein of SEQ ID NO:80 (KSPI1) is a 267-amino-acid long protein, and is a new variant of the bA108L7.1 gene (Genbank accession number AL133215). The 255 first amino-acids are identical between the two proteins, but the 12 last amino-acids of KSPI1 are unique. KSPI1 displays a signal peptide (MLPPPRPAAALALPVLLLLLVVLTPPPT-GA(SEQ ID NO:218)), a kazal-type serine protease inhibitor (Ki) domain (VPEPLCACRSQSPLCGSDGHTYSQI-CRLQEAARARPDANLTVAHPGPC (SEQ ID NO:219)), an Immunoglobulin-like (Ig) domain (QDVIFGCEVFAYP-MASIEWRKDGLDIQLPGDDPHISVQFRG-GPQRFEVTGWLQIQAVRP SDEGTYRCLG (SEQ ID NO:220)) and an Insulin-like growth factor-binding domain (CAPCRPEECAAPRGCLAGRVRDACGC-CWECANLEGQLC (SEQ ID NO:221)). Furthermore, KSPI 1 displays homologies with many Insulin-like growth factor-binding proteins (IGFBP) from positions 1 to 255, and highest homology with a well-known IGFBP is obtained with human MAC25.

The protein of SEQ ID NO:80 (KSPI1) is a 267-amino-acid long protein, and is a new variant of the bA108L7.1 gene (Genbank accessionnumber AL133215). The 255 first amino-acids are identical between the two proteins, but the 12 last amino-acids of KSPI 1 are unique. KSPI1 displays a signal peptide (MLPPPRPAAALALPVLLLLLVVLTP-PPTGA), a kazal-type serine protease inhibitor (Ki) domain (VPEPLCACRSQSPLCGSDGHTYSQICR-LQEAARARPDANLTVAHPGPC), an Immunoglobulin-like (1g) domain.

(QDVIFGCEVFAYPMASIEWRKDG-LDIQLPGDDPIHSVQFRGGPQRFEVTGWLQIQAVRPS DEGTYRCLG) and an Insulin-like growth factor-binding domain.

(CAPCRPEECAAPRGCLAGRVRDACGC-CWECANLEGQLC). Furthermore, KSPI1 displays homologies with many Insulin-like growth factor-binding proteins (IGFBP) from positions 1 to 255, and highest homology with a well-known IGFBP is obtained with human MAC25.

KSPI1 is a new. Kazal-type serine protease inhibitor Protease inhibitors are important tools of nature for regulating the proteolytic activity of their target proteases, for blocking these in emergency cases, or for signaling receptor interaction or clearance. Kazal-type serine proteases inhibitors have been shown to inhibit a number of serine proteases such as trypsin, elastase, acrosin, and thrombin. As these proteases are involved in major biological processes such as haemostasis, inflammation and apoptosis, their inhibitors may have a wide range of therapeutical applications (Dahlback, Lancet, 355:1627-32 (2000); Watorek et al., Adv. Exp Med Biol, 240:23-31 (1988); Martin et al, Cell, 82:349-52 (1995)).

Moreover, KSPI1 belongs to the low affinity. IGFBP family. IGFBPs are soluble proteins that bind insulinike growth factors (IGFs). IGFs are involved in the regulation of cellular growth and metabolism, and the principal function of IGFBPs is to regulate IGF availability in body fluids. Some serine protease inhibitors have been shown to be implicated in the activation of growth factors (Kawaguchi et al, J Biol Chem 272:27558-64 (1997)). As KSPI1 is a serine protease that belongs to the low affinity IGFBP family, KSPI1 binds to IGFs and modulates IGF activation by inhibiting a serine protease.

An embodiment of the present invention relates to methods of using KSPI1 or fragment thereof to inhibit contaminating proteases in a sample. In particular, KSPI1 can be used in a "cocktail" of protease inhibitors that is able to inhibit a wide range of proteases without knowing the specificity of any of the proteases. Such protease inhibitor cocktails are widely used in laboratory assays to prevent degradation of protein samples by contaminating proteases.

In another embodiment, KSPI1 or fragment thereof can be used to treat and/or attenuate thrombin-mediated and thrombin-associated diseases. Thrombin is a serine protease that regulates the last step in the coagulation cascade, and has a central regulatory role in haemostasis and thrombus formation. Any compositions and methods containing, e.g., KSPI1 or fragment thereof, a polynucleotide encoding the protein, or a compound that increases the expression or activity of KSPI1. Such compounds can be readily identified, e.g. by screening test agents against cells expressing KSPI1 and detecting the ability of the test agents to increase the level of KSPI1 expression. A method for determining the ability of the polypeptides of the invention to block the proteolytic activity of thrombin is described in U.S. Pat. No. 6,218,365. The compositions of the invention can be administered directly to the patient using any suitable method, for example by intravenous perfusion or by oral administration. The compositions of the invention can also be used in extracorporeal circuits, as necessary in dialysis and surgery. Effective doses of the polypeptides of the present invention are determined according to the, relevant techniques. The compositions of the invention may be administered alone or in combination with other known agents inhibiting proteases of the coagulation cascade. Thrombin-mediated and thrombin-associated diseases in which the coagulation cascade is activated include but are not limited to deep vein thrombosis, pulmonary embolism, thrombophlebitis, arterial occlusion from thrombosis or embolism, arterial reocclusion during or after angioplasty or thrombolysis, restenosis following arterial injury or invasive cardiological procedures, postoperative venous thrombosis or embolism, acute or chronic atherosclerosis, stroke, myocardial infarction.

In another preferred embodiment, KSPI1 or fragment thereof can be used to treat and/or attenuate diseases associated with neutrophil-released proteases. Activated neutrophils release serine proteases such as elastase or cathepsin G, which result in abnormal connective tissue turnover and in severe damage to healthy tissues if not properly controlled [Watorek et al., Adv Exp Med Biol, 240:23-31 (1988)]. KSPI1 or fragment thereof inhibit neutrophil-released proteases, and inhibition efficiency of the polypeptides of the invention can be determined by measuring in vitro the apparent equilibrium dissociation constants using methods derived for tight-binding inhibitors [Bieth, Proteinase Inhibitors. 463-9 (1974); Williams et al, Methods Enzymol. 63:437-67 (1979)]. The compositions of the invention can be administered directly to the patient using any suitable method, for example by intravenous perfusion or by oral administration. Effective doses of the polypeptides of the present invention are determined according to the relevant techniques. The compositions of the invention may be administered alone or in combination with other known agents inhibiting neutrophil-released proteases. Diseases caused by neutrophil-released proteases include but are not limited to emphysema, idiopathic pulmonary fibrosis, adult respiratory distress syndrome, cystic fibrosis, rheumatoid arthritis, organ failure, glomerulonephritis and various inflarumatory diseases.

Another embodiment of the invention relates to the inhibition and/or attenuation of proteases produced by pathogenic microorganisms. This embodiment relates to the administration of KSPI1 or fragment thereof, or a compound that increases the expression or activity of KSPI1, alone or in combination with other known agents, for preventing and/or treating parasitic infections in human, in animals and in cell cultures. It has previously been shown that protease inhibitors can prevent dissemination of a virus, a protozoa, a bacteria or a fungus in the host organism. Methods for determining the ability of the polypeptides of the invention to block the proteolytic activity of serine proteases from various pathogenic microorganisms, for preparing and evaluating the pharmaceutical compositions, and for administrating the compositions are described in U.S. Pat. No. 5,739,283, which disclosure is hereby incorporated in its entirety. Accordingly, the polypeptides of the present invention may be used to prevent or to treat, e.g., coccidiosis, staphylococcal infection, infection by the influenza virus, *P. gingivalis* or *T. denticola*, and invasive pulmonary, aspergillosis.

Another embodiment of the present invention relates to methods of using KSPI1 or fragment thereof to remove or to purify serine proteases in a sample. Such methods can be useful either for removing contaminating proteases from a sample or for purifying a given protease in a sample. Preferred polypeptides are KSPI1 in its entirety, polypeptides containing the Ki domain, and polypeptides containing the Ki and the Ig domains. Recombinant proteins that display the Ki and/or Ig of KSPI1 may also be used. The binding efficacity of KSPI1 to a given serine protease can be tested using any suitable method, e.g., immunoprecipitation and Western blots analysis. Any method of binding KSPI1 to the protease and of purifying the complex can be used in such methods. In a preferred embodiment, KSPI1 or fragment thereof may be bound to a chromatographic support, either alone or in combination with other proteases inhibitors, to form an affinity chromatography column. The sample to analyse could then be run through this affinity chromatography column.

Another embodiment of the present invention relates to methods of using KSPI1 or fragment thereof to detect and/or to quantify the amount of protease in a sample, and thus to, use these methods in assays and diagnostic kits for the quantification of proteases in samples, bodily fluids or cell cultures. Such assays can be used to calculate the yield of a serine protease purification, and such diagnosis kits, which also contain a sample representative of the amount of protease found in a normal subject, can be used to detect diseases and disorders caused as a result of protease activity, including those listed above. Preferred polypeptides are KSPI1 in its entirety, polypeptides containing the Ki domain, and polypeptides containing the Ki and the Ig domains. Any method of detecting the protease inhibitor activity of KSPI1 or fragment thereof can be used in such methods. For example, the sample is assayed using a standard protease substrate. A known concentration of KSPI1 or fragment thereof is added, and allowed to bind to a particular protease present. The protease assay is then rerun, and the loss of activity is then correlated to the protease inhibitor activity using techniques well-known to those skilled in the art.

Still another embodiment of the invention relates to compositions and methods for modulating IGF activity by decreasing binding of KSPI1 to IGFs. Compounds that inhibit the interaction of an IGF with any one of its binding proteins and not to a human IGF receptor are useful to, increase serum and tissue levels of active IGFs in a mammal. Thus, compositions and methods for decreasing binding of KSPI1 to IGFs can be used, for example, in any treatments where IGFs are usually administrated, e.g., treatment of hyperglycemic, obesity-related, neurological, cardiac, renal, immunologic, and anabolic disorders. The inhibition and/or reduction of binding of KSPI1 to IGFs can be achieved using any suitable method, e.g. through the administration of a therapeutically effective amount of an antibody that specifically recognizes KSPI1 or fragment thereof to a patient. Preferably, two antibodies are used, separately or simultaneously, one recognizing the Ig domain and the other recognizing the Ki domain. The antibody can be administered alone or in combination with one or more agent known in the art, e.g those described in U.S. Pat. No. 6,251,865, which disclosure is hereby incorporated by reference in its entirety. Effective doses of the antibodies of the present invention are determined according to the relevant techniques. Decreased binding of KSPI1 to IGFs can also be obtained by using methods and compounds decreasing KSPI1 expression or activity. Such methods and compounds include, but are not limited to, antisense molecules, ribozymes, dominant negative forms of KSPI1, and compounds that decrease the activity or expression of KSPI1 in a cell.

Another embodiment of the present invention relates to methods of using KSPI1 or fragment thereof to purify IGFs in a sample. Such methods of purifying IGFs can be used to analyse the different IGFs present in a patient suffering of one of the diseases listed above. The binding efficacity of KSPI1 to a given IGF can be tested using any suitable method, e.g., immunoprecipitation and Western blots analysis. Any method of binding KSPI1 to IGFs and of purifying the complex can be used in such methods. In a preferred embodiment, KSPIl or fragment thereof may be bound to a chromatographic support, either alone or in combination with other IGFBPs, to, form an affinity chromatography column. The sample to purify could then be run through this affinity chromatography column.

In another series of embodiments, KSPI1 or fragment thereof can be used to detect and/or to quantify IGFs in a sample. Such methods may then be used in assays and diagnostic kits for the quantification of KSPI1-IGF complexes in, e.g., bodily fluids or tissue samples. Any method of detecting the presence or level of KSPI1-IGF complexes can be used. In particular, the methods described by Khosravi et al [Clin Chem 43:523-32 (1997)]and in U.S. Pat. No. 6,248,546, which disclosures are hereby incorporated by reference in their entirety, may be adapted., In a preferred embodiment, the diagnosis kit, which contains a sample representative of the level of KSPI1-IGF complexes found in a normal subject, can be used to detect diseases caused as a result of impaired IGF level, or to monitor the effects of a treatment aiming to increase or decrease IGF level in a patient.

Protein of SEQ ID NOS: 82 (Internal Designation Clone 517778_184-5-3-0-G3-F)

The cDNA of Clone 517778_184-5-3-0-G3-F (SEQ ID NO:81) encodes the Amyloid Apoptotic Receptor (AAR) protein comprising the amino acid sequence:

MAGGVRPLRGLRALCRVLL-FLSQFCILSGGESTEIP-PYVMKCPSNGLCSRLPADGIDCTTNF SCTYGKPVT-FDCAVKPSVTCVDQDFKSQKNFIINMTCRFCWQLPE-TDYECTNSTSCMTVS CPRQRYPANCTVRDHVH-CLGNRTFPKMLYCNWTGGYKWSTALAL-SITLGGFGADRFYLG QWREGLGKLFSFGGLGI-WTLIDVLLIGVGYVGPADGSLYI (SEQ ID NO:82). Accordingly, it will be appreciated that all characteristics and uses of the polypeptides of SEQ ID NO:82 described throughout the present application also pertain to the polypeptides encoded by the nucleic acids included in Clone 517778_184-5-3-0-G3-F. In addition, it will be appreciated that all characteristics and uses of the polynucleotides of SEQ ID NO:81 described throughout the present application also pertain to the nucleic acids included in Clone 517778_184-5-3-0-G3-F. A preferred embodiment of the invention is directed toward the compositions of SEQ ID NO:81, SEQ ID NO:82, and Clone 517778_184-5-3-0-G3-F. Also preferred are polypeptide fragments having a biological activity as described herein and the polynucleotides encoding the fragments.

AAR is a 221 amino acid receptor with two transmembrane segments. The resulting protein has a hydrophilic intracellular loop, and extracellular amino- and carboxy-terminal ends. The transmembrane domains and intracellular loop of AAR are very similar to the third and forth transmembrane domains and intervening sequence of seven transmembrane G protein coupled receptors. The G protein-binding amino acid sequence DRF is found near the first transmembrane region of AAR. The extracellular portion of AAR binds to ligands that include amyloidgenic peptides. Ligand binding leads to apoptosis for the AAR-expressing cell. AAR has biological activities that-comprise binding G protein components and ligands such as amyloidgenic peptides.

Preferred embodiments of the invention include:

A method of preventing cell death wherein a ligand-binding polypeptide fragment of AAR is contacted with ligand in an amount effective to competitively inhibit ligand binding to AAR expressed on a cell.

Preferred polypeptide fragments of AAR include but are not limited to those starting at an amino acid chosen from amino acids 1-40 and ending at amino acid chosen from amino acids 165-180. The most preferred polypeptide fragment comprises amino acids 1-180 of AAR.

Preferred forms of inhibited cell death include those associated with amyloidgenic peptides. A method of inducing apoptotic cell death wherein an AAR ligand is contacted with a cell in an amount effective to induce apoptosis of the cell. Preferred AAR ligands include amyloidgenic peptides. Further preferred AAR ligands are compounds that bind specifically to AAR and cause apoptosis in the cell expressing AAR. Further preferred AAR ligands include AAR-specific antibodies. Preferred AAR-specific antibodies include those that bind an epitope within the amino-terminal extracellular region of AAR. Preferred cells to be contacted with AAR ligand include neoplastic cells. Further preferred cells include neoplastic cells that express AAR.

A preferred solution of AAR ligand further comprises a hydrogel-forming polymer solution to improve localization of delivery. A preferred solution of AAR ligand further comprises one or more alkaline salts to improve ligand binding. A preferred solution of AAR ligand further comprises one or more chemotherapeutic agents to improve efficacy of treatment. A preferred method of contacting a cell includes catheter injection. A preferred method of contacting a cell further includes tumor imaging to improve accuracy of localized delivery. A preferred method of contacting a cell further includes computer, modeling and administration of AAR ligand to improve accuracy of localized delivery.

The amino-terminus of AAR is capable of binding to ligands such as amyloidgenic peptides (i.e., the β-amyloid peptide associated with Alzheimer's disease, Amyloid Precursor Like Proteins (APLP) 1 and 2, immunoglobulin light chain, prealbumin, β-2-microglobulin, transthyretin, amylin, insulin, atrial natriuretic peptide (ANP), apolipoproteins and glucagon). The amyloidgenic fragments of these proteins form predominantly beta-pleated sheet structures that may adopt the fibrillar configuration of amyloid in certain pathologic states. Amyloid deposits often lead to cell death in affected tissues. Amyloid-associated disorders include, most notably, Alzheimer's disease, diabetes, systemic amyloidosis, familial visceral amyloidosis, cutaneous amyloidosis, Muckle-Wells syndrome, Gerstrnan-Straussler disease, dialysis-related and hemodialysis-related amyloidosis. Amyloid deposits may lead to further pathogenic outcomes depending on the affected tissue. For instance, hemodialysis-related amyloidosis can result in carpal tunnel syndrome, erosive arthropathy, spondyloarthropathy, lytic bone lesions, and pathologic fractures. β-amyloid peptide deposition in the tunica media of leptomeningeal and parenchymal vessels causes degradation of smooth muscle cells and subsequent cortical hemorrhages. Furthermore, the neuronal cell death observed in Alzheimer's disease is associated with the senility that accompanies the later stages of the disease and pancreatic β-islet cell death is a causative factor of disrupted insulin regulation in diabetes. Reducing the level of amyloidgenic peptides is a desired therapy for disorders such as those listed herein.

In a preferred embodiment of the invention, a ligand-binding polypeptide fragment of AAR is used to prevent cell death. This method comprises the step of contacting a ligand-binding fragment of AAR with ligand in an amount effective to competitively inhibit binding of ligand to AAR expressed on a cell. Preferred polypeptide fragments of AAR include but are not limited to those starting at an ammino acid chosen from amino acids 1-40 and ending at an amino acid chosen from amino acids 165-180. Any single AAR fragment or combination of AAR fragments included in said list may be excluded from this embodiment of the invention. The most preferred fragment comprises amino acids 1-180 of AAR. Preferred forms of inhibited cell death include those associated with amyloidgenic peptides, such as pancreatic K-islet cell death and others listed herein. AAR fragments may be applied by methods common to the art such as those discussed herein. For example, AAR fragments may be delivered to cells of the pancreas in physiologically acceptable form by direct injection or catheter. For prolonged treatment, AAR fragments may be released from an implantable polypeptide-releasing stent (U.S. Pat. No. 5,683,345 and U.S. Pat. No. 5,500,013, which disclosures are hereby incorporated by reference in their entireties).

In the absence of ligand, AAR expression protects a cell from apoptotic cell death. AAR is expressed in many different cell types, including leukocytes and cells of the heart, brain, placenta, ovaries, testes, lung, liver, muscle, kidney, pancreas, colon, intestine, and prostate. Therefore, AAR may be exploited to cause cell death by addition of ligand. This inducible cell death is useful for treating neoplastic cell growth in a number of different tissues. As a preferred embodiment of the invention, an AAR ligand is used in a method to promote apoptotic cell death. This method comprises the step of contacting an AAR ligand with a cell in an amount effective to induce apoptotic cell death. Preferred AAR ligands include but are not limited to those listed herein (i.e., amyloidgenic peptides). Any single amyloidgenic, peptide ligand or combination of amyloidgenic peptide ligands may be excluded from this embodiment of the invention. Further preferred AAR ligands are compounds that bind specifically to AAR and cause apoptosis in the cell expressing AAR, such as an AAR-specific antibody. Preferred antibodies for use in this method include those that bind an epitope within the amino-terminal extracellular region of AAR. Any single antibody or combination of antibodies that bind to an epitope of AAR may be excluded from this embodiment of the invention. Preferred cells to be contacted with AAR ligand include neoplastic cells including but not limited to: neoplastic leukocytes and neoplastic cells of the heart, brain, placenta, ovaries, testes, lung, liver, muscle, kidney, pancreas, colon, intestine, and prostate. Further preferred cells include those that express AAR.

Delivery of AAR ligand to specific cells may be accomplished by methods common to the art such as those discussed herein. For example, an effective amount of AAR ligand in physiologically acceptable solution may be injected locally by syringe or catheter into a tumor mass to promote apoptotic cell death. AAR ligand may be used as the sole active agent in the solution, or may be used in combination with other chemotherapeutic drugs to increase the efficacy of treatment. A problem with direct delivery of AAR ligand into a solid tumor may be resistance of the tissue to the influx of the fluid. Increased penetration and/or reduced backflow through the point of entry, so that more material is introduced into and remains in the tumor, is obtained through the use of a viscous vehicle for the AAR ligand. Preferred materials include solutions or suspensions of a polymeric material which form a hydrogel at the time of or shortly after injection or implantation. The hydrogel solution of AAR ligand is injected via a catheter into regions of the tumor to be treated as described in U.S. Pat. No. 5,945,100, which disclosure is hereby incorporated by reference in its entirety. Another problem with direct delivery of AAR ligand is that cancerous tumors generate localized areas of relatively high acidity due to a metabolic process known as "anaerobic glycolysis."This acidic environment may interfere with ligand binding to AAR. A physiologically acceptable solution of AAR ligand may therefore include a variety of alkaline salts, as described in U.S. Pat. No. 5,681,857, which disclosure is hereby incorporated by reference in its entirety. To further increase the accuracy of treatment, tumor imaging, alone or in combination with computer modeling and administration of the AAR ligand solution may be employed (U.S. Pat. No. 5,438,989 and U.S. Pat. No. 5,823,993, which disclosures are hereby incorporated by reference in their entireties)

Proteins of SEQ ID NOs:84, 86, and 98 (Internal Designation Clones 100038__105-017-4-0-E4-F, 100523__105-019-1-0-F3-F, and 100545__105-019-2-0-E3-F)

The cDNAs of Clones 100038__105-017-4-0-E4F and 100523__105-019-1-0-F3-F (SEQ ID NOs:83 and 85, respectively) encode the Soluble Activator of Wnt (SAW)-1 protein comprising the amino acid sequence:

The cDNA of Clone 100545__105-019-2-0-E3-F (SEQ ID NO:97) encodes the SAW-2 protein comprising the amino acid sequence:

MLPPLPSRLGLLLLLLLCPAHVGGLW-
WAVGSPLVMDPTSICRKARRLAGRQAELCQAEPE
VVAELARGARLGVRECQFQFRFRRWNC-
SSHSKAFGRILQQGQCGEGHPARTLPPRPLGQP
SRRRFQVPGPS (SEQ ID NOs:84 and 86). The cDNA of Clone 100545_105-019-2-0-E3-F (SEQ ID NO: 97) encodes the SAW-2 protein comprising the amino acid sequence:

MLPPLPSRLGLLLLLLLCPAHVGGLW-
WAVGSPLVMDPTSICRKARRLAGRQAELCQAEPE
VVAELARGARLGVRECQFQFRFRRWNC-
SSHSKAFGRILQQGQCGEGAEVGLLSPCCGTR GEEN-
WFAEVA (SEQ ID NO:98).Accordingly, it will be appreciated that all characteristics and uses of the polypeptides of SEQ ID NOs:84, 86, and 98 described throughout the present application also pertain to the polypeptides encoded by the nucleic acids included in Clones 100038__105-017-4-0-E4-F, 100523__105-019-1-0-F3-F, and 100545__105-019-0E3-F, respectively. In addition, it will be appreciated that all characteristics and uses of the polynucleetides of SEQ ID NOs:83; 85, and 97 described throughout the present application also pertain to the nucleic acids included in Clones 100038__105-017-4-0-E4-F, 100523__105-3-F, and 100545__105-019-2-0-E3-F, respectively. A preferred embodiment of the invention is directed toward the compositions of SEQ ID NO:83, SEQ ID NO:84, SEQ ID NO:85, SEQ ID NO:86, SEQ ID NO:97, SEQ ID NO:98, Clone. 100038__105-017-4-0-E4-F, Clone: 100523$_{13}$ 105-019-1-0-F3-F, and Clone 100545$_{13\ 105}$-019-2-0-E3-F. Also preferred are fragments having a biological activity described herein and the polynucleotides encoding the fragments. A preferred fragment of the polypeptides of SEQ ID NOs:84 and 86 comprises:

MLPPLPSRLGLLLLLLLCPAHVGGLW-WAVGSPLVMDPTSICRKARRLAGRQAELCQAEPE VVAELARGARLGVRECQFQFRFRRWNC-SSHSKAFGRILQQGQCGEGHPARTLPP. A preferred fragment of the polypeptides of SEQ ID NO:98 comprises:

MLPPLPSRLGLLLLLLLCPAHVGGLW-WAVGSPLVMDPTSICRKARRLAGRQAELCQAEPE VVAELARGARLGVRECQFQFRFRRWNC-SSHSKAFGRILQQGQCGEGAEVGLLSP. A further preferred fragment of the polypeptide, sequences of SEQ ID NOs: 84, 86, and 98 comprises:

MLPPLPSRLGLLLLLLLCPAHVGGLW-WAVGSPLVMDPTSICRKARRLAGRQAELCQAEPE VVAELARGARLGVRECQFQFRFRRWNC-SSHSKAFGRILQQGQ.

A list of preferred embodiments of the invention follows.

A preferred embodiment is a composition, comprising a SAW-1 polypeptide sequence of SEQ ID NO:84.

A preferred embodiment is a composition, comprising a SAW-1 polypeptide sequence of SEQ ID NO:86.

A preferred embodiment is a composition, comprising a SAW-1 polypeptide fragment having biological activity.

A preferred embodiment is a composition, comprising a SAW-2 polypeptide sequence of SEQ ID NO:98.

A preferred embodiment is a composition, comprising a SAW-2 polypeptide fragment having biological activity.

A preferred embodiment is a composition, comprising a polynucleotide sequence of SEQ ID NO: 83 encoding a SAW-1 polypeptide.

A preferred embodiment is a composition, comprising a polynucleotide sequence of SEQ ID NO:85 encoding a SAW-1 polypeptide.

A preferred embodiment is a composition, comprising a polynucleotide sequence encoding a biologically active SAW-1 polypeptide fragment.

A preferred embodiment is a composition, comprising a polynucleotide sequence of SEQ ID NO:97 encoding a SAW-2 polypeptide.

A preferred embodiment is a composition, comprising a polynucleotide sequence encoding a biologically active SAW-2 polypeptide fragment.

A preferred embodiment is a method of increasing Wnt-dependent signaling to facilitate stem cell growth comprising the step of: contacting a SAW-1 or SAW-2 polypeptide or biologically active fragment thereof with a stem cell.

Preferred stem cells include those capable of growth or proliferation in response to Wnt.

Further preferred stem cells include those capable of giving rise to hematopoetic cells.

Further preferred stem cells include those capable of giving rise to neuronal or neuroglial cells.

Further preferred stem cells include those capable of giving rise to hepatocytes Further preferred stem cells include those capable of giving rise to pancreatic cells.

Further preferred stem cells include osteoblasts.

Further preferred stem cells include chondroblasts.

Further preferred stem cells include those found in cord blood.

Also preferred is the addition of one or more cell-type specific growth factor to the stem cell before, during or subsequent to contact with SAW-1 or SAW-2 polypeptide.

A preferred embodiment is a method of increasing Wnt-dependent signaling to prevent apoptosis comprising the step of: contacting a SAW-1 or SAW-2 polypeptide or biologically active fragment thereof with a cell at risk of apoptosis.

Preferred cells are those capable of responding to Wnt.

Preferably, the method is applied to prevent apoptosis of cells in culture.

Preferably, the method is applied to treat an apoptosis-related disorder.

Preferably, the method is applied to prevent an apoptosis-related disorder.

A preferred apoptosis-related disorder is chosen from the list consisting of: neurodegenerative diseases, Spinal Muscular Atrophy (SMA) types I-III, Amyltrophic Lateral Sclerosis (ALS), Huntington's disease, Alzheimer's disease, Parkinson's disease, retinal degeneration, retinitis pigmentosa, cerebellar degeneration, myelodysplasis, aplastic anemia, ischemia-related degeneration, myocardial infarction, stroke, hepatic degeneration diseases, alcoholic hepatitis, hepatitis B, hepatitis C, fulminant hepatitis, joint degeneration diseases, osteoarthritis, and diabetes.

SAW-1 and SAW-2 are splice variants of the Wnt-6 gene. In the case of SAW-1,the 135-nucleotide cassette inserted into the Wnt-6 cDNA encodes an early termination codon. The resulting SAW-1 polypeptide is 131 amino acids in length, compared to the 365-amino acid Wnt-6 protein. In the case of SAW-2, a 236-nucleotide insertion also encodes for an early termination codon. SAW-2 polypeptide is 129 amino acids in length and possesses a biological activity identical to that of SAW-1. The Wnt family of proteins is crucial for determining cell polarity and fate, patterning of a number of tissues in the developing embryo, cell proliferation, and maintenance of stem cell populations throughout life. The role of Wnt proteins in promoting cell survival may explain the prevalence of Wnt overexpression in human cancers. Wnt proteins are secreted factors that generally associate with the extracellular matrix or cell surface. Receptors for Wnt proteins include the Frizzled (Fz) family of seven transmembrane spanning receptors and the low-density lipoprotein receptor-related proteins (LRP) 5 and 6. These receptors can act synergistically as Wnt coreceptors to transmit signals and upregulate target gene expression. Inhibitors of Wnt signaling include a soluble form of the Fz receptor, which acts as a competitive dominant negative inhibitor, and the extracellular factors Cerberus and Wnt-Inhibitory Factors (WIFs). Therefore, Wnt proteins are targets for multiple protein-protein interactions. SAW-1 and SAW-2 are novel, truncated splice variants of Wnt-6 that interact with Cerberus and WIF proteins. The biological activities of SAW-1 and SAW-2 are defined by those interactions.

Wnt proteins are important in maintaining stem cell populations throughout adulthood. Stem cells comprise an undifferentiated or partially undifferentiated self-renewing population. As used herein, "stem cell" refers to any cell that retains undifferentiated character, is capable of self-renewal, and that gives rise to a further, differentiated cell. These cells are important for renewing cell populations of nearly every type, especially the high-turnover populations of epithelial linings, dermal layers, and the reproductive and hematopoetic systems. Defects in stem cell populations or drastic cell loss, whether caused by genetic predisposition, trauma, injury, disease, or medical treatments such as chemotherapy, have a disastrous effect on an individual. These defects may be overcome by stimulating growth of the remaining stem cell population in vivo. Alternatively, in vitro culture and transplantation of stem cells, preferably derived from the individual in need of treatment, but also from other sources such as cord blood, may be effective. Mature cells derived from the cultured stem cells may be transplanted as well. As Wnt proteins are effective growth and survival factors for stem cells, these proteins are useful for either strategy of cell replacement. However, Wnt proteins are difficult to purify in soluble form and do not diffuse readily, making Wnt-based treatments difficult to execute. A preferred method of increasing Wnt signaling is to decrease interaction of Wnt with soluble inhibitors such as Cerberus and WIF.

In a preferred embodiment of the invention, a SAW-1 or SAW-2 polypeptide or biologically active fragment thereof is used to increase Wnt-dependent signaling and facilitate stem cell growth. This method comprises the step of contacting a SAW-1 or SAW-2 polypeptide or biologically active fragment thereof with a stem cell. Preferred stem cells include those capable of growth or proliferation in response to Wnt. Also preferred is the addition of one or more cell-type specific growth factors or cytokines in combination with SAW-1 or SAW-2 polypeptide. Examples include the interleukins (e.g., IL-3), granulocyte-macrophage colony-stimulating factor (GM-CSF), macrophage colony-stimulating factor (M-CSF), granulocyte colony-stimulating factor (G-CSF), erythropoietin (Epo), lymphotoxin, steel factor (SLF), tumor necrosis factor (TNF) and gamma-interferon. IL-3 acts on multipotent stem cells as well as progenitors restricted to the granulocyte, macrophage, eosinophil, megakaryocyte, erythroid or mast cell lineages, while Epo acts on fairly mature erythroid progenitor cells. SAW-1 or SAW-2 polypeptide or a biologically active fragment thereof may be-used to facilitatestem cell proliferation in culture by adding a physiologically acceptable solution comprising said polypeptide to a stem cell in culture (e.g., liver stem cells, neural or neuroglial stem cells, osteoblasts, chondroblasts, pancreatic stem cells, hematopoetic stem cells, cord blood, etc.) in an amount effective to promote Wnt-dependent growth or proliferation. A physiologically acceptable solution comprising a SAW-1 or SAW-2 polypeptide or a biologically active fragment thereof may further be added upon transplantation or reintroduction of cultured cells into an individual to provide additional growth potential for the cells in vivo. Cell transplantation and reintroduction methods are determined by one skilled in the art and include injection of a single-cell suspension by syringe or catheter and surgical implantation (also see U.S. Pat. No. 5,869,463 for neuroglial cell transplants; U.S. Pat. No. 6,068,836 for bone marrow transplants; Noel et al., Metabolism, 31:184-7 (1982) for pancreatic cell transplants; and U.S. Pat. No. 4,950,296, U.S. Pat. No. 5,385,566, and U.S. Pat. No. 6,200,324 for bone transplants, which disclosures are hereby incorporated by reference in their entireties). Additionally this method may be applied to increase Wnt-dependent stem cell growth and proliferation in vivo. For example, a physiologically acceptable solution comprising SAW-1 or SAW-2 polypeptide or a biologically active fragment thereof may be directly injected to the site of interest (e.g., the bone marrow for hematopoetic stem cell treatment) or by other methods common to the art.

Given that stem cells are, at the earliest stage, able to differentiate into almost any kind of mature, functional cell, a wide variety of conditions rnay be addressed by stem cell treatment. As an example, hematopoetic stem cell growth or replacement may benefit those predisposed to or suffering from, any one or more of the following exemplary conditions: lymphocytopenia; lymphorrhea; lymphostasis; immunodeficiency (e.g., HIV and AIDS); infections (including, for example, opportunistic infections and tuberculosis (TB)); lupus; disorders characterized by lymphocyte deficiency, erythrocytopenia; erthrodegenerative disorders; erythroblastopenia; leukoerythroblastosis; erythroclasis; thalassemia; anemia (e.g., hemolytic anemia, such as acquired, autoimmune, or microangiopathichemolyticanemia; aplastic anemia; congenital anemia, e.g., congenital dyserythropoietic anemia, congenital hemolytic anemia or congenital hypoplastic anemia; dyshemopoietic anemia; Faconi's anemia; genetic anemia; hemorrhagic anemia; hyperchromic or hypochromic anemia; nutritional, hypoferric, or iron deficiency anemia; hypoplastic anemia; infectious aneia; lead anemia; local anemia; macrocytic or microcytic anemia; malignant or pernicious anemia; megaloblastic anemia; molecular anemia; normocytic anemia; physiologic, anemia; traumatic or posthemorrhagic anemia; refractory anemia; radiation anemia; sickle cell anemia; splenic anemia; and toxic anemia); myelofibrosis; thrombocytopenia; hypoplasia; disseminated intravascular-coagulation (DIC); immune (autoimmune) thrombocytopenio purpura (ITP); HIV inducted ITP; myelodysplasia; thrombocytotic diseases and thrombocytosis. Stem cells giving rise to neural or neuroglial cells may be applied to treat disorders including but not limited to: Alzheimer's disease, frontotemporal dementia, bipolar disorder, Huntington's chorea; multiple sclerosis, amyotrophic lateral sclerosis, Tay-Sach's disease, Gaucher's disease, and dopamine-related disorders such as Parkinson's disease and schizophrenia. Pancreatic, stem cell cultures may be applied to treatment of metabolic disorders such as diabetes. Stem cells from bone tissue (osteoblasts), may be used to treat to bone loss, atrophy, or malformation due to injury, congenital or chronic conditions, osteopenia, osteoporosis, rickets, malignant melanoma-induced bone degradation, and bone fissures or fractures due to injury, elective surgery. (e.g., plastic surgery), reconstructive surgery, and dental procedures or surgeries.

Wnt proteins act to inhibit apoptosis and promote survival of Wnt-responsive cells. A specific activator of Wnt signaling is desirable both for cell or tissue growth in vitro and for treating apoptosis-related disorders in vivo. Examples of such disorders include: neurodegenerative diseases such as Spinal Muscular Atrophy (SMA) types I-III, Amyltrophic. Lateral Sclerosis (ALS), Alzheimer's disease, Huntington's disease, Parkinson's disease, retinal degeneration, retinitis pigmentosa and cerebellar degeneration; myelodysplasis such as aplastic anemia; ischemic diseases such as myocardial infarction and stroke; hepatic diseases such as alcoholic hepatitis, hepatitis B, hepatitis C, and filminant hepatitis; joint diseases such as osteoarthritis; and metabolic disorders such as diabetes. In a preferred embodiment of the invention, a SAW-1 or SAW-2 polypeptide or biologically active fragment thereof is used to prevent apoptosis-related degeneration. This method comprises the step of contacting a SAW-1 or SAW-2 polypeptide or biologically active fragment thereof with a cell. Preferred cells are those capable of responding to Wnt. Further preferred cells are those at risk of apoptosis. For example, a physiologically acceptable composition comprising SAW-1 or SAW-2 polypeptides may be added to a mixed culture of hippocampal neurons to improve cell survival in culture. Alternatively, a physiologically acceptable composition comprising SAW-1 or SAW-2 polypeptide or biologically active fragment thereof may be delivered to an individual diagnosed with or at risk of an apoptosis-related disorder, as determined by one skilled in the art. SAW-1 or SAW-2 polypeptide may be used alone or in combination with agents that modulate Wnt signaling, apoptosis, or cell type-specific, processes. Furthermore, SAW-1 or SAW-2 polypeptide may be fused to a ligand for the purpose of stabilizing and/or targeting said polypeptide (for example, tetanus toxin, calcium channel blocking agents, transferrin, poliovirus epitopes, neuropeptide fragments, or steroid hormone androgens, or fragments thereof which are sufficient for neuronal targeting). As an example, a physiologically acceptable composition comprising SAW-1 or SAW-2 polypeptides may be delivered to an individual to prevent osteoarthritis-associated joint degeneration. As an additional example, said composition may be administered to an individual that has or is likely to experience an ischemic event. Appropriate delivery methods, such as those discussed herein, may be determined on a case by case basis by one skilled in the art.

Protein of SEQ ID NOs:88 and 90 (Internal Designation Clone 116470_105-063-3-0-H7-F and Clone 122600_105-077-3-0-F9-F)

The cDNAs of Clone 116470_105-063-3-0-H7-F and Clone 122600_105-077-3-0-F (SEQ ID NOs:87 and 89, respectively) encode the Dopamine AMPhetamine INhibitor. (Dampin). protein comprising the amino acid sequence:

MLFRLSEHSSPEEEASPHQRAS-GEGHHLKSKRPNPCAYTPPSLKAVQRI-AESHLQSISNLNE NQASEEEDELGELREL-GYPREEDEEEEEDDEEEEEEEDSQAEVLKVIRQSAG-QKTTCGQGL EGPWERPPPLDESERDGGSEDQVED-PALSEPGEEPQRPSPSEPGT (SEQ ID NOs:88 and 90).

Accordingly, it will be appreciated that all characteristics and uses of the polypeptides of SEQ ID. NOs:88 and 90 described throughout the present application also pertain to the polypeptides encoded by the nucleic acids included in Clone 116470_105-063-3-0-H7-F and Clone 122600_105-077-3-0-F9-F, respectively. In addition, it will be appreciated that all characteristics and uses of the polynucleotides of SEQ ID NOs:87 and 89 described throughout the present application also pertain to the nucleic acids included in Clone 116470_105-063-3-0-H7-F and Clone. 122600_105-077-3-0-F9-F, respectively. A preferred embodiment of the invention is directed toward the compositions of SEQ ID NO:87, SEQ ID NO:88, SEQ ID NO:89, SEQ ID NO:90, Clone 116470_105-063-3-0-H7-F and Clone 122600_105-077-3-0 are polypeptide fragments having a biological activity as described herein and the polynucleotides encoding the fragments.

Dampin is a splice variant of the Dopamine and cAMP-Regulated PhosphoProtein-32 (DARPP-32) that utilizes a different translation start site and lacks the first 37 amino acids of DARPP-32. DARPP-32 is a cytoplasmnic signaling molecule that is regulated by phosphorylation at residues T34 by Protein Kinase A (PKA) to function as an inhibitor of Protein Phosphatase 1. (PP1). This increases the effect of PKA on downstream targets. In neurons, PKA phosphorylates DARPP-32 in response to dopamine or psychoactive drugs that act on doparrine signaling pathways (e.g., cocaine and amphetamines). Alternatively, phosphorylation of T75 by Cdk5 results in DARPP-32 inhibition of PKA. Dampin, as a splice variant, is not phosphorylated in response to PKA signaling and does not act as an inhibitor of PP1 However, Dampin has a Cdk5 phosphorylation site and is able to inhibit PKA signaling.

Abnormal signaling through dopaminergic pathways has been implicated in several major neurological and psychiatric disorders, including Parkinson's disease, Tourette's syndrome, Attention Deficit Disorder. (ADD), Huntington's disease, schizophrenia, and drug(alcohol abuse. In particular, cocaine and amphetamines activate the dopaminergic pathways through PKA. Furthermore, addictive behavior is associated with increased dopaminergic signaling and PKA activity. Therefore, diminished PKA activity may be desired to address addictive behavior and drug and alcohol abuse. Increases in dopamine responses may be desired to treat disorders such as Parkinson's disease, Tourette's syndrome, ADD, Huntington's disease, and schizophrenia.

Progesterone, similar to dopamine, also activates PKA, which leads to DARPP-32 phosphorylation at T34 and inhibition of PP1. Dampin inhibits both dopamine and progesterone signaling by attenuating PKA activity. Progesterone is required for ovulation and implantation of a fertilized egg in the uterine wall. In addition, progesterone, in combination with dopamine increases female sexual receptivity. Therefore, high levels of Dampin relative to DARPP-32 would be effective for female birth control as well as behavioral modification (e.g., for purposes of animal training). Alternatively, high levels of DARPP-32, relative to Dampin would be effective for increasing female fertility and sexual receptivity.

PP1 activates glycogen synthase in response to insulin. Glycogen synthesis is one mechanism by which blood glucose levels are regulated by insulin. DARPP-32 inhibition of PP1 is in turn inhibited by insulin. However, insufficient insulin or insulin resistance may lead to inappropriate inhibition of PP1 and dysregulation of blood glucose, levels. Such dysregulation may result from disorders that include: Noninsulin dependent diabetes mellitus (MIDDM), Insulin dependent diabetes mellitus (IDDM), insulin resistance and insulin resistant disorders such as acanthosis nigricans, leprechaunism, and lipoatropahy. As Dampin does not inhibit PP1, high levels of Dampin relative to DARPP-32 would be effective for modulating blood glucose levels by increasing glycogen synthase activity.

Preferred embodiments of the invention include:

A composition comprising a Dampin polypeptide sequence of SEQ ID NOs:88 and 90. A composition comprising a Dampin polypeptide fragment having biological activity. A composition comprising a polynucleotide sequence of SEQ ID NOs:87 and 89 encoding a Dampin polypeptide. A composition comprising a polynucleotide sequence encoding a Dampin polypeptide fragment having biological activity.

A method of screening test substances for modulators of Dampin expression comprising the steps of: i) contacting a cell with a test substance; and ii) comparing Dampin expression in the cell after exposure to the test substance to that of an unexposed control cell.

A method of screening for test substances that modify the ratio of DARPP-32 relative to Dampin comprising the steps of: i) contacting a cell with a test substance; ii) comparing Dampin expression in the cell after exposure to the test substance to that of an unexposed control cell; iii) comparing DARPP-32 expression in the cell after exposure to that of an unexposed control cell; iv) quanting said expression levels; and v) determining the level of DARPP-32 relative to, Dampin in the exposed and unexposed cells.

Preferably, the test substance modifies the ratio of Dampin relative to DARPP-32 in a specific cell type while not in others. Further preferably, the test substance is conjugated to a cell type-specific ligand. Preferably, the method screens for test substances that decrease the ratio of DARPP-32 relative to Dampin.

Alternatively, the method screens for test substances that increase the ratio of DARPP-32 relative to Dampin.

A method of differentiating Dampin polypeptides from DARPP-32 polypeptides comprising the steps of: i) contacting a first antibody that binds specifically to DARPP-32 and not Dampin with a protein sample; ii) contacting a second antibody that binds specifically to both DARPP-32 and Dampin with a protein sample; and iii) detecting protein-bound antibody. Preferably, the first and second antibodies are labeled with a different detectable conjugate. Preferably, the method follows immunohistochemical protocols.

A substance that decreases the ratio of DARPP-32 relative to Dampin made by the process comprising the steps of: i) contacting a cell with a test substance; ii) comparing Dampin expression in the cell after exposure to the test substance to that of an unexposed control cell; iii) comparing DARPP-32 expression in the cell after exposure to that of an unexposed control cell; iv) quantifying said expression levels; v) determining the level of DARPP-32 relative to Dampin in the exposed and unexposed cells.

Preferably, the substance decreases the ratio of DARPP-32 relative to Dampin in a specific cell type while not in others. Further preferably, the substance is contained in a physiologically acceptable composition.

A substance that increases the ratio of DARPP-32 relative to Dampin made by the process comprising the steps of: i) contacting a cell with a test substance: ii) comparing Dampin expression in the cell after exposure to the test substance to that of an unexposed control cell; iii) comparing DARPP-32 expression in the cell after exposure to that of an unexposed control cell; iv) quantifying said expression levels; v) determining the level of DARPP-32 relative to Dampin in the exposed and unexposed cells.

Preferably, the substance increases the ratio of DARPP-32 relative to Dampin in a specific cell type while not in others. Further preferably, the substance is contained in a physiologically acceptable composition.

A method of screening for test substances that specifically bind to Dampin and prevent binding to PKA comprising the steps of: i) contacting a test substance with Dampin polypeptide in the presence of PKA, under conditions that allow binding of Dampin to PKA and ii) detecting the amount of PKA bound to Dampin in the presence and absence of the test substance.

Preferably, the test substance is able to inhibit Dampin interaction with PKA in a certain cell type and not in others. Further preferable are test substances conjugated to cell-type specific. ligands or portions thereof.

A substance that specifically binds to Dampin and prevents binding to PKA made by the process comprising the steps of: i) contacting a test substance with Dampin polypeptide in the presence of PKA, under conditions that allow binding of Dampin to PKA and ii) detecting the amount of PKA bound to Dampin in the presence and absence of the test substance by methods common to the art.

A method of decreasing PKA activity in a neuron comprising the step of contacting a substance capable of increasing the ratio of Dampin to DARPP-32 with a neuron. Preferably, the substance is capable of passing through the blood brain barrier. Preferably, this method is used to decrease cocaine- or amphetamine-dependent responses. Preferably, this method is used to diminish addictive behavior. Further preferably, this method is used to diminish alcohol addiction.

A method of decreasing PKA activity in a cell of the female reproductive tract comprising the step of contacting a substance, capable of increasing the ratio of Dampin to DARPP-32 with a cell of the female reproductive tract. Preferred cells include ovarian granulosa cells and luteal cells of the uterus. Preferably, this method is used to inhibit progesterone-dependent ovulation and implantation of a fertilized egg. Preferably, this method is used for female birth control.

A method of modulating blood glucose levels comprising the step of contacting a substance capable of increasing the ratio of Dampin to DARPP-32 with a glycogen-storing cell. Preferred glycogen-storing cells include myocytes and hepatocytes.

A method of inhibiting PKA activity comprising the step of introducing a Dampin polypeptide into a cell. Preferably, Dampin polypeptide is delivered to a cell by introducing a polynucleotide encoding Dampin polypeptide into the cell. Preferably, the polynucleotide is a polynucleotide construct comprising an expression control unit and a polynucleotide encoding Dampin polypeptide. Preferred cells include neurons, ovarian granulosa cells, uterine cells, hepatocytes, and myocytes.

A method of increasing neuronal PKA activity comprising the step of contacting a substance capable of decreasing the ratio of Dampin to DARPP-32 with a neuron. Preferably, the substance is capable of passing through the blood brain barrier. Preferably, this method is used to increase PKA activity in dopaminergic neurons affected by neurological disorders.

Preferred neurological disorders include: Parkinson's disease, Huntington's disease, ADD, Tourette's syndrome, and schizophrenia. Preferably, this method is used to increase, PKA activity in hypothalamic neurons that express both dopaminergic and progesterone receptors. Preferably, increasing PKA activity in the hypothalamus is directed toward increasing sexual receptivity in a female individual.

A method of increasing Atrial Natriuretic Factor (ANF) activity comprising the step of contacting a substance capable of decreasing the ratio of Dampin to DARPP-32 with a nephronic kidney cell. Preferably, this method is used to reduce blood volume. Further preferably, this method is used to reduce hypertension.

An embodiment of the invention provides for a method of screening test substances for modulators of Dampin expression. This method comprises the steps of: i) contacting a cell with a test substance; and ii) comparing Dampin expression in the cell after exposure to the test substance to that of an unexposed control cell. Darmin expression is determined by methods common to the art or included herein, by detecting Dampin polynucleotides or polypeptides. An example of this method comprises the steps of: i) culturing two equivalent cell samples; ii) adding a test substance to one of the cultures and not the other; i) harvesting both cultures at a specified time; iv) purifying the mRNA from each sample of cells; v) comparing the level of Dampin mRNA in each sample by Northern blot, RTPCR, or another method common to the art. The invention provides for design and use of specific polynucleotide probes and primers, as discussed herein. An additional example comprises the steps of: i) having two equivalent cultures of cells; ii) adding a test substance to one of the cultures and not the other; iii) harvesting both cultures; iv) purifying the protein from each sample of cells; v) comparing the level of Dampin polypeptides in each sample by Western blot, immunohistochemistry, or another method common to the art. The invention provides for design and use of specific antibodies and antibody fragments, as discussed herein.

A preferred embodiment of the invention provides a method of screening for test substances that modify the ratio of DARPP-32 relative to Dampin. This method comprises the steps of: i) contacting a cell with a test substance; ii)

comparing Dampin expression in the cell after exposure to the test substance to that of an unexposed control cell; iii) comparing DARPP-32 expression in the cell after exposure to the test substance to that of an unexposed control cell; iv) quantifying said expression levels; and v) determining the level of DARPP-32 relative to Dampin in the exposed (i.e., test) and unexposed (i.e., control) cells.

A further preferred embodiment of the invention provides a method of screening for test substances that modify the ratio of DARPP-32 relative to Dampin in a specific cell type while not in others. Included in this method are test substances that are conjugated to cell-type specific ligands or portions thereof. For example, a test substance may be conjugated to a hydrophilic neuropeptide (e.g., interferon alpha, endorphin, somatostatin) for targeting to the brain (U.S. Pat. No. 4,902,505, which disclosure is hereby incorporated by reference in its entirety).

A preferred embodiment of the invention provides a method of screening for test substances that decrease the ratio of DARPP-32 relative to Dampin. An alternative preferred embodiment of the invention provides a method of screening for test substances that increase the ratio of DARPP-32 relative to Dampin.

In a preferred embodiment of the invention, a substance that decreases the ratio of DARPP-32 relative to Dampin is made by the process comprising the steps of: i) contacting a cell with a test substance; ii) comparing Dampin expression in the cell after exposure to the test substance to that of an unexposed control cell; iii) comparing DARPP-32 expression in the cell after exposure to that of an unexposed control cell; iv) quantifying said expression levels; v) determining the level of DARPP-32 relative to Dampin in the exposed and unexposed cells. This substance is used for purposes discussed herein.

In a preferred embodiment of the invention, a substance that increases the ratio of DARPP-32 relative to Dampin is made by the process comprising the steps of: i) contacting a cell with a test substance; ii) comparing Dampin expression in the cell after exposure to the test substance to that of an unexposed control cell; iii) comparing DARPP-32 expression in the cell after exposure to that of an unexposed control cell; iv) quantifying said expression levels; v) determining the level of DARPP-32 relative to Dampin in the exposed and unexposed cells. The substance that increases the relative level of DARPP-32 is used for purposes discussed herein.

Methods of detecting Dampin polynucleotides and polypeptides may be used to detect DARPP-32 polynucleotides and polypeptides and are addressed herein (e.g., mRNA detection methods, antibody-based detection methods). A simple method for differentiating between the Dampin and DARPP-32 splice variants is desirable. A preferred embodiment of the invention provides a method for differentiating Dampin polypeptides from DARPP-32 polypeptides. This method comprises the steps of: i) contacting a first antibody that binds specifically to DARPP-32 and not Dampin with a protein sample; ii) contacting a second antibody that binds specifically to both DARPP-32 and Dampin with a protein sample; and iii) detecting protein-bound antibody. Preferably, the first and second antibodies are labeled with a different detectable conjugate. This allows the method to be carried out with a single protein sample. Preferably, the protein sample is a fixed, semi-permeablized cell sample. Preferably, the detection method follows immunohistochemical protocols, as discussed herein.

Dampin inhibits PKA by a competitive binding mechanism. Therefore, the inhibitory effect of Dampin may be ablated by a substance that blocks the interaction of Dampin with PKA. A preferred embodiment of the invention provides a method of screening for test substances that specifically bind to Dampin and prevent binding to PKA. This method comprises the steps of: i). contacting a test substance with Dampin polypeptide in the presence of PKA, under conditions that allow binding of Dampin to PKA (e.g., an intact cell); and ii) detecting the amount of PKA bound to Dampin in the presence and absence of the test substance by methods common to the art (e.g., antibody-based methods such as coimmunopreciptation and Western blotting). Preferably, the test substance is able to inhibit Dampin interaction with PKA in a certain cell type and not in others. Included in this method are test substances that are conjugated to cell-type specific ligands or portions thereof.

In a preferred embodiment of the invention, a substance that inhibits Dampin binding to PKA is made by the process comprising the steps of: i) contacting a test substance with Dampin polypeptide in the presence of PKA, under conditions that allow binding of Dampin to PKA (e.g., a biological solution, preferably an intact cell); and ii) detecting the amount of PKA bound to Dampin in the presence and absence of the test substance by methods common to the art (e.g., antibody-based methods such as coimmunopreciptation and Western blotting).

In a preferred embodiment of the invention, a substance capable of increasing the ratio of Dampin to DARPP-32 is used in a method to decrease PKA activity in a neuron. Preferred substances are additionally capable of passing through the blood brain barrier in vivo. This method comprises the step of contacting a neuron with said substance. Diminished activity can be measured by an altered modulation of calcium channel function in response to dopamine, in situ. This diminished activity may also to be measured as a loss of dopamine-mediated inhibition of the sodium-potassium ATPase (Na,KATPase) in situ or an increased excitability of striatal and cortical neurons. This method may also be applied to: i) diminish release of dopamine in response to amphetamines, as determined in situ; ii) diminish release of GABA (4-Aminobutyric acid) in response to amphetamines, as determined in situ; iii) increase levels of substance P in the striatum and cortex, as determined in situ; iv) increase levels of neurotensin in the striatum and cortex, as determined in situ; v) attenuate increase in locomotor activity of an individual in response to cocaine; vi) attenuate increase in the protein Fos in response to an amphetamine, as determined in situ; vii) attenuate increase in the protein Chronic Fos Related Antigen (FRA) in response to cocaine, as determined in situ; and viii) diminish inhibition of the activity of the brain sodium-potassium-ATPase in response to dopamine, as determined in situ; and ix) decrease addictive behavior in an individual at risk of or displaying such behavior, as determined by family history or clinical assessment.

In a preferred embodiment of the invention, a substance capable of increasing the ratio of Dampin to DARPP-32 is used in a method to decrease PKA activity in a cell of the female reproductive tract. This method comprises the step of contacting a cell of the female reproductive tract with said substance. Preferred cells include ovarian granulosa cells and luteal cells of the uterine tract. Dampin inhibits progesterone-mediated PKA activity, which is required for ovulation and implantation of a fertilized egg in the uterine wall. This method is directed toward female birth control.

In a preferred embodiment of the invention, a substance capable of increasing the ratio of Dampin to DARPP-32 in glycogen-storing cells is used to modulate blood glucose levels. This method comprises the step of contacting said substance with glycogen-storing cells. Preferred cells include hepatocytes and myocytes. DARPP-32 inhibits PP, which is required for glycogen synthase activity in response to insulin. Dampin does not inhibit PP1 and therefore will allow glucose processing and blood glucose modulation. This method is particularly useful for modulating glucose levels in insulin-deficient and diabetic individuals.

As Dampin acts as a dominant negative inhibitor of DARPP-32, Dampin polypeptides may be expressed in a cell to inhibit PKA activity. In a preferred embodiment of the invention, a Dampin polypeptide or polynucleotide encoding said polypeptide in used to inhibit PKA activity in a cell. This method comprises the step of: introducing a Dampin polypeptide or polynucleotide construct comprising an expression control unit operably linked to a Dampin-encoding polynucleotide into a cell. Preferred cells include but are not limited to: neurons, ovarian granulosa cells, uterine cells, hepatocytes, and myocytes. Methods of delivering a polypeptide or polynucleotide construct to a specific cell type are discussed herein. For example, a polynucleotide construct may be introduced to cells in culture by transfection, electroporation, or viral transduction, as commonly practiced in the art. As a further example, a polynucleotide construct may be introduced to a hepatocyte by packaging said polynucleotide construct into a liposomal vector; targeting the liposomal vector to the liver by embedding a hepatocyte-specific ligand in the membrane (e.g., hepatocyte growth factor); and introducing the liposome in a physiologically acceptable manner to an individual (e.g., orally or by injection). Preferably, this embodiment is directed toward: decreasing addictive behavior, especially in the case of alcohol addiction; reducing cocaine- or amphetamine-dependent responses; reducing progesterone-dependent ovulation and egg implantation; or increasing glycogen synthesis to control blood glucose levels, as discussed herein.

In a preferred embodiment of the invention, a substance capable of decreasing the ratio of Dampin to DARPP-32 is used in a method to increase PKA activity in a neuron. Preferred compounds are additionally capable of passing through the blood brain barrier in vivo. This method comprises the step of contacting a neuron with said substance. Deficient dopaminergic signaling (and thus PKA activity) has been implicated in several major neurological and psychiatric disorders, including Parkinson's disease, Tourette's syndrome, ADD, Huntington's disease, and schizophrenia. As DARPP-32 is a vital downstream component the dopaminergic pathway, this method is preferably directed toward treatment of these disorders. Increased activity can be measured by an altered modulation of calcium channel function in response to dopamine, in situ, dopamine-mediated inhibition of the sodium-potassium ATPase (Na,K ATPase) in situ, an increased excitability of striatal and cortical neurons, or dopamine-mediated inhibition of brain sodium-potassium-ATPase activity, as determined in situ. Furthermore, this method may be used to increase sexual receptivity in a female individual. Preferred neurons for use in this method include hypothalamic neurons that express both the dopamine receptor and the progesterone receptor. Preferred individuals include breeding animals. Further preferred individuals include humans.

In a further preferred embodiment of the invention, a substance that blocks the inhibition of PKA by Dampin is used in a method to increase PKA activity in a neuron. Preferred compounds are additionally capable of passing through the blood brain barrier in vivo. This method comprises the step of contacting a neuron with said substance. This method is directed toward treatment of neurological and psychiatric disorders, including Parkinson's disease, Tourette's syndrome, ADD, Huntington's disease, and schizophrenia. Furthermore, this method may be used to increase sexual receptivity in a female individual. Preferred neurons for use in this method include hypothalamic neurons that express both the dopamine receptor and the progesterone receptor. Preferred individuals include breeding animals. Further preferred individuals include humans.

DARPP-32 is required for proper Atrial Natriuretic Factor (ANF) activity in the kidney. ANF modulates blood sodium levels and reduces blood volume by inhibiting the renal sodium-potassium-ATPase, the sole active sodium transporter in the renal basolateral epithelia throughout the nephron. In a preferred embodiment of the invention, a substance capable of decreasing the ratio of Dampin to DARPP-32 expression is used in a method to activate ANF in a cell. Preferred cells are nephronic kidney cells. This method is applied to inhibit the activity of the renal sodium-potassium-ATPase in response to ANF, as determined in situ, and increase ANF-mediated sodium excretion in vivo. Preferably, this method is directed toward decreasing blood volume and hypertension.

In a further preferred embodiment of the invention, a substance that blocks the inhibition of PKA by Dampin is used in a method to activate ANF in a cell. Preferred cells are nephronic kidney cells. This method is applied to inhibit the activity of the renal sodium-potassium-ATPase in response to ANF, as determined in situ, and increase ANF-mediated sodium excretion in vivo. Preferably, this method is directed toward decreasing blood volume and hypertension.

Protein of SEQ ID NO:92 (Internal Designation Clone 651658_181-35-2-0C8-F)

The cDNA of clone 651658—181-35-2-0C8-F (SEQ ID NO:91) encodes the protein of SEQ ID NO:92, comprising the amino acid sequence:

MPSSVSWGILLLAGLCCLVPVSLAEDPQGDAAQKTDTSHHDQDHPTFNKITPNLAEFAFSLYRQLAHQSNSTNIFFSPVSIATAFAMLSLGTKADTHDEILESLNFNLTEIPEAQIHEGFQELLRTLNQPDSQLQLTTGNGLFLSEGLKLVDKFLEDVKKLYHSEAFTVNFGDTEEAKKQINDYVEKGTQGKIVDLVKELDRDTVFALVNYIFFKGKWERPFEVKDTEEEDFHVDQATTVKVPMMKRLGMFNIQHCKKLSSWVLLMKYLGNATAIFFLPDEGKLQHLENELTHDIITKFLENEDRRSASLHLPKLSITGTYDLKSVLGQLGITKVFSNGADLSGVTEEAPLKLSKAVHKAVLTIDEKGTEAAGAMFLEAIPMSIPPEVKFNKPFVFLMIEQNTKSPLFMGKVVNPTQK (SEQ ID NO:92). Accordingly, it will be appreciated that all characteristics and uses of polypeptides of SEQ ID NO:92 described throughout the present application also pertain to the polypeptides encoded by the nucleic acids included in clone 651658—181-35-2-0-C8-F. In addition, it will be appreciated that all characteristics and uses of the polynucleotides of SEQ ID NO:91 described throughout the present application also pertain to the nucleic acids included in clone 651658—181-35-2-0-C8-F. A preferred embodiment of the invention is directed toward the compositions of SEQ ID NO:91 and SEQ ID NO:92. Also preferred are polypeptide fragments having a biological activity as described herein and the polynucleotides encoding the fragments.

The cDNA of SEQ ID NO:91 is a novel variant of the human alpha 1 anti-trypsin protein named VAGS, encoded by a gene located on chromosome 14, specifically at position 14q32.1. The cDNA of SEQ ID NO:91 encodes a 418 amino-acid protein of SEQ ID NO:92.

Proteases are key components of a broad range of biological pathways and can be classified into four groups according to their catalytic mechanisms: the serine, cysteine (thiol), aspartic (carboxyl), and metalloproteases. VAGS displays serpin motif and thus belongs to the serine protease inhibitor family of protein named serpin. Serpins are irreversible suicide inhibitors of proteases that have a central role in regulating proteolysis in diverse physiological processes such as blood coagulation, fibrinolysis, complement activation, angiogenesis, apoptosis, inflammation, neoplasia and viral pathogenesis. VAGS neutralizes any trypsin formed prematurely within the cells by binding to its active site forming stable complexes with its target enzymes, which is a general property of serpin/serine protease interactions. VAGS is synthesized in the liver and, in response to inflammatory stimuli, inhibits the proteolytic enzyme neutrophil elastase, released from activated neutrophils at sites of inflammation. In hepatocytes, VAGS. expression is increased by the cytokine interleukin-6 (IL-6). Synthesis of VAGS is tightly regulated by the net balance of neutrophil elastase and VAGS at sites of inflammation/tissue injury. Alterations of a serpin which can affect its functional levels may result in pathology., Congenital serpin deficiencies cause specific clinical syndromes such as thrombosis with anti-thrombin III deficiency. Individuals with VAGS deficiency are susceptible to premature development of emphysema and liver diseases. In addition, changes in the balance between serine proteases and their cognate inhibitors may lead to pathological states similar to those associated with some neurodegenerative diseases such as Alzheimer's disease.

In one embodiment, VAGS, or fragment thereof, provide an in vitro assay to test the specific sensitivity of various proteases to VAGS. The protease inhibitor activity of VAGS may be assessed using any techniques known to those skilled in the art including those disclosed in the U.S. Pat. No. 5,955,284, which disclosure is hereby incorporated by reference in its entirety. Possible substrates for the protein of the invention include, but are not limited to, serine proteases such as elastase, trypsin, chymotrypsin, thrombin III, plasmin, heparin, complement II, plasminogen activator, protein C, interleukin-1beta converting enzyme, preferably trypsin, elastase and chymotrypsin. Methods to assess the activity of such proteases inhibitors include the steps of contacting the inhibitor to be tested with one or several protease substrate in a competition system, and detecting the amount of inhibition of the present protein that occurs. Competitive system can also be used to determine the respective affinities of VAGS among all protease substrates.

In another embodiment, VAGS, or fragment thereof, may be used to remove, identify or inhibit contaminating proteases in a sample. Compositions comprising the polypeptides of the present invention may be added to biological samples as a "cocktail" with other protease inhibitors to prevent degradation of protein samples. The advantage of using a cocktail of protease inhibitors is that one is able to inhibit a wide range of proteases without knowing the specificity of any of the proteases. Using a cocktail of protease inhibitors also protects a protein sample from a wide range of future unknown proteases which may contaminate a protein sample from a vast number of sources. For example, the protein of the invention or fragment thereof are added to samples where proteolytic degradation by contaminating proteases is undesirable. Such protease inhibitor cocktails are widely used in assays to inhibit proteases susceptible of degrading a protein of interest for which the assay is to be performed. Alternatively, the protein of the invention or fragment thereof may be bound to a chromatographic support, either alone or in combination with other protease inhibitor, using techniques well known in the art, to form an affinity chromatography column. A sample containing the undesirable protease is run through the column to remove the protease. Alternatively, the same methods may be used to identify new target proteases of the protein of the invention.

In one embodiment, VAGS, or fragment thereof, may be useful to quantify the amount of a given protease in a biological sample, and thus used in assays and diagnostic kits for the quantification of proteases in bodily fluids or other tissue samples, in addition to bacterial, fungal, plant, yeast, viral or mammalian cell cultures. In a preferred embodiment, the sample is assayed using a standard protease substrate. A known concentration of protease inhibitor is added, and allowed to bind to a particular protease present. The protease assay is then rerun, and the loss of activity is correlated to the protease inhibitor activity using techniques well known to those skilled in the art. Preferred proteases in this embodiment are seine protease, more preferably elastase, trypsin and chymotrypsin.

In another preferred embodiment, VAGS, or fragment thereof may be used as anti-microbial agent useful to inhibit exogenous proteases implicated in a number of infectious diseases including, but not limited to, bacterial and parasite-borne infections. For example, protease inhibitors are able to inhibit growth of all strains of group. A streptococci, including antibiotic-resistant strains. Accordingly, the present invention may be used to retard or inhibit the growth of certain microbes either in vitro or in vivo.

The present invention provides a method for identify other molecules which specifically binds VAGS. For example, the composition of the balance proteases/proteases inhibitors of a diseased tissue can be determined by isolating the present protein under conditions that do not disrupt protein-protein interactions, and determining the identity of proteins associated with the present protein. Such associated proteins can be identified by any standard method including, but not limited to, immunoprecipitation and immuno-affinity columns. It can also comprise an investigation using the yeast-2-hybrid trap for identification of new interactions involving relevant targets of the present protein that could be implicated in some diseases affecting serpin biology. Another method can comprise the combination of the present protein with the library of molecules under conditions suitable to allow complex formation, and detecting complex formation, wherein the presence of the complex identifies a molecule which specifically binds the protein of the invention and that could be accumulated in some disorders.

In a further embodiment, VAGS provides a method of producing a recombinant serpin capable of effectively modulating serine protease activity. Despite the availability of human alpha 1 anti-trypsin from serum, quantities large enough for therapeutic uses have been unobtainable, due in large part to the limited availability of human serum. Consequently, there is a great need for other sources of alpha 1 anti-trypsin to fill the needs created by therapeutic uses. In one preferred embodiment, milkers animal can be used to produce the protein of the invention in the milk, thereby generating a significant amount of this particular protein after purification. Any type of animal that produce enough quantity of milk can be used in this aim such as, but not limited to, sheep, goat, and cow. These animals can be generated with any method of targeting overexpression of the present protein in the milk. Also in this embodiment, the protein of the invention can be produced in host cells that have been transfected with an appropriate expression vector comprising a nucleic acid sequence coding for the present protein. The host cells are cultured under conditions whereby the nucleic acid sequence coding for this particular protein is expressed. After a suitable amount of time for the product to accumulate, the protein is purified from the host cells or medium surrounding the cells. Introduction of an expression vector incorporating a nucleic acid sequence coding for the protein of the invention into a host cell can be performed in a variety of ways, such as but not limited to calcium or lithium chloride treatment, electroporation, lipofection.

In another embodiment, use of VAGS provides a method of effectively modulating serine proteases activity in cells. For example, the level or activity of the present protein can be increased in cells to decrease the rate or inhibit specific serine proteases by contacting the biological sample with an amount of the present protein sufficient to decrease the rate or inhibit specific serine proteases of one or more cells within the sample, or with a compound that increases the activity or expression of the present protein within one or more cells of the sample. Such methods can be performed either in vitro or in vivo. The level of the present protein can be increased in cells in any of a number of ways, including by administering purified protein to the cells, transfecting the cells with a polynucleotide encoding the protein, or administering a compound to the cells that causes an increase in the activity or expression of the protein. Alternatively, serine proteases level can be increase by decreasing the level of the present protein in cells, for example using antisense molecules, or more specifically inhibit the activity, of the present protein using direct or indirect inhibitor molecules or antagonistic antibodies directed against the present protein.

The present invention also provides animal models generated by modulating the expression or activity of the present protein in one or more tissues of the animal. Such animals are useful for a number of purposes, for example to assist with the study of the human alpha 1 anti-trypsin deficiency disease, because they represent an in vivo assay method for testing candidate molecules potentially useful for the treatment of various pathophysiological aspects of diseases specifically related to the activity of the present protein. Study of the phenotype of such models can also allow the identification of additional human equivalent diseases caused by or linked with alpha 1 anti-trypsin deficiency. These animals can be generated with any method of targeting overexpression or inactivation of the present protein. Such models are extremely useful, e.g. in the assessment of candidate therapies and drugs for the treatment of inflammatory diseases and conditions.

In other embodiment, VAGS, or fragment thereof, is used to diagnose diseases or disorders associated with altered expression or activity of the present protein. In particular, it is useful in diagnosing patients with deficient amounts of the present invention which results in uncontrolled activity of target proteases. Examples of such diseases and disorders include, but are not limited to, alpha 1 anti-trypsin deficiency associated disorders and more specifically liver diseases, or diseases associated with an excess level of elastase, such as rheumatoid arthritis, emphysema, and psoriasis. The method includes the steps of contacting a fluid or tissue sample obtained from an individual suspected of suffering from the disease or condition, or at risk of developing the disease or condition, with a compound capable of selectively binding the present protein or nucleic acids, e.g. a polyclonal or monoclonal antibody or any immunologically active fragment thereof, a nucleic acid probe, etc., and detecting the level, or any other detectable property of the present protein in the sample, where a difference in the level or other property in the sample relative to in a control sample indicates the presence of the disease or disorder, or of a propensity for developing the disease or disorder. In this embodiment, the identification of mutations using well known PCR or RT-PCR techniques and in particular in with real time PCR system that could facilitate diagnosis of such conditions. Alternatively, using such a method, the present invention provides a tool to correlate modulations in the expression of the specific variant of the invention with some pathologies which have never been linked to. Thus, the present invention provides a novel candidate gene for such conditions.

A further embodiment of the present invention is to provide novel methods and compositions useful for the treatment of diseases and conditions related to the abnormal function of proteases or their inhibitors. The VAGS, or fragment thereof, may be used to inhibit proteases implicated in a number of diseases where cellular proteolysis occur such as diseases characterized by tissue degradation preferably including, but not limited to, arthritis, muscular dystrophy, inflammation, tumor invasion, glomerulonephritis, parasite-borne infections, Alzheimer's disease, periodontal disease, and cancer metastasis. The methods and compositions can also be useful for treatment of septic shock, pancreatitis, coagulation disorders. In a more preferably embodiment, the invention relates to compositions and methods to use the protein of the invention or fragment thereof in diseases characterized by an abnormally elevated levels of trypsin, chymotrypsin, or elastase, including but not limited to, chronic emphysema of the lungs, cirrhosis, liver diseases, cystic fibrosis, and more specifically for alpha 1 anti-trypsin deficiency associated disorders such as aneurysm or toxic shock. In this embodiment, the present invention is preferably applied in the treatment of diseases associated with an excess level of elastase, such as rheumatoid arthritis, emphysema, and psoriasis. Indeed, uncontrolled secretion of elastase which frequently results from aging of the cells or genetic defects may cause non-specific proteolysis and trigger destructive processes associated with those various chronic diseases. Such methods comprise the administration of a therapeutically-effective amount of the present protein to mammals suffering from the disease or condition, where "effective amount" is meant a concentration of the present protein which is capable of modulating the activity of serine proteases. The compositions of the invention are preferably delivered to the affected mammals in combination with a physiologically acceptable liquid, such as a saline solution or other buffer, or physiologically acceptable carrier. For treatment of skin inflammation, the compositions of the invention may be applied to the affected area in combination with a physiologically acceptable ointment or cream. The proportional ratio of active ingredient to pharmaceutical carrier will naturally depend on the chemical nature, solubility, and stability of the recombinant serine protease inhibitor. The particular amount of the compositions of the invention that will be administered to the mammal for any particular condition will depend on the clinical condition of the patient and the type of illness, and other factors such as the weight, age, the patient and route of delivery. Such composition can be administered by any suitable route including, but not limited to, intravenous, intramuscular, intraperitoneal, subcutaneous routes, and topically to an affected area of the skin or by absorption through epithelial or mucocutaneous linings such as nasal, oral, vaginal, rectal. Alternatively, for treatment purposes, the protein of the invention may be administrated using any of the gene therapy methods known in the art. These compositions can comprise the protein of the invention, and, optionally, one or more other types of protease inhibitors, or any other compound of interest. Indeed, in this embodiment, the present invention find use in drug potentiation applications. For example, therapeutic agents such as antibiotics or antitumor drugs can be inactivated through proteolysis by endogenous proteases, thus rendering the administrated drug less effective or inactive. Accordingly, the protease inhibitor of the invention may be administrated to a patient in conjunction with a therapeutic agent in order to potentiate or increase the activity of the drug. This co-administration may be by simultaneous administration, such as a mixture of the protease inhibitor and the drug, of by separate or sequential administrations. All of these components may be either obtained from natural sources or produced by recombinant genetic engineering techniques and/or chemical modification.

Since the regulation of serine proteases by their inhibitors are critical for the control of tissue destruction in the diseases described above, in a further embodiment, VAGS, or fragment thereof provides an assay for the monitoring of markers in vivo for characterisation of disease states. The invention thus includes test kits useful for the quantification in a biological sample of the amount of the, present protein. The kits comprise at least one immunological binding partner, e.g. a monoclonal or polyclonal antibody specific for the protein of the invention and coupled to detectable markers. In this embodiment, the application of such assays can be used to monitor the progress of therapy administered to treat these or other conditions. Further, the assays can be used as a measure of toxicity, or during clinical testing of new drugs to assess the impact on tissue degradation. Thus the assays may be applied in any situation wherein the present invention can be used as an index of the condition, treatment, or effect of substances directly administered to the subject or to which the subject is exposed in the environment. This marker may thus also play a role as prognostic indicators, preferably concerning inflammatory diseases. For example, it can be used in the Alzheimer's disease where chronic inflammation is an accompanying physiological contributor to this multifactor pathology. Also in a preferred embodiment, the present invention provides a method of detecting the presence and/or monitoring the metastatic progress of a malignancy. Indeed, metastatic potential can be influenced by the interaction between the neoplastic cells and their microenvironment such as extracellular matrix and proteolytic enzymes including the present protein. The invention thus includes test kits useful for quantify the amount of the present protein in a biological sample comprising the steps of contacting the biological sample with a specific monoclonal or polyclonal antibody specific for the present protein and coupled to detectable markers. Thus, the condition of a patient can be monitored continuously and the quantified amount of such proteins measured in the pathological sample can be compared with the amount quantified in a biological sample of a normal individual or with the previous analysis of the same patient. In all this embodiment, this marker can be measured effectively in plasma, serum or blood, by any suitable method, including immunoassays. It can also preferably be measured in tissues and fluids recovered from inflammatory sites. Thus, the condition of a subject can be monitored continuously and the quantified amount of this particular protein measured in the pathological sample can be compared with the amount quantified in a biological sample of a normal individual.

Polynucleotides of SEQ ID NO:93 (Internal Designation Clone 150011_110-006-3-0-D5-F) and SEQ ID NO:95 (Internal designation Clone 500737461_205-43-3-0-E3-F)

The cDNA of clone 150011_110-006-3-0-D5-F (SEQ ID NO:93) encodes an allele of Tissue Factor Pathway Inhibitor-1 (TFPI-1), comprising the nucleotide sequence:

CTCTTTGCTCTAACAGACAGCAGC-
GACTTTAGGCTGGATAATAGTCAAATTCTTACC
TCGCTCTTTCACTGCTAGTAAGATCA-
GATTGCGTTTCTTTCAGTTACTCTTCAATCGC
CAGTTTCTTGATCTGCTTCTAAAA-
GAARAAGTAGAGAAGATAAATCCTGTCTTCAAT
ACCTGGAAGGAAAAACAAAATAACCT-
CAACTCCGTTTTGAAAAAAACATTCCAAGA
ACTTTCATCAGAGATTTTACTTAGAT-
GATTTACACAATGAAGAAAGTACATGCACTT
TGGGCTTCTGTCCCTGCTGCTTAATCT-
TGCCCCTGCCCCTCTTAATGCTGATTCTGAG GAA-
GATGAAGAACACACAATTATCACA-
GATACGGAGTTGCCACCACTGAAACTTAT
GCATTCATTTTGTGCATTCAAGGCGGAT-
GATAGCCCATGTAAAGCAATCATGAAAAG
ATTTTTCTTCAATATTTTCACTCGA-
CAGTGCGAAGAATTTATATATGGGGGATGTGAA
GGAAATCAGAATCGATTTGAAAGTCTG-
GAAGAGTGCAAAAAAATGTGTACAAGAGA TAMT-
GCAAACAGGATTATAAAGACAACATTG-
CAACAAGAAAAGCCAGATTTCTGCT
TTTTGGAAGAAGATCCTGGAATATGTC-
GAGGTTATATTACCAGGTATTTTTATAACA ATCAGA-
CAAAACATGTGAACGTTTCAAGTATG-
GTGGATGCCTGGGCAATATGAACA
ATTTTGAGACACTGGAAGAATGCAAGAA-
CATTTGTGAAGATGGTCCGAATGGTTTCC AGGTG-
GATAATTATGGAACCCAGCTCAATGCT-
GTGAATAACTCCCTGACTCCGCAAT
CAACCAAGGTTCCCAGCCTTTTTGTTA-
CAAAAGAAGGAACAAATGATGGTTGGAAG AAT-
GCGGCTCATATTTACCAAGTCTTTYT-
GAACGCCTTCTGCATTCATGCATCCATGT
TCTTTCTAGGATTGGATAGCATTTCAT-
GCCTATGTTAATATTTGTGCTTTTGGCATTTC
CTTAATATTTATATGTATACGTGATGC-
CTTTGATAGCATACTGCTAATAAAGTTTTAA TATT-
TACATGCATAGGAAAAAAAAAAAAAAA (SEQ ID NO:93). Accordingly, it will be appreciated that all characteristics and uses of the polypeptides of SEQ ID NO:94 and polynucleotides of SEQ ID NO:93 described throughout the present application also pertain to the nucleic acids included in Clone 150011_$_{110}$-006-3-0-D5-F. Clone 150011_110-006-3-0-D5-F is alternatively referred to herein as TFPI-C16Pfs in reference to the nucleotide polymorphism that is a subject of the present invention. A preferred embodiment of the invention is directed toward the compositions of SEQ ID NO:93, SEQ ID NO:94, and Clone 150011—110-006-3-0-D5-F. Also preferred are polypeptide fragments having a biological activity as described herein and the polynucleotides encoding the fragments.

The cDNA of clone 500737461—205-43-3-0-E3-F (SEQ ID:95) encodes an allele of Tissue Factor Pathway Inhibitor-1 (TFPI-1), comprising the nucleotide sequence: CTCTTTGCTCTAACAGACAGCAGC-GACTTTAGGCTGGATAATAGTCAAATTCTTACC TCGCTCTTTCACTGCTAGTAAGATCA-GATTGCGTTTCTTTCAGTTACTCTTCAATCGC CAGTTTCTTGATCTGCTTCTAAAAGAA-GAAGTAGAGAAGATAAATCCTGTCTTCAAT ACCTG-GAAGGAAAAACAGAATAACCTCAACTC-CGTTTTGAAAAAAACATTCCAAGA ACTTTCATCAGAGATTTTACTTAGAT-GATTTACACAATGAAGAAAGTACATGCACTT TGGGCTTCTGTATGCCTGCTGCT-TAATCTTGCCCCTGCCCCTCTTAATGCTGATTCTG AGGAAGATGAAGAACACACAATTATCA-CAGATACGGAGTTGCCACCACTGAAACTT ATGCAT-TCATTTTGTGCATTCAAGGCGGATGATG-GCCCATGTAAAGCAATCATGAAA AGATTTTTCTTCAATATTTTCACTCGA-CAGTGCGAAGAATTTATATATGGGGGATGTG AAG-GAAATCAGAATCGATTTGAAAGTCTG-GAAGAGTGCAAAAAAATGTGTACAAGA GATAATGCAAACAGGATTATAAAGACAA-CATTGCAACAAGAAAAGCCAGATTTCTG CTTTTTG-GAAGAAGATCCTGGAATATGTCGAGGT-TATATTACCAGGTATTTTTATAAC AATCAGACAAAACAGTGT-GAACGTTTCAAGTATGGTGGATGC-CTGGGCAATCAACAATTTTGAGACACTGGAACAAT-GCAAGAACATTTGTGAAGATGGTCCGAATGGTTTC-C AGGTGGATAATTATGGAACCCAGCT-CAATGCTGTGAATAACTCCCTGACTCCGCAAT CAACCAAGGTTCCCAGC-CTTTTTGAATTTCACGGTCCCTCATGGT-GTCTCACTCCAGC AGACAGAGGATTGTGTCGTGC-CAATGAGAACAGATTCTACTACAATTCAGTCATTGG GAAATGCCGCCCATTTAAGTACAGTG-GATGTGGGGGAAATGAAAACAATTTTACTTC CAAACAAGAATGTCTGAGGGCATG-TAAAAAAGGTTTCATCCAAAGAATATCAAAAG GAGGCCTAATTAAAACCAAAAGAAAAA-GAAAGAAGCAGAGAGTGAAAATAGCATA TGAA-GAAATTTTTGTTAAAAATATGT-GAATTTGTTATAGCAATGTAACATTAATTCTA CTAAATATTTTATATGAAATGTTTCAC-TATGATTTTCTATTTTTCTTCTAAAATGCTTT TAAT-TAATATGTTCATTAAATTTTCTATGCT-TATTGCAAAAAAAAAAAA (SEQ ID NO:95). Accordingly, it will be appreciated that all characteristics and uses of the polynucleotides of SEQ ID NO:95 and polypeptides of SEQ ID NO:96 described throughout the present application also pertain to the nucleic acids included in Clone 500737461—205-43-3-0-E3-F. Clone 500737461—205-43-3-0-E3-F is alternatively referred to herein as TFPI-M162Qfs in reference to the nucleotide polymorphism that is a subject of the present invention. A preferred embodiment of the invention is directed toward the compositions of SEQ ID NO:95, SEQ ID NO:96, and Clone 500737461—205-43-3-0-E3-F. Also preferred are polypeptide fragments having a biological activity as described herein and the polynucleotides encoding the fragments.

The extrinsic coagulation pathway is initiated on exposure of Tissue factor (TF) to plasma (McVey J H, Bailliere's Clinical Haematology 12:361-72 (1999) which disclosure is hereby incorporated by reference in its entirety). Tissue Factor Pathway Inhibitor-1. (TFPI-1) is a negative regulator of the extrinsic coagulation pathway (U.S. Pat. No. 5,849,875 which disclosure is hereby incorporated by reference in its entirety).

TFPI-1 is a secreted trivalent Kunitz-type plasma proteinase inhibitor. TFPI-1 negatively regulates the initiation of coagulation through a mechanism of activated factor X (FXa) feedback inhibition of the catalytic complex of activated factor VII (FVa) and TF. That is, TFPI-1 directly inhibits FXa and, in a FXa-dependent fashion, produces feedback inhibition of the TF-FVIIa complex by allosteric enablement of TF-FVIIa binding TFPI-1 is the major inhibitor of the protease activity of the TF-FVIIa complex. The second Kunitz domain of TFPI-1 binds and inhibits FXa, whereas the first Kunitz domain is responsible for the inhibition of FVIIa in the TF-FVIIa complex. The function of the third Kunitz domain is unknown, although there is evidence, that it contains a heparin binding site. Heparin binding site(s) have also been mapped carboxyl-terminal to the third Kunitz domain.

Tissue factor pathway of coagulation plays a dominant role during normal haemostasis. TFPI-1, expressed primarily by the microvascular endothelium, appears to be the major physiologic inhibitor of TF-induced coagulation. TF-initiated coagulation also plays an important role in the pathophysiology of many diseases, including coronary thrombosis, disseminated intravascular coagulation, stroke, and atheriosclerosis. Several animal studies have found a beneficial effect of recombinant TFPI-1 in some of these clinical conditions.

TFPI-1 plays an important role in modulating TF-dependent thrombogenesis. Recombinant full-length TFPI-1 prevents thrombosis formation and rethrombosis after lysis in a rabbit model of jugular vein thrombosis (Kaiser, B. et al. Thromb. Haemost. 76:615-20 (1996) which disclosure is hereby incorporated by reference in its entirety). In a rat model of disseminated intravascular coagulation, TFPI-1 was found to inhibit thrombus formation (Elsayed, YA et al., Am. J. Clin. Pathol. 106:574-83 (1996) which disclosure is hereby incorporated by reference in its entirety).

High levels of TF antigen and activity are detected in atheriosclerotic lesions, particularly in the advanced lesions. When the plaques are ruptured or eroded, exposure of cellular and extracellular TF to circulating blood plays a pivotal role in mediating fibrin-rich thrombus formation leading to acute coronary syndromes. Presence of TFPI-1 in atheriosclerotic plaques is associated with reduced tissue factor activity and reduced plaque thrombogenicity. (Caplice, N M et al., Circulation 98:1051-7 (1998); Badimon, 33 et al., Circulation 99:1780-7 (1999) which disclosures are hereby incorporated by reference in their entirety).

A recent study in mice using the gene knockout technology unambiguously established that deficiency of TFPI-1 promotes atheriosclerosis and thrombosis. In this work, it was found that TFPI-1 protects from atheriosclerosis and is an important regulator of the thrombosis that occurs in the setting of atheriosclerosis (Westrick, RJ et al., Circulation, 103:3044-6 (2001) which disclosure is hereby incorporated by reference in its entirety). Importantly, it was found that in this model inactivation of only one of the two copies of the TFPI-1 gene was sufficient to promote atheriosclerosis and thrombosis.

Recently several amino acid polymorphisms have been identified for human TFPI-1. A mutation at nucleotide position 1 of exon 7 results in the substitution of leucine for proline at position 179 (numbered from the initiating methionine of TFPI-1). (Kleesiek, K et al., Blood 10:3976-7 (1998) which disclosure is hereby incorporated by reference in its entirety). This mutation occurs immediately downstream of Kunitz domain 2. (U.S. Pat. No. 5,849,875 which disclosure is hereby incorporated by reference in its entirety). This mutation has been found to be statistically associated with a higher risk for venous thrombosis (Kleesiek, K et al., Thromb. Haemost. 82:1-5 (1999) which disclosure is hereby incorporated by reference in its entirety).

A second amino acid polymorphism results in the substitution of methionine for valine at position 292 (numbered from the initiating methionine of TFPI-1). This mutation occurs very near the carboxy-terminus of TFPI-1. As might be expected for a mutation so far downstream of Kunitz domains 1 and 2, no lick was found between this mutation and venous thromboernbolic disease (Arnaud, E et al., Thromb. Haemost. 82:159-60 (1999) which disclosure is hereby incorporated by reference in its entirety).

The cDNA of clone 150011 encodes the protein of SEQ ID NO:94. In the case of TFPI-C16Pfs, a deletion of two nucleotides in codon 16 (numbered from the initiating methionine of TFPI-1).results in the substitution of proline for cysteine and in the introduction of a frame-shift leading to premature termination of the protein within the signal sequence (exon 3). Specifically, whereas codon 16 of TFPI-1 reads TGC (U.S. Pat. No. 5,849,875 which disclosure is hereby incorporated by reference in its entirety), in TFP1_C16Pfs nucleotides T and G have been deleted. As protein TFPI-C16Pfs terminates upstream of Kunitz domains 1 and 2, the protein of SEQ. ID NO:94 is nonfunctional.

The cDNA of clone 500737461 encodes the protein of SEQ ID NO:96. In the case of TFPI-M162Qfs, a deletion of two nucleotides in codon 162 (numbered from the initiating methionine of TFPI-1) and mutation of the remaining nucleotide results in the substitution of glutamine for methionine and in the introduction of a frame-shift leading to premature termination of the protein within Kunitz domain 2 (exon 6). Specifically, whereas codon 162 of TFPI-1 reads ATG (U.S. Pat. No. 5,849,875 which disclosure is hereby incorporated by reference in its entirety), in TFPI-M162Qfs two of the nucleotides have been deleted and the third changed to C. As protein TFP1-M162Qfs terminates within Kunitz domain 2, neither FXa binding nor the consequential enablement of TF-FVIIa-binding by Kunitz domain 1 occurs, leading to nonfunctional protein of SEQ ID NO:96.

The availability of informative genetic screenings and diagnostic markers for genetic predisposition to thrombosis would be of considerable value. On one hand, said information can be used by the patient to make appropriate lifestyle changes. On the other hand, said information can be used by the physician to anticipate thrombotic complications that might arise in the course of clinical procedures. In both cases, said information results in health benefit to the patient and in reduced medical costs born by the patient as well as by society in general.

The nucleotide polymorphisms that are described herein for clones 150011 (TFPI-C16Pfs) and 500737461 (TFPI-M162Qfs) and that are the subject of the present invention lead to nonfunctional TFPI-1. There is clear evidence that having even just one of the two copies of the TFPI-1 gene inactivated predisposes the patient to atheriosclerosis and thrombosis. It follows therefore that the nucleotide polymorphisms described here within the coding region of TFPI-1 that lead to nonfunctional TFPI-1 have genetic screening and diagnostic value in identifying patients that are genetically predisposed to atheriosclerosis and thrombosis.

In a preferred embodiment, the present invention provides for a method of diagnosing genetic predisposition to atheriosclerosis and thrombosis through the identification of a dinucleotide deletion in TFPI-1 codon 16 (numbered from the initiating methionine of TFPI-1). Methods of identifying such a dinucleotide deletion are well known to those skilled in the art and include, but are not restricted to, to PCR-SSCP (polymerase chain reaction followed by single-strand conformation polymorphism) (Kleesiek, K et al., Blood 10:3976-7 (1998) which disclosure is hereby incorporated by reference in its entirety).

In a further preferred embodiment, the present invention is drawn to a method of determining if an individual is at increased risk of developing atheriosclerosis and thrombosis comprising the step of identifying a dinucleotide deletion in TFPI-1 codon 16 (numbered from the initiating methionine of TFPI-1), preferably using the method of PCR-SSCP, in a biological sample, preferably blood, wherein said deletion indicates increased risk.

In an additional preferred embodiment, the present invention provides for a method of diagnosing genetic predisposition to atheriosclerosis and thrombosis through the identification of a dinucleotide deletion in TFPI-1 codon 162 (numbered from the initiating methionine of TFPI-1). Methods of identifying such a dinucleotide deletion are well known to those skilled in the art and include, but are not restricted to, to PCR-SSCP (polymerase chain reaction followed by single-strand conformation polymorphism) (Kleesiek, K et al., Blood 10:3976-7 (1998) which disclosure is hereby incorporated by reference in its entirety).

In a further preferred embodiment, the present invention is drawn to a method of determining if an individual is at increased risk of developing atheriosclerosis and thrombosis comprising the step of identifying a dinucleotide deletion in TFPI-1 codon 162. (numbered from the initiating methionine of TFPI-1), preferably using the method of PCR-SSCP, in a biological sample, preferably blood, wherein said deletion indicates increased risk.

Protein of SEQ ID NO:100 (Internal Designation Clone 479155_1744-4-4-0-C8-F).

The cDNA of clone 479155—174-4-4-0-C8-F (SEQ ID NO:99) encodes the protein of SEQ ID NO:100 comprising the amino acid sequence MIVKGVASRTVVSRPFPGNWLFSSIQLT-DDQGPVLMTTVAMPVFSKQNETRSKGILLGV VGTD-VPVKELLKTIPKYKLGIHGYAFAIT-NNGYILTHPELRLLYEEGKKRRKPNYSSVDLS EVEWEDRDDVLRNAMVNRKTGKFS-MEVKKTVDKGVHFSQTFLLLNLKQTTVKN (SEQ ID NO:100). Accordingly it will be appreciated that all characteristics and uses of polypeptides of SEQ ID NO:100 described throughout the present application also pertain to the polypeptides encoded by the nucleic acids included in Clone 479155—174-4-4-0-C8-F. In addition, it will be appreciated that all characteristics and uses of the polynucleotides of SEQ ID NO:99 described throughout the present application also pertain to the nucleic acids included in Clone 479155—174-4-4-0-C8-F. A preferred embodiment of the invention is directed toward the compositions of SEQ ID NO:99, SEQ ID NO:100, and Clone 479155—174-4-4-0-C8-F. Also preferred are polypeptide fragments having a biological activity as described herein and the polynucleotides encoding the fragments.

The protein of SEQ ID NO:100 encodes ADEVAR, a variant of calcium channel alpha2delta3 subunit resulting from alternative splicing. ADEVAR has novel function as described below.

Alpha2delta3 subunit is a component of voltage-gated Ca2+ channels. The alpha2 subunit has several hydrophobic sequences, but biosynthetic studies indicate that it is an extracellular, extrinsic membrane protein attached to the membrane through disulfide linkage to the delta subunit. The delta subunit is encoded by the 3' end of the coding sequence of the same gene as the alpha2 subunit, and the mature forms of these two subunits are produced by post-translational proteolytic processing and disulfide linkage (Catterall, W A, Annu. Rev. Cell Dev. Biol. 16:521-55. (2000) which disclosure is hereby incorporated by reference in its entirety). Alpha2delta3 subunit is expressed exclusively in the brain (Klugbauer, N et al., J. Neuroscience 19:684-691 (1999) which disclosure is hereby incorporated by reference in its entirety). Alpha2delta3 subunit plays a role in regulating neuronal Ca2+ currents (Catteral, W A, Annu. Rev. Cell Dev. Biol., 16:521-55 (2000); Stefani, A et al., Neuropharmacology. 37:83-91 (1998) which disclosures are hereby incorporated by reference in their entirety). Alpha2delata3 subunit has been implicated in epileptic seizures (Gee NS et al., J. Biol. Chem. 271:5768-76 (1996); Bryans J S et al., J. Med. Chem. 41:1838-1845 (1998) which disclosures are hereby incorporated by reference in their entirely).

ADEVAR is a product of alternative splicing leading to a soluble protein truncated at both it amino- and carboxyl-termini. ADEVAR plays a negative regulatory role in Ca2+ channel function. Diminished ADEVAR expression leads to dysregulated Ca2+ flux through the channel and reduced neuronal excitability.

In a preferred embodiment, the present invention provides for an antibody that specifically binds ADEVAR of the present invention. Further preferred is a method of making said antibody wherein said antibody recognizes a non-conformational or conformational epitope of ADEVAR.

Further preferred is a method wherein a mouse is immunized with ADEVAR. Further preferred is said immunization with ADEVAR, wherein ADEVAR is produced by recombinant DNA methodology. Further preferred is a method wherein monoclonal antibodies from said mouse are screened for binding to ADEVAR but not to full-length alpha2delta3 subunit. Further preferred is a method wherein monoclonal antibodies derived from said mouse are screened by enzyme-linked immunosorbent assay (ELISA) for binding to ADEVAR but not to full-length alpha2delta3 subunit. Methods of expressing protein by recombinant DNA methodology are well known to those skilled in the art. Methods of generating said monoclonal antibody and of establishing specificity by methods including ELISA are well known to those skilled in the art.

In a further preferred embodiment, the present invention provides for a method wherein said ADEVAR antibody is used in a method of quantitating ADEVAR in bodily fluid. Further preferred is a method of quantitating ADEVAR in bodily fluid, wherein the method of quantitation is a sandwich ELISA format. Further preferred is a method wherein said ADEVAR antibody is used to measure ADEVAR concentration in cerebrospinal fluid. In a preferred embodiment, the present invention provides for a method of contacting said antibody and specifically binding it with ADEVAR. Further preferred is a method for using said antibody diagnostically to stratify seizures and thereby add value to therapeutic strategies. Further preferred is a method of diagnosis, wherein reduced ADEVAR level is associated with predisposition to seizure in a subset of patients manifesting seizure.

Protein of SEQ ID NO:102 (Internal Designation Clone 586587_181-9-2-0-C5-F)

The cDNA of Clone 586587—181-9-2-0-C5-F (SEQ ID NO: 101) encodes hABC of SEQ ID NO:102, comprising the amino acid sequence: MACWPQLRLLLWKNLTFR-RRQTCQLLLEVAWPLFIFLILISVRL-SYPPYEQHECHFPNKA MPSAGTLPWVQGIICNAN-NPCFRYPTPGEAPGVVGNFNKSIVARLFSDARRLLL-YSQKDT SMKDMRKVLRTLQQIKKSSSRGD-KRHFLNWQKGLKPLPQALL (SEQ ID NO:102). Accordingly, it will be appreciated that all characteristics and uses of the polypeptides of SEQ ID NO:102 described throughout the present application also pertain to the polypeptides encoded by the nucleic acids included in Clone 586587—181-9-2-0-C5-F. In addition, it will be appreciated that all characteristics and uses of the polynucleotides of SEQ ID NOs:101 described throughout the present application also pertain to the nucleic acids included in Clone 586587—181-9-2-0-C5-F. A preferred embodiment of the invention is directed toward the compositions of SEQ ID NO:102, SEQ ID NO:101, and Clone 586587—181-9-2-0-C5-F. Also preferred are polypeptide fragments having a biological activity as described herein and the polynucleotides encoding the fragments.

hABC is a novel splice variant of the ATP-binding cassette 1. As a splice variant, hABC is only 162 amino-acid long whereas ABCA1 is 2261 amino acid long. hABC displays 100% identity with ABCA1 over its 140 amino-terminal residues, whereas the 22 carboxyl-terminal amino acids are unique to hABC. hABC does not display the Walker A and B motifs nor the active transport signature. The 140 common amino acids correspond to the cytoplasmic amino-terminal tail of ABCA1 that plays a role in cholesterol-binding. Furthermore, hABC displays one transmembrane domain (TCQLLLEVAWPLFIFLILISV(SEO ID NO:222)) and a "positive-hydrophobic-polar" signal peptide that is required for translocation to the plasma membrane. Moreover, the hABC splice variant is specifically expressed in liver cells. Thus, hABC plays an important role in clearing HDL from the bloodstream by binding to HDL-cholesterol, thus allowing HDL-cholesterol import to liver cells where lipids are catabolized and excreted.

An embodiment of the invention is directed to a composition comprising a hABC polypeptide sequence of SEQ ID NO:102.

A further embodiment of the invention is directed to a composition comprising a hABC polypeptide fragment having biological activity.

An embodiment of the invention is directed to a composition comprising a polynucleotide sequence of SEQ ID NO:101 encoding a hABC polypeptide.

A further embodiment of the invention is directed to a composition comprising a polynucleotide sequence encoding a hABC polypeptide fragment having biological activity.

An embodiment of the invention is directed to a composition comprising a polynucleotide sequence that yields an RNA that is complementary to the sequence of SEQ ID NO:101 encoding a hABC polypeptide.

A further embodiment of the invention is directed to a composition comprising a polynucleotide sequence that yields an RNA that is complementary to a polynucleotide sequence encoding a hABC polypeptide fragment. Preferred such a polynucleotide sequence is the polynucleotide sequence that yields an RNA that is complementary to GAGGGGACAAACGCCATTTCCTCAACTG-GCAGAAGGGACTGAAGCCTCTCCCTCAA GCCCTTTTA (SEQ ID NO:223).

A further embodiment of the invention is directed to compositions comprising an antibody directed against a hABC polypeptide or against a hABC polypeptide fragment having the same biological activity. Preferably, the antibody specifically binds to the hABC polypeptide or and not to the ABCA1 polypeptide. Even more preferably, the antibody recognizes the LQQIKKSSSRGDKRHFL (SEQ ID NO:224) amino-acid sequence or the RHFLNWQKGLK-PLP (SEQ ID NO:225) amino-acid sequence.

An embodiment of the present invention relates to methods of measuring the circulating HDL-cholesterol in bodily fluids. Methods of detecting measuring the circulating HDL-cholesterol comprise the steps of i) labeling by standard methods of the hABC polypeptide with a molecule which can be used to provide a quantifiable signal, ii) addition of this probe, under conditions suitable for the formation of hybridization complexes, to a fluid obtained from a patient and to control fluids containing a known amount of HDL-cholesterol, iii) washing of the samples, after a suitable incubation period, in order to remove all hABC polypeptides that are not complexed with HDL-cholesterol, and iv) comparison of the resulting signal with control samples containing a known amount of HDL-cholesterol. Such methods can be used in diagnostic kits for detecting diseases associated with low circulating HDL-cholesterol level, for evaluating the efficacy of a particular therapeutic treatment regimen in animal studies and in clinical trials, and for monitoring the treatment of an individual patient. The binding efficiency of hABC to HDL-cholesterol can be determined using any technique familiar to those skilled in the art, e.g. using the. assay described in U.S. Pat. No. 5,962,322, which disclosure is hereby incorporated by reference in its entirety.

An embodiment of the present invention relates to compositions comprising an antibody directed against hABC or fragment thereof, and to a method to decrease uptake of HDL-cholesterol comprising the step of inhibiting hABC binding to HDL-cholesterol using an anti-hABG antibody.

Preferably, such compositions comprise the preferred antibodies described above. Such compositions can be administered to a cell, a tissue sample or a patient. Preferably, this method is directed to treating an individual with low circulating HDL-cholesterol level by decreasing HDL-cholesterol clearance.

Another embodiment relates a method to decrease uptake of HDL-cholesterol comprising the step of inhibiting hABC expression without affecting ABCA1 expression using an antisense polynucleotide. In such a method, recombinant expression vectors comprising a polypeptide that yields an RNA that is complementary to the sequence of the hABC mRNA can be administered to cell, a tissue sample or a patient. Preferred such an antisense polynucleotide is described above. Preferred expression vectors include viral vectors, especially adenoviral and lentiviral vectors. Preferably, the antisense polynucleotides of the present invention are administered to hepatocytes.

In another embodiment, genetic modification of a cell with a vector comprising a polynucleotide that yields an RNA that is complementary to the sequence of the hABC mRNA may be accomplished using one or more techniques well known in the gene therapy field. For example, one of the methods described in Mulligan (Mulligan, Science, 260:926-32 (1993)), which disclosure is hereby incorporated by reference in its entirety, can be used. Preferably, such a method is directed to treating an individual with low circulating HDL-cholesterol level by decreasing HDL-cholesterol clearance.

A further embodiment of the present invention is directed to substances that decrease hABC expression without affecting ABCA1 expression, and to, a method of screening for such substances comprising the steps of: i) contacting a cell with a test substance, ii) comparing hABC expression in the cell after exposure to that of an unexposed control cell, iii) comparing ABCA1 expression in the cell after exposure to, that of an unexposed control cell, iv) quantifying said expression levels, and v) determining the ratios of hABC and ABCA1 expression in an exposed cell relative to the expression in an unexposed cell. Preferably, hABC expression is studied in an hepatocyte and ABCA1 expression is studied in a macrophage.

In another preferred embodiment, compositions comprising substances that decrease hABC expression without affecting ABCA1 expression can be administered to patients presenting low levels of HDL-cholesterol.

Additionally, the compositions comprising an antibody directed against HABG or substances that decrease hABC expression without affecting ABCA1 expression can be processed in accordance with conventional methods of pharmacy to produce medicinal agents for administration to patients. For example, the pharmaceutical composition comprising an antibody directed against hABC substances that decrease hABC expression without affecting ABCA1 expression may be made up in a solid form (e.g. granules for oral administration, powders for inhalation) or in a liquid form (e.g. solutions for oral administration or for injection).

Effectiveness of the compositions can be verified in vivo by measuring the plasma HDL-cholesterol level of an animal model before and after administration of the composition of the present invention. The circulating IDL-cholesterol level can for example be measured using the fast pressure liquid chromatography technique as described in U.S. Pat. No. 5,962,322, which disclosure is hereby incorporated by reference in its entirety. The dosage regimen for treating a human patient presenting low circulating HDL-cholesterol with compositions of the present invention may vary widely, but can be determined using standard methods. For example, the amount of antibody directed against or substances that decrease hABC expression without affecting ABCA1 expression is an amount sufficient to increase circulating low HDL-cholesterol in the plasma of a subject.

The compositions of the invention may be administered alone or in combination with other known agents increasing circulating HDL-cholesterol level, e.g., gemfibrozil, niacin and the SR-BI HDL-cholesterol receptor. Diseases associated with low circulating HDL-cholesterol level that may be treated by compositions and methods of the present invention include, but are not limited to, artherosclerosis, angioplasty, dyslipidemia associated with non insulin-dependant diabetes mellitus, obesity and various other coronary artery diseases.

Protein of SEQ ID NO:104 (Internal Designation Clone 620315_188-13-1-0-G12-F)

The cDNA of Clone 620315_188-13-1-0-G12-F (SEQ ID NO: 103) encodes MOBP-81h of SEQ ID NO:104, comprising the amino acid sequence: MSQKPAKEGPRL-SKNQKYSEHFSIHCCPPFTFLN-SKKEIVDRKYSICKSGCFYQKKEEDW ICCACQKTR-LKRKIRPTPKKK (SEQ ID NO:104). Accordingly, it will be appreciated that all characteristics and uses of the polypeptides of SEQ ID NO:104 described throughout the present application also pertain to the polypeptides encoded by the nucleic acids included in Clone 620315_188-13-1-0-G12-F. In addition, it will be appreciated that all characteristics and uses of the polynucleotides of SEQ ID NOs:103 described throughout the present application also pertain to the nucleic acids included in Clone 620315_188-13-1-0-G12-F. A preferred embodiment of the invention is directed toward the compositions of SEQ ID NO:104, SEQ ID NO:103, and Clone 620315_1 88-13-1-O-G 12-F. Also preferred are polypeptide fragments having a biological activity as described herein and the polynucleotides encoding the fragments.

The protein of the present invention, named MOBP-81h, is a novel splice variant of the myelin-associated oligodendrocytic basic protein (MOBP, Genbank accession number. BAA05659). MOBP-81h is only 81 amino acids long, whereas MOBP is 183 amino acids long. The first exon is identical between the two cDNAs. MOBP-81h lacks the second exon of MOBP, and the twelve carboxyl-terminal amino acids of MOBP-81h are unique to this splice variants. MOBP-81h, is the first splice variant described for the human MOBP protein. MOBP-81h is specifically expressed in CNS oligodendrocytes, and plays a role in maintaining myelin sheath integrity.

An embodiment of the invention is directed to a composition comprising a MOBP-81h polypeptidesequence of SEQ ID NO:104.

A further embodiment of the invention is directed to a composition comprising a MOBP-81h polypeptide fragment having biological activity.

A further embodiment of the invention is directed to a composition comprising a polynucleotide sequence of SEQ ID NO:103 encoding a MOBP-81h polypeptide.

A further embodiment of the invention is directed to a composition comprising a polynucleotide sequence encoding a MOBP-81h polypeptide fragment having biological activity., In another embodiment, the compositions of the present invention comprise MOBP-81h polypeptides. The method of producing MOBP-81h polypeptides comprises the steps of: i). transfecting a mammalian host cell with a recombinant expression vector comprising a polynucleotide of the present invention, and ii) purifying the produced protein. The purification of the protein can be done following any technique well-known to those skilled in the art. Preferably, an antibody directed against MOBP-81h or fragment thereof may be bound to a chromatographic support to form an affinity chromatography column. Even more preferably, the: antibody recognizes the twelve carboxyl-terinai amino acids of MOBP-81h.

An embodiment of the present invention relates to methods of using the polypeptides and the polynucleotides of the present invention to treat or to reduce in severity demyelinating disorders. Any compositions and methods containing, e.g., MOBP-81h polypeptide or fragment thereof, a polynucleotide encoding the protein, or a compound that increases the expression or activity of MOBP-81h can be used.

In an embodiment, the methods of the present invention relate to the administration of a recombinant expression vector comprising one of the polynucleotides of the invention to a patient suffering from a demyelinating disease. Preferred expression vectors include viral vectors, especially adenoviral and lentiviral vectors.

In another embodiment, genetic modification of a cell with a vector comprising one of the polynucleotides of the invention may be accomplished using one or more techniques well known in the gene therapy field. For example, one of the methods described in Mulligan (Mulligan, Science, 260:926-32 (1993)), which disclosure is hereby incorporated by reference in its entirety, can be used.

In still another embodiment, the compositions of the present invention comprise a substance that increases MOBP-81h expression.

Additionally, the methods of the present invention relate to methods of screening test substances that increase MOBP-81h expression. These methods comprise the steps of: i). contacting a cell with a test substance; and ii) comparing MOBP-81h expression in the cell after exposure to the test substance to that of an unexposed control cell. Preferably, the test substance modifies the expression of MOBP-81h in oligodendrocytes while not in other cell types.

Effectiveness of compositions and methods of the present invention to treat demyelinating diseases can be verified in vitro by studying the effects of the compositions of the present invention on the morphology of myelin sheaths by immunoelectron microscopy. Effectiveness of compositions and methods of the present invention to treat demyelinating diseases can be verified in vivo using experimental models of demyelinating disorders, e.g., TMEV-infected mice. Effective doses of the polypeptides or polynucleotides of the present invention for treating a patient suffering from demyelinating disorders can be determined according to the relevant techniques. For example, the effective amounts of compositions of the present invention can be determined by measuring the necessary and sufficient amount of composition for disappearance or reduction in severity of clinical manifestations associated with demyelinating disorders (e.g., tremor, tonic seizure, unstable locomotion, ataxia).

In a preferred embodiment, MOBP-81h polypeptides or a substance that increases MOBP-81h expression can be processed in accordance with conventional methods of pharmacy to produce medicinal agents for administration to patients. Thus, the pharmaceutical composition comprising MOBP-81h or fragment thereof or a substance that increases MOBP-81h expression may be made up in a solid form (e.g. granules for oral administration, powders for inhalation) or in a liquid form (e.g. solutions for oral administration or for injection).

The compositions of the invention may be administered alone or in combination with other known agents treating demyelinating disorders, e.g., imidazol derivatives or MBP molecules.

Demyelinating disorders that may be treated by a composition containing MOBP-81h or fragment thereof include but are not limited to leukodystrophies (e.g. Krabbe's disease, metacbromatic leukodistrophy, AUD, Canavan disease, Alexander disease), leukoencephalopathies, multiple sclerosis and virus-induced inflammatory detyelination.

Protein of SEQ ID NO: 106 (Internal designation Clone 646477_181-19-2-0-F4-F)

The cDNA of Clone 646477_181-19-2-0-F4-F (SEQ ID NO:105) encodes novel Apolipoprotein H (NAPOH) of SEQ ID NO:106, comprising the amino acid sequence: MISPV-LILFSSFLCHVAIAGRTCPKPD-DLPFSTVVPLKTFYEPGEEITYSCKPGYVSRGGMR KFICPLTGLWLINTLKCTPRVCPFAG-ILENGAVRYfTFEYPNTISFSCNTGFYLNGADSAK CTEEGKWSPELPVCAPIICPPPSIPT-FATLRVYKPSAGNNSLYRDTAVFECLPQHAMFGND TITCTTHGNWTKLPECREVKCPFPSRPD-NGFVNYPAKpTLYYKDTFGCHDGYSLDGP EEIECT- KLGNWSAMPSCKASCKVPVKKATV-VYQGERVKIQEKFKNGMLHGDKVSFFCK NKEKKCSYTEDAQCIDGTIEVPKCFKEH-SSLAFWKTDASDVKPC (SEQ ID NO:106). Accordingly, it will be appreciated that all characteristics and uses of the polypeptides of SEQ ID NO:106 described throughout the present application also pertain to the polypeptides encoded by the nucleic acids included in Clone 646477__181-19-2-0-F4-F. In addition, it will be appreciated that all characteristics and uses of the polynucleotides of SEQ ID NO:105 described throughout the present application also pertain to the nucleic acids included in Clone 646477__181-19-2-0-F4-F. A preferred embodiment of the invention is directed toward the compositions of SEQ ID NO:105, SEQ ID NO:106, and Clone 646477__181-19-2-0-F4-F. Also preferred are polypeptide fragments having a biological activity as described herein and the polynucleotides encoding the fragments.

The protein of SEQ ID NO:106 is a polymorphic variant of the sequence of apolipoprotein H or beta-2-glycoprotein I precursor (swissprot accession number P02749). Like apoliprotein H, the protein of the invention displays 4 Sushi domains (PF00084) and one sushi-like domain, from amino acids 23 to 79 (Sushi 1), amino acids 84 to 137 (Sushi 2), amino acids 142 to 200 (Sushi 3), amino acids 205 to 260 (Sushi 4) and amino acids 263 to 345 (Sushi-like). Sushi domains are also known as Complement control protein (CCP) modules, or short consensus repeats (SCR), exist in a wide variety of complement and adhesion proteins. Also, it has been reported that the domain V (sushi-like domain) specifically interacts with hydrophobic ligands (Hong, D.P. et al., Biochemistry 40:8092-8100 (2001)). Novel apolipoprotein H, the protein of SEQ ID NO:106, is highly expressed in liver.

Novel apolipoprotein H is a plasma protein with the ability to bind with various kinds of negatively charged substances. Novel apolipoprotein H (NAPOH) may prevent activation of the intrinsic blood coagulation cascade by binding to phospholipids on the surface of damaged cells. NAPOH is a strong auto-antigen that stimulates a vigorous B. cell-humoral response and T cell immunity response. NAPOH has been implicated in a variety of physiologic pathways including lipoprotein metabolism, artherosclerosis and in the production of antiphospholipid autoantibodies ("aPA"). NAPOH also binds to platelets, mitochondria, heparin, DNA, and anionic phospholipids, and has been shown to, be involved in the blood coagulation pathway, platelet aggregation, and prothrombinase activity of platelets. NAPOH exerts multiple inhibitory effects on the coagulation pathway and platelet aggregation. NAPOH is considered to be a required cofactor for anionic phospholipids antigen by the aPA found in sera of many patients with chronic inflammatory disease, like systemic lupus erythematosus, and primary antiphospholipid syndrome, but it does not seem to be required for the reactivity of aPA associated with infections. These studies suggest that the NAPOH-phospholipid compex forms the antigen to which aPA are directed. Autoantibodies to phospholipid-free. NAPOH are present in patients with primary antiphospolipid syndrome. Antiphospholipid autoantibodies are a heterogeneous group of autoantibodies including most commonly a lupus anticoagulant and anticardiolipin antibodies which are directed against negatively charged phospholipids. The presence of antiphospholipid autoantibodies has been associated with recurrent deep vein thrombosis and other thrombotic complications, including pulmonary, renal, and retinal thrombosis, as well as Budd-Chiari syndrome. In addition, antiphospholipid autoantibodies have been associated with arterial thrombosis including cerebral, retinal, and peripheral arteries. Recurrent fetal losses, usually occurring in the second and third trimester, felt to be due in part to thrombosis of the placental vessels and subsequent infarction resulting in placental insufficiency and ultimately fetal loss are associated with antiphospholipid autoantibodies.

An embodiment of the invention is directed to a composition comprising a novel Apolipoprotein H (NAPOH) polypeptide sequence of SEQ ID NO: 106.

A further embodiment of the invention is directed to a composition comprising a NAPOH polypeptide fragment having biological activity.

A further embodiment of the invention is directed to a composition comprising a polynucleotide sequence of SEQ ID NO: 105 encoding a NAPOH polypeptide.

A further embodiment of the invention is directed to a composition comprising a polynucleotide sequence encoding a NAPOH polypeptide fragment having biological activity.

Preparation and purification of the protein of SEQ ID NO:106 or fragments thereof may be carried out as described in Patent U.S. Pat. No. 5,859,213, the disclosure of which is incorporated herein by reference in its entirety. For example, a method of purifying NAPOH from human blood plasma comprising the steps: i) heating and cooling the plasma to obtain a precipitate and a supernatant, ii) separating the supernatant and acidifying the supernatant, iii) adding a precipitation agent to the supernatant and separating aqueous albumin solution from second precipitate, iv) subjecting the aqueous albumin solution to affinity chromatography; and v) eluting the particulate support to obtain NAPOH.

A further embodiment of the invention is directed to a method of screening test substances for activators or inhibitors of NAPOH expression comprising the steps of: i) contacting a cell with a test substance; and ii) comparing NAPOH expression in the cell after exposure to the test substance to that of an unexposed control cell. As a result, such NAPOH activators are of great potential as new drugs due to their ability to induce coagulation and are expected to be useful in treatment of various coagulation disorders (including but not limited to hereditary disorders, such as hemophilias and disseminated intravascular coagulation, a severe hemorragic syndrome) or to enhance coagulation and other hemostatic events in treating wounds resulting from trauma, surgery or other causes. Alternatively, such NAPOH inhibitors can be useful in treatment of autoimmune diseases and thrombotic diseases.

A further embodiment of the invention is directed to a method of screening for test substances that specifically bind to NAPOH and prevent binding to antiphospholipid autoantibodies to comprising the steps of: i) contacting a test substance with NAPOH polypeptide in the presence of antiphospholipid autoantibodies, under conditions that allow binding of NAPOH to antiphospholipid autoantibodies and ii) detecting the amount of antiphospholipid autoantibodies bound to NAPOH in the presence and absence of the test substance by methods common to the art. Preferably, the test substance is able to inhibit NAPOH interaction with antiphospholipid autoantibodies. Interaction of NAPOH with autoantibodies is linked to antiphopoholipid syndrome and more specifically to autoimmune artherogenesis.

A further, embodiment of the invention is directed to a method of screening substances for modulators of NAPOH expression comprising the steps of: i) contacting a cell with a test substance; and ii) comparing NAPOH expression in the cell after exposure to the test substance to that of an unexposed control cell. NAPOH expression is determined by methods common to the art or included herein, by detecting NAPOH polynucleotides or polypeptides An example of this method comprises the step of i) culturing two equivalent cell samples; ii) adding a test substances to one of the cultures and not the other; ii) harvesting both cultures at a specified time; iv). purifying the mRNA from each sample of cells; v) comparing the level of NAPOH mRNA in each sample by Northern Blot, RTPCR, or another method common to the art. The invention provides for design and use of specific polynucleotide probes and primers, as described herein. An additional example comprises the step of: i) having two equivalent cultures of cells; ii) adding a test substance to one of the cultures and not the other; iii) harvesting both cultures; iv) purifying the protein from each sample of cells; v) comparing the level of NAPOH polypeptides in each sample by Western blot, immunohistochemistry, or another method common to the art. The invention provides for design and use of specific antibodies and antibody fragments, as discussed herein. As a result, such NAPOH activators are of great potential as new drugs due to their ability to induce coagulation and are expected to be useful in treatment of various coagulation disorders (including but not limited to hereditary disorders, such as hemophilias and disseminated intravascular coagulation, a severe hemorragic syndrome) or to enhance coagulation and other hemostatic events in treating wounds resulting from trauma, surgery or other causes. Alternatively, such NAPOH inhibitors can be useful in treatment of autoimmune diseases and thrombotic diseases by decreasing the level of inflammatory aPAs. In another embodiment, the invention relates to methods for using the protein of the invention or fragments to identify autoantibodies which are related to autoimmune disease and systemic lupus erythematosus (SLE). Accordingly, the present protein may be used to detect the presence of autoantibodies. In a typical embodiment, the protein of SEQ ID NO:106 is labeled with any detectable moiety including, but are not limited to, a fluorescent label, a radioactive atom, a paramagnetic ion, biotin, a chemiluminescent label or a label which can be detected through a secondary enzymatic or binding step. The invention further provides a method of diagnosing SLE, and distinguishing such processes from other diseases.

An antagonist of the protein of SEQ ID NO:106 may be produced using methods which are generally know in the art. The antagonist will affect the binding activity of NAPOH to negatively charged phopholipids which are implicated in autoimmune disorders. In one aspect, the protein of the invention or a fragment thereof may be used to synthesize specific antibodies using any techniques known to those skilled in the art including those described therein. In particular, purified NAPOH may be used to produce antibodies or to screen libraries of pharmaceutical agents to identify those which specifically bind NAPOH. NAPOH may thus be used for the characterization and assay of antibody against this protein in patients suffering from autoimmune disorder.

The ability of the protein of the invention or fragment thereof to function as a major antigen for antiphospholipid antibodies may be assessed using techniques well known to those skilled in the art. The ability of the protein of the invention or fragment thereof, especially fragments containing Sushi motifs and Sushi-like motifs, to bind to antiphospholipid autoantibodies may be assessed using techniques well known to those skilled in the art including those described herein. For example, the protein of SEQ ID NO:106 or a fragment thereof may be fixed to a solid support, such as a chromatography matrix. A preparation containing antiphospholipid autoantibodies is placed in contact with the protein of the invention under conditions which facilitate binding to NAPOH. The support is washed and then the antiphospholipid autoantibodies are released from the support by contacting the support with agents which cause antiphospholipid autoantibodies to dissociate from the NAPOH.

An embodiment of the present invention relates to methods of using the protein of the invention or fragment thereof, particularly polypeptides containing Sushi motifs, or derivative thereof to identify and/or quantify binding autoantibodies, preferably anti phospholipid autoantibodies, in a biological sample, and thus used in assays and diagnostic kits for the quantification of such binding proteins in bodily fluids in tissue samples, and in mammalian cell cultures. Such assays may be particularly useful as diagnostic or prognostic tools in the detection and monitoring of a disorder linked to primary antiphospholipid syndrome. The binding activity of the protein of the invention or fragment thereof may be assessed using any method familiar to those skilled in the art. Preferably, a defined quantity of the protein of the invention or fragment thereof is added to the sample under conditions allowing the formation of a complex between the protein of the invention or fragment thereof and the binding protein to be identified and/or quantified. Then, the presence of the complex and/or or the free protein of the invention or fragment thereof is assayed and eventually compared to a control using any of the techniques known by those skilled in the art.

In another embodiment, an array of oligonucleotides probes comprising the nucleotide sequence of SEQ ID NO:105 or fragments thereof can be constructed to conduct efficient screening of e.g., genetic mutations. The microarray can be used to monitor the expression level of large numbers of genes simultaneously and to identify genetic variants, mutations, and polymorphisms. This information may be used to determine gene function, to understand the genetic basis of a disorder, to diagnose a disorder, and to develop and monitor the activities of therapeutic agents (see for example: Chee, M. et al., Science, 274:610-614 (1996) which disclosure is hereby incorporated by reference in its entirety). For example, it has been shown that genetic variants, mutations, and polymorphisms are related to thrombotic related disease and chronic inflammatory disease (described in U.S. Pat. No. 6,203,980 B1, the disclosure of which is incorporated herein by reference in its entirety). In addition, NAPOH is involved in the fertilization process. The addition of the purified protein to prepared sperm samples from normospermic men increases significantly the straight line velocity. (VSL) and the amplitude of lateral head displacement (ALH). Storage of sperm is of widespread importance in commercial animal breeding programs, human sperm donor programs, and in the treatment of certain disease states. For example, sperm samples may be frozen for men who have been diagnosed with cancer or other diseases that may eventually interfere with sperm production, as well as for assisted reproduction purposes where sperm may be stored for use at other locations or times. The procedures utilized in such cases include: washing a sperm sample to separate out the sperm-rich fraction from non-sperm components of a sample such as seminal plasma or debris; further isolating the healthy, motile sperm from dead sperm or from white blood cells in an ejaculate; freezing or refrigerating of sperm for use at a later date or for shipping to females at differing locations; extending or diluting sperm for culture in diagnostic testing or for use in therapeutic interventions such as in vitro fertilization or intracytoplasrnic sperm injection (Cohen et al. 12:994-1001 (1997)). Once sperm have been washed or isolated, they are then extended (or diluted) in culture or holding media for a variety of uses (sperm analysis, diagnostic tests, assisted reproduction). Each of these uses for extended or diluted sperm requires a somewhat different formulation of basal medium (see, for review, U.S. Pat. No. 6,140,121 Ellington et al. October 2000); however, in all cases sperm survival is suboptimal outside of the female reproductive tract. Novel additional components of a dilution or storage medium which could improve the functional preservation of sperm would be useful. Therefore, in another preferred embodiment of this invention, purified recombinant proteins encoded by SEQ ID NO:106 or fragments thereof can be added as components of pharmacological media designed to protect spermatozoa. The methods used to compose such preservation media are generally known by those skilled in the art (for example, Oliver. S. A., et al. U.S. Pat. No. 5,897,987 April 1999; Cohen J.et al., supra). Inversely, in yet another embodiment of this invention, ligands, inhibitors, neutralizing antibodies or other biological agents which recognize the protein of the invention and which bind it and which block it can be used as components of pharmacological formulations designed for male contraception purposes.

Protein of SEQ ID NO:108 (Internal Designation Clone 113165_105-056-3-0-G12-F)

The cDNA of clone 113165 (SEQ ID NO:107) encodes, the protein of SEQ ID NO:108, comprising the amino acid sequence:

MAAGGSGVGGKRSSKSDADSGFLGL-RPTSVDPALRRRRRGPRNKKRGWRRLAQE PLGLEVDQFLEDVRLQERTSGGLLSEAP-NEKLFFVDTGSKEKGLTKKRTKVQKKSLLLKK PLRVDLILENTSKVPAPKDVLAHQVP-NAKKLRRKEQLWEKLAKQGELPREVRRAQARLL NPSATRAKPGPQDTVERPFYDLWASDN-PLDRPLVGQDEFFLEQTKKKGVKRPARLHTKPS QAPAVEVAPAGASYNPSFEDHQTLLSAA-HEVELQRQKEAEKLERQLALPATEQAATQEST FQEL-CEGLLEESDGEGEPGQGEGPEAGDAE-VCPTPARLATTEKKThQQRRREKAVHRLRV QQAALRAARLRHQELFRLRGIKAQVALR-LAELARRQRRRQARREAEADKPRRLGRLKYQ APDIDVQLSSELTDSLRTLKPEGNIL-RDRFKSFQRRNMIEPRERAKFKRKYKVKLVEKRAF REIQL. Accordingly, it will be appreciated that all characteristics and uses of polypeptides of SEQ ID NO:108 described throughout the present application also pertain to the polypeptides encoded by the nucleic acids included in clone 113165_105-056-3-0-G12-F. In addition, it will be appreciated that all characteristics and uses of the polynucleotides of SEQ ID NO:107 described throughout the present application also pertain to the nucleic acids included in clone 113165_105-056-3-0-G12-F. A preferred embodiment of the invention is directed toward the compositions of SEQ ID NO:107, SEQ ID NO:108, and clone 113165_105-056-3-0-G12-F. Also preferred are polypeptide fragments having a biological activity as described herein and the polynucleotides encoding the fragments.

The cDNA of SEQ ID NO:107 is a novel human JNK3-binding protein named hJNK3-BP, homologous to a murine JNK3-binding protein (GSP:AAB12882). The cDNA of SEQ ID NO:107 encodes a 478 amino-acid protein of SEQ ID NO:108, which is predominantly expressed in the brain.

The c-Jun NH2-terminal kinase (JNK) signal transduction pathway is activated in response to various environmental stress and by the engagement of several classes of cell surface receptors. In mammalian cells, JNK has been implicated in the immune response, oncogenic transformation and apoptosis. These effects of JNK are mediated, at least in part, by increased gene expression. Three mammalian genes encode JNK protein kinases. JNK1 and JNK2 are expressed ubiquitously, while JNK3 is expressed primarily in the brain (Ip. Y T, Davis R J Curr Opin Cell Biol 1998. April; 10(2):205-19). By performing a yeast two-hybrid screen specifically with JNK3 as a bait, Ito M, et al. (Ito M, Yoshioka K, Akechi M, Yamashita S, Takamatsu N, Sugiyama K, Hibi M, Nakabeppu Y, Shiba T, Yamamoto K I. Mol Cell Biol 1999. Nov;19(11):753948) isolated mouse Jsap1 (for JNK/stress-activated protein kinase-associated protein 1), also known as Jip-3 (Kelkar. N, Gupta S, Dickens M, Davis R J, Mol Cell Bio 2000.20:1030-1043). Jip-3 represents a JNK-interacting proteins (JIPs), such as Jip-1 and Jip-2, acting as scaffolding proteins that may regulate signal transduction by the JNK signaling pathway. The protein of the invention hJNK3-BP specifically binds JNK3 protein kinase, modulating the biological effects of JNK3 signaling pathway in cells . . . hJNK3-BP represents the founding member of a new class of scaffold protein involved in the regulation of the JNK3 cascade.

An embodiment of the invention is directed to a composition comprising a hJNK3-BP polypeptide sequence of SEQ ID NO:108.

A further embodiment of the invention is directed to a composition comprising a hJNK3-BP polypeptide fragment having biological activity.

A further embodiment of the invention is directed to a composition comprising a polynucleotide sequence of SEQ ID NO:107 encoding a UNK3-BP polypeptide.

A further embodiment of the invention is directed to a composition comprising a polynucleotide sequence encoding a hJNK3-BP polypeptide fragment having biological activity.

In one embodiment, the present invention provides a method of producing a recombinant protein capable of effectively modulating JNK activity. The protein of the invention can be produced in host cells that have been transfected with an appropriate expression vector comprising a nucleic acid sequence coding for hJNK3-BP polypeptides. Introduction of an expression vector incorporating a nucleic acid sequence coding for the protein of the invention into a host cell can be performed in a variety of ways, including but not limited to calcium or lithium chloride treatment, electroporation, or lipofection. Any of a wide variety of expression systems can be used to provide the recombinant proteins. Suitable expression vehicles include, but are not limited to plasmids, viral particles and baculovirus for insect cells. The expression vehicle can be integrated into the host cell genome. In some circumstances, it is desirable to employ an inducible expression vector. The host cells harboring the expression vehicle are cultured in conventional nutrient media, under conditions whereby the nucleic acid sequence coding for this particular protein is expressed. After a suitable amount of time for the product to accumulate, the protein is purified from the host cells.

In another embodiment, the present invention provides a method of effectively modulating JNK activity in cells. The, level or activity of hJNK3-BP can be increased in cells to decrease or inhibit specific. JNK protein kinase activity, thereby preventing JNK3-associated apoptosis hJNK3-BP levels may be increased by introducing hJNK3-BP polynucleotides or polypeptides into a cell in an amount sufficient to specifically inhibit JNK protein kinase activity of one or more cells within the sample. Such methods can be performed either in vitro or in vivo. The level of hJNK3-BP can be increased in cells in any of a number of ways. For instance, purified hJNK3-BP protein may be introduced to the cells by microinjection or by liposome or micelle-mediated transport. Such liposomal or micellar microcapsule may optionally be combined with a cell type-specific target, such as an antibody or receptor ligand. Alternatively, hJNK3-BP polynucleotides may be introduced to a cell by methods common to the art such as transfection, electroporation, or viral transduction. Cyclodextrin, liposome or micelle-mediated transport may also be used to introduce hJNK3-BP polynucleotides to a cell. Useful examples of the above methods are described in U.S. Pat. Nos. 5,019,369, 5,616,565, 6,110,490, 6,204,060, and P.C.T. WO9704748, disclosures of which are hereby incorporated by reference in their entireties. In addition, any compound that increases the expression of hJNK3-BP.polypeptides can be used to decrease JNK protein kinase activity within one or more cells of the sample. Such compounds can be identified by screening for test substances that increase hJNK3-BP expression comprising the steps of: contacting a cell with a test substance and comparing hJNK3-BP expression in the cell after, exposure to the test substance to that of an unexposed control cell.

The present invention provides an in vitro method to inhibit apoptosis induced by JNK activation to keep cells alive in culture. Preferably, the present invention is suited to the culturing of cells for purposes including transplantation or implantation of such cells in vivo after an ex vivo introduction of hJNK3-BP polynucleotides. Said polynucleotides may be introduced to a cell of interest by methods known in the art, such as those listed above. Furthermore, such a method can be used with neurons or other cell types which undergo apoptosis in culture. Transplantation of healthy neurons expressing a hJNK3-BP into subjects whose neurons are degenerating can alleviate some effects of the neuronal diseases or disorders. Treated cells can be grafted, in particular, into the brain, either as cells cultured in vitro on a support matrix using techniques disclosed in the U.S. Pat. No. 6,264,943, which disclosure is hereby incorporated by reference in its entirety, or as dispersed cells.

The present invention also provides animal models generated by modulating the expression or activity of the present protein in one or more tissues of the animal. Preferably, the expression of hJNK3-BP polypeptides is targeted in the brain. The transgene can be integrated as a single transgene or in concatamers, e.g., head-to-head tandems or head-to-tail tandems., The transgene can also be selectively introduced into and activated in a particular cell type using a conditional expression system. Such animals are useful for a number of purposes, because they represent an in vivo assay method for testing candidate molecules potentially useful for the treatment of various pathophysiological aspects of diseases specifically related to the activity or consequence of the activity of hJNK3-BP polypeptides on JNK biological effects. Study of the phenotype of such models can also allow the identification of additional human diseases associated with JNK abnormal activity. These animals can be generated with any method of targeting over-expression or inactivation of hJNK3-BP to produce the founder lines of transgenic animals. Such models are extremely useful, e.g., in the assessment of candidate therapies and drugs for the treatment of neurodegenerative diseases and autoimmune or malignancy conditions.

In other embodiment, the protein of the invention or fragment thereof is used to diagnose diseases or disorders associated with abnormal hJNK3-BP activity and in particular with altered JNK biological effects. In particular, it is useful in diagnosing patients with deficient amounts of JNK3-BP which results in uncontrolled activity of JNK protein kinase and monitor hJNK3-BP expression in such conditions. Preferably, the present invention provides a method of diagnose pathologies linked to altered apoptosis or inflammatory responses such as, but are not limited to, neurodegenerative diseases characterized by apoptosis, including Parkinson's disease and Alzheimer's disease, autoimmune diseases such as arthritis or other conditions characterized by inflammation and malignancies such as leukemias. The method comprises the steps of contacting a tissue sample obtained from an individual suspected of suffering from the disease or condition or at risk of developing the disease or condition, with a detectably labeled compound capable of selectively binding hJNK3-BP polypeptides or nucleic acids. For example, a polyclonal or monoclonal antibody or any immunologically active fragment thereof or a nucleic acid probe may be used.

This marker may thus also play a role as prognostic indicators, preferably concerning inflammatory diseases. More preferably, it can be measured in tissues and fluids recovered from inflammatory sites. Thus, the condition of a subject can be monitored continuously and the quantified amount of this particular protein measured in the pathological sample can be compared with the amount quantified in a biological sample of a normal individual or with previous samples of the same patient.

A further embodiment of the present invention is to, provide novel methods and compositions useful for the treatment or prevention of diseases and conditions related to the abnormal JNK biological effects and preferably with abnormal apoptosis. The protein of the, invention or fragment thereof may be used to treat neurodegenerative diseases characterized by apoptosis, including Parkinson's disease and Alzheimer's disease. Other conditions that can be treated using the compositions and methods of the invention are autoimmune diseases such as arthritis, other conditions characterized by inflammation such as inflammatory arthritis and bronchial asthma, and malignancies such as, but not limited to leukemias.

In another embodiment of the present invention is to provide novel methods and compositions useful for the treatment or prevention of diseases and conditions associated with oxidative damage dependent on abnormal JNK biological effects. The protein of the invention or fragment thereof can be used to treat or prevent oxidative damage to organs such as the liver and kidney, and in particular, damage due to ischemia/reperfusion in heart disease and cardiomyopathy. More preferably, such methods and compositions can also be used to treat donor organs for transplantation. Indeed these organs are exposed to substantial environmental stress which can affect the normal functioning of the organs; effects of which can be blocked by JNK modulators such as hJNK3-BP.

Such methods comprise the administration of a therapeutically-effective amount of hJNK3-BP polypeptides to mammals suffering from the disease or condition, where "effective amount" is meant a concentration of hJNK3-BP polypeptides which is capable of modulating JNK biological effects. The compositions of the invention are preferably delivered to an individual in combination with a pharmaceutically acceptable carrier, such as a saline solution or other physiological buffer suitable for administration to a patient. The particular amount of the compositions of the invention that will be administered to the mammal for any particular condition will depend on the clinical condition of the patient, and other factors such as the weight, age, and route of delivery. Such composition can be administered by any suitable route. Alternatively, for treatment purposes, nucleic acids can be administered to the patient using any of the standard vectors and/or gene delivery methods known in the art. Suitable gene delivery systems include, but are not limited to liposomes, naked DNA and viral vectors. These compositions can comprise the protein of the invention, and, optionally, one or more other compounds of interest. Indeed, in this embodiment, the present invention find use in drug potentiation applications. This co-administration may be by simultaneous administration or by separate or sequential administrations. All of these components may be either obtained from natural sources or produced by recombinant genetic engineering techniques and/or chemical modification.

Protein of SEQ ID NO:110 (Internal Designation Clone 231462_117-065-1-0-G11-F)

The cDNA of Clone 231462_117-065-1-0-Gil-F (SEQ ID NO:109) encodes the 386 amino acid long polypeptide, DROCK2, of SEQ ID NO:110 comprising the amino acid sequence: MCLLLSCPCHPSAHGQSMWIERTS-FVTAYKLPGILRWFEVVHMSQTTISPLENAIETMST ANEKILMMINQYQSDETLPINPLSMLLN-GIVDPAVMGGFAKYEKAFFTEEYVRDHPEDQ DKLTHLKDLIAWQIPFLGAGIKJHEK-RVSDNLRPFHDRMEECFKNLKMKVEKEYGVREM PDFDDRRVGRPRSMLRSYRQMSIIS-LASMNSDCSTPSKPTSESFDLEASPKTPRVEQEEPI SPGSTLPEVKLRRSKKRTKRSSVVFADE-KAAAESDLKRLSRKHEFMSDTNLSEHAAIPLK ASV-LSQMSFASQSMPTIPALALSVA-GIPGLDEANTSPRLSQTFLQLSDGDKKTLTRKKVN QFFKTMLASKSAEEGKQIPDSLSTDL (SEQ ID NO:110). Accordingly, it will be appreciated that all characteristics and uses of polypeptides of SEQ ID NO:110 described throughout the present application also pertain to the polypeptides encoded by the nucleic acids included in Clone 231462 117-065-1-0-G11-F. In addition, it will be appreciated that all characteristics and uses of the polynucleotides of SEQ ID NO:109 described throughout the present application also pertain to the nucleic acids included in Clone 231462 117-065-1-0-G11-F. A preferred embodiment of the invention is directed toward the compositions of SEQ ID NO:109, SEQ ID NO:110, and Clone 231462 117-065-1-0-G11-F. Also preferred are polypeptide fragments having a biological activity as described herein and the polynucleotides encoding the fragments.

DROCK2, the protein of SEQ ID NO:110, is a splicing variant of DOCK2 (EMBL entry Q92608) retaining the last 370 amino acid of DOCK2, while the first sixteen amino acids (MCLLLSCPCHPSAHGQ) represent specificDROCK2 amino acids corresponding to signal sequence. The resulting isoform is thus lacking the N-terminal sequences of the DOCK2 isoform. However, it retains DOCK2's C-terminal domain comprising a twenty amino acid sequence (LASKSAEEGKQIPDSLSTDL) which has been shown to be involved in protein-protein interactions by interacting with PDZ domain of membrane-associated proteins.

DROCK2 belongs with DOCK2 to the CDM family of signaling proteins which also comprises the human DOCK180 protein and its homologues, the Ced-5 protein in Caenorhabditis elegans and Mbc polypeptide in *Drosophila* melanagaster. These proteins share extensive similarities at the amino acid level, except in their carboxyl-terminal regions that are divergent. CDM proteins have been implicated in polarized extension of the cell surface in their respective organisms. Mbc in *Drosophila* is necessary for myoblast fusion and for migration of epithelial cells, both of which require reorganization of the cytoskeleton. Ced-5 has also been shown to be involved in the regulation of the cytoskeleton in the nematode, loss of function of which results in defects in engulfing dead cells and in the migration of distal tip cells. Finally, the human DOCK180 protein which was originally identified as one of the major proteins bound to the CrkII adaptator protein, is involved in membrane ruffling and cell migration in nonadherent cells. It has been shown to transduce signals from the CrkII-p130Cas complex to both the cytoskeleton and JNK pathway by activating the low molecular weight Rac GTPase.

DROCK2, in contrast to DOCK180, which is expressed in all tissues except in peripheral blood cells, is expressed only in circulating blood cells, lymphocytes and macrophages present in organs. Thus the protein is specifically expressed by nonadherent cells. DROCK2 is involved in blood cell migration and phagocytosis of apoptotic cells by macrophages where it binds to and activates Rac GTPAses.

An embodiment of the invention is directed to a composition comprising a DROCK2 polypeptide sequence of SEQ ID NO:110.

A further embodiment of the invention is directed to a composition comprising a DROCK2 polypeptide fragment having biological activity.

A further embodiment of the invention is directed to a composition comprising a polynucleotide sequence of SEQ ID NO:109 encoding a DROCK2 polypeptide.

A further embodiment of the invention is directed to a composition comprising a polynucleotide sequence encoding a DROCK2 polypeptide fragment having biological activity.

A further embodiment of the invention is directed to a method of screening test substances for modulators of DROCK2 expression comprising the steps of: i) contacting a cell with a substance to be tested; and ii) comparing DROCK2 expression in the cell after exposure to the test substance to that of an untreated control cell.

In one embodiment, the present invention provides a method of producing a recombinant protein capable of effectively increasing Rac. GTPase activity. The protein of the invention can be produced in host cells that have been transfected with an appropriate expression vector comprising a nucleic acid sequence coding for the protein of the invention. Introduction into a host cell of such expression vector for DROCK2 can be performed in a variety of ways, including but not limited to calcium or lithium chloride treatment, electroporation, or lipofection. Any of a wide variety of expression systems can be used to provide the recombinant proteins. Suitable expression vehicles include, but are not limited to plasmids, viral particles or baculovirus for insect cells. The expression vehicle can be integrated into the host cell genome. Optionally, an inducible expression vector can be used to achieve tight controlled expression of the gene in the host cell.

Another embodiment the present invention provides methods to purify from cellular extracts proteins harboring one or more. PDZ domain, preferably proteins belonging to the MAGUK (Membrane Associated and Guanylate Kinase) family, more preferably proteins selected from the group consisting of DLG, syntenin or PSD95 proteins, by using the present protein, preferably its C-terminal twenty amino acid sequence to copurify those proteins. Methods to affinity purify proteins are well known for those skilled in the art. For example, the PDZ-containing proteins can be purified on an affinity column or on solid support like beads using the polypeptides of the invention. The protein to be purified using the present method can be derived from any source, e.g. protein expressed in vitro using an invertebrate, yeast or bacterial heterologous expression system.

Another embodiment of the invention is directed to a method to increase phagocytosis of apoptotic cells. Preferably, this method is applied in vivo to an individual. The method comprises the steps of: i) removing a sample of monocytes, ii) introducing a polynucleotide encoding a DROCK-2 polypeptide or fragment thereof ex vivo to those cells, and iii) reinjecting the recombinant cells into an individual. Using such a method in combination with anti-cancer or antiviral therapies would be of particular interest for the rapid elimination of apoptotic cancer or infected cells.

An embodiment of the invention provides for a method of screening test substances for modulators of DROCK-2 expression. This method comprises the steps of: i) contacting a cell with a test substance; and ii) comparing DROCK-2 expression in the cell after exposure to the test substance to that of an unexposed control cell. DROCK-2 expression is determined by methods common to the art or included herein, by detecting DROCK-2 polynucleotides or polypeptides. An example of this method comprises the steps of: i) culturing two equivalent cell samples; ii). adding a test substance to one of the cultures and not the other; iii) harvesting both cultures at a specified time; iv) purifying the mRNA from each sample of cells; v) comparing the level of DROCK-2 mRNA in each sample by Northern blot, RTPCR, or another method common to the art. The invention provides for design and use of specific polynucleotide probes and primers, as discussed herein. An additional example comprises the steps of: i) having two equivalent cultures of cells; ii) adding a test substance to one of the cultures and not the other; iii) harvesting both cultures; iv) purifying the protein from each sample of cells; v) comparing the level of DROCK-2 polypeptides in each sample by Western blot, immunohistochemistry, or another method common to the art. The invention provides for design and use of specific antibodies and antibody fragments, as discussed herein. Substances that increase DROCK-2 expression (agonists) may be used to increase cytoskeletal remodeling and Rac activation. Substances that decrease DROCK-2 expression (antagonists) may be, used to inhibit cytoskeletal remodeling and Rac activation. Methods utilizing DROCK-2 agonists and antagonists are included herein.

A preferred embodiment of the invention provides a method of screening for test substances that bind DROCK-2 polypeptides. This method comprises the steps of: i) contacting a test substance with a DROCK-2 polypeptide or fragment thereof under conditions that allow binding; and ii) detecting the binding of the test substance by methods common to the art (e.g., competitive antibody-based methods such as coimmunopreciptation and Western blotting). Included in this method are test substances that are conjugated to an antibody, antibody fragment, cell-type specific ligand or a portion thereof.

A further preferred embodiment of the invention provides a method of screening test substances that bind to. DROCK-2 for antagonists of DROCK-2 activity. This method comprises the steps of: i) contacting a cell with a test substance; and ii) comparing DROCK-2 biological activity after exposure to the test substance to that of an unexposed control cell. Detection of DROCK-2 biological activity may be detected by detecting activity of Rac GTPase. An example of an assay detecting Rac activity comprises the steps of: exposing Rac GTPase to radiolabeled GTP and detecting the amount of hydrolysis by detecting the amount of free, radiolabeled phosphate.

A further embodiment of the present invention is also directed to a method to reduce the elimination rate of apoptotic cells in a patient subjected to an antiapoptotic, treatment, such method comprising removing a sample of the monocytes/macrophages of said patient, inhibiting or reducing the expression of the present protein in the isolated cells ex vivo, and reinjecting the modified cells to the patient. Methods to inhibit the expression of a given gene in a cell are well known in the art, e.g. using antisense or ribozyme strategies, any of which can be used in the present method. Alternatively, reduced phagocytosis of apoptotic cells in said patient can be achieved by interfering with the normal activity of the present protein. In such a method, the isolated monocytes are transfected ex vivo with a DROCK2 fragment corresponding to the last twenty carboxy-terminal amino acid prior to reinjection into the patient. Because reducing phagocytosis of apoptotic cells concomitantly with the administration of the antiapoptotic agent would help maintaining more dying cells alive and therefore available for the, action of the antiapoptotic agent, such method would be of particular interest to increase the treatment efficiency of diseases associated with abnormal cell apoptosis, including but not limited to neurodegenerative disorders.

A preferred embodiment provides a method of preventing and treating invasive neoplasms that require cytoskeletal remodeling (e.g., for extravasation). This method comprises the step of contacting an antagonist of DROCK-2 expression or activity with a cell. Preferred cells include nonadherent cells. Further preferred cells include lymphocytes and macrophages. Preferably, the DROCK-2 antagonist is delivered to a specific cell type, for example, by conjugating the antagonist to a cell-type specific targeting moiety. (e.g., a ligand or antibody fragment). DROCK-2 antagonists in a physiologically acceptable solution may be delivered by methods common to the art, such as orally or parenterally. This method is useful for prevention and treatment of leukemias and other invasive neoplasms.

Protein of SEQ ID NO:112 (Internal Designation Clone 500723589_205-34-3-0-G4-F)

The cDNA of clone 500723589_205-34-3-0-G4-F (SEQ ID NO:111) encodes Novel 17 beta-hydroxysteroid dehydrogenase type 2 (NBHSD2) of SEQ ID NO:112, comprising the amino acid sequence:

MSTFFSDTAWICLAVPTVLCGTVFCK-YKKSSGQLWSWMVCLAGLCAVCLLILSPFWGLI LFS-VSCFLMYTYLSGQELLPVDQKAVLVTG-GDCGLGHALCKYLDELGFTVFAGVLNEN GPGAEELRRTCSPRLSVLQMDITKPV-QIKDAYSKVAAMLQDRGLWAVINNAGVLGFPTD GELLLMTDYKQCMAVNFFGTVEVTKT-FLPLLRKSKGRLVNVSSMGGGAPVERLASYGS SKAAVTMFSSVMRLELSKWGIKVA-SIQPGGFLTNIAGTSDKWEKLEKDILDHLPAEVQE DYCQDYILAQRNFLLLINSLASKDFSPV-LRDIQHAILAKSPFAYYTPGKGAYLWICLAHYL PIGIYDYFAKRHFGQDKPMPRALRMPNYKKKAP (SEQ ID NO:112). Accordingly, it will be appreciated that all characteristics and uses of the polypeptides of SEQ ID NO:112 described throughout the present application also pertain to the polypeptides encoded by the nucleic acids included in Clone 500723589_205-34-3-0-G4-F. In addition, it will be appreciated that all characteristics and uses of the polynucleotides of SEQ ID NO:111 described throughout the present application also pertain to the nucleic acids included in Clone 500723589_205-34-3-0-G4-F. A preferred embodiment of the invention is directed toward the compositions of SEQ ID NO:111, SEQ ID NO:112, and clone 500723589_205-34-3-0-G4-F. Also preferred are polypeptide fragments having a biological activity as described herein and the polynucleotides encoding the fragments.

The protein of SEQ ID NO:112 is a polymorphic variant of the sequence of 17 beta estradiol dehydrogenase (swissprot accession number P37059). Like 17 beta-hydroxysteroid dehydrogenase type 2, the protein of the invention displays a short chain dehydrogenase domain (PF00106) spanning from positions 83 to 268, a ferredoxin doain (PS00197) spanning from positions 40 to 48 and an ADH-short domain spanning from positions 219 to 247.

Novel 17 beta-hydroxysteroid dehydrogenase type 2 (NBHSD2) is an enzyme of the 17 beta-hydroxysteroid dehydrogenase. (17 beta-HSD) gene family. The 17 beta-hydroxysteroid dehydrogenases are pivotal in controlling the biological potency of steroid hormones by catalyzing oxidation or reduction at position 17.

17 Beta-hydroxysteroid dehydrogenases catalyze the interconversion between high-activity 17 beta-hydroxysteroids and low-activity 17-ketosteroids. Because both estrogens and androgens have the highest affinity towards their receptors in the 17 beta-hydroxy form, the 17 beta-HSD enzymes regulate the biological activity of sex hormones. Several 17 beta-HSD may metabolize further substrates including alcohols, bile acids, fatty acids and retinol. The activities of 17 beta HSDs are essential for gonadal sex steroid biosynthesis and they are also involved in the modulation of steroid hormone action in peripheral tissues. This family of steroidogenic enzymes constitutes an interesting target in the control of the concentration of estrogens and androgens since this family is involved in the formation and inactivation of sex steroids.

NBHSD2 catalyzes the oxidative reaction or the inactivation of sex steroids thereby reducing the exposure of tissues to the action of sex steroids. NBHSD2 preferentially catalyzes the oxidation of estradiol (E(2)) to inactive estrogen, estrone (E(1)), testosterone to 4-dione, dihydrotestosterone (DHT), 20alpha-dihydroprogesterone (20alpha-DHP), and androst-5-ene-3, 17-diol (5-diol) to DHEA with NAD+: as the coenzyme. Therefore, NBHSD2 is involved in the regulation of clearance and/or metabolism of sex steroids.

Local formation of sex steroids plays a major role in both normal and neoplastic hormone-sensitive tissues. 40% of all cancers, namely, breast, prostate, ovarian and uterine cancers, are sex steroid-sensitive and are thus prime candidates for approaches based upon the control of synthesis of active steroids in peripheral target tissues. Thus, the rate of formation of each sex steroid depends upon the activity of the specific androgen- and estrogen-synthesizing enzymes in each cell of each tissue. Local hormone metabolism plays a key role in determining tissue responsiveness to oestrogen. High capacity for inactivation of oestrogens is associated with the presence of 17beta-HSD isozymes in epithelial cells. By inactivating oestrogens, NBHSD2 plays a role in cancers, especially hormone-dependent cancers such as those stimulated by androgens or estrogens, for example, colon, breast, prostate, ovarian and uterine cancer. In the colon, NBHSD2 plays a role as attenuator of estradiol E2 bioavailability. (estradiol (E2) stimulates the growth of colonic cancer cell lines), and possibly as modulators of colonic cell proliferation in the pathogenesis of colon cancer.

Also, bioavailibility of estradiol, one of the most potent human sex steroid hormones of placental origin, is essential to the maintenance of pregnancy, the timing of parturition, the maturation of many fetal organs, and the preparation of the maternal reproductive system.

Several inhibitors of the functions of NBHSD2 have been characterized. These include: lindane which induces oxidative stress, progestins (promegestone, nomegestrol acetate, medrogestone)>and tibolone and its metabolite which will provide a new possibility in the treatment of breast cancer, chalcones (naringenin chalcone and 4-hydroxychalcone), steroidal spirolactones inhibitors, isoflavones which have been suggested to be anticarcinogenic, propylthiouracil (PTJ) which is an anti-thyroid drug., Such inhibitors are useful tools to regulate the level of active estrogens, androgens and progesterone and can exert cancer-preventive effects.

Alternatively, retinoic acids stimulate the expression of NHBSD2 and may be involved in modulation of in situ estrogen metabolism in both normal and neoplastic human endometrium.

An embodiment of the invention is directed to a composition comprising a NBHSD2 polypeptide sequence of SEQ ID NO:112.

A further embodiment of the invention is directed to a composition comprising a NBHSD2 polypeptide fragment having biological activity.

A further embodiment of the invention is directed to a composition comprising a polynucleotide sequence of SEQ ID NO:111 encoding a NBHSD2 polypeptide.

A further embodiment of the invention is directed to a composition comprising a polynucleotide sequence encoding a NBHSD2 polypeptide fragment having biological activity.

An embodiment of the invention provides for a method of screening test substances for modulators of NBHSD2 expression. This method comprises the steps of: i) contacting a cell with a test substance; and ii) comparing NBHSD2 expression in the cell after exposure to the test substance to that of an unexposed control cell. NBHSD2 expression is determined by methods common to the art or included herein, by detecting NBHSD2 polynucleotides or polypeptides. An example of this method comprises the steps of: i) culturing two equivalent cell samples; ii) adding a test substance to one of the cultures and not the other; iii) harvesting both cultures at a specified time; iv) purifying the nmRNA from each sample of cells; v) comparing the level of NBHSD2 mRNA in each sample by Northern blot, RTPCR, or another method common to the art. The invention provides for design and use of specific polynucleotide probes and primers, as discussed herein. An additional example comprises the steps of: i) having two equivalent cultures of cells; ii). adding a test substance to, one of the cultures and not the other; iii) harvesting both cultures; iv) purifying the protein from each sample of cells; v) comparing the level of NBHSD2 polypeptides in each sample by Western blot, immunohistochernistry, or another method common to the art. The invention provides for design and use of specific antibodies and antibody fragments, as discussed herein.

Agents which modulate the expression or activity of the NBHSD2 of the subject invention include, but are not limited to, antisense oligonucleotides, ribozymes, drugs, and antibodies. These agents may be made and used according to methods well known in the art. Also, the protein of the invention, or biologically active fragments thereof, may be used in screening assays for therapeutic. compounds. A variety of drug screening techniques may be employed. In this aspect of the invention, the protein or biologically active fragment thereof, may be free in solution, affixed to a solid support, recombinantly expressed on, or chemically attached to, a cell surface, or located intracellularly. The formation of binding complexes, between the protein of the invention, or biologically active fragments thereof, and the compound being tested, may then be measured.

Another technique for drug screening which may be used provides for high throughput screening of compounds having suitable binding affinity to the protein of the invention as described in published PCT application WO84/03564, and incorporated herein by reference in its entirety.

Another embodiment of the subject invention provides compositions and methods of selectively modulating the activity of the protein of the invention. Modulation of the NBHSD2 activity would allow for the successful treatment and/or management of diseases or biochemical abnormalities associated with the NBHSD2. Antagonists, able to reduce or inhibit the expression or the activity of the protein of the invention, would be useful in the treatment of diseases associated with decreased estradiol and testosterone biosynthesis. For example, estradiol deficiency is an important pathogenetic factor in female osteoporosis. Also, antagonists of NBHSD2 provide methods of treating diseases including, and not limited to, cancers, especially hormone-dependent cancers such as those stimulated by androgens or estrogens. Andogen-sentitive diseases, i.e diseases whose onset or progress is aided by androgeneic activity, are known, included but are not limited to prostate cancer, benign prostatic hyperplasia; acne, seborrhea, hirsutism, androgenic alopecia, precocious puberty, adrenal hyperplasia and polycystic ovarian syndrome. Estrogen sensitive diseases, i.e diseases whose onset or progress is aided by estrogenic activity, included but are not limited to breast cancer, endometriosis, leiomyoma, and precocious puberty.

Alternatively, the subject invention provides methods of treating diseases or disorders associated with decreased levels of the protein of the NBHSD2. Thus, agonists of NBHSD2 provide methods for treating diseases with increases in estradiol and testosterone levels.

In one embodiment, the subject method utilizes eukaryotic or prokaryotic host cells which are stably transformed with recombinant nucleic acids expressing the NBHSD2 polypeptide or biologically active fragments thereof. The transformed cells may be viable or fixed. Drugs or compounds which are candidates for the modulation of the NBHSD2, or biologically active fragments thereof, are screened against such transformed cells in binding assays well known to those skilled in the art. Alternatively, assays such as those taught in Geysen H. N., WO. Application 84/03564, published on Sep. 13, 1984, and incorporated herein by reference in its entirety, may be used to screen for peptide compounds which demonstrate binding affinity for, or the ability to modulate, the NBHSD2, or biologically active fragments thereof. In another embodiment, competitive drug screening assays using neutralizing antibodies specifically compete with a test compound for binding to the NBHSD2 protein of the invention, or biologically active fragments thereof.

Agents which stimulate or inhibit the activity of the protein of the invention include but are not limited to agonist and antagonist drugs respectively. These drugs can be obtained using any of a variety of drug screening techniques as discussed above.

Antagonists of the NBHSD2 polypeptide encoded by SEQ ID NO:112 include agents which decrease the levels of expressed mRNA encoding the protein of SEQ ID NO:112. These include, but are not limited to, RNAi, one or more ribozymes capable of digesting the protein of the invention mRNA, or antisense oligonucleotides capable of hybridizing to mRNA encoding the NBHSD2 polypeptide of SEQ ID NO:112. Antisense oligonucleotides can be administrated as DNA, as DNA entrapped in proteoliposomes containing viral envelope receptor proteins [Kanoda, Y. et al. (1989) *Science* 243:375, which disclosure is hereby incorporated by reference in its entirety] or as part of a vector which can be expressed in the target cell and provide antisense DNA or RNA. Vectors which are expressed in particular cell types are known in the art. Alternatively, the DNA can be injected along with a carrier. A carrier can be a protein such as a cytokine, for example interleukin 2, or polylysine-glycoprotein carriers. Carrier proteins, vectors, and methods of making and using polylysine carrier systems are known in the art. Alternatively, nucleic acid encoding antisense molecules may be coated onto gold beads and introduced into the skin with, for example, a gene gun [Ulmer, J. B. et al. (1993) *Science* 259:1745, which disclosure is hereby incorporated by reference in its entirety].

Antibodies, or other polypeptides, capable of reducing or inhibiting the activity of NBHSD2 may be provided as in isolated and substantially purified foL. Alternatively, antibodies or other polypeptides capable of inhibiting or reducing the activity of the protein of the invention, may be recombinantly expressed in the target cell to provide a modulating effect. In addition, compounds which inhibit or reduce the activity of the protein of the subject invention may be incorporated into biodegradable polymers being implanted in the vicinity of where drug delivery is. desired. For example, biodegradable polymers containing antagonists/agonists may be implanted to slowly release the compounds systemically. Biodegradable polymers, and their use, are known to those of skill in the art (see, for example, Brem et al., *J. Neurosurg*. 74:441-446(1991) which disclosure is hereby incorporated by reference in its entirety).

In one embodiment, methods of increasing the levels of NBHSD2 in tissues or cell types maybe practiced by utilizing nucleic acids encoding the protein of the subject invention, or biologically active fragments thereof, to introduce biologically active polypeptide into targeted cell types. Vectors useful in such methods are known to those skilled in the art as are, methods of introducing such nucleic acids into target tissues. Preferred expression vectors include viral vectors, especially adenoviral and lentiviral vectors. For example, one of the methods described in Mulligan (Mulligan, Science, 260:926-32 (1993)), which disclosure is hereby incorporated by reference in its entirety, can be used.

In another embodiment, the invention provides methods and compositions for detecting the level of expression of the mRNA of the protein of the invention. Quantification of mRNA levels of the NBHSD2 protein of the invention may be useful for the diagnosis or prognosis of diseases associated with an altered expression of the protein of the invention. Assays for the detection and quantification of the mRNA of the protein of the invention are well known in the art (see, for example, Maniatis, Fitsch and Sambrook, Molecular. Cloning; A Laboratory. Manual (1982), or Current Protocols in Molecular. Biology, Ausubel, F. M. et al. (Eds), Wiley & Sons, Inc.).

Polynucleotides probes or primers for the detection of NBHSD2 cDNA can be designed from the cDNA of SEQ ID NO:111 Methods for designing probes and primers are known in the art. In another embodiment, the subject invention provides diagnostic kits for the detection of NBHSD2 cDNA in cells. The kit comprises a package having one or more containers of oligonucleotide primers for detection of NBHSD2 cDNA in PCR assays or one or more containers of polynucleotide probes for the detection of NBHSD2 cDNA by in situ hybridization or Northern analysis. Kits may, optionally, include containers of various reagents used in various hybridization assays. The kit may also, optionally, contain one or more of the following items: polymerization enzymes, buffers, instructions, controls, or detection labels. Kits may also, optionally, include containers of reagents mixed together in suitable proportions for performing the hybridization assay methods in accordance with the invention. Reagent containers preferably contain reagents in unit quantities that obviate measuring steps when performing the subject methods.

In another embodiment, the invention relates to methods and compositions for detecting and quantifying the level of the protein of the invention present in a particular biological sample. These methods are useful for the diagnosis or prognosis of diseases associated with an altered levels of the protein of the invention. Diagnostic assays to detect the protein of the invention may comprise a biopsy, in situ assay of cells from organ or tissue sections, or an aspirate of cells from a tumor or normal tissue. In addition, assays may be conducted upon cellular extracts from organs, tissues, cells, urine, or serum or blood or any other body fluid or extract.

Assays for the quantification of the NBHSD2 polypeptide of SEQ ID NO:112 may be performed according to methods well known in the art. Typically, these assays comprise contacting the sample with a ligand of the protein of the invention or an antibody (polyclonal or monoclonal) which recognizes the protein of the invention or a fragment thereof, and detecting the complex formed between the protein of the invention present in the sample and the ligand or antibody. Fragments of the ligands and antibodies may also be used in the binding assays, provided these fragments are capable of specifically interacting with the NBHSD2 of the subject invention. Further, the ligands and antibodies which bind to the NBHSD2 of the invention may be labeled according to methods known in the art. Labels which are useful in the subject invention include, but are not limited to, enzymes labels, radioisotopic labels, paramagnetic labels, and chemiluminescent labels. Typical techniques are described by Kennedy, J. H., et al. (1976). *Clin. Chim. Acta* 70:1-31; and Schurs, A. H. et al. (1977) *Clin. Chim. Acta* 81: 140 which disclosure is hereby incorporated by reference in its entirety).

In another embodiment, the invention relates to compositions and methods using the proteins of the invention or fragment thereof to screen for compounds that bind an NBHSD2 polypeptide or fragment thereof. In a preferred embodiment, the proteins of the invention or fragment thereof may be used to identify and/or quantify substrates using any techniques known to those skilled in the art. To find substrates, the proteins of the invention, or fragment thereof, or derivative thereof, may be used for screening libraries of compounds in any of a variety of drug screening techniques. The fragment employed in such screening may be free in solution, affixed to a solid support, borne on a cell surface, or located intracellularly. The: formation of binding complexes, between the proteins of the invention, or fragment thereof, or derivative thereof, and the agent being tested, may be measured by methods well known to those skilled in the art, like, but not limited to, the BIAcore (Upsala, Sweden). Antagonists or inhibitors of the proteins of the invention may be produced using methods which are generally known in the art, including the screening of libraries of pharmaceutical agents to identify those which specifically bind the protein of the invention. Another technique for drug screening which may be used provides for high throughput screening of compounds having suitable binding affinity to the protein of the invention.

In another embodiment, the present invention includes the use of NBHSD2 polypeptides, or fragments having a desired biological activity to treat or ameliorate a condition in an individual. For example, the condition may be deficiency of the sex steroid biosynthesis such as hormone-25 dependent disorders, or an abnormality in any of the functions of the sex steroid metabolism. In such embodiments, AN. NBHSD2 polypeptide, or a fragment thereof, is administered to an individual in whom it is desired to increase or decrease any of the activities of NBHSD2 polypeptides. A NBHSD2 polypeptide or fragment thereof may be administered directly to the individual or, alternatively, a nucleic acid encoding a NBHSD2 polypeptide or a fragment thereof may be administered to the individual. Alternatively, an agent which increases the activity of NBHSD2 polypeptides may be administered to the individual. Such agents may be identified by contacting a NBHSD2 polypeptide or a cell or preparation containing NBHSD2 polypeptides with a test agent and assaying whether the test agent increases the activity of the protein. For example, the test agent may be a chemical compound or a polypeptide or peptide. Alternatively, the activity of NBHSD2 polypeptides may be decreased by administering an agent which interferes with such activity to an individual. Agents which interfere with the activity of NBHSD2 polypeptides may be identified by contacting A NBHSD2 polypeptide or a cell or preparation containing NBHSD2 polypeptides with a test agent and assaying whether the test agent decreases the activity of the protein. Decrreasing the activity of NHBSD2 would be useful for the successful treatment and/or management of diseases or biochemical abnormalities associated with decrease of oestradiol. For example, the agent may be a chemical compound, a polypeptide or peptide, an antibody, or a nucleic acid such as an antisense nucleic acid or a triple helix-forming nucleic acid. Another embodiment of the invention relates to composition and methods using polynucleotide sequences encoding the protein of the invention or fragment thereof to establish transgenic model animals (*D. melanogaster, M. musculus*), by any method familiar to those skilled in the art. By modulating in vivo the expression of the transgene with drugs or modifier genes (activator or suppressor genes), animal models can be developed that mimic human hormone-dependent disorders such as cancers. These animal models would thus allow the identification of potential therapeutic agents for treatment of the disorders. In addition, recombinant cell lines derived from these transgenic animals may be used for similar approaches ex vivo.

In another embodiment, an array of oligonucleotides probes comprising the nucleotide sequence of SEQ ID NO:111 or fragments thereof can be constructed to conduct efficient screening of e.g., genetic mutations or deletion. The microarray can be used to monitor the expression level of large numbers of genes simultaneously and to identify genetic variants, mutations, and polymorphisms. This information may be used to determine gene function, to understand the genetic basis of a disorder, to diagnose a disorder, and to develop and monitor the activities of therapeutic agents. (see for example: Chee, M. et al., Science, 274:610-614 (1996). which disclosure is hereby incorporated by reference in its entirety). For example, deletion of genes NBHSD2 locus is a frequent target of deletion in human hepatocellular carcinoma.

Uses of Antibodies

Antibodies of the present invention have uses that include, but are not limited to, methods known in the art to purify, detect, and target the polypeptides of the present invention including both in vitro and in vivo diagnostic and therapeutic, methods. An example of such use using immunoaffinity chromatography is given below. The antibodies of the present invention may be used either alone or in combination with other compositions. For example, the antibodies have use in immunoassays for qualitatively and quantitatively measuring levels of antigen-bearing substances, including the polypeptides of the, present invention, in biological samples (See, e.g., Harlow et al., 1988). (Incorporated by reference in the entirety). The antibodies may also be used in therapeutic compositions for killing cells expressing the protein or reducing the levels of the protein in the body.

The invention further relates to antibodies that act as agonists or antagonists of the polypeptides of the present invention. For example, the present invention includes antibodies that disrupt the receptor/ligand interactions with the polypeptides of the invention either partially or fully. Included are both receptor-specific antibodies and ligand-specific antibodies. Included are receptor-specific antibodies, which do not prevent ligand binding but prevent receptor activation. Receptor activation (i.e., signaling) may be determined by techniques described herein or otherwise known in the art. Also include are receptor-specific antibodies which both prevent ligand binding and receptor activation. Likewise, included are neutralizing antibodies that bind the ligand and prevent binding of the ligand to the receptor, as well as antibodies that bind the ligand, thereby preventing receptor activation, but do not prevent the ligand from binding the receptor. Further included are antibodies that activate the receptor. These antibodies may act as agonists for either all or less than all of the biological activities affected by ligand-mediated receptor activation. The antibodies may be specified as agonists or antagonists for biological activities comprising specific activities disclosed herein. The above antibody agonists can be made using methods known in the art. See e.g., WO 96/40281; U.S. Pat. No. 5,811,097; Deng et al., (1998). Blood. 92(6):1981-1988; Chen et al., (1998), Cancer Res. 58(16):3668-3678; Harrop et al., (1998), J. Immunol. 161(4):1786-1794; Zhu, et al. (1998), Cancer Res.58(15):3209-3214; Yoon, et al. (1998), J. Immunol. 160(7):3170-3179; Prat et al., (1998), J. Cell. Sci. 111 (Pt2):237-247; Pitard et al., (1997), J. hmnunol. Methods. 205(2):177-190; Liautard et al., (1997), Cytokine. 9(4):233-241; Carlson et al., (1997), J. Biol. Chem., 272 (17):11295-11301; Taryman, et al., (1995), Neuron. 14(4): 755-762; Muller et al., (1998), Structure. 6(9):1153-1167; Bartunek et al., (1996), Cytokine. 8(1): 14-20 (said references incorporated by reference in their entireties).

As discussed above, antibodies of the polypeptides of the invention can, in turn, be utilized to generate anti-idiotypic antibodies that "mimic" polypeptides of the invention using techniques well known to those skilled in the art [See, e.g. Greenspan and Bona (1989), FASEB. J. 7(5):437-444 and Nissinoff, (1991), J. Immunol. 147(8):2429-2438, which disclosures are hereby incorporated by reference in their entireties]. For example, antibodies which bind to and competitively inhibit polypeptide multimerization or binding of a pqlypeptide of the invention to ligand can be used to generate anti-idiotypes that "mimic" the polypeptide multimerization or binding domain and, as a consequence, bind to and neutralize polypeptide or its ligand. Such neutralization anti-idiotypic antibodies can be used to bind a polypeptide of the invention or to bind its ligands/receptors, and thereby block its biological activity.

Immunoaffinity Chromatography

Antibodies prepared as described herein are coupled to a support. Preferably, the antibodies are monoclonal antibodies, but polyclonal antibodies may also be used. The support may be any of those typically employed in immunoaffinity chromatography, including Sepharose CL-4B (Pharmacia, Piscataway, N.J.), Sepharose CL-2B (Pharmacia, Piscataway, N.J.), Affi-gel 10 (Biorad, Richmond, Calif.), or glass beads.

The antibodies may be coupled to the support using any of the coupling reagents typically used in immunoaffinity chromatography, including cyanogen bromide. After coupling the antibody to the support, the support is contacted with a sample which contains a target polypeptide whose isolation, purification or enrichment is desired. The target polypeptide may be a polypeptide selected from the group consisting of polypeptide sequences of the Sequence Listing, those encoded by the clone inserts of the deposited clone pool, variants and fragments thereof, or a fusion protein comprising said selected polypeptide or a fragment thereof.

Preferably, the sample is placed in contact with the support for a sufficient amount of time and under appropriate conditions to allow at least 50% of the target polypeptide to specifically bind to the antibody coupled to the support.

Thereafter, the support is washed with an appropriate wash solution to remove polypeptides which have non-specifically adhered to the support. The wash solution may be any of those typically employed in immunoaffinity chromatography, including PBS, Tris-lithium chloride buffer (0.1M lysine base and 0.5M lithium chloride, pH 8.0), Tris-hydrochloride buffer (0.05M Tris-hydrochloride, pH 8.0), or Tris/TritonlNaCl buffer (50 mM Tris.cl, pH 8.0 or 9.0, 0.1% Triton X-100, and 0.5 M NaCl).

After washing, the specifically bound target polypeptide is eluted from the support using the high pH or low pH elution solutions typically employed in immunaffinity chromatography. In particular, the elution solutions may contain an eluant such as triethanolamine, diethylamine, calcium chloride, sodium thiocyanate, potasssium bromide, acetic acid, or glycine. In some embodiments, the elution solution may also contain a detergent such as Triton X-100 or octyl-beta-D-glucoside.

Expression of Genset Gene Products

Evaluation of Expression Levels and Patterns of GENSET Polypeptide-Encoding mRNAs The spatial and temporal expression patterns of GENSET polypeptide-encoding mRNAs, as well as their expression levels, may be determined as follows.

Expression levels and patterns of GENSET polypeptide-encoding mRNAs, may be analyzed by solution hybridization with long probes as described in International Patent Application No. WO 97/05277, the entire contents of which are hereby incorporated by reference. Briefly, a GENSET polynucleotide, or fragment thereof, corresponding to the gene encoding the mRNA to be characterized is inserted at a cloning site immediately downstream of a bacteriophage (T3, T7 or SP6). RNA polymerase promoter to produce antisense RNA. Preferably, the GENSET polynucleotide is at least a 100 nucleotides in length. The plasmid is linearized and transcribed in the presence of ribonucleotides comprising modified ribonucleotides (i.e biotin-UTP and DIG-UTP). An excess of this doubly labeled RNA is hybridized in solution with mRNA isolated from cells or tissues of interest. The hybridizations are performed under standard stringent conditions (40-50° C. for 16 hours in an 80% formamide, 0.4 M NaCl buffer, pH 7-8). The unhybridized probe is removed by digestion with ribonucleases specific for single-stranded RNA (i.e. RNases CL3, T1, Phy M, U2 or A). The presence of the biotin-UTP modification enables capture of the hybrid on a microtitration plate coated with streptavidin. The presence of the DIG modification enables the hybrid to, be detected and quantified by ELISA using an anti-DIG antibody coupled to alkaline phosphatase.

The GENSET polypeptide-encoding cDNAs, or fragments thereof, may also be tagged with nucleotide sequences for the serial analysis of gene expression (SAGE) as disclosed in UK Patent Application No. 2 305 241 A, the entire contents of which are incorporated by reference. In this method, cDNAs are prepared from a cell, tissue, organism or other source of nucleic acid for which it is desired to determine gene expression patterns. The resulting cDNAs are separated into two pools. The cDNAs in each pool are cleaved with a first restriction endonuclease, called an "anchoring enzyme," having a recognition site which is likely to be present at least once in most cDNAs. The fragments which contain the 5' or 3' most region of the cleaved cDNA are isolated by binding to a capture medium such as streptavidin coated beads. A first oligonucleotide linker having a first sequence for hybridization of an amplification primer, and an internal restriction site for a "tagging endonuclease" is ligated to, the digested cDNAs in the first pool. Digestion with the second endonuclease produces short "tag" fragments from the cDNAs. A second oligonucleotide having a second sequence for hybridization of an amplification primer and an internal restriction site is ligated to the digested cDNAs in the second pool. The cDNA fragments in the second pool are also digested with the "tagging endonuclease" to generate short "tag" fragments derived from the cDNAs in the second pool. The "tags" resulting from digestion of the first and second pools with the anchoring enzyme and the tagging endonuclease are ligated to one another to produce "ditags.". In some embodiments, the ditags are concatamerized to produce ligation products containing from 2 to 200 ditags. The tag sequences are then determined and compared to the sequences of the GENSET polypeptide-encoding cDNAs to determine which genes are expressed in the cell, tissue, organism, or other source of nucleic acids from which the tags were derived. In this way, the expression pattern of a GENSET polypeptide-encoding gene in the cell, tissue, organism, or other source of nucleic acids is obtained.

Quantitative analysis of GENSET gene expression may also be performed using arrays. For example, quantitative analysis of gene expression may be performed with GENSET polynucleotides, or fragments thereof in a complementary DNA microarray as described by Schena et al. (1995). *Science* 270:467-470 and Schena et al. (1996), Proc Natl Acad Sci U S A, 93(20): 10614-10619 which disclosures are hereby incorporated by reference in their entireties. GENSET polypeptide-encoding cDNAs or fragments thereof are amplified by PCR and arrayed from 96-well microtiter plates onto, silylated microscope slides using high-speed robotics. Printed arrays are incubated in a humid chamber to allow rehydration of the array elements and rinsed, once in 0.2% SDS for 1 min, twice in water for 1 min and once for 5 min in sodium borohydride solution. The arrays are submerged in water for 2 min at 95° C., transferred into 0.2% SDS for 1 min, rinsed twice with water, air dried and stored in the dark at 25° C. Cell or tissue mRNA is isolated or commercially obtained and probes are prepared by a single round of reverse transcription. Probes are hybridized to 1 $cm^2$ microarrays under a 14×14 mm glass coverslip for 6-12 hours at 60° C. Arrays are washed for 5 min at 25° C. in low stringency wash buffer (1×SSC/0.2% SDS), then for 10 min at room temperature, in high stringency wash buffer (0.1×SSC/0.2% SDS). Arrays are scanned in 0.1×SSC using a fluorescence laser scanning device fitted with a custom filter set. Accurate differential expression measurements are obtained by taking the average of the ratios of two independent hybridizations.

Quantitative analysis of the expression of genes may also be performed with GENSET polypeptide-encoding cDNAs or fragments thereof in complementary. DNA arrays as described by Pietu et al., (1996). Genome. Research 6:492-503, which disclosure is hereby incorporated by reference in its entirety., The GENSET polynucleotides of the invention or fragments thereof are PCR amplified and spotted on membranes. Then, mRNAs originating from various tissues or cells are labeled with radioactive nucleotides. After hybridization and washing in controlled conditions, the hybridized mRNAs are detected by phospho-imaging or autoradiography. Duplicate experiments are performed and a quantitative analysis of differentially expressed mRNAs is then performed.

Alternatively, expression analysis of GENSET genes can be done through high density. nucleotide arrays as described by Lockhart et al., (1996). Nature Biotechnology 14:1675-1680 and Sosnowski, et al., (1997). Proc Natl Acad Sci U.S.A. 94:1119-1123, which disclosures are hereby incorporated by reference in their entireties. Oligonucleotides of 15-50 nucleotides corresponding to sequences of a GENSET polynucleotide or fragments thereof are synthesized directly on the chip. (Lockhart et al., supra) or synthesized and then addressed to the chip. (Sosnowski et al., supra). Preferably, the oligonucleotides are about 20 nucleotides in length. cDNA probes labeled with an appropriate compound, such as biotin, digoxigenin or fluorescent dye, are synthesized from the appropriate mRNA population and then randomly fragmented to an average size of 50 to 100 nucleotides. The said probes are then hybridized to the chip. After washing as described in Lockhart et al., (supra) and application of different electric fields (Sosnowsky et al., supra), the dyes or labeling compounds are detected and quantified. Duplicate hybridizations are performed. Comparative analysis of the intensity of the signal originating from cDNA probes on the same target oligonucleotide in different cDNA samples indicates a differential expression of the GENSET polypeptide-encoding mRNA.

Uses of GENSET Gene Expression Data

Once the expression levels and patterns of a GENSET polypeptide-encoding mRNA has been determined using any technique known to those skilled in the art, in particular those described in the section entitled "Evaluation of Expression Levels and Patterns of GENSET polypeptide-encoding mRNAs", or using the instant disclosure, these information may beused to design GENSET gene specific markers for detection, identification, screening and diagnosis purposes as well as to design DNA constructs with an expression pattern similar to a GENSET gene expression pattern.

Detection of GENSET Polypeptide Expression and/or Biological Activity

The invention further relates to methods of detection of GENSET polypeptide expression and/or biological activity in a biological sample using the polynucleotide and polypeptide sequences described herein. Such method scan be used, for example, as a screen for normal or abnormal GENSET polypeptide expression and/or biological activity and, thus, can be used diagnostically. The biological sample for use in the methods of the present invention includes a suitable sample from, for example, a mammal, particularly a human.

Detection of GENSET Polypeptides

The invention further relates to methods of detection of GENSET polypeptide or encoding polynucleotides in a sample using the sequences described herein and any techniques known to those skilled in the art. For example, a labeled polynucleotide probe having all or a functional portion of the nucleotide sequence of a GENSET polypeptide-encoding polynucleotide can be used in a method to detect a GENSET polypeptide-encoding polynucleotide in a sample. In one embodiment, the sample is treated to render the polynucleotides in the sample available for hybridization to a polynucleotide probe, which can be DNA or RNA. The resulting treated sample is combined with a labeled polynucleotide probe having all or a portion of the nucleotide sequence of the GENSET polypeptide-encoding cDNA or genomic sequence, under conditions appropriate for hybridization of complementary sequences to occur. Detection of hybridization of polynucleotides from the sample with the labeled nucleic probe indicates the presence of GENSET polypeptide-encoding polynucleotides in a sample. The presence of GENSET polypeptide-encoding mRNA is indicative of GENSET polypeptide-encoding gene expression.

Consequently, the invention comprises methods for detecting the presence of a polynucleotide comprising a nucleotide sequence selected from a group consisting of the polynucleotide sequences of the Sequence Listing, those of human cDNA clone inserts of the deposited clone pool, sequences fully complementary thereto, fragments and variants thereof in a sample. In a first embodiment, said method comprises the following steps of:

a) bringing into contact said sample and a nucleic acid probe or a plurality of nucleic acid probes which hybridize to said selected nucleotide sequence; and
b) detecting the hybrid complex formed between said probe or said plurality of probes and said polynucleotide., In a preferred embodiment of the above detection method, said nucleic acid probe or said plurality of nucleic acid probes is labeled with a detectable molecule. In another preferred embodiment of the above detection method, said nucleic acid probe or said plurality of nucleic acid probes has been immobilized on a substrate. In still another preferred embodiment, said nucleic acid probe or said plurality of nucleic acid probes has a sequence comprised in a sequence complementary to said selected sequence.

In a second embodiment, said method comprises the steps of:

a) contacting said sample with amplification reaction reagents comprising a pair of amplification primers located on either side of the region of said nucleotide sequence to be amplified;
b) performing an amplification reaction to synthesize amplification products containing said region of said selected nucleotide sequence; and
c) detecting said amplification products.

In a preferred embodiment of the above detection method, when the polynucleotide to be amplified is a RNA molecule, preliminary reverse transcription and synthesis of a second cDNA strand are necessary to provide a DNA template to be amplified. In another preferred embodiment of the above detection method, the amplification product is detected by hybridization with a labeled probe having a sequence which is complementary to the amplified region. In still another preferred embodiment, at least one of said amplification primer has a sequence comprised in said selected sequence or in the sequence complementary to said selected sequence.

Alternatively, a method of detecting GENSET polypeptide expression in a test sample can be accomplished using any product which binds to a GENSET olypeptide of the present invention or a portion of a GENSET polypeptide. Such products may be antibodies, binding fragments of antibodies, polypeptides able to bind specifically to GENSET polypeptides or fragments thereof, including GENSET polypeptide agonists and antagonists. Detection of specific binding to the antibody indicates the presence of a GENSET polypeptide in the sample (e.g., ELISA).

Consequently, the invention is also directed to a method for detecting specifically the presence of a GENSET polypeptide according to the invention in a biological sample, said method comprising the steps of:

a) bringing into contact said biological sample with a product able to bind to a polypeptide of the invention or fragments thereof;
b) allowing said product to bind to said polypeptide to, form a complex; and
c) detecting said complex.

In a preferred embodiment of the above detection method, the product is an antibody. In a more preferred embodiment, said antibody is labeled with a detectable molecule. In another more preferred embodiment of the above detection method, said antibody has been immobilized on a substrate.

In addition, the invention also relates to methods of determining whether a GENSET gene product (e.g. a polynucleotide or polypeptide) is present or absent in a biological sample, said methods comprising the steps of:

a) obtaining said biological sample from a human or non-human animal, preferably a mammal;
b) contacting said biological sample with a product able to bind to a GENSET polypeptide or encoding polynucleotide of the invention; and
c) determining the presence or absence of said GENSET polypeptide-encoding gene product in said biological sample.

The present invention also relates to kits that can be used in the detection of GENSET polypeptide-encoding gene expression products. The kit can comprise a compound that specifically binds a GENSET polypeptide (e.g. binding proteins, antibodies or binding fragments thereof (e.g. F(ab')2 fragments) or a GENSET polypeptide-encoding mRNA (e.g. a complementary probe or primer), for example, disposed within a container means. The kit can further comprise ancillary reagents, including buffers and the like.

Detection of GENSET Polypeptide Biological Activity

The invention further includes methods of detecting specifically a GENSET polypeptide biological activity, and to identify compounds capable of modulating the activity of a GENSET polypeptide. Assessing the GENSET polypeptide biological activity may be performed by the detection of a change in any cellular property associated with the GENSET polypeptide, using a variety of techniques, including those described herein. To identify modulators of the polypeptides, a control is preferably used. For example, a control sample includes all of the same reagents but lacks the compound or agent being assessed; it is treated in the same manner as the test sample.

The present invention also relates to kits that can be used in the detection of GENSET polypeptide biological activity. The kit can comprise, e.g. substrates for GENSET polypeptides, GENSET-binding compounds, antibodies to GENSET polypeptides, etc., for example, disposed within a container means. The kit can further comprise ancillary reagents, including buffers and the like.

Identification of a Specific Context of GENSET Polypeptide-Encoding Gene Expression When the expression pattern of a GENSET polypeptide-encoding mRNA shows that a GENSET polypeptide-encoding gene is specifically expressed in a given context, probes and primers specific for this gene as well as antibodies binding to the GENSET polypeptide-encoding polynucleotide may then be used as markers for the specific context. Examples of specific contexts are: specific expression in a given tissue/cell or tissue/cell type, expression at a given stage of development of a process such as embryo development or disease development, or specific expression in a given organelle. Such primers, probes, and antibodies are useful commercially to identify, tissues/cells/organelles of unknown origin, for example, forensic samples, differentiated tumor tissue that has metastasized to foreign bodily sites, or to differentiate different tissue types in a tissue cross-section using any technique known to those skilled in the art including in situ. PCR or immunochemistry for example.

For example, the cDNAs and proteins of the sequence listing and fragments thereof, may be used to distinguish human tissues/cells from non-human tissues/cells and to distinguish between human tissues/cells/organelles that do and do not express the, polynucleotides comprising the cDNAs. By knowing the expression pattern of a given GENSET polypeptide, either through routine experimentation or by using the instant disclosure, the polynucleotides and polypeptides of the present invention may be used in methods of determining the identity of an unknown tissue/cell sample/organelle. As part of determining the identity of an unknown tissue/cell sample/organelle, the polynucleotides and polypeptides of the present invention may be used to determine what the unknown tissue/cell sample is and what the unknown sample is not. For example, if a cDNA is expressed in a particular tissue/cell type/organelle, and the unknown tissue/cell sample/organelle does not express the cDNA, it may be inferred that the unknown tissue/cells are either not human or not the same human tissue/cell type/organelle as that which expresses the cDNA. Determination of tissue/cell/organelle identity is based on methods that detect the presence or absence of the mRNA (or corresponding cDNA) in a tissue/cell sample using methods well known in the art (e.g., hybridization, PCR based methods, immunoassays, immunochemistry, ELISA). Examples of such techniques are described in more detail below. Therefore, the invention encompasses uses of the polynucleotides and polypeptides of the invention as tissue markers. Consequently, the present invention encompasses methods of identification of a tissue/cell type/subcellular compartment, wherein said method includes the steps of:

a) contacting a biological sample which identity is to be assayed with a product able to bind a GENSET gene product; and b) determining whether a GENSET gene product is expressed in said biological sample.

Products that are able to bind specifically to a GENSET gene product, namely a GENSET polypeptide or a GENSET polypeptide-encoding mRNA, include GENSET polypeptide binding proteins, antibodies or binding fragments thereof (e.g. F(ab')2 fragments), as well as GENSET polynucleotide complementary probes and primers.

Step b) may be performed using any detection method known to those skilled in the art including those disclosed herein, especially in the section entitled "Detection of GENSET polypeptide expression and/or biological activity".

Identification of Tissue Types or Cell Species by Means of Labeled Tissue Specific Antibodies Identification of specific tissues is accomplished by the visualization of tissue specific antigens by means of antibody preparations which are conjugated, directly (e.g., green fluorescent protein) or indirectly to a detectable marker. Selected labeled antibody species bind to their specific antigen binding partner in tissue sections, cell suspensions, or in extracts of soluble proteins from a tissue sample to provide a pattern for qualitative or semi-qualitative interpretation.

A. Immunohistochemical Techniques

Purified, high-titer antibodies, prepared as described above, are conjugated to a detectable marker, as described, for example, by Fudenberg, (1980). Chap. 26 in: Basic 503 Clinical Immunology, 3rd Ed. Lange, Los Altos, Calif. or Rose et al., (1980) Chap. 12 in: Methods in Immunodiagnosis, 2d Ed. John Wiley 503 Sons, New York, which disclosures are hereby incorporated by reference in their entireties.

A fluorescent marker, either fluorescein or rhodamine, is preferred, but antibodies can also be labeled with an enzyme that supports a color producing reaction with a substrate, such as horseradish peroxidase. Markers can be added to tissue-bound antibody in a second step, as described below. Alternatively, the specific anti-tissue antibodies can be labeled with ferritin or other electron dense particles, and localization of the ferritin coupled antigen-antibody complexes achieved by means of an electron microscope. In yet another approach, the antibodies are, radiolabeled, with, for example $^{125}$I, and detected by overlaying the antibody treated preparation with photographic emulsion. Preparations to carry out the procedures can comprise monoclonal or polyclonal antibodies to a single protein or peptide identified as specific to a tissue type, for example, brain tissue, or antibody preparations to several antigenically distinct tissue specific antigens can be used in panels, independently or in mixtures, as required. Tissue sections and cell suspensions are prepared for immunohistocherical examination according to common histological techniques. Multiple cryostat sections (about 4 um, unfixed) of the unknown tissue and known control, are mounted and each slide covered with different dilutions of the antibody preparation.

Sections of known and unknown tissues should also be treated with preparations to provide a positive control, a negative control, for example, pre-immune sera, and a control for non-specific staining, for example, buffer. Treated sections are incubated in a humid chamber for 30 min at room temperature, rinsed, then washed in buffer for 30-45 min. Excess fluid is blotted away, and the marker developed. If the tissue specific antibody was not labeled in the first incubation, it can be labeled at this time in a second antibody-antibody reaction, for example, by adding fluorescein or enzyme-conjugated antibody against the immunoglobulin class of the antiserum-producing species, for example, fluorescein labeled antibody to mouse IgG. Such labeled sera are commercially available. The antigen found in the tissues by the above procedure can be quantified by measuring the intensity of color or fluorescence on the tissue section, and calibrating that signal using appropriate standards.

B. Identification of Tissue Specific Soluble Proteins

The visualization of tissue specific proteins and identification of unknown tissues from that procedure is carried out using the labeled antibody reagents and detection strategy as described for immunohistochemistry; however the sample is prepared according to an electrophoretic technique to distribute the proteins extracted from the tissue in an orderly array on the basis of molecular weight for detection. For example, Western Blot Analysis, see, e.g., Davis et al., Basic. Methods in Molecular. Biology, ed., Elsevier. Press, NY (1986), Section 19-3.

In either procedure A or B, a detectable label can be attached to the primary tissue antigen-primary antibody complex according to various strategies and permutations thereof. In a straightforward approach, the primary specific antibody can be labeled; alternatively, the unlabeled complex can be bound by a labeled secondary anti-IgG antibody. In other approaches, either the primary or secondary antibody is conjugated to a biotin molecule, which can, in a subsequent step, bind an avidin conjugated marker. According to yet another strategy, enzyme labeled or radioactive protein A, which has the property of binding to any IgG, is bound in a final step to either the primary or secondary antibody. The visualization of tissue specific antigen binding at levels above those seen in control tissues to one or more tissue specific antibodies, prepared from the gene sequences identified from cDNA sequences, can identify tissues of unknown origin, for example, forensic samples, or differentiated tumor tissue that has metastasized to foreign bodily sites.

Screening and Diagnosis of Abnormal GENSET Polypeptide Expression and/or Biological Activity Moreover, antibodies and/or primers specific for GENSET polypeptide expression may also be used to identify abnormal GENSET polypeptide expression and/or biological activity, and subsequently to screen and/or diagnose disorders associated with abnormal GENSET polypeptide expression. For example, a particular disease may result from lack of expression, over expression, or under expression of a GENSET polypeptide-encoding mRNA. By comparing mRNA expression patterns and quantities in samples taken from healthy individuals with those from individuals suffering from a particular disorder, genes responsible for this disorder may be identified. Primers, probes and antibodies specific for this GENSET polypeptide may then be used to elaborate kits of screening and diagnosis for a disorder in which the gene of interest is specifically expressed or in which its expression is specifically dysregulated, i.e underexpressed or overexpressed.

Screening for Specific Disorders

The present invention also relates to methods and uses of GENSET polypeptides for identifying individuals having elevated or reduced levels of GENSET polypeptides, which individuals are likely to benefit from therapies to suppress or enhance GENSET polypeptide-encoding gene expression, respectively. One example of such methods and uses comprises the steps of:

a) obtaining from a mammal a biological sample;
b) detecting the presence in said sample of a GENSET polypeptide-encoding gene product (mRNA or protein);
c) comparing the amount of said GENSET polypeptide-encoding gene product present in said sample with that of a control sample; and
d) determining whether said human or non-human mammal has a reduced or elevated level of GENSET gene expression compared to the control sample.

A biological sample from a subject affected by, or at risk of developing, any disease or condition associated with a GENSET polypeptide can be screened for the presence of increased or decreased levels of GENSET gene product, relative to a normal population (standard or control), with an increased or decreased level of the GENSET polypeptide relative to the normal population being indicative of predisposition to or a present indication of the disease or condition, or any sympton associated with the disease or condition. Such individuals would be candidates for therapies, e.g., treatment with pharmaceutical compositions comprising the GENSET polypeptide, a polynucleotide encoding the GENSET polypeptide, or any other compound that affects the expression or activity of the GENSET polypeptide. Generally, the identification of elevated levels of the GENSET polypeptide in a patient would be indicative of an individual that would benefit from treatment with agents that suppress GENSET polypeptide expression or activity, and the identification of low levels of the GENSET polypeptide in a patient would be indicative of an individual that would benefit from agents that induce GENSET expression or activity.

Biological samples suitable for use in this method include any biological fluids, including, but not limited to, blood, saliva, milk, and urine. Tissue samples (e.g. biopsies) can also be used in the method of the, invention, including samples derived from any tissue associated with GENSET gene expression as determined by any method common to the art such as those described herein. Cell cultures or cell extracts derived, for example, from tissue biopsies can also be used. The detection step of the present method can be performed using standard protocols for protein/mRNA detection. Examples of suitable protocols include Northern blot analysis, immunoassays (e.g. RIA, Western blots, immunohistocheimcal analyses), and PCP.

Thus, the present invention further relates to methods and uses of GENSET polypeptides for identifying individuals or non-human animals at increased risk for developing, or present state of having, certain diseases/disorders associated with abnormal GENSET polypeptide expression or biological activity. One example of such methods comprises the steps of:

a) obtaining from a human or non-human mammal a biological sample;

b) detecting the presence in said sample of a GENSET gene product (mRNA or protein);

c) comparing the amount of said GENSET gene product present in said sample with that of a control sample; and d) determing whether said human or non-human mammal is at increased risk for developing, or present state of having, a diseases or disorder.

In preferred embodiments, the biological sample is taken from animals presenting any symptom associated with any disease or condition associated with a GENSET gene product. In accordance with this method, the presence in the sample of altered (e.g. increased or decreased). levels of the GENSET product indicates that the subject is predisposed to the disease or condition. Biological samples suitable for use in this method include biological fluids including, but not limited to, blood, saliva, milk, and urine. Tissue samples (e.g. biopsies) can also be used in the method of the invention. Cell cultures or cell extracts derived, for example, from tissue biopsies can also be used.

The diagnostic methodologies described herein are applicable to both humans and non-human mammals.

Detection of GENSET Gene Mutations

The invention also encompasses methods and uses of GENSET polynucleotides to detect mutations in GENSET polynucleotides of the invention. Such methods may advantageously be used to detect mutations occurring in GENSET genes and preferably in their regulatory regions. When the mutation was proven to be associated with a disease, the detection of such mutations may be used for screening and diagnosis purposes.

In one embodiment of the oligonucleotide arrays of the invention, an oligonucleotide probe matrix may advantageously be used to detect mutations occurring in GENSET genes and preferably in their regulatory regions. For this particular purpose, probes are specifically designed to have a nucleotide sequence allowing their, hybridization to the genes that carry known mutations (either by deletion, insertion or substitution of one or several nucleotides). By known mutations, it is meant, mutations on the GENSET genes that have been identified according, for example to the technique used by Huang et al., (1996). Cancer Res 56(5):1137-1141 or Samson et al., (1996) Nature, 382(6593):722-725, which disclosures are hereby incorporated by reference in their entireties.

Another technique that is used to detect mutations in GENSET genes is the use of a high-density. DNA array. Each oligonucleotide probe constituting a unit element of the high density DNA array is designed to match a specific subsequence of a GENSET genomic DNA or cDNA. Thus, an array consisting of oligonucleotides complementary to subsequences of the target gene sequence is used to determine the identity of the target sequence with the wild gene sequence, measure its amount, and detect differences between the target sequence and the reference wild gene sequence of the GENSET gene. In one such design, termed 4L tiled array, is implemented a set of four probes (A, C, G, T), preferably 15-nucleotide oligomers. In each set of four probes, the perfect complement will hybridize more strongly than mismatched probes. Consequently, a nucleic acid target of length L is scanned for mutations with a tiled array containing 4L probes, the whole probe set containing all the possible mutations in the known wild reference sequence. The hybridization signals of the 15-mer probe set tiled array are perturbed by a single base change in the target sequence. As a consequence, there is a characteristic loss of signal or a "footprint" for the probes flanking a mutation position. This technique was described by Chee et al., (1996) *Science*. 274:610-614, which disclosure is hereby incorporated by reference in its entirety.

Construction of DNA Constructs with a Genset Gene Expression Pattern

In addition, characterization of the spatial and temporal expression patterns and expression levels of GENSET polypeptide-encoding mRNAs is also useful for constructing expression vectors capable of producing a desired level of gene product in a desired spatial or temporal manner, as discussed below.

DNA Constructs that Direct Temporal and Spatial GENSET Gene Expression in Recombinant Cell Hosts and in Transgenic Animals.

In order to study the physiological and phenotypic consequences of a lack of synthesis of a GENSET polypeptide., both at the cellular, level and at the multi cellular organism level, the invention also encompasses DNA constructs and recombinant vectors enabling a conditional expression of a specific allele of a GENSET polypeptide-encoding genomic sequence or cDNA and also of a copy of this genomic sequence or cDNA harboring substitutions, deletions, or additions of one or more bases as regards to a polynucleotide of the present regulatory sequence, but preferably in the 5'-egulatory sequence or in an exon of the GENSET polypeptide-encoding genomic sequence or within the GENSET polypeptide-encoding cDNA.

A first preferred DNA construct is based on the tetracycline resistance operon tet from *E. coli* transposon Tn10 for controlling the GENSET gene expression, such as described by Gossen et al., (1992). Proc. Natl. Acad. Sci. USA. 89:5547-5551; Gossen et al., (1995) Science 268:1766-1769, and Furth P. A. et al. (1994). Proc. Natl. Acad. Sci USA. 91:9302-9306, which disclosures are hereby incorporated by reference in their entireties. Such a DNA construct contains seven tet operator sequences from Tn10 (tetop) that are fused to either a minimal promoter or a 5'-regulatory sequence of the GENSET gene, said minimal promoter or said GENSET polynucleotide regulatory sequence being operably linked to a polynucleotide of interest that codes either for a sense or an antisense oligonucleotide or for a polypeptide, including a GENSET polypeptide, or a peptide fragment thereof. This DNA construct is functional as a conditional expression system for the nucleotide sequence of interest when the same cell also comprises a nucleotide sequence coding for either the wild type (tTA) or the mutant (rTA) repressor fused to the activating domain of viral protein VP 16 of herpes simplex virus, placed under the control of a promoter, such as the HCMVIE1 enhancer/promoter or the MMTV-LTR. Indeed, a preferred DNA construct of the invention comprise both the polynucleotide containing the tet operator sequences and the polynucleotide containing a sequence coding for the tTA or the rTA repressor. In a specific embodiment, the conditional expression DNA construct contains the sequence encoding the mutant tetracycline repressor rTA, the expression of the polynucleotide of interest is silent in the absence of tetracycline and induced in its presence.

DNA Constructs Allowing Homologous Recombination: Replacement Vectors

A second preferred DNA construct will comprise, from 5'-end to 3'-end: (a) a first nucleotide sequence that is found in the GENSET polypeptide-encoding genomic sequence; (b) a nucleotide sequence comprising a positive selection marker, such as the marker for neomycin resistance (neo); and (c) a second nucleotide sequence that is found in the GENSET polypeptide-encoding genomic sequence, and is located on the genome downstream the first GENSET polypeptide-encoding nucleotide sequence (a).

In a preferred embodiment, this DNA construct also comprises a negative selection marker located upstream of the nucleotide sequence (a) or downstream from the nucleotide sequence (c). Preferably, the negative selection marker comprises the thymidine kinase (tk) gene [Thomas et al. (1986), Cell. 44:419-428], the hygromycine beta gene [Te Riele et al. (1990), Nature. 348:649-651], the hprt gene [Van der Lugt et al. (1991), Gene. 105:263-267; Reid et al., (1990). Proc. Natl. Acad. Sci. U.S.A. 87:4299-4303]or the Diphteria toxin A fragment (Dt-A) gene [Nada et al., (1993) Cell 73:1125-1135; Yagi, T., et al. (1990), Proc. Natl. Acad. Sci. U.S.A. 87:9918-992], which disclosures are hereby incorporated by reference in their entireties. Preferably, the positive selection marker.is located within a GENSET exon sequence so as to interrupt the sequence encoding a GENSET polypeptide. These replacement vectors are described, for example, by Thomas et al. (1986;1987), Mansour et al. (1988) and Koller et al., (1992). Annu. Rev Immunol. 10:705-730.

The first and second nucleotide sequences (a) and (c) may be indifferently located within a GENSET polypeptide-encoding regulatory sequence, an intronic sequence, an exon sequence or a sequence containing both regulatory and/or intronic and/or exon sequences. The size of the nucleotide sequences (a) and (c) ranges from 1 to 50 kb, preferably from 1 to 10 kb, more preferably from 2 to 6 kb and most preferably from 2 to 4 kb.

DNA Constructs Allowing Homologous Recombination: Cre-LoxP System.

These new. DNA constructs make use of the site specific recombination system of the P1 phage. The P1 phage possesses a recombinase called Cre which interacts specifically with a 34 base pairs loxP site. The loxP site iscomposed of two palindromic sequences of 13 bp separated by a 8 bp, conserved sequence [Hoess et al., (1986). Nucleic Acids Res. 14:2287-2300], which disclosure is hereby incorporated by reference in its entirety., The recombination by the Cre enzyme between two loxp sites having an identical orientation leads to the deletion of the DNA fragment.

The Cre-loxP system used in combination with a homologous recombination technique has been first described by Gu H. et al., (1993) Cell 73:1155-1164 and Gu H. et al., (1994) *Science* 265:103-106, which disclosures are hereby incorporated by reference in their entireties. Briefly, a nucleotide sequence of interest to be inserted in a targeted location of the genome harbors at least two loxP sites in the same orientation and located at the respective ends of a nucleotide sequence to be excised from the recombinant genome. The excision event requires the, presence of the recombinase (Cre) enzyme within the nucleus of the recombinant cell host. The recombinase enzyme may be brought at the desired time either by (a) incubating the recombinant cell hosts in a culture medium containing this enzyme, by injecting the Cre enzyme directly into the desired cell, such as described by Araki et al., (1995) Proc. Natl. Acad. Sci. U.S.A. 92(1): 1604, which disclosure is hereby incorporated by reference in its entirety, or by lipofection of the enzyme into the cells, such as described by Baubonis et at (1993) Nucleic Acids Res. 21(9):2025-9), which disclosure is hereby incorporated by reference in its entirety; (b) transfecting the cell host with a vector comprising the Cre coding sequence operably linked to a promoter functional in the recombinant cell host, which promoter being optionally inducible, said vector being introduced in the recombinant cell host, such as described by Gu et al. (1993) and Sauer et al., (1988). Proc. Natl. Acad. Sci. U.S.A. 85:5166-5170, which disclosures are hereby incorporated by reference in their entireties; (c) introducing in the genome of the cell host a polynucleotide comprising the Cre coding sequence operably linked to a promoter functional in the recombinant cell host, which promoter is optionally inducible, and said polynucleotide being inserted in the genome of the cell host either by a random insertion event or an homologous recombination event, such as described by Gu et al. (1994).

In a specific embodiment, the vector containing the sequence to be inserted in the GENSET gene by homologous recombination is constructed in such a way that selectable markers are flanked by loxP sites of the same orientation, it is possible, by treatment by the Cre enzyme, to eliminate the selectable marker is while leaving the GENSET sequences of interest that have been inserted by an homologous recombination event. Again, two selectable markers are needed: a positive selection marker to select for the recombination event and a negative selection marker to select for the homologous recombination event. Vectors and methods using the Cre-loxP. system are described by Zou, et al., (1994) Curr. Biol. 4:1099-1103, which disclosure is hereby incorporated by reference in its entirety.

Thus, a third preferred DNA construct of the invention comprises, from 5'-end to 3'-end:

(a) a first nucleotide sequence that is comprised in the GENSET genomic sequence; (b) a nucleotide sequence comprising a polynucleotide encoding a positive selection marker, said nucleotide sequence comprising additionally two sequences defining a site recognized by a recombinase, such as a loxP site, the two, sites being placed in the same orientation; and (c) a second nucleotide sequence that is comprised in the GENSET genomic sequence, and is located on the genome downstream of the first GENSET nucleotide sequence (a)

The sequences defining a site recognized by a recombinase, such as a loxP site, are preferably located within the nucleotide sequence (b) at suitable locations bordering the nucleotide sequence for which the conditional excision is sought. In one specific embodiment, two loxP sites are located at each side of the positive selection marker sequence, in order to allow its excision at a desired time after the occurrence of the homologous recombination event.

In a preferred embodiment of a method using the third DNA construct described above, the excision of the polynucleotide fragment bordered by the two sites recognized by a recombinase, preferably two loxP sites, is performed at a desired time, due to the presence within the genome of the recombinant host cell of a sequence encoding the Cre enzyme operably linked to a promoter sequence, preferably an inducible promoter, more preferably a tissue-specific promoter sequence and most preferably a promoter sequence which is both inducible and tissue-specific, such as described by Gu et al. (1994).

The presence of the Cre enzyme within the genome of the recombinant cell host may result from the breeding of two transgenic animals, the first transgenic animal bearing the GENSET-derived sequence of interest containing the loxP. sites as described above and the second transgenic. animal bearing the Cre coding sequence operably linked to a suitable promoter sequence, such as described by Gu et al. (1994).

Spatio-temporal control of the Cre enzyme expression may also be achieved with an adenovirus based vector that contains the Cre gene thus allowing infection of cells, or in vivo infection of organs, for delivery of the Cre enzyme, such as described by Anton and Graharn, (1995), J. Virol., 69:4600-4606 and Kanegae et al., (1995). Nucl. Acids Res. 23:3816-3821, which disclosures are hereby incorporated by reference in their entireties.

The DNA constructs described above may be used to introduce a desired nucleotide sequence of the invention, preferably a GENSET genomic, sequence or a GENSET cDNA sequence, and most preferably an altered copy of a GENSET genomic or cDNA sequence, within a predetermined location of the targeted genome, leading either to the generation of an altered copy of a targeted gene (knock-out homologous recombination) or to, the, replacement of a copy of the targeted gene by another copy sufficiently homologous to, allow an homologous recombination event to occur (knock-in homologous recombination).

Modifying GENSET Polypoptide Expression and/or Biological Activity

Modifying endogenous GENSET expression and/or biological activity is expressly contemplated by the present invention.

Screening for Compounds that Modulate GENSET Expression and/or Biological Activity The present invention further relates to compounds able to modulate GENSET expression and/or biological activity and methods to use these compounds. Such compounds may interact with the regulatory sequences of GENSET genes or they may interact with GENSET polypeptides directly or indirectly.

Compounds Interacting with GENSET Regulatory Sequences

The present invention also concerns a method for screening substances or molecules that are able to interact with the regulatory sequences of a GENSET gene, such as for example promoter or enhancer sequences in untranscribed regions of the genomic. DNA, as determined using any techniques known to those skilled in the art including those described in the section entitled "Identification of Promoters in Cloned Upstream Sequences, or such as regulatory sequences located in untranslated regions of GENSET mRNA.

Sequences within untranscribed or untranslated regions of polynucleotides of the invention may be identified by comparison to databases containing known regulatory sequence such as transcription start sites, transcription factor binding sites, promoter sequences, enhancer sequences, 5'UTR and 3'UTR elements [Pesole et al., (2000) Nucleic. Acids Res, 28(1):193-196]. Alternatively, the regulatory sequences of interest may be identified through conventional mutagenesis or deletion analyses of reporter plasmids using, for instance, techniques described in the section entitled "Identification of Promoters in Cloned Upstream Sequences".

Following the identification of potential GENSET regulatory sequences, proteins which interact with these regulatory sequences may be identified as described below.

Gel retardation assays may be performed independently in order to screen candidate molecules that are able to interact with the regulatory sequences of the GENSET gene, such as described by Fried and Crothers, (1981) Nucleic Acids Res. 9:6505-6525, Garner and Revzin, (1981). Nucleic. Acids Res 9:3047-3060 and Dent and Latchman (1993). The DNA mobility shift assay In: Transcription Factors: A Practical Approach (Latchman D S, ed.) pp1-26. Oxford: IRL Press, the teachings of these publications being herein incorporated by reference. These techniques are based on the principle according to which a DNA or mRNA fragment which is bound to a protein migrates slower than the same unbound DNA or mRNA fragment. Briefly, the target nucleotide sequence is labeled. Then the labeled target nucleotide sequence is brought into contact with either a total nuclear extract from cells containing regulation factors, or with different candidate molecules to be tested. The interaction between the target regulatory sequence of the GENSET gene and the candidate molecule or the regulation factor is detected after gel or capillary electrophoresis through a retardation in the migration.

Nucleic acids encoding proteins which are able to interact with the promoter sequence of the GENSET gene, more particularly the polynucleotides of the 5' and 3' regulatory region or a fragment or variant thereof, may be identified by using a one-hybrid system, such as that described in the booklet enclosed in the Matchmaker One-Hybrid System kit from Clontech (Catalog Ref no. K1603-1, the technical teachings of which are herein incorporated by reference).

Ligands Interacting with GENSET Polypeptides

For the purpose of the present invention, a ligand means a molecule, such as a protein, a peptide, an antibody or any synthetic chemical compound capable of binding to a GENSET protein or one of its fragments or variants or to modulate the expression of the polynucleotide coding for GENSET or a fragment or variant thereof.

In the ligand screening method according to the present invention, a biological sample or a defined molecule to be tested as a putative ligand of a GENSET protein is brought into contact with the corresponding purified GENSET protein, for example the corresponding purified recombinant GENSET protein produced by a recombinant cell host as described herein, in order to form a complex between this protein and the putative ligand molecule to be tested.

As an illustrative example, to study the interaction of a polypeptide of the invention, with drugs or small molecules, such as molecules generated through combinatorial chemistry approaches, the microdialysis coupled to. HPLC method described by Wang, et al. (1997), Chromatographia, 44: 205-208 or the affinity capillary electrophoresis method described by Bush et al., (1997), J. Chromatogr., 777: 311-328, the disclosures of which are incorporated by reference, can be used.

In further methods, peptides, drugs, fatty acids, lipoproteins, or small molecules which interact with a may be identified using assays known in the art. For example, the molecule to be tested for binding is labeled with a detectable label, such as a fluorescent, radioactive, or enzymatic tag and placed in contact with immobilized GENSET protein, or a fragment thereof under conditions which permit specific binding to occur. After removal of non-specifically bound molecules, bound molecules are detected using appropriate means.

Various candidate substances or molecules can be assayed for interaction with a GENSET polypeptide. These substances or molecules include, without being limited to, natural or synthetic organic compounds or molecules of biological origin such as polypeptides. When the candidate substance or molecule comprises a polypeptide, this polypeptide may be the resulting expression product of a phage clone belonging to a phage-based random peptide library, or alternatively the polypeptide may be the resulting expression product of a cDNA library cloned in a vector suitable for performing a two-hybrid screening assay.

A. Candidate Ligands Obtained from Random Peptide Libraries

In a particular embodiment of the screening method, the putative ligand is the expression product of a DNA insert contained in a phage vector [Parmley and Smith, (1988). Gene 73:305-318]. Specifically, random peptide phages libraries are used. The random DNA inserts encode for peptides of 8 to 20 amino acids in length (Oldenburg et al., (1992), Proc. Natl. Acad. Sci. USA 89:5393-5397; Valadon et al., (1996), J. Mol. Biol., 261:11-22; Lucas (1994), In: Development and Clinical Uses of Haempophilus b Conjugate; Westerink (1995), Prbc. Natl. Acad. Sci USA., 92:4021-4025; Felici, (1991), J. Mol. Biol., 222:301-310], which disclosures are hereby incorporated by reference in their entireties. According to this particular embodiment, the recombinant phages expressing a protein that binds to an immobilized GENSET protein is retained and the complex formed between the GENSET protein and the recombinant phage may be subsequently immunoprecipitated by a polyclonal or a monoclonal antibody directed against the GENSET protein.

Once the ligand library in recombinant phages has been constructed, the phage population is brought into contact with the immobilized GENSET protein. Then the preparation of complexes is washed in order to remove the non-specifically bound recombinant phages. The phages that bind specifically to the GENSET protein are then eluted by a buffer, (acid pH) or immunoprecipitated by the monoclonal antibody produced by the hybridoma anti-GENSET, and this phage population is subsequently amplified by an over-infection of bacteria (for example *E. coli*). The selection step may be repeated several times, preferably 24 times, in order to select the more specific recombinant phage clones. The last step comprises characterizing the peptide produced by the selected recombinant phage clones either by expression in infected bacteria and isolation, expressing the phage insert in another host-vector system, or sequencing the insert contained in the selected recombinant phages.

B. Candidate Ligands Obtained by Competition Experiments.

Alternatively, peptides, drugs or small molecules which bind to polypeptide of the present invention may be identified in competition experiments. In such assays, the GENSET protein, or a fragment thereof, is immobilized to a surface, such as a plastic plate. Increasing amounts of the peptides, drugs or small molecules are placed in contact with the immobilized GENSET protein, or a fragment thereof, in the presence of a detectable labeled known GENSET protein ligand. For example, the GENSET ligand may be detectably labeled with a fluorescent, radioactive, or enzymatic tag. The ability of the test molecule to bind the GENSET protein, or a fragment thereof, is determined by measuring the amount of detectably labeled known ligand bound in the presence of the test molecule. A decrease in the amount of known ligand bound to the GENSET protein, or a fragment thereof, when the test molecule is present indicated that the test molecule is able to bind to the GENSET protein, or a fragment thereof.

C. Candidate Ligands Obtained by Affinity Chromatoraphy.

Proteins or other molecules interacting with a polypeptide of the present invention, can also be found using affinity columns which contain the GENSET protein, or a fragment thereof. The GENSET protein, or a fragment thereof, may be attached to the column using conventional techniques including chemical coupling to a suitable column matrix such as agarose, AFFI-GEL, or other matrices familiar to those of skill in art. In some embodiments of this method, the affinity column contains chimeric proteins in which the GENSET protein, or a fragment thereof, is fused to glutathion S transferase (GST). A mixture of cellular proteins or pool of expressed proteins as described above is applied to the affinity column. Proteins or other molecules interacting with the GENSET protein, or a fragment thereof, attached to the column can then be isolated and analyzed on 2-D electrophoresis gel as described in Ramunsen et al., (1997), Electrophoresis, 18: 588-598, the disclosure of which is incorporated by reference. Alternatively, the proteins retained on the affinity column can be purified by electrophoresis based methods and sequenced. The same method can be used to isolate antibodies, to screen phage display products, or to screen phage display human antibodies.

D. Candidate Ligands Obtained by Optical Biosensor Methods

Proteins interacting with a polypeptide of the present invention, can also be screened by using an Optical Biosensor as described in Edwards and Leatherbarrow, (1997) Analytical Biochemistry, 246, 1-6 and also in Szabo et al., (1995) Curr Opin Struct Biol 5, 699-705, the disclosures of which are incorporated by reference. This technique permits the detection of interactions between molecules in real time, without the need of labeled molecules. This technique is based on the surface plasmon resonance (SPR) phenomenon. Briefly, the candidate ligand molecule to be tested is attached to a surface (such as a carboxymethyl dextran matrix). A light beam is directed towards the side of the surface that does not contain the sample to be tested and is reflected by said surface. The SPR phenomenon causes a decrease in the intensity of the reflected light with a specific association of angle and wavelength. The binding of candidate ligand molecules cause a change in the refraction index on the surface, which change is detected as a change in the SPR signal. For screening of candidate ligand molecules or substances that are able to interact with the GENSET protein, or a fragment thereof, the GENSET protein, or a fragment thereof, is immobilized onto a surface. This surface comprises one side of a cell through which flows the candidate molecule to be assayed. The binding of the candidate molecule on the GENSET protein, or a fragment thereof, is detected. as a change of the SPR signal. The candidate molecules tested may be proteins, peptides, carbohydrates, lipids, or small molecules generated by combinatorial chemistry. This technique may also be performed by immobilizing eukaryotic or prokaryotic cells or lipid vesicles exhibiting an endogenous or a recombinantly expressed GENSET protein at their surface.

The main advantage of the method is that it allows the determination of the association rate between the GENSET protein and molecules interacting with the GENSET protein. It is thus possible to select specifically ligand molecules interacting with the GENSET protein, or a fragment thereof, through strong or conversely weak association constants., E. Candidate Ligands Obtained through a Two-Hybrid Screening Assay.

The yeast two-hybrid system is designed to study protein-protein interactions in vivo (Fields and Song, 1989), which disclosure is hereby incorporated by reference in its entirety, and relies upon the fusion of a bait protein to the DNA binding domain of the yeast Gal4 protein. This technique is also described in the U.S. Pat. No. US 5,667,973 and the U.S. Pat. No. 5,283,173, the technical teachings of both patents being herein incorporated by reference.

The general procedure of library screening by the two-hybrid assay may be performed as described by Harper et al., (1993), Cell, 75: 805-816 or as described by Cho et al., (1998), Proc. Natl. Acad. Sci. USA, 95(7):3752-3757 or also Fromont-Racine et al., (1997), Nature Genetics, 16(3):277-282, which disclosures are hereby incorporated by reference in their entireties.

The bait protein or polypeptide comprises a polypeptide of the present invention.

More precisely, the nucleotide sequence encoding the GENSET polypeptide or a fragment or variant thereof is fused to a polynucleotide encoding the DNA binding domain of the GAL4 protein, the fused nucleotide sequence, being inserted in a suitable expression vector, for example pAS2 or pM3.

Then, a human cDNA library is constructed in a specially designed vector, such that the human cDNA insert is fused to a nucleotide sequence in the vector that encodes the transcriptional domain of the GAL4 protein. Preferably, the vector used is the pACT vector. The polypeptides encoded by the nucleotide inserts of the human cDNA library are termed "prey" polypeptides.

A third vector contains a detectable marker gene, such as beta galactosidase gene or CAT gene that is placed under the control of a regulation sequence that is responsive to the binding of a complete Gal4 protein containing both the transcriptional activation domain and the DNA binding domain. For example, the vector pGSEC maybe used.

Two different yeast strains are also used. As an illustrative but non limting example the two different yeast strains may be the followings:

190, the phenotype of which is (MATa, Leu2-3, 112 ura-12, trp1-901, his3-D200, ade2-101, gal4Dgall80D URA3. GAL-LacZ, LYS. GAL-HIS3, cyh$^r$);

187, the phenotype of which is (MATa gal4 gal80his3 trp 1-901 ade2-1 01 ura3-52 leu2-3, -112. URA3. GAL-lacZmet$^-$), which is the opposite mating type of Y190.

Briefly, 20 tig of pAS2/GENSET and 20 μg of pACT-cDNA library are co-transformed into yeast strain YI90. The transformants are selected for growth on minimal media lacking histidine, leucine and tryptophan, but containing the histidine synthesis inhibitor 3-AT (50 mM). Positive colonies are screened for beta galactosidase by filter lift assay. The: double positive colonies. (His$^+$, beta-gal$^+$) are then grown on plates lacking histidine, leucine, but containing tryptophan and cycloheximide (10 mg/ml) to select for loss of pAS2/GENSET plasmids but retention of pACT-cDNA library plasmids. The resulting Y190 stins are mated with Y187 strains expressing GENSET or non-related control proteins; such as cyclophilin B, lamin, or SNF1, as Gal4 fusions as described by Harper et al. (1993) and by Bram et al., (1993), Mol. Cell Biol., 13:4760-4769, which disclosures are hereby incorporated by reference in their entireties, and screened for beta galactosidase by filter lift assay. Yeast clones that are beta gal- after mating with the control Gal4 fusions are considered false positives.

In another embodiment of the two-hybrid method according to the invention, interaction between the GENSET or a fragment or variant thereof with cellular proteins may be assessed using the Matchmaker Two Hybrid System 2 (Catalog No. K1604-1, Clontech). As described in the manual accompanying the kit, the disclosure of which is incorporated herein by reference, nucleic acids encoding the GENSET protein or a portion thereof, are inserted into, an expression vector such that they are in frame with DNA encoding the DNA binding domain of the yeast transcriptional activator GAL4. A desired cDNA, preferably human cDNA, is inserted into a second expression vector such that they are in frame with DNA encoding the activation domain of GAL4. The two expression plasmids are transformed into yeast and the yeast are plated on selection medium which selects for expression of selectable markers on each of the expression vectors as well as GAL4 dependent expression of the HIS3 gene. Transformants capable of growing on medium lacking histidine are screened for GALA dependent lacZ expression. Those cells which are positive in both the histidine selection and the lacZ assay contain interaction between GENSET and the protein or peptide encoded by the initially selected cDNA insert.

Compounds Modulating GENSET Biological Activity

Another method of screening for compounds that modulate GENSET expression and/or biological activity is by measuring the effects of test compounds on specific biological activity, e.g. a GENSET biological activity in a host cell. In one embodiment, the present invention relates to a method of identifying an agent which alters GENSET biological activity, wherein a nucleic acid construct comprising a nucleic acid which encodes a mammalian GENSET polypeptide is introduced into a host cell. The host cells produced are maintained under conditions appropriate for expression of the encoded mammalian GENSET polypeptides, whereby the nucleic acid is expressed. The host cells are then contacted with a compound to be assessed (an "agent," or "test agent"), and the properties of the, cells are assessed. Detection of a change in any GENSET polypeptide-associated property in the presence of the agent indicates that the agent alters GENSET activity. In a particular embodiment, the invention relates to a method of identifying an agent which is an activator of GENSET activity, wherein detection of an increase of any GENSET polypeptide-associated property in the presence of the agent indicates that the agent activates GENSET activity. In another particular embodiment, the invention relates to a method of identifying an agent which is an inhibitor of GENSET activity, wherein detection of a decrease of any GENSET polypeptide-associated property in the presence of the agent indicates that the agent inhibits GENSET activity.

In a particular embodiment, a high throughput screen can be used to identify agents that activate (enhance) or inhibit GENSET activity. (See e.g., PCT publication WO 98/45438, which disclosure is hereby incorporated by reference in its entirety). For example, the method of identifying an agent which alters GENSET activity can be performed as follows. A nucleic acid construct comprising a polynucleotide which encodes a mammalian GENSET polypeptide is introduced into a host cell to produce recombinant host cells. The recombinant host cells are then maintained under conditions appropriate for expression of the encoded mammalian GENSET polypeptide, whereby the nucleic acid is expressed. The compound to be assessed is added to the recombinant host cells; the resulting combination is referred to as a test sample. A detectable, GENSET polypeptide-associated property of the cells is detected. A control can be used in the methods of detecting agents which alter GENSET activity. For example, the control sample includes the same reagents but lacks the compound or agent being assessed; it is treated in the same manner as the test sample.

Methods of Screening for Compounds Modulating GENSET Expression and/or Activity.

The present invention also relates to methods of screening compounds for their ability, to modulate (e.g. increase or inhibit) the activity or expression of GENSET. More specifically, the present invention relates to methods of testing compounds for their ability either, to increase or to decrease expression or activity of GENSET. The assays are performed in vitro or in vivo.

In Vitro Methods

In vitro, cells expressing GENSET polypeptides are incubated in the presence and absence of the test compound. By determining the level of GENSET expression in the presence of the test compound or the level of GENSET activity, in the presence of the test compound, compounds can be identified that suppress or enhance GENSET, expression or activity. Alternatively, constructs comprising a GENSET regulatory sequence operably linked to a reporter gene (e.g. luciferase, chloramphenicol acetyl transferase, LacZ, green fluorescent protein, etc.) can be introduced into host cells and the effect of the test compounds on expression of the reporter gene detected. Cells suitable for use in the foregoing assays include, but are not limited to, cells having the same origin as tissues or cell lines in which the polypeptide has been determined to be expressed by methods common to the art such as discussed herein. Consequently, the present invention encompasses a method for screening molecules that modulate the expression of a GENSET gene, said screening method comprising the steps of:

a) cultivating a prokaryotic or an eukaryotic cell that has been transfected with a nucleotide sequence encoding a GENSET protein or a variant or a fragment thereof, placed under the control of its own promoter;
b) bringing into contact said cultivated cell with a molecule to be tested;
c) quantifying the expression of said GENSET protein or a variant or a fragment thereof in the presence of said molecule.

Using DNA recombination techniques well known by the one skill in the art, the GENSET protein encoding DNA sequence is inserted into an expression vector, downstream from its promoter sequence. As an illustrative example, the promoter sequence of the GENSET gene is contained in the 5' untranscribed region of the GENSET genomic. DNA.

The quantification of the expression of a GENSET protein may be realized either at the. mRNA level (using for example Northern blots, RT-PCR, preferably quantitative. RT-PCR with primers and probes specific for the GENSET mRNA of interest) or at the protein level (using polyclonal or monoclonal antibodies in immunoassays such as ELISA or RIA assays, Western blots, or immunochemistry).

The present invention also concerns a method for screening substances or molecules that are able to increase, or in contrast to decrease, the level of expression of a GENSET gene. Such a method may allow the one skilled in the art to select substances exerting a regulating effect on the expression level of a GENSET gene and which may be useful as active ingredients included in pharmaceutical compositions for treating patients suffering from disorders associated with abnormal levels of GENSET products.

Thus, another part of the present invention is a method for screening a candidate molecule that modulates the expression of a GENSET gene, this method comprises the following steps:

a) providing a recombinant cell host containing a nucleic acid, wherein said nucleic acid comprises a GENSET 5' regulatory region or a regulatory active fragment or variant thereof, operably linked to a polynucleotide encoding a detectable protein;
b) obtaining a candidate molecule; and
c) determining the ability of said candidate molecule to modulate the expression levels of said polynucleotide encoding the detectable protein., In a further embodiment, said nucleic acid comprising a GENSET 5' regulatory region or a regulatory active fragment or variant thereof, includes the 5'UTR region of a GENSET cDNA selected from the group comprising of the 5'UTRs of the polynucleotide sequences of the Sequence Listing, those of human cDNA clone inserts of the deposited clone pool, regulatory active fragments, and variants thereof. In a more preferred embodiment of the above screening method, said nucleic acid includes a promoter sequence which is endogenous with respect to the GENSET 5'UTR sequence. In another more preferred embodiment of the above screening method, said nucleic acid includes a promoter sequence which is exogenous with respect to the GENSET 5'UTR sequence defined therein.

Preferred polynucleotides encoding a detectable protein are polynucleotides encoding beta galactosidase, green fluorescent protein (GFP) and chloramphenicol acetyl transferase (CAT).

The invention further relates to a method for the production of a pharmaceutical composition comprising a method of screening a candidate molecule that modulates the expression of a GENSET gene and furthermore mixing the identified molecule with a physiologically acceptable carrier.

The invention also pertains to kits for the screening of a candidate substance modulating the expression of a GENSET gene. Preferably, such kits comprise a recombinant vector that allows the expression of a GENSET 5' regulatory region or a regulatory active fragment or a variant thereof, operably linked to a polynucleotide encoding a detectable protein or a GENSET protein or a fragment or a variant thereof. More preferably, such kits include a recombinant vector that comprises a nucleic acid including the 5'UTR region of a GENSET cDNA selected from the group comprising the 5'UTR of the polynucleotide sequences of the Sequence Listing, those of human cDNA clone inserts of the deposited clone pool, regulatory active fragments and variants thereof, being operably linked to a polynucleotide encoding a detectable protein.

For the design of suitable recombinant vectors useful for performing the screening methods described above, it will be referred to the section of the present specification wherein the preferred recombinant vectors of the invention are detailed.

Another object of the present invention comprises methods and kits for the screening of candidate substances that interact with a GENSET polypeptide, fragments or variants thereof. By their capacity to bind covalently or non-covalently to a GENSET protein, fragments or variants thereof, these substances or molecules may be advantageously used both in vitro and in vivo.

In vitro, said interacting molecules may be used as detection means in order to identify the presence of a GENSET protein in a sample, preferably a biological sample.

A method for the screening of a candidate substance that interact with a GENSET polypeptide, fragments or variants thereof, said methods comprising the following steps:

a) providing a polypeptide comprising, consisting essentially of, or consisting of a GENSET protein or a fragment comprising a contiguous span of at least 6 amino acids, preferably at least 8 to 10 amino acids, more preferably at least 12, 15, 20, 25, 30, 40, 50, or 100 aminoacids of a polypeptide of the present invention;

b) obtaining a candidate substance;

c) bringing into contact said polypeptide with said candidate substance;

d) detecting the complexes formed between said polypeptide and said candidate substance.

The invention further relates to a method for the production of a pharmaceutical composition comprising a method for the screening of a candidate substance that interact with a GENSET polypeptide, fragments or variants thereof and furthermore mixing the identified substance with a physiologically acceptable carrier.

The invention further concerns a kit for the screening of a candidate substance interacting with the GENSET polypeptide, wherein said kit comprises:

a) polypeptide comprising, consisting essentially of, or consisting of a GENSET protein or a fragment comprising a contiguous span of at least 6 amino acids, preferably at least 8 to 10 amino acids, more preferably at least 12, 15, 20, 25, 30, 40, 50, or 100 amino acids of a polypeptide of the present invention; and.

b) optionally means useful to detect the complex formed between said polypeptide or a variant thereof and the candidate substance.

In a preferred embodiment of the kit described above, the detection means comprises a monoclonal or polyclonal antibody binding to, said GENSET protein or fragment or variant thereof.

In Vivo Methods

Compounds that suppress or enhance GENSET expression can also be identified using in vivo screens. In these assays, the test compound is administered (e.g. intravenously, intraperitoneally, intramuscularly, orally, or otherwise), to the animal, for example, at a variety of dose levels. The effect of the compound on GENSET expression is, determined by comparing GENSET levels, for example in tissues known to express the gene of interest using Northern blots, immunoassays, PCR, etc., as described above. Suitable test animals include, but are not limited to, rodents (e.g., mice and rats), primates, and rabbits. Humanized mice can also be used as test animals, that is maice in which the endogenous mouse protein is ablated (knocked out) and the homologous human protein added back by standard transgenic approaches. Such mice express only the human form of a protein. Humanized mice expressing only the human GENSET can be used to study in vivo responses to potential agents regulating GENSET protein or mRNA levels. As an example, transgenic mice have been produced carrying the human apoE4 gene. They are then bred with a mouse line that lacks endogenous apoE, to produce an animal model carrying human proteins believed to be instrumental in development of Alzheimer's pathology. Such transgenic animals are useful for dissecting the biochemical and physiological steps of disease, and for development of therapies for disease intervention (Loring, et al, 1996). (incorporated herein by reference in its entirety).

Uses for Compounds Modulating Genset Expression and/or Biological Activity

Using in vivo (or in vitro) systems, it may be possible to identify compounds that exert a tissue specific effect, for example, that increase GENSET expression or activity only in tissues of interest, such as the adrenal gland, bone marrow, brain, cerebellum, colon, fetal brain, fetal kidney, fetal liver, heart, hypertrophic prostate, kidney, liver, lung, lymph ganglia, lymphocytes, muscle, ovary, pancreas, pituitary gland, placenta, prostate, salivary gland, spinal cord, spleen, stomach, intestine, substantia nigra, testis, thyroid, umbilical cord, and uterus. Screening procedures such as those described above are also useful for identifying agents for their potential use in pharmacological intervention strategies. Agents that enhance GENSET gene expression or stimulate its activity may thus be used to induce any phenotype associated with a GENSET gene, or to treat disorders resulting from a deficiency of a GENSET polypeptide activity or expression. Compounds that suppress GENSET polypeptide expression or inhibit its activity can be used to treat any disease or condition associated with increased or deleterious GENSET polypeptide activity or expression.

Also encompassed by the present invention is an agent which interacts with a GENSET gene or polypeptide directly or indirectly, and inhibits or enhances GENSET polypeptide expression and/or function. In one embodiment, the agent is an inhibitor which interferes with a GENSET polypeptide directly (e.g., by binding the GENSET polypeptide) or indirectly (e.g., by blocking the ability of the GENSET polypeptide to have a GENSET biological activity). In a particular embodiment, an inhibitor of a GENSET protein is an antibody specific for the GENSET protein or a functional portion of the GENSET protein; that is, the antibody binds a GENSET, polypeptide. For example, the antibody can be specific for a polypeptide encoded by one of the nucleic acid sequences of human GENSET nucleic acids, a mammalian GENSET nucleic acid, or portions thereof. Alternatively, the inhibitor can be an agent other than an antibody. (e.g., small organic molecule, protein or peptide) which binds the GENSET polypeptide and blocks its activity. For example, the inhibitor can be an agent which mimics the GENSET polypeptide structurally, but lacks its function. Alternatively, it can be an agent which binds to or interacts with a molecule which the GENSET polypeptide normally binds to or interacts with, thus blocking the GENSET. polypepetide from doing so and preventing it from exerting the effects it would normally exert.

In another embodiment, the agent is an enhancer (activator) of a GENSET polypeptide which increases the activity of the GENSET polypeptide (increases the effect of a given amount or level of GENSED, increases the length of time it is effective (by preventing its degradation or otherwise prolonging the time during which it is active) or both either directly or indirectly. For example, GENSET polynucleotides and polypeptides can be used to identify drugs which increase or decrease the ability of GENSET polypeptides to induce GENSET biological activity, which drugs are useful for the treatment or prevention of any disease or condition associated with a GENSET biological activity.

The GENSET sequences of the present invention can also be used to generate nonhuman gene knockout animals, such as mice, whichlack a GENSET gene or transgenically overexpress a GENSET gene. For example, such GENSET gene knockout mice can be generated and used to obtain further insight into the function of the GENSET gene as well as assess the specificity of GENSET activators and inhibitors. Also, over expression of the GENSET gene (e.g., a human GENSET gene) in transgenic mice can be used as a means of creating a test system for GENSET activators and inhibitors (e.g., against a human GENSET polypeptide). In addition, the GENSET gene can be used to clone the GENSET promoter/enhancer in order to identify regulators of GENSET gene transcription. GENSET gene knockout animals include animals which completely or partially lack the GENSET gene and/or GENSET activity or function. Thus the present invention relates to a method of inhibiting artilly or completely) a GENSET biological activity in a mammal (e.g., a human), the method comprising administering to the mammal an effective amount of an inhibitor of a GENSET polypeptide or polynucleotide., The invention also relates to a method of enhancing a GENSET biological activity in a mammal, the method comprising administering to the mammal an effective amount of an enhancer of a GENSET polypeptide or polynucleotide.

Inhibiting GENSET Gene Expression

Therapeutic compositions according to the present invention may comprise advantageously one or several GENSET oligonucleotide fragments as an antisense tool or a triple helix tool that inhibits the expression of the corresponding GENSET gene.

Antisense Approach

In antisense approaches, nucleic acid sequences complementary to an mRNA are hybridized to the mRNA intracellularly, thereby blocking the expression of the protein encoded by the mRNA. The antisense nucleic acid molecules to be used in gene therapy may be either. DNA or RNA sequences. Preferred methods using antisense polynucleotide according to the present invention are the procedures described by Sczakiel et al., (1995). Trends Microbiol. 3(6):213-217, which disclosure is hereby incorporated by reference in its entirety.

Preferably, the antisense tools are chosen among the polynucleotides (15-200 bp long) that are complementary to GENSET mRNA, more preferably to the 5'end of the GENSET. mRNA. In another embodiment, a combination of different antisense polynucleotides complementary to different parts of the desired targeted gene are used.

Other preferred antisense polynucleotides according to the present invention are sequences complementary to either a sequence of GENSET mRNAs comprising the translation initiation codon ATG or a sequence of GENSET genomnic. DNA containing a splicing donor or acceptor site. Preferably, the antisense polynucleotides of the invention have a 3' polyadenylation signal that has been replaced with a self-cleaving ribozyme sequence, such that RNA polymerase II transcripts, are produced without poly(A) at their 3' ends, these antisense polynucleotides being incapable of export from the nucleus, such as described by Liu et al. (1994), Proc. Natl. Acad. Sci. USA 91: 4528-4262, which disclosure is hereby incorporated by reference in its entirety. In a preferred embodiment, these GENSET antisense polynucleotides also comprise, within the ribozyme cassette, a histone stem-loop structure to stabilize cleaved transcripts against 3'-5' exonucleolytic degradation, such as the structure described by Eckner et al., (199 1) EMBO J. 10:3513-3522, which disclosure is hereby incorporated by reference in its entirety.

The antisense nucleic acids should have a length and melting temperature sufficient to permit formation of an intracellular duplex having sufficient stability to inhibit the expression of the GENSET mRNA in the duplex. Strategies for designing antisense nucleic acids suitable for use in gene therapy are disclosed in Green et al., (1986). Ann. Rev. Biochem. 55:569-597 and Izant and Weintraub, (1984). Cell 36(4):1007-15, the disclosures of which are incorporated herein by reference.

In some strategies, antisense molecules are obtained by reversing the orientation of the GENSET coding region with respect to a promoter, so as to transcribe the opposite strand from that which is normally transcribed in the cell. The antisense molecules may be transcribed using in vitro transcription systems such as those which employ T7 or SP6 polymerase to generate the transcript. Another approach involves transcription of GENSET antisense nucleic acids in vivo by operably linking DNA containing the antisense sequence to a promoter in a suitable expression vector. Alternatively, oligonucleotides which are complementary to the strand normally transcribed in the cell may be synthesized in vitro. Thus, the antisense nucleic acids are complementary to the corresponding mRNA and are capable of hybridizing to the rnR A to create a duplex.

Specific examples of preferred antisense compounds useful in this invention include oligonucleotides containing modified backbones or non-natural internucleoside linkages. As defined in this specification, oligonucleotides having modified backbones include those that retain a phosphorus atom in the backbone and those that do not have a phosphorus atom in the backbone. For the purposes of this specification, and as sometimes referenced in the art, modified oligonucleotides that do not have a phosphorus atom in their internucleoside backbone can also be considered to be oligonucleosides.

Preferred modified oligonucleotide backbones include, for example, phosphorothioates, chiral phosphorothioates, phosphorodithioates, phosphotriesters, aminoalkylphosphotriesters, methyl and other alkyl phosphonates including 3'-alkylene phosphonates and chiral phosphonates, phosphinates, phosphorarmidates including 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2'. Various salts, mixed salts and free acid forms are also included.

Preferred modified oligonucleotide backbones that do not include a phosphorus atom therein have backbones that are formed by short chain alkyl or cycloalkyl intemucleoside linkages, mixed heteroatom and alkyl or cycloalkyl intemucleoside linkages, or one or more short chain heteroatomic or heterocyclic intemucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and $CH_2$, component parts.

In other preferred oligonucleotide mimetics, both the sugar and the intemucleoside linkage, i.e., the backbone, of the nucleotide units are replaced with novel groups. The base units are maintained for hybridization with an appropriate nucleic acid target compound. One such oligomeric compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, in particular an aminoethylglycine backbone. The nucleobases are retained and are bound directly or indirectly to aza nitrogen atoms of the amide portion of the backbone.

Oligonucleotides may also include nueleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazandenine. Further nucleobases include those disclosed in U.S. Pat. No. 3,687,808, those disclosed in The Concise Encyclopedia Of Polymer Science And Engineering, pages 858-859, Kroschwitz, J. I., ed. John Wiley & Sons, 1990, those disclosed by Englisch et al., Angewandte Chemie, International Edition, 1991, 30, 613, and those disclosed by Sanghvi, Y. S., Chapter 15, Antisense Research and Applications, pages 289-302, Crooke, S. T. and Lebleu, B. ed., CRC Press, 1993. Certain of these nucleobases are particularly useful for increasing the binding affinity of the oligomeric compounds of the invention. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6-1.2° C. (Sanghvi, Y. S., Crooke, S. T. and Lebleu, B., eds., Antisense Research and Applications, CRC Press, Boca Raton, 1993, pp. 276-278) and are presently preferred base substitutions, even more particularly when combined with 2'-O-methoxyethyl sugar modifications (U.S. Patent 6,242,590, hereby incorporated by reference).

Various types of antisense oligonucleotides complementary to the sequence of the GENSET cDNA or genomic. DNA may be used. In one preferred embodiment, stable and semi-stable antisense oligonucleotides described in International Application No. PCT WO94/23026, hereby incorporated by reference, are used. In these molecules, the 3' end or both the 3' and 5' ends are engaged in intramolecular hydrogen bonding between complementary base pairs. These molecules are better able to withstand exonuclease attacks and exhibit increased stability compared to conventional antisense oligonucleotides.

In another preferred embodiment, the antisense oligodeoxynucleotides against herpes simplex virus types 1 and 2 described in International Application No. WO 95/04141, hereby incorporated by reference, are used.

In yet another preferred embodiment, the covalently cross-linked antisense oligonucleotides described in International Application No. WO 96/31523, hereby incorporated by reference, are used. These double- or single-stranded oligonucleotides comprise one or more, respectively, inter- or intra-oligonucleotide covalent cross-linkages, wherein the linkage consists of an amide bond between a primary amine group of one strand and a carboxyl group of the other strand or of the same strand, respectively, the primary amine group being directly substituted in the 2' position of the strand nucleotide monosaccharide ring, and the carboxyl group being carried by an aliphatic spacer group substituted on a nucleotide or nucleotide analog of the other strand or the same strand, respectively.

The antisense oligodeoxynucleotides and oligonucleotides disclosed in International Application No. WO 92/18522, incorporated by reference, may also be used. These molecules are stable to degradation and contain at least one transcription control recognition sequence which binds to control proteins and are effective as decoys therefor. These molecules may contain "hairpin" structures, "dumbbell" structures, "modified dumbbell" structures, "cross-linked" decoy structures and "loop" structures.

In another preferred embodiment, the cyclic double-stranded oligonucleotides described in European Patent Application No. 0.572.287. A2, hereby incorporated by reference, are used. These ligated oligonucleotide "dumbbells" contain the binding site for a transcription factor and inhibit expression of the gene under control of the transcription factor by sequestering the factor.

Use of the closed antisense oligonucleotides disclosed in International Application No. WO 92/19732, hereby incorporated by reference, is also contemplated. Because these molecules have no free ends, they are more resistant to degradation by exonucleases than are conventional oligonucleotides. These oligonucleotides may be multifunctional, interacting with several regions which are not adjacent to the target mRNA.

Another modification of the oligonucleotides of the invention involves chemically linking to the oligonucleotide one or more moieties or conjugates which enhance the activity, cellular distribution or cellular uptake of the oligonucleotide. Such moieties include but are not limited to lipid moieties such as a cholesterol moiety (Letsinger et al., Proc., Natl. Acad. Sci. USA (1989). 86: 6553-6556), cholic acid (Manoharan et al., Bioorg. Med. Chem. Let. (1994). 4:1053-1060), a thioether, e.g., hexyl-S-tritylthiol (Manoharan et al., Ann. N.Y. Acad. Sci. (1992). 660:306-309; Manoharan et al., Bioorg. Med. Chem. Let., (1993). 3:2765-2770), a thiocholesterol (Oberhauser et al., Nucl. Acids Res. (1992). 20:533-538), an aliphatic chain, e.g., dodecandiol or undecyl residues (Saison-Behinoaras et al., EMBO. J. (1991).10: 1111-1118; Kabanov et al., FEBS. Lett. (1990) 259: 327-33.0; Svinarchuk et al., Biochimie (1993) 75:49-54), a phospholipid, e.g., di-hexadecyl-rac-glycerol or triethylammonium 1, 2-di-O-hexadecyl-rac-glycero-3-H-phosphonate (Manoharan et al., Tetrahedron Lett., 1995, 36, 3651-3654; Shea et al., Nucl. Acids Res. (1990). 18:3777-3783), a polyamine or a polyethylene glycol chain (Manoharan et al., Nucleosides & Nucleotides (1995).14: 969-973), or adamantane acetic acid (Manoharan et al., Tetrahedron Lett. (1995).36:3651-3654), a paimityl moiety (Mishra et al., Biochim. Biophys. Acta (1995).1264:229-237), or an octadecylamine or hexylamino-carbonyl-oxycholesterol moiety (Crooke et al., J. Pharmacol., Exp. Ther. (1996) 277:923-937; U.S. Pat. No. 6,242,590, which disclosures are hereby incorporated by reference in their entireties It is not necessary for all positions in a given compound to be uniformly modified, and in fact more than one of the aforementioned modifications may be incorporated in a single compound or even at a single nucleoside within an oligonucleotide. The present invention also includes antisense compounds which are chimeric compounds., "Chimeric" antisense compounds or "chimeras," in the context of this invention, are antisense compounds, particularly oligonucleotides, which contain two or more chemically distinct regions, each made up of at least one monomer unit, i.e., a nucleotide in the case of an oligonucleotide compound. These oligonucleotides typically contain at least one region wherein the oligonucleotide is modified so as to confer upon the oligonucleotide increased resistance to nuclease degradation, increased cellular uptake, and/or increased binding affinity for the target nucleic acid. An additional region of the oligonucleotide may serve as a substrate for enzymes capable of cleaving RNA:DNA or RNA:RNA hybrids. By way of example, RNase H is a cellular endonuclease which cleaves the RNA strand of an RNA: DNA duplex. Activation of RNase H, therefore, results in cleavage of the RNA target, thereby greatly enhancing the efficiency of oligonucleotide inhibition of gene expression. Consequently, comparable results can often be obtained with shorter oligonucleotides when chimeric oligonucleotides are used, compared to phosphorothioate deoxyoligonucleotides hybridizing to the same target region. Cleavage of the RNA target can be routinely detected by gel electrophoresis and, if necessary, associated nucleic acid hybridization techniques known in the art (U.S. Pat. No. 6,242,590, hereby incorporated by reference).

Further included in the present invention is a method of high throughput screening of antisense nucleic acids and modified versions thereof for binding to targeted GENSET polynucleotide sequences or fragments thereof. This method is directed toward determining optimally targeted sequences and/or optimal species of targeting antisense molecules for binding. A preferred method comprises the steps of: contacting a random pool of test molecules with a set array of GENSET polynucleotide sequences or fragments thereof; detecting and quantifying binding of test molecules to said array; and purification and identification of binding test molecules as discussed in U.S. Pat. No. 6,022,691, which disclosure is hereby incorporated by reference.

Preferred test molecules are antisense oligonucleotides, oligonucleosides, and modified versions thereof as discussed herein. Further preferred test molecules are those that are capable of forming hydrogen bonds with GENSET polynucleotide sequences or fragments thereof.

The appropriate level of antisense nucleic acids required to inhibit gene expression may be determined using in vitro expression analysis. The antisense molecule may be introduced into the cells by diffusion, injection, infection or transfection using procedures known in the art. For example, the antisense nucleic acids can be introduced into the body as a bare or naked oligonucleotide, oligonucleotide encapsulated in lipid, oligonucleotide sequence encapsidated by viral protein, or as an oligonucleotide operably linked to a promoter contained in an expression vector. The expression vector may be any of a variety of expression vectors known in the art, including retroviral or viral vectors, vectors capable of extrachromosomal replication, or integrating vectors. The vectors may be DNA or RNA.

The antisense compounds of the invention encompass any physiologically acceptable salts, esters, or salts of such esters, or any other compound which, upon administration to an animal including a human, is capable of providing (directly or indirectly) the biologically active metabolite or residue thereof. Accordingly, for example, the disclosure is also drawn to prodrugs and physiologically acceptable salts of the compounds of the invention, physiologically acceptable salts of such prodrugs, and other bioequivalents as discussed herein.

The antisense molecules are introduced onto cell samples at a number of different concentrations preferably between $1\times10^{-10}$M to $1\times10^{-4}$M. Once the minimum concentration that can adequately control gene expression is identified, the optimized dose is translated into a dosage suitable for use in vivo. For example, an inhibiting concentration in culture of $1\times10^{-7}$ translates into a dose of approximately 0.6 mg/kg bodyweight. Levels of oligonucleotide approaching 100 mg/kg bodyweight or higher may be possible after testing the toxicity of the oligonucleotide in laboratory animals. It is additionally contemplated that cells from the, vertebrate are removed, treated with the antisense oligonucleotide, and reintroduced into the vertebrate.

In a preferred application of this invention, the polypeptide encoded by the gene is first identified, so that the effectiveness of antisense inhibition on translation can be monitored using techniques that include but are not limited to antibody-mediated tests such as RIAs and ELISA, functional assays, or radiolabeling.

An alternative to the antisense technology that is used according to the present invention comprises using ribozymes that will bind to a target sequence via their complementary polynucleotide tail and that will cleave the corresponding RNA by hydrolyzing its target site (namely. "hammerhead ribozymes"). Briefly, the simplified cycle of a hammerhead ribozyme comprises (1) sequence specific binding to the target RNA via complementary antisense sequences; (2) site-specific hydrolysis of the cleavable motif of the target str and; and (3) release of cleavage products, which gives rise to another catalytic cycle. Indeed, the use of long-chain antisense polynucleotide (at least 30 bases long) or ribozymes with long antisense arms are advantageous. A preferred delivery system for antisense ribozyme is achieved by covalently linking these antisense ribozymes to lipophilic groups or to use liposomes as a convenient vector. Preferred antisense ribozymes according to the present invention are prepared as described by Rossi et al., (1991). Pharmacol. Ther. 50:245-254 and Sczakiel et al. (1995), the specific preparation procedures being referred to in said articles being herein incorporated by reference.

Triple Helix Approach

The GENSET genomic DNA may also be used to inhibit the expression of the GENSET gene based on intracellular triple helix formation.

Triple helix oligonucleotides are used to inhibit transcription from a genome. They are particularly useful for studying alterations in cell activity when it is associated with a particular. gene. The GENSET cDNAs or genomic DNAs of the present invention or, more preferably, a fragment of those sequences, can be used to inhibit gene expression in individuals having diseases associated with expression of a particular gene. Similarly, a portion of the GENSET genomic. DNA can be used to study the effect of inhibiting GENSET gene transcription within a cell. Traditionally, homopurine sequences were considered the most useful for triple helix strategies. However, homopyrimidine sequences can also inhibit gene expression. Such homopyrimidine oligonucleotides bind to the major groove at homopurine: homopyrimidine sequences. Thus, both types of sequences from the GENSET genomic DNA are contemplated within the scope of this invention.

To carry out gene therapy strategies using the triple helix approach, the sequences of the GENSET genomic DNA are first scanned to identify 10-mer to 20-mer homopyrimidine or homopurine stretches which could be used in triple-helix based strategies for inhibiting GENSET expression. Following identification of candidate homopyrinidine or homopurine stretches, their efficiency in inhibiting GENSET expression is assessed by introducing varying amounts of oligonucleotides containing the candidate sequences into, tissue culture cells which express the GENSET gene.

The oligonucleotides can be introduced into the cells using a variety of methods known to those skilled in the art, including but not limited to calcium phosphate precipitation, DEAE-Dextran, electroporation, liposome-mediated transfection or native uptake.

Treated cells are monitored for altered cell function or reduced GENSET expression using techniques such as Northern blotting, RNase protection assays, or PCR based strategies to monitor the transcription levels of the GENSET gene in cells which have been treated with the oligonucleotide. The cell functions to be monitored are predicted based upon the homologies of the target gene corresponding to the cDNA from which the oligonucleotide was derived with known gene sequences that have been associated with a particular function. The cell functions can also be predicted based on the presence of abnormal physiology within cells derived from individuals with a particular inherited disease, particularly when the cDNA is associated with the disease using techniques described in the section entitled "Identification of genes associated with hereditary diseases or drug response".

The oligonucleotides which are effective in inhibiting gene expression in tissue culture cells may then be introduced in vivo using the techniques and at a dosage calculated based on the in vitro results, as described in the section entitled "Antisense Approach".

In some embodiments, the natural (beta) anomers of the oligonucleotide units can be replaced with alpha anomers to render the oligonucleotide more resistant to nucleases. Further, an intercalating agent such as ethidium bromide, or the like, can be attached to the 3' end of the alpha oligonucleotide to stabilize the triple helix. For information on the generation of oligonucleotides suitable for triple helix formation. See Griffin et al., (1989) Science 245:967-971, which is hereby incorporated by this reference.

Treating GENSET Gene-Related Disorders

The present invention further relates to methods, uses of GENSET polypeptides and polynucleotides, and uses of modulators of GENSET polypeptides and polynucleotides, for treating diseases/disorders associated with GENSET genes by increasing or decreasing GENSET, gene activity and/or expression. These methodologies can be effected using compounds selected using screening protocols such as those described herein and/or by using the gene therapy and antisense approaches described in the art and herein. Gene therapy can be used to effect targeted expression of GENSET genes in any tissue, e.g. a tissue associated with the disease or condition to be treated. The GENSET coding sequence can be cloned into an appropriate expression vector and targeted to a particular cell type(s) to achieve efficient, high level expression. Introduction of the GENSET coding sequence into, target cells can be achieved, for example, using particle mediated DNA delivery, [Haynes et al., (1996). 3 Biotechnol. 44(1-3):3742 and Maurer et al., (1999). Mol Membr Biol. 16(1):12940], direct injection of naked DNA, [Levy et al., (1996). Gene Ther. 3(3):201-11; and Felgner (1996). Hum Gene Ther. 7(15): 1791-3], or viral vector mediate transport [(Smith et al., (1996). Antiviral Res. 32(2):99-115, Stone et al., (2000). J Endocrinol. 164(2): 103-18; Wu and Ataai (2000), Curr Opin Biotechnol. 11(2): 205-8], each of which disclosures are hereby incorporated by reference in their entireties. Tissue specific effects can be achieved, for example, in the case of virus mediated transport by using viral vectors that are tissue specific, or by the use of promoters that are tissue specific. For instance, any tissue-specific promoter may be used to achieve specific expression, for example albumin promoters (liver specific; Pinkert et al., 1987 Genes. Dev. 1:268-277), lymphoid specific promoters. (Calame et al., 1988 Adv. Immunol. 43:235-275), promoters of T-cell receptors (Winoto et al., 1989. EMBO. J. 8:729-733) and immunoglobulins (Banedi et al., 1983. Cell 33:729-740; Queen and Baltimore 1983. Cell 33:741-748), neuron-specific promoters (e.g. the neurofilament promoter; Byrne et al., 1989. Proc. Natl. Acad. Sci. USA 86:5473-5477), pancreas-specific promoters (Edlunch et al., 1985: Science 230:912-916) or mammary gland-specific promoters (milk whey promoter, U.S. Pat. No. 4,873,316 and European Application Publication No. 264, 166). Developmentally-regulated promoters can also be used, such as the murine homeobox promoters (Kessel et al., 1990 Science 249:374-379) or the alpha-fetoprotein promoter. (Campes et al., 1989. Genes Dev. 3:537-546).

Combinatorial approaches can also be used to ensure that the GENSET coding sequence is activated in the target tissue [Butt and Karathanasis (1995) Gene Expr. 4(6):3 19-36; Miller and Whelan, (1997). Hum Gene Ther. 8(7): 803-15], which disclosures are hereby incorporated by reference in their entireties. Antisense oligonucleotides complementary to GENSET mRNA can be used to selectively diminish or ablate the expression of the protein, for example, at sites of inflammation. More specifically, antisense constructs or antisense oligonucleotides can be used to inhibit the production of GENSET in high expressing cells such as determined by methods common to the art or discussed herein. Antisense mRNA can be produced by transfecting into target cells an expression vector with the GENSET gene sequence, or a portion thereof, oriented in an antisense direction relative to the direction of transcription. Appropriate vectors include viral vectors, including retroviral, adenoviral, and adeno-associated viral vectors, as well as nonviral vectors. Tissue specific promoters can be used, as described supra. Alternatively, antisense oligonucleotides can be introduced directly into target cells to achieve the same goal. (See also other delivery methodologies described herein in connection with gene therapy.). Oligonucleotides can be selected/designed to achieve a high level of specificity. [Wagner, et al. (1996), Nat Biotechnol. 14(7):8404], which disclosure is hereby inco rporated by reference in its entirety. The therapeutic methodologies described herein are applicable to both human and non-human mammals (including cats and dogs).

Pharmaceutical and Physiologically Acceptable Compositions

The present invention also relates to pharmaceutical or physiologically acceptable compositions comprising, as active agent, the polypeptides, nucleic acids or antibodies of the invention. The invention also relates to compositions comprising, as active agent, compounds selected using the above-described screening protocols. Such compositions include the active agent in combination with a pharmaceutical or physiologically acceptable carriers such as a physiologically acceptable salt, ester, or salt of such esters. In the case of naked DNA, the "carrier" may be gold particles. The amount of active agent in the composition can vary with the agent, the patient and the effect sought. Likewise, the dosing regimen can vary depending on the composition and the disease/disorder to be treated.

Therefore, the invention related to methods for the production of pharmaceutical composition comprising a method for selecting an active agent, compound, substance or molecule using any of the screening method described herein and furthermore mixing the identified active agent, compound, substance or molecule with a physiologically acceptable carrier.

The term "physiologically acceptable salts" refers to physiologically and pharmaceutically acceptable salts of the compounds of the invention: i.e., salts that retain the desired biological activity of the parent compound and do not impart undesired toxicological effects thereto. Physiologically acceptable base addition salts are formed with metals or amines, such as alkali and alkaline earth metals or organic amines Examples of metals used as cations are sodium, potassium, magnesium, calcium, and the like Examples of suitable amines are N,N'-dibenzylethylenediamine, chloroprocaine, choline, diethanolamine, dicyclohexylamine, ethylenediamine, N-methylglucamine, and procaine (see, for example, Berge et al., "Pharmaceutical Salts,". J. of Pharma Sci. (1977) 66:1-19). The base addition salts of said acidic compounds are prepared by contacting the free acid form with a sufficient amount of the desired base to produce the salt in the. conventional manner. The free acid form may be regenerated by contacting the salt form with an acid and isolating the free acid in the conventional manner. The free acid forms differ from their respective salt forms somewhat in certain physical properties such as solubility in polar solvents, but otherwise the salts are equivalent to their respective free acid for purposes of the present invention. As used herein, a "pharmaceutical addition salt" includes a physiologically acceptable salt of an acid form of one of the components of the compositions of the invention. These include organic or inorganic acid salts of the amines. Preferred acid salts are the hydrochlorides, acetates, salicylates, nitrates and phosphates. Other suitable physiologically acceptable salts are; well known to those skilled in the art and include basic salts of a variety of inorganic and organic acids, such as, for example, with inorganic acids, such as for example hydrochloric acid, hydrobromic acid, sulfuric acid or phosphoric acid; with organic carboxylic, sulfonic, sulfo or phospho acids or N-substituted sulfamic acids, for example acetic acid, propionic acid, glycolic acid, succinic acid, maleic acid, hydroxymaleic acid, methylmaleic acid, fumaric acid, malic acid, tartaric acid, lactic acid, oxalic acid, gluconic acid, glucaric acid, glucuronic acid, citric acid, benzoic acid, cinnamic acid, mandelic acid, salicylic acid, 4-aminosalicylic acid, 2-phenoxybenzoic acid, 2-acetoxybenzoic acid, embonic acid, nicotinic acid or isonicotinic acid; and with amino acids, such as the 20 alpha-amino acids involved in the synthesis of proteins in nature, for example glutamic acid or aspartic acid, and also with phenylacetic acid, methanesulfonic acid, ethanesulfonic acid, 2-hydroxyethanesulfonic acid, ethane-1, 2-disulfonic acid, benzenesulfonic acid, 4-methylbenzenesulfonic acid, naphthalene-2-sulfonic acid, naphthalene-1, 5sulfonic acid, 2- or 3-phosphoglycerate, glucose-6-phosphate, N-cyclohexylsulfamic acid (with the formation of cyclamates), or with other acid organic compounds, such as ascorbic acid. Physiologically acceptable salts of compounds may also be prepared with a physiologically acceptable cation. Suitable physiologically acceptable cations are well known to those skilled in the art and include alkaline, alkaline earth, ammonium and quaternary ammonium cations. Carbonates or hydrogen carbonates are also possible. For oligonucleotides, preferred examples of physiologically acceptable salts include but are not limited to (a) salts formed with cations such as sodium, potassium, ammonium, magnesium, calcium, polyamines such as spermine and spermidine, etc.; (b) acid addition salts formed with inorganic acids, for example hydrochloric acid, hydrobromnic acid, sulfuric acid, phosphoric acid, nitric acid and the like; (c) salts formed with organic acids such as, for example, acetic acid, oxalic acid, tartaric acid, succinic acid, maleic acid, flmaric acid, gluconic acid, citric acid, malic acid, ascorbic acid, benzoic acid, tannic acid, palmitic acid, alginic acid, polyglutarnic acid, naphthalenesulfonic acid, methanesulfonic acid, p-toluenesulfonic acid, naphthalenedisulfonic acid, polygalacturonic acid, and the like; and (d) salts formed from elemental anions such as chlorine, bromine, and iodine.

The term "prodrug" indicates a therapeutic agent that is prepared in an inactive form that is converted to an active form (i.e., drug) within the body or cells thereof by the action of endogenous enzymes or other chemicals and/or conditions. In particular, prodrug versions of the oligonucleotides of the invention are prepared as SATE. [(S-acetyl-2-thioethyl) phosphate]. derivatives according to the methods disclosed in WO 93/24510 to Gosselin et al., published Dec. 9, 1993 or in WO 94/26764 and U.S. Pat. No. 5,770,713 to Imbach, et al.

The pharmaceutical compositions utilized in this invention may be administered by any number of routes including, but not limited to: parenteral, intracranial, intraorbital, intracapsular, intraspinal, intracistemal, intrapulmonary, oral, intravenous, intramuscular, intra-arterial, intramedullary, intrathecal, intraventricular, transderaal, subcutaneous, intraperitoneal, intranasal, enteral, topical, sublingual, or rectal means. In addition to the active ingredients, these pharmaceutical compositions may contain suitable physiologically acceptable carriers comprising excipients and auxiliaries which facilitate processing of the active compounds into preparations which can be used pharmaceutically. Further details on techniques for formulation and administration may be found in the latest edition of Remington's Pharmaceutical Sciences (Maack PublishingCo. Easton, Pa.).

Pharmaceutical compositions for, oral administration can be formulated using physiologically acceptable carriers well known in the art in dosages suitable for oral administration. Such carriers enable the pharmaceutical compositions to be formulated as powders, tablets, pills, dragees, capsules, liquids, gels, syrups, slurries, suspensions, and the like, for ingestion by the patient.

Pharmaceutical preparations for oral use can be obtained through combining active compounds with solid excipient, optionally grinding the resulting mixture, and processing the mixture of granules, after adding suitable auxiliaries, if desired, to obtain tablets or dragee cores. Suitable excipients are carbohydrate or protein fillers, such as sugars, including lactose, sucrose, mannitol, or sorbitol; starch from corn, wheat, rice, potato, or other plants; cellulose, such as methyl cellulose, hydroxypropylmethyl-cellulose, or sodium carboxymethylcellulose; gums including arabic and tragacanth; and proteins such as gelatin and collagen. If desired, disintegrating or solubilizing agents may be added, such as the cross-linked polyvinyl pyrrolidone, agar, alginic acid, or a salt thereof, such as sodium alginate.

Dragee cores may be used in conjunction with suitable coatings, such as concentrated sugar solutions, which may also contain gum arabic, talc, polyvinylpyrrolidone, carbopol gel, polyethylene glycol, and/or titaniumdioxide, lacquer solutions, and suitable organic solvents or solvent mixtures. Dyestuffs or pigments may be added to the, tablets or dragee coatings for product identification or to characterize the quantity of active compound, i.e., dosage.

Pharmaceutical preparations which can be used orally include push-fit capsules made of gelatin, as well as soft, sealed capsules made of gelatin and a coating, such as glycerol or sorbitol. Push-fit capsules can contain active ingredients mixed with a filler or binders, such as lactose or starches, lubricants, such as talc or magnesium stearate, and, optionally, stabilizers. In soft capsules, the active compounds may be dissolved or suspended in suitable liquids, such as fatty oils, liquid, or liquid polyethylene glycol with or without stabilizers.

Formulations suitable for pulmonary or respiratory delivery include dry powders, liquid solutions or suspensions suitable for nebulization, and propellant formulations suitable for use in metered dose inhalers (MDI's). The preparation of such formulations is well described in the patent, scientific, and medical literatures, and the following descriptions are intended to be exemplary only.

Dry powder formulations will have a particle size within a preferred range for deposition within the alveolar region of the lung, typically from 0.5 μm to 5 μm. Respirable powders of pharmaceutical compositions within the preferred size range can be produced by a variety of conventional techniques, such as jet-milling, spray-drying, solvent precipitation, and the like. Dry powders can then be administered to the patient in conventional dry powder inhalers (DPI's) that use the patient's inspiratory breath through the device to disperse the powder or in air-assisted devices that use an external power source to disperse the powder into an aerosol cloud, as described in U.S. Pat. No. 5,458,135, the full disclosure of which is incorporated herein by reference.

Dry powder devices typically require a powder mass in the range from about 1 mg to 10 mg to produce a single aerosolized dose, which may necessitate addition of a dry bulking powder to the pharmaceutical formulation. Preferred dry bulking powders include sucrose, lactose, trehalose, human serum albumin (HSA), and glycine. Other suitable dry bulking powders include cellobiose, dextrans, maltotriose, pectin, sodium citrate, sodium ascorbate, mannitol, and the like. Furthermore, stabilizing buffers and salts may be used. Other additives, such as chelating agents, peptidase inhibitors, and the like, which would facilitate the biological activity of the pharmaceutical composition once it is dissolved within the lung would be appropriate. For example, ethylenediaminetetraacetic acid (F4DA EDTA) would be useful as a chelator for divalent cations which are peptidase cofactors.

Liquid formulations for use in nebulizer systems preferably employ slightly acidic buffers (pH 4-6) such as acetate, ascorbate, and citrate, at concentrations of 5 mM to 50 mM. These buffers can act as antioxidants. Physiologically acceptable components to enhance or maintain chemical stability include: antioxidants, chelating agents, protease inhibitors, isotonic modifiers, inert gases, and the like A preferred type of nebulizer suitable for delivering such liquid formulations is described in U.S. Pat. No. 5,458,135, the disclosure of which is incorporated herein by reference.

For use in MDI's, the pharmaceutical composition will be dissolved or suspended in a suitable aerosol propellant, such as a chlorofluorocarbon (CFC) or a hydrofluorocarbon (HFC). Suitable CFC's include trichloromonofluoromethane (propellant 11), dichlorotetrafluoromethane (propellant 114), and dichlorodifluoromethane (propellant 12). Suitable HFC's. include tetrafluoroethane (HFC-134a) and heptafluoropropane (MFC-227).

Preferably, for incorporation into the aerosol propellant, the pharmaceutical composition will be processed into respirable particles as described for the dry powder formulations. The particles are then suspended in the propellant, typically being coated with a surfactant to enhance their dispersion. Suitable surfactants include oleic acid, sorbitan trioleate, and various long chain diglycerides and phospholipids. Such aerosol propellant formulations may further include a lower alcohol, such as ethanol (up to. 30% by weight) and other additives to maintain or enhance chemical stability and physiological acceptability (U.S. Pat. No. 6,080,721, which disclosure is hereby incorporated by reference in its entirety).

For topical or nasal administration, penetrants appropriate to the particular barrier to be permeated are used in the formulation. Such penetrants are generally known in the art.

Pharmaceutical formulations suitable for parenteral administration may be formulated in aqueous solutions, preferably in physiologically compatible buffers such as Hanks solution, Ringer's solution, or physiologically buffered saline. Aqueous injection suspensions may contain substances which increase the viscosity of the suspension, such as sodium carboxymethylcellulose, sorbitol, or dextran. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Optionally, the suspension may also contain suitable stabilizers or agents which increase the solubility of the compounds to allow for the preparation of highly concentrated solutions.

The pharmaceutical compositions of the present invention may be manufactured in a manner that is known in the art, e.g., by means of conventional mixing, dissolving, granulating, dragee-making, levigating, emulsifying, encapsulating, entrapping, or lyophilizing processes.

The pharmaceutical composition may be provided as a salt and can be formed with many acids, including but not limited to, hydrochloric, sulfuric, acetic, lactic, tartaric, malic, succinic, etc. Salts tend to be more soluble in aqueous or other protonic solvents than are the corresponding free base forms. In other cases, the preferred preparation may be a lyophilized powder which may contain any or all of the following: 1-50 mM histidine, 0.1%-2% sucrose, and 2-7% mannitol, at a pH range of 4.5 to 5.5, that is combined with buffer prior to use.

After pharmaceutical compositions have been prepared, they can be placed in an appropriate container and labeled for treatment of an indicated condition. For administration of a GENSET polypeptide, such labeling would include amount, frequency, and method of administration.

Pharmaceutical compositions suitable for use in the invention include compositions wherein the active ingredients are contained in an effective amount to achieve the intended purpose. The determination of an effective dose is well within the capability of those skilled in the art.

For any compound, the therapeutically effective dose can be estimated initially either in cell culture assays, e.g., of neoplastic cells, or in animal models, usually mice, rabbits, dogs, or pigs. The animal model may also be used to determine the appropriate concentration range and route of administration. Such information can then be used to: determine useful doses and routes for administration in humans.

A therapeutically effective dose refers to that amount of active ingredient, for example a GENSET polypeptide or fragments thereof, antibodies specific to GENSET polypeptides, agonists, antagonists or inhibitors of GENSET polypeptides, which ameliorates the symptoms or condition. Therapeutic efficacy and toxicity may be determined by standard pharmaceutical procedures in cell cultures or experimental animals, e.g., ED50 (the dose therapeutically effective in 500% of the population) and LD50 (the dose lethal to 50% of the population). The dose ratio between therapeutic and toxic effects is the therapeutic index, and it can be expressed as the ratio, LD50/ED50. Pharmaceutical compositions which exhibit large therapeutic indices are preferred. The data obtained from cell culture assays and animal studies is used in formulating a range of dosage for human use. The dosage contained in such compositions is preferably within a range of circulating concentrations that include the ED50 with little or no toxicity. The dosage varies within this range depending upon the dosage form employed, sensitivity of the patient, and the route of administration.

The exact dosage will be determined by the practitioner, in light of factors related to the subject that requires treatment. Dosage and administration are adjusted to provide sufficient levels of the active moiety or to maintain the desired effect. Factors which may be taken into account include the severity of the disease state, general health of the subject, age, weight, and gender of the subject, diet, time and frequency of administration, drug combination(s), reaction sensitivities, and tolerance/response to therapy. Other factors that may be considered when evaluating the proper dosage include the chemical nature of the compound destined for delivery, the biological responses associated with the compound (both intended and coincidental) and anticipated contraindications. Additionally, the mode of delivery (including but not limited to systemic and/or local applications: oral, oral enteric, intramuscular injection, subcutaneous injection, intradermal injection, interarticular space, intravascular injection, intravenous infusion, suppository, topical preparation, transdermal system), the duration and frequency of administration (e.g. n doses per hours, n doses per day, n doses per week, cumulative dosage per day, cumulative dosage per week), the biologically effective dose delivered to target site, often indicated by plasma level concentrations, and the rate or efficiency of compound clearance from the body may be considered. Long-acting pharmaceutical compositions maybe administered every. 3 to 4 days, every week, or once every two weeks depending on half-life and clearance rate of the particular formulation.

Normal dosage amounts may vary depending upon the route of administration. Guidance as to particular dosages and methods of delivery is provided in the literature and generally available to practitioners in the art. Those skilled in the art will employ different formulations for nucleotides than for proteins or their inhibitors. Similarly, delivery, of polynucleotides or polypeptides will be specific to particular cells, conditions, locations, etc. In general, for a 75 kg individual the normal dosage range are as follows: for a small molecule compound an effective does is usually between 0.3-50 mg/kg; for recombinant polypeptides an effective dose is usually between 0.25-7.5 mg/kg; for compounds used for mediating humoral immune responses (e.g., polyvalent pneumococcal vaccine, $Rh_o$ (D) immune globulin, Hepatitis B. vaccine, anti-CD20 antigen) the effective dose is usually between 0.0015-1.5 mg/kg; for hormone supplemental compounds. (e.g. estradiol, norethindrone) the effective dose is usually between 0.0005-0.5 mg/kg depending upon delivery system utilized (e.g. transdermal, oral, topical).

Transdermal delivery systems (e.g. estradiol transdermal system, transdermal scopolamine system, transferal nicotine patch) must be calibrated for nominal delivery dosages based upon efficiency of percutaneous delivery for the individual and specific compounds, surface area ($cm^2$). of transdermal system contact, quantity and form of compound integrated into transdermal delivery. system and anatomical location of positioned transdermal system. The effective dosage range, of compounds administered in this manner is usually between 0.005-0.5 mg/kg Uses of GENSET Sequences: Computer-Related Embodiments As used herein the term “GENSET cDNAs” encompasses the nucleotide sequences of the present invention.

It will be appreciated by those skilled in the art that the nucleic acid codes of the invention and polypeptide codes of the invention can be stored, recorded, and manipulated on any medium which can be read and accessed by a computer. As used herein, the words. “recorded” and “stored” refer to a process for storing information on a computer medium. A skilled artisan can readily adopt any of the presently known methods for recording information on a computer readable medium to generate manufactures comprising one or more of the nucleic acid codes of the invention, or one or more of the polypeptide codes of the invention. Another aspect of the present invention is a computer readable medium having recorded thereon at least 1, 2, 5, 10, 15, 20, 25, 30, or 50 nucleic acid codes of the invention. Another aspect of the present invention is a computer readable medium having recorded thereon at least 1, 2, 5, 10, 15, 20, 25, 30, or 50 polypeptide codes of the invention.

Computer readable media include magnetically readable media, optically readable media, electronically readable media and magnetic/optical media. For example, the computer readable media may be a hard disk, a floppy disk, a magnetic tape, CD-ROM, Digital Versatile Disk (DVD), Random Access Memory (RAM), or Read Only Memory (ROM) as well as other types of other media known to those skilled in the art.

Embodiments of the present invention include systems, particularly computer systems which store and manipulate the sequence information described herein. One example of a computer system 100 is illustrated in block diagram form in FIG. 1. As used herein, “a computer system” refers to the hardware components, software components, and data storage components used to analyze the nucleotide sequences of the nucleic acid codes of the invention or the amino acid sequences of the polypeptide codes of the invention. In one embodiment, the computer system 100 is a Sun Enterprise 1000 server, (Sun Microsystems, Palo Alto, Calif.). The computer system 100 preferably includes a processor for processing, accessing and manipulating the sequence data. The processor 105 can be any well-known type of central processing unit, such as the Pentium III from Intel Corporation, or similar processor from Sun, Motorola, Compaq or International Business Machines.

Preferably, the computer system 100 is a general purpose system that comprises the processor 105 and one or more internal data storage components 110 for storing data, and one or more data retrieving devices for retrieving the data stored on the data storage components. A skilled artisan can readily appreciate that any one of the currently available computer systems are suitable.

In one particular embodiment, the computer system 100 includes a processor 105. connected to a bus which is connected to a main memory 115 (preferably implemented as RAM) and one or more internal data storage devices 110, such as a hard drive and/or other computer readable media having data recorded thereon. In some embodiments, the computer system 100 further includes one or more data retrieving device 118 for reading the data stored on the internal data storage devices 110.

The data retrieving device 118 may represent, for example, a floppy disk drive, a compact disk drive, a magnetic tape drive, etc. In some embodiments, the internal data storage device 110 is a removable computer readable medium such as a floppy disk, a compact disk, a magnetic tape, etc containing control logic and/or data recorded thereon. The computer system 100 may advantageously include or be programmed by appropriate software for reading the control logic and/or the data from the data storage component once inserted in the data retrieving device.

The computer system 100 includes a display 120 which is used to display output to a computer user. It should also be noted that the computer system 100 can be linked to other computer systems 125*a-c* in a network or wide area network to provide centralized access to the computer system 100.

Software for accessing and processing the nucleotide sequences of the nucleic acid codes of the invention or the amino acid sequences of the polypeptide codes of the invention (such as search tools, compare tools, and modeling tools etc.) may reside in main memory 115 during execution.

In some embodiments, the computer system 100 may further comprise a sequence comparer for comparing the above-described nucleic acid codes of the invention or the polypeptide codes of the invention stored on a computer readable medium to reference nucleotide or polypeptide sequences stored on a computer readable medium. A "sequence comparer" refers to one or more programs which are implemented on the computer system 100 to compare a nucleotide or polypeptide sequence with other nucleotide or polypeptide sequences and/or compounds including but not limited to peptides, peptidomimetics, and chemicals stored within the data storage means. For example, the sequence comparer may compare the nucleotide sequences of nucleic acid codes of the invention or the amino acid sequences of the polypeptide codes of the invention stored on a computer readable medium to reference sequences stored on a computer readable medium to, identify homologies, motifs implicated in biological function, or structural motifs. The various sequence comparer programs identified elsewhere in this patent specification are particularly contemplated for use in this aspect of the invention.

Figure 2:
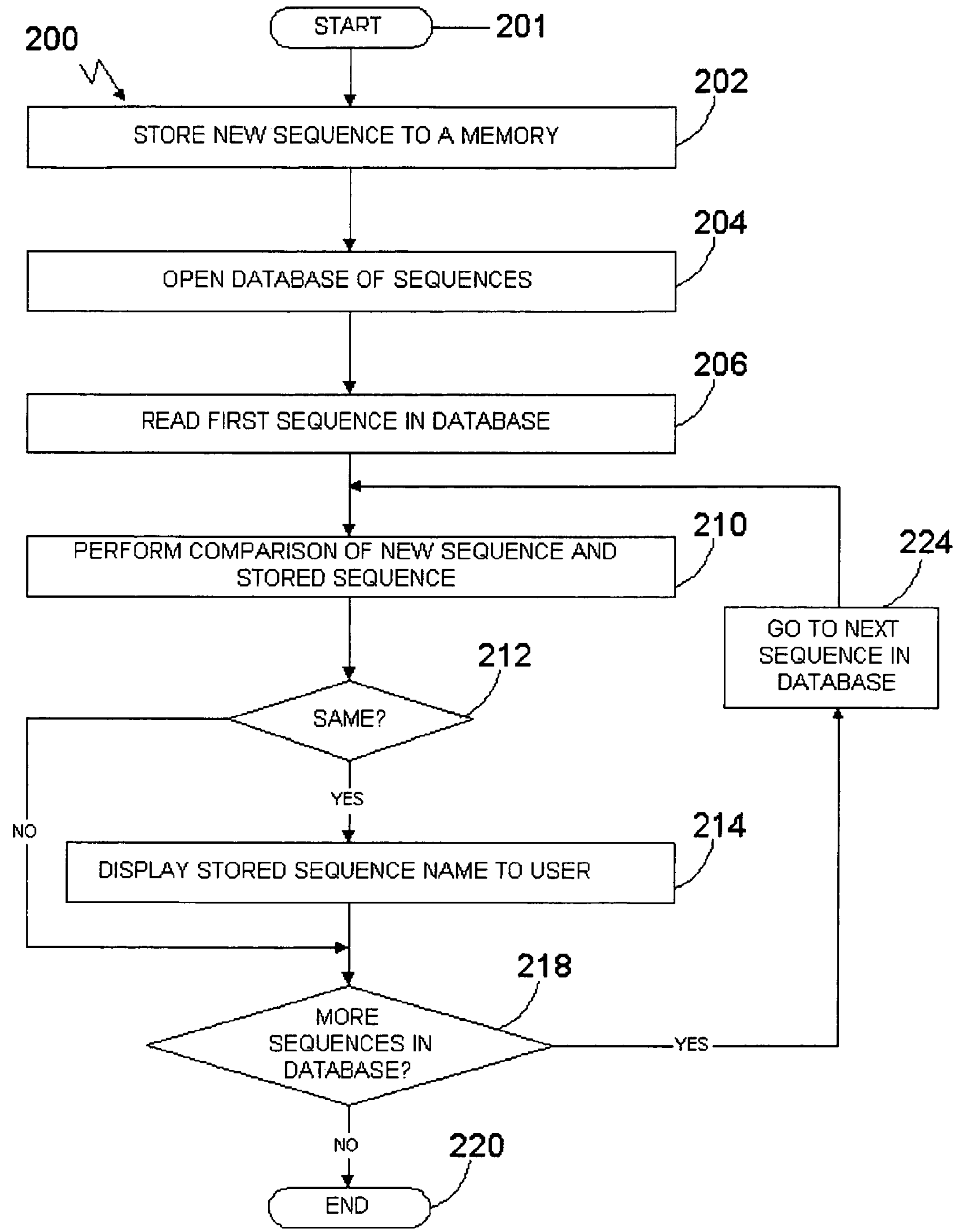
FIG. 2 is a flow diagram illustrating one embodiment of a process 200 for comparing a new nucleotide or protein sequence with a database of sequences in order to determine the identity levels between the new sequence and the sequences in the database.

FIG. 2 is a flow diagram illustrating one embodiment of a process 200 for comparing a new nucleotide or protein sequence with a database of sequences in order to determine the homology levels between the new sequence and the sequences in the database. The database of sequences can be a private database stored within the computer system 100, or a public database such as GENBANK, PIR OR SWISSPROT that is available through the Internet.

The process 200 begins at a start state 201 and then moves to a state 202 wherein the new sequence to be compared is stored to a memory in a computer system 100. As discussed above, the memory could be any type of memory, including RAM or an internal storage device.

The process 200 then moves to a state 204 wherein a database of sequences is opened for analysis and comparison. The process 200 then moves to a state 206 wherein the first sequence stored in the database is read into a memory on the computer. A comparison is then performed at a state 210 to determine if the first sequence is the same as the second sequence. It is important to note that this step is not limited to performing an exact comparison between the new sequence and the first sequence in the database. Well-known methods are known to those of skill in the art for comparing two nucleotide or protein sequences, even if they are not identical. For example, gaps can be introduced into one sequence in order to raise the homology level between the two tested sequences. The parameters that control whether gaps or other features are introduced into a sequence during comparison are normally entered by the user of the computer system.

Once a comparison of the two sequences has been performed at the state 210, a determination is made at a decision state 210 whether the two sequences are the same. Of course, the term "same" is not limited to sequences that are absolutely identical. Sequences that are within the homology parameters entered by the user will be marked as "same" in the process 200.

If a determination is made that the two sequences are the same, the process 200 moves to a state 214 wherein the name of the sequence from the database is displayed to the user. This state notifies the user that the sequence with the displayed name fulfills the homology constraints that were entered. Once the name of the stored sequence is displayed to the user, the process 200 moves to a decision state 218 wherein a determination is made whether more sequences exist in the database. If no more sequences exist in the database, then the process 200 terminates at an end state 220. However, if more sequences do exist in the database, then the process 200 moves to a state 224 wherein a pointer is moved to the next sequence in the database so that it can be compared to the new sequence. In this manner, the new sequence is aligned and compared with every sequence in the database.

It should be noted that if a determination had been made at the decision state 212 that the sequences were not homologous, then the process 200 would move immediately to the decision state 218 in order to determine if any other sequences were available in the database for comparison.

Accordingly, one aspect of the present invention is a computer system comprising a processor, a data storage device having stored thereon a nucleic acid code of the invention or a polypeptide code of the invention, a data storage device having retrievably stored thereon reference nucleotide sequences or polypeptide sequences to be compared to the nucleic acid code of the, invention or polypeptide code of the invention and a sequence comparer for conducting the comparison. The sequence comparer may indicate a homology level between the sequences compared or identify motifs implicated in biological function and structural motifs in the nucleic acid code of the invention and polypeptide codes of the invention or it may, identify structural motifs in sequences which are compared to these nucleic acid codes and polypeptide codes. In some embodiments, the data storage device may have stored thereon the sequences of at least 2, 5, 10, 15, 20, 25, 30, or 50 of the nucleic acid codes of the invention or polypeptide codes of the. invention Another aspect of the present invention is a method for determining the level of homology between a nucleic acid code of the invention and a reference nucleotide sequence, comprising the steps of reading the nucleic acid code and the reference nucleotide sequence through the use of a computer program which determines homology levels and determining homology between the nucleic acid code and the reference nucleotide sequence with the computer program. The computer program may be any of a number of computer programs for determining homology levels, including those specifically enumerated herein, including BLAST2N with the default parameters or with any modified parameters. The method may be implemented using the computer systems described above. The method may also be performed by reading 2, 5, 10, 15, 20, 25, 30, or 50 of the above described nucleic acid codes of the invention through the use of the computer program and determining homology between the nucleic acid codes and reference nucleotide sequences.

Figure 3:
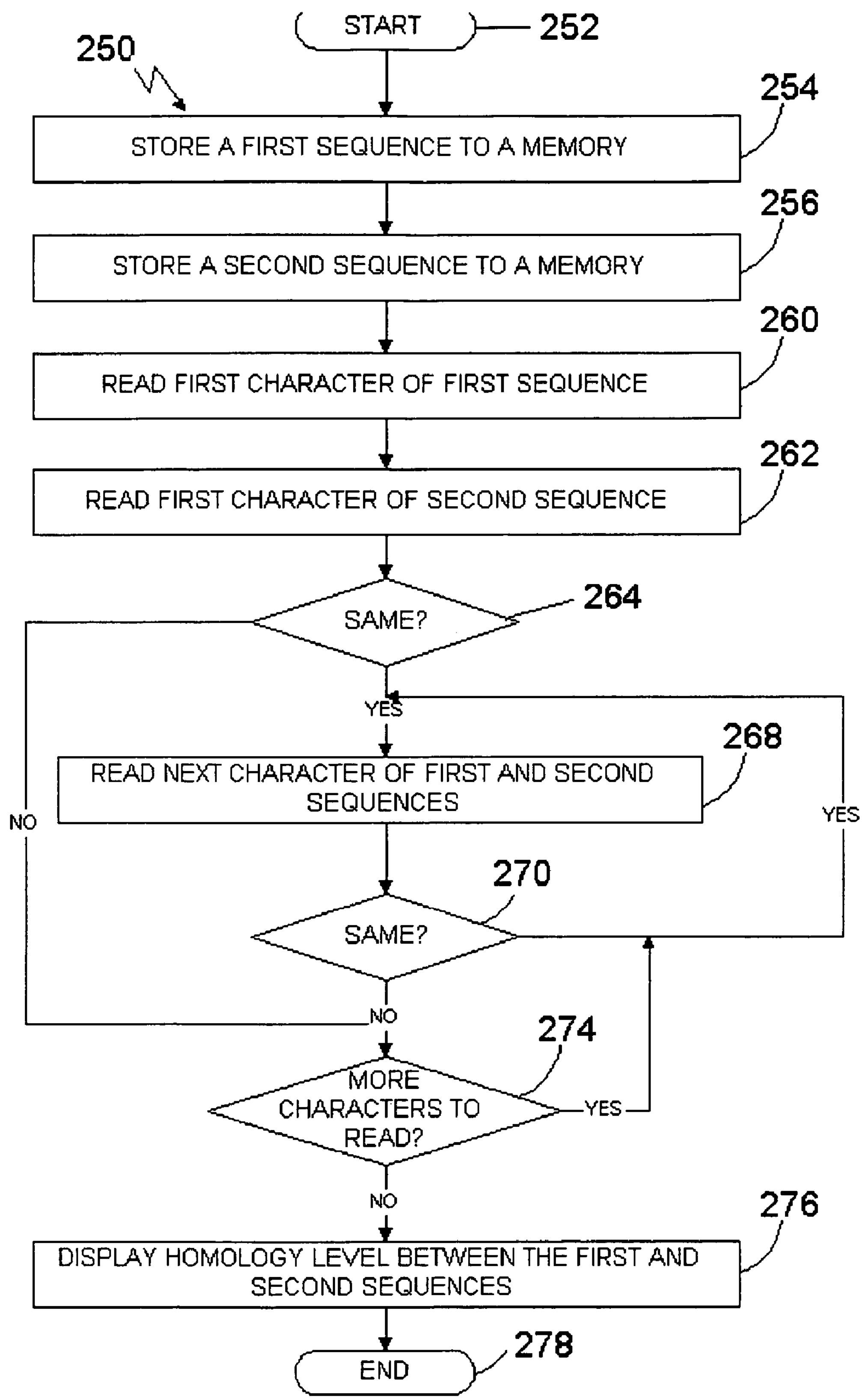
FIG. 3 is a flow diagram illustrating one embodiment of a process 250 in a computer for determining whether two sequences are homologous.

FIG. 3. is a flow diagram illustrating one embodiment of a process 250 in a computer for determining whether two sequences are homologous. The process 250 begins at a start state 252. and then moves to a state 254 wherein a first sequence to be compared is stored to a memory. The second sequence to be compared is then stored to a memory at a state 256. The process 250 then moves to a state 260 wherein the first character in the first sequence is read and then to a state 262 wherein the first character of the second sequence is read. It should be understood that if the sequence is a nucleotide sequence, then the character would normally be either. A, T, C, G or U. If the sequence is a protein sequence, then it should be in the single letter amino acid code so that the first and sequence sequences can be easily compared.

A determination is then made at a decision state 264 whether the two characters are the same. If they are the same, then the process 250 moves to a state 268 wherein the next characters in the first and second sequences are read. A determination is then made whether the next characters are the same. If they are, then the process 250 continues this loop until two characters are not the same. If a determination is made that the next two characters are not the same, the process 250 moves to a decision state 274 to determine whether there are any more characters either sequence to read.

If there are no more characters to read, then the process 250 moves to a state 276 wherein the level of homology between the first and second sequences is displayed to the user. The level of homology is determined by calculating the proportion of characters between the sequences that were the same out of the total number of sequences in the first sequence. Thus, if every character in a first 100 nucleotide sequence aligned with a every character in a second sequence, the homology level would be 100%, Alternatively, the computer program may be a computer program which compares the nucleotide sequences of the nucleic acid codes of the present invention, to reference nucleotide sequences in order to determine whether the nucleic acid code of the invention differs from a reference nucleic acid sequence at one or more positions. Optionally such a program records the length and identity of inserted, deleted or substituted nucleotides with respect to the sequence of either the reference polynucleotide or the nucleic acid code of the invention. In one embodiment, the computer program may be a program which determines whether the nucleotide sequences of the nucleic, acid codes of the invention contain one or more single nucleotide polymorphisms (SNP) with respect to a reference nucleotide sequence. These single nucleotide polymorphisms may each comprise a single base substitution, insertion, or deletion.

Another aspect of the present invention is a method for determining the level of homology between a polypeptide code of the invention and a reference polypeptide sequence, comprising the steps of reading the polypeptide code of the invention and the referencepolypeptide sequence through use of a computer program which determines homology levels and determining homology between the polypeptide code and the reference polypeptide sequence using the computer program.

Accordingly, another aspect of the present invention is a method for determining whether a nucleic acid code of the invention differs at one or more nucleotides from a reference nucleotide sequence comprising the steps of reading the nucleic acid code and the reference nucleotide sequence through use of a computer program which identifies differences between nucleic acid sequences and identifying differences between the nucleic acid code and the reference nucleotide sequence with the computer program. In some embodiments, the computer program is a program which identifies single nucleotide polymorphisms. The method may be implemented by the computer systems described above and the method illustrated in FIG. 3. The method may also be performed by reading at least 2, 5, 10, 15, 20, 25, 30, or 50 of the nucleic acid codes of the invention and the reference nucleotide sequences through the use of the computer program and identifying differences between the nucleic acid codes and the reference nucleotide sequences with the computer program.

In other embodiment the computer based system may further comprise an identifier for identifying features within the nucleotide sequences of the nucleic acid codes of the invention or the amino acid sequences of the polypeptide codes of the invention. An "identifier" refers to one or more programs which identifies certain features within the above-described nucleotide sequences of the nucleic acid codes of the invention or the amino acid sequences of the polypeptide codes of the invention. In one embodiment, the identifier may comprise a program which identifies an open reading frame in the cDNAs codes of the invention.

Figure 4:
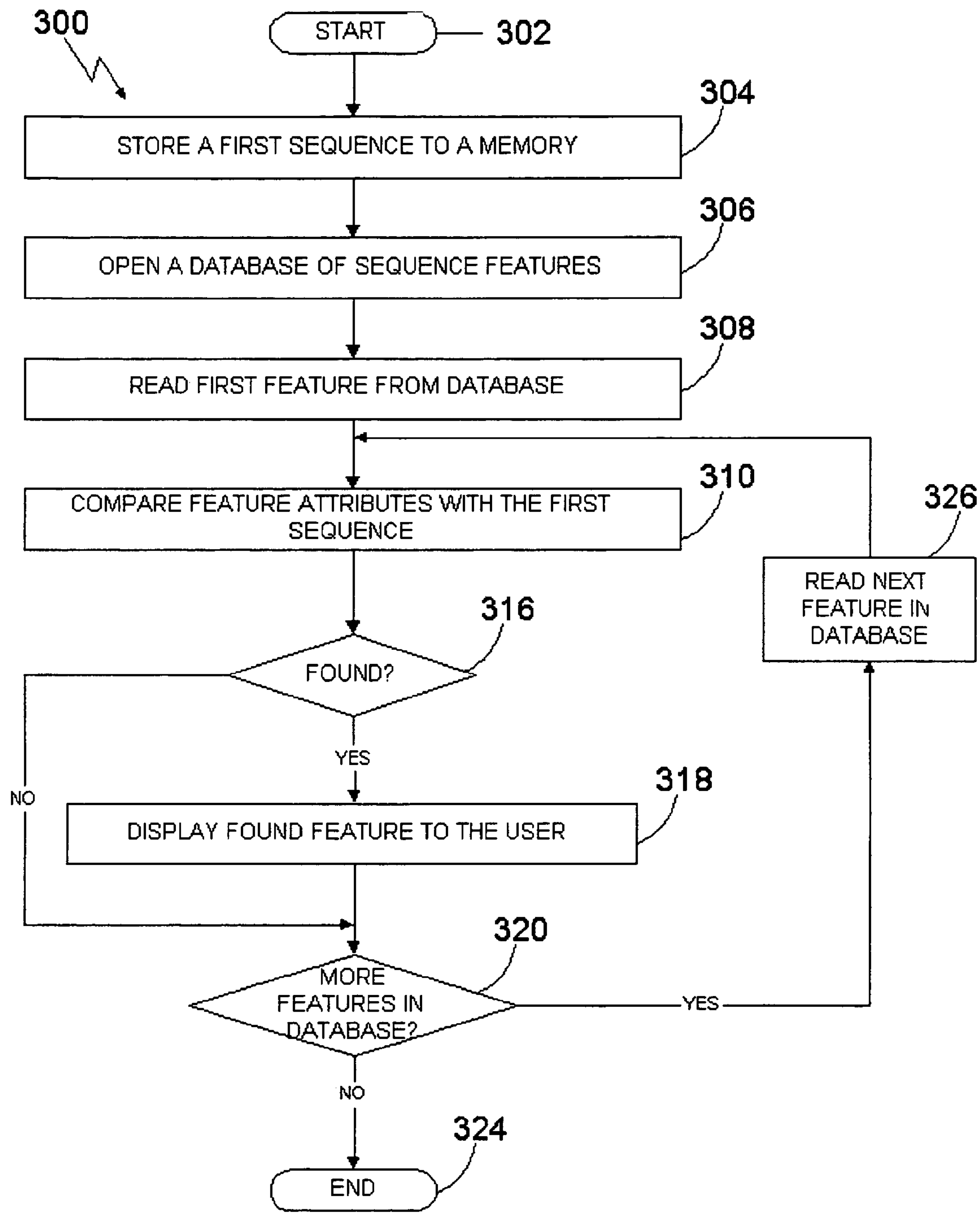
FIG. 4 is a flow diagram illustrating one embodiment of an identifier process 300 for detecting the presence of a feature in a sequence.

FIG. 4 is a flow diagram illustrating one embodiment of an identifier process 300 for detecting the presence of a feature in a sequence. The process 300 begins at a start state 302 and then moves to a state 304 wherein a first sequence that is to be checked for features is stored to a memory 115 in the computer system 100. The process 300 then moves to a state 306 wherein a database of sequence features is opened. Such a database would include a list of each feature's attributes along with the name of the feature. For example, a feature name could be "Initiation Codon" and the, attribute would be "ATO". Another example would be the feature name. "TAATAA Box" and the feature attribute would be "TAATAA". An example of such a database is produced by the University of Wisconsin Genetics Computer Group.

Once the database of features is opened at the state 306, the process 300 moves to a state 308 wherein the first feature is read from the database. A comparison of the attribute of the first feature with the first sequence is then made at a state 310. A determination is then made at a decision state 316 whether the attribute of the feature was found in the first sequence. If the attribute was found, then the process 300 moves to a state 318 wherein the name of the found feature is displayed to the user.

The process 300 then moves to a decision state 320 wherein a determination is made whether move features exist in the database. If no more features do exist, then the process 300 terminates at an end state 324. However, if more features do exist in the database, then the process 300 reads the next sequence feature at a state 326 and loops back to the state 310 wherein the attribute of the next feature is compared against the first sequence.

It should be noted that if the feature attribute is not found in the first sequence at the decision state 316, the process 300 directly to the decision state 320 in order to determine if any more features exist in the database.

In another embodiment, the identifier may comprise a molecular modeling program which determines the 3-dimensional structure of the polypeptides codes of the invention. Such programs may use any methods known to those skilled in the art including methods based on homology-modeling, fold recognition and ab initio methods as described in Sternberg et al., (1999). Curr Opin Struct Biol. 9(3):368-73, which disclosure is hereby incorporated by reference in its entirety. In some embodiments, the molecular modeling program identifies target sequences that are most compatible with profiles representing the structural environments of the residues in known three-dimensional protein structures. (See, e.g., Eisenberg et al., U.S. Pat. No. 5,436,850 issued Jul. 25, 1995, which disclosure is hereby incorporated by reference in its entirety). In another technique, the known three-dimensional structures of proteins in a given family are superimposed to define the structurally conserved regions in that family. This protein modeling technique also uses the known three-dimensional structure of a homologous protein to, approximate the structure of the polypeptide codes of the invention. (See e.g., Srinivasan, et al., U.S. Pat. No. 5,557,535 issued Sep. 17, 1996, which disclosure is hereby incorporated by reference in its entirety). Conventional homology modeling techniques have been used routinely to build models of proteases and antibodies. [Sowdhamini et al. (1997), Protein Engineering 10:207, 215]. Comparative approaches can also be used to develop three-dimensional protein models when the protein of interest has poor sequence identity to template proteins. In some, cases, proteins fold into similar three-dimensional structures despite having very weak sequence identities. For example, the three-dimensional structures of a number of helical cytokines fold in similar three-dimensional topology in spite of weak sequence homology.

The recent development of threading methods now enables the identification of likely folding patterns in a number of situations where the structural relatedness between target and template(s) is not detectable at the sequence level. Hybrid methods, in which fold recognition is performed using Multiple Sequence Threading (MST), structural equivalencies are deduced from the threading output using a distance geometry program DRAGON to construct a low resolution model, and a full-atom representation is constructed using a molecular modeling package such as QUANTA.

According to this 3-step approach, candidate templates are first identified by using the novel fold recognition algorithm MST, which is capable of performing simultaneous threading of multiple aligned sequences onto one or more 3-D structures. In a second step, the structural equivalencies obtained from the MST output are converted into interresidue distance restraints and fed into the distance geometry program DRAGON, together with auxiliary information obtained from secondary structure predictions. The program combines the restraints in an imbiased manner and rapidly generates a large number of low resolution model confirmations. In a third step, these low resolution model confirmations are converted into full-atom models and subjected to energy minimization using the molecular modeling package QUANTA. (See e.g., Aszódi et al., (1997). Proteins: Structure, Function, and Genetics, Supplement 1:3842).

The results of the molecular modeling analysis may then be used in rational drug design techniques to identify agents which modulate the activity of the polypeptide codes of the invention.

Accordingly, another aspect of the present invention is a method of identifying a feature within the nucleic acid codes of the invention or the polypeptide codes of the invention comprising reading the nucleic acid code(s) or the polypeptide code(s) through the use of a computer program which identifies features therein and identifying features within the nucleic acid code(s) or polypeptide code(s) with the computer program. In one embodiment, computer program comprises a computer program which identifies open reading frames. In a further embodiment, the computer program identifies linear or structural motifs in a polypeptide sequence. In another embodiment, the computer program comprises a molecular modeling program. The method may be performed by reading a single sequence or at least 2, 5, 10, 15, 20, 25, 30, or 50 of the nucleic acid codes of the invention or the polypeptide codes of the invention through the use of the computer program and identifying features within the nucleic acid codes or polypeptide codes with the computer program.

The nucleic acid codes of the invention or the polypeptide codes of the invention may be stored and manipulated in a variety of data processor programs in a variety of formats. For example, they may be stored as text in a word processing file, such as MicrosoftWORD or, WORDPERFECT or as an ASCII file in a variety of database programs familiar to those of skill in the art, such as DB2, SYBASE, or ORACLE. In addition, many computer programs and databases may be used as sequence comparers, identifiers, or sources of reference nucleotide or polypeptide sequences to be compared to the nucleic acid codes of the invention or the polypeptide codes of the invention. The following list is intended not to limit the invention but to provide guidance to programs and databases which are useful with the nucleic acid codes of the invention or the polypeptide codes of the invention. The programs and databases which may be used include, but are not limited to: MacPattern (EMBL), DiscoveryBase (Molecular. Applications Group), GeneMine (Molecular Applications Group), Look (Molecular Applications Group), MacLook (Molecular Applications Group), BLAST and BLASI2 (NCBI), BLASTN and BLASTX (Altschul et al, 1990), FASTA (Pearson and Lipman, 1988), FASTDB (Brutlag et al., 1990), Catalyst (Molecular Simulations Inc.), Catalyst/SHAPE (Molecular Simulations Inc.), Cerius2 DBAccess. (Molecular Simulations Inc.), HypoGen (Molecular Simulations Inc.), Insight II, (Molecular. Simulations Inc.), Discover. (Molecular. Simulations Inc.), CHARMM (Molecular Simulations Inc.), Felix (Molecular. Simulations Inc.), DelPhi, (Molecular. Simulations Inc.), QuanteMM, (Molecular. Simulations Inc.), Homology. (Molecular. Simulations Inc.), Modeler. (Molecular. Simulations Inc.), ISIS (Molecular Simulations Inc.), Quanta/Protein Design (Molecular Simulations Inc.), WebLab (Molecular. Simulations Inc.), WebLab Diversity. Explorer, (Molecular, Simulations Inc.), Gene Explorer (Molecular. Simulations Inc.), SeqFold (Molecular. Simulations Inc.), the EMBL/Swissprotein database, the MDL Available Chemicals Directory database, the MDL Drug Data Report data base, the Comprehensive Medicinal Chemistry database, Derwents's World Drug Index database, the BioByteMasterFile database, the Genbank database, and the Genseqn database. Many other programs and data bases would be apparent to one of skill in the art given the present disclosure.

Motifs which may be detected using the above programs include sequences encoding leucine zippers, helix-turn-helix motifs, glycosylation sites, ubiquitination sites, alpha helices, and beta sheets, signal sequences encoding signal peptides which direct the secretion of the encoded proteins, sequences implicated in transcription regulation such as homeoboxes, acidic stretches, enzymatic active sites, substrate binding sites, and enzymatic cleavage sites.

Conclusion

As discussed above, the GENSET polynucleotides and polypeptides of the present invention or fragments thereof can be used for various purposes. The polynucleotides can be used to express recombinant protein for analysis, characterization or therapeutic use; as markers for tissues in which the corresponding protein is preferentially expressed (either constitutively or at a particular stage of tissue differentiation or development or in disease states); as molecular weight markers on Southern gels; as chromosome markers or tags (when labeled) to identify chromosomes or to map related gene positions; as a reagent (including a labeled reagent) in assays designed to quantitatively determine levels of GENSET expression in biological samples; to compare with endogenous DNA sequences in patients to identify potential genetic disorders; as probes to hybridize and thus discover novel, related DNA sequences; as a source of information to derive PCR primers for genetic fingerprinting; for selecting and making oligomers for attachment to a "gene chip" or other support, including for examination for expression patterns; to raise anti-protein antibodies using DNA immunization techniques; and as an antigen to raise anti-DNA antibodies or elicit another immune response. Where the polynucleotide encodes a protein which binds or potentially binds to another protein (such as, for example, in a receptor-ligand interaction), the polynucleotide can also be used in interaction trap assays (such as, for example, that described in Gyuris et al., (1993). Cell 75:791-803 to identify polynucleotides encoding the other protein with which binding occurs or to identify inhibitors of the binding interaction.

The proteins or polypeptides provided by the present invention can similarly be used in assays to determine biological activity, including in a panel of multiple proteins for high-throughput screening; to raise antibodies or to elicit another immune response; as a reagent (including the labeled reagent) in assays designed to quantitatively determine levels of the protein (or its receptor) in biological fluids; as markers for tissues in which the corresponding protein is preferentially expressed (either constitutively or at a particular stage of tissue differentiation or development or in a disease state); and, of course, to isolate correlative receptors or ligands. Where the protein binds or potentially binds to another protein (such as, for example, in a receptor-ligand interaction), the protein can be used to identify the other protein with which binding occurs or to identify inhibitors of the binding interaction. Proteins involved in these binding interactions can also be used to screen for peptide or small molecule inhibitors, or agonists of the binding interaction.

Any, or all of these research utilities are capable of being developed into reagent grade or kit format for commercialization as research products.

Methods for performing the uses listed above are well known to those skilled in the art. References disclosing such methods include without limitation "Molecular. Cloning; A Laboratory Manual", 2d ed., Cole Spring Harbor Laboratory. Press, Sambrook, J., E. F. Fritsch and T. Maniatis eds., 1989, and "Methods in Enzymology; Guide to Molecular. Cloning Techniques", Academic Press, Berger and Kimmel eds., 1987, which disclosures are hereby incorporated by reference in their entireties.

Although this invention has been described in terms of certain preferred embodiments, other embodiments which will be apparent to those of ordinary, skill in the art in view of the disclosure herein are also within the scope of this invention. Accordingly, the, scope of the invention is intended to be defined only by reference to the appended claims.

EXAMPLES

Example 1

Preparation of Antibody Compositions to the GENSET Protein

Substantially pure protein or polypeptide is isolated from transfected or transformed cells containing an expression vector encoding the GENSET protein or a portion thereof. The concentration of protein in the final preparation is adjusted, for example, by concentration on an Amicon filter device, to the level of a few micrograms/ml. Monoclonal or polyclonal antibody to the protein can then be prepared as follows:

A. Monoclonal Antibody Production by Hybridoma Fusion

Monoclonal antibody to epitopes in the GENSET protein or a portion thereof can be prepared from murine hybridomas according to the classical method of Kohler and Milstein, (1975) Nature 256:495 or derivative methods thereof. Also see Harlow and Lane. (1988).

Briefly, a mouse is repetitively inoculated with a few micrograms of the GENSET protein, or a portion thereof, over a period of a few weeks. The mouse is then sacrificed, and the antibody producing cells of the spleen isolated. The spleen cells are fused by means of polyethylene glycol with mouse myeloma cells, and the excess unfused cells destroyed by growth of the system on selective media comprising aminopterin (HAT media). The successfully fused cells are, diluted and aliquots of the dilution placed in wells of a microtiter plate where growth of the culture is continued. Antibody-producing clones are identified by detection of antibody, in the supernatant fluid of the wells by immunoassay procedures, such as ELISA, as originally described by Engvall, (1980). Meth. Enzymol. 70:419, which disclosure is hereby incorporated by reference in its entirety, and derivative methods thereof. Selected positive clones can be expanded and their monoclonal antibody product harvested for use. Detailed procedures for monoclonal antibody production are described in Davis, et al. (1986). Section 21-2.

B. Polyclonal Antibody Production by Immunization.

Polyclonal antiserum containing antibodies to heterogeneous epitopes in the GENSET protein or a portion thereof can be prepared by immunizing suitable non-human animal with the GENSET protein or a portion thereof, which can be unmodified or, modified to enhance immunogenicity. A suitable non-human animal is preferably a non-human mammal is selected, usually a mouse, rat, rabbit, goat, or horse. Alternatively, a crude preparation which has been enriched for GENSET concentration can be used to generate antibodies. Such proteins, fragments or preparations are introduced into the non-human mammal in the presence of an appropriate adjuvant (e.g. aluminum hydroxide, RIBI, etc.) which is known in the art., In addition the protein, fragment or preparation can be pretreated with an agent which will increase antigenicity, such agents are known in the art and include, for example, methylated bovine serum albumin (mBSA), bovine serum albumin (BSA), Hepatitis B surface antigen, and keyhole limpet hemocyanin (KLH). Serum from the immunized animal is collected, treated and tested according to known procedures. If the serum contains polyclonal antibodies to undesired epitopes, the polyclonal antibodies can be purified by immunoaffinity chromatography.

Effective polyclonal antibody production is affected by many factors related both to the antigen and the host species. Also, host animals vary in response to site of inoculations and doses with both inadequate or excessive doses of antigen resulting in low titer antisera. Small doses (ng level) of antigen administered at multiple intradermal sites appears to, be most reliable. Techniques for producing and processing polyclonal antisera are known in the art. An effective immunization protocol for rabbits can be found in Vaitukaitis et al., (1971) J. Clin. Endocrinol. Metab. 33:988-991, which disclosure is hereby incorporated by reference in its entirety.

Booster injections can be given at regular intervals, and antiserum harvested when antibody titer thereof, as determined semi-quantitatively, for example, by double immunodiffusion in agar against known concentrations of the antigen, begins to fall. See, for example, Ouchterlony et al., (1973) Chap 19 in: Handbook of Experimental Immunology. D. Wier (ed). Blackwell, which disclosure is hereby incorporated by reference in its entirety. Plateau concentration of antibody is usually in the range of 0.1 to 0.2 mg/ml of serun (about 12 uM). Affinity of the antisera for the antigen is determined by preparing competitive binding curves, as described, for example, by Fisher, (1980) Chap. 42 in: Manual of Clinical Immunology, 2d Ed. (Rose and Friedman, Eds.). Amer. Soc. For Microbiol., Washington, D.C., which disclosure is hereby incorporated by reference in its entirety.

Antibody preparations prepared according to either the monoclonal or the polygonal protocol are useful in quantitative immunoassays which determine concentrations of antigen-bearing substances in biological samples; they are also used semi-quantitatively or qualitatively to identify the presence of antigen in a biological sample. The antibodies may also be used in therapeutic compositions for killing cells expressing the protein or reducing the levels of the protein in the body.

TABLE I

| SEQ ID NO. | Sequence Type | Clone ID_Clone Name | Name | ATCC Deposit | ATCC Deposit Date |
|---|---|---|---|---|---|
| 1 | DNA | 223583_114-044-2-0-E11-F | S-100A10rP | PTA-2732 | Nov. 27, 2000 |
| 2 | Protein | 223583_114-044-2-0-E11-F | S-100A10rP | PTA-2732 | Nov. 27, 2000 |
| 3 | DNA | 1000848582_181-40-4-0-A11-F | SCPhx | PTA-2732 | Nov. 27, 2000 |
| 4 | Protein | 1000848582_181-40-4-0-A11-F | SCPhx | PTA-2732 | Nov. 27, 2000 |
| 5 | DNA | 1000839315_220-26-1-0-F3-F | Chimerin | PTA-2732 | Nov. 27, 2000 |
| 6 | Protein | 1000839315_220-26-1-0-F3-F | Chimerin | PTA-2732 | Nov. 27, 2000 |
| 7 | DNA | 1000770704_208-27-3-0-G6-F | CalX | PTA-2732 | Nov. 27, 2000 |
| 8 | Protein | 1000770704_208-27-3-0-G6-F | CalX | PTA-2732 | Nov. 27, 2000 |
| 9 | DNA | 147103_106-024-1-0-H6-F | sLRP10 | PTA-2534 | Sep. 27, 2000 |
| 10 | Protein | 147103_106-024-1-0-H6-F | sLRP10 | PTA-2534 | Sep. 27, 2000 |
| 11 | DNA | 224168_116-096-3-0-G11-F | sLRP10 | PTA-2534 | Sep. 27, 2000 |
| 12 | Protein | 224168_116-096-3-0-G11-F | sLRP10 | PTA-2534 | Sep. 27, 2000 |
| 13 | DNA | 243303_116-118-4-0-A3-F | sLRP10 | PTA-2534 | Sep. 27, 2000 |
| 14 | Protein | 243303_116-118-4-0-A3-F | sLRP10 | PTA-2534 | Sep. 27, 2000 |
| 15 | DNA | 225432_116-083-3-0-C6-F | sLRP10 | PTA-2534 | Sep. 27, 2000 |
| 16 | Protein | 225432_116-083-3-0-C6-F | sLRP10 | PTA-2534 | Sep. 27, 2000 |
| 17 | DNA | 229633_114-049-1-0-D3-F | STAMSAP | PTA-2534 | Sep. 27, 2000 |
| 18 | Protein | 229633_114-049-1-0-D3-F | STAMSAP | PTA-2534 | Sep. 27, 2000 |
| 19 | DNA | 158523_106-030-2-0-A3-F | OAR | PTA-2732 | Nov. 27, 2000 |
| 20 | Protein | 158523_106-030-2-0-A3-F | OAR | PTA-2732 | Nov. 27, 2000 |
| 21 | DNA | 589198_184-11-1-0-E4-F | COVI | PTA-2732 | Nov. 27, 2000 |
| 22 | Protein | 589198_184-11-1-0-E4-F | COVI | PTA-2732 | Nov. 27, 2000 |
| 23 | DNA | 47-14-1-C3-CL0 5 | APIP | 98921 | Oct. 15, 1998 |
| 24 | Protein | 47-14-1-C3-CL0 5 | APIP | 98921 | Oct. 15, 1998 |
| 25 | DNA | 545542_182-1-2-0-D12-F | FGF-22 | PTA-2534 | Sep. 27, 2000 |
| 26 | Protein | 545542_182-1-2-0-D12-F | FGF-22 | PTA-2534 | Sep. 27, 2000 |
| 27 | DNA | 117401_106-006-4-0-B11-F | Frangiopogen | PTA-2534 | Sep. 27, 2000 |
| 28 | Protein | 117401_106-006-4-0-B11-F | Frangiopogen | PTA-2534 | Sep. 27, 2000 |
| 29 | DNA | 133431_105-092-4-0-G11-F | Armapoptin | PTA-2534 | Sep. 27, 2000 |
| 30 | Protein | 133431_105-092-4-0-G11-F | Armapoptin | PTA-2534 | Sep. 27, 2000 |
| 31 | DNA | 477709_174-8-2-0-C10-F | Pretactilin | PTA-2534 | Sep. 27, 2000 |
| 32 | Protein | 477709_174-8-2-0-C10-F | Pretactilin | PTA-2534 | Sep. 27, 2000 |
| 33 | DNA | 145606_106-023-2-0-B3-F | MS4A5 | PTA-2534 | Sep. 27, 2000 |
| 34 | Protein | 145606_106-023-2-0-B3-F | MS4A5 | PTA-2534 | Sep. 27, 2000 |
| 35 | DNA | 1000769575_208-22-1-0-B2-F | Antaginin | PTA-2732 | Nov. 27, 2000 |
| 36 | Protein | 1000769575_208-22-1-0-B2-F | Antaginin | PTA-2732 | Nov. 27, 2000 |
| 37 | DNA | 146994_106-023-4-0-C9-F | Beferin | PTA-2732 | Nov. 27, 2000 |
| 38 | Protein | 146994_106-023-4-0-C9-F | Beferin | PTA-2732 | Nov. 27, 2000 |
| 39 | DNA | 1000838788_228-28-4-0-F7-F | RP | PTA-2732 | Nov. 27, 2000 |
| 40 | Protein | 1000838788_228-28-4-0-F7-F | RP | PTA-2732 | Nov. 27, 2000 |
| 41 | DNA | 1000943975_160-213-2-0-A5-F | SSSPI | PTA-2732 | Nov. 27, 2000 |
| 42 | Protein | 1000943975_160-213-2-0-A5-F | SSSPI | PTA-2732 | Nov. 27, 2000 |

TABLE I-continued

| SEQ ID NO. | Sequence Type | Clone ID_Clone Name | Name | ATCC Deposit | ATCC Deposit Date |
|---|---|---|---|---|---|
| 43 | DNA | 147441_106-025-2-0-C11-F | CPI-1 | | |
| 44 | Protein | 147441_106-025-2-0-C11-F | CPI-1 | | |
| 45 | DNA | 124610_113-003-3-0-H5-F | RET-A-MODULIN | PTA-2732 | Nov. 27, 2000 |
| 46 | Protein | 124610_113-003-3-0-H5-F | RET-A-MODULIN | PTA-2732 | Nov. 27, 2000 |
| 47 | DNA | 1000855165_205-99-1-0-A5-F | Tifapinix | PTA-2732 | Nov. 27, 2000 |
| 48 | Protein | 1000855165_205-99-1-0-A5-F | Tifapinix | PTA-2732 | Nov. 27, 2000 |
| 49 | DNA | 588098_184-11-4-0-H4-F | CrypAAT | PTA-2732 | Nov. 27, 2000 |
| 50 | Protein | 588098_184-11-4-0-H4-F | CrypAAT | PTA-2732 | Nov. 27, 2000 |
| 51 | DNA | 500721700_204-43-4-0-H10-F | Tifapinix-A58S | | |
| 52 | Protein | 500721700_204-43-4-0-H10-F | Tifapinix-A58S | | |
| 53 | DNA | 789749_182-14-3-0-C12-F | Plasminute | PTA-2732 | Nov. 27, 2000 |
| 54 | Protein | 789749_182-14-3-0-C12-F | Plasminute | PTA-2732 | Nov. 27, 2000 |
| 55 | DNA | 519757_184-4-2-0-F7-F | CALSIGN | PTA-2732 | Nov. 27, 2000 |
| 56 | Protein | 519757_184-4-2-0-F7-F | CALSIGN | PTA-2732 | Nov. 27, 2000 |
| 57 | DNA | 625004_188-15-4-0-H6-F | vCOL16A1 | PTA-2534 | Sep. 27, 2000 |
| 58 | Protein | 625004_188-15-4-0-H6-F | vCOL16A1 | PTA-2534 | Sep. 27, 2000 |
| 59 | DNA | 422353_145-11-3-0-E7-F | NK5 | PTA-2534 | Sep. 27, 2000 |
| 60 | Protein | 422353_145-11-3-0-E7-F | NK5 | PTA-2534 | Sep. 27, 2000 |
| 61 | DNA | 500715621_204-15-3-0-C6-F | PLasminogen Carrier Protein (PLCP) | PTA-2534 | Sep. 27, 2000 |
| 62 | Protein | 500715621_204-15-3-0-C6-F | PLasminogen Carrier Protein (PLCP) | PTA-2534 | Sep. 27, 2000 |
| 63 | DNA | 165843_116-008-4-0-G4-F | Novel Calpastatin 1 (NC1) | PTA-2534 | Sep. 27, 2000 |
| 64 | Protein | 165843_116-008-4-0-G4-F | Novel Calpastatin 1 (NC1) | PTA-2534 | Sep. 27, 2000 |
| 65 | DNA | 335752_157-15-4-0-B11-F | Novel Calpastatin 2 (NC2) | | |
| 66 | Protein | 335752_157-15-4-0-B11-F | Novel Calpastatin 2 (NC2) | | |
| 67 | DNA | 646607_181-15-2-0-E2-F | Benzodiazepine Receptor 2 (BZRP-R2) | PTA-2534 | Sep. 27, 2000 |
| 68 | Protein | 646607_181-15-2-0-E2-F | Benzodiazepine Receptor 2 (BZRP-R2) | PTA-2534 | Sep. 27, 2000 |
| 69 | DNA | 229654_114-049-1-0-F12-F | LAP | | |
| 70 | Protein | 229654_114-049-1-0-F12-F | LAP | | |
| 71 | DNA | 338116_174-1-1-0-B10-F | Short Histone Deacetylase (SHDAC) | PTA-2534 | Sep. 27, 2000 |
| 72 | Protein | 338116_174-1-1-0-B10-F | Short Histone Deacetylase (SHDAC) | PTA-2534 | Sep. 27, 2000 |
| 73 | DNA | 500716683_204-24-2-0-D12-F | Protease-associated Paraplegin (PAP) | PTA-2534 | Sep. 27, 2000 |
| 74 | Protein | 500716683_204-24-2-0-D12-F | Protease-associated Paraplegin (PAP) | PTA-2534 | Sep. 27, 2000 |
| 75 | DNA | 500760207_205-58-4-0-H6-F | Ketothiolase (KT) | | |
| 76 | Protein | 500760207_205-58-4-0-H6-F | Ketothiolase (KT) | | |
| 77 | DNA | 122421_105-076-4-0-H1-F | BASI2 | | |
| 78 | Protein | 122421_105-076-4-0-H1-F | BASI2 | | |
| 79 | DNA | 99483_105-016-1-0-D7-F | KSPI1 | PTA-2534 | Sep. 27, 2000 |
| 80 | Protein | 99483_105-016-1-0-D7-F | KSPI1 | PTA-2534 | Sep. 27, 2000 |

TABLE I-continued

| SEQ ID NO. | Sequence Type | Clone ID_Clone Name | Name | ATCC Deposit | ATCC Deposit Date |
|---|---|---|---|---|---|
| 81 | DNA | 517778_184-5-3-0-G3-F | Amyloid Apoptotic Receptor (AAR) | | |
| 82 | Protein | 517778_184-5-3-0-G3-F | Amyloid Apoptotic Receptor (AAR) | | |
| 83 | DNA | 100038_105-017-4-0-E4-F | Soluble Activator of Wnt 1 (SAW-1) | | |
| 84 | Protein | 100038_105-017-4-0-E4-F | Soluble Activator of Wnt 1 (SAW-1) | | |
| 85 | DNA | 100523_105-019-1-0-F3-F | Soluble Activator of Wnt 1 (SAW-1) | | |
| 86 | Protein | 100523_105-019-1-0-F3-F | Soluble Activator of Wnt 1 (SAW-1) | | |
| 87 | DNA | 116470_105-063-3-0-H7-F | Dopamine AMPhetamine INhibitor (Dampin) | | |
| 88 | Protein | 116470_105-063-3-0-H7-F | Dopamine AMPhetamine INhibitor (Dampin) | | |
| 89 | DNA | 122600_105-077-3-0-F9-F | Dopamine AMPhetamine INhibitor (Dampin) | PTA-2732 | Nov. 27, 2000 |
| 90 | Protein | 122600_105-077-3-0-F9-F | Dopamine AMPhetamine INhibitor (Dampin) | PTA-2732 | Nov. 27, 2000 |
| 91 | DNA | 651658_181-35-2-0-C8-F | VAGS | | |
| 92 | Protein | 651658_181-35-2-0-C8-F | VAGS | | |
| 93 | DNA | 150011_110-006-3-0-D5-F | TFPI-C16Pfs | | |
| 94 | Protein | 150011_110-006-3-0-D5-F | TFPI-C16Pfs | | |
| 95 | DNA | 500737461_205-43-3-0-E3-F | TFPI-M162Qfs | | |
| 96 | Protein | 500737461_205-43-3-0-E3-F | TFPI-M162Qfs | | |
| 97 | DNA | 100545_105-019-2-0-E3-F | Soluble Activator, of Wnt 2 (SAW-2) | | |
| 98 | Protein | 100545_105-019-2-0-E3-F | Soluble Activator of Wnt 2 (SAW-2) | | |
| 99 | DNA | 479155_174-4-4-0-C8-F | ADEVAR | PTA-2732 | Nov. 27, 2000 |
| 100 | Protein | 479155_174-4-4-0-C8-F | ADEVAR | PTA-2732 | Nov. 27, 2000 |
| 101 | DNA | 586587_181-9-2-0-C5-F | ATP-binding cassette 1, hABC | | |
| 102 | Protein | 586587_181-9-2-0-C5-F | ATP-binding cassette, hABC | | |
| 103 | DNA | 620315_188-13-1-0-G12-F | MOBP-81h | PTA-2534 | Sep. 27, 2000 |
| 104 | Protein | 620315_188-13-1-0-G12-F | MOBP-81h | PTA-2534 | Sep. 27, 2000 |
| 105 | DNA | 646477_181-19-2-0-F4-F | novel Apolipoprotein H (NAPOH) | | |
| 106 | Protein | 646477_1 81-19-2-0-F4-F | novel Apolipoprotein H (NAPOH) | | |

TABLE I-continued

| SEQ ID NO. | Sequence Type | Clone ID_Clone Name | Name | ATCC Deposit | ATCC Deposit Date |
|---|---|---|---|---|---|
| 107 | DNA | 113165_105-056-3-0-G12-F | human JNK3-binding protein (hJNK3-BP) | | |
| 108 | Protein | 113165_105-056-3-0-G12-F | human JNK3-binding (hJNK3-BP) | | |
| 109 | DNA | 231462_117-065-1-0-G11-F | DROCK2 | | |
| 110 | Protein | 231462_117-065-1-0-G11-F | DROCK2 | | |
| 111 | DNA | 500723589_205-34-3-0-G4-F | Novel 17 beta-hydroxysteroid dehydrogenase type 2 (NBHSD2) | | |
| 112 | Protein | 500723589_205-34-3-0-G4-F | Novel 17 beta-hydroxysteroid dehydrogenase type 2 (NBHSD2) | | |

TABLE II

| SEQ ID NO: | ORF | Signal Peptide | Mature peptide | Polyadenylation Signal | PolyA tail |
|---|---|---|---|---|---|
| 1 | [1435-1836] | — | — | [1965-1970] | [2001-2016] |
| 3 | [39-917] | [39-116] | [117-917] | [1045-1050] | [1066-1081] |
| 5 | [84-317] | [84-140] | [141-317] | [397-402] | [423-438] |
| 7 | [32-748] | [32-91] | [92-748] | [928-933] | [953-968] |
| 9 | [254-574] | [254-295] | [296-574] | — | — |
| 11 | [254-574] | [254-295] | [296-574] | — | — |
| 13 | [254-574] | [254-295] | [296-574] | — | — |
| 15 | [254-574] | [254-295] | [296-574] | — | — |
| 17 | [327-1013] | — | — | [1131-1136] | [1160-1175] |
| 19 | [112-813] | [112-162] | [163-813] | — | — |
| 21 | [127-1020] | [127-183] | [184-1020] | — | — |
| 23 | [10-1212] | [10-60] | [61-1212] | [1709-1714] | [1733-1746] |
| 25 | [127-879] | [127-198] | [199-879] | — | [1224-1239] |
| 27 | [116-961] | — | — | [1145-1150] | [1164-1179] |
| 29 | [345-1118] | [345-404] | [405-1118] | — | [1103-1118] |
| 31 | [14-1048] | [14-91] | [92-1048] | [1234-1239] | [1258-1273] |
| 33 | [73-672] | — | — | [689-694] | [708-723] |
| 35 | [119-655] | — | — | [809-814] | [830-845] |
| 37 | [17-259] | — | — | — | — |
| 39 | [260-1048] | [260-319] | [320-1048] | [1782-1787] | [1801-1816] |
| 41 | [91-462] | [91-180] | [181-462] | [607-612] | [628-643] |
| 43 | [228-501] | [228-326] | [327-501] | — | — |
| 45 | [98-934] | — | — | — | — |
| 47 | [267-1139] | [267-350] | [351-1139] | [1246-1251] | [1279-1294] |
| 49 | [48-1100] | [48-119] | [120-1100] | [1159-1164] | [1179-1194] |
| 51 | [290-1162] | [290-373] | [374-1162] | [1269-1274] | [1302-1317] |
| 53 | [1044-1664] | — | — | [1869-1874] | [1892-1907] |
| 55 | [26-628] | — | — | [766-771] | [795-809] |
| 57 | [476-964] | — | — | [1101-1106] | [1118-1133] |
| 59 | [79-642] | — | — | [799-804] | [823-838] |
| 61 | [159-764] | [159-221] | [222-764] | — | — |
| 63 | [195-587] | [195-260] | [261-587] | [578-583] | [604-618] |
| 65 | [177-767] | [177-242] | [243-767] | [814-819] | [822-836] |
| 67 | [63-572] | — | — | [750-755] | [774-789] |
| 69 | [67-2427] | [67-114] | [115-2427] | [2522-2527] | [2541-2556] |
| 71 | [8-763] | [8-58] | [59-763] | [1562-1567] | [1588-1603] |
| 73 | [9-395] | [9-56] | [57-395] | — | [864-879] |
| 75 | [88-1269] | — | — | [1594-1599] | [1619-1634] |
| 77 | [69-875] | [69-131] | [132-875] | [1599-1604] | [1627-1642] |
| 79 | [344-1144] | [344-433] | [434-1144] | — | — |
| 81 | [27-689] | [27-122] | [123-689] | [1302-1307] | [1325-1406] |
| 83 | [118-510] | [118-189] | [190-510] | [1718-1723] | [1739-1754] |
| 85 | [118-510] | [118-189] | [190-510] | [1718-1723] | [1739-1754] |
| 87 | [152-655] | — | — | [1399-1404] | [1416-1431] |
| 89 | [152-655] | — | — | [1399-1404] | [1416-1431] |
| 91 | [48-1301] | [48-119] | [120-1301] | [1360-1365] | [1402-1417] |
| 93 | [278-733] | [278-334] | [335-733] | [1072-1077] | [1101-1115] |

TABLE II-continued

| SEQ ID NO: | ORF | Signal Peptide | Mature peptide | Polyadenylation Signal | PolyA tail |
|---|---|---|---|---|---|
| 95 | [253-744] | [253-336] | [337-744] | [1269-1274] | [1292-1307] |
| 97 | [118-504] | [118-189] | [190-504] | [1819-1824] | [1840-1855] |
| 99 | [95-613] | — | — | [636-641] | [652-667] |
| 101 | [154-639] | — | — | [1023-1028] | [1047-1062] |
| 103 | [150-392] | — | — | — | [63-933] |
| 105 | [35-1069] | [35-91] | [92-1069] | [1146-1151] | [1172-1187] |
| 107 | [16-1449] | — | — | [1483-1488] | [1505-1520] |
| 109 | [95-1252] | [95-139] | [140-1252] | [1751-1756] | [1774-1789] |
| 111 | [103-1263] | — | — | [1341-1346] | [1365-1408] |

TABLE III

| SEQ ID NO: | Positions of immunogenic epitopes |
|---|---|
| 2 | 21 . . . 28:34 . . . 42:56 . . . 65:80 . . . 85:95 . . . 105:128 . . . 133 |
| 4 | 32 . . . 39:57 . . . 66:78 . . . 84:92 . . . 105:152 . . . 157:165 . . . 171:262 . . . 270:277 . . . 287 |
| 6 | 23 . . . 33:34 . . . 41:49 . . . 63 |
| 8 | 42 . . . 48:53 . . . 69:76 . . . 94:145 . . . 154:165 . . . 171:179 . . . 188:186 . . . 200:229 . . . 238 |
| 10 | 11 . . . 20:36 . . . 55:63 . . . 70:79 . . . 94 |
| 12 | 11 . . . 20:36 . . . 55:63 . . . 70:79 . . . 94 |
| 14 | 11 . . . 20:36 . . . 55:63 . . . 70:79 . . . 94 |
| 16 | 11 . . . 20:36 . . . 55:63 . . . 70:79 . . . 94 |
| 18 | 10 . . . 22:80 . . . 91:100 . . . 110:122 . . . 128:134 . . . 141:151 . . . 162:160 . . . 173:191 . . . 202:216 . . . 227 |
| 20 | 21 . . . 28:54 . . . 62:70 . . . 81:83 . . . 91:95 . . . 101:110 . . . 124:134 . . . 139:180 . . . 190 |
| 22 | 20 . . . 29:33 . . . 39:43 . . . 53:82 . . . 92:253 . . . 264 |
| 24 | 16 . . . 27:87 . . . 97:152 . . . 159:169 . . . 175:178 . . . 188:213 . . . 221:273 . . . 282:308 . . . 313:339 . . . 347:385 . . . 395 |
| 26 | 45 . . . 55:52 . . . 63:106 . . . 117:118 . . . 128:126 . . . 131:148 . . . 155:157 . . . 164:172 . . . 190:212 . . . 221:232 . . . 247 |
| 28 | 44 . . . 53:55 . . . 65:82 . . . 90:93 . . . 114:119 . . . 132:148 . . . 163:174 . . . 179:176 . . . 181:199 . . . 219:218 . . . 228:242 . . . 253:272 . . . 278 |
| 30 | 1 . . . 6:41 . . . 46:92 . . . 102:133 . . . 139:143 . . . 163:161 . . . 181:185 . . . 195:214 . . . 221 |
| 32 | 53 . . . 77:120 . . . 130:144 . . . 159:159 . . . 169:196 . . . 202:266 . . . 272:331 . . . 344 |
| 34 | 147 . . . 157:189 . . . 199 |
| 36 | 113 . . . 125:139 . . . 151:149 . . . 160 |
| 38 | 1 . . . 8:49 . . . 63:66 . . . 76 |
| 40 | 27 . . . 35:106 . . . 111:183 . . . 194:222 . . . 228:241 . . . 247:255 . . . 262 |
| 42 | 38 . . . 49:49 . . . 54:71 . . . 82:92 . . . 116 |
| 44 | 1 . . . 19 |
| 46 | 1 . . . 8:9 . . . 14:70 . . . 80:85 . . . 92:110 . . . 116:145 . . . 158:202 . . . 216:231 . . . 246:244 . . . 253:262 . . . 276 |
| 48 | 57 . . . 63:85 . . . 96:104 . . . 111:114 . . . 121:127 . . . 142:159 . . . 169:169 . . . 178:185 . . . 191:206 . . . 214:213 . . . 222:228 . . . 250 |
| 50 | 58 . . . 67:116 . . . 125:149 . . . 154:188 . . . 193:213 . . . 218:233 . . . 241:332 . . . 339 |
| 52 | 56 . . . 63:85 . . . 96:104 . . . 111:114 . . . 121:127 . . . 142:159 . . . 169:169 . . . 178:185 . . . 191:206 . . . 214:213 . . . 222:228 . . . 250 |
| 54 | 21 . . . 30:124 . . . 137:147 . . . 159:181 . . . 189 |
| 56 | 55 . . . 64:80 . . . 86:167 . . . 174 |
| 58 | 3 . . . 15:12 . . . 42:40 . . . 66:75 . . . 85:90 . . . 107:123 . . . 142:147 . . . 159 |
| 60 | 30 . . . 39:73 . . . 89:96 . . . 102:163 . . . 187 |
| 62 | 20 . . . 31:89 . . . 101:106 . . . 116:157 . . . 172:180 . . . 194 |
| 64 | 28 . . . 34:37 . . . 45:49 . . . 61:61 . . . 77:102 . . . 108 |
| 66 | 27 . . . 35:37 . . . 45:49 . . . 61:61 . . . 77:102 . . . 109:144 . . . 152:170 . . . 180:179 . . . 188 |
| 68 | 22 . . . 36:151 . . . 156:161 . . . 169 |
| 70 | 19 . . . 24:34 . . . 45:79 . . . 94:100 . . . 107:146 . . . 152:161 . . . 168:174 . . . 179:199 . . . 204:238 . . . 246:259 . . . 269:329 . . . 342:380 . . . 393:390 . . . 395:393 . . . 398:395 . . . 400:397 . . . 404:408 . . . 414:427 . . . 434:447 . . . 456:461 . . . 474:481 . . . 489:492 . . . 499:506 . . . 513:520 . . . 540:556 . . . 563:561 . . . 568:584 . . . 590:596 . . . 604:626 . . . 632:629 . . . 634:634 . . . 656:654 . . . 659:675 . . . 681:714 . . . 731:730 . . . 743:745 . . . 766:768 . . . 786 |
| 72 | 97 . . . 110:234 . . . 245 |
| 74 | 10 . . . 23:27 . . . 32:33 . . . 44:103 . . . 108:111 . . . 122 |
| 76 | 116 . . . 122:182 . . . 188:205 . . . 215:223 . . . 231:234 . . . 241:351 . . . 356:364 . . . 374 |
| 78 | 67 . . . 73:71 . . . 85:142 . . . 148:176 . . . 195:229 . . . 237:236 . . . 246:248 . . . 268 |
| 80 | 25 . . . 44:54 . . . 61:93 . . . 99:99 . . . 108:107 . . . 123:129 . . . 144:164 . . . 172:176 . . . 185:203 . . . 210:214 . . . 221:225 . . . 233:243 . . . 253 |
| 82 | 42 . . . 48:84 . . . 93:104 . . . 118:122 . . . 132:141 . . . 147:153 . . . 161 |
| 84 | 42 . . . 51:76 . . . 94:97 . . . 126 |
| 86 | 42 . . . 51:76 . . . 94:97 . . . 126 |
| 88 | 6 . . . 14:13 . . . 23:25 . . . 39:36 . . . 42:59 . . . 67:79 . . . 86:110 . . . 120:123 . . . 132:133 . . . 145:153 . . . 167 |
| 90 | 6 . . . 14:13 . . . 23:25 . . . 39:36 . . . 42:59 . . . 67:79 . . . 86:110 . . . 120:123 . . . 132:133 . . . 145:153 . . . 167 |
| 92 | 25 . . . 33:31 . . . 48:65 . . . 73:125 . . . 134:183 . . . 192:216 . . . 221:255 . . . 260:280 . . . 285:300 . . . 308:400 . . . 405 |
| 94 | 48 . . . 54:76 . . . 87:95 . . . 102:107 . . . 115:118 . . . 125:131 . . . 141 |
| 96 | 57 . . . 63:85 . . . 96:104 . . . 111:116 . . . 124:127 . . . 134:140 . . . 155 |
| 98 | 42 . . . 51:76 . . . 94:116 . . . 123 |
| 100 | 26 . . . 33:46 . . . 54:104 . . . 117:125 . . . 130 |

TABLE III-continued

| SEQ ID NO: | Positions of immunogenic epitopes |
|---|---|
| 102 | 15 . . . 23:44 . . . 55:52 . . . 62:77 . . . 83:83 . . . 88:115 . . . 124:132 . . . 148:145 . . . 156 |
| 104 | 2 . . . 23:34 . . . 39:41 . . . 46:50 . . . 60:67 . . . 80 |
| 106 | 21 . . . 30:40 . . . 50:49 . . . 62:99 . . . 106:123 . . . 133:156 . . . 169:189 . . . 198:197 . . . 205:203 . . . 216:224 . . . 232:232 . . . 246:300 . . . 315:336 . . . 344 |
| 108 | 9 . . . 20:33 . . . 52:68 . . . 75:91 . . . 97:123 . . . 130:175 . . . 189:186 . . . 193:195 . . . 204:216 . . . 227:229 . . . 234:246 . . . 252:249 . . . 254:302 . . . 320:386 . . . 396:402 . . . 412:409 . . . 415:429 . . . 451 |
| 110 | 8 . . . 17:70 . . . 78:111 . . . 123:142 . . . 155:176 . . . 191:189 . . . 194:191 . . . 198:206 . . . 220:235 . . . 240:250 . . . 262:285 . . . 291:331 . . . 340:346 . . . 355 |
| 112 | 25 . . . 35:115 . . . 131:207 . . . 214:230 . . . 235:272 . . . 278:291 . . . 298:313 . . . 318:336 . . . 345:362 . . . 374:377 . . . 386 |

TABLE IV

| SEQ ID NO: | Preferentially excluded fragments | Preferentially included fragments |
|---|---|---|
| 1 | [1-507]; [1524-2004] | [508-1523]; [2005-2016] |
| 3 | [1-477]; [507-849]; [851-1081] | [478-506]; [850-850] |
| 5 | [1-430] | [431-438] |
| 7 | [1-816] | [817-968] |
| 9 | [1-190]; [205-336]; [338-527] | [191-204]; [337-337]; [528-730] |
| 11 | [1-190]; [205-336]; [338-527] | [191-204]; [337-337]; [528-733] |
| 13 | [1-190]; [205-336]; [338-527] | [191-204]; [337-337]; [528-732] |
| 15 | [1-190]; [205-336]; [338-527] | [191-204]; [337-337]; [528-733] |
| 17 | [31-415]; [417-476] | [1-30]; [416-416]; [477-1175] |
| 19 | [1-239]; [241-593]; [673-732] | [240-240]; [594-672]; [733-844] |
| 21 | [1-533]; [1323-1455]; [1459-1751] | [534-1322]; [1456-1458]; [1752-1997] |
| 23 | [1-289]; [291-320] | [290-290]; [321-1746] |
| 25 | [1-528] | [529-1239] |
| 27 | [1-417]; [814-1162] | [418-813]; [1163-1179] |
| 29 | [1-172]; [178-334] | [173-177]; [335-1118] |
| 31 | [1-122]; [385-435] | [123-384]; [436-1816] |
| 33 | [1-585] | [586-643] |
| 35 | [1-436]; [444-487] | [437-443]; [488-501] |
| 37 | [1-71]; [73-466] | [72-72]; [467-845] |
| 39 | [1-500] | [501-517] |
| 41 | [1-575]; [683-1045]; [1047-1141]; [1149-1178] | [576-682]; [1046-1046]; [1142-1148]; [1179-1194] |
| 43 | [1-558] | [559-960] |
| 45 | [1-510]; [533-572] | [511-532]; [573-1294] |
| 47 | [1-519]; [523-552] | [520-522]; [553-1273] |
| 49 | [1-723] | None |
| 51 | [1-533]; [556-595] | [534-555]; [596-1317] |
| 53 | [1-64]; [67-441]; [1035-1306]; [1406-1488]; [1514-1711]; [1713-1787]; [1789-1892] | [65-66]; [442-1034]; [1307-1405]; [1489-1513]; [1712-1712]; [1788-1788]; [1893-1907] |
| 55 | [1-483] | [484-809] |
| 57 | [1-494] | [495-1133] |
| 59 | [2-523] | [1-1]; [524-838] |
| 61 | [1-427] | [428-862] |
| 63 | [1-30]; [125-299]; [301-570] | [31-124]; [300-300]; [571-618] |
| 65 | [14-105] | [1-13]; [106-836] |
| 67 | [1-293]; [304-541] | [294-303]; [542-789] |
| 69 | [1-466]; [900-974] | [467-899]; [975-2556] |
| 71 | [1-486]; [526-560]; [987-1588] | [487-525]; [561-986]; [1589-1603] |
| 73 | [1-435]; [486-517]; [599-708]; [728-803]; [812-879] | [436-485]; [518-598]; [709-727]; [804-811] |
| 75 | [1-465] | [466-1634] |
| 77 | [2-394]; [396-564]; [681-832]; [1207-1294] | [1-1]; [395-395]; [565-680]; [833-1206]; [1295-1642] |
| 79 | [1-218]; [220-591]605-663] | [219-219]; [592-604]; [664-1466] |
| 81 | [1-432] | [433-1406] |
| 83 | [1-339] | [340-1754] |
| 85 | [1-339] | [340-1754] |
| 87 | [1-433]; [1261-1355] | [434-1260]; [1356-1431] |
| 89 | [1-433]; [1261-1355] | [434-1260]; [1356-1431] |
| 91 | [1-738]; [884-1342]; [1350-1380] | [739-883]; [1343-1349]; [1381-1417] |
| 93 | [1-494]; [517-581] | [495-516]; [582-1115] |
| 95 | [1-189]; [191-496]; [519-583] | [190-190]; [497-518]; [584-1307] |
| 97 | [1-339] | [340-1855] |
| 99 | [1-405]; [426-457] | [406-425]; [458-667] |
| 101 | [1-44]; [666-753]; [783-813]; [899-965]; [981-1013] | [45-665]; [754-782]; [814-898]; [966-980]; [1014-1062] |

TABLE IV-continued

| SEQ ID NO: | Preferentially excluded fragments | Preferentially included fragments |
|---|---|---|
| 103 | [1-77]; [79-412]; [418-456]; [758-916] | [78-78]; [413-417]; [457-757]; [917-933] |
| 105 | [1-287]; [289-635] | [288-288]; [636-1187] |
| 107 | [1-501]; [680-719]; [721-816]; [822-853]; [982-1180]; [1182-1235]; [1237-1383]; [1404-1520] | [502-679]; [720-720]; [817-821]; [854-981]; [1181-1181]; [1236-1236]; [1384-1403] |
| 109 | [1-393]; [409-503] | [394-408]; [504-1789] |
| 111 | [1-777]; [779-860]; [1365-1408] | [778-778]; [861-1364] |

Throughout this application, various publications, patents and published patent applications are cited. The disclosures of these publications, patents and published patent specification referenced in this application are hereby incorporated by reference into the present disclosure to more fully describe the state of the art to which this invention pertains.

We claim:

1. An isolated, recombinant, or purified polynucleotide:

a) encoding an amyloid processing inhibitor protein (APIP) polypeptide comprising SEQ ID NO: 24;

b) comprising the open reading frame of the human cDNA sequence of deposited clone 47-14-1-C3-CL0_5 (ATCC deposit number 98921), which encodes the APIP polypeptide of SEQ ID NO: 24; or c) that is at least 95%, 96%, 97%, 98%, or 99% identical to the polynucleotide of SEQ ID NO:23 and encodes a polypeptide that reduces or inhibits amyloid processing.

2. The isolated, recombinant, or purified polynucleotide according to claim 1, wherein the polynucleotide comprises the open reading frame of the human cDNA of deposited clone 47-14-1-C3-CLO_5 (ATCC deposit number 98921), which encodes the APIP polypeptide of SEQ ID NO: 24.

3. The isolated, recombinant, or purified polynucleotide according to claim 1, wherein said polynucleotide encodes a polypeptide comprising SEQ ID NO: 24.

4. The isolated, recombinant, or purified polynucleotide according to claim 1, wherein said polynucleotide comprises SEQ ID NO: 23.

5. The isolated, recombinant, or purified polynucleotide according to claim 1, wherein said polynucleotide comprises nucleotides 10 to 1212 of SEQ ID NO: 23.

6. The isolated, recombinant, or purified polynucleotide according to claim 1, wherein said polynucleotide comprises nucleotides 61 to 1212 of SEQ ID NO:23.

7. A composition comprising a physiologically acceptable carrier and an isolated, recombinant, or purified polynucleotide:

a) encoding a protein comprising the APIP polypeptide of SEQ ID NO: 24;

b) comprising the open reading frame of the human cDNA sequence of deposited clone 47-14-1-C3-CL0_5 (ATCC deposit number 98921), which encodes the APIP polypeptide of SEQ ID NO: 24; or c) that is at least 95%, 96%, 97%, 98%, or 99% identical to the polynucleotide of SEQ ID NO:23 and encodes a polypeptide that reduces or inhibits amyloid processing.

8. The composition according to claim 7, wherein said polynucleotide comprises the open reading frame of the human cDNA of deposited clone 47-14-1-C3-CLO_5 (ATCC deposit number 98921), which encodes the APIP polypeptide of SEQ ID NO: 24.

9. The composition according to claim 7, wherein said polynucleotide encodes a polypeptide comprising SEQ ID NO: 24.

10. The composition according to claim 7, wherein said polynucleotide further comprises a portion of a vector.

11. The composition according to claim 7, wherein said polynucleotide comprises SEQ ID NO: 23.

12. The composition according to claim 7, wherein said polynucleotide comprises nucleotides 10 to 1212 of SEQ ID NO: 23.

13. The composition according to claim 7, wherein said polynucleotide comprises nucleotides 61 to 1212 of SEQ ID NO: 23.

14. A vector comprising a polynucleotide:

a) encoding a protein comprising the APIP polypeptide comprising SEQ ID NO: 24;

b) comprising the open reading frame of the human cDNA sequence of deposited clone 47-14-1-C3-CL0_5 (ATCC deposit number 98921), which encodes the APIP polypeptide of SEQ ID NO: 24; or c) that is at least 95%, 96%, 97%, 98%, or 99% identical to the polynucleotide of SEQ ID NO:23 and encodes a polypeptide that reduces or inhibits amyloid processing.

15. The vector according to claim 14, wherein the polynucleotide comprises the open reading frame of the human cDNA of deposited clone 47-14-1-C3-CLO_5 (ATCC deposit number 98921), which encodes the APIP polypeptide of SEQ ID NO: 24.

16. The vector according to claim 14, wherein said polynucleotide encodes a polypeptide comprising SEQ ID NO: 24.

17. The vector according to claim 14, wherein said polynucleotide comprises SEQ ID NO: 23.

18. The vector according to claim 14, wherein said polynucleotide comprises nucleotides 10 to 1212 of SEQ ID NO: 23.

19. The vector according to claim 14, wherein said polynucleotide comprises nucleotides 61 to 1212 of SEQ ID NO: 23.

20. A host cell comprising a polynucleotide:

a) encoding a protein comprising the APIP polypeptide comprising SEQ ID NO: 24;

b) comprising the open reading frame of the human cDNA sequence of deposited clone 47-14-1-C3-CL0_5 (ATCC deposit number 98921), which encodes the APIP polypeptide of SEQ ID NO: 24;

c) that is at least 95%, 96%, 97%, 98%, or 99% identical to the polynucleotide of SEQ ID NO:23 and encodes a polypeptide that reduces or inhibits amyloid processing; or d) a vector comprising a polynucleotide:

i) encoding a protein comprising the APIP polypeptide comprising SEQ ID NO: 24;

ii) comprising the open reading frame of the human cDNA sequence of deposited clone 47-14-1-C3-CL0_5 (ATCC deposit number 98921), which encodes the APIP polypeptide of SEQ ID NO: 24; or iii) that is at least 95%, 96%, 97%, 98%, or 99% identical to the polynucleotide of SEQ ID NO:23 and encodes a polypeptide that reduces or inhibits amyloid processing.

21. The host cell according to claim 20, wherein said host cell comprises a polynucleotide comprising the open reading frame of the human cDNA of deposited clone 47-14-1-C3-CLO_5 (ATCC deposit number 98921), which encodes the APIP polypeptide of SEQ ID NO: 24.

22. The host cell according to claim 20, wherein said host cell comprises a polynucleotide encoding a polypeptide comprising SEQ ID NO: 24.

23. The host cell according to claim 20, wherein said host cell comprises a vector comprising the open reading frame of the human cDNA of deposited clone 47-14-1-C3-CLO_5 (ATCC deposit number 98921), which encodes the APIP polypeptide of SEQ ID NO: 24.

24. The host cell according to claim 20, wherein said host cell comprises a vector comprising a polynucleotide encoding a polypeptide comprising SEQ ID NO: 24.

25. The host cell according to claim 20, wherein said host cell comprises a polynucleotide comprising SEQ ID NO: 23.

26. The host cell according to claim 20, wherein said host cell comprises a polynucleotide comprising nucleotides 10 to 1212 of SEQ ID NO: 23.

27. The host cell according to claim 20, wherein said host cell comprises a polynucleotide comprising nucleotides 61 to 1212 of SEQ ID NO: 23.

28. The host cell according to claim 20, wherein said host cell comprises a vector comprising a polynucleotide comprising SEQ ID NO: 23.

29. The host cell according to claim 20, wherein said host cell comprises a vector comprising a polynucleotide comprising nucleotides 10 to 1212 of SEQ ID NO: 23.

30. The host cell according to claim 20, wherein said host cell comprises a vector comprising a polynucleotide comprising nucleotides 61 to 1212 of SEQ ID NO: 23.

31. A method of making an APIP polypeptide comprising culturing the host cell according to claim 20 under conditions that allow for the production of said polypeptide.

32. The method according to claim 31, further comprising the step of purifying said polypeptide.

33. The method according to claim 31, wherein said host cell comprises a polynucleotide comprising the open reading frame of the human cDNA of deposited clone 47-14-1-C3-CLO_5 (ATCC deposit number 98921), which encodes the APIP polypeptide of SEQ ID NO: 24.

34. The method according to claim 31, wherein said host cell comprises a polynucleotide encoding a polypeptide comprising SEQ ID NO: 24.

35. The method according to claim 31, wherein said host cell comprises a vector comprising the open reading frame of the human cDNA of deposited clone 47-14-1-C3-CLO_5 (ATCC deposit number 98921), which encodes the APIP polypeptide of SEQ ID NO: 24.

36. The method according to claim 31, wherein said host cell comprises a vector comprising a polynucleotide encoding a polypeptide comprising SEQ ID NO: 24.

37. The method according to claim 31, wherein said host cell comprises a polynucleotide comprising SEQ ID NO: 23.

38. The method according to claim 31, wherein said host cell comprises a polynucleotide comprising nucleotides 10 to 1212 of SEQ ID NO: 23.

39. The method according to claim 31, wherein said host cell comprises a polynucleotide comprising nucleotides 61 to 1212 of SEQ ID NO: 23.

40. The method according to claim 31, wherein said host cell comprises a vector comprising a polynucleotide comprising SEQ ID NO: 23.

41. The method according to claim 31, wherein said host cell comprises a vector comprising a polynucleotide comprising nucleotides 10 to 1212 of SEQ ID NO: 23.

42. The method according to claim 31, wherein said host cell comprises a vector comprising a polynucleotide comprising nucleotides 61 to 1212 of SEQ ID NO: 23.

43. The isolated, recombinant or purified polynucleotide according to claim 1, wherein said polynucleotide is at least 95%, 96%, 97%, 98%, or 99identical to the polynucleotide of SEQ ID NO:23 and said polynucleotide encodes apolypeptide that reduces or inhibits amyloid processing.

44. The composition according to claim 7, wherein said polynucleotide is at least 95%, 96%, 97%, 98%, or 99% identical to the polynucleotide of SEQ ID NO:23 and said polynucleotide encodes a polypeptide that reduces or inhibits amyloid processing.

45. The vector according to claim 14, wherein said polynucleotide is at least 95%, 96%, 97%, 98%, or 99% identical to the polynucleotide of SEQ ID NO:23 and said polynucleotide encodes a polypeptide that reduces or inhibits amyloid processing.

46. The host cell according to claim 20, wherein said polynucleotide is at least 95%, 96%, 97%, 98%, or 99% identical to the polynucleotide of SEQ ID NO:23 and said polynucleotide encodes a polypeptide that reduces or inhibits amyloid processing.

47. The method according to claim 31, wherein said host cell comprises a polynucleotide that is at least 95%, 96%, 97%, 98%, or 99% identical to the polynucleotide of SEQ ID NO:23 and said polynucleotide encodes a polypeptide that reduces or inhibits amyloid processing.

48. The method according to claim 31, wherein said host cell comprises a vector comprising a polynucleotide that is at least 95%, 96%, 97%, 98%, or 99% identical to the polynucleotide of SEQ ID NO:23 and said polynucleotide encodes apolypeptide that reduces or inhibits amyloid processing.

* * * * *

SEQUENCE LISTING

```
<160> NUMBER OF SEQ ID NOS: 112

<210> SEQ ID NO 1
<211> LENGTH: 2016
<212> TYPE: DNA
<213> ORGANISM: Homo sapiens
<220> FEATURE:
<221> NAME/KEY: 5'UTR
<222> LOCATION: 1..1434
<220> FEATURE:
<221> NAME/KEY: CDS
<222> LOCATION: 1435..1836
<220> FEATURE:
<221> NAME/KEY: 3'UTR
<222> LOCATION: 1837..2016
<220> FEATURE:
<221> NAME/KEY: polyA_signal
<222> LOCATION: 1965..1970
<220> FEATURE:
<221> NAME/KEY: polyA_site
<222> LOCATION: 2001..2016

<400> SEQUENCE: 1

aaggtctctc tgcatgcata caccaaggaa aagccacatg aggacataac caggaagaga     60

gccatcacca agaacccgaa catgcggaca ccctgatctc ggacttctag ccttcagaac    120

cgttgccaca gttttgatga tcatctctct cccaaccaag atggtggaaa aagcaaaaac    180

gtggtgaatc ttggagcaat ccgacaaggc atgaaacgct tccaatttct gttaaactgc    240

tgtgagccag ggacaattcc tgatgcctcc atcctagcag ctgccttgga tctactatgc    300

ggcattcttc tgattcattt ttctccattt gtgctgtttt tctctgtgat gtgaatccat    360

ccctatccat tatgtcatgc ctccatcttt tgctgcttct tcagattgca ctgagccata    420

agaggaagcc cctgtggtgg ccagagcagc cttgttcctg gaatgtgctc gttttgttca    480

ccgctgcaac cgtggcaact ggccagagtg gatgaaaggg caccacgtga acatcaccaa    540

gaaaggactt tcccggggac gctctcccat tgtgggcaac aagcgaaacc agaagctgca    600

gtggaatgca gccaagctct tctaccaatg ggagacaag gaaaaaaggt gaagaataaa     660

aggaaattca agaggaccaa gtttctgcta attttagaca gagctgaaca taaacacaca    720

taaagaggtt ccatatattc ctcttttctt aaagattact tggaataact gttacaattt    780

ccgttaataa ttcagctgaa tgtgtctacc aatgtgctta ccaactaagg caattggcgt    840

ccgattgaat gagctgtgcc acggggaaag tgagagccca gccaacctgc tgggtctcat    900
```

-continued

```
ttacgatgaa gagaccaaga ggagacttag aaaggaggat gaggaggaag actttttaga    960

tgacattcca ctttcaagtc aatacacagc tcatcttgca tttaaaagct gattatggtg   1020

caagcaactt tcgggctgga aattctacag aagcttgtct tttccattct tgatgagagg   1080

caaagtcccc ggcaacaaat taactcagga gagaaaatgg ttttcctgaa aaaaacgata   1140

gcttaaatat ctacagaaag accgtaattt ccacctattt tcaaatgaaa tcgtgaaaaa   1200

cacatttgga ctagagctga aacaacttca ctgccctcaa aacagcaaga cagacatccc   1260

tcataaaatg aactgacaga atttttatag ctccaaatct agttcactgc catatacata   1320

gtctaaatct gattgaatag cagcgtagaa atcttgcgaa attacttccc atttctgttt   1380

tcgttaaaag gtactgtgaa cccctctaaa tgcggttgcc cctttgcctt gaag atg     1437
                                                            Met
                                                            1

gca gca tgt cag ctt ctt ctg gag att acc acc ttc ctg cga gag acc     1485
Ala Ala Cys Gln Leu Leu Leu Glu Ile Thr Thr Phe Leu Arg Glu Thr
            5                   10                  15

ttt tct tgc ctg ccc aga cct cgc act gag cct ctg gtg gct tca acg     1533
Phe Ser Cys Leu Pro Arg Pro Arg Thr Glu Pro Leu Val Ala Ser Thr
        20                  25                  30

gac cac acc aaa atg cca tct caa atg gaa cac gcc atg gaa acc atg     1581
Asp His Thr Lys Met Pro Ser Gln Met Glu His Ala Met Glu Thr Met
    35                  40                  45

atg ttt aca ttt cac aaa ttc gct ggg gat aaa ggc tac tta aca aag     1629
Met Phe Thr Phe His Lys Phe Ala Gly Asp Lys Gly Tyr Leu Thr Lys
50                  55                  60                  65

gag gac ctg aga gta ctc atg gaa aag gag ttc cct gga ttt ttg gaa     1677
Glu Asp Leu Arg Val Leu Met Glu Lys Glu Phe Pro Gly Phe Leu Glu
                70                  75                  80

aat caa aaa gac cct ctg gct gtg gac aaa ata atg aag gac ctg gac     1725
Asn Gln Lys Asp Pro Leu Ala Val Asp Lys Ile Met Lys Asp Leu Asp
            85                  90                  95

cag tgt aga gat ggc aaa gtg ggc ttc cag agc ttc ttt tcc cta att     1773
Gln Cys Arg Asp Gly Lys Val Gly Phe Gln Ser Phe Phe Ser Leu Ile
        100                 105                 110

gcg ggc ctc acc att gca tgc aat gac tat ttt gta gta cac atg aag     1821
Ala Gly Leu Thr Ile Ala Cys Asn Asp Tyr Phe Val Val His Met Lys
    115                 120                 125

cag aag gga aag aag taggcagaaa tgagcagttc gctcctccct gataagagtt     1876
Gln Lys Gly Lys Lys
130

gtcccaaagg gtcgcttaag gaatctgccc cacagcttcc cccatagaag gatttcatga   1936

gcagatcagg acacttagca aatgtaaaaa taaaatctaa ctctcatttg acaagcagag   1996

aaagaaaaaa aaaaaaaaat                                               2016
```

<210> SEQ ID NO 2
<211> LENGTH: 134
<212> TYPE: PRT
<213> ORGANISM: Homo sapiens

<400> SEQUENCE: 2

```
Met Ala Ala Cys Gln Leu Leu Leu Glu Ile Thr Thr Phe Leu Arg Glu
1               5                   10                  15

Thr Phe Ser Cys Leu Pro Arg Pro Arg Thr Glu Pro Leu Val Ala Ser
            20                  25                  30

Thr Asp His Thr Lys Met Pro Ser Gln Met Glu His Ala Met Glu Thr
        35                  40                  45
```

```
Met Met Phe Thr Phe His Lys Phe Ala Gly Asp Lys Gly Tyr Leu Thr
    50                  55                  60

Lys Glu Asp Leu Arg Val Leu Met Glu Lys Glu Phe Pro Gly Phe Leu
65                  70                  75                  80

Glu Asn Gln Lys Asp Pro Leu Ala Val Asp Lys Ile Met Lys Asp Leu
                85                  90                  95

Asp Gln Cys Arg Asp Gly Lys Val Gly Phe Gln Ser Phe Phe Ser Leu
            100                 105                 110

Ile Ala Gly Leu Thr Ile Ala Cys Asn Asp Tyr Phe Val Val His Met
        115                 120                 125

Lys Gln Lys Gly Lys Lys
    130


<210> SEQ ID NO 3
<211> LENGTH: 1081
<212> TYPE: DNA
<213> ORGANISM: Homo sapiens
<220> FEATURE:
<221> NAME/KEY: 5'UTR
<222> LOCATION: 1..38
<220> FEATURE:
<221> NAME/KEY: CDS
<222> LOCATION: 39..917
<220> FEATURE:
<221> NAME/KEY: 3'UTR
<222> LOCATION: 918..1081
<220> FEATURE:
<221> NAME/KEY: polyA_signal
<222> LOCATION: 1045..1050
<220> FEATURE:
<221> NAME/KEY: polyA_site
<222> LOCATION: 1066..1081

<400> SEQUENCE: 3

gtccagcctg ttgctgatgc tgccgtgcgg tacttgtc atg gag ctg gca ctg cgg      56
                                          Met Glu Leu Ala Leu Arg
                                          -25                 -20

cgc tct ccc gtc ccg cgg tgg ttg ctg ctg ctg ccg ctg ctg ctg ggc       104
Arg Ser Pro Val Pro Arg Trp Leu Leu Leu Leu Pro Leu Leu Leu Gly
                -15                 -10                 -5

ctg aac gca gga gct gtc att gac tgg ccc aca gag gag ggc aag gaa       152
Leu Asn Ala Gly Ala Val Ile Asp Trp Pro Thr Glu Glu Gly Lys Glu
            1               5                   10

gta tgg gat tat gtg acg gtc cgc aag gat gcc tac atg ttc tgg tgg       200
Val Trp Asp Tyr Val Thr Val Arg Lys Asp Ala Tyr Met Phe Trp Trp
    15                  20                  25

ctc tat tat gcc acc aac tcc tgc aag aac ttc tca gaa ctg ccc ctg       248
Leu Tyr Tyr Ala Thr Asn Ser Cys Lys Asn Phe Ser Glu Leu Pro Leu
30                  35                  40                  45

gtc atg tgg ctt cag ggc ggt cca ggc ggt tct agc act gga ttt gga       296
Val Met Trp Leu Gln Gly Gly Pro Gly Gly Ser Ser Thr Gly Phe Gly
                50                  55                  60

aac ttt gag gaa att ggg ccc ctt gac agt gat ctc aaa cca cgg aaa       344
Asn Phe Glu Glu Ile Gly Pro Leu Asp Ser Asp Leu Lys Pro Arg Lys
            65                  70                  75

acc acc tgg ctc cag gct gcc agt ctc cta ttt gtg gat aat ccc gtg       392
Thr Thr Trp Leu Gln Ala Ala Ser Leu Leu Phe Val Asp Asn Pro Val
        80                  85                  90

ggc act ggg ttc agt tat gtg aat ggt agt ggt gcc tat gcc aag gac       440
Gly Thr Gly Phe Ser Tyr Val Asn Gly Ser Gly Ala Tyr Ala Lys Asp
    95                  100                 105

ctg gct atg gtg gct tca gac atg atg gtt ctc ctg aag acc ttc ttc       488
Leu Ala Met Val Ala Ser Asp Met Met Val Leu Leu Lys Thr Phe Phe
```

-continued

```
110                 115                 120                 125

agt tgc cac aaa gaa ttc cag aca gtt cca ttc tac att ttc tca gag      536
Ser Cys His Lys Glu Phe Gln Thr Val Pro Phe Tyr Ile Phe Ser Glu
                130                 135                 140

tcc tat gga gga aaa atg gca gct ggc att ggt cta gag ctt tat aag      584
Ser Tyr Gly Gly Lys Met Ala Ala Gly Ile Gly Leu Glu Leu Tyr Lys
            145                 150                 155

gcc att cag cga ggg acc atc aag tgc aac ttt gcg ggg gtt gcc ttg      632
Ala Ile Gln Arg Gly Thr Ile Lys Cys Asn Phe Ala Gly Val Ala Leu
        160                 165                 170

ggt gat tcc tgg atc tcc cct gtt gat tcg gtg ctc tcc tgg gga cct      680
Gly Asp Ser Trp Ile Ser Pro Val Asp Ser Val Leu Ser Trp Gly Pro
    175                 180                 185

tac ctg tac agc atg tct ctt ctc gaa gac aaa ggt ctg gca gag gtg      728
Tyr Leu Tyr Ser Met Ser Leu Leu Glu Asp Lys Gly Leu Ala Glu Val
190                 195                 200                 205

tct aag gtt gca gag caa gta ctg aat gcc gta aat aag ggg ctc tac      776
Ser Lys Val Ala Glu Gln Val Leu Asn Ala Val Asn Lys Gly Leu Tyr
                210                 215                 220

aga gag gcc aca gag ctg tgg ggg aaa gca gaa atg atc att gaa cag      824
Arg Glu Ala Thr Glu Leu Trp Gly Lys Ala Glu Met Ile Ile Glu Gln
            225                 230                 235

gta aaa agg gga aac act cag agg cta gcc tgc ttg gct ttt tct ggt      872
Val Lys Arg Gly Asn Thr Gln Arg Leu Ala Cys Leu Ala Phe Ser Gly
        240                 245                 250

ggg tac agg gcc cat ggt tgg tgt tgt caa act tgg agt cta cac          917
Gly Tyr Arg Ala His Gly Trp Cys Cys Gln Thr Trp Ser Leu His
    255                 260                 265

tgaggctccc cacatatctg caaatgattg catgctggat aataaatctc ttgggtctaa    977

gcagtgatgt agtggctcct tacagagtca gaaagccacc caggcctgca agacttgctt   1037

gtccttcact aaatgtatgg attctattaa aaaaaaaaaa aaaa                    1081


<210> SEQ ID NO 4
<211> LENGTH: 293
<212> TYPE: PRT
<213> ORGANISM: Homo sapiens
<220> FEATURE:
<221> NAME/KEY: SIGNAL
<222> LOCATION: 1..26

<400> SEQUENCE: 4

Met Glu Leu Ala Leu Arg Arg Ser Pro Val Pro Arg Trp Leu Leu Leu
    -25                 -20                 -15

Leu Pro Leu Leu Leu Gly Leu Asn Ala Gly Ala Val Ile Asp Trp Pro
-10                 -5                  1                   5

Thr Glu Glu Gly Lys Glu Val Trp Asp Tyr Val Thr Val Arg Lys Asp
            10                  15                  20

Ala Tyr Met Phe Trp Trp Leu Tyr Tyr Ala Thr Asn Ser Cys Lys Asn
        25                  30                  35

Phe Ser Glu Leu Pro Leu Val Met Trp Leu Gln Gly Gly Pro Gly Gly
    40                  45                  50

Ser Ser Thr Gly Phe Gly Asn Phe Glu Glu Ile Gly Pro Leu Asp Ser
55                  60                  65                  70

Asp Leu Lys Pro Arg Lys Thr Thr Trp Leu Gln Ala Ala Ser Leu Leu
                75                  80                  85

Phe Val Asp Asn Pro Val Gly Thr Gly Phe Ser Tyr Val Asn Gly Ser
            90                  95                  100
```

-continued

```
Gly Ala Tyr Ala Lys Asp Leu Ala Met Val Ala Ser Asp Met Met Val
        105                 110                 115

Leu Leu Lys Thr Phe Phe Ser Cys His Lys Glu Phe Gln Thr Val Pro
    120                 125                 130

Phe Tyr Ile Phe Ser Glu Ser Tyr Gly Gly Lys Met Ala Ala Gly Ile
135                 140                 145                 150

Gly Leu Glu Leu Tyr Lys Ala Ile Gln Arg Gly Thr Ile Lys Cys Asn
                155                 160                 165

Phe Ala Gly Val Ala Leu Gly Asp Ser Trp Ile Ser Pro Val Asp Ser
            170                 175                 180

Val Leu Ser Trp Gly Pro Tyr Leu Tyr Ser Met Ser Leu Leu Glu Asp
        185                 190                 195

Lys Gly Leu Ala Glu Val Ser Lys Val Ala Glu Gln Val Leu Asn Ala
    200                 205                 210

Val Asn Lys Gly Leu Tyr Arg Glu Ala Thr Glu Leu Trp Gly Lys Ala
215                 220                 225                 230

Glu Met Ile Ile Glu Gln Val Lys Arg Gly Asn Thr Gln Arg Leu Ala
                235                 240                 245

Cys Leu Ala Phe Ser Gly Gly Tyr Arg Ala His Gly Trp Cys Cys Gln
            250                 255                 260

Thr Trp Ser Leu His
        265


<210> SEQ ID NO 5
<211> LENGTH: 438
<212> TYPE: DNA
<213> ORGANISM: Homo sapiens
<220> FEATURE:
<221> NAME/KEY: 5'UTR
<222> LOCATION: 1..83
<220> FEATURE:
<221> NAME/KEY: CDS
<222> LOCATION: 84..317
<220> FEATURE:
<221> NAME/KEY: 3'UTR
<222> LOCATION: 318..438
<220> FEATURE:
<221> NAME/KEY: polyA_signal
<222> LOCATION: 397..402
<220> FEATURE:
<221> NAME/KEY: polyA_site
<222> LOCATION: 423..438

<400> SEQUENCE: 5

atagaaaagg acatctcttg agacttcact tcagcttcac tgacttcttg actctcctct      60

tgagtaaaag gactcagcca act atg aag ttt ttt gtc ttt gct tta gtc ttg     113
                          Met Lys Phe Phe Val Phe Ala Leu Val Leu
                                      -15                 -10

gct ctc atg att tcc atg att agc gct gat tca cat gaa aag aga cat       161
Ala Leu Met Ile Ser Met Ile Ser Ala Asp Ser His Glu Lys Arg His
            -5                  1               5

cat ggg tat aga aga aaa ttc cat gaa aag cat cat tca tac cat atc       209
His Gly Tyr Arg Arg Lys Phe His Glu Lys His His Ser Tyr His Ile
    10                  15                  20

aca cta cta cca ctt ttt gaa gaa tca tca aag agc aat gca aat gaa       257
Thr Leu Leu Pro Leu Phe Glu Glu Ser Ser Lys Ser Asn Ala Asn Glu
25                  30                  35                  40

aaa cac tat aat tta ctg tat act ctt tgt ttc agg ata ctt gcc ttt       305
Lys His Tyr Asn Leu Leu Tyr Thr Leu Cys Phe Arg Ile Leu Ala Phe
                45                  50                  55
tca att gtc act tgatgatata attgcaattt aaactgttaa gctgtgttca           357
Ser Ile Val Thr
```

```
        60

gtactgtttc tgaataatag aaatcacttc tctaaaagca ataaatttca agcacatttt    417

taaataaaaa aaaaaaaaaa a                                              438


<210> SEQ ID NO 6
<211> LENGTH: 78
<212> TYPE: PRT
<213> ORGANISM: Homo sapiens
<220> FEATURE:
<221> NAME/KEY: SIGNAL
<222> LOCATION: 1..19

<400> SEQUENCE: 6

Met Lys Phe Phe Val Phe Ala Leu Val Leu Ala Leu Met Ile Ser Met
                -15                 -10                 -5

Ile Ser Ala Asp Ser His Glu Lys Arg His His Gly Tyr Arg Arg Lys
            1               5                   10

Phe His Glu Lys His His Ser Tyr His Ile Thr Leu Leu Pro Leu Phe
    15                  20                  25

Glu Glu Ser Ser Lys Ser Asn Ala Asn Glu Lys His Tyr Asn Leu Leu
30                  35                  40                  45

Tyr Thr Leu Cys Phe Arg Ile Leu Ala Phe Ser Ile Val Thr
                50                  55


<210> SEQ ID NO 7
<211> LENGTH: 968
<212> TYPE: DNA
<213> ORGANISM: Homo sapiens
<220> FEATURE:
<221> NAME/KEY: 5'UTR
<222> LOCATION: 1..31
<220> FEATURE:
<221> NAME/KEY: CDS
<222> LOCATION: 32..748
<220> FEATURE:
<221> NAME/KEY: 3'UTR
<222> LOCATION: 749..968
<220> FEATURE:
<221> NAME/KEY: polyA_signal
<222> LOCATION: 928..933
<220> FEATURE:
<221> NAME/KEY: polyA_site
<222> LOCATION: 953..968

<400> SEQUENCE: 7

tgatcaggac tcctcagttc accttctcac a atg agg ctc cct gct cag ctc        52
                                   Met Arg Leu Pro Ala Gln Leu
                                                   -15

ctg ggg ctg cta atg ctc tgg gtc tct gga tcc agt ggg gat att gtg      100
Leu Gly Leu Leu Met Leu Trp Val Ser Gly Ser Ser Gly Asp Ile Val
        -10                 -5                  1

atg act cag tct cca ctc ttc ctg ccc gtc acc cct gga gag ccg gcc      148
Met Thr Gln Ser Pro Leu Phe Leu Pro Val Thr Pro Gly Glu Pro Ala
5                   10                  15                  20

tcc atc tcc tgc agg tct agt cag agc ctc ctg cat gtt caa ggg tcc      196
Ser Ile Ser Cys Arg Ser Ser Gln Ser Leu Leu His Val Gln Gly Ser
                25                  30                  35

aac tat ttg gat tgg tac cac cag aag cca ggg cag tct cca caa ctc      244
Asn Tyr Leu Asp Trp Tyr His Gln Lys Pro Gly Gln Ser Pro Gln Leu
            40                  45                  50

ctg ata tac ttg ggt tct aat cgg gcc tcc ggg gtc cct gac agg ttc      292
Leu Ile Tyr Leu Gly Ser Asn Arg Ala Ser Gly Val Pro Asp Arg Phe
        55                  60                  65
```

-continued

```
agt ggc agt gga tca ggc aca gat ttc aca ctg aaa atc agt aga gtg      340
Ser Gly Ser Gly Ser Gly Thr Asp Phe Thr Leu Lys Ile Ser Arg Val
    70                  75                  80

gag gct gag gat gtt ggg gtt tat tac tgc atg caa gct cta caa act      388
Glu Ala Glu Asp Val Gly Val Tyr Tyr Cys Met Gln Ala Leu Gln Thr
85                  90                  95                  100

cca ttc act ttc ggc cct ggg acc aga gtg gat atc aag cga act gtg      436
Pro Phe Thr Phe Gly Pro Gly Thr Arg Val Asp Ile Lys Arg Thr Val
                105                 110                 115

gct gca cca tct gtc ttc atc ttc ccg cca tct gat gag cag ttg aaa      484
Ala Ala Pro Ser Val Phe Ile Phe Pro Pro Ser Asp Glu Gln Leu Lys
            120                 125                 130

tct gga act gcc tct gtt gtg tgc ctg ctg aat aac ttc tat ccc aga      532
Ser Gly Thr Ala Ser Val Val Cys Leu Leu Asn Asn Phe Tyr Pro Arg
        135                 140                 145

gag gcc aaa gta cag tgg aag gtg gat aac gcc ctc caa tcg ggt aac      580
Glu Ala Lys Val Gln Trp Lys Val Asp Asn Ala Leu Gln Ser Gly Asn
    150                 155                 160

tcc cag gag agt gtc aca gag cag gac agc aag gac agc acc tac agc      628
Ser Gln Glu Ser Val Thr Glu Gln Asp Ser Lys Asp Ser Thr Tyr Ser
165                 170                 175                 180

ctc agc agc acc ctg acg ctg agc aaa gca gac tac gag aaa cac aaa      676
Leu Ser Ser Thr Leu Thr Leu Ser Lys Ala Asp Tyr Glu Lys His Lys
                185                 190                 195

gtc tac gcc tgc gaa gtc acc cat cag ggc ctg agc tcg ccc gtc aca      724
Val Tyr Ala Cys Glu Val Thr His Gln Gly Leu Ser Ser Pro Val Thr
            200                 205                 210

aag agc ttc aac agg gga gag tgt tagagggaga agtgccccca cctgctcctc      778
Lys Ser Phe Asn Arg Gly Glu Cys
        215                 220

agttccagcc tgacccctc ccatcctttg gcctctgacc ctttttccac aggggaccta      838

cccctattgc ggtcctccag ctcatctttc acctcacccc cctcctcctc cttggcttta      898

attatgctaa tgttggagga gaatgaataa ataaagtgaa tctttgcacc tgttaaaaaa      958

aaaaaaaaaa                                                              968


<210> SEQ ID NO 8
<211> LENGTH: 239
<212> TYPE: PRT
<213> ORGANISM: Homo sapiens
<220> FEATURE:
<221> NAME/KEY: SIGNAL
<222> LOCATION: 1..20

<400> SEQUENCE: 8

Met Arg Leu Pro Ala Gln Leu Leu Gly Leu Leu Met Leu Trp Val Ser
-20                 -15                 -10                 -5

Gly Ser Ser Gly Asp Ile Val Met Thr Gln Ser Pro Leu Phe Leu Pro
                1               5                   10

Val Thr Pro Gly Glu Pro Ala Ser Ile Ser Cys Arg Ser Ser Gln Ser
        15                  20                  25

Leu Leu His Val Gln Gly Ser Asn Tyr Leu Asp Trp Tyr His Gln Lys
    30                  35                  40

Pro Gly Gln Ser Pro Gln Leu Leu Ile Tyr Leu Gly Ser Asn Arg Ala
45                  50                  55                  60

Ser Gly Val Pro Asp Arg Phe Ser Gly Ser Gly Ser Gly Thr Asp Phe
                65                  70                  75

Thr Leu Lys Ile Ser Arg Val Glu Ala Glu Asp Val Gly Val Tyr Tyr
            80                  85                  90
```

-continued

```
Cys Met Gln Ala Leu Gln Thr Pro Phe Thr Phe Gly Pro Gly Thr Arg
        95                  100                 105

Val Asp Ile Lys Arg Thr Val Ala Ala Pro Ser Val Phe Ile Phe Pro
    110                 115                 120

Pro Ser Asp Glu Gln Leu Lys Ser Gly Thr Ala Ser Val Val Cys Leu
125                 130                 135                 140

Leu Asn Asn Phe Tyr Pro Arg Glu Ala Lys Val Gln Trp Lys Val Asp
                145                 150                 155

Asn Ala Leu Gln Ser Gly Asn Ser Gln Glu Ser Val Thr Glu Gln Asp
            160                 165                 170

Ser Lys Asp Ser Thr Tyr Ser Leu Ser Ser Thr Leu Thr Leu Ser Lys
        175                 180                 185

Ala Asp Tyr Glu Lys His Lys Val Tyr Ala Cys Glu Val Thr His Gln
    190                 195                 200

Gly Leu Ser Ser Pro Val Thr Lys Ser Phe Asn Arg Gly Glu Cys
205                 210                 215


<210> SEQ ID NO 9
<211> LENGTH: 730
<212> TYPE: DNA
<213> ORGANISM: Homo sapiens
<220> FEATURE:
<221> NAME/KEY: 5'UTR
<222> LOCATION: 1..253
<220> FEATURE:
<221> NAME/KEY: CDS
<222> LOCATION: 254..574
<220> FEATURE:
<221> NAME/KEY: 3'UTR
<222> LOCATION: 575..730

<400> SEQUENCE: 9

agatgagtgt tcagctctca gcagagaggt tagctcctct ctgcagcttg tcctgttgtc      60

tcctcaagtc tggctgagtc cggagttttt atgagcctca gaggggagga agtgcatgct     120

gattaatcca tgggcaggcc tggaaaagtt cccactccag tctgcgggac ccacagcctg     180

gccctcaggc ctcaggcctt cccaggcttg aagattgggc ttcacctggg acctacccct     240

tctgcctagg agc atg tct gcc tcc tgc tgc ctt tca tgg tgc cca gcc        289
               Met Ser Ala Ser Cys Cys Leu Ser Trp Cys Pro Ala
                           -10                 -5

aag gct aag tcg aaa tgt ggc cca acc ttc ttc ccc tgt gcc agc ggc       337
Lys Ala Lys Ser Lys Cys Gly Pro Thr Phe Phe Pro Cys Ala Ser Gly
    1               5                   10                  15

atc cat tgc atc att ggt cgc ttc cgg tgc aat ggg ttt gag gac tgt       385
Ile His Cys Ile Ile Gly Arg Phe Arg Cys Asn Gly Phe Glu Asp Cys
                20                  25                  30

ccc gat ggc agc gat gaa gag aac tgc aca gca aac cct ctg ctt tgc       433
Pro Asp Gly Ser Asp Glu Glu Asn Cys Thr Ala Asn Pro Leu Leu Cys
            35                  40                  45

tcc acc gcc cgc tac cac tgc aag aac ggc ctc tgt att gac aag agc       481
Ser Thr Ala Arg Tyr His Cys Lys Asn Gly Leu Cys Ile Asp Lys Ser
        50                  55                  60

ttc atc tgc gat gga cag aat aac tgt caa gac aac agt gat gag gaa       529
Phe Ile Cys Asp Gly Gln Asn Asn Cys Gln Asp Asn Ser Asp Glu Glu
    65                  70                  75

agc tgt gaa agt tct caa gct att ttt cca caa att act gtg tcc           574
Ser Cys Glu Ser Ser Gln Ala Ile Phe Pro Gln Ile Thr Val Ser
80                  85                  90

tgagccctga gctaattaag tgctggataa gcatcacctc ccagtaatcc tgttatcagc     634
```

```
ctttgaaatg taggtagctt tattatccac attttgcaga tgaggaaaca gagtcaggtg    694

aagtgtcttt tccaaggcca agctcctgag ggcagg                              730


<210> SEQ ID NO 10
<211> LENGTH: 107
<212> TYPE: PRT
<213> ORGANISM: Homo sapiens
<220> FEATURE:
<221> NAME/KEY: SIGNAL
<222> LOCATION: 1..14

<400> SEQUENCE: 10

Met Ser Ala Ser Cys Cys Leu Ser Trp Cys Pro Ala Lys Ala Lys Ser
                -10                 -5                  1

Lys Cys Gly Pro Thr Phe Phe Pro Cys Ala Ser Gly Ile His Cys Ile
        5                   10                  15

Ile Gly Arg Phe Arg Cys Asn Gly Phe Glu Asp Cys Pro Asp Gly Ser
    20                  25                  30

Asp Glu Glu Asn Cys Thr Ala Asn Pro Leu Leu Cys Ser Thr Ala Arg
35                  40                  45                  50

Tyr His Cys Lys Asn Gly Leu Cys Ile Asp Lys Ser Phe Ile Cys Asp
                55                  60                  65

Gly Gln Asn Asn Cys Gln Asp Asn Ser Asp Glu Glu Ser Cys Glu Ser
            70                  75                  80

Ser Gln Ala Ile Phe Pro Gln Ile Thr Val Ser
        85                  90


<210> SEQ ID NO 11
<211> LENGTH: 733
<212> TYPE: DNA
<213> ORGANISM: Homo sapiens
<220> FEATURE:
<221> NAME/KEY: 5'UTR
<222> LOCATION: 1..253
<220> FEATURE:
<221> NAME/KEY: CDS
<222> LOCATION: 254..574
<220> FEATURE:
<221> NAME/KEY: 3'UTR
<222> LOCATION: 575..733

<400> SEQUENCE: 11

agatgagtgt tcagctctca gcagagaggt tagctcctct ctgcagcttg tcctgttgtc     60

tcctcaagtc tggctgagtc cggagttttt atgagcctca gaggggagga agtgcatgct    120

gattaatcca tgggcaggcc tggaaaagtt cccactccag tctgcgggac ccacagcctg    180

gccctcaggc ctcaggcctt ccctggcttg aagattgggc ttcacctggg acctacccct    240

tctgcctagg agc atg tct gcc tcc tgc tgc ctt tca tgg tgc cca gcc       289
               Met Ser Ala Ser Cys Cys Leu Ser Trp Cys Pro Ala
                           -10                 -5

aag gct aag tcg aaa tgt ggc cca acc ttc ttc ccc tgt gcc agc ggc      337
Lys Ala Lys Ser Lys Cys Gly Pro Thr Phe Phe Pro Cys Ala Ser Gly
    1               5                   10                  15

atc cat tgc atc att ggt cgc ttc cgg tgc aat ggg ttt gag gac tgt      385
Ile His Cys Ile Ile Gly Arg Phe Arg Cys Asn Gly Phe Glu Asp Cys
                20                  25                  30

ccc gat ggc agc gat gaa gag aac tgc aca gca aac cct ctg ctt tgc      433
Pro Asp Gly Ser Asp Glu Glu Asn Cys Thr Ala Asn Pro Leu Leu Cys
            35                  40                  45

tcc acc gcc cgc tac cac tgc aag aac ggc ctc tgt att gac aag agc      481
```

-continued

```
Ser Thr Ala Arg Tyr His Cys Lys Asn Gly Leu Cys Ile Asp Lys Ser
        50                  55                  60

ttc atc tgc gat gga cag aat aac tgt caa gac aac agt gat gag gaa      529
Phe Ile Cys Asp Gly Gln Asn Asn Cys Gln Asp Asn Ser Asp Glu Glu
    65                  70                  75

agc tgt gaa agt tct caa gct att ttt cca caa att act gtg tcc          574
Ser Cys Glu Ser Ser Gln Ala Ile Phe Pro Gln Ile Thr Val Ser
80                  85                  90

tgagccctga gctaattaag tgctggataa gcatcacctc ccagtaatcc tgttatcagc    634

ctttgaaatg taggtagctt tattatccac attttgcaga tgaggaaaca gagtcaggtg    694

aagtgtcttt tccaaggcca agctcctgag ggcaggggc                           733


<210> SEQ ID NO 12
<211> LENGTH: 107
<212> TYPE: PRT
<213> ORGANISM: Homo sapiens
<220> FEATURE:
<221> NAME/KEY: SIGNAL
<222> LOCATION: 1..14

<400> SEQUENCE: 12

Met Ser Ala Ser Cys Cys Leu Ser Trp Cys Pro Ala Lys Ala Lys Ser
                -10                 -5                  1

Lys Cys Gly Pro Thr Phe Phe Pro Cys Ala Ser Gly Ile His Cys Ile
        5                   10                  15

Ile Gly Arg Phe Arg Cys Asn Gly Phe Glu Asp Cys Pro Asp Gly Ser
    20                  25                  30

Asp Glu Glu Asn Cys Thr Ala Asn Pro Leu Leu Cys Ser Thr Ala Arg
35                  40                  45                  50

Tyr His Cys Lys Asn Gly Leu Cys Ile Asp Lys Ser Phe Ile Cys Asp
                55                  60                  65

Gly Gln Asn Asn Cys Gln Asp Asn Ser Asp Glu Glu Ser Cys Glu Ser
            70                  75                  80

Ser Gln Ala Ile Phe Pro Gln Ile Thr Val Ser
        85                  90


<210> SEQ ID NO 13
<211> LENGTH: 732
<212> TYPE: DNA
<213> ORGANISM: Homo sapiens
<220> FEATURE:
<221> NAME/KEY: 5'UTR
<222> LOCATION: 1..253
<220> FEATURE:
<221> NAME/KEY: CDS
<222> LOCATION: 254..574
<220> FEATURE:
<221> NAME/KEY: 3'UTR
<222> LOCATION: 575..732

<400> SEQUENCE: 13

agatgagtgt tcagctctca gcagagaggt tagctcctct ctgcagcttg tcctgttgtc     60

tcctcaagtc tggctgagtc cggagttttt atgagcctca gaggggagga agtgcatgct    120

gattaatcca tgggcaggcc tggaaaagtt cccactccag tctgcgggac ccacagcctg    180

gccctcaggc ctcaggcctt ccctggcttg aagattgggc ttcacctggg acctacccct    240

tctgcctagg agc atg tct gcc tcc tgc tgc ctt tca tgg tgc cca gcc       289
               Met Ser Ala Ser Cys Cys Leu Ser Trp Cys Pro Ala
                           -10                 -5

aag gct aag tcg aaa tgt ggc cca acc ttc ttc ccc tgt gcc agc ggc      337
```

-continued

```
Lys Ala Lys Ser Lys Cys Gly Pro Thr Phe Phe Pro Cys Ala Ser Gly
    1               5                   10                  15

atc cat tgc atc att ggt cgc ttc cgg tgc aat ggg ttt gag gac tgt      385
Ile His Cys Ile Ile Gly Arg Phe Arg Cys Asn Gly Phe Glu Asp Cys
                20                  25                  30

ccc gat ggc agc gat gaa gag aac tgc aca gca aac cct ctg ctt tgc      433
Pro Asp Gly Ser Asp Glu Glu Asn Cys Thr Ala Asn Pro Leu Leu Cys
            35                  40                  45

tcc acc gcc cgc tac cac tgc aag aac ggc ctc tgt att gac aag agc      481
Ser Thr Ala Arg Tyr His Cys Lys Asn Gly Leu Cys Ile Asp Lys Ser
        50                  55                  60

ttc atc tgc gat gga cag aat aac tgt caa gac aac agt gat gag gaa      529
Phe Ile Cys Asp Gly Gln Asn Asn Cys Gln Asp Asn Ser Asp Glu Glu
    65                  70                  75

agc tgt gaa agt tct caa gct att ttt cca caa att act gtg tcc          574
Ser Cys Glu Ser Ser Gln Ala Ile Phe Pro Gln Ile Thr Val Ser
80                  85                  90

tgagccctga gctaattaag tgctggataa gcatcacctc ccagtaatcc tgttatcagc    634

ctttgaaatg taggtagctt attatccaca ttttgcagat gaggaaacag agtcaggtga    694

agtgtctttt ccaaggccaa gctcctgagg gcaggggc                            732


<210> SEQ ID NO 14
<211> LENGTH: 107
<212> TYPE: PRT
<213> ORGANISM: Homo sapiens
<220> FEATURE:
<221> NAME/KEY: SIGNAL
<222> LOCATION: 1..14

<400> SEQUENCE: 14

Met Ser Ala Ser Cys Cys Leu Ser Trp Cys Pro Ala Lys Ala Lys Ser
                -10                 -5                  1

Lys Cys Gly Pro Thr Phe Phe Pro Cys Ala Ser Gly Ile His Cys Ile
        5                   10                  15

Ile Gly Arg Phe Arg Cys Asn Gly Phe Glu Asp Cys Pro Asp Gly Ser
    20                  25                  30

Asp Glu Glu Asn Cys Thr Ala Asn Pro Leu Leu Cys Ser Thr Ala Arg
35                  40                  45                  50

Tyr His Cys Lys Asn Gly Leu Cys Ile Asp Lys Ser Phe Ile Cys Asp
                55                  60                  65

Gly Gln Asn Asn Cys Gln Asp Asn Ser Asp Glu Glu Ser Cys Glu Ser
            70                  75                  80

Ser Gln Ala Ile Phe Pro Gln Ile Thr Val Ser
        85                  90


<210> SEQ ID NO 15
<211> LENGTH: 733
<212> TYPE: DNA
<213> ORGANISM: Homo sapiens
<220> FEATURE:
<221> NAME/KEY: 5'UTR
<222> LOCATION: 1..253
<220> FEATURE:
<221> NAME/KEY: CDS
<222> LOCATION: 254..574
<220> FEATURE:
<221> NAME/KEY: 3'UTR
<222> LOCATION: 575..733

<400> SEQUENCE: 15

agatgagtgt tcagctctca gcagagaggt tagctcctct ctgcagcttg tcctgttgtc     60
```

```
tcctcaagtc tggctgagtc cggagttttt atgagcctca gaggggagga agtgcatgct    120

gattaatcca tgggcaggcc tggaaaagtt cccactccag tctgcgggac ccacagcctg    180

gccctcaggc ytcaggcctt cccaggcttg aagattgggc ttcacctggg acctacccct    240

tctgcctagg agc atg tct gcc tcc tgc tgc ctt tca tgg tgc cca gcc       289
               Met Ser Ala Ser Cys Cys Leu Ser Trp Cys Pro Ala
                           -10                 -5

aag gct aag tcg aaa tgt ggc cca acc ttc ttc ccc tgt gcc agc ggc      337
Lys Ala Lys Ser Lys Cys Gly Pro Thr Phe Phe Pro Cys Ala Ser Gly
    1               5                   10                  15

atc cat tgc atc att ggt cgc ttc cgg tgc aat ggg ttt gag gac tgt      385
Ile His Cys Ile Ile Gly Arg Phe Arg Cys Asn Gly Phe Glu Asp Cys
                20                  25                  30

ccc gat ggc agc gat gaa gag aac tgc aca gca aac cct ctg ctt tgc      433
Pro Asp Gly Ser Asp Glu Glu Asn Cys Thr Ala Asn Pro Leu Leu Cys
            35                  40                  45

tcc acc gcc cgc tac cac tgc aag aac ggc ctc tgt att gac aag agc      481
Ser Thr Ala Arg Tyr His Cys Lys Asn Gly Leu Cys Ile Asp Lys Ser
        50                  55                  60

ttc atc tgc gat gga cag aat aac tgt caa gac aac agt gat gag gaa      529
Phe Ile Cys Asp Gly Gln Asn Asn Cys Gln Asp Asn Ser Asp Glu Glu
    65                  70                  75

agc tgt gaa agt tct caa gct att ttt cca caa att act gtg tcc          574
Ser Cys Glu Ser Ser Gln Ala Ile Phe Pro Gln Ile Thr Val Ser
80                  85                  90

tgagccctga gctaattaag tgctggataa gcatcacctc ccagtaatcc tgttatcagc    634

ctttgaaatg taggtagctt tattatccac attttgcaga tgaggaaaca gagtcaggtg    694

aagtgtcttt tccaaggcca agctcctgag ggcaggggc                           733


<210> SEQ ID NO 16
<211> LENGTH: 107
<212> TYPE: PRT
<213> ORGANISM: Homo sapiens
<220> FEATURE:
<221> NAME/KEY: SIGNAL
<222> LOCATION: 1..14

<400> SEQUENCE: 16

Met Ser Ala Ser Cys Cys Leu Ser Trp Cys Pro Ala Lys Ala Lys Ser
                -10                 -5                  1

Lys Cys Gly Pro Thr Phe Phe Pro Cys Ala Ser Gly Ile His Cys Ile
        5                   10                  15

Ile Gly Arg Phe Arg Cys Asn Gly Phe Glu Asp Cys Pro Asp Gly Ser
    20                  25                  30

Asp Glu Glu Asn Cys Thr Ala Asn Pro Leu Leu Cys Ser Thr Ala Arg
35                  40                  45                  50

Tyr His Cys Lys Asn Gly Leu Cys Ile Asp Lys Ser Phe Ile Cys Asp
                55                  60                  65

Gly Gln Asn Asn Cys Gln Asp Asn Ser Asp Glu Glu Ser Cys Glu Ser
            70                  75                  80

Ser Gln Ala Ile Phe Pro Gln Ile Thr Val Ser
        85                  90


<210> SEQ ID NO 17
<211> LENGTH: 1175
<212> TYPE: DNA
<213> ORGANISM: Homo sapiens
<220> FEATURE:
```

-continued

```
<221> NAME/KEY: 5'UTR
<222> LOCATION: 1..326
<220> FEATURE:
<221> NAME/KEY: CDS
<222> LOCATION: 327..1013
<220> FEATURE:
<221> NAME/KEY: 3'UTR
<222> LOCATION: 1014..1175
<220> FEATURE:
<221> NAME/KEY: polyA_signal
<222> LOCATION: 1131..1136
<220> FEATURE:
<221> NAME/KEY: polyA_site
<222> LOCATION: 1160..1175

<400> SEQUENCE: 17

gaagcggagc ggtctaggga gccgcggccg cgggtcaccc ggcgggtagc agttgctgag     60

tgtcagctag acagcagcga ctagggctcg ggcgccggcg agatgccttt gttcaccgcc    120

aaccccttcg agcaagacgt ggtgatgcca attggtggaa aggagaaaat cacagaggaa    180

taggactttt cccatccaat tttgtaacaa ctaatttaaa catagagact gaggcagcgg    240

ctgtggacaa attgaatgta attgatgatg atgtggagga aattaagaaa tcagagcctg    300

agcctgttta tatagatgag gataag atg gat aga gcc ctg cag gta ctt cag     353
                             Met Asp Arg Ala Leu Gln Val Leu Gln
                             1               5

agt ata gat cca aca gat tca aaa cca gac tcc caa gac ctt ttg gat     401
Ser Ile Asp Pro Thr Asp Ser Lys Pro Asp Ser Gln Asp Leu Leu Asp
10                  15                  20                  25

tta gaa gat atc tgc caa cag atg ggt cca atg ata gat gaa aaa ctt     449
Leu Glu Asp Ile Cys Gln Gln Met Gly Pro Met Ile Asp Glu Lys Leu
                30                  35                  40

gaa gaa att gat agg aag cat tca gaa ttg tct gaa ttg aat gtt aaa     497
Glu Glu Ile Asp Arg Lys His Ser Glu Leu Ser Glu Leu Asn Val Lys
            45                  50                  55

gtc ctg gaa gct ctg gaa cta tat aac aaa ttg gtg aat gaa gca cca     545
Val Leu Glu Ala Leu Glu Leu Tyr Asn Lys Leu Val Asn Glu Ala Pro
        60                  65                  70

gtg tac tca gtc tat tca aag ctc cac cct cca gca cat tac cca cct     593
Val Tyr Ser Val Tyr Ser Lys Leu His Pro Pro Ala His Tyr Pro Pro
    75                  80                  85

gca tca tct ggg gtt cca atg cag aca tat cca gtt caa tca cat ggt     641
Ala Ser Ser Gly Val Pro Met Gln Thr Tyr Pro Val Gln Ser His Gly
90                  95                  100                 105

gga aac tat atg ggt cag agc att cac caa gta act gtt gcc caa agc     689
Gly Asn Tyr Met Gly Gln Ser Ile His Gln Val Thr Val Ala Gln Ser
                110                 115                 120

tat agc cta gga ccc gat caa att ggt cca ctg aga tct ctg cct cca     737
Tyr Ser Leu Gly Pro Asp Gln Ile Gly Pro Leu Arg Ser Leu Pro Pro
            125                 130                 135

aat gtg aat tcc tca gtg aca gca cag cct gct caa act tca tat tta     785
Asn Val Asn Ser Ser Val Thr Ala Gln Pro Ala Gln Thr Ser Tyr Leu
        140                 145                 150

agc act gga caa gac act gtt tcc aat cct act tat atg aac cag aac     833
Ser Thr Gly Gln Asp Thr Val Ser Asn Pro Thr Tyr Met Asn Gln Asn
    155                 160                 165

tct aac cta cag tca gct act ggt aca act gct tac aca cag caa atg     881
Ser Asn Leu Gln Ser Ala Thr Gly Thr Thr Ala Tyr Thr Gln Gln Met
170                 175                 180                 185

ggg atg tct gtg gat atg tca tct tat cag aac act act tcc aat ttg     929
Gly Met Ser Val Asp Met Ser Ser Tyr Gln Asn Thr Thr Ser Asn Leu
                190                 195                 200
```

-continued

```
cct caa ctg gca ggc ttt ccg gtg aca gtt cca gct cat cca gtt gca      977
Pro Gln Leu Ala Gly Phe Pro Val Thr Val Pro Ala His Pro Val Ala
            205                 210                 215

cag cag cac aca aat tac cat cag cag cct ctc ctt tagaaacaaa          1023
Gln Gln His Thr Asn Tyr His Gln Gln Pro Leu Leu
        220                 225

tcaagcattt tcttgaaagc cttcataagt gtattattca gtccttgtga taccaacctg   1083

aaaatattaa aactttttc cctctcaact caaaaggacc atgaataaat aaagcacaaa   1143

aacctctctt attctgaaaa aaaaaaaaaa at                                 1175


<210> SEQ ID NO 18
<211> LENGTH: 229
<212> TYPE: PRT
<213> ORGANISM: Homo sapiens

<400> SEQUENCE: 18

Met Asp Arg Ala Leu Gln Val Leu Gln Ser Ile Asp Pro Thr Asp Ser
1               5                   10                  15

Lys Pro Asp Ser Gln Asp Leu Leu Asp Leu Glu Asp Ile Cys Gln Gln
            20                  25                  30

Met Gly Pro Met Ile Asp Glu Lys Leu Glu Glu Ile Asp Arg Lys His
        35                  40                  45

Ser Glu Leu Ser Glu Leu Asn Val Lys Val Leu Glu Ala Leu Glu Leu
    50                  55                  60

Tyr Asn Lys Leu Val Asn Glu Ala Pro Val Tyr Ser Val Tyr Ser Lys
65                  70                  75                  80

Leu His Pro Pro Ala His Tyr Pro Pro Ala Ser Ser Gly Val Pro Met
                85                  90                  95

Gln Thr Tyr Pro Val Gln Ser His Gly Gly Asn Tyr Met Gly Gln Ser
            100                 105                 110

Ile His Gln Val Thr Val Ala Gln Ser Tyr Ser Leu Gly Pro Asp Gln
        115                 120                 125

Ile Gly Pro Leu Arg Ser Leu Pro Pro Asn Val Asn Ser Ser Val Thr
    130                 135                 140

Ala Gln Pro Ala Gln Thr Ser Tyr Leu Ser Thr Gly Gln Asp Thr Val
145                 150                 155                 160

Ser Asn Pro Thr Tyr Met Asn Gln Asn Ser Asn Leu Gln Ser Ala Thr
                165                 170                 175

Gly Thr Thr Ala Tyr Thr Gln Gln Met Gly Met Ser Val Asp Met Ser
            180                 185                 190

Ser Tyr Gln Asn Thr Thr Ser Asn Leu Pro Gln Leu Ala Gly Phe Pro
        195                 200                 205

Val Thr Val Pro Ala His Pro Val Ala Gln Gln His Thr Asn Tyr His
    210                 215                 220

Gln Gln Pro Leu Leu
225


<210> SEQ ID NO 19
<211> LENGTH: 844
<212> TYPE: DNA
<213> ORGANISM: Homo sapiens
<220> FEATURE:
<221> NAME/KEY: 5'UTR
<222> LOCATION: 1..111
<220> FEATURE:
<221> NAME/KEY: CDS
<222> LOCATION: 112..813
<220> FEATURE:
```

```
<221> NAME/KEY: 3'UTR
<222> LOCATION: 814..844

<400> SEQUENCE: 19

tttcctgttg cctgtctcta aacccctcca cattcccgcg gtccttcaga ctgcccggag      60

agcgcgctct gcctgccgcc tgcctgcctg ccactgaggg ttcccagcac c atg agg      117
                                                          Met Arg
                                                              -15

gcc tgg atc ttc ttt ctc ctt tgc ctg gcc ggg agg gcc ttg gca gcc      165
Ala Trp Ile Phe Phe Leu Leu Cys Leu Ala Gly Arg Ala Leu Ala Ala
                -10                 -5                  1

cct cag caa gaa gcc ctg cct gat gag aca gag gtg gtg gaa gaa act      213
Pro Gln Gln Glu Ala Leu Pro Asp Glu Thr Glu Val Val Glu Glu Thr
        5                   10                  15

gtg gca gag gtg act gag gta tct gtt gga gct aat cct gtc cag gtg      261
Val Ala Glu Val Thr Glu Val Ser Val Gly Ala Asn Pro Val Gln Val
    20                  25                  30

gaa gta gga gaa ttt gat gat ggt gca gag gaa acc gaa gag gag gtg      309
Glu Val Gly Glu Phe Asp Asp Gly Ala Glu Glu Thr Glu Glu Glu Val
35                  40                  45                  50

gtg gcg gaa aat ccc tgc cag aac cac cac tgc aaa cac ggc aag gtg      357
Val Ala Glu Asn Pro Cys Gln Asn His His Cys Lys His Gly Lys Val
                55                  60                  65

tgc gag ctg gat gag aac aac acc ccc atg tgc gtg tgc cag gac ccc      405
Cys Glu Leu Asp Glu Asn Asn Thr Pro Met Cys Val Cys Gln Asp Pro
            70                  75                  80

acc agc tgc cca gcc ccc att ggc gag ttt gag aag gtg tgc agc aat      453
Thr Ser Cys Pro Ala Pro Ile Gly Glu Phe Glu Lys Val Cys Ser Asn
        85                  90                  95

gac aac aag acc ttc gac tct tcc tgc cac ttc ttt gcc aca aag tgc      501
Asp Asn Lys Thr Phe Asp Ser Ser Cys His Phe Phe Ala Thr Lys Cys
    100                 105                 110

acc ctg gag ggc acc aag aag ggc cac aag ctc cac ctg gac tac atc      549
Thr Leu Glu Gly Thr Lys Lys Gly His Lys Leu His Leu Asp Tyr Ile
115                 120                 125                 130

ggg cct tgc aaa tac atc ccc cct tgc ctg gac tct gag ctg acc gaa      597
Gly Pro Cys Lys Tyr Ile Pro Pro Cys Leu Asp Ser Glu Leu Thr Glu
                135                 140                 145

ttc ccc ctg cgc atg cgg gac tgg ctc aag aac gtc ctg gtc acc ctg      645
Phe Pro Leu Arg Met Arg Asp Trp Leu Lys Asn Val Leu Val Thr Leu
            150                 155                 160

tat gag agg gat gag gac aac aac ctt ctg act gag aag cag aag ctg      693
Tyr Glu Arg Asp Glu Asp Asn Asn Leu Leu Thr Glu Lys Gln Lys Leu
        165                 170                 175

cgg gtg aag aag atc cat gag aat gag aag cgc ctg gag gca gga gac      741
Arg Val Lys Lys Ile His Glu Asn Glu Lys Arg Leu Glu Ala Gly Asp
    180                 185                 190

cac ccc gtg gag ctg ctg gcc cgg gac tgc cag gct gtt tca gcc agg      789
His Pro Val Glu Leu Leu Ala Arg Asp Cys Gln Ala Val Ser Ala Arg
195                 200                 205                 210

aag gcc aaa atc aag agt gag atg tagaaagttg taaaatagaa aaagtggagt      843
Lys Ala Lys Ile Lys Ser Glu Met
                215

t                                                                     844


<210> SEQ ID NO 20
<211> LENGTH: 234
<212> TYPE: PRT
<213> ORGANISM: Homo sapiens
<220> FEATURE:
```

```
<221> NAME/KEY: SIGNAL
<222> LOCATION: 1..17

<400> SEQUENCE: 20

Met Arg Ala Trp Ile Phe Phe Leu Leu Cys Leu Ala Gly Arg Ala Leu
        -15                 -10                 -5

Ala Ala Pro Gln Gln Glu Ala Leu Pro Asp Glu Thr Glu Val Val Glu
    1               5                   10                  15

Glu Thr Val Ala Glu Val Thr Glu Val Ser Val Gly Ala Asn Pro Val
                20                  25                  30

Gln Val Glu Val Gly Glu Phe Asp Asp Gly Ala Glu Glu Thr Glu Glu
            35                  40                  45

Glu Val Val Ala Glu Asn Pro Cys Gln Asn His His Cys Lys His Gly
        50                  55                  60

Lys Val Cys Glu Leu Asp Glu Asn Asn Thr Pro Met Cys Val Cys Gln
    65                  70                  75

Asp Pro Thr Ser Cys Pro Ala Pro Ile Gly Glu Phe Glu Lys Val Cys
80                  85                  90                  95

Ser Asn Asp Asn Lys Thr Phe Asp Ser Ser Cys His Phe Phe Ala Thr
                100                 105                 110

Lys Cys Thr Leu Glu Gly Thr Lys Lys Gly His Lys Leu His Leu Asp
            115                 120                 125

Tyr Ile Gly Pro Cys Lys Tyr Ile Pro Pro Cys Leu Asp Ser Glu Leu
        130                 135                 140

Thr Glu Phe Pro Leu Arg Met Arg Asp Trp Leu Lys Asn Val Leu Val
    145                 150                 155

Thr Leu Tyr Glu Arg Asp Glu Asp Asn Asn Leu Leu Thr Glu Lys Gln
160                 165                 170                 175

Lys Leu Arg Val Lys Lys Ile His Glu Asn Glu Lys Arg Leu Glu Ala
                180                 185                 190

Gly Asp His Pro Val Glu Leu Leu Ala Arg Asp Cys Gln Ala Val Ser
            195                 200                 205

Ala Arg Lys Ala Lys Ile Lys Ser Glu Met
        210                 215


<210> SEQ ID NO 21
<211> LENGTH: 1997
<212> TYPE: DNA
<213> ORGANISM: Homo sapiens
<220> FEATURE:
<221> NAME/KEY: 5'UTR
<222> LOCATION: 1..126
<220> FEATURE:
<221> NAME/KEY: CDS
<222> LOCATION: 127..1020
<220> FEATURE:
<221> NAME/KEY: 3'UTR
<222> LOCATION: 1021..1997

<400> SEQUENCE: 21

atcctctaag cttttaaata ttgcttcgat ggtctgaatt tttatttcca gggaaaaaga      60

gagttttgtc ccacagtcag caggccacta gtttattaac ttccagtcac cttgattttt     120

gctaaa atg aag act ctg cag tct aca ctt ctc ctg tta ctg ctt gtg       168
       Met Lys Thr Leu Gln Ser Thr Leu Leu Leu Leu Leu Leu Val
                   -15                 -10                 -5

cct ctg ata aag cca gca cca cca acc cag cag gac tca cgc att atc      216
Pro Leu Ile Lys Pro Ala Pro Pro Thr Gln Gln Asp Ser Arg Ile Ile
                1               5                   10
```

```
tat gat tat gga aca gat aat ttt gaa gaa tcc ata ttt agc caa gat      264
Tyr Asp Tyr Gly Thr Asp Asn Phe Glu Glu Ser Ile Phe Ser Gln Asp
        15                  20                  25

tat gag gat aaa tac ctg gat gga aaa aat att aag gaa aaa gaa act      312
Tyr Glu Asp Lys Tyr Leu Asp Gly Lys Asn Ile Lys Glu Lys Glu Thr
    30                  35                  40

gtg ata ata ccc aat gag aaa agt ctt caa tta caa aaa gat gag gca      360
Val Ile Ile Pro Asn Glu Lys Ser Leu Gln Leu Gln Lys Asp Glu Ala
45                  50                  55                  60

ata aca cca tta cct ccc aag aaa gaa aat gat gaa atg ccc acg tgt      408
Ile Thr Pro Leu Pro Pro Lys Lys Glu Asn Asp Glu Met Pro Thr Cys
                65                  70                  75

ctg ctg tgt gtt tgt tta agt ggc tct gta tac tgt gaa gaa gtt gac      456
Leu Leu Cys Val Cys Leu Ser Gly Ser Val Tyr Cys Glu Glu Val Asp
            80                  85                  90

att gat gct gta cca ccc tta cca aag gaa tca gcc tat ctt tac gca      504
Ile Asp Ala Val Pro Pro Leu Pro Lys Glu Ser Ala Tyr Leu Tyr Ala
        95                  100                 105

cga ttc aac aaa att aaa aag ctg act gcc aaa gat ttt gca gac ata      552
Arg Phe Asn Lys Ile Lys Lys Leu Thr Ala Lys Asp Phe Ala Asp Ile
    110                 115                 120

cct aac tta aga aga ctc gat ttt aca gga aat ttg ata gaa gat ata      600
Pro Asn Leu Arg Arg Leu Asp Phe Thr Gly Asn Leu Ile Glu Asp Ile
125                 130                 135                 140

gaa gat ggt act ttt tca aaa ctt tct ctg tta gaa gaa ctt tca ctt      648
Glu Asp Gly Thr Phe Ser Lys Leu Ser Leu Leu Glu Glu Leu Ser Leu
                145                 150                 155

gct gaa aat caa cta cta aaa ctt cca gtt ctt cct ccc aag ctc act      696
Ala Glu Asn Gln Leu Leu Lys Leu Pro Val Leu Pro Pro Lys Leu Thr
            160                 165                 170

tta ttt aat gca aaa tac aac aaa atc aag agt agg gga atc aaa gca      744
Leu Phe Asn Ala Lys Tyr Asn Lys Ile Lys Ser Arg Gly Ile Lys Ala
        175                 180                 185

aat gca ttc aaa aaa ctg aat aac ctc acc ttc ctc tac ttg gac cat      792
Asn Ala Phe Lys Lys Leu Asn Asn Leu Thr Phe Leu Tyr Leu Asp His
    190                 195                 200

aat gcc ctg gaa tcc gtg cct ctt aat tta cca gaa agt cta cgt gta      840
Asn Ala Leu Glu Ser Val Pro Leu Asn Leu Pro Glu Ser Leu Arg Val
205                 210                 215                 220

att cat ctt cag ttc aac aac ata gct tca att aca gat gac aca ttc      888
Ile His Leu Gln Phe Asn Asn Ile Ala Ser Ile Thr Asp Asp Thr Phe
                225                 230                 235

tgc aag gct aat gac acc agt tac atc cgg gac cgc att gaa gag ata      936
Cys Lys Ala Asn Asp Thr Ser Tyr Ile Arg Asp Arg Ile Glu Glu Ile
            240                 245                 250

cgc ctg gag ggc aat cca atc gtc ctg gga aag cat cca aac agt ttt      984
Arg Leu Glu Gly Asn Pro Ile Val Leu Gly Lys His Pro Asn Ser Phe
        255                 260                 265

att tgc tta aaa aga tta ccg ata ggg tca tac ttt taacctctat          1030
Ile Cys Leu Lys Arg Leu Pro Ile Gly Ser Tyr Phe
    270                 275                 280

tggtacaaca tataaatgaa agtacaccta cactaatagt ctgtctcaac aatgagtaaa   1090

ggaacttaag tattggttta atattaacct tgtatctcat tttgaaggaa tttaatattt   1150

taagcaagga tgttcaaaat cttacatata ataagtaaaa agtaagactg aatgtctacg   1210

ttcgaaacaa agtaatatga aaatatttaa acagcattac aaaatcctag tttatactag   1270

actaccattt aaaaatcatg tttttatata aatgcccaaa tttgagatgc attattccta   1330
```

-continued

```
ttactaatga tgtaagtacg aggataaatc caagaaactt tcaactcttt gcctttcctg   1390

gcctttactg gatcccaaaa gcatttaagg tacatgttcc aaaaactttg aaaagctaaa   1450

tgtttcccat gatcgctcat tcttctttta tgattcatac gttattcctt ataaagtaag   1510

aactttgttt tcctcctatc aaggcagcta ttttattaaa tttttcactt agtctgagaa   1570

atagcagata gtctcatatt taggaaaact ttccaaataa aataaatgtt attctctgat   1630

aaagagctaa tacagaaatg ttcaagttat tttactttct ggtaatgtct tcagtaaaat   1690

attttcttta tctaaatatt aacattctaa gtctaccaaa aaaagtttta aactcaagca   1750

ggccaaaacc aatatgctta taagaaataa tgaaaagttc atccatttct gataaagttc   1810

tctatggcaa agtctttcaa atacgagata actgcaaaat attttccttt tatactacag   1870

aaatgagaat ctcatcaata aattagttca agcataagat gaaaacagaa tattctgtgg   1930

tgccagtgca cactaccttc ccacccatac acatccatgt tcactgtaac aaactgaata   1990

ttcacaa                                                             1997
```

```
<210> SEQ ID NO 22
<211> LENGTH: 298
<212> TYPE: PRT
<213> ORGANISM: Homo sapiens
<220> FEATURE:
<221> NAME/KEY: SIGNAL
<222> LOCATION: 1..19

<400> SEQUENCE: 22

Met Lys Thr Leu Gln Ser Thr Leu Leu Leu Leu Leu Leu Val Pro Leu
                -15                 -10                 -5

Ile Lys Pro Ala Pro Pro Thr Gln Gln Asp Ser Arg Ile Ile Tyr Asp
            1               5                   10

Tyr Gly Thr Asp Asn Phe Glu Glu Ser Ile Phe Ser Gln Asp Tyr Glu
    15                  20                  25

Asp Lys Tyr Leu Asp Gly Lys Asn Ile Lys Glu Lys Glu Thr Val Ile
30                  35                  40                  45

Ile Pro Asn Glu Lys Ser Leu Gln Leu Gln Lys Asp Glu Ala Ile Thr
                50                  55                  60

Pro Leu Pro Pro Lys Lys Glu Asn Asp Glu Met Pro Thr Cys Leu Leu
            65                  70                  75

Cys Val Cys Leu Ser Gly Ser Val Tyr Cys Glu Glu Val Asp Ile Asp
        80                  85                  90

Ala Val Pro Pro Leu Pro Lys Glu Ser Ala Tyr Leu Tyr Ala Arg Phe
    95                  100                 105

Asn Lys Ile Lys Lys Leu Thr Ala Lys Asp Phe Ala Asp Ile Pro Asn
110                 115                 120                 125

Leu Arg Arg Leu Asp Phe Thr Gly Asn Leu Ile Glu Asp Ile Glu Asp
                130                 135                 140

Gly Thr Phe Ser Lys Leu Ser Leu Leu Glu Glu Leu Ser Leu Ala Glu
            145                 150                 155

Asn Gln Leu Leu Lys Leu Pro Val Leu Pro Pro Lys Leu Thr Leu Phe
        160                 165                 170

Asn Ala Lys Tyr Asn Lys Ile Lys Ser Arg Gly Ile Lys Ala Asn Ala
    175                 180                 185

Phe Lys Lys Leu Asn Asn Leu Thr Phe Leu Tyr Leu Asp His Asn Ala
190                 195                 200                 205

Leu Glu Ser Val Pro Leu Asn Leu Pro Glu Ser Leu Arg Val Ile His
                210                 215                 220
```

```
Leu Gln Phe Asn Asn Ile Ala Ser Ile Thr Asp Asp Thr Phe Cys Lys
            225                 230                 235

Ala Asn Asp Thr Ser Tyr Ile Arg Asp Arg Ile Glu Glu Ile Arg Leu
        240                 245                 250

Glu Gly Asn Pro Ile Val Leu Gly Lys His Pro Asn Ser Phe Ile Cys
    255                 260                 265

Leu Lys Arg Leu Pro Ile Gly Ser Tyr Phe
270                 275


<210> SEQ ID NO 23
<211> LENGTH: 1746
<212> TYPE: DNA
<213> ORGANISM: Homo sapiens
<220> FEATURE:
<221> NAME/KEY: 5'UTR
<222> LOCATION: 1..9
<220> FEATURE:
<221> NAME/KEY: CDS
<222> LOCATION: 10..1212
<220> FEATURE:
<221> NAME/KEY: 3'UTR
<222> LOCATION: 1213..1746
<220> FEATURE:
<221> NAME/KEY: polyA_signal
<222> LOCATION: 1709..1714
<220> FEATURE:
<221> NAME/KEY: polyA_site
<222> LOCATION: 1733..1746

<400> SEQUENCE: 23

gcctcacca atg gtt ccc ttc atc tat ctg caa gcc cac ttt aca ctc tgt      51
          Met Val Pro Phe Ile Tyr Leu Gln Ala His Phe Thr Leu Cys
              -15                 -10                 -5

tct ggg tgg tcc agc aca tac cgg gac ctc cgg aag ggt gtg tat gtg        99
Ser Gly Trp Ser Ser Thr Tyr Arg Asp Leu Arg Lys Gly Val Tyr Val
        1               5                   10

ccc tac acc cag ggc aag tgg gaa ggg gag ctg ggc acc gac ctg gta       147
Pro Tyr Thr Gln Gly Lys Trp Glu Gly Glu Leu Gly Thr Asp Leu Val
15                  20                  25                  30

agc atc ccc cat ggc ccc aac gtc act gtg cgt gcc aac att gct gcc       195
Ser Ile Pro His Gly Pro Asn Val Thr Val Arg Ala Asn Ile Ala Ala
                35                  40                  45

atc act gaa tca gac aag ttc ttc atc aac ggc tcc aac tgg gaa ggc       243
Ile Thr Glu Ser Asp Lys Phe Phe Ile Asn Gly Ser Asn Trp Glu Gly
            50                  55                  60

atc ctg ggg ctg gcc tat gct gag att gcc agg cct gac gac tcc ccg       291
Ile Leu Gly Leu Ala Tyr Ala Glu Ile Ala Arg Pro Asp Asp Ser Pro
        65                  70                  75

gag cct ttc ttt gac tct ctg gta aag cag acc cac gtt ccc aac ctc       339
Glu Pro Phe Phe Asp Ser Leu Val Lys Gln Thr His Val Pro Asn Leu
    80                  85                  90

ttc tcc ctg cag ctt tgt ggt gct ggc ttc ccc ctc aac cag tct gaa       387
Phe Ser Leu Gln Leu Cys Gly Ala Gly Phe Pro Leu Asn Gln Ser Glu
95                  100                 105                 110

gtg ctg gcc tct gtc gga ggg agc atg atc att gga ggt atc gac cac       435
Val Leu Ala Ser Val Gly Gly Ser Met Ile Ile Gly Gly Ile Asp His
                115                 120                 125

tcg ctg tac aca ggc agt ctc tgg tat aca ccc atc cgg cgg gag tgg       483
Ser Leu Tyr Thr Gly Ser Leu Trp Tyr Thr Pro Ile Arg Arg Glu Trp
            130                 135                 140

tat tat gag gtg atc att gtg cgg gtg gag atc aat gga cag gat ctg       531
Tyr Tyr Glu Val Ile Ile Val Arg Val Glu Ile Asn Gly Gln Asp Leu
        145                 150                 155
```

-continued

```
aaa atg gac tgc aag gag tac aac tat gac aag agc att gtg gac agt      579
Lys Met Asp Cys Lys Glu Tyr Asn Tyr Asp Lys Ser Ile Val Asp Ser
    160                 165                 170

ggc acc acc aac ctt cgt ttg ccc aag aaa gtg ttt gaa gct gca gtc      627
Gly Thr Thr Asn Leu Arg Leu Pro Lys Lys Val Phe Glu Ala Ala Val
175                 180                 185                 190

aaa tcc atc aag gca gcc tcc tcc acg gag aag ttc cct gac ggt ttc      675
Lys Ser Ile Lys Ala Ala Ser Ser Thr Glu Lys Phe Pro Asp Gly Phe
                195                 200                 205

tgg cta gga gag cag ctg gtg tgc tgg caa gca ggc acc acc cct tgg      723
Trp Leu Gly Glu Gln Leu Val Cys Trp Gln Ala Gly Thr Thr Pro Trp
            210                 215                 220

aac att ttc cca gtc atc tca ctc tac cta atg ggt gag gtt acc aac      771
Asn Ile Phe Pro Val Ile Ser Leu Tyr Leu Met Gly Glu Val Thr Asn
        225                 230                 235

cag tcc ttc cgc atc acc atc ctt ccg cag caa tac ctg cgg cca gtg      819
Gln Ser Phe Arg Ile Thr Ile Leu Pro Gln Gln Tyr Leu Arg Pro Val
    240                 245                 250

gaa gat gtg gcc acg tcc caa gac gac tgt tac aag ttt gcc atc tca      867
Glu Asp Val Ala Thr Ser Gln Asp Asp Cys Tyr Lys Phe Ala Ile Ser
255                 260                 265                 270

cag tca tcc acg ggc act gtt atg gga gct gtt atc atg gag ggc ttc      915
Gln Ser Ser Thr Gly Thr Val Met Gly Ala Val Ile Met Glu Gly Phe
                275                 280                 285

tac gtt gtc ttt gat cgg gcc cga aaa cga att ggc ttt gct gtc agc      963
Tyr Val Val Phe Asp Arg Ala Arg Lys Arg Ile Gly Phe Ala Val Ser
            290                 295                 300

gct tgc cat gtg cac gat gag ttc agg acg gca gcg gtg gaa ggc cct     1011
Ala Cys His Val His Asp Glu Phe Arg Thr Ala Ala Val Glu Gly Pro
        305                 310                 315

ttt gtc acc ttg gac atg gaa gac tgt ggc tac aac att cca cag aca     1059
Phe Val Thr Leu Asp Met Glu Asp Cys Gly Tyr Asn Ile Pro Gln Thr
    320                 325                 330

gat gag tca acc ctc atg acc ata gcc tat gtc atg gct gcc atc tgc     1107
Asp Glu Ser Thr Leu Met Thr Ile Ala Tyr Val Met Ala Ala Ile Cys
335                 340                 345                 350

gcc ctc ttc atg ctg cca ctc tgc ctc atg gtg tgt cag tgg cgc tgc     1155
Ala Leu Phe Met Leu Pro Leu Cys Leu Met Val Cys Gln Trp Arg Cys
                355                 360                 365

ctc cgc tgc ctg cgc cag cag cat gat gac ttt gct gat gac atc tcc     1203
Leu Arg Cys Leu Arg Gln Gln His Asp Asp Phe Ala Asp Asp Ile Ser
            370                 375                 380

ctg ctg aag tgaggaggcc catgggcaga agatagggat tcccctggac             1252
Leu Leu Lys
        385

cacacctccg tggttcactt tggtcacaag taggagacac agatggcacc tgtggccaga   1312

gcacctcagg accctcccca cccaccaaat gcctctgcct tgatggagaa ggaaaaggct   1372

ggcaaggtgg gttccaggga ctgtacctgt aggagacaga aaagagaaga aagaagcact   1432

ctgctggcgg gaatactctt ggtcacctca aatttaagtc gggaaattct gctgcttgaa   1492

acttcagccc tgaacctttg tcaccattcc tttaaattct ccaacccaaa gtattcttct   1552

tttcttagtt tcagaagtac tggcatcaca cgcaggttac cttggcgtgt gtccctgtgg   1612

taccctggca gagaagagac caagcttgtt tccctgctgg ccaaagtcag taggagagga   1672

tgcacagttt gctatttgct ttagagacag ggactgtata aacaagccta acattggtgc   1732

aaaaaaaaaa aaaa                                                     1746
```

<210> SEQ ID NO 24
<211> LENGTH: 401
<212> TYPE: PRT
<213> ORGANISM: Homo sapiens
<220> FEATURE:
<221> NAME/KEY: SIGNAL
<222> LOCATION: 1..17

<400> SEQUENCE: 24

```
Met Val Pro Phe Ile Tyr Leu Gln Ala His Phe Thr Leu Cys Ser Gly
        -15                 -10                 -5

Trp Ser Ser Thr Tyr Arg Asp Leu Arg Lys Gly Val Tyr Val Pro Tyr
    1               5                   10                  15

Thr Gln Gly Lys Trp Glu Gly Glu Leu Gly Thr Asp Leu Val Ser Ile
                20                  25                  30

Pro His Gly Pro Asn Val Thr Val Arg Ala Asn Ile Ala Ala Ile Thr
            35                  40                  45

Glu Ser Asp Lys Phe Phe Ile Asn Gly Ser Asn Trp Glu Gly Ile Leu
        50                  55                  60

Gly Leu Ala Tyr Ala Glu Ile Ala Arg Pro Asp Asp Ser Pro Glu Pro
    65                  70                  75

Phe Phe Asp Ser Leu Val Lys Gln Thr His Val Pro Asn Leu Phe Ser
80                  85                  90                  95

Leu Gln Leu Cys Gly Ala Gly Phe Pro Leu Asn Gln Ser Glu Val Leu
                100                 105                 110

Ala Ser Val Gly Gly Ser Met Ile Ile Gly Gly Ile Asp His Ser Leu
            115                 120                 125

Tyr Thr Gly Ser Leu Trp Tyr Thr Pro Ile Arg Arg Glu Trp Tyr Tyr
        130                 135                 140

Glu Val Ile Ile Val Arg Val Glu Ile Asn Gly Gln Asp Leu Lys Met
    145                 150                 155

Asp Cys Lys Glu Tyr Asn Tyr Asp Lys Ser Ile Val Asp Ser Gly Thr
160                 165                 170                 175

Thr Asn Leu Arg Leu Pro Lys Lys Val Phe Glu Ala Ala Val Lys Ser
                180                 185                 190

Ile Lys Ala Ala Ser Ser Thr Glu Lys Phe Pro Asp Gly Phe Trp Leu
            195                 200                 205

Gly Glu Gln Leu Val Cys Trp Gln Ala Gly Thr Thr Pro Trp Asn Ile
        210                 215                 220

Phe Pro Val Ile Ser Leu Tyr Leu Met Gly Glu Val Thr Asn Gln Ser
    225                 230                 235

Phe Arg Ile Thr Ile Leu Pro Gln Gln Tyr Leu Arg Pro Val Glu Asp
240                 245                 250                 255

Val Ala Thr Ser Gln Asp Asp Cys Tyr Lys Phe Ala Ile Ser Gln Ser
                260                 265                 270

Ser Thr Gly Thr Val Met Gly Ala Val Ile Met Glu Gly Phe Tyr Val
            275                 280                 285

Val Phe Asp Arg Ala Arg Lys Arg Ile Gly Phe Ala Val Ser Ala Cys
        290                 295                 300

His Val His Asp Glu Phe Arg Thr Ala Ala Val Glu Gly Pro Phe Val
    305                 310                 315

Thr Leu Asp Met Glu Asp Cys Gly Tyr Asn Ile Pro Gln Thr Asp Glu
320                 325                 330                 335

Ser Thr Leu Met Thr Ile Ala Tyr Val Met Ala Ala Ile Cys Ala Leu
                340                 345                 350
```

```
Phe Met Leu Pro Leu Cys Leu Met Val Cys Gln Trp Arg Cys Leu Arg
            355                 360                 365

Cys Leu Arg Gln Gln His Asp Asp Phe Ala Asp Asp Ile Ser Leu Leu
        370                 375                 380

Lys


<210> SEQ ID NO 25
<211> LENGTH: 1239
<212> TYPE: DNA
<213> ORGANISM: Homo sapiens
<220> FEATURE:
<221> NAME/KEY: 5'UTR
<222> LOCATION: 1..126
<220> FEATURE:
<221> NAME/KEY: CDS
<222> LOCATION: 127..879
<220> FEATURE:
<221> NAME/KEY: 3'UTR
<222> LOCATION: 880..1239
<220> FEATURE:
<221> NAME/KEY: polyA_site
<222> LOCATION: 1224..1239

<400> SEQUENCE: 25

agtctaggat cctcacacca gctacttgca agggagaagg aaaaggccag taaggcctgg      60

gccaggagag tcccgacagg agtgtcaggt ttcaatctca gcaccagcca ctcagagcag     120

ggcacg atg ttg ggg gcc cgc ctc agg ctc tgg gtc tgt gcc ttg tgc        168
       Met Leu Gly Ala Arg Leu Arg Leu Trp Val Cys Ala Leu Cys
                   -20                 -15                 -10

agc gtc tgc agc atg agc gtc ctc aga gcc tat ccc aat gcc tcc cca       216
Ser Val Cys Ser Met Ser Val Leu Arg Ala Tyr Pro Asn Ala Ser Pro
                -5                  1               5

ctg ctc ggc tcc agc tgg ggt ggc ctg atc cac ctg tac aca gcc aca       264
Leu Leu Gly Ser Ser Trp Gly Gly Leu Ile His Leu Tyr Thr Ala Thr
        10                  15                  20

gcc agg aac agc tac cac ctg cag atc cac aag aat ggc cat gtg gat       312
Ala Arg Asn Ser Tyr His Leu Gln Ile His Lys Asn Gly His Val Asp
    25                  30                  35

ggc gca ccc cat cag acc atc tac agt gcc ctg atg atc aga tca gag       360
Gly Ala Pro His Gln Thr Ile Tyr Ser Ala Leu Met Ile Arg Ser Glu
40                  45                  50                  55

gat gct ggc ttt gtg gtg att aca ggt gtg atg agc aga aga tac ctc       408
Asp Ala Gly Phe Val Val Ile Thr Gly Val Met Ser Arg Arg Tyr Leu
                60                  65                  70

tgc atg gat ttc aga ggc aac att ttt gga tca cac tat ttc gac ccg       456
Cys Met Asp Phe Arg Gly Asn Ile Phe Gly Ser His Tyr Phe Asp Pro
            75                  80                  85

gag aac tgc agg ttc caa cac cag acg ctg gaa aac ggg tac gac gtc       504
Glu Asn Cys Arg Phe Gln His Gln Thr Leu Glu Asn Gly Tyr Asp Val
        90                  95                  100

tac cac tct cct cag tat cac ttc ctg gtc agt ctg ggc cgg gcg aag       552
Tyr His Ser Pro Gln Tyr His Phe Leu Val Ser Leu Gly Arg Ala Lys
    105                 110                 115

aga gcc ttc ctg cca ggc atg aac cca ccc ccg tac tcc cag ttc ctg       600
Arg Ala Phe Leu Pro Gly Met Asn Pro Pro Pro Tyr Ser Gln Phe Leu
120                 125                 130                 135

tcc cgg agg aac gag atc ccc cta att cac ttc aac acc ccc ata cca       648
Ser Arg Arg Asn Glu Ile Pro Leu Ile His Phe Asn Thr Pro Ile Pro
                140                 145                 150

cgg cgg cac acc cgg agc gcc gag gac gac tcg gag cgg gac ccc ctg       696
Arg Arg His Thr Arg Ser Ala Glu Asp Asp Ser Glu Arg Asp Pro Leu
```

-continued

```
          155                 160                 165

aac gtg ctg aag ccc cgg gcc cgg atg acc ccg gcc ccg gcc tcc tgt      744
Asn Val Leu Lys Pro Arg Ala Arg Met Thr Pro Ala Pro Ala Ser Cys
        170                 175                 180

tca cag gag ctc ccg agc gcc gag gac aac agc ccg atg gcc agt gac      792
Ser Gln Glu Leu Pro Ser Ala Glu Asp Asn Ser Pro Met Ala Ser Asp
    185                 190                 195

cca tta ggg gtg gtc agg ggc ggt cga gtg aac acg cac gct ggg gga      840
Pro Leu Gly Val Val Arg Gly Gly Arg Val Asn Thr His Ala Gly Gly
200                 205                 210                 215

acg ggc ccg gaa ggc tgc cgc ccc ttc gcc aag ttc atc tagggtcgct      889
Thr Gly Pro Glu Gly Cys Arg Pro Phe Ala Lys Phe Ile
                220                 225

ggaagggcac cctctttaac ccatccctca gcaaacgcag ctcttcccaa ggaccaggtc    949

ccttgacgtt ccgaggatgg gaaaggtgac aggggcatgt atggaatttg ctgcttctct   1009

ggggtccctt ccacaggagg tcctgtgaga accaaccttt gaggcccaag tcatggggtt   1069

tcaccgcctt cctcactcca tatagaacac ctttcccaat aggaaacccc aacaggtaaa   1129

ctagaaattt ccccttcatg aaggtagaga gaaggggtct ctcccaacat atttctcttc   1189

cttgtgcctc tcctctttat cacttttaag catgaaaaaa aaaaaaaaaa              1239


<210> SEQ ID NO 26
<211> LENGTH: 251
<212> TYPE: PRT
<213> ORGANISM: Homo sapiens
<220> FEATURE:
<221> NAME/KEY: SIGNAL
<222> LOCATION: 1..24

<400> SEQUENCE: 26

Met Leu Gly Ala Arg Leu Arg Leu Trp Val Cys Ala Leu Cys Ser Val
            -20                 -15                 -10

Cys Ser Met Ser Val Leu Arg Ala Tyr Pro Asn Ala Ser Pro Leu Leu
            -5                  1               5

Gly Ser Ser Trp Gly Gly Leu Ile His Leu Tyr Thr Ala Thr Ala Arg
    10                  15                  20

Asn Ser Tyr His Leu Gln Ile His Lys Asn Gly His Val Asp Gly Ala
25                  30                  35                  40

Pro His Gln Thr Ile Tyr Ser Ala Leu Met Ile Arg Ser Glu Asp Ala
                45                  50                  55

Gly Phe Val Val Ile Thr Gly Val Met Ser Arg Arg Tyr Leu Cys Met
            60                  65                  70

Asp Phe Arg Gly Asn Ile Phe Gly Ser His Tyr Phe Asp Pro Glu Asn
        75                  80                  85

Cys Arg Phe Gln His Gln Thr Leu Glu Asn Gly Tyr Asp Val Tyr His
    90                  95                  100

Ser Pro Gln Tyr His Phe Leu Val Ser Leu Gly Arg Ala Lys Arg Ala
105                 110                 115                 120

Phe Leu Pro Gly Met Asn Pro Pro Pro Tyr Ser Gln Phe Leu Ser Arg
                125                 130                 135

Arg Asn Glu Ile Pro Leu Ile His Phe Asn Thr Pro Ile Pro Arg Arg
            140                 145                 150

His Thr Arg Ser Ala Glu Asp Asp Ser Glu Arg Asp Pro Leu Asn Val
        155                 160                 165

Leu Lys Pro Arg Ala Arg Met Thr Pro Ala Pro Ala Ser Cys Ser Gln
    170                 175                 180
```

```
Glu Leu Pro Ser Ala Glu Asp Asn Ser Pro Met Ala Ser Asp Pro Leu
185                 190                 195                 200

Gly Val Val Arg Gly Gly Arg Val Asn Thr His Ala Gly Gly Thr Gly
                205                 210                 215

Pro Glu Gly Cys Arg Pro Phe Ala Lys Phe Ile
            220                 225


<210> SEQ ID NO 27
<211> LENGTH: 1179
<212> TYPE: DNA
<213> ORGANISM: Homo sapiens
<220> FEATURE:
<221> NAME/KEY: 5'UTR
<222> LOCATION: 1..115
<220> FEATURE:
<221> NAME/KEY: CDS
<222> LOCATION: 116..961
<220> FEATURE:
<221> NAME/KEY: 3'UTR
<222> LOCATION: 962..1179
<220> FEATURE:
<221> NAME/KEY: polyA_signal
<222> LOCATION: 1145..1150
<220> FEATURE:
<221> NAME/KEY: polyA_site
<222> LOCATION: 1164..1179

<400> SEQUENCE: 27

acaaattccc aatgcagtta caggatcctg ggaagcagag tgtctggatg gaacctgagc     60

tgggtctctg actcacttct gactttaggc gctcgaggac tgtgcccagg agcag atg     118
                                                             Met
                                                             1

cgg ctc aga gcc cag gtg cgc ctg ctt gag acc cgg gtc aaa cag caa      166
Arg Leu Arg Ala Gln Val Arg Leu Leu Glu Thr Arg Val Lys Gln Gln
            5                   10                  15

cag gtc aag atc aag cag ctt ttg cag gag aat gaa gtc cag ttc ctt      214
Gln Val Lys Ile Lys Gln Leu Leu Gln Glu Asn Glu Val Gln Phe Leu
        20                  25                  30

gat aaa gga gat gag aat act gtc gtt gat ctt gga agc aag agg cag      262
Asp Lys Gly Asp Glu Asn Thr Val Val Asp Leu Gly Ser Lys Arg Gln
    35                  40                  45

tat gca gat tgt tca gag att ttc aat gat ggg tat aag ctc agt gga      310
Tyr Ala Asp Cys Ser Glu Ile Phe Asn Asp Gly Tyr Lys Leu Ser Gly
50                  55                  60                  65

ttt tac aaa atc aaa cct ctc cag agc cca gca gaa ttt tct gtt tat      358
Phe Tyr Lys Ile Lys Pro Leu Gln Ser Pro Ala Glu Phe Ser Val Tyr
                70                  75                  80

tgt gac atg tcc gat gga gga gga tgg act gta att cag aga cga tct      406
Cys Asp Met Ser Asp Gly Gly Gly Trp Thr Val Ile Gln Arg Arg Ser
            85                  90                  95

gat ggc agt gaa aac ttt aac aga gga tgg aaa gac tat gaa aat ggc      454
Asp Gly Ser Glu Asn Phe Asn Arg Gly Trp Lys Asp Tyr Glu Asn Gly
        100                 105                 110

ttt gga amt ttt gtc caa aaa cat ggt gaa tat tgg ctg ggc aat aaa      502
Phe Gly Xaa Phe Val Gln Lys His Gly Glu Tyr Trp Leu Gly Asn Lys
    115                 120                 125

aat ctt cac ttc ttg acc act caa gaa gac tac act tta aaa atc gac      550
Asn Leu His Phe Leu Thr Thr Gln Glu Asp Tyr Thr Leu Lys Ile Asp
130                 135                 140                 145

ctt gca gat ttt gaa aaa aat agc cgt tat gca caa tat aag aat ttc      598
Leu Ala Asp Phe Glu Lys Asn Ser Arg Tyr Ala Gln Tyr Lys Asn Phe
                150                 155                 160
```

-continued

```
aaa gtt gga gat gaa aag aat ttc tac gag ttg aat att ggg gaa tat      646
Lys Val Gly Asp Glu Lys Asn Phe Tyr Glu Leu Asn Ile Gly Glu Tyr
            165                 170                 175

tct gga aca gct gga gat tcc ctt gcg ggg aat ttt cat cct gag gtg      694
Ser Gly Thr Ala Gly Asp Ser Leu Ala Gly Asn Phe His Pro Glu Val
        180                 185                 190

cag tgg tgg gct agt cac caa aga atg aaa ttc agc acg tgg gac aga      742
Gln Trp Trp Ala Ser His Gln Arg Met Lys Phe Ser Thr Trp Asp Arg
    195                 200                 205

gat cat gac aac tat gaa ggg aac tgc gca gaa gaa gat cag tct ggc      790
Asp His Asp Asn Tyr Glu Gly Asn Cys Ala Glu Glu Asp Gln Ser Gly
210                 215                 220                 225

tgg tgg ttt aac agg tgt cac tyt gca aac ctg aat ggt gta tac tac      838
Trp Trp Phe Asn Arg Cys His Xaa Ala Asn Leu Asn Gly Val Tyr Tyr
                230                 235                 240

agc ggc ccc tac acg gct aaa aca gac aat ggg att gtc tgg tac acc      886
Ser Gly Pro Tyr Thr Ala Lys Thr Asp Asn Gly Ile Val Trp Tyr Thr
            245                 250                 255

tgg cat ggg tgg tgg tat tct ctg aaa tct gtg gtt atg aaa att agg      934
Trp His Gly Trp Trp Tyr Ser Leu Lys Ser Val Val Met Lys Ile Arg
        260                 265                 270

cca aat gat ttt att cca aat gta att taattgctgc tgttgggctt            981
Pro Asn Asp Phe Ile Pro Asn Val Ile
    275                 280

tcgtttctgc aattcagctt tgtttaaagt gatttgaaaa atactcattc tgaacatatc   1041

catgcgcaat catgataact gttgtgagta gtgcttttca ttcttctcac ttgcctttgt   1101

tacttaatgt gctttcagta cagcagatat gcaatattca ccaaataaat gtagactgtg   1161

tcaaaaaaaa aaaaaaa                                                   1179


<210> SEQ ID NO 28
<211> LENGTH: 282
<212> TYPE: PRT
<213> ORGANISM: Homo sapiens
<220> FEATURE:
<221> NAME/KEY: UNSURE
<222> LOCATION: 116
<223> OTHER INFORMATION: Xaa = Asn,Thr
<220> FEATURE:
<221> NAME/KEY: UNSURE
<222> LOCATION: 233
<223> OTHER INFORMATION: Xaa = Phe,Ser

<400> SEQUENCE: 28

Met Arg Leu Arg Ala Gln Val Arg Leu Leu Glu Thr Arg Val Lys Gln
1               5                   10                  15

Gln Gln Val Lys Ile Lys Gln Leu Leu Gln Glu Asn Glu Val Gln Phe
            20                  25                  30

Leu Asp Lys Gly Asp Glu Asn Thr Val Val Asp Leu Gly Ser Lys Arg
        35                  40                  45

Gln Tyr Ala Asp Cys Ser Glu Ile Phe Asn Asp Gly Tyr Lys Leu Ser
    50                  55                  60

Gly Phe Tyr Lys Ile Lys Pro Leu Gln Ser Pro Ala Glu Phe Ser Val
65                  70                  75                  80

Tyr Cys Asp Met Ser Asp Gly Gly Gly Trp Thr Val Ile Gln Arg Arg
                85                  90                  95

Ser Asp Gly Ser Glu Asn Phe Asn Arg Gly Trp Lys Asp Tyr Glu Asn
            100                 105                 110

Gly Phe Gly Xaa Phe Val Gln Lys His Gly Glu Tyr Trp Leu Gly Asn
        115                 120                 125
```

```
Lys Asn Leu His Phe Leu Thr Thr Gln Glu Asp Tyr Thr Leu Lys Ile
    130                 135                 140

Asp Leu Ala Asp Phe Glu Lys Asn Ser Arg Tyr Ala Gln Tyr Lys Asn
145                 150                 155                 160

Phe Lys Val Gly Asp Glu Lys Asn Phe Tyr Glu Leu Asn Ile Gly Glu
                165                 170                 175

Tyr Ser Gly Thr Ala Gly Asp Ser Leu Ala Gly Asn Phe His Pro Glu
            180                 185                 190

Val Gln Trp Trp Ala Ser His Gln Arg Met Lys Phe Ser Thr Trp Asp
        195                 200                 205

Arg Asp His Asp Asn Tyr Glu Gly Asn Cys Ala Glu Glu Asp Gln Ser
    210                 215                 220

Gly Trp Trp Phe Asn Arg Cys His Xaa Ala Asn Leu Asn Gly Val Tyr
225                 230                 235                 240

Tyr Ser Gly Pro Tyr Thr Ala Lys Thr Asp Asn Gly Ile Val Trp Tyr
                245                 250                 255

Thr Trp His Gly Trp Trp Tyr Ser Leu Lys Ser Val Val Met Lys Ile
            260                 265                 270

Arg Pro Asn Asp Phe Ile Pro Asn Val Ile
        275                 280


<210> SEQ ID NO 29
<211> LENGTH: 1118
<212> TYPE: DNA
<213> ORGANISM: Homo sapiens
<220> FEATURE:
<221> NAME/KEY: 5'UTR
<222> LOCATION: 1..344
<220> FEATURE:
<221> NAME/KEY: CDS
<222> LOCATION: 345..1118
<220> FEATURE:
<221> NAME/KEY: polyA_site
<222> LOCATION: 1103..1118

<400> SEQUENCE: 29

aatcctagtc ttcgtttggt ccggttgcac tcttcctata gcccagaggg cgagagggcc      60

tgtggcctgg gggaaggagg acgaggttct gcctggatcc cagcaggacg ctgtgccatt     120

tgggaacaaa ggaatagtct gcctggaatc cctgcagatc ttggggccgg aggccagtcc     180

aacccttgga gcaggaagaa acgcaaagtt gtcaagaacc aagtcgagct gcctcagagc     240

cggcccgcag tagctgcaga ctccgcccgc gacgtgtgcg cgcttctctg ggccagagcg     300

agcctgtttt gtgctcgggt taagagattt gtcccagcta tacc atg ggc cgc act      356
                                                 Met Gly Arg Thr

cgg gaa gct ggc tgc gtg gcc gct ggt gtg gtt atc ggg gct ggt gcc       404
Arg Glu Ala Gly Cys Val Ala Ala Gly Val Val Ile Gly Ala Gly Ala
-15                 -10                 -5                  1

tgc tac tgt gta tac aga ctg gct tgg gga aga gac gag aac gag aaa       452
Cys Tyr Cys Val Tyr Arg Leu Ala Trp Gly Arg Asp Glu Asn Glu Lys
            5                   10                  15

atc tgg gac gaa gac gag gag tct acg gac acc tca kag att ggg gtt       500
Ile Trp Asp Glu Asp Glu Glu Ser Thr Asp Thr Ser Xaa Ile Gly Val
        20                  25                  30

gag act gtg aaa gga gct aaa act aac gct ggg gca ggg tct ggg gcc       548
Glu Thr Val Lys Gly Ala Lys Thr Asn Ala Gly Ala Gly Ser Gly Ala
    35                  40                  45

aaa ctt cag ggt gat tca gag gtc aag cct gag gtg agt ttg gga ctc       596
Lys Leu Gln Gly Asp Ser Glu Val Lys Pro Glu Val Ser Leu Gly Leu
```

-continued

```
50                  55                  60                  65

gag gat tgt ccg ggt gta aaa gag aag gcc cat tca gga tcc cac agc      644
Glu Asp Cys Pro Gly Val Lys Glu Lys Ala His Ser Gly Ser His Ser
                70                  75                  80

gga ggt ggc cta gag gcc aag gcc aag gcc ctt ttc aac acg ctg aag      692
Gly Gly Gly Leu Glu Ala Lys Ala Lys Ala Leu Phe Asn Thr Leu Lys
            85                  90                  95

gaa cag gca agt gca aag gca ggc aaa ggg gct agg gtg ggt acc atc      740
Glu Gln Ala Ser Ala Lys Ala Gly Lys Gly Ala Arg Val Gly Thr Ile
        100                 105                 110

tct ggg aac agg acc ctt gca ccg agt tta ccc tgc cca gga ggc agg      788
Ser Gly Asn Arg Thr Leu Ala Pro Ser Leu Pro Cys Pro Gly Gly Arg
    115                 120                 125

ggt gga ggc tgc cac ccc acc agg agt gga tct agg gcc ggg ggc agg      836
Gly Gly Gly Cys His Pro Thr Arg Ser Gly Ser Arg Ala Gly Gly Arg
130                 135                 140                 145

gca agt gga aaa tcc aag gga aag gcc cga agt aag agc acc agg gct      884
Ala Ser Gly Lys Ser Lys Gly Lys Ala Arg Ser Lys Ser Thr Arg Ala
                150                 155                 160

cca gct aca aca tgg cct gtc cgg aga ggc aag ttc aac ttt cct tat      932
Pro Ala Thr Thr Trp Pro Val Arg Arg Gly Lys Phe Asn Phe Pro Tyr
            165                 170                 175

aaa att gat gat att ctg agt gct ccc gac ctc caa aag gtc ctc aac      980
Lys Ile Asp Asp Ile Leu Ser Ala Pro Asp Leu Gln Lys Val Leu Asn
        180                 185                 190

atc ctg gag cga aca aat gat cct ttt att caa gaa gta gcc ttg gtc     1028
Ile Leu Glu Arg Thr Asn Asp Pro Phe Ile Gln Glu Val Ala Leu Val
    195                 200                 205

act ctg ggt aac aat gca gca tat tca ttt aac cag aat gcc ata cgt     1076
Thr Leu Gly Asn Asn Ala Ala Tyr Ser Phe Asn Gln Asn Ala Ile Arg
210                 215                 220                 225

gaa ttg ggt ggt gtc cca att att gca aaa aaa aaa aaa aaa             1118
Glu Leu Gly Gly Val Pro Ile Ile Ala Lys Lys Lys Lys Lys
                230                 235


<210> SEQ ID NO 30
<211> LENGTH: 258
<212> TYPE: PRT
<213> ORGANISM: Homo sapiens
<220> FEATURE:
<221> NAME/KEY: SIGNAL
<222> LOCATION: 1..20
<220> FEATURE:
<221> NAME/KEY: UNSURE
<222> LOCATION: 49
<223> OTHER INFORMATION: Xaa = Glu, *

<400> SEQUENCE: 30

Met Gly Arg Thr Arg Glu Ala Gly Cys Val Ala Ala Gly Val Val Ile
-20                 -15                 -10                 -5

Gly Ala Gly Ala Cys Tyr Cys Val Tyr Arg Leu Ala Trp Gly Arg Asp
                1               5                   10

Glu Asn Glu Lys Ile Trp Asp Glu Asp Glu Glu Ser Thr Asp Thr Ser
        15                  20                  25

Xaa Ile Gly Val Glu Thr Val Lys Gly Ala Lys Thr Asn Ala Gly Ala
    30                  35                  40

Gly Ser Gly Ala Lys Leu Gln Gly Asp Ser Glu Val Lys Pro Glu Val
45                  50                  55                  60

Ser Leu Gly Leu Glu Asp Cys Pro Gly Val Lys Glu Lys Ala His Ser
                65                  70                  75
```

-continued

```
Gly Ser His Ser Gly Gly Gly Leu Glu Ala Lys Ala Lys Ala Leu Phe
            80                  85                  90

Asn Thr Leu Lys Glu Gln Ala Ser Ala Lys Ala Gly Lys Gly Ala Arg
        95                  100                 105

Val Gly Thr Ile Ser Gly Asn Arg Thr Leu Ala Pro Ser Leu Pro Cys
    110                 115                 120

Pro Gly Gly Arg Gly Gly Gly Cys His Pro Thr Arg Ser Gly Ser Arg
125                 130                 135                 140

Ala Gly Gly Arg Ala Ser Gly Lys Ser Lys Gly Lys Ala Arg Ser Lys
                145                 150                 155

Ser Thr Arg Ala Pro Ala Thr Thr Trp Pro Val Arg Arg Gly Lys Phe
            160                 165                 170

Asn Phe Pro Tyr Lys Ile Asp Asp Ile Leu Ser Ala Pro Asp Leu Gln
        175                 180                 185

Lys Val Leu Asn Ile Leu Glu Arg Thr Asn Asp Pro Phe Ile Gln Glu
    190                 195                 200

Val Ala Leu Val Thr Leu Gly Asn Asn Ala Ala Tyr Ser Phe Asn Gln
205                 210                 215                 220

Asn Ala Ile Arg Glu Leu Gly Gly Val Pro Ile Ile Ala Lys Lys Lys
                225                 230                 235

Lys Lys


<210> SEQ ID NO 31
<211> LENGTH: 1273
<212> TYPE: DNA
<213> ORGANISM: Homo sapiens
<220> FEATURE:
<221> NAME/KEY: 5'UTR
<222> LOCATION: 1..13
<220> FEATURE:
<221> NAME/KEY: CDS
<222> LOCATION: 14..1048
<220> FEATURE:
<221> NAME/KEY: 3'UTR
<222> LOCATION: 1049..1273
<220> FEATURE:
<221> NAME/KEY: polyA_signal
<222> LOCATION: 1234..1239
<220> FEATURE:
<221> NAME/KEY: polyA_site
<222> LOCATION: 1258..1273

<400> SEQUENCE: 31

agaggttggg aag atg gcg tgg cga ggc tgg gcg cag aga ggc tgg ggc       49
               Met Ala Trp Arg Gly Trp Ala Gln Arg Gly Trp Gly
               -25                 -20                 -15

tgc ggc cag gcg tgg ggt gcg tcg gtg ggc ggc cgc agc tgc gag gag       97
Cys Gly Gln Ala Trp Gly Ala Ser Val Gly Gly Arg Ser Cys Glu Glu
            -10                 -5                  1

ctc act gcg gtc cta acc ccg ccg cag ctc ctc gga cgc agg ttt aac      145
Leu Thr Ala Val Leu Thr Pro Pro Gln Leu Leu Gly Arg Arg Phe Asn
    5                   10                  15

ttc ttt att caa caa aaa tgc gga ttc aga aaa gca ccc agg aag gtt      193
Phe Phe Ile Gln Gln Lys Cys Gly Phe Arg Lys Ala Pro Arg Lys Val
20                  25                  30                  35

gaa cct cga aga tca gac cca ggg aca agt ggt gaa gca tac aag aga      241
Glu Pro Arg Arg Ser Asp Pro Gly Thr Ser Gly Glu Ala Tyr Lys Arg
                40                  45                  50

agt gct ttg att cct cct gtg gaa gaa aca gtc ttt tat cct tct ccc      289
Ser Ala Leu Ile Pro Pro Val Glu Glu Thr Val Phe Tyr Pro Ser Pro
            55                  60                  65
```

-continued

```
tat cct ata agg agt ctc ata aaa cct tta ttt ttt act gtt ggg ttt      337
Tyr Pro Ile Arg Ser Leu Ile Lys Pro Leu Phe Phe Thr Val Gly Phe
        70                  75                  80

aca ggc tgt gca ttt gga tca gct gct att tgg caa tat gaa tca ctg      385
Thr Gly Cys Ala Phe Gly Ser Ala Ala Ile Trp Gln Tyr Glu Ser Leu
    85                  90                  95

aaa tcc agg gtc cag agt tat ttt gat ggt ata aaa gct gat tgg ttg      433
Lys Ser Arg Val Gln Ser Tyr Phe Asp Gly Ile Lys Ala Asp Trp Leu
100                 105                 110                 115

gat agc ata aga cca caa aaa gaa gga gac ttc aga aag gag att aac      481
Asp Ser Ile Arg Pro Gln Lys Glu Gly Asp Phe Arg Lys Glu Ile Asn
                120                 125                 130

aag tgg tgg aat aac cta agt gat ggc cag cgg act gtg aca ggt att      529
Lys Trp Trp Asn Asn Leu Ser Asp Gly Gln Arg Thr Val Thr Gly Ile
            135                 140                 145

ata gct gca aat gtc ctt gta ttc tgt tta tgg aga gta cct tct ctg      577
Ile Ala Ala Asn Val Leu Val Phe Cys Leu Trp Arg Val Pro Ser Leu
        150                 155                 160

cag cgg aca atg atc aga tat ttc aca tcg aat cca gcc tca aag gtc      625
Gln Arg Thr Met Ile Arg Tyr Phe Thr Ser Asn Pro Ala Ser Lys Val
    165                 170                 175

ctt tgt tct cca atg ttg ctg tca aca ttc agt cat ttc tcc tta ttt      673
Leu Cys Ser Pro Met Leu Leu Ser Thr Phe Ser His Phe Ser Leu Phe
180                 185                 190                 195

cac atg gca gca aat atg tat gtt ttg tgg agc ttc tct tcc agc ata      721
His Met Ala Ala Asn Met Tyr Val Leu Trp Ser Phe Ser Ser Ser Ile
                200                 205                 210

gtg aac att ctg ggt caa gag cag ttc atg gca gtg tac cta tct gca      769
Val Asn Ile Leu Gly Gln Glu Gln Phe Met Ala Val Tyr Leu Ser Ala
            215                 220                 225

ggt gtt att tcc aat ttt gtc agt tac gtg ggt aaa gtt gcc aca gga      817
Gly Val Ile Ser Asn Phe Val Ser Tyr Val Gly Lys Val Ala Thr Gly
        230                 235                 240

aga tat gga cca tca ctt ggt gca gcc ctg aaa gcc att atc gcc atg      865
Arg Tyr Gly Pro Ser Leu Gly Ala Ala Leu Lys Ala Ile Ile Ala Met
    245                 250                 255

gat aca gca gga atg atc ctg gga tgg aaa ttt ttt gat cat gcg gca      913
Asp Thr Ala Gly Met Ile Leu Gly Trp Lys Phe Phe Asp His Ala Ala
260                 265                 270                 275

cat ctt ggg gga gct ctt ttt gga ata tgg tat gtt act tac ggt cat      961
His Leu Gly Gly Ala Leu Phe Gly Ile Trp Tyr Val Thr Tyr Gly His
                280                 285                 290

gaa ctg att tgg aag aac agg gag ccg cta gtg aaa atc tgg cat gaa     1009
Glu Leu Ile Trp Lys Asn Arg Glu Pro Leu Val Lys Ile Trp His Glu
            295                 300                 305

ata agg act aat ggc ccc aaa aaa gga ggt ggc tct aag taaaactggg     1058
Ile Arg Thr Asn Gly Pro Lys Lys Gly Gly Gly Ser Lys
        310                 315                 320

attggacagt agtggtgcat ctggtccttg ccgcctgaga gccccaggag acatcggcta   1118

gagtgaccat ggctatgctc ccgtctggaa gatgccagca tctggcctcc cactttttc   1178

agctgtgtcc cccagtccgt gtctttttag aatgtgaatg atgataaagt tgtgaaataa   1238

aggtttctat ctagtttgca aaaaaaaaaa aaaaa                              1273
```

<210> SEQ ID NO 32
<211> LENGTH: 345
<212> TYPE: PRT
<213> ORGANISM: Homo sapiens
<220> FEATURE:
<221> NAME/KEY: SIGNAL

```
<222> LOCATION: 1..26

<400> SEQUENCE: 32

Met Ala Trp Arg Gly Trp Ala Gln Arg Gly Trp Gly Cys Gly Gln Ala
    -25                 -20                 -15

Trp Gly Ala Ser Val Gly Gly Arg Ser Cys Glu Glu Leu Thr Ala Val
-10                 -5                  1               5

Leu Thr Pro Pro Gln Leu Leu Gly Arg Arg Phe Asn Phe Phe Ile Gln
            10                  15                  20

Gln Lys Cys Gly Phe Arg Lys Ala Pro Arg Lys Val Glu Pro Arg Arg
        25                  30                  35

Ser Asp Pro Gly Thr Ser Gly Glu Ala Tyr Lys Arg Ser Ala Leu Ile
    40                  45                  50

Pro Pro Val Glu Glu Thr Val Phe Tyr Pro Ser Pro Tyr Pro Ile Arg
55                  60                  65                  70

Ser Leu Ile Lys Pro Leu Phe Phe Thr Val Gly Phe Thr Gly Cys Ala
                75                  80                  85

Phe Gly Ser Ala Ala Ile Trp Gln Tyr Glu Ser Leu Lys Ser Arg Val
            90                  95                  100

Gln Ser Tyr Phe Asp Gly Ile Lys Ala Asp Trp Leu Asp Ser Ile Arg
        105                 110                 115

Pro Gln Lys Glu Gly Asp Phe Arg Lys Glu Ile Asn Lys Trp Trp Asn
    120                 125                 130

Asn Leu Ser Asp Gly Gln Arg Thr Val Thr Gly Ile Ile Ala Ala Asn
135                 140                 145                 150

Val Leu Val Phe Cys Leu Trp Arg Val Pro Ser Leu Gln Arg Thr Met
                155                 160                 165

Ile Arg Tyr Phe Thr Ser Asn Pro Ala Ser Lys Val Leu Cys Ser Pro
            170                 175                 180

Met Leu Leu Ser Thr Phe Ser His Phe Ser Leu Phe His Met Ala Ala
        185                 190                 195

Asn Met Tyr Val Leu Trp Ser Phe Ser Ser Ser Ile Val Asn Ile Leu
    200                 205                 210

Gly Gln Glu Gln Phe Met Ala Val Tyr Leu Ser Ala Gly Val Ile Ser
215                 220                 225                 230

Asn Phe Val Ser Tyr Val Gly Lys Val Ala Thr Gly Arg Tyr Gly Pro
                235                 240                 245

Ser Leu Gly Ala Ala Leu Lys Ala Ile Ile Ala Met Asp Thr Ala Gly
            250                 255                 260

Met Ile Leu Gly Trp Lys Phe Phe Asp His Ala Ala His Leu Gly Gly
        265                 270                 275

Ala Leu Phe Gly Ile Trp Tyr Val Thr Tyr Gly His Glu Leu Ile Trp
    280                 285                 290

Lys Asn Arg Glu Pro Leu Val Lys Ile Trp His Glu Ile Arg Thr Asn
295                 300                 305                 310

Gly Pro Lys Lys Gly Gly Gly Ser Lys
                315


<210> SEQ ID NO 33
<211> LENGTH: 723
<212> TYPE: DNA
<213> ORGANISM: Homo sapiens
<220> FEATURE:
<221> NAME/KEY: 5'UTR
<222> LOCATION: 1..72
<220> FEATURE:
```

```
<221> NAME/KEY: CDS
<222> LOCATION: 73..672
<220> FEATURE:
<221> NAME/KEY: 3'UTR
<222> LOCATION: 673..723
<220> FEATURE:
<221> NAME/KEY: polyA_signal
<222> LOCATION: 689..694
<220> FEATURE:
<221> NAME/KEY: polyA_site
<222> LOCATION: 708..723

<400> SEQUENCE: 33

acaagaaaag aacatggtct agactgaagt accaactaaa tcatctcctt tcaaattatc      60

accgacacca tc atg gat tca agc acc gca cac agt ccg gtg ttt ctg gta     111
              Met Asp Ser Ser Thr Ala His Ser Pro Val Phe Leu Val
              1               5                   10

ttt cct cca gaa atc act gct tca gaa tat gag tcc aca gaa ctt tca      159
Phe Pro Pro Glu Ile Thr Ala Ser Glu Tyr Glu Ser Thr Glu Leu Ser
    15                  20                  25

gcc acg acc ttt tca act caa agc ccc ttg caa aaa tta ttt gct aga      207
Ala Thr Thr Phe Ser Thr Gln Ser Pro Leu Gln Lys Leu Phe Ala Arg
30                  35                  40                  45

aaa atg aaa atc tta ggg act atc cag atc ctg ttt gga att atg acc      255
Lys Met Lys Ile Leu Gly Thr Ile Gln Ile Leu Phe Gly Ile Met Thr
                50                  55                  60

ttt tct ttt gga gtt atc ttc ctt ttc acc ttg tta aaa cca tat cca      303
Phe Ser Phe Gly Val Ile Phe Leu Phe Thr Leu Leu Lys Pro Tyr Pro
            65                  70                  75

agg ttt ccc ttt ata ttt ctt tca gga tat cca ttc tgg ggc tct gtt      351
Arg Phe Pro Phe Ile Phe Leu Ser Gly Tyr Pro Phe Trp Gly Ser Val
        80                  85                  90

ttg ttc att aat tct gga gcc ttc cta att gca gtg aaa aga aaa acc      399
Leu Phe Ile Asn Ser Gly Ala Phe Leu Ile Ala Val Lys Arg Lys Thr
    95                  100                 105

aca gaa act ctg ata ata ttg agc cga ata atg aat ttt ctt agt gcc      447
Thr Glu Thr Leu Ile Ile Leu Ser Arg Ile Met Asn Phe Leu Ser Ala
110                 115                 120                 125

ctg gga gca ata gct gga atc att ctc ctc aca ttt ggt ttc atc cta      495
Leu Gly Ala Ile Ala Gly Ile Ile Leu Leu Thr Phe Gly Phe Ile Leu
                130                 135                 140

gat caa aac tac att tgt ggt tat tct cac caa aat agt cag tgt aag      543
Asp Gln Asn Tyr Ile Cys Gly Tyr Ser His Gln Asn Ser Gln Cys Lys
            145                 150                 155

gct gtt act gtc ctg ttc ttg gga att ttg att aca ttg atg act ttc      591
Ala Val Thr Val Leu Phe Leu Gly Ile Leu Ile Thr Leu Met Thr Phe
        160                 165                 170

agc att att gaa tta ttc att tct ctg cct ttc tca att ttg ggg tgc      639
Ser Ile Ile Glu Leu Phe Ile Ser Leu Pro Phe Ser Ile Leu Gly Cys
    175                 180                 185

cac tca gag gat tgt gat tgt gaa caa tgt tgt tgactagcac tgtgagaata    692
His Ser Glu Asp Cys Asp Cys Glu Gln Cys Cys
190                 195                 200

aagatgtgtt aaaataaaaa aaaaaaaaaa t                                    723


<210> SEQ ID NO 34
<211> LENGTH: 200
<212> TYPE: PRT
<213> ORGANISM: Homo sapiens

<400> SEQUENCE: 34

Met Asp Ser Ser Thr Ala His Ser Pro Val Phe Leu Val Phe Pro Pro
```

```
1               5                   10                  15

Glu Ile Thr Ala Ser Glu Tyr Glu Ser Thr Glu Leu Ser Ala Thr Thr
            20                  25                  30

Phe Ser Thr Gln Ser Pro Leu Gln Lys Leu Phe Ala Arg Lys Met Lys
        35                  40                  45

Ile Leu Gly Thr Ile Gln Ile Leu Phe Gly Ile Met Thr Phe Ser Phe
    50                  55                  60

Gly Val Ile Phe Leu Phe Thr Leu Leu Lys Pro Tyr Pro Arg Phe Pro
65                  70                  75                  80

Phe Ile Phe Leu Ser Gly Tyr Pro Phe Trp Gly Ser Val Leu Phe Ile
                85                  90                  95

Asn Ser Gly Ala Phe Leu Ile Ala Val Lys Arg Lys Thr Thr Glu Thr
            100                 105                 110

Leu Ile Ile Leu Ser Arg Ile Met Asn Phe Leu Ser Ala Leu Gly Ala
        115                 120                 125

Ile Ala Gly Ile Ile Leu Leu Thr Phe Gly Phe Ile Leu Asp Gln Asn
    130                 135                 140

Tyr Ile Cys Gly Tyr Ser His Gln Asn Ser Gln Cys Lys Ala Val Thr
145                 150                 155                 160

Val Leu Phe Leu Gly Ile Leu Ile Thr Leu Met Thr Phe Ser Ile Ile
                165                 170                 175

Glu Leu Phe Ile Ser Leu Pro Phe Ser Ile Leu Gly Cys His Ser Glu
            180                 185                 190

Asp Cys Asp Cys Glu Gln Cys Cys
        195                 200


<210> SEQ ID NO 35
<211> LENGTH: 845
<212> TYPE: DNA
<213> ORGANISM: Homo sapiens
<220> FEATURE:
<221> NAME/KEY: 5'UTR
<222> LOCATION: 1..118
<220> FEATURE:
<221> NAME/KEY: CDS
<222> LOCATION: 119..655
<220> FEATURE:
<221> NAME/KEY: 3'UTR
<222> LOCATION: 656..845
<220> FEATURE:
<221> NAME/KEY: polyA_signal
<222> LOCATION: 809..814
<220> FEATURE:
<221> NAME/KEY: polyA_site
<222> LOCATION: 830..845

<400> SEQUENCE: 35

acaaatagcc ccggatatct gtgttaccag ccttgtctcg gccacctcaa ggataatcac      60

taaattctgc caaaaggact gaggaacggt gcctggaaaa gggcaagaat atcacggc       118

atg ggc atg agt agc ttg aaa ctg ctg aag tat gtc ctg ttt ttc ttc       166
Met Gly Met Ser Ser Leu Lys Leu Leu Lys Tyr Val Leu Phe Phe Phe
1               5                   10                  15

aac ttg ctc ttt tgg atc tgt ggc tgc tgc att ttg ggc ttt ggg atc       214
Asn Leu Leu Phe Trp Ile Cys Gly Cys Cys Ile Leu Gly Phe Gly Ile
            20                  25                  30

tac ctg ctg atc cac aac aac ttc gga gtg ctc ttc cat aac ctc ccc       262
Tyr Leu Leu Ile His Asn Asn Phe Gly Val Leu Phe His Asn Leu Pro
        35                  40                  45

tcc ctc acg ctg ggc aat gtg ttt gtc atc gtg ggc tct att atc atg       310
Ser Leu Thr Leu Gly Asn Val Phe Val Ile Val Gly Ser Ile Ile Met
```

-continued

```
    50                  55                  60

gta gtt gcc ttc ctg ggc tgc atg ggc tct atc aag gaa aac aag tgt      358
Val Val Ala Phe Leu Gly Cys Met Gly Ser Ile Lys Glu Asn Lys Cys
65                  70                  75                  80

ctg ctt atg tcg ttc ttc atc ctg ctg ctg att atc ctc ctt gct gag      406
Leu Leu Met Ser Phe Phe Ile Leu Leu Leu Ile Ile Leu Leu Ala Glu
                85                  90                  95

gtg acc ttg gcc atc ctg ctc ttt gtg gct aag ggt ctg acc gac agc      454
Val Thr Leu Ala Ile Leu Leu Phe Val Ala Lys Gly Leu Thr Asp Ser
            100                 105                 110

atc cac cgt tac cac tca gac aat agc acc aag gca gcg tgg gac tcc      502
Ile His Arg Tyr His Ser Asp Asn Ser Thr Lys Ala Ala Trp Asp Ser
        115                 120                 125

atc cag tca ttt ctg cag tgt tgt ggt ata aat ggc acg agt gat tgg      550
Ile Gln Ser Phe Leu Gln Cys Cys Gly Ile Asn Gly Thr Ser Asp Trp
    130                 135                 140

acc agt ggc cca cca gca tct tgc ccc tca gat cga aaa gtg gag ggt      598
Thr Ser Gly Pro Pro Ala Ser Cys Pro Ser Asp Arg Lys Val Glu Gly
145                 150                 155                 160

tgc tat gcg aaa gca aga ctg tgg ttt cat tcc aat ttc ttt att aga      646
Cys Tyr Ala Lys Ala Arg Leu Trp Phe His Ser Asn Phe Phe Ile Arg
                165                 170                 175

ggg cct tat tgatgtgttc taagtctttc cagaaaaaaa ctatccagtg              695
Gly Pro Tyr

atttatatcc tgatttcaac cagtcactta gctgataatc acagtaagaa gacttctggt    755

attatctctc tatcagataa gattttgtta atgtactatt ttactcttca ataaataaaa    815

cagtttatta tcgcaaaaaa aaaaaaaaaa                                      845


<210> SEQ ID NO 36
<211> LENGTH: 179
<212> TYPE: PRT
<213> ORGANISM: Homo sapiens

<400> SEQUENCE: 36

Met Gly Met Ser Ser Leu Lys Leu Leu Lys Tyr Val Leu Phe Phe Phe
1               5                   10                  15

Asn Leu Leu Phe Trp Ile Cys Gly Cys Cys Ile Leu Gly Phe Gly Ile
            20                  25                  30

Tyr Leu Leu Ile His Asn Asn Phe Gly Val Leu Phe His Asn Leu Pro
        35                  40                  45

Ser Leu Thr Leu Gly Asn Val Phe Val Ile Val Gly Ser Ile Ile Met
    50                  55                  60

Val Val Ala Phe Leu Gly Cys Met Gly Ser Ile Lys Glu Asn Lys Cys
65                  70                  75                  80

Leu Leu Met Ser Phe Phe Ile Leu Leu Leu Ile Ile Leu Leu Ala Glu
                85                  90                  95

Val Thr Leu Ala Ile Leu Leu Phe Val Ala Lys Gly Leu Thr Asp Ser
            100                 105                 110

Ile His Arg Tyr His Ser Asp Asn Ser Thr Lys Ala Ala Trp Asp Ser
        115                 120                 125

Ile Gln Ser Phe Leu Gln Cys Cys Gly Ile Asn Gly Thr Ser Asp Trp
    130                 135                 140

Thr Ser Gly Pro Pro Ala Ser Cys Pro Ser Asp Arg Lys Val Glu Gly
145                 150                 155                 160

Cys Tyr Ala Lys Ala Arg Leu Trp Phe His Ser Asn Phe Phe Ile Arg
                165                 170                 175
```

```
Gly Pro Tyr

<210> SEQ ID NO 37
<211> LENGTH: 517
<212> TYPE: DNA
<213> ORGANISM: Homo sapiens
<220> FEATURE:
<221> NAME/KEY: 5'UTR
<222> LOCATION: 1..16
<220> FEATURE:
<221> NAME/KEY: CDS
<222> LOCATION: 17..259
<220> FEATURE:
<221> NAME/KEY: 3'UTR
<222> LOCATION: 260..517

<400> SEQUENCE: 37

ttccatagaa tgggag atg tca cca ggg cag cct atg aca ttc ccc cca gag     52
                  Met Ser Pro Gly Gln Pro Met Thr Phe Pro Pro Glu
                  1               5                   10

gcc ctg tgg gtg acc gtg ggg ctg tct gtc tgt ctc att gca ctg ctg      100
Ala Leu Trp Val Thr Val Gly Leu Ser Val Cys Leu Ile Ala Leu Leu
        15                  20                  25

gtg gcc ctg gct ttc gtg tgc tgg aga aag atc aaa cag agc tgt gag      148
Val Ala Leu Ala Phe Val Cys Trp Arg Lys Ile Lys Gln Ser Cys Glu
    30                  35                  40

gag gag aat gca gga gct gag gac cag gat ggg gag gga gaa ggc tcc      196
Glu Glu Asn Ala Gly Ala Glu Asp Gln Asp Gly Glu Gly Glu Gly Ser
45                  50                  55                  60

aag aca gcc ctg cag cct ctg aaa cac tct gac agc aaa gaa gat gat      244
Lys Thr Ala Leu Gln Pro Leu Lys His Ser Asp Ser Lys Glu Asp Asp
                65                  70                  75

gga caa gaa ata gcc tgaccatgag gaccagggag ctgctacccc tccctacagc      299
Gly Gln Glu Ile Ala
            80

tcctaccctc tggctgcaat ggggctgcac tgtgagccct gcccccaaca gatgcatcct    359

gctctgacag gtgggctcct tctccaaagg atgcgataca cagaccactg tgcagcctta    419

tttctccaat ggacatgatt cccaagtcat cctgctgcct tttttcttat agacacaatg    479

aacagaccac ccacaacctt agttctctaa gtcatcct                            517


<210> SEQ ID NO 38
<211> LENGTH: 81
<212> TYPE: PRT
<213> ORGANISM: Homo sapiens

<400> SEQUENCE: 38

Met Ser Pro Gly Gln Pro Met Thr Phe Pro Pro Glu Ala Leu Trp Val
1               5                   10                  15

Thr Val Gly Leu Ser Val Cys Leu Ile Ala Leu Leu Val Ala Leu Ala
            20                  25                  30

Phe Val Cys Trp Arg Lys Ile Lys Gln Ser Cys Glu Glu Glu Asn Ala
        35                  40                  45

Gly Ala Glu Asp Gln Asp Gly Glu Gly Glu Gly Ser Lys Thr Ala Leu
    50                  55                  60

Gln Pro Leu Lys His Ser Asp Ser Lys Glu Asp Asp Gly Gln Glu Ile
65                  70                  75                  80

Ala


<210> SEQ ID NO 39
```

```
<211> LENGTH: 1816
<212> TYPE: DNA
<213> ORGANISM: Homo sapiens
<220> FEATURE:
<221> NAME/KEY: 5'UTR
<222> LOCATION: 1..259
<220> FEATURE:
<221> NAME/KEY: CDS
<222> LOCATION: 260..1048
<220> FEATURE:
<221> NAME/KEY: 3'UTR
<222> LOCATION: 1049..1816
<220> FEATURE:
<221> NAME/KEY: polyA_signal
<222> LOCATION: 1782..1787
<220> FEATURE:
<221> NAME/KEY: polyA_site
<222> LOCATION: 1801..1816

<400> SEQUENCE: 39

actctggggc cattgccagc cggctgtagg cattcagggc agtgtcttct gcatctccta     60

ggaacctcgg gagcggcagc tccggcgcct ggtagcgaga ggcgggttcc ggagatcccg    120

gcctcacttc gtcccactgt ggttaggggt gagtcctgcg aatgttaagt gatttgctca    180

aggtgcccat ttcgcaggaa ttggagccca ggccagttct ctgagcctat cattagggct    240

aaaggagtgc gtgatcaga atg gtg tct gga cgg ttc tac ttg tcc tgc ctg     292
                     Met Val Ser Gly Arg Phe Tyr Leu Ser Cys Leu
                                     -15                 -10

ctg ctg ggg tcc ctg ggc tct atg tgc atc ctc ttc act atc tac tgg      340
Leu Leu Gly Ser Leu Gly Ser Met Cys Ile Leu Phe Thr Ile Tyr Trp
            -5                  1               5

atg cag tac tgg cgt ggt ggc ttt gcc tgg aat ggc agc atc tac atg      388
Met Gln Tyr Trp Arg Gly Gly Phe Ala Trp Asn Gly Ser Ile Tyr Met
    10                  15                  20

ttc aac tgg cac cca gtg ctt atg gtt gct ggc atg gtg gta ttc tat      436
Phe Asn Trp His Pro Val Leu Met Val Ala Gly Met Val Val Phe Tyr
25                  30                  35                  40

gga ggt gcg tca ctg gtg tac cgc ctg ccc cag tcg tgg gtg ggg ccc      484
Gly Gly Ala Ser Leu Val Tyr Arg Leu Pro Gln Ser Trp Val Gly Pro
                45                  50                  55

aaa ctg ccc tgg aaa ctc ctc cat gca gcg ctg cac ctg atg gcc ttc      532
Lys Leu Pro Trp Lys Leu Leu His Ala Ala Leu His Leu Met Ala Phe
            60                  65                  70

gtc ctc act gtt gtg ggg ctg gtt gct gtc ttt acg ttt cac aac cat      580
Val Leu Thr Val Val Gly Leu Val Ala Val Phe Thr Phe His Asn His
        75                  80                  85

gga agg act gcc aac ctc tac tcc ctt cac agc tgg ctg ggc atc acc      628
Gly Arg Thr Ala Asn Leu Tyr Ser Leu His Ser Trp Leu Gly Ile Thr
    90                  95                  100

act gtc ttc ctc ttc ggc tgc cag tgg ttc ctg ggc ttt gct gtc ttc      676
Thr Val Phe Leu Phe Gly Cys Gln Trp Phe Leu Gly Phe Ala Val Phe
105                 110                 115                 120

ctc ctg ccc tgg gcg tcc atg tgg ctg cgc agc ctc cta aaa cct atc      724
Leu Leu Pro Trp Ala Ser Met Trp Leu Arg Ser Leu Leu Lys Pro Ile
                125                 130                 135

cac gtc ttt ttt gga gcc gcc atc ctc tct ctg tcc atc gca tcc gtc      772
His Val Phe Phe Gly Ala Ala Ile Leu Ser Leu Ser Ile Ala Ser Val
            140                 145                 150

att tcg ggc att aat gag aag ctt ttc ttc agt ttg aaa aac acc acc      820
Ile Ser Gly Ile Asn Glu Lys Leu Phe Phe Ser Leu Lys Asn Thr Thr
        155                 160                 165

agg cca tac cac agc ctg ccc agt gag gcg gtc ttt gcc aac agc acc      868
Arg Pro Tyr His Ser Leu Pro Ser Glu Ala Val Phe Ala Asn Ser Thr
```

-continued

```
    170                 175                 180

ggg atg ctg gtg gtg gcc ttt ggg ctg ctg gtg ctc tac atc ctt ctg      916
Gly Met Leu Val Val Ala Phe Gly Leu Leu Val Leu Tyr Ile Leu Leu
185                 190                 195                 200

gct tca tct tgg aag cgc cca gag ccg ggg atc ctg acc gac aga cag      964
Ala Ser Ser Trp Lys Arg Pro Glu Pro Gly Ile Leu Thr Asp Arg Gln
                205                 210                 215

ctg ctg cta cag ctg agg cct gga tcc cgg cct ttc cct gtg act tac     1012
Leu Leu Leu Gln Leu Arg Pro Gly Ser Arg Pro Phe Pro Val Thr Tyr
            220                 225                 230

gtg tct gtc acc ggc agg cag ccc tac aaa tcc tgg tgacctgctc          1058
Val Ser Val Thr Gly Arg Gln Pro Tyr Lys Ser Trp
        235                 240

tcccaagaac agagcctgtc cccagatgtc ccagtagcga tgagtaacag aggtggctgt   1118

ggacttcctc tacttctcct tgctggatca gggccttcct gcctcccgct gggcaggtct   1178

ggccttgctc tcttggcagg gccccagccc ctctgaccac tctgcagctc accatgcagc   1238

tgatgccaaa gttgtggtgt ccagtgtgca gcagccctgg gagccactgc caccttcaga   1298

ggggttcctt gctgagaccc acattgcttc acctggcccc accatggctg cttgcctggc   1358

ccaacctagc gttctgtgcc atgctagaac ttgagctgtt gctcttcttc aggggaggaa   1418

atagggtgga gagcgggaag ggtcttgctc ctaagtgttg ctgctgtggc tttttttgcct  1478

tctccaaaga cgcactgcca ggtcccaagc ttcagactgc tgtgcttagt aagcaagtga   1538

gaagcctggg gtttggagcc cacctactct ctggcagcat cagcatccta ctcctggcaa   1598

catcaggcca acgtccaccc cagcctcaca ttgccagatg ttggcagaag ggctaatatt   1658

gaccgtcttg actggctgga gccttcaaag ccactgggat gtcctccagg cacctgggtc   1718

ccatgaccag ctccccgtct ccataggggt aggcatttca ctggtttatg aagctcgagt   1778

ttcattaaat atgttaagaa tcaaaaaaaa aaaaaaaa                           1816


<210> SEQ ID NO 40
<211> LENGTH: 263
<212> TYPE: PRT
<213> ORGANISM: Homo sapiens
<220> FEATURE:
<221> NAME/KEY: SIGNAL
<222> LOCATION: 1..20

<400> SEQUENCE: 40

Met Val Ser Gly Arg Phe Tyr Leu Ser Cys Leu Leu Leu Gly Ser Leu
-20                 -15                 -10                  -5

Gly Ser Met Cys Ile Leu Phe Thr Ile Tyr Trp Met Gln Tyr Trp Arg
                1               5                   10

Gly Gly Phe Ala Trp Asn Gly Ser Ile Tyr Met Phe Asn Trp His Pro
        15                  20                  25

Val Leu Met Val Ala Gly Met Val Val Phe Tyr Gly Gly Ala Ser Leu
    30                  35                  40

Val Tyr Arg Leu Pro Gln Ser Trp Val Gly Pro Lys Leu Pro Trp Lys
45                  50                  55                  60

Leu Leu His Ala Ala Leu His Leu Met Ala Phe Val Leu Thr Val Val
                65                  70                  75

Gly Leu Val Ala Val Phe Thr Phe His Asn His Gly Arg Thr Ala Asn
            80                  85                  90

Leu Tyr Ser Leu His Ser Trp Leu Gly Ile Thr Thr Val Phe Leu Phe
        95                  100                 105
```

```
Gly Cys Gln Trp Phe Leu Gly Phe Ala Val Phe Leu Leu Pro Trp Ala
    110                 115                 120

Ser Met Trp Leu Arg Ser Leu Leu Lys Pro Ile His Val Phe Phe Gly
125                 130                 135                 140

Ala Ala Ile Leu Ser Leu Ser Ile Ala Ser Val Ile Ser Gly Ile Asn
                145                 150                 155

Glu Lys Leu Phe Phe Ser Leu Lys Asn Thr Thr Arg Pro Tyr His Ser
            160                 165                 170

Leu Pro Ser Glu Ala Val Phe Ala Asn Ser Thr Gly Met Leu Val Val
        175                 180                 185

Ala Phe Gly Leu Leu Val Leu Tyr Ile Leu Leu Ala Ser Ser Trp Lys
    190                 195                 200

Arg Pro Glu Pro Gly Ile Leu Thr Asp Arg Gln Leu Leu Leu Gln Leu
205                 210                 215                 220

Arg Pro Gly Ser Arg Pro Phe Pro Val Thr Tyr Val Ser Val Thr Gly
                225                 230                 235

Arg Gln Pro Tyr Lys Ser Trp
            240


<210> SEQ ID NO 41
<211> LENGTH: 643
<212> TYPE: DNA
<213> ORGANISM: Homo sapiens
<220> FEATURE:
<221> NAME/KEY: 5'UTR
<222> LOCATION: 1..90
<220> FEATURE:
<221> NAME/KEY: CDS
<222> LOCATION: 91..462
<220> FEATURE:
<221> NAME/KEY: 3'UTR
<222> LOCATION: 463..643
<220> FEATURE:
<221> NAME/KEY: polyA_signal
<222> LOCATION: 607..612
<220> FEATURE:
<221> NAME/KEY: polyA_site
<222> LOCATION: 628..643

<400> SEQUENCE: 41

acccctaccc cacgcccccct cccgcgcgcg cggttaaatc cccgcacctg agcatcggct      60

cacacctgca ccccgcccgg gcatagcacc atg cct gct tgt cgc cta ggc ccg     114
                                 Met Pro Ala Cys Arg Leu Gly Pro
                                                 -25

cta gcc gcc gcc ctc ctc ctc agc ctg ctg ctg ttc ggc ttc acc cta      162
Leu Ala Ala Ala Leu Leu Leu Ser Leu Leu Leu Phe Gly Phe Thr Leu
    -20                 -15                 -10

gtc tca ggc aca gga gca gag aag act ggc gtg tgc ccc gag ctc cag      210
Val Ser Gly Thr Gly Ala Glu Lys Thr Gly Val Cys Pro Glu Leu Gln
-5                  1               5                   10

gct gac cag aac tgc acg caa gag tgc gtc tcg gac agc gaa tgc gcc      258
Ala Asp Gln Asn Cys Thr Gln Glu Cys Val Ser Asp Ser Glu Cys Ala
            15                  20                  25

gac aac ctc aag tgc tgc agc gcg ggc tgt gcc acc ttc tgc tct ctg      306
Asp Asn Leu Lys Cys Cys Ser Ala Gly Cys Ala Thr Phe Cys Ser Leu
        30                  35                  40

ccc aat gat aag gag ggt tcc tgc ccc cag gtg aac att aac ttt ccc      354
Pro Asn Asp Lys Glu Gly Ser Cys Pro Gln Val Asn Ile Asn Phe Pro
    45                  50                  55

cag ctc ggc ctc tgt cgg gac cag tgc cag gtg gac agc cag tgt cct      402
Gln Leu Gly Leu Cys Arg Asp Gln Cys Gln Val Asp Ser Gln Cys Pro
60                  65                  70                  75
```

-continued

```
ggc cag atg aaa tgc tgc cgc aat ggc tgt ggg aag gtg tcc tgt gtc      450
Gly Gln Met Lys Cys Cys Arg Asn Gly Cys Gly Lys Val Ser Cys Val
                80                  85                  90

act ccc aat ttc tgagctccag ccaccaccag gctgagcagt gaggagagaa          502
Thr Pro Asn Phe
            95

agtttctgcc tggccctgca tctggttcca gcccacctgc cctccccttt ttcgggactc    562

tgtattccct cttgggctga ccacagcttc tccctttccc aaccaataaa gtaaccactt    622

tcagcaaaaa aaaaaaaaaa a                                              643


<210> SEQ ID NO 42
<211> LENGTH: 124
<212> TYPE: PRT
<213> ORGANISM: Homo sapiens
<220> FEATURE:
<221> NAME/KEY: SIGNAL
<222> LOCATION: 1..30

<400> SEQUENCE: 42

Met Pro Ala Cys Arg Leu Gly Pro Leu Ala Ala Ala Leu Leu Leu Ser
-30                 -25                 -20                 -15

Leu Leu Leu Phe Gly Phe Thr Leu Val Ser Gly Thr Gly Ala Glu Lys
                -10                 -5                  1

Thr Gly Val Cys Pro Glu Leu Gln Ala Asp Gln Asn Cys Thr Gln Glu
        5                   10                  15

Cys Val Ser Asp Ser Glu Cys Ala Asp Asn Leu Lys Cys Cys Ser Ala
    20                  25                  30

Gly Cys Ala Thr Phe Cys Ser Leu Pro Asn Asp Lys Glu Gly Ser Cys
35                  40                  45                  50

Pro Gln Val Asn Ile Asn Phe Pro Gln Leu Gly Leu Cys Arg Asp Gln
                55                  60                  65

Cys Gln Val Asp Ser Gln Cys Pro Gly Gln Met Lys Cys Cys Arg Asn
            70                  75                  80

Gly Cys Gly Lys Val Ser Cys Val Thr Pro Asn Phe
        85                  90


<210> SEQ ID NO 43
<211> LENGTH: 501
<212> TYPE: DNA
<213> ORGANISM: Homo sapiens
<220> FEATURE:
<221> NAME/KEY: 5'UTR
<222> LOCATION: 1..227
<220> FEATURE:
<221> NAME/KEY: CDS
<222> LOCATION: 228..501

<400> SEQUENCE: 43

actcttactc tttctctctc actctctctc ttttcccacc cttaagccaa gtacagggat     60

agttgtctca tcattggtgg cttaaaatga tgtttttgaa caagaagaca ccccatggga    120

ctgatctcaa atgcagctgt gactaaaacc tctaggtgct gtgctgtcct gaggcctggg    180

ccatggtgcc caaggaaagc ccctgaagct caccaggagg aagaagc atg cag ggc      236
                                                    Met Gln Gly
                                                            -30

act cct gga ggc ggg acg cgc cct ggg cca tcc ccc gtg gac agg cgg      284
Thr Pro Gly Gly Gly Thr Arg Pro Gly Pro Ser Pro Val Asp Arg Arg
                -25                 -20                 -15

aca ctc ctg gtc ttc agc ttt atc ctg gca gca gct ttg ggc caa atg      332
```

```
Thr Leu Leu Val Phe Ser Phe Ile Leu Ala Ala Ala Leu Gly Gln Met
            -10                 -5                  1

aat ttc aca ggg gac cag gtt ctt cga gtc ctg gcc aaa gat gag aag      380
Asn Phe Thr Gly Asp Gln Val Leu Arg Val Leu Ala Lys Asp Glu Lys
    5                   10                  15

cag ctt tca ctt ctc ggg gat ctg gag ggc ctg aaa ccc cag aag gtg      428
Gln Leu Ser Leu Leu Gly Asp Leu Glu Gly Leu Lys Pro Gln Lys Val
20                  25                  30                  35

gac ttc tgg cgt ggc cca gcc agg ccc agc ctc cct gtg gat atg aga      476
Asp Phe Trp Arg Gly Pro Ala Arg Pro Ser Leu Pro Val Asp Met Arg
                40                  45                  50

gtt cct ttc tcc gaa ctg aaa gac a                                    501
Val Pro Phe Ser Glu Leu Lys Asp
            55


<210> SEQ ID NO 44
<211> LENGTH: 91
<212> TYPE: PRT
<213> ORGANISM: Homo sapiens
<220> FEATURE:
<221> NAME/KEY: SIGNAL
<222> LOCATION: 1..33

<400> SEQUENCE: 44

Met Gln Gly Thr Pro Gly Gly Gly Thr Arg Pro Gly Pro Ser Pro Val
            -30                 -25                 -20

Asp Arg Arg Thr Leu Leu Val Phe Ser Phe Ile Leu Ala Ala Ala Leu
        -15                 -10                 -5

Gly Gln Met Asn Phe Thr Gly Asp Gln Val Leu Arg Val Leu Ala Lys
    1               5                   10                  15

Asp Glu Lys Gln Leu Ser Leu Leu Gly Asp Leu Glu Gly Leu Lys Pro
                20                  25                  30

Gln Lys Val Asp Phe Trp Arg Gly Pro Ala Arg Pro Ser Leu Pro Val
            35                  40                  45

Asp Met Arg Val Pro Phe Ser Glu Leu Lys Asp
        50                  55


<210> SEQ ID NO 45
<211> LENGTH: 960
<212> TYPE: DNA
<213> ORGANISM: Homo sapiens
<220> FEATURE:
<221> NAME/KEY: 5'UTR
<222> LOCATION: 1..97
<220> FEATURE:
<221> NAME/KEY: CDS
<222> LOCATION: 98..934
<220> FEATURE:
<221> NAME/KEY: 3'UTR
<222> LOCATION: 935..960

<400> SEQUENCE: 45

ataatcacct ctcattccag actatgttag gtcttaatgg tgggaggacg cccgagtgct      60

cggcccgttt caccccgagg aggaaggaca ctgggtc atg acg cca tca gaa ggc      115
                                         Met Thr Pro Ser Glu Gly
                                         1               5

gcc aga gca ggg acc gga cgc gag ttg gag atg ttg gac tcg ctg ttg      163
Ala Arg Ala Gly Thr Gly Arg Glu Leu Glu Met Leu Asp Ser Leu Leu
            10                  15                  20

gcc ttg ggc ggc ctg gtg ctg ctt cgg gat tcc gtg gag tgg gag ggg      211
Ala Leu Gly Gly Leu Val Leu Leu Arg Asp Ser Val Glu Trp Glu Gly
        25                  30                  35
```

-continued

```
cgc agt ctc ttg aag gcg ctt gtc aag aaa tct gca ctg tgt ggg gag      259
Arg Ser Leu Leu Lys Ala Leu Val Lys Lys Ser Ala Leu Cys Gly Glu
    40                  45                  50

caa gtg cat atc ctg ggc tgt gaa gtg agc gag gaa gag ttt cgt gaa      307
Gln Val His Ile Leu Gly Cys Glu Val Ser Glu Glu Glu Phe Arg Glu
55                  60                  65                  70

ggt ttt gac tct gat atc aac aat cgg ctg gtt tac cat gac ttc ttc      355
Gly Phe Asp Ser Asp Ile Asn Asn Arg Leu Val Tyr His Asp Phe Phe
                75                  80                  85

aga gac cct ctc aac tgg tca aaa act gag gag gcc ttt cct ggg ggg      403
Arg Asp Pro Leu Asn Trp Ser Lys Thr Glu Glu Ala Phe Pro Gly Gly
            90                  95                  100

ccg ctg gga gcc ttg aga gcc atg tgc aag agg aca gat cct gtt cct      451
Pro Leu Gly Ala Leu Arg Ala Met Cys Lys Arg Thr Asp Pro Val Pro
        105                 110                 115

gtc acc att gct ctc gat tca ctc agc tgg ctg cta ctt cgc ctt ccc      499
Val Thr Ile Ala Leu Asp Ser Leu Ser Trp Leu Leu Leu Arg Leu Pro
    120                 125                 130

tgc acc aca ctc tgc cag gtc ctg cat gct gtg agc cat cag gac tct      547
Cys Thr Thr Leu Cys Gln Val Leu His Ala Val Ser His Gln Asp Ser
135                 140                 145                 150

tgt cct ggt gac agc tcc tca gtg ggg aaa gtg agt gtg ctg ggc ttg      595
Cys Pro Gly Asp Ser Ser Ser Val Gly Lys Val Ser Val Leu Gly Leu
                155                 160                 165

cta cat gaa gag ctt cat gga cca ggc cct gtg gga gct ctc agc agc      643
Leu His Glu Glu Leu His Gly Pro Gly Pro Val Gly Ala Leu Ser Ser
            170                 175                 180

ctt gct cag act gag gtg acc ctg ggc ggt acc atg ggc cag gcc tcg      691
Leu Ala Gln Thr Glu Val Thr Leu Gly Gly Thr Met Gly Gln Ala Ser
        185                 190                 195

gcc cac atc ctg tgt cgg agg ccc cga cag cgc cca act gac cag act      739
Ala His Ile Leu Cys Arg Arg Pro Arg Gln Arg Pro Thr Asp Gln Thr
    200                 205                 210

cag tgg ttc tcc atc ctt ccg gac ttc agc ctg gat ctc caa gag ggg      787
Gln Trp Phe Ser Ile Leu Pro Asp Phe Ser Leu Asp Leu Gln Glu Gly
215                 220                 225                 230

ccc tct gta gag tcc cag ccc tac tcc gat cct cat ata ccc ccg gta      835
Pro Ser Val Glu Ser Gln Pro Tyr Ser Asp Pro His Ile Pro Pro Val
                235                 240                 245

tct aag aat gcc aag gcc aga aca agg aaa tgt agt tta gta tct ggt      883
Ser Lys Asn Ala Lys Ala Arg Thr Arg Lys Cys Ser Leu Val Ser Gly
            250                 255                 260

cac ggg aga gaa aat aaa agc tgc aga ggt tgg ggg tgg ggt cag gga      931
His Gly Arg Glu Asn Lys Ser Cys Arg Gly Trp Gly Trp Gly Gln Gly
        265                 270                 275

ttc tagggatggg gcagagtggc agcatc                                     960
Phe


<210> SEQ ID NO 46
<211> LENGTH: 279
<212> TYPE: PRT
<213> ORGANISM: Homo sapiens

<400> SEQUENCE: 46

Met Thr Pro Ser Glu Gly Ala Arg Ala Gly Thr Gly Arg Glu Leu Glu
1               5                   10                  15

Met Leu Asp Ser Leu Leu Ala Leu Gly Gly Leu Val Leu Leu Arg Asp
            20                  25                  30

Ser Val Glu Trp Glu Gly Arg Ser Leu Leu Lys Ala Leu Val Lys Lys
        35                  40                  45
```

```
Ser Ala Leu Cys Gly Glu Gln Val His Ile Leu Gly Cys Glu Val Ser
    50                  55                  60

Glu Glu Glu Phe Arg Glu Gly Phe Asp Ser Asp Ile Asn Asn Arg Leu
65                  70                  75                  80

Val Tyr His Asp Phe Phe Arg Asp Pro Leu Asn Trp Ser Lys Thr Glu
                85                  90                  95

Glu Ala Phe Pro Gly Gly Pro Leu Gly Ala Leu Arg Ala Met Cys Lys
            100                 105                 110

Arg Thr Asp Pro Val Pro Val Thr Ile Ala Leu Asp Ser Leu Ser Trp
        115                 120                 125

Leu Leu Leu Arg Leu Pro Cys Thr Thr Leu Cys Gln Val Leu His Ala
    130                 135                 140

Val Ser His Gln Asp Ser Cys Pro Gly Asp Ser Ser Ser Val Gly Lys
145                 150                 155                 160

Val Ser Val Leu Gly Leu Leu His Glu Glu Leu His Gly Pro Gly Pro
                165                 170                 175

Val Gly Ala Leu Ser Ser Leu Ala Gln Thr Glu Val Thr Leu Gly Gly
            180                 185                 190

Thr Met Gly Gln Ala Ser Ala His Ile Leu Cys Arg Arg Pro Arg Gln
        195                 200                 205

Arg Pro Thr Asp Gln Thr Gln Trp Phe Ser Ile Leu Pro Asp Phe Ser
    210                 215                 220

Leu Asp Leu Gln Glu Gly Pro Ser Val Glu Ser Gln Pro Tyr Ser Asp
225                 230                 235                 240

Pro His Ile Pro Pro Val Ser Lys Asn Ala Lys Ala Arg Thr Arg Lys
                245                 250                 255

Cys Ser Leu Val Ser Gly His Gly Arg Glu Asn Lys Ser Cys Arg Gly
            260                 265                 270

Trp Gly Trp Gly Gln Gly Phe
        275


<210> SEQ ID NO 47
<211> LENGTH: 1294
<212> TYPE: DNA
<213> ORGANISM: Homo sapiens
<220> FEATURE:
<221> NAME/KEY: 5'UTR
<222> LOCATION: 1..266
<220> FEATURE:
<221> NAME/KEY: CDS
<222> LOCATION: 267..1139
<220> FEATURE:
<221> NAME/KEY: 3'UTR
<222> LOCATION: 1140..1294
<220> FEATURE:
<221> NAME/KEY: polyA_signal
<222> LOCATION: 1246..1251
<220> FEATURE:
<221> NAME/KEY: polyA_site
<222> LOCATION: 1279..1294

<400> SEQUENCE: 47

gactctgagg ctccctcttt gctctaacag acagcagcga ctttaggctg gataatagtc      60

aaattcttac ctcgctcttt cactgctagt aagatcagat tgcgtttctt tcagttactc     120

ttcaatcgcc agtttcttga tctgcttcta aaagaagaag tagagaagat aaatcctgtc     180

ttcaatacct ggaaggaaaa acaaaataac ctcaactccg ttttgaaaaa aacattccaa     240

gaactttcat cagagatttt acttag atg att tac aca atg aag aaa gta cat      293
                             Met Ile Tyr Thr Met Lys Lys Val His
```

-continued

```
                                    -25                 -20

gca ctt tgg gct tct gta tgc ctg ctg ctt aat ctt gcc cct gcc cct        341
Ala Leu Trp Ala Ser Val Cys Leu Leu Leu Asn Leu Ala Pro Ala Pro
            -15                 -10                 -5

ctt aat gct gat tct gag gaa gat gaa gaa cac aca att atc aca gat        389
Leu Asn Ala Asp Ser Glu Glu Asp Glu Glu His Thr Ile Ile Thr Asp
        1               5                   10

acg gag ttg cca cca ctg aaa ctt atg cat tca ttt tgt gca ttc aag        437
Thr Glu Leu Pro Pro Leu Lys Leu Met His Ser Phe Cys Ala Phe Lys
15                  20                  25                  30

gcg gat gat ggc cca tgt aaa gca atc atg aaa aga ttt ttc ttc aat        485
Ala Asp Asp Gly Pro Cys Lys Ala Ile Met Lys Arg Phe Phe Phe Asn
                35                  40                  45

att ttc act cga cag tgc gaa gaa ttt ata tat ggg gga tgt gaa gga        533
Ile Phe Thr Arg Gln Cys Glu Glu Phe Ile Tyr Gly Gly Cys Glu Gly
            50                  55                  60

aat cag aat cga ttt gaa agt ctg gaa gag tgc aaa aaa atg tgt aca        581
Asn Gln Asn Arg Phe Glu Ser Leu Glu Glu Cys Lys Lys Met Cys Thr
        65                  70                  75

aga gaa aag cca gat ttc tgc ttt ttg gaa gaa gat cct gga ata tgt        629
Arg Glu Lys Pro Asp Phe Cys Phe Leu Glu Glu Asp Pro Gly Ile Cys
    80                  85                  90

cga ggt tat att acc agg tat ttt tat aac aat cag aca aaa cag tgt        677
Arg Gly Tyr Ile Thr Arg Tyr Phe Tyr Asn Asn Gln Thr Lys Gln Cys
95                  100                 105                 110

gaa cgt ttc aag tat ggt gga tgc ctg ggc aat atg aac aat ttt gag        725
Glu Arg Phe Lys Tyr Gly Gly Cys Leu Gly Asn Met Asn Asn Phe Glu
                115                 120                 125

aca ctg gaa gaa tgc aag aac att tgt gaa gat ggt ccg aat ggt ttc        773
Thr Leu Glu Glu Cys Lys Asn Ile Cys Glu Asp Gly Pro Asn Gly Phe
            130                 135                 140

cag gtg gat aat tat gga acc cag ctc aat gct gtg aat aac tcc ctg        821
Gln Val Asp Asn Tyr Gly Thr Gln Leu Asn Ala Val Asn Asn Ser Leu
        145                 150                 155

act ccg caa tca acc aag gtt ccc agc ctt ttt gaa ttt cac ggt ccc        869
Thr Pro Gln Ser Thr Lys Val Pro Ser Leu Phe Glu Phe His Gly Pro
    160                 165                 170

tca tgg tgt ctc act cca gca gac aga gga ttg tgt cgt gcc aat gag        917
Ser Trp Cys Leu Thr Pro Ala Asp Arg Gly Leu Cys Arg Ala Asn Glu
175                 180                 185                 190

aac aga ttc tac tac aat tca gtc att ggg aaa tgc cgc cca ttt aag        965
Asn Arg Phe Tyr Tyr Asn Ser Val Ile Gly Lys Cys Arg Pro Phe Lys
                195                 200                 205

tac agt gga tgt ggg gga aat gaa aac aat ttt act tcc aaa caa gaa       1013
Tyr Ser Gly Cys Gly Gly Asn Glu Asn Asn Phe Thr Ser Lys Gln Glu
            210                 215                 220

tgt ctg agg gca tgt aaa aaa ggt ttc atc caa aga ata tca aaa gga       1061
Cys Leu Arg Ala Cys Lys Lys Gly Phe Ile Gln Arg Ile Ser Lys Gly
        225                 230                 235

ggc cta att aaa acc aaa aga aaa aga aag aag cag aga gtg aaa ata       1109
Gly Leu Ile Lys Thr Lys Arg Lys Arg Lys Lys Gln Arg Val Lys Ile
    240                 245                 250

gca tat gaa gaa att ttt gtt aaa aat atg tgaatttgtt atagcaatgt         1159
Ala Tyr Glu Glu Ile Phe Val Lys Asn Met
255                 260
aacattaatt ctactaaata ttttatatga aatgtttcac tatgattttc tatttttctt     1219

ctaaaatgct tttaattaat atgttcatta aattttctat gcttattgta cttgttacca     1279

aaaaaaaaaa aaaaa                                                       1294
```

```
<210> SEQ ID NO 48
<211> LENGTH: 291
<212> TYPE: PRT
<213> ORGANISM: Homo sapiens
<220> FEATURE:
<221> NAME/KEY: SIGNAL
<222> LOCATION: 1..28

<400> SEQUENCE: 48

Met Ile Tyr Thr Met Lys Lys Val His Ala Leu Trp Ala Ser Val Cys
            -25                 -20                 -15

Leu Leu Leu Asn Leu Ala Pro Ala Pro Leu Asn Ala Asp Ser Glu Glu
        -10                 -5                  1

Asp Glu Glu His Thr Ile Ile Thr Asp Thr Glu Leu Pro Pro Leu Lys
5                   10                  15                  20

Leu Met His Ser Phe Cys Ala Phe Lys Ala Asp Asp Gly Pro Cys Lys
                25                  30                  35

Ala Ile Met Lys Arg Phe Phe Phe Asn Ile Phe Thr Arg Gln Cys Glu
            40                  45                  50

Glu Phe Ile Tyr Gly Gly Cys Glu Gly Asn Gln Asn Arg Phe Glu Ser
        55                  60                  65

Leu Glu Glu Cys Lys Lys Met Cys Thr Arg Glu Lys Pro Asp Phe Cys
    70                  75                  80

Phe Leu Glu Glu Asp Pro Gly Ile Cys Arg Gly Tyr Ile Thr Arg Tyr
85                  90                  95                  100

Phe Tyr Asn Asn Gln Thr Lys Gln Cys Glu Arg Phe Lys Tyr Gly Gly
                105                 110                 115

Cys Leu Gly Asn Met Asn Asn Phe Glu Thr Leu Glu Glu Cys Lys Asn
            120                 125                 130

Ile Cys Glu Asp Gly Pro Asn Gly Phe Gln Val Asp Asn Tyr Gly Thr
        135                 140                 145

Gln Leu Asn Ala Val Asn Asn Ser Leu Thr Pro Gln Ser Thr Lys Val
    150                 155                 160

Pro Ser Leu Phe Glu Phe His Gly Pro Ser Trp Cys Leu Thr Pro Ala
165                 170                 175                 180

Asp Arg Gly Leu Cys Arg Ala Asn Glu Asn Arg Phe Tyr Tyr Asn Ser
                185                 190                 195

Val Ile Gly Lys Cys Arg Pro Phe Lys Tyr Ser Gly Cys Gly Gly Asn
            200                 205                 210

Glu Asn Asn Phe Thr Ser Lys Gln Glu Cys Leu Arg Ala Cys Lys Lys
        215                 220                 225

Gly Phe Ile Gln Arg Ile Ser Lys Gly Gly Leu Ile Lys Thr Lys Arg
    230                 235                 240

Lys Arg Lys Lys Gln Arg Val Lys Ile Ala Tyr Glu Glu Ile Phe Val
245                 250                 255                 260

Lys Asn Met


<210> SEQ ID NO 49
<211> LENGTH: 1194
<212> TYPE: DNA
<213> ORGANISM: Homo sapiens
<220> FEATURE:
<221> NAME/KEY: 5'UTR
<222> LOCATION: 1..47
<220> FEATURE:
<221> NAME/KEY: CDS
<222> LOCATION: 48..1100
<220> FEATURE:
```

-continued

```
<221> NAME/KEY: 3'UTR
<222> LOCATION: 1101..1194
<220> FEATURE:
<221> NAME/KEY: polyA_signal
<222> LOCATION: 1159..1164
<220> FEATURE:
<221> NAME/KEY: polyA_site
<222> LOCATION: 1179..1194

<400> SEQUENCE: 49

ctcctcagct tcaggcacca ccactgacct gggacagtga atcgaca atg ccg tct       56
                                                    Met Pro Ser

tct gtc tcg tgg ggc atc ctc ctg ctg gca ggc ctg tgc tgc ctg gtc      104
Ser Val Ser Trp Gly Ile Leu Leu Leu Ala Gly Leu Cys Cys Leu Val
-20                 -15                 -10                 -5

cct gtc tcc ctg ggg acc aag gct gac act cac gat gaa atc ctg gag      152
Pro Val Ser Leu Gly Thr Lys Ala Asp Thr His Asp Glu Ile Leu Glu
                1               5                   10

ggc ctg aat ttc aac ctc acg gag att ccg gag gct cag atc cat gaa      200
Gly Leu Asn Phe Asn Leu Thr Glu Ile Pro Glu Ala Gln Ile His Glu
        15                  20                  25

ggc ttc cag gaa ctc ctc cgt acc ctc aac cag cca gac agc cag ctc      248
Gly Phe Gln Glu Leu Leu Arg Thr Leu Asn Gln Pro Asp Ser Gln Leu
    30                  35                  40

cag ctg acc acc ggc aat ggc ctg ttc ctc agc gag ggc ctg aag cta      296
Gln Leu Thr Thr Gly Asn Gly Leu Phe Leu Ser Glu Gly Leu Lys Leu
45                  50                  55                  60

gtg gat aag ttt ttg gag gat gtt aaa aag ttg tac cac tca gaa gcc      344
Val Asp Lys Phe Leu Glu Asp Val Lys Lys Leu Tyr His Ser Glu Ala
                65                  70                  75

ttc act gtc aac ttc ggg gac acc gaa gag gcc aag aaa cag atc aac      392
Phe Thr Val Asn Phe Gly Asp Thr Glu Glu Ala Lys Lys Gln Ile Asn
            80                  85                  90

gat tac gtg gag aag ggt act caa ggg aaa att gtg gat ttg gtc aag      440
Asp Tyr Val Glu Lys Gly Thr Gln Gly Lys Ile Val Asp Leu Val Lys
        95                  100                 105

gag ctt gac aga gac aca gtt ttt gct ctg gtg aat tac atc ttc ttt      488
Glu Leu Asp Arg Asp Thr Val Phe Ala Leu Val Asn Tyr Ile Phe Phe
    110                 115                 120

aaa ggc aaa tgg gag aga ccc ttt gaa gtc aag gac acc gag gaa gag      536
Lys Gly Lys Trp Glu Arg Pro Phe Glu Val Lys Asp Thr Glu Glu Glu
125                 130                 135                 140

gac ttc cac gtg gac cag gtg acc acc gtg aag gtg cct atg atg aag      584
Asp Phe His Val Asp Gln Val Thr Thr Val Lys Val Pro Met Met Lys
                145                 150                 155

cgt tta ggc atg ttt aac atc cag cac tgt aag aag ctg tcc agc tgg      632
Arg Leu Gly Met Phe Asn Ile Gln His Cys Lys Lys Leu Ser Ser Trp
            160                 165                 170

gtg ctg ctg atg aaa tac ctg ggc aat gcc acc gcc atc ttc ttc ctg      680
Val Leu Leu Met Lys Tyr Leu Gly Asn Ala Thr Ala Ile Phe Phe Leu
        175                 180                 185

cct gat gag ggg aaa cta cag cac ctg gaa aat gaa ctc acc cac gat      728
Pro Asp Glu Gly Lys Leu Gln His Leu Glu Asn Glu Leu Thr His Asp
    190                 195                 200

atc atc acc aag ttc ctg gaa aat gaa gac aga agg tct gcc agc tta      776
Ile Ile Thr Lys Phe Leu Glu Asn Glu Asp Arg Arg Ser Ala Ser Leu
205                 210                 215                 220

cat tta ccc aaa ctg tcc att act gga acc tat gat ctg aag agc gtc      824
His Leu Pro Lys Leu Ser Ile Thr Gly Thr Tyr Asp Leu Lys Ser Val
                225                 230                 235

ctg ggt caa ctg ggc atc act aag gtc ttc agc aat ggg gct gac ctc      872
```

-continued

```
Leu Gly Gln Leu Gly Ile Thr Lys Val Phe Ser Asn Gly Ala Asp Leu
            240                 245                 250

tcc ggg gtc aca gag gag gca ccc ctg aag ctc tcc aag gcc gtg cat      920
Ser Gly Val Thr Glu Glu Ala Pro Leu Lys Leu Ser Lys Ala Val His
        255                 260                 265

aag gct gtg ctg acc atc gac gag aaa ggg act gaa gct gct ggg gcc      968
Lys Ala Val Leu Thr Ile Asp Glu Lys Gly Thr Glu Ala Ala Gly Ala
    270                 275                 280

atg ttt tta gag gcc ata ccc atg tct atc ccc ccc gag gtc aag ttc     1016
Met Phe Leu Glu Ala Ile Pro Met Ser Ile Pro Pro Glu Val Lys Phe
285                 290                 295                 300

aac aaa ccc ttt gtc ttc tta atg att gac caa aat acc aag tct ccc     1064
Asn Lys Pro Phe Val Phe Leu Met Ile Asp Gln Asn Thr Lys Ser Pro
                305                 310                 315

ctc ttc atg gga aaa gtg gtg aat ccc acc caa aaa taactgcctc          1110
Leu Phe Met Gly Lys Val Val Asn Pro Thr Gln Lys
            320                 325

tcgctcctca accccctcccc tccatccctg gccccctccc tggatgacat taaagaaggg  1170

ttgagctgaa aaaaaaaaaa aaaa                                          1194


<210> SEQ ID NO 50
<211> LENGTH: 351
<212> TYPE: PRT
<213> ORGANISM: Homo sapiens
<220> FEATURE:
<221> NAME/KEY: SIGNAL
<222> LOCATION: 1..24

<400> SEQUENCE: 50

Met Pro Ser Ser Val Ser Trp Gly Ile Leu Leu Leu Ala Gly Leu Cys
                -20                 -15                 -10

Cys Leu Val Pro Val Ser Leu Gly Thr Lys Ala Asp Thr His Asp Glu
            -5                  1               5

Ile Leu Glu Gly Leu Asn Phe Asn Leu Thr Glu Ile Pro Glu Ala Gln
    10                  15                  20

Ile His Glu Gly Phe Gln Glu Leu Leu Arg Thr Leu Asn Gln Pro Asp
25                  30                  35                  40

Ser Gln Leu Gln Leu Thr Thr Gly Asn Gly Leu Phe Leu Ser Glu Gly
                45                  50                  55

Leu Lys Leu Val Asp Lys Phe Leu Glu Asp Val Lys Lys Leu Tyr His
            60                  65                  70

Ser Glu Ala Phe Thr Val Asn Phe Gly Asp Thr Glu Glu Ala Lys Lys
        75                  80                  85

Gln Ile Asn Asp Tyr Val Glu Lys Gly Thr Gln Gly Lys Ile Val Asp
    90                  95                  100

Leu Val Lys Glu Leu Asp Arg Asp Thr Val Phe Ala Leu Val Asn Tyr
105                 110                 115                 120

Ile Phe Phe Lys Gly Lys Trp Glu Arg Pro Phe Glu Val Lys Asp Thr
                125                 130                 135

Glu Glu Glu Asp Phe His Val Asp Gln Val Thr Thr Val Lys Val Pro
            140                 145                 150

Met Met Lys Arg Leu Gly Met Phe Asn Ile Gln His Cys Lys Lys Leu
        155                 160                 165

Ser Ser Trp Val Leu Leu Met Lys Tyr Leu Gly Asn Ala Thr Ala Ile
    170                 175                 180

Phe Phe Leu Pro Asp Glu Gly Lys Leu Gln His Leu Glu Asn Glu Leu
185                 190                 195                 200
```

```
Thr His Asp Ile Ile Thr Lys Phe Leu Glu Asn Glu Asp Arg Arg Ser
                205                 210                 215

Ala Ser Leu His Leu Pro Lys Leu Ser Ile Thr Gly Thr Tyr Asp Leu
            220                 225                 230

Lys Ser Val Leu Gly Gln Leu Gly Ile Thr Lys Val Phe Ser Asn Gly
        235                 240                 245

Ala Asp Leu Ser Gly Val Thr Glu Glu Ala Pro Leu Lys Leu Ser Lys
    250                 255                 260

Ala Val His Lys Ala Val Leu Thr Ile Asp Glu Lys Gly Thr Glu Ala
265                 270                 275                 280

Ala Gly Ala Met Phe Leu Glu Ala Ile Pro Met Ser Ile Pro Pro Glu
                285                 290                 295

Val Lys Phe Asn Lys Pro Phe Val Phe Leu Met Ile Asp Gln Asn Thr
            300                 305                 310

Lys Ser Pro Leu Phe Met Gly Lys Val Val Asn Pro Thr Gln Lys
        315                 320                 325


<210> SEQ ID NO 51
<211> LENGTH: 1317
<212> TYPE: DNA
<213> ORGANISM: Homo sapiens
<220> FEATURE:
<221> NAME/KEY: 5'UTR
<222> LOCATION: 1..289
<220> FEATURE:
<221> NAME/KEY: CDS
<222> LOCATION: 290..1162
<220> FEATURE:
<221> NAME/KEY: 3'UTR
<222> LOCATION: 1163..1317
<220> FEATURE:
<221> NAME/KEY: polyA_signal
<222> LOCATION: 1269..1274
<220> FEATURE:
<221> NAME/KEY: polyA_site
<222> LOCATION: 1302..1317

<400> SEQUENCE: 51

aactgccagt gatctctgaa gccgactctg aggctccctc tttgctctaa cagacagcag      60

cgactttagg ctggataata gtcaaattct tacctcgctc tttcactgct agtaagatca     120

gattgcgttt ctttcagtta ctcttcaatc gccagtttct tgatctgctt ctaaaagaag     180

aagtagagaa gataaatcct gtcttcaata cctggaagga aaaacaaaat aacctcaact     240

ccgttttgaa aaaaacattc caagaacttt catcagagat tttacttag atg att tac     298
                                                      Met Ile Tyr
                                                              -25

aca atg aag aaa gta cat gca ctt tgg gct tct gta tgc ctg ctg ctt      346
Thr Met Lys Lys Val His Ala Leu Trp Ala Ser Val Cys Leu Leu Leu
                -20                 -15                 -10

aat ctt gcc cct gcc cct ctt aat gct gat tct gag gaa gat gaa gaa      394
Asn Leu Ala Pro Ala Pro Leu Asn Ala Asp Ser Glu Glu Asp Glu Glu
            -5                  1               5

cac aca att atc aca gat acg gag ttg cca cca ctg aaa ctt atg cat      442
His Thr Ile Ile Thr Asp Thr Glu Leu Pro Pro Leu Lys Leu Met His
    10                  15                  20

tca ttt tgt gca ttc aag tcg gat gat ggc cca tgt aaa gca atc atg      490
Ser Phe Cys Ala Phe Lys Ser Asp Asp Gly Pro Cys Lys Ala Ile Met
25                  30                  35                  40

aaa aga ttt ttc ttc aat att ttc act cga cag tgc gaa gaa ttt ata      538
Lys Arg Phe Phe Phe Asn Ile Phe Thr Arg Gln Cys Glu Glu Phe Ile
                45                  50                  55
```

```
tat ggg gga tgt gaa gga aat cag aat cga ttt gaa agt ctg gaa gag     586
Tyr Gly Gly Cys Glu Gly Asn Gln Asn Arg Phe Glu Ser Leu Glu Glu
            60                  65                  70

tgc aaa aaa atg tgt aca aga gaa aag cca gat ttc tgc ttt ttg gaa     634
Cys Lys Lys Met Cys Thr Arg Glu Lys Pro Asp Phe Cys Phe Leu Glu
        75                  80                  85

gaa gat cct gga ata tgt cga ggt tat att acc agg tat ttt tat aac     682
Glu Asp Pro Gly Ile Cys Arg Gly Tyr Ile Thr Arg Tyr Phe Tyr Asn
    90                  95                  100

aat cag aca aaa cag tgt gaa cgt ttc aag tat ggt gga tgc ctg ggc     730
Asn Gln Thr Lys Gln Cys Glu Arg Phe Lys Tyr Gly Gly Cys Leu Gly
105                 110                 115                 120

aat atg aac aat ttt gag aca ctg gaa gaa tgc aag aac att tgt gaa     778
Asn Met Asn Asn Phe Glu Thr Leu Glu Glu Cys Lys Asn Ile Cys Glu
                125                 130                 135

gat ggt ccg aat ggt ttc cag gtg gat aat tat gga acc cag ctc aat     826
Asp Gly Pro Asn Gly Phe Gln Val Asp Asn Tyr Gly Thr Gln Leu Asn
            140                 145                 150

gct gtg aat aac tcc ctg act ccg caa tca acc aag gtt ccc agc ctt     874
Ala Val Asn Asn Ser Leu Thr Pro Gln Ser Thr Lys Val Pro Ser Leu
        155                 160                 165

ttt gaa ttt cac ggt ccc tca tgg tgt ctc act cca gca gac aga gga     922
Phe Glu Phe His Gly Pro Ser Trp Cys Leu Thr Pro Ala Asp Arg Gly
    170                 175                 180

ttg tgt cgt gcc aat gag aac aga ttc tac tac aat tca gtc att ggg     970
Leu Cys Arg Ala Asn Glu Asn Arg Phe Tyr Tyr Asn Ser Val Ile Gly
185                 190                 195                 200

aaa tgc cgc cca ttt aag tac agt gga tgt ggg gga aat gaa aac aat    1018
Lys Cys Arg Pro Phe Lys Tyr Ser Gly Cys Gly Gly Asn Glu Asn Asn
                205                 210                 215

ttt act tcc aaa caa gaa tgt ctg agg gca tgt aaa aaa ggt ttc atc    1066
Phe Thr Ser Lys Gln Glu Cys Leu Arg Ala Cys Lys Lys Gly Phe Ile
            220                 225                 230

caa aga ata tca aaa gga ggc cta att aaa acc aaa aga aaa aga aag    1114
Gln Arg Ile Ser Lys Gly Gly Leu Ile Lys Thr Lys Arg Lys Arg Lys
        235                 240                 245

aag cag aga gtg aaa ata gca tat gaa gaa att ttt gtt aaa aat atg    1162
Lys Gln Arg Val Lys Ile Ala Tyr Glu Glu Ile Phe Val Lys Asn Met
    250                 255                 260

tgaatttgtt atagcaatgt aacattaatt ctactaaata ttttatatga aatgtttcac  1222

tatgattttc tatttttctt ctaaaatgct tttaattaat atgttcatta aattttctat  1282

gcttattgta cttgttatca aaaaaaaaaa aaaaa                              1317


<210> SEQ ID NO 52
<211> LENGTH: 291
<212> TYPE: PRT
<213> ORGANISM: Homo sapiens
<220> FEATURE:
<221> NAME/KEY: SIGNAL
<222> LOCATION: 1..28

<400> SEQUENCE: 52

Met Ile Tyr Thr Met Lys Lys Val His Ala Leu Trp Ala Ser Val Cys
            -25                 -20                 -15

Leu Leu Leu Asn Leu Ala Pro Ala Pro Leu Asn Ala Asp Ser Glu Glu
        -10                 -5                  1

Asp Glu Glu His Thr Ile Ile Thr Asp Thr Glu Leu Pro Pro Leu Lys
5                   10                  15                  20
```

```
Leu Met His Ser Phe Cys Ala Phe Lys Ser Asp Asp Gly Pro Cys Lys
                25                  30                  35

Ala Ile Met Lys Arg Phe Phe Phe Asn Ile Phe Thr Arg Gln Cys Glu
            40                  45                  50

Glu Phe Ile Tyr Gly Gly Cys Glu Gly Asn Gln Asn Arg Phe Glu Ser
        55                  60                  65

Leu Glu Glu Cys Lys Lys Met Cys Thr Arg Glu Lys Pro Asp Phe Cys
    70                  75                  80

Phe Leu Glu Glu Asp Pro Gly Ile Cys Arg Gly Tyr Ile Thr Arg Tyr
85                  90                  95                  100

Phe Tyr Asn Asn Gln Thr Lys Gln Cys Glu Arg Phe Lys Tyr Gly Gly
                105                 110                 115

Cys Leu Gly Asn Met Asn Asn Phe Glu Thr Leu Glu Glu Cys Lys Asn
            120                 125                 130

Ile Cys Glu Asp Gly Pro Asn Gly Phe Gln Val Asp Asn Tyr Gly Thr
        135                 140                 145

Gln Leu Asn Ala Val Asn Asn Ser Leu Thr Pro Gln Ser Thr Lys Val
    150                 155                 160

Pro Ser Leu Phe Glu Phe His Gly Pro Ser Trp Cys Leu Thr Pro Ala
165                 170                 175                 180

Asp Arg Gly Leu Cys Arg Ala Asn Glu Asn Arg Phe Tyr Tyr Asn Ser
                185                 190                 195

Val Ile Gly Lys Cys Arg Pro Phe Lys Tyr Ser Gly Cys Gly Gly Asn
            200                 205                 210

Glu Asn Asn Phe Thr Ser Lys Gln Glu Cys Leu Arg Ala Cys Lys Lys
        215                 220                 225

Gly Phe Ile Gln Arg Ile Ser Lys Gly Gly Leu Ile Lys Thr Lys Arg
    230                 235                 240

Lys Arg Lys Lys Gln Arg Val Lys Ile Ala Tyr Glu Glu Ile Phe Val
245                 250                 255                 260

Lys Asn Met


<210> SEQ ID NO 53
<211> LENGTH: 1907
<212> TYPE: DNA
<213> ORGANISM: Homo sapiens
<220> FEATURE:
<221> NAME/KEY: 5'UTR
<222> LOCATION: 1..1043
<220> FEATURE:
<221> NAME/KEY: CDS
<222> LOCATION: 1044..1664
<220> FEATURE:
<221> NAME/KEY: 3'UTR
<222> LOCATION: 1665..1907
<220> FEATURE:
<221> NAME/KEY: polyA_signal
<222> LOCATION: 1869..1874
<220> FEATURE:
<221> NAME/KEY: polyA_site
<222> LOCATION: 1892..1907

<400> SEQUENCE: 53

caaaaaaatt ctaggtcatg atccccataa atgaagagtg atcagtccaa tcccagggaa      60

cctggacatt ttgggtattg tttcagtgga acatgccttt cataagttcc attttcttgg     120

gtatctctta ggaagcaagc ataggaaaca ggcccatccg tctgcctgtt ttgcttcctc     180

atctcacttc tacacgaggg tgcctgtgct caattgctgt tttcccctaa agagactctt     240

ttccataagt ttgtgaaatg ccatcgacaa acctgatcgc attgcatttc actctgctgt     300
```

```
tgagtcgatt tttctttatt ttatcattta gtaactcctt gctctacaga gctttcacct    360

tccacatatt tcagattcat tctttcctaa actatgtggt ggtctacgtc ctcactgact    420

tatcaacatg ctaccatcat gcacttccta tctctattcc tcttctttaa atttggttcc    480

aaatggctca caccattatt ctgagctatt acctgcctac gcagtcctag aaagtaagtg    540

attcaggaaa cattccccaa aagtaaagtt tctcaggtaa gatcagaaga ctcccatgag    600

tcactgctgc tcaggatcac atctggctcc ttgaagagtg attcatcaga ccttacatag    660

atcttgtcat aaaaatgaaa gaggcctcgg gggaaggtct tgggctggtg gcttctgttg    720

gagtcctggg ctgtggggtg aaagccgtgg ctgtagagct tcatgcggag ttacttagct    780

ttgctctcct gtggacaggc catgcctgtg cctcccccaa gcatcggaaa aattggcata    840

gatgggccct tctcaaaaat cccactcctg gagcactggc caaaattact accatcctga    900

tgctgggctt gcagtccttt cctttgggaa tatgaacatg gtcaaaatta agtgaacgtg    960

tctttctggc tttctgtaca atggagcaga acaaagtatc aatttaacta aaatttgaac   1020

taaatcctct ttccaggttt gga atg cac ttc tgt gga ggc acc ttg ata tcc   1073
                           Met His Phe Cys Gly Gly Thr Leu Ile Ser
                           1               5                   10

cca gag tgg gtg ttg act gct gcc cac tgc ttg gag aag tcc cca agg     1121
Pro Glu Trp Val Leu Thr Ala Ala His Cys Leu Glu Lys Ser Pro Arg
                15                  20                  25

cct tca tcc tac aag gtc atc ctg ggt gca cac caa gaa gtg aat ctc     1169
Pro Ser Ser Tyr Lys Val Ile Leu Gly Ala His Gln Glu Val Asn Leu
            30                  35                  40

gaa ccg cat gtt cag gaa ata gaa gtg tct agg ctg ttc ttg gag ccc     1217
Glu Pro His Val Gln Glu Ile Glu Val Ser Arg Leu Phe Leu Glu Pro
        45                  50                  55

aca cga aaa gat att gcc ttg cta aag cta agc agt cct gcc gtc atc     1265
Thr Arg Lys Asp Ile Ala Leu Leu Lys Leu Ser Ser Pro Ala Val Ile
    60                  65                  70

act gac aaa gta atc cca gct tgt ctg cca tcc cca aat tat gtg gtc     1313
Thr Asp Lys Val Ile Pro Ala Cys Leu Pro Ser Pro Asn Tyr Val Val
75                  80                  85                  90

gct gac cgg acc gaa tgt ttc atc act ggc tgg gga gaa acc caa ggt     1361
Ala Asp Arg Thr Glu Cys Phe Ile Thr Gly Trp Gly Glu Thr Gln Gly
                95                  100                 105

act ttt gga gct ggc ctt ctc aag gaa gcc cag ctc cct gtg att gag     1409
Thr Phe Gly Ala Gly Leu Leu Lys Glu Ala Gln Leu Pro Val Ile Glu
            110                 115                 120

aat aaa gtg tgc aat cgc tat gag ttt ctg aat gga aga gtc caa tcc     1457
Asn Lys Val Cys Asn Arg Tyr Glu Phe Leu Asn Gly Arg Val Gln Ser
        125                 130                 135

acc gaa ctc tgt gct ggg cat ttg gcc gga ggc act gac agt tgc cag     1505
Thr Glu Leu Cys Ala Gly His Leu Ala Gly Gly Thr Asp Ser Cys Gln
    140                 145                 150

ggt gac agt gga ggt cct ctg gtt tgc ttc gag aag gac aaa tac att     1553
Gly Asp Ser Gly Gly Pro Leu Val Cys Phe Glu Lys Asp Lys Tyr Ile
155                 160                 165                 170

tta caa gga gtc act tct tgg ggt ctt ggc tgt gca cgc ccc aat aag     1601
Leu Gln Gly Val Thr Ser Trp Gly Leu Gly Cys Ala Arg Pro Asn Lys
                175                 180                 185

cct ggt gtc tat gtt cgt gtt tca agg ttt gtt act tgg att gag gga     1649
Pro Gly Val Tyr Val Arg Val Ser Arg Phe Val Thr Trp Ile Glu Gly
            190                 195                 200

gtg atg aga aat aat taattggacg ggagacagag tgacgcactg actcacctag     1704
Val Met Arg Asn Asn
```

```
        205

aggctggaac gtgggtaggg atttagcatg ctggaaataa ctggcagtaa tcaaacgaag   1764

acactgtccc cagctaccag ctatgccaaa cctcggcatt ttttgtgtta ttttctgact   1824

gctggattct gtagtaaggt gacatagcta tgacatttgt taaaaataaa ctctgtactt   1884

aactttgaaa aaaaaaaaaa aaa                                           1907


<210> SEQ ID NO 54
<211> LENGTH: 207
<212> TYPE: PRT
<213> ORGANISM: Homo sapiens

<400> SEQUENCE: 54

Met His Phe Cys Gly Gly Thr Leu Ile Ser Pro Glu Trp Val Leu Thr
1               5                   10                  15

Ala Ala His Cys Leu Glu Lys Ser Pro Arg Pro Ser Ser Tyr Lys Val
            20                  25                  30

Ile Leu Gly Ala His Gln Glu Val Asn Leu Glu Pro His Val Gln Glu
        35                  40                  45

Ile Glu Val Ser Arg Leu Phe Leu Glu Pro Thr Arg Lys Asp Ile Ala
    50                  55                  60

Leu Leu Lys Leu Ser Ser Pro Ala Val Ile Thr Asp Lys Val Ile Pro
65                  70                  75                  80

Ala Cys Leu Pro Ser Pro Asn Tyr Val Val Ala Asp Arg Thr Glu Cys
                85                  90                  95

Phe Ile Thr Gly Trp Gly Glu Thr Gln Gly Thr Phe Gly Ala Gly Leu
            100                 105                 110

Leu Lys Glu Ala Gln Leu Pro Val Ile Glu Asn Lys Val Cys Asn Arg
        115                 120                 125

Tyr Glu Phe Leu Asn Gly Arg Val Gln Ser Thr Glu Leu Cys Ala Gly
    130                 135                 140

His Leu Ala Gly Gly Thr Asp Ser Cys Gln Gly Asp Ser Gly Gly Pro
145                 150                 155                 160

Leu Val Cys Phe Glu Lys Asp Lys Tyr Ile Leu Gln Gly Val Thr Ser
                165                 170                 175

Trp Gly Leu Gly Cys Ala Arg Pro Asn Lys Pro Gly Val Tyr Val Arg
            180                 185                 190

Val Ser Arg Phe Val Thr Trp Ile Glu Gly Val Met Arg Asn Asn
        195                 200                 205


<210> SEQ ID NO 55
<211> LENGTH: 809
<212> TYPE: DNA
<213> ORGANISM: Homo sapiens
<220> FEATURE:
<221> NAME/KEY: 5'UTR
<222> LOCATION: 1..25
<220> FEATURE:
<221> NAME/KEY: CDS
<222> LOCATION: 26..628
<220> FEATURE:
<221> NAME/KEY: 3'UTR
<222> LOCATION: 629..809
<220> FEATURE:
<221> NAME/KEY: polyA_signal
<222> LOCATION: 766..771
<220> FEATURE:
<221> NAME/KEY: polyA_site
<222> LOCATION: 795..809

<400> SEQUENCE: 55
```

```
agaaaggtgt ggttggcatg gggca atg ctt gag gta tca gat gca ctg gga       52
                            Met Leu Glu Val Ser Asp Ala Leu Gly
                            1               5

gga cct gga aga gta cca ggg gcc aca gca ggg atg aat gga gtg gac      100
Gly Pro Gly Arg Val Pro Gly Ala Thr Ala Gly Met Asn Gly Val Asp
10                  15                  20                  25

acg tcg ctt ctc tgt gat ttg ttg cag gcc ctg acc ttc ctg acc aga      148
Thr Ser Leu Leu Cys Asp Leu Leu Gln Ala Leu Thr Phe Leu Thr Arg
                30                  35                  40

aat gaa att ctg tgc atc cat gac acc ttc ctg aag ctc tgc cct cct      196
Asn Glu Ile Leu Cys Ile His Asp Thr Phe Leu Lys Leu Cys Pro Pro
            45                  50                  55

ggg aag tac tac aag gag gca acg ctc acc atg gac cag gtc agc tcc      244
Gly Lys Tyr Tyr Lys Glu Ala Thr Leu Thr Met Asp Gln Val Ser Ser
        60                  65                  70

ctg cca gct ctg cgg gtc aac cct ttc aga gac cgt atc tgc aga gtg      292
Leu Pro Ala Leu Arg Val Asn Pro Phe Arg Asp Arg Ile Cys Arg Val
    75                  80                  85

ttc tcc cac aaa ggc atg ttc tcc ttt gag gat gtg ctg ggc atg gca      340
Phe Ser His Lys Gly Met Phe Ser Phe Glu Asp Val Leu Gly Met Ala
90                  95                  100                 105

tct gtg ttc agc gag cag gcc tgc cca agc ctg aag att gag tat gcc      388
Ser Val Phe Ser Glu Gln Ala Cys Pro Ser Leu Lys Ile Glu Tyr Ala
                110                 115                 120

ttt cgc atc tat gat ttt aat gag aat ggc ttc att gat gag gag gat      436
Phe Arg Ile Tyr Asp Phe Asn Glu Asn Gly Phe Ile Asp Glu Glu Asp
            125                 130                 135

ctg cag agg atc atc ctg cga ctg ctg aac agt gat gac atg tct gag      484
Leu Gln Arg Ile Ile Leu Arg Leu Leu Asn Ser Asp Asp Met Ser Glu
        140                 145                 150

gac ctc ctg atg gac ctc acg aac cac gtc ctg agt gag tcg gat ctg      532
Asp Leu Leu Met Asp Leu Thr Asn His Val Leu Ser Glu Ser Asp Leu
    155                 160                 165

gac aat gac aac atg ctg tcc ttc tca gag ttt gaa cat gca atg gcc      580
Asp Asn Asp Asn Met Leu Ser Phe Ser Glu Phe Glu His Ala Met Ala
170                 175                 180                 185

aag tct cca gat ttc atg aac tcc ttt cgg att cac ttc tgg gga tgc      628
Lys Ser Pro Asp Phe Met Asn Ser Phe Arg Ile His Phe Trp Gly Cys
                190                 195                 200

tgatgtagcg gcaaatacct gacatggcag cctcgaggga gaccacagga atcgaacccc    688

ctccagcact ggagggagct ggtttgaagt atgactttgt actgggccca cactcacctc    748

tagaatattg tttattagat aaaagaaaaa gcttttcctt agcccgaaaa aaaaaaaaaa    808

t                                                                    809


<210> SEQ ID NO 56
<211> LENGTH: 201
<212> TYPE: PRT
<213> ORGANISM: Homo sapiens

<400> SEQUENCE: 56

Met Leu Glu Val Ser Asp Ala Leu Gly Gly Pro Gly Arg Val Pro Gly
1               5                   10                  15

Ala Thr Ala Gly Met Asn Gly Val Asp Thr Ser Leu Leu Cys Asp Leu
            20                  25                  30

Leu Gln Ala Leu Thr Phe Leu Thr Arg Asn Glu Ile Leu Cys Ile His
        35                  40                  45

Asp Thr Phe Leu Lys Leu Cys Pro Pro Gly Lys Tyr Tyr Lys Glu Ala
```

```
    50                  55                  60

Thr Leu Thr Met Asp Gln Val Ser Ser Leu Pro Ala Leu Arg Val Asn
65                  70                  75                  80

Pro Phe Arg Asp Arg Ile Cys Arg Val Phe Ser His Lys Gly Met Phe
                85                  90                  95

Ser Phe Glu Asp Val Leu Gly Met Ala Ser Val Phe Ser Glu Gln Ala
            100                 105                 110

Cys Pro Ser Leu Lys Ile Glu Tyr Ala Phe Arg Ile Tyr Asp Phe Asn
        115                 120                 125

Glu Asn Gly Phe Ile Asp Glu Glu Asp Leu Gln Arg Ile Ile Leu Arg
    130                 135                 140

Leu Leu Asn Ser Asp Asp Met Ser Glu Asp Leu Leu Met Asp Leu Thr
145                 150                 155                 160

Asn His Val Leu Ser Glu Ser Asp Leu Asp Asn Asp Asn Met Leu Ser
                165                 170                 175

Phe Ser Glu Phe Glu His Ala Met Ala Lys Ser Pro Asp Phe Met Asn
            180                 185                 190

Ser Phe Arg Ile His Phe Trp Gly Cys
        195                 200


<210> SEQ ID NO 57
<211> LENGTH: 1133
<212> TYPE: DNA
<213> ORGANISM: Homo sapiens
<220> FEATURE:
<221> NAME/KEY: 5'UTR
<222> LOCATION: 1..475
<220> FEATURE:
<221> NAME/KEY: CDS
<222> LOCATION: 476..964
<220> FEATURE:
<221> NAME/KEY: 3'UTR
<222> LOCATION: 965..1133
<220> FEATURE:
<221> NAME/KEY: polyA_signal
<222> LOCATION: 1101..1106
<220> FEATURE:
<221> NAME/KEY: polyA_site
<222> LOCATION: 1118..1133

<400> SEQUENCE: 57

gacataatca gagctatgct ggaggagaag agggcagcca tttgctggct ggcttgcagt      60

gagccaggag gtggcaggac gagttaggag gctggttcag tagctcgggc aagagcaggg     120

ccccccagga tctgaaggcc tcccaggccc cccaggccca gcgggtccca gaggagagcg     180

aggaccccaa ggtaactccg gtgagaaggg cgaccaggga tttcaaggcc agccaggctt     240

tccgggccca ccgggtcccc ctggattccc aggcaaagtt ggatcacctg gcccacctgg     300

ccctcaagca gagaagggca gcgaagggat tcgaggccca tcaggcctgc ctggctcccc     360

tgggccaccg ggacctcctg ggattcaggg ccccgccggt ctggatggtt tggatgggaa     420

ggatggcaag cctggcttga ggggggaccc tggtcctgct ggcccccctg gactc atg      478
                                                             Met
                                                             1

gga cca ccg ggc ttt aag ggg aaa aca gga cat cct ggc ctc cca gga       526
Gly Pro Pro Gly Phe Lys Gly Lys Thr Gly His Pro Gly Leu Pro Gly
            5                   10                  15

cct aag ggt gac tgt ggc aaa cca ggt cct cct ggc agc act ggc cgg       574
Pro Lys Gly Asp Cys Gly Lys Pro Gly Pro Pro Gly Ser Thr Gly Arg
        20                  25                  30

cct ggc gca gag ggt gaa cct ggt gcc atg gga ccc cag gga aga ccc       622
```

-continued

```
Pro Gly Ala Glu Gly Glu Pro Gly Ala Met Gly Pro Gln Gly Arg Pro
    35                  40                  45

ggt ccc ccg gga cac gtt ggg cca cca ggg cct cca ggc cag cca gga      670
Gly Pro Pro Gly His Val Gly Pro Pro Gly Pro Pro Gly Gln Pro Gly
50                  55                  60                  65

cca gct ggg atc tct gca gtg ggt ctg aaa gga gac cga gga gcc acc      718
Pro Ala Gly Ile Ser Ala Val Gly Leu Lys Gly Asp Arg Gly Ala Thr
                70                  75                  80

gga gaa agg ggc ctt gca ggc ctc cca ggc cag ccc ggc ccc cca ggt      766
Gly Glu Arg Gly Leu Ala Gly Leu Pro Gly Gln Pro Gly Pro Pro Gly
            85                  90                  95

cct caa ggt cct cca ggc tat ggc aag atg ggt gca aca gga cca atg      814
Pro Gln Gly Pro Pro Gly Tyr Gly Lys Met Gly Ala Thr Gly Pro Met
        100                 105                 110

ggc cag caa ggc atc cct ggc atc cct ggg ccc ccg ggt ccc atg ggc      862
Gly Gln Gln Gly Ile Pro Gly Ile Pro Gly Pro Pro Gly Pro Met Gly
    115                 120                 125

cag cca ggc aag gct ggc cac tgt aat ccc tct gac tgc ttt ggg gcc      910
Gln Pro Gly Lys Ala Gly His Cys Asn Pro Ser Asp Cys Phe Gly Ala
130                 135                 140                 145

atg ccg atg gag cag cag tac cca ccc atg aaa acc atg aag ggg cct      958
Met Pro Met Glu Gln Gln Tyr Pro Pro Met Lys Thr Met Lys Gly Pro
                150                 155                 160
ttt ggc tgaaattccc cacctgcctt tggatgaaag actccgttgg gaataaatgg      1014
Phe Gly

ccaaagctta taggactctg tgacaggttg tgaatgtttt ttttgttgtt gttgttgttt   1074

ttaattgctg ttaatatttt ttaaataata aagaaacaaa actaaaaaaa aaaaaaaaa    1133


<210> SEQ ID NO 58
<211> LENGTH: 163
<212> TYPE: PRT
<213> ORGANISM: Homo sapiens

<400> SEQUENCE: 58

Met Gly Pro Pro Gly Phe Lys Gly Lys Thr Gly His Pro Gly Leu Pro
1               5                   10                  15

Gly Pro Lys Gly Asp Cys Gly Lys Pro Gly Pro Pro Gly Ser Thr Gly
            20                  25                  30

Arg Pro Gly Ala Glu Gly Glu Pro Gly Ala Met Gly Pro Gln Gly Arg
        35                  40                  45

Pro Gly Pro Pro Gly His Val Gly Pro Pro Gly Pro Pro Gly Gln Pro
    50                  55                  60

Gly Pro Ala Gly Ile Ser Ala Val Gly Leu Lys Gly Asp Arg Gly Ala
65                  70                  75                  80

Thr Gly Glu Arg Gly Leu Ala Gly Leu Pro Gly Gln Pro Gly Pro Pro
                85                  90                  95

Gly Pro Gln Gly Pro Pro Gly Tyr Gly Lys Met Gly Ala Thr Gly Pro
            100                 105                 110

Met Gly Gln Gln Gly Ile Pro Gly Ile Pro Gly Pro Pro Gly Pro Met
        115                 120                 125

Gly Gln Pro Gly Lys Ala Gly His Cys Asn Pro Ser Asp Cys Phe Gly
    130                 135                 140

Ala Met Pro Met Glu Gln Gln Tyr Pro Pro Met Lys Thr Met Lys Gly
145                 150                 155                 160

Pro Phe Gly


<210> SEQ ID NO 59
```

```
<211> LENGTH: 838
<212> TYPE: DNA
<213> ORGANISM: Homo sapiens
<220> FEATURE:
<221> NAME/KEY: 5'UTR
<222> LOCATION: 1..78
<220> FEATURE:
<221> NAME/KEY: CDS
<222> LOCATION: 79..642
<220> FEATURE:
<221> NAME/KEY: 3'UTR
<222> LOCATION: 643..838
<220> FEATURE:
<221> NAME/KEY: polyA_signal
<222> LOCATION: 799..804
<220> FEATURE:
<221> NAME/KEY: polyA_site
<222> LOCATION: 823..838

<400> SEQUENCE: 59

aaagactgcg tgcagaaggt gactgtctca gtggagctgg gtcatctcag gccttggctc     60

cttgaacttt tggccgcc atg tgc ttc ccg aag gtc ctc tct gat gac atg      111
                    Met Cys Phe Pro Lys Val Leu Ser Asp Asp Met
                    1               5                   10

aag aag ctg aag gcc cga atg cac cag gcc ata gaa aga ttt tat gat      159
Lys Lys Leu Lys Ala Arg Met His Gln Ala Ile Glu Arg Phe Tyr Asp
            15                  20                  25

aaa atg caa aat gca gaa tca gga cgt gga cag gtg atg tcg agc ctg      207
Lys Met Gln Asn Ala Glu Ser Gly Arg Gly Gln Val Met Ser Ser Leu
        30                  35                  40

gca gag ctg gag gac gac ttc aaa gag ggc tac ctg gag aca gtg gcg      255
Ala Glu Leu Glu Asp Asp Phe Lys Glu Gly Tyr Leu Glu Thr Val Ala
    45                  50                  55

gct tat tat gag gag cag cac cca gag ctc act cct cta ctt gaa aaa      303
Ala Tyr Tyr Glu Glu Gln His Pro Glu Leu Thr Pro Leu Leu Glu Lys
60                  65                  70                  75

gaa aga gat gga tta cgg tgc cga ggc aac aga tcc cct gtc ccg gat      351
Glu Arg Asp Gly Leu Arg Cys Arg Gly Asn Arg Ser Pro Val Pro Asp
                80                  85                  90

gtt gag gat ccc gca acc gag gag cct ggg gag agc ttt tgt gac aag      399
Val Glu Asp Pro Ala Thr Glu Glu Pro Gly Glu Ser Phe Cys Asp Lys
            95                  100                 105

gtc atg aga tgg ttc cag gcc atg ctg cag cgg ctg cag acc tgg tgg      447
Val Met Arg Trp Phe Gln Ala Met Leu Gln Arg Leu Gln Thr Trp Trp
        110                 115                 120

cac ggg gtt ctg gcc tgg gtg aag gag aag gtg gtg gcc ctg gtc cat      495
His Gly Val Leu Ala Trp Val Lys Glu Lys Val Val Ala Leu Val His
    125                 130                 135

gca gtg cag gcc ctc tgg aaa cag ttc cag agt ttc tgc tgc tct ctg      543
Ala Val Gln Ala Leu Trp Lys Gln Phe Gln Ser Phe Cys Cys Ser Leu
140                 145                 150                 155

tca gag ctc ttc atg tcc tct ttc cag tcc tac gga gcc cca cgg ggg      591
Ser Glu Leu Phe Met Ser Ser Phe Gln Ser Tyr Gly Ala Pro Arg Gly
                160                 165                 170

gac aag gag gag ctg aca ccc cag aag tgc tct gaa ccc caa tcc tca      639
Asp Lys Glu Glu Leu Thr Pro Gln Lys Cys Ser Glu Pro Gln Ser Ser
            175                 180                 185

aaa tgaagatact gacaccacct ttgccctccc cgtcaccgcg cacccaccct          692
Lys

gacccctccc tcagctgtcc tgtgccccgc cctctcccgc acactcagtc cccctgcctg    752

gcgttcctgc cgcagctctg acctggtgct gtcgccctgg catcttaata aamcctgctt    812

atacttccct aaaaaaaaaa aaaaaa                                         838
```

<210> SEQ ID NO 60
<211> LENGTH: 188
<212> TYPE: PRT
<213> ORGANISM: Homo sapiens

<400> SEQUENCE: 60

```
Met Cys Phe Pro Lys Val Leu Ser Asp Asp Met Lys Lys Leu Lys Ala
1               5                   10                  15

Arg Met His Gln Ala Ile Glu Arg Phe Tyr Asp Lys Met Gln Asn Ala
            20                  25                  30

Glu Ser Gly Arg Gly Gln Val Met Ser Ser Leu Ala Glu Leu Glu Asp
        35                  40                  45

Asp Phe Lys Glu Gly Tyr Leu Glu Thr Val Ala Ala Tyr Tyr Glu Glu
    50                  55                  60

Gln His Pro Glu Leu Thr Pro Leu Leu Glu Lys Glu Arg Asp Gly Leu
65                  70                  75                  80

Arg Cys Arg Gly Asn Arg Ser Pro Val Pro Asp Val Glu Asp Pro Ala
                85                  90                  95

Thr Glu Glu Pro Gly Glu Ser Phe Cys Asp Lys Val Met Arg Trp Phe
            100                 105                 110

Gln Ala Met Leu Gln Arg Leu Gln Thr Trp Trp His Gly Val Leu Ala
        115                 120                 125

Trp Val Lys Glu Lys Val Val Ala Leu Val His Ala Val Gln Ala Leu
    130                 135                 140

Trp Lys Gln Phe Gln Ser Phe Cys Cys Ser Leu Ser Glu Leu Phe Met
145                 150                 155                 160

Ser Ser Phe Gln Ser Tyr Gly Ala Pro Arg Gly Asp Lys Glu Glu Leu
                165                 170                 175

Thr Pro Gln Lys Cys Ser Glu Pro Gln Ser Ser Lys
            180                 185
```

<210> SEQ ID NO 61
<211> LENGTH: 862
<212> TYPE: DNA
<213> ORGANISM: Homo sapiens
<220> FEATURE:
<221> NAME/KEY: 5'UTR
<222> LOCATION: 1..158
<220> FEATURE:
<221> NAME/KEY: CDS
<222> LOCATION: 159..764
<220> FEATURE:
<221> NAME/KEY: 3'UTR
<222> LOCATION: 765..862

<400> SEQUENCE: 61

```
attttttttt ttggcacgcc tgcagccaag ttggggaggg tttcctggac agaggtcctt     60

tggctgctgc cttaagacgt gcagcctggg ccgtggctgt cactgcgttc ggacccagac    120

ccgctgcagg cagcagcagc ccccgcccgc gcagcagc atg gag ctc tgg ggg gcc    176
                                          Met Glu Leu Trp Gly Ala
                                          -20                 -15

tac ctc ctc ctc tgc ctc ttc tcc ctc ctg acc cag gtc acc acc gag      224
Tyr Leu Leu Leu Cys Leu Phe Ser Leu Leu Thr Gln Val Thr Thr Glu
                -10                 -5                  1

cca cca acc cag aag ccc aag aag att gta aat gcc aag aaa gat gtt      272
Pro Pro Thr Gln Lys Pro Lys Lys Ile Val Asn Ala Lys Lys Asp Val
        5                   10                  15

gtg aac aca aag atg ttt gag gag ctc aag agc cgt ctg gac acc ctg      320
```

-continued

```
Val Asn Thr Lys Met Phe Glu Glu Leu Lys Ser Arg Leu Asp Thr Leu
    20                  25                  30

gcc cag gag gtg gcc ctg ctg aag gag cag cag gcc ctg cag acg gtc      368
Ala Gln Glu Val Ala Leu Leu Lys Glu Gln Gln Ala Leu Gln Thr Val
35                  40                  45                  50

tgc ctg aag ggg acc aag gtg cac atg aaa tgc ttt ctg gcc ttc acc      416
Cys Leu Lys Gly Thr Lys Val His Met Lys Cys Phe Leu Ala Phe Thr
                55                  60                  65

cag acg aag acc ttc cac gag tcc agc gag gac tgc atc tcg cgc ggg      464
Gln Thr Lys Thr Phe His Glu Ser Ser Glu Asp Cys Ile Ser Arg Gly
            70                  75                  80

ggc acc ctg agc acc cct cag act ggc tcg gag aac gac gcc ctg tat      512
Gly Thr Leu Ser Thr Pro Gln Thr Gly Ser Glu Asn Asp Ala Leu Tyr
        85                  90                  95

gag tac ctg cgc cag agc gtg ggc aac gag gcc gag atc tgg ctg ggc      560
Glu Tyr Leu Arg Gln Ser Val Gly Asn Glu Ala Glu Ile Trp Leu Gly
    100                 105                 110

ctc aac gac atg gcg gcc gag ggc acc tgg gtg gac atg acc ggc gcc      608
Leu Asn Asp Met Ala Ala Glu Gly Thr Trp Val Asp Met Thr Gly Ala
115                 120                 125                 130

cgc atc gcc tac aag aac tgg gag act gag atc acc gcg caa ccc gat      656
Arg Ile Ala Tyr Lys Asn Trp Glu Thr Glu Ile Thr Ala Gln Pro Asp
                135                 140                 145

ggc ggc aag acc gag aac tgc gcg gtc ctg tca ggc gcg gcc aac ggc      704
Gly Gly Lys Thr Glu Asn Cys Ala Val Leu Ser Gly Ala Ala Asn Gly
            150                 155                 160

aag tgg ttc gac aag cgc tgc cgc gat cag ctg ccc tac atc tgc cag      752
Lys Trp Phe Asp Lys Arg Cys Arg Asp Gln Leu Pro Tyr Ile Cys Gln
        165                 170                 175

ttc ggg atc gtg tagccggcgg ggcgggggcc gtgggggccc tggaggaggg         804
Phe Gly Ile Val
    180

caggagccgc gggaggccgg gaggagggtg gggaccttgc agcccccatc ctctccgt      862


<210> SEQ ID NO 62
<211> LENGTH: 202
<212> TYPE: PRT
<213> ORGANISM: Homo sapiens
<220> FEATURE:
<221> NAME/KEY: SIGNAL
<222> LOCATION: 1..21

<400> SEQUENCE: 62

Met Glu Leu Trp Gly Ala Tyr Leu Leu Leu Cys Leu Phe Ser Leu Leu
    -20                 -15                 -10

Thr Gln Val Thr Thr Glu Pro Pro Thr Gln Lys Pro Lys Lys Ile Val
-5                  1               5                   10

Asn Ala Lys Lys Asp Val Val Asn Thr Lys Met Phe Glu Glu Leu Lys
            15                  20                  25

Ser Arg Leu Asp Thr Leu Ala Gln Glu Val Ala Leu Leu Lys Glu Gln
        30                  35                  40

Gln Ala Leu Gln Thr Val Cys Leu Lys Gly Thr Lys Val His Met Lys
    45                  50                  55

Cys Phe Leu Ala Phe Thr Gln Thr Lys Thr Phe His Glu Ser Ser Glu
60                  65                  70                  75

Asp Cys Ile Ser Arg Gly Gly Thr Leu Ser Thr Pro Gln Thr Gly Ser
                80                  85                  90

Glu Asn Asp Ala Leu Tyr Glu Tyr Leu Arg Gln Ser Val Gly Asn Glu
            95                  100                 105
```

```
Ala Glu Ile Trp Leu Gly Leu Asn Asp Met Ala Ala Glu Gly Thr Trp
        110                 115                 120

Val Asp Met Thr Gly Ala Arg Ile Ala Tyr Lys Asn Trp Glu Thr Glu
    125                 130                 135

Ile Thr Ala Gln Pro Asp Gly Gly Lys Thr Glu Asn Cys Ala Val Leu
140                 145                 150                 155

Ser Gly Ala Ala Asn Gly Lys Trp Phe Asp Lys Arg Cys Arg Asp Gln
                160                 165                 170

Leu Pro Tyr Ile Cys Gln Phe Gly Ile Val
            175                 180


<210> SEQ ID NO 63
<211> LENGTH: 618
<212> TYPE: DNA
<213> ORGANISM: Homo sapiens
<220> FEATURE:
<221> NAME/KEY: 5'UTR
<222> LOCATION: 1..194
<220> FEATURE:
<221> NAME/KEY: CDS
<222> LOCATION: 195..587
<220> FEATURE:
<221> NAME/KEY: 3'UTR
<222> LOCATION: 588..618
<220> FEATURE:
<221> NAME/KEY: polyA_signal
<222> LOCATION: 578..583
<220> FEATURE:
<221> NAME/KEY: polyA_site
<222> LOCATION: 604..618

<400> SEQUENCE: 63

atttgcttag gtctgatcaa tctgctccac acaatttctc agtgatcctc tgcatctctg     60

cctacaaggg cctccctgac acccaagttc atattgctca gaaacagtga acttgagttt    120

ttcgttttac cttgatctct ctctgacaaa gaaatccaga tgatgcgaga cctgatgaag    180

acaatacatg gaaa atg aca gtc ttg gaa ata act ttg gct gtc atc ctg      230
                Met Thr Val Leu Glu Ile Thr Leu Ala Val Ile Leu
                    -20                 -15                 -10

act cta ctg gga ctt gcc atc ctg gct att ttg tta aca aga tgg gca      278
Thr Leu Leu Gly Leu Ala Ile Leu Ala Ile Leu Leu Thr Arg Trp Ala
                -5                  1               5

cga cgt aag caa agt gaa atg cat atc tcc aga tac agt tca gaa caa      326
Arg Arg Lys Gln Ser Glu Met His Ile Ser Arg Tyr Ser Ser Glu Gln
        10                  15                  20

agt gct aga ctt ctg gac tat gag gat ggt aga gga tcc cga cat gca      374
Ser Ala Arg Leu Leu Asp Tyr Glu Asp Gly Arg Gly Ser Arg His Ala
    25                  30                  35

tat tca aca caa agt gag aga tcc aaa aga gat tac aca cca tca acc      422
Tyr Ser Thr Gln Ser Glu Arg Ser Lys Arg Asp Tyr Thr Pro Ser Thr
40                  45                  50                  55

aac tct cta gca ctg tct cga tca agt att gct tta cct caa gga tcc      470
Asn Ser Leu Ala Leu Ser Arg Ser Ser Ile Ala Leu Pro Gln Gly Ser
                60                  65                  70

atg agt agt ata aaa tgt tta caa aca act gaa gaa ctt cct tcc aga      518
Met Ser Ser Ile Lys Cys Leu Gln Thr Thr Glu Glu Leu Pro Ser Arg
            75                  80                  85

act gca gga gcc atg agt aag ttc ttt ttc tgc cct tta att ctc atg      566
Thr Ala Gly Ala Met Ser Lys Phe Phe Phe Cys Pro Leu Ile Leu Met
        90                  95                  100

tgc ttt gct tta cta aac tgt tagaatatgt aagacgaaaa aaaaaaaaa a        618
Cys Phe Ala Leu Leu Asn Cys
```

```
    105                 110


<210> SEQ ID NO 64
<211> LENGTH: 131
<212> TYPE: PRT
<213> ORGANISM: Homo sapiens
<220> FEATURE:
<221> NAME/KEY: SIGNAL
<222> LOCATION: 1..22

<400> SEQUENCE: 64

Met Thr Val Leu Glu Ile Thr Leu Ala Val Ile Leu Thr Leu Leu Gly
        -20                 -15                 -10

Leu Ala Ile Leu Ala Ile Leu Leu Thr Arg Trp Ala Arg Arg Lys Gln
    -5                  1               5                   10

Ser Glu Met His Ile Ser Arg Tyr Ser Ser Glu Gln Ser Ala Arg Leu
                15                  20                  25

Leu Asp Tyr Glu Asp Gly Arg Gly Ser Arg His Ala Tyr Ser Thr Gln
            30                  35                  40

Ser Glu Arg Ser Lys Arg Asp Tyr Thr Pro Ser Thr Asn Ser Leu Ala
        45                  50                  55

Leu Ser Arg Ser Ser Ile Ala Leu Pro Gln Gly Ser Met Ser Ser Ile
    60                  65                  70

Lys Cys Leu Gln Thr Thr Glu Glu Leu Pro Ser Arg Thr Ala Gly Ala
75                  80                  85                  90

Met Ser Lys Phe Phe Phe Cys Pro Leu Ile Leu Met Cys Phe Ala Leu
                95                  100                 105

Leu Asn Cys


<210> SEQ ID NO 65
<211> LENGTH: 836
<212> TYPE: DNA
<213> ORGANISM: Homo sapiens
<220> FEATURE:
<221> NAME/KEY: 5'UTR
<222> LOCATION: 1..176
<220> FEATURE:
<221> NAME/KEY: CDS
<222> LOCATION: 177..767
<220> FEATURE:
<221> NAME/KEY: 3'UTR
<222> LOCATION: 768..836
<220> FEATURE:
<221> NAME/KEY: polyA_signal
<222> LOCATION: 814..819
<220> FEATURE:
<221> NAME/KEY: polyA_site
<222> LOCATION: 822..836

<400> SEQUENCE: 65

aatctgctcc acgcaatttc tcagtgatcc tctgcatctc tgcctacaag ggcctccctg      60

acacccaagt tcatattgct cagaaacagt gaacttgagt tttcatttt  accttgatct     120

ctctctgaca aagaaatcca gatgatgcga gacctgatga agacaataca tggaaa atg     179
                                                              Met

aca gtc ttg gaa ata act ttg gct gtc atc ctg act cta ctg gga ctt      227
Thr Val Leu Glu Ile Thr Leu Ala Val Ile Leu Thr Leu Leu Gly Leu
-20                 -15                 -10                 -5

gcc atc ctg gct att ttg tta aca aga tgg gca cga cgt aag caa agt      275
Ala Ile Leu Ala Ile Leu Leu Thr Arg Trp Ala Arg Arg Lys Gln Ser
                1               5                   10

gaa atg tat atc tcc aga tac agt tca gaa caa agt gct aga ctt ctg      323
Glu Met Tyr Ile Ser Arg Tyr Ser Ser Glu Gln Ser Ala Arg Leu Leu
```

-continued

```
        15                  20                  25

gac tat gag gat ggt aga gga tcc cga cat gca tat tca aca caa agt       371
Asp Tyr Glu Asp Gly Arg Gly Ser Arg His Ala Tyr Ser Thr Gln Ser
    30                  35                  40

gag aga tcc aaa aga gat tac aca cca tca acc aac tct cta gca ctg       419
Glu Arg Ser Lys Arg Asp Tyr Thr Pro Ser Thr Asn Ser Leu Ala Leu
45                  50                  55                  60

tct cga tca agt att gct tta cct caa gga tcc atg agt agt ata aaa       467
Ser Arg Ser Ser Ile Ala Leu Pro Gln Gly Ser Met Ser Ser Ile Lys
                65                  70                  75

tgt tta caa aca act gaa gaa cct cct tcc aga act gca gga gcc atg       515
Cys Leu Gln Thr Thr Glu Glu Pro Pro Ser Arg Thr Ala Gly Ala Met
            80                  85                  90

atg caa ttc aca gcc cct att ccc gga gct aca gga cct atc aag ctc       563
Met Gln Phe Thr Ala Pro Ile Pro Gly Ala Thr Gly Pro Ile Lys Leu
        95                  100                 105

tct caa aaa acc att gtg caa act cta gga cct att gta caa tat cct       611
Ser Gln Lys Thr Ile Val Gln Thr Leu Gly Pro Ile Val Gln Tyr Pro
    110                 115                 120

gga tcc aat ggg agg ata aac ata agc cag ctc acc tca gag gat ctc       659
Gly Ser Asn Gly Arg Ile Asn Ile Ser Gln Leu Thr Ser Glu Asp Leu
125                 130                 135                 140

act ggg gct aaa gga agg gtc aca tct ggt cca cag ttc cct aat agc       707
Thr Gly Ala Lys Gly Arg Val Thr Ser Gly Pro Gln Phe Pro Asn Ser
                145                 150                 155

cac cat gtg cca gag aat cta cat gga tac atg aat tcc ctt tcc ctt       755
His His Val Pro Glu Asn Leu His Gly Tyr Met Asn Ser Leu Ser Leu
            160                 165                 170

ttc tcc cct gct tgactccctc tcccttatgt gtaaacaatt taaaaatatg           807
Phe Ser Pro Ala
        175

atagtgtata aatgaaaaaa aaaaaaaaa                                       836

<210> SEQ ID NO 66
<211> LENGTH: 197
<212> TYPE: PRT
<213> ORGANISM: Homo sapiens
<220> FEATURE:
<221> NAME/KEY: SIGNAL
<222> LOCATION: 1..22

<400> SEQUENCE: 66

Met Thr Val Leu Glu Ile Thr Leu Ala Val Ile Leu Thr Leu Leu Gly
        -20                 -15                 -10

Leu Ala Ile Leu Ala Ile Leu Leu Thr Arg Trp Ala Arg Arg Lys Gln
    -5                  1               5                   10

Ser Glu Met Tyr Ile Ser Arg Tyr Ser Ser Glu Gln Ser Ala Arg Leu
                15                  20                  25

Leu Asp Tyr Glu Asp Gly Arg Gly Ser Arg His Ala Tyr Ser Thr Gln
            30                  35                  40

Ser Glu Arg Ser Lys Arg Asp Tyr Thr Pro Ser Thr Asn Ser Leu Ala
        45                  50                  55

Leu Ser Arg Ser Ser Ile Ala Leu Pro Gln Gly Ser Met Ser Ser Ile
    60                  65                  70

Lys Cys Leu Gln Thr Thr Glu Glu Pro Pro Ser Arg Thr Ala Gly Ala
75                  80                  85                  90

Met Met Gln Phe Thr Ala Pro Ile Pro Gly Ala Thr Gly Pro Ile Lys
                95                  100                 105

Leu Ser Gln Lys Thr Ile Val Gln Thr Leu Gly Pro Ile Val Gln Tyr
```

```
            110                 115                 120

Pro Gly Ser Asn Gly Arg Ile Asn Ile Ser Gln Leu Thr Ser Glu Asp
        125                 130                 135

Leu Thr Gly Ala Lys Gly Arg Val Thr Ser Gly Pro Gln Phe Pro Asn
    140                 145                 150

Ser His His Val Pro Glu Asn Leu His Gly Tyr Met Asn Ser Leu Ser
155                 160                 165                 170

Leu Phe Ser Pro Ala
                175


<210> SEQ ID NO 67
<211> LENGTH: 789
<212> TYPE: DNA
<213> ORGANISM: Homo sapiens
<220> FEATURE:
<221> NAME/KEY: 5'UTR
<222> LOCATION: 1..62
<220> FEATURE:
<221> NAME/KEY: CDS
<222> LOCATION: 63..572
<220> FEATURE:
<221> NAME/KEY: 3'UTR
<222> LOCATION: 573..789
<220> FEATURE:
<221> NAME/KEY: polyA_signal
<222> LOCATION: 750..755
<220> FEATURE:
<221> NAME/KEY: polyA_site
<222> LOCATION: 774..789

<400> SEQUENCE: 67

atatgtcatc aggccccccg cctgggaggt gtgctgccag agattttgcc tcttcaaggt      60

ga atg cgg ctt caa ggg gct atc ttt gtg ctc ctg ccc cac ctg ggg       107
   Met Arg Leu Gln Gly Ala Ile Phe Val Leu Leu Pro His Leu Gly
   1               5                   10                  15

ccc atc ctg gtc tgg ctg ttc act cgt gat cac atg tct ggt tgg tgt      155
Pro Ile Leu Val Trp Leu Phe Thr Arg Asp His Met Ser Gly Trp Cys
                20                  25                  30

gag ggc ccg agg atg ctg tcc tgg tgc cca ttc tac aaa gtc tta ttg      203
Glu Gly Pro Arg Met Leu Ser Trp Cys Pro Phe Tyr Lys Val Leu Leu
            35                  40                  45

ctt gta cag aca gcc atc tac tct gtc gtg ggc tat gcc tcc tac ctg      251
Leu Val Gln Thr Ala Ile Tyr Ser Val Val Gly Tyr Ala Ser Tyr Leu
        50                  55                  60

gtg tgg aag gac ctg gga ggg ggc ttg ggg tgg ccc ctg gcc ctg cct      299
Val Trp Lys Asp Leu Gly Gly Gly Leu Gly Trp Pro Leu Ala Leu Pro
    65                  70                  75

ctt cgc ctc tat gct gtt cag ctc acc atc agc tgg act gtc ctg gtt      347
Leu Arg Leu Tyr Ala Val Gln Leu Thr Ile Ser Trp Thr Val Leu Val
80                  85                  90                  95

ctc ttt ttc aca gtc cac aac cct ggt ctg gcc ctg ctg cac ctg ctg      395
Leu Phe Phe Thr Val His Asn Pro Gly Leu Ala Leu Leu His Leu Leu
                100                 105                 110

ctg ctg tat ggg ctg gtg gtg agc aca gca ctg atc tgg cat ccc atc      443
Leu Leu Tyr Gly Leu Val Val Ser Thr Ala Leu Ile Trp His Pro Ile
            115                 120                 125

aac aaa ctg gct gcc ctg tta ctg ctg ccc tac cta gcc tgg ctc acc      491
Asn Lys Leu Ala Ala Leu Leu Leu Leu Pro Tyr Leu Ala Trp Leu Thr
        130                 135                 140

gtg act tca gcc ctc acc tac cac ctg tgg agg gac agc ctt tgt cca      539
Val Thr Ser Ala Leu Thr Tyr His Leu Trp Arg Asp Ser Leu Cys Pro
    145                 150                 155
```

```
gtg cac cag cct cag ccc acg gag aag agt gac tgaggcccta gggcatggga    592
Val His Gln Pro Gln Pro Thr Glu Lys Ser Asp
160                 165                 170

gaggagggac gcccagggtg gggaggaaga gtctgcaagc agggctgtgg agttagggtt    652

caccccaatg ggaccaccct cctgggtccc ctggtgccgt tttccttag aaatcagaga     712

aatgggaaag ggggggaaac tgattttaca cttaaataat aaaatcctat tagtaactcc    772

gaaaaaaaaa aaaaaaa                                                   789


<210> SEQ ID NO 68
<211> LENGTH: 170
<212> TYPE: PRT
<213> ORGANISM: Homo sapiens

<400> SEQUENCE: 68

Met Arg Leu Gln Gly Ala Ile Phe Val Leu Leu Pro His Leu Gly Pro
1               5                   10                  15

Ile Leu Val Trp Leu Phe Thr Arg Asp His Met Ser Gly Trp Cys Glu
            20                  25                  30

Gly Pro Arg Met Leu Ser Trp Cys Pro Phe Tyr Lys Val Leu Leu Leu
        35                  40                  45

Val Gln Thr Ala Ile Tyr Ser Val Val Gly Tyr Ala Ser Tyr Leu Val
    50                  55                  60

Trp Lys Asp Leu Gly Gly Gly Leu Gly Trp Pro Leu Ala Leu Pro Leu
65                  70                  75                  80

Arg Leu Tyr Ala Val Gln Leu Thr Ile Ser Trp Thr Val Leu Val Leu
                85                  90                  95

Phe Phe Thr Val His Asn Pro Gly Leu Ala Leu Leu His Leu Leu Leu
            100                 105                 110

Leu Tyr Gly Leu Val Val Ser Thr Ala Leu Ile Trp His Pro Ile Asn
        115                 120                 125

Lys Leu Ala Ala Leu Leu Leu Leu Pro Tyr Leu Ala Trp Leu Thr Val
    130                 135                 140

Thr Ser Ala Leu Thr Tyr His Leu Trp Arg Asp Ser Leu Cys Pro Val
145                 150                 155                 160

His Gln Pro Gln Pro Thr Glu Lys Ser Asp
                165                 170


<210> SEQ ID NO 69
<211> LENGTH: 2556
<212> TYPE: DNA
<213> ORGANISM: Homo sapiens
<220> FEATURE:
<221> NAME/KEY: 5'UTR
<222> LOCATION: 1..66
<220> FEATURE:
<221> NAME/KEY: CDS
<222> LOCATION: 67..2427
<220> FEATURE:
<221> NAME/KEY: 3'UTR
<222> LOCATION: 2428..2556
<220> FEATURE:
<221> NAME/KEY: polyA_signal
<222> LOCATION: 2522..2527
<220> FEATURE:
<221> NAME/KEY: polyA_site
<222> LOCATION: 2541..2556

<400> SEQUENCE: 69

gtccccgcgt ccctggcaat tcccgacttc ccaacggctt cctgctggca gccccgaagc     60

cgcacc atg ttc cgc ctc tgg ttg ctg ctg gcc ggg ctc tgc ggc ctc       108
```

-continued

```
     Met Phe Arg Leu Trp Leu Leu Leu Ala Gly Leu Cys Gly Leu
     -15                -10                 -5

ctg gcg tca aga ccc ggt ttt caa aat tca ctt cta cag atc gta att      156
Leu Ala Ser Arg Pro Gly Phe Gln Asn Ser Leu Leu Gln Ile Val Ile
  1               5                  10                  15

cca gag aaa atc caa aca aat aca aat gac agt tca gaa ata gaa tat      204
Pro Glu Lys Ile Gln Thr Asn Thr Asn Asp Ser Ser Glu Ile Glu Tyr
             20                  25                  30

gaa caa ata tcc tat att att cca ata gat gag aaa ctg tac act gtg      252
Glu Gln Ile Ser Tyr Ile Ile Pro Ile Asp Glu Lys Leu Tyr Thr Val
         35                  40                  45

cac ctt aaa caa aga tat ttt tta aca gat aat ttt atg atc tat ttg      300
His Leu Lys Gln Arg Tyr Phe Leu Thr Asp Asn Phe Met Ile Tyr Leu
     50                  55                  60

tac aat caa gga tct atg aat act tat tct tca gat att cag act caa      348
Tyr Asn Gln Gly Ser Met Asn Thr Tyr Ser Ser Asp Ile Gln Thr Gln
 65                  70                  75

tgc tac tat caa gga aat att gaa gaa tat cca gat tcc atg gtc aca      396
Cys Tyr Tyr Gln Gly Asn Ile Glu Glu Tyr Pro Asp Ser Met Val Thr
80                  85                  90                  95

ctc agc acg tgc tct gga cta aga gga ata ctg caa ttt gaa aat gtt      444
Leu Ser Thr Cys Ser Gly Leu Arg Gly Ile Leu Gln Phe Glu Asn Val
            100                 105                 110

tct tat gga att gag cct ctg gaa tct gca gtt gaa ttt cag cat gtt      492
Ser Tyr Gly Ile Glu Pro Leu Glu Ser Ala Val Glu Phe Gln His Val
        115                 120                 125

ctt cac aaa tta aag aat gaa gac aat gat att gca att ttt att gac      540
Leu His Lys Leu Lys Asn Glu Asp Asn Asp Ile Ala Ile Phe Ile Asp
    130                 135                 140

aga agc ctg aaa gaa caa cca atg gat gac aac att ttt ata agt gaa      588
Arg Ser Leu Lys Glu Gln Pro Met Asp Asp Asn Ile Phe Ile Ser Glu
    145                 150                 155

aaa tca gaa cca gct gtt cca gat tta ttt cct ctt tat cta gaa atg      636
Lys Ser Glu Pro Ala Val Pro Asp Leu Phe Pro Leu Tyr Leu Glu Met
160                 165                 170                 175

cat att gtg gtg gac aaa act ttg tat gat tac tgg ggc tct gat agc      684
His Ile Val Val Asp Lys Thr Leu Tyr Asp Tyr Trp Gly Ser Asp Ser
                180                 185                 190

atg ata gta aca aat aaa gtc atc gaa att gtt ggc ctt gca aat tca      732
Met Ile Val Thr Asn Lys Val Ile Glu Ile Val Gly Leu Ala Asn Ser
            195                 200                 205

atg ttc acc caa ttt aaa gtt act att gtg ctg tca tca ttg gag tta      780
Met Phe Thr Gln Phe Lys Val Thr Ile Val Leu Ser Ser Leu Glu Leu
        210                 215                 220

tgg tca gat gaa aat aag att tct aca gtt ggt gag gca gat gaa tta      828
Trp Ser Asp Glu Asn Lys Ile Ser Thr Val Gly Glu Ala Asp Glu Leu
    225                 230                 235

ttg caa aaa ttt tta gaa tgg aaa caa tct tat ctt aac cta agg cct      876
Leu Gln Lys Phe Leu Glu Trp Lys Gln Ser Tyr Leu Asn Leu Arg Pro
240                 245                 250                 255

cat gat att gca tat cta cta att tat atg gat tat cct cgt tat ttg      924
His Asp Ile Ala Tyr Leu Leu Ile Tyr Met Asp Tyr Pro Arg Tyr Leu
                260                 265                 270

gga gca gtg ttt cct gga aca atg tgt att act cgt tat tct gca gga      972
Gly Ala Val Phe Pro Gly Thr Met Cys Ile Thr Arg Tyr Ser Ala Gly
            275                 280                 285

gtc gca ttg tac ccc aag gag ata act ctg gag gca ttt gca gtt att     1020
Val Ala Leu Tyr Pro Lys Glu Ile Thr Leu Glu Ala Phe Ala Val Ile
        290                 295                 300
```

-continued

```
gtc acc cag atg ctg gca ctc agt ctg gga ata tca tat gac gac cca      1068
Val Thr Gln Met Leu Ala Leu Ser Leu Gly Ile Ser Tyr Asp Asp Pro
    305                 310                 315

aag aaa tgt caa tgt tca gaa tcc acc tgt ata atg aat cca gaa gtt      1116
Lys Lys Cys Gln Cys Ser Glu Ser Thr Cys Ile Met Asn Pro Glu Val
320                 325                 330                 335

gtg caa tcc aat ggt gtg aag act ttt agc agt tgc agt ttg agg agc      1164
Val Gln Ser Asn Gly Val Lys Thr Phe Ser Ser Cys Ser Leu Arg Ser
                340                 345                 350

ttt caa aat ttc att tca aat gtg ggt gtc aaa tgt ctt cag aat aag      1212
Phe Gln Asn Phe Ile Ser Asn Val Gly Val Lys Cys Leu Gln Asn Lys
            355                 360                 365

cca caa atg caa aaa aaa tct ccg aaa cca gtc tgt ggc aat ggc aga      1260
Pro Gln Met Gln Lys Lys Ser Pro Lys Pro Val Cys Gly Asn Gly Arg
        370                 375                 380

ttg gag gga aat gaa atc tgt gat tgt ggt act gag gct caa tgt gga      1308
Leu Glu Gly Asn Glu Ile Cys Asp Cys Gly Thr Glu Ala Gln Cys Gly
    385                 390                 395

cct gca agc tgt tgt gat ttt cga act tgt gta ctg aaa gac gga gca      1356
Pro Ala Ser Cys Cys Asp Phe Arg Thr Cys Val Leu Lys Asp Gly Ala
400                 405                 410                 415

aaa tgt tat aaa gga ctg tgc tgc aaa gac tgt caa att tta caa tca      1404
Lys Cys Tyr Lys Gly Leu Cys Cys Lys Asp Cys Gln Ile Leu Gln Ser
                420                 425                 430

ggc gtt gaa tgt agg ccg aaa gca cat cct gaa tgt gac atc gct gaa      1452
Gly Val Glu Cys Arg Pro Lys Ala His Pro Glu Cys Asp Ile Ala Glu
            435                 440                 445

aat tgt aat gga agc tca cca gaa tgt ggt cct gac ata act tta atc      1500
Asn Cys Asn Gly Ser Ser Pro Glu Cys Gly Pro Asp Ile Thr Leu Ile
        450                 455                 460

aat gga ctt tca tgc aaa aat aat aag ttt att tgt tat gac gga gac      1548
Asn Gly Leu Ser Cys Lys Asn Asn Lys Phe Ile Cys Tyr Asp Gly Asp
    465                 470                 475

tgc cat gat ctc gat gca cgt tgt gag agt gta ttt gga aaa ggt tca      1596
Cys His Asp Leu Asp Ala Arg Cys Glu Ser Val Phe Gly Lys Gly Ser
480                 485                 490                 495

aga aat gct cca ttt gcc tgc tat gaa gaa ata caa tct caa tca gac      1644
Arg Asn Ala Pro Phe Ala Cys Tyr Glu Glu Ile Gln Ser Gln Ser Asp
                500                 505                 510

aga ttt ggg aac tgt ggt agg gat aga aat aac aaa tat gtg ttc tgt      1692
Arg Phe Gly Asn Cys Gly Arg Asp Arg Asn Asn Lys Tyr Val Phe Cys
            515                 520                 525

gga tgg agg aat ctt ata tgt gga aga tta gtt tgt acc tac cct act      1740
Gly Trp Arg Asn Leu Ile Cys Gly Arg Leu Val Cys Thr Tyr Pro Thr
        530                 535                 540

cga aag cct ttc cat caa gaa aat ggt gat gtg att tat gct ttc gta      1788
Arg Lys Pro Phe His Gln Glu Asn Gly Asp Val Ile Tyr Ala Phe Val
    545                 550                 555

cga gat tct gta tgc ata acc gta gac tac aaa ttg cct cga aca gtt      1836
Arg Asp Ser Val Cys Ile Thr Val Asp Tyr Lys Leu Pro Arg Thr Val
560                 565                 570                 575

cca gat cca ctg gct gtc aaa aat ggc tct cag tgt gat att ggg agg      1884
Pro Asp Pro Leu Ala Val Lys Asn Gly Ser Gln Cys Asp Ile Gly Arg
                580                 585                 590

gtt tgt gta aat cgt gaa tgt gta gaa tca agg ata att aag gct tca      1932
Val Cys Val Asn Arg Glu Cys Val Glu Ser Arg Ile Ile Lys Ala Ser
            595                 600                 605

gca cat gtt tgt tca caa cag tgt tct gga cat gga gtg tgt gat tcc      1980
Ala His Val Cys Ser Gln Gln Cys Ser Gly His Gly Val Cys Asp Ser
        610                 615                 620
```

```
aga aac aag tgc cat tgt tcg cca ggc tat aag cct cca aac tgc caa     2028
Arg Asn Lys Cys His Cys Ser Pro Gly Tyr Lys Pro Pro Asn Cys Gln
    625                 630                 635

ata cgt tcc aaa gga ttt tcc ata ttt cct gag gaa gat atg ggt tca     2076
Ile Arg Ser Lys Gly Phe Ser Ile Phe Pro Glu Glu Asp Met Gly Ser
640                 645                 650                 655

atc atg gaa aga gca tct ggg aag act gaa aac acc tgg ctt cta ggt     2124
Ile Met Glu Arg Ala Ser Gly Lys Thr Glu Asn Thr Trp Leu Leu Gly
                660                 665                 670

ttc ctc att gct ctt cct att ctc att gta aca acc gca ata gtt ttg     2172
Phe Leu Ile Ala Leu Pro Ile Leu Ile Val Thr Thr Ala Ile Val Leu
            675                 680                 685

gca agg aaa cag ttg aaa aac tgg ttc gcc aag gaa gag gaa ttc cca     2220
Ala Arg Lys Gln Leu Lys Asn Trp Phe Ala Lys Glu Glu Glu Phe Pro
        690                 695                 700

agt agc gaa tct aaa tcg gaa ggt agc aca cag aca tat gcc agc caa     2268
Ser Ser Glu Ser Lys Ser Glu Gly Ser Thr Gln Thr Tyr Ala Ser Gln
    705                 710                 715

tcc agc tca gaa ggc agc act cag aca tat gcc ggc caa acc aga tca     2316
Ser Ser Ser Glu Gly Ser Thr Gln Thr Tyr Ala Gly Gln Thr Arg Ser
720                 725                 730                 735

gaa agc agc agt caa gct gat act agc aaa tcc aaa tca gaa gat agt     2364
Glu Ser Ser Ser Gln Ala Asp Thr Ser Lys Ser Lys Ser Glu Asp Ser
                740                 745                 750

gct gaa gca tat act agc aga tcc aaa tca cag gac agt acc caa aca     2412
Ala Glu Ala Tyr Thr Ser Arg Ser Lys Ser Gln Asp Ser Thr Gln Thr
            755                 760                 765

caa agc agt agt aac tagtgattcc ttcagaaggc aacggataac atcgagagtc     2467
Gln Ser Ser Ser Asn
        770

tcgctaagaa atgaaaattc tgtctttcct tccgtggtca cagctgaaag aaacaataaa   2527

ttgagtgtgg accaaaaaaa aaaaaaaat                                     2556


<210> SEQ ID NO 70
<211> LENGTH: 787
<212> TYPE: PRT
<213> ORGANISM: Homo sapiens
<220> FEATURE:
<221> NAME/KEY: SIGNAL
<222> LOCATION: 1..16

<400> SEQUENCE: 70

Met Phe Arg Leu Trp Leu Leu Leu Ala Gly Leu Cys Gly Leu Leu Ala
    -15                 -10                 -5

Ser Arg Pro Gly Phe Gln Asn Ser Leu Leu Gln Ile Val Ile Pro Glu
1               5                   10                  15

Lys Ile Gln Thr Asn Thr Asn Asp Ser Ser Glu Ile Glu Tyr Glu Gln
            20                  25                  30

Ile Ser Tyr Ile Ile Pro Ile Asp Glu Lys Leu Tyr Thr Val His Leu
        35                  40                  45

Lys Gln Arg Tyr Phe Leu Thr Asp Asn Phe Met Ile Tyr Leu Tyr Asn
    50                  55                  60

Gln Gly Ser Met Asn Thr Tyr Ser Ser Asp Ile Gln Thr Gln Cys Tyr
65                  70                  75                  80

Tyr Gln Gly Asn Ile Glu Glu Tyr Pro Asp Ser Met Val Thr Leu Ser
                85                  90                  95

Thr Cys Ser Gly Leu Arg Gly Ile Leu Gln Phe Glu Asn Val Ser Tyr
            100                 105                 110
```

-continued

```
Gly Ile Glu Pro Leu Glu Ser Ala Val Glu Phe Gln His Val Leu His
        115                 120                 125

Lys Leu Lys Asn Glu Asp Asn Asp Ile Ala Ile Phe Ile Asp Arg Ser
    130                 135                 140

Leu Lys Glu Gln Pro Met Asp Asp Asn Ile Phe Ile Ser Glu Lys Ser
145                 150                 155                 160

Glu Pro Ala Val Pro Asp Leu Phe Pro Leu Tyr Leu Glu Met His Ile
                165                 170                 175

Val Val Asp Lys Thr Leu Tyr Asp Tyr Trp Gly Ser Asp Ser Met Ile
            180                 185                 190

Val Thr Asn Lys Val Ile Glu Ile Val Gly Leu Ala Asn Ser Met Phe
        195                 200                 205

Thr Gln Phe Lys Val Thr Ile Val Leu Ser Ser Leu Glu Leu Trp Ser
    210                 215                 220

Asp Glu Asn Lys Ile Ser Thr Val Gly Glu Ala Asp Glu Leu Leu Gln
225                 230                 235                 240

Lys Phe Leu Glu Trp Lys Gln Ser Tyr Leu Asn Leu Arg Pro His Asp
                245                 250                 255

Ile Ala Tyr Leu Leu Ile Tyr Met Asp Tyr Pro Arg Tyr Leu Gly Ala
            260                 265                 270

Val Phe Pro Gly Thr Met Cys Ile Thr Arg Tyr Ser Ala Gly Val Ala
        275                 280                 285

Leu Tyr Pro Lys Glu Ile Thr Leu Glu Ala Phe Ala Val Ile Val Thr
    290                 295                 300

Gln Met Leu Ala Leu Ser Leu Gly Ile Ser Tyr Asp Asp Pro Lys Lys
305                 310                 315                 320

Cys Gln Cys Ser Glu Ser Thr Cys Ile Met Asn Pro Glu Val Val Gln
                325                 330                 335

Ser Asn Gly Val Lys Thr Phe Ser Ser Cys Ser Leu Arg Ser Phe Gln
            340                 345                 350

Asn Phe Ile Ser Asn Val Gly Val Lys Cys Leu Gln Asn Lys Pro Gln
        355                 360                 365

Met Gln Lys Lys Ser Pro Lys Pro Val Cys Gly Asn Gly Arg Leu Glu
    370                 375                 380

Gly Asn Glu Ile Cys Asp Cys Gly Thr Glu Ala Gln Cys Gly Pro Ala
385                 390                 395                 400

Ser Cys Cys Asp Phe Arg Thr Cys Val Leu Lys Asp Gly Ala Lys Cys
                405                 410                 415

Tyr Lys Gly Leu Cys Cys Lys Asp Cys Gln Ile Leu Gln Ser Gly Val
            420                 425                 430

Glu Cys Arg Pro Lys Ala His Pro Glu Cys Asp Ile Ala Glu Asn Cys
        435                 440                 445

Asn Gly Ser Ser Pro Glu Cys Gly Pro Asp Ile Thr Leu Ile Asn Gly
    450                 455                 460

Leu Ser Cys Lys Asn Asn Lys Phe Ile Cys Tyr Asp Gly Asp Cys His
465                 470                 475                 480

Asp Leu Asp Ala Arg Cys Glu Ser Val Phe Gly Lys Gly Ser Arg Asn
                485                 490                 495

Ala Pro Phe Ala Cys Tyr Glu Glu Ile Gln Ser Gln Ser Asp Arg Phe
            500                 505                 510

Gly Asn Cys Gly Arg Asp Arg Asn Asn Lys Tyr Val Phe Cys Gly Trp
        515                 520                 525
```

-continued

```
Arg Asn Leu Ile Cys Gly Arg Leu Val Cys Thr Tyr Pro Thr Arg Lys
    530                 535                 540

Pro Phe His Gln Glu Asn Gly Asp Val Ile Tyr Ala Phe Val Arg Asp
545                 550                 555                 560

Ser Val Cys Ile Thr Val Asp Tyr Lys Leu Pro Arg Thr Val Pro Asp
                565                 570                 575

Pro Leu Ala Val Lys Asn Gly Ser Gln Cys Asp Ile Gly Arg Val Cys
            580                 585                 590

Val Asn Arg Glu Cys Val Glu Ser Arg Ile Ile Lys Ala Ser Ala His
        595                 600                 605

Val Cys Ser Gln Gln Cys Ser Gly His Gly Val Cys Asp Ser Arg Asn
    610                 615                 620

Lys Cys His Cys Ser Pro Gly Tyr Lys Pro Pro Asn Cys Gln Ile Arg
625                 630                 635                 640

Ser Lys Gly Phe Ser Ile Phe Pro Glu Glu Asp Met Gly Ser Ile Met
                645                 650                 655

Glu Arg Ala Ser Gly Lys Thr Glu Asn Thr Trp Leu Leu Gly Phe Leu
            660                 665                 670

Ile Ala Leu Pro Ile Leu Ile Val Thr Thr Ala Ile Val Leu Ala Arg
        675                 680                 685

Lys Gln Leu Lys Asn Trp Phe Ala Lys Glu Glu Glu Phe Pro Ser Ser
    690                 695                 700

Glu Ser Lys Ser Glu Gly Ser Thr Gln Thr Tyr Ala Ser Gln Ser Ser
705                 710                 715                 720

Ser Glu Gly Ser Thr Gln Thr Tyr Ala Gly Gln Thr Arg Ser Glu Ser
                725                 730                 735

Ser Ser Gln Ala Asp Thr Ser Lys Ser Lys Ser Glu Asp Ser Ala Glu
            740                 745                 750

Ala Tyr Thr Ser Arg Ser Lys Ser Gln Asp Ser Thr Gln Thr Gln Ser
        755                 760                 765

Ser Ser Asn
    770


<210> SEQ ID NO 71
<211> LENGTH: 1603
<212> TYPE: DNA
<213> ORGANISM: Homo sapiens
<220> FEATURE:
<221> NAME/KEY: 5'UTR
<222> LOCATION: 1..7
<220> FEATURE:
<221> NAME/KEY: CDS
<222> LOCATION: 8..763
<220> FEATURE:
<221> NAME/KEY: 3'UTR
<222> LOCATION: 764..1603
<220> FEATURE:
<221> NAME/KEY: polyA_signal
<222> LOCATION: 1562..1567
<220> FEATURE:
<221> NAME/KEY: polyA_site
<222> LOCATION: 1588..1603

<400> SEQUENCE: 71

gagaagg atg ggg ccg cat cta cac ctg tgc ctg tgt gtg cct gac ctg       49
        Met Gly Pro His Leu His Leu Cys Leu Cys Val Pro Asp Leu
            -15                 -10                 -5

cgg tca ctc cgt gtc tgt gtg tcc ctc tgg tct gtc cac cac agg cca       97
Arg Ser Leu Arg Val Cys Val Ser Leu Trp Ser Val His His Arg Pro
        1               5                   10
```

-continued

```
cac gag tcc ctg gcc cgg gag gag gcc ctc act gca ctt ggg aag ctc      145
His Glu Ser Leu Ala Arg Glu Glu Ala Leu Thr Ala Leu Gly Lys Leu
15                  20                  25                  30

ctg tac ctc tta gat ggg atg ctg gat ggg cag gtg aac agt ggt ata      193
Leu Tyr Leu Leu Asp Gly Met Leu Asp Gly Gln Val Asn Ser Gly Ile
                35                  40                  45

gca gcc act cca gcc tct gct gca gca gcc acc ctg gat gtg gct gtt      241
Ala Ala Thr Pro Ala Ser Ala Ala Ala Ala Thr Leu Asp Val Ala Val
            50                  55                  60

cgg aga ggc ctg tcc cac gca gcc cag agg ctg ctg tgc gtg gcc ctg      289
Arg Arg Gly Leu Ser His Ala Ala Gln Arg Leu Leu Cys Val Ala Leu
        65                  70                  75

gga cag ctg gac cgg cct cca gac ctc gcc cat gac ggg agg agt ctg      337
Gly Gln Leu Asp Arg Pro Pro Asp Leu Ala His Asp Gly Arg Ser Leu
    80                  85                  90

tgg ctg aac atc agg ggc aag gag gcg gct gcc cta tcc atg ttc cat      385
Trp Leu Asn Ile Arg Gly Lys Glu Ala Ala Ala Leu Ser Met Phe His
95                  100                 105                 110

gtc tcc acg cca ctg cca gtg atg acc ggt ggt ttc ctg agc tgc atc      433
Val Ser Thr Pro Leu Pro Val Met Thr Gly Gly Phe Leu Ser Cys Ile
                115                 120                 125

ttg ggc ttg gtg ctg ccc ctg gcc tat ggc ttc cag cct gac ctg gtg      481
Leu Gly Leu Val Leu Pro Leu Ala Tyr Gly Phe Gln Pro Asp Leu Val
            130                 135                 140

ctg gtg gcg ctg ggg cct ggc cat ggc ctg cag ggc ccc cac gst gca      529
Leu Val Ala Leu Gly Pro Gly His Gly Leu Gln Gly Pro His Xaa Ala
        145                 150                 155

ctc ctg gct gca atg ctt cgg ggg ctg gca ggg ggc cga gtc ctg gcc      577
Leu Leu Ala Ala Met Leu Arg Gly Leu Ala Gly Gly Arg Val Leu Ala
    160                 165                 170

ctc ctg gag gag aac tcc aca ccc cag cta gca ggg atc ctg gcc cgg      625
Leu Leu Glu Glu Asn Ser Thr Pro Gln Leu Ala Gly Ile Leu Ala Arg
175                 180                 185                 190

gtg ctg aat gga gag gca cct cct agc cta ggc cct tcc tct gtg gcc      673
Val Leu Asn Gly Glu Ala Pro Pro Ser Leu Gly Pro Ser Ser Val Ala
                195                 200                 205

tcc cca gag gac gtc cag gcc ctg atg tac ctg aga ggg cag ctg gag      721
Ser Pro Glu Asp Val Gln Ala Leu Met Tyr Leu Arg Gly Gln Leu Glu
            210                 215                 220

cct cag tgg aag atg ttg cag tgc cat cct cac ctg gtg gct              763
Pro Gln Trp Lys Met Leu Gln Cys His Pro His Leu Val Ala
        225                 230                 235

tgaaatcggc caaggtggga gcatttacac cgcagaaatg acaccgcacg ccagcgcccc    823

gcggccgcga tccggacccc aagcccacgg ctccctcgac tctggggcac ggaaccccgc    883

ccactcccaa tccccgcgcc ccgccctctc ccacccgtgc ttcccccgct ccacccctca    943

cctcacctcg cccccgcccc acccatcgcg ccccggcggc tgttattgtt cggctgggct   1003

cggtcgggcg ctgtctccct cggctctgcg ggtgtcagtt cgtccggctt cctcacagcc   1063

cctcactccc ggcggctgac agcagcagcg gcggcggcgg gcggcgcctg gcgtttcgag   1123

gctgagcggc accggggttg gggcgcggag gaggagcagc agcgggagga ggagccgtgt   1183

gccctggcac tgagcggccg cggccatggc gtacgcctat ctcttcaagt acatcataat   1243

cggcgacaca ggtgttggta aatcatgctt attgctacag tttacagaca agaggttcag   1303

ccagtgcatg accttactat tggtgtagag ttcggtgctc gaatgataac tattgatggg   1363

aaacagataa aacttcagat atgggatacg gcagggcaag aatcctttcg ttccatcaca   1423

aggtcgtatt acagaggtgc agcaggagct ttactagttt acgatattac acggagagat   1483
```

```
acattcaacc acttgacaac ctggttagaa gatgcccgcc agcattccaa ttccaacatg   1543

gtcattatgc ttattggaaa taaaagtgat ttagaatcta gaagaaaaaa aaaaagaaaa   1603


<210> SEQ ID NO 72
<211> LENGTH: 252
<212> TYPE: PRT
<213> ORGANISM: Homo sapiens
<220> FEATURE:
<221> NAME/KEY: SIGNAL
<222> LOCATION: 1..17
<220> FEATURE:
<221> NAME/KEY: UNSURE
<222> LOCATION: 173
<223> OTHER INFORMATION: Xaa = Ala,Gly

<400> SEQUENCE: 72

Met Gly Pro His Leu His Leu Cys Leu Cys Val Pro Asp Leu Arg Ser
        -15                 -10                 -5

Leu Arg Val Cys Val Ser Leu Trp Ser Val His His Arg Pro His Glu
    1               5                   10                  15

Ser Leu Ala Arg Glu Glu Ala Leu Thr Ala Leu Gly Lys Leu Leu Tyr
                20                  25                  30

Leu Leu Asp Gly Met Leu Asp Gly Gln Val Asn Ser Gly Ile Ala Ala
            35                  40                  45

Thr Pro Ala Ser Ala Ala Ala Ala Thr Leu Asp Val Ala Val Arg Arg
        50                  55                  60

Gly Leu Ser His Ala Ala Gln Arg Leu Leu Cys Val Ala Leu Gly Gln
    65                  70                  75

Leu Asp Arg Pro Pro Asp Leu Ala His Asp Gly Arg Ser Leu Trp Leu
80                  85                  90                  95

Asn Ile Arg Gly Lys Glu Ala Ala Ala Leu Ser Met Phe His Val Ser
                100                 105                 110

Thr Pro Leu Pro Val Met Thr Gly Gly Phe Leu Ser Cys Ile Leu Gly
            115                 120                 125

Leu Val Leu Pro Leu Ala Tyr Gly Phe Gln Pro Asp Leu Val Leu Val
        130                 135                 140

Ala Leu Gly Pro Gly His Gly Leu Gln Gly Pro His Xaa Ala Leu Leu
    145                 150                 155

Ala Ala Met Leu Arg Gly Leu Ala Gly Gly Arg Val Leu Ala Leu Leu
160                 165                 170                 175

Glu Glu Asn Ser Thr Pro Gln Leu Ala Gly Ile Leu Ala Arg Val Leu
                180                 185                 190

Asn Gly Glu Ala Pro Pro Ser Leu Gly Pro Ser Ser Val Ala Ser Pro
            195                 200                 205

Glu Asp Val Gln Ala Leu Met Tyr Leu Arg Gly Gln Leu Glu Pro Gln
        210                 215                 220

Trp Lys Met Leu Gln Cys His Pro His Leu Val Ala
    225                 230                 235


<210> SEQ ID NO 73
<211> LENGTH: 879
<212> TYPE: DNA
<213> ORGANISM: Homo sapiens
<220> FEATURE:
<221> NAME/KEY: 5'UTR
<222> LOCATION: 1..8
<220> FEATURE:
<221> NAME/KEY: CDS
<222> LOCATION: 9..395
```

-continued

```
<220> FEATURE:
<221> NAME/KEY: 3'UTR
<222> LOCATION: 396..879
<220> FEATURE:
<221> NAME/KEY: polyA_site
<222> LOCATION: 864..879

<400> SEQUENCE: 73

aggccaac atg gcc gtg ctg ctg ctg ctg ctc cgt gcc ctc cgc cgg ggt      50
         Met Ala Val Leu Leu Leu Leu Leu Arg Ala Leu Arg Arg Gly
         -15                -10                 -5

cca ggc ccg ggt cct cgg ccg ctg tgg ggc cca ggc ccg gcc tgg agt       98
Pro Gly Pro Gly Pro Arg Pro Leu Trp Gly Pro Gly Pro Ala Trp Ser
    1               5                   10                  15

cca ggg ttc ccc gcc agg ccc ggg agg ggg cgg ccg tac atg gcc agc      146
Pro Gly Phe Pro Ala Arg Pro Gly Arg Gly Arg Pro Tyr Met Ala Ser
                20                  25                  30

agg cct ccg ggg gac ctc gcc gag gct gga ggc cga gct ctg cag agc      194
Arg Pro Pro Gly Asp Leu Ala Glu Ala Gly Gly Arg Ala Leu Gln Ser
            35                  40                  45

tta caa ttg aga ctg cta acc cct acc ttt gaa ggg atc aac gga ttg      242
Leu Gln Leu Arg Leu Leu Thr Pro Thr Phe Glu Gly Ile Asn Gly Leu
        50                  55                  60

ttg ttg aaa caa cat tta gtt cag aat cca gtc aga ctc tgg caa ctt      290
Leu Leu Lys Gln His Leu Val Gln Asn Pro Val Arg Leu Trp Gln Leu
    65                  70                  75

tta ggt ggt act ttc tat ttt aac acc tca agg ttg aag cag aag aat      338
Leu Gly Gly Thr Phe Tyr Phe Asn Thr Ser Arg Leu Lys Gln Lys Asn
80                  85                  90                  95

aag gag aag gat aag tcg aag ggg aag gcg cct gaa gag gac gaa ggt      386
Lys Glu Lys Asp Lys Ser Lys Gly Lys Ala Pro Glu Glu Asp Glu Gly
                100                 105                 110
ata ttc atc tgatgttctt cagtcagtag ctgcctctgg atgtctttac              435
Ile Phe Ile

rtttctgttt wccttttagc aaggtgaaac cagtctggam aatggggaga tgggccgggt    495

gcagtggctc acacttgtaa tcgaaacgct ttgggaggcc caggtggaag gatcacttga    555

ggcctatacc acatagctag accctgtctc actgcaaatt aaaaggctgg gcgtggtggc    615

tcacacctgt aatcccagca ctttgggagg ctgaggcagg cggatcacct gcaccctggc    675

caacatggtg aaaccccgtc tttactaaaa atagaaaatt agccgggcgt gatggcacac    735

gcctgtaatc ccagctactc gggaggctga ggcaggagaa ttgcttgaac ctgggaggtg    795

gaggttgctg tgagtggaga tcatgccatt gcactccagc ctgagcaaca agagcaaaac    855

tccatcccaa aaaaaaaaaa aaaa                                           879


<210> SEQ ID NO 74
<211> LENGTH: 129
<212> TYPE: PRT
<213> ORGANISM: Homo sapiens
<220> FEATURE:
<221> NAME/KEY: SIGNAL
<222> LOCATION: 1..16

<400> SEQUENCE: 74

Met Ala Val Leu Leu Leu Leu Leu Arg Ala Leu Arg Arg Gly Pro Gly
    -15                 -10                 -5

Pro Gly Pro Arg Pro Leu Trp Gly Pro Gly Pro Ala Trp Ser Pro Gly
1               5                   10                  15

Phe Pro Ala Arg Pro Gly Arg Gly Arg Pro Tyr Met Ala Ser Arg Pro
            20                  25                  30
```

-continued

```
Pro Gly Asp Leu Ala Glu Ala Gly Gly Arg Ala Leu Gln Ser Leu Gln
        35                  40                  45

Leu Arg Leu Leu Thr Pro Thr Phe Glu Gly Ile Asn Gly Leu Leu Leu
    50                  55                  60

Lys Gln His Leu Val Gln Asn Pro Val Arg Leu Trp Gln Leu Leu Gly
65                  70                  75                  80

Gly Thr Phe Tyr Phe Asn Thr Ser Arg Leu Lys Gln Lys Asn Lys Glu
                85                  90                  95

Lys Asp Lys Ser Lys Gly Lys Ala Pro Glu Glu Asp Glu Gly Ile Phe
            100                 105                 110

Ile


<210> SEQ ID NO 75
<211> LENGTH: 1634
<212> TYPE: DNA
<213> ORGANISM: Homo sapiens
<220> FEATURE:
<221> NAME/KEY: 5'UTR
<222> LOCATION: 1..87
<220> FEATURE:
<221> NAME/KEY: CDS
<222> LOCATION: 88..1269
<220> FEATURE:
<221> NAME/KEY: 3'UTR
<222> LOCATION: 1270..1634
<220> FEATURE:
<221> NAME/KEY: polyA_signal
<222> LOCATION: 1594..1599
<220> FEATURE:
<221> NAME/KEY: polyA_site
<222> LOCATION: 1619..1634

<400> SEQUENCE: 75

aaagttcctc agcccttggc tcctgcccag tgtttagggt gttggcggag acaaagggga      60

agagtcatcg cctgtcgggg ctaggat atg atg ggt gtg ttt gta gtt gct gct     114
                              Met Met Gly Val Phe Val Val Ala Ala
                              1               5

aag cga acg ccc ttt gga gct tac gga ggc ctt ctg aaa gac ttc act       162
Lys Arg Thr Pro Phe Gly Ala Tyr Gly Gly Leu Leu Lys Asp Phe Thr
10                  15                  20                  25

gct act gac ttg tct gaa ttt gct gcc aag gct gcc ttg tct gct ggc       210
Ala Thr Asp Leu Ser Glu Phe Ala Ala Lys Ala Ala Leu Ser Ala Gly
                30                  35                  40

aaa gtc tca cct gaa aca gtt gac agt gtg att atg ggc aat gtc ctg       258
Lys Val Ser Pro Glu Thr Val Asp Ser Val Ile Met Gly Asn Val Leu
            45                  50                  55

cag agt tct tca gat gct ata tat ttg gca agg cat gtt ggt ttg cgt       306
Gln Ser Ser Ser Asp Ala Ile Tyr Leu Ala Arg His Val Gly Leu Arg
        60                  65                  70

gtg gga atc cca aag gag acc cca gct ctc acg att aat agg ctc tgt       354
Val Gly Ile Pro Lys Glu Thr Pro Ala Leu Thr Ile Asn Arg Leu Cys
    75                  80                  85

ggt tct ggt ttt cag tcc att gtg aat gga tgt cag gaa att tgt gtt       402
Gly Ser Gly Phe Gln Ser Ile Val Asn Gly Cys Gln Glu Ile Cys Val
90                  95                  100                 105

aaa gaa gct gaa gtt gtt tta tgt gga gga acc gaa agc atg agc caa       450
Lys Glu Ala Glu Val Val Leu Cys Gly Gly Thr Glu Ser Met Ser Gln
                110                 115                 120

gct ccc tac tgt gtc aga aat gtg cgt ttt gga acc aag ctt gga tca       498
Ala Pro Tyr Cys Val Arg Asn Val Arg Phe Gly Thr Lys Leu Gly Ser
            125                 130                 135

gat atc aag ctg gaa gat tct tta tgg gta tca tta aca gat cag cat       546
```

-continued

```
Asp Ile Lys Leu Glu Asp Ser Leu Trp Val Ser Leu Thr Asp Gln His
        140                 145                 150

gtc cag ctc ccc atg gca atg act gca gag aat ctt gct gta aaa cac      594
Val Gln Leu Pro Met Ala Met Thr Ala Glu Asn Leu Ala Val Lys His
    155                 160                 165

aaa ata agc aga gaa gaa tgt gac aaa tat gcc ctg cag tca cag cag      642
Lys Ile Ser Arg Glu Glu Cys Asp Lys Tyr Ala Leu Gln Ser Gln Gln
170                 175                 180                 185

aga tgg aaa gct gct aat gat gct ggc tac ttt aat gat gaa atg gca      690
Arg Trp Lys Ala Ala Asn Asp Ala Gly Tyr Phe Asn Asp Glu Met Ala
                190                 195                 200

cca att gaa gtg aag aca aag aaa gga aaa cag aca atg cag gta gac      738
Pro Ile Glu Val Lys Thr Lys Lys Gly Lys Gln Thr Met Gln Val Asp
            205                 210                 215

gag cat gct cgg ccc caa acc acc ctg gaa cag tta cag aaa ctt cct      786
Glu His Ala Arg Pro Gln Thr Thr Leu Glu Gln Leu Gln Lys Leu Pro
        220                 225                 230

cca gta ttc aag aaa gat gga act gtt act gca ggg aat gca tcg ggt      834
Pro Val Phe Lys Lys Asp Gly Thr Val Thr Ala Gly Asn Ala Ser Gly
    235                 240                 245

gta gct gat ggt gct gga gct gtt atc ata gct agt gaa gat gct gtt      882
Val Ala Asp Gly Ala Gly Ala Val Ile Ile Ala Ser Glu Asp Ala Val
250                 255                 260                 265

aag aaa cat aac ttc aca cca ctg gca aga att gtg ggc tac ttt gta      930
Lys Lys His Asn Phe Thr Pro Leu Ala Arg Ile Val Gly Tyr Phe Val
                270                 275                 280

tct gga tgt gat ccc tct atc atg ggt att ggt cct gtc cct gct atc      978
Ser Gly Cys Asp Pro Ser Ile Met Gly Ile Gly Pro Val Pro Ala Ile
            285                 290                 295

agt ggg gca ctg aag aaa gca gga ctg agt ctt aag gac atg gat ttg     1026
Ser Gly Ala Leu Lys Lys Ala Gly Leu Ser Leu Lys Asp Met Asp Leu
        300                 305                 310

gta gag gtg aat gaa gct ttt gct ccc cag tac ttg gct gtt gag agg     1074
Val Glu Val Asn Glu Ala Phe Ala Pro Gln Tyr Leu Ala Val Glu Arg
    315                 320                 325

agt ttg gat ctt gac ata agt aaa acc aat gtg aat gga gga gcc att     1122
Ser Leu Asp Leu Asp Ile Ser Lys Thr Asn Val Asn Gly Gly Ala Ile
330                 335                 340                 345

gct ttg ggt cac cca ctg gga gga tct gga tca aga att act gca cac     1170
Ala Leu Gly His Pro Leu Gly Gly Ser Gly Ser Arg Ile Thr Ala His
                350                 355                 360

ctg gtt cac gaa tta agg cgt cga ggt gga aaa tat gcc gtt gga tca     1218
Leu Val His Glu Leu Arg Arg Arg Gly Gly Lys Tyr Ala Val Gly Ser
            365                 370                 375

gct tgc att gga ggt ggc caa ggt att gct gtc atc att cag agc aca     1266
Ala Cys Ile Gly Gly Gly Gln Gly Ile Ala Val Ile Ile Gln Ser Thr
        380                 385                 390

gcc tgaagagacc agtgagctca ctgtgaccca tccttactct acttggccag          1319
Ala

gccacagtaa aacaagtgac cttcagagca gctgccacaa ctggccatgc cctgccattg   1379

aaacagtgat taagtttgat caagccatgg tgacacaaaa atgcattgat catgaatagg   1439

agcccatgct agaagtacat tctctcagat ttgaaccagt gaaatatgat gtatttctga   1499

gctaaaactc aactatagaa gacattaaaa gaaatcgtat tcttgccaag taaccaccac   1559

ttctgcctta gataatatga ttataaggaa atcaaataaa tgttgcctta acttcaaaca   1619

aaaaaaaaaa aaaaa                                                    1634
```

<210> SEQ ID NO 76
<211> LENGTH: 394
<212> TYPE: PRT
<213> ORGANISM: Homo sapiens

<400> SEQUENCE: 76

```
Met Met Gly Val Phe Val Val Ala Ala Lys Arg Thr Pro Phe Gly Ala
1               5                   10                  15

Tyr Gly Gly Leu Leu Lys Asp Phe Thr Ala Thr Asp Leu Ser Glu Phe
            20                  25                  30

Ala Ala Lys Ala Ala Leu Ser Ala Gly Lys Val Ser Pro Glu Thr Val
        35                  40                  45

Asp Ser Val Ile Met Gly Asn Val Leu Gln Ser Ser Ser Asp Ala Ile
    50                  55                  60

Tyr Leu Ala Arg His Val Gly Leu Arg Val Gly Ile Pro Lys Glu Thr
65                  70                  75                  80

Pro Ala Leu Thr Ile Asn Arg Leu Cys Gly Ser Gly Phe Gln Ser Ile
                85                  90                  95

Val Asn Gly Cys Gln Glu Ile Cys Val Lys Glu Ala Glu Val Val Leu
            100                 105                 110

Cys Gly Gly Thr Glu Ser Met Ser Gln Ala Pro Tyr Cys Val Arg Asn
        115                 120                 125

Val Arg Phe Gly Thr Lys Leu Gly Ser Asp Ile Lys Leu Glu Asp Ser
    130                 135                 140

Leu Trp Val Ser Leu Thr Asp Gln His Val Gln Leu Pro Met Ala Met
145                 150                 155                 160

Thr Ala Glu Asn Leu Ala Val Lys His Lys Ile Ser Arg Glu Glu Cys
                165                 170                 175

Asp Lys Tyr Ala Leu Gln Ser Gln Gln Arg Trp Lys Ala Ala Asn Asp
            180                 185                 190

Ala Gly Tyr Phe Asn Asp Glu Met Ala Pro Ile Glu Val Lys Thr Lys
        195                 200                 205

Lys Gly Lys Gln Thr Met Gln Val Asp Glu His Ala Arg Pro Gln Thr
    210                 215                 220

Thr Leu Glu Gln Leu Gln Lys Leu Pro Pro Val Phe Lys Lys Asp Gly
225                 230                 235                 240

Thr Val Thr Ala Gly Asn Ala Ser Gly Val Ala Asp Gly Ala Gly Ala
                245                 250                 255

Val Ile Ile Ala Ser Glu Asp Ala Val Lys Lys His Asn Phe Thr Pro
            260                 265                 270

Leu Ala Arg Ile Val Gly Tyr Phe Val Ser Gly Cys Asp Pro Ser Ile
        275                 280                 285

Met Gly Ile Gly Pro Val Pro Ala Ile Ser Gly Ala Leu Lys Lys Ala
    290                 295                 300

Gly Leu Ser Leu Lys Asp Met Asp Leu Val Glu Val Asn Glu Ala Phe
305                 310                 315                 320

Ala Pro Gln Tyr Leu Ala Val Glu Arg Ser Leu Asp Leu Asp Ile Ser
                325                 330                 335

Lys Thr Asn Val Asn Gly Gly Ala Ile Ala Leu Gly His Pro Leu Gly
            340                 345                 350

Gly Ser Gly Ser Arg Ile Thr Ala His Leu Val His Glu Leu Arg Arg
        355                 360                 365

Arg Gly Gly Lys Tyr Ala Val Gly Ser Ala Cys Ile Gly Gly Gly Gln
    370                 375                 380
```

```
Gly Ile Ala Val Ile Ile Gln Ser Thr Ala
385                 390


<210> SEQ ID NO 77
<211> LENGTH: 1642
<212> TYPE: DNA
<213> ORGANISM: Homo sapiens
<220> FEATURE:
<221> NAME/KEY: 5'UTR
<222> LOCATION: 1..68
<220> FEATURE:
<221> NAME/KEY: CDS
<222> LOCATION: 69..875
<220> FEATURE:
<221> NAME/KEY: 3'UTR
<222> LOCATION: 876..1642
<220> FEATURE:
<221> NAME/KEY: polyA_signal
<222> LOCATION: 1599..1604
<220> FEATURE:
<221> NAME/KEY: polyA_site
<222> LOCATION: 1627..1642

<400> SEQUENCE: 77

attttatagc ggccgcgggc ggcggcggca gcggttggag gttgtaggac cggcgaggaa      60

taggaatc atg gcg gct gcg ctg ttc gtg ctg ctg gga ttc gcg ctg ctg      110
         Met Ala Ala Ala Leu Phe Val Leu Leu Gly Phe Ala Leu Leu
         -20                -15                 -10

ggc acc cac gga gcc tcc ggg gct gcc ggc aca gtc ttc act acc gta      158
Gly Thr His Gly Ala Ser Gly Ala Ala Gly Thr Val Phe Thr Thr Val
    -5                  1               5                   10

gaa gac ctt ggc tcc aag ata ctc ctc acc tgc tcc ttg aat gac agc      206
Glu Asp Leu Gly Ser Lys Ile Leu Leu Thr Cys Ser Leu Asn Asp Ser
                15                  20                  25

gcc aca gag gtc aca ggg cac cgc tgg ctg aag ggg ggc gtg gtg ctg      254
Ala Thr Glu Val Thr Gly His Arg Trp Leu Lys Gly Gly Val Val Leu
            30                  35                  40

aag gag gac gcg ctg ccc ggc cag aaa acg gag ttc aag gtg gac tcc      302
Lys Glu Asp Ala Leu Pro Gly Gln Lys Thr Glu Phe Lys Val Asp Ser
        45                  50                  55

gac gac cag tgg gga gag tac tcc tgc gtc ttc ctc ccc gag ccc atg      350
Asp Asp Gln Trp Gly Glu Tyr Ser Cys Val Phe Leu Pro Glu Pro Met
    60                  65                  70

ggc acg gcc aac atc cag ctc cac ggg cct ccc aga gtg aag gcc gtg      398
Gly Thr Ala Asn Ile Gln Leu His Gly Pro Pro Arg Val Lys Ala Val
75                  80                  85                  90

aag tcg tca gaa cac atc aac gag ggg gag acg gcc atg ctg gtc tgc      446
Lys Ser Ser Glu His Ile Asn Glu Gly Glu Thr Ala Met Leu Val Cys
                95                  100                 105

aag tca gag tcc gtg cca cct gtc act gac tgg gcc tgg tac aag atc      494
Lys Ser Glu Ser Val Pro Pro Val Thr Asp Trp Ala Trp Tyr Lys Ile
            110                 115                 120

act gac tct gag gac aag gcc ctc atg aac ggc tcc gag agc agg ttc      542
Thr Asp Ser Glu Asp Lys Ala Leu Met Asn Gly Ser Glu Ser Arg Phe
        125                 130                 135

ttc gtg agt tcc tcg cag ggc ctg tca gag cta cac att gag aac ctg      590
Phe Val Ser Ser Ser Gln Gly Leu Ser Glu Leu His Ile Glu Asn Leu
    140                 145                 150

aac atg gag gcc gac ccc ggc cag tac cgg tgc aac ggc acc agc tcc      638
Asn Met Glu Ala Asp Pro Gly Gln Tyr Arg Cys Asn Gly Thr Ser Ser
155                 160                 165                 170

aag ggc tcc gac cag gcc atc atc acg ctc cgc gtg cgc agc cac ctg      686
Lys Gly Ser Asp Gln Ala Ile Ile Thr Leu Arg Val Arg Ser His Leu
                175                 180                 185
```

```
gcc gcc ctc tgg ccc ttc ctg ggc atc gtg gct gag gtg ctg gtg ctg      734
Ala Ala Leu Trp Pro Phe Leu Gly Ile Val Ala Glu Val Leu Val Leu
            190                 195                 200

gtc acc atc atc ttc atc tac gag aag cgc cgg aag ccc gag gac gtc      782
Val Thr Ile Ile Phe Ile Tyr Glu Lys Arg Arg Lys Pro Glu Asp Val
        205                 210                 215

ctg gat gat gac gac gcc ggc tct gca ccc ctg aag agc agc ggg cag      830
Leu Asp Asp Asp Asp Ala Gly Ser Ala Pro Leu Lys Ser Ser Gly Gln
    220                 225                 230

cac cag aat gac aaa ggc aag aac gtc cgc cag agg aac tct tcc          875
His Gln Asn Asp Lys Gly Lys Asn Val Arg Gln Arg Asn Ser Ser
235                 240                 245

tgaggcaggt ggcccgagga cgctccctgc tccgcgtctg cgccgccgcc ggagtccact    935

cccagtgctt gcaagattcc aagttctcac ctcttaaaga aaacccaccc cgtagattcc    995

catcatacac ttccttcttt tttaaaaaag ttgggttttc tccattcagg attctgttcc   1055

ttaggatttt ttccttctga agtgtttcac gagagcccgg gagctgctgc cctgcggccc   1115

cgtctgtggc tttcagcctc tgggtctgag tcatggccgg gtgggcggca cagccttctc   1175

cactggccgg agtcagtgcc aggtccttgc cctttgtgga aagtcacagg tcacacgagg   1235

ggccccgtgt cctgcctgtc tgaagccaat gctgtctggt tgcgccattt ttgtgctttt   1295

atgtttaatt ttatgagggc cacgggtctg tgttcgactc agcctcaggg acgactctga   1355

cctcttggcc acagaggact cacttgccca caccgagggc gaccccgtca cagcctcaag   1415

tcactcccaa gccccctcct tgtctgtgca tccgggggca gctctggagg gggtttgctg   1475

gggaactggc gccatcgccg ggactccaga accgcagaag cctccccagc tcacccctgg   1535

aggacggccg gctctctata gcaccagggc tcacgtggga acccccctcc cacccaccgc   1595

cacaataaag atcgccccca cctccaccct caaaaaaaaa aaaaaaa                 1642


<210> SEQ ID NO 78
<211> LENGTH: 269
<212> TYPE: PRT
<213> ORGANISM: Homo sapiens
<220> FEATURE:
<221> NAME/KEY: SIGNAL
<222> LOCATION: 1..21

<400> SEQUENCE: 78

Met Ala Ala Ala Leu Phe Val Leu Leu Gly Phe Ala Leu Leu Gly Thr
    -20                 -15                 -10

His Gly Ala Ser Gly Ala Ala Gly Thr Val Phe Thr Thr Val Glu Asp
-5                  1               5                   10

Leu Gly Ser Lys Ile Leu Leu Thr Cys Ser Leu Asn Asp Ser Ala Thr
            15                  20                  25

Glu Val Thr Gly His Arg Trp Leu Lys Gly Gly Val Val Leu Lys Glu
        30                  35                  40

Asp Ala Leu Pro Gly Gln Lys Thr Glu Phe Lys Val Asp Ser Asp Asp
    45                  50                  55

Gln Trp Gly Glu Tyr Ser Cys Val Phe Leu Pro Glu Pro Met Gly Thr
60                  65                  70                  75

Ala Asn Ile Gln Leu His Gly Pro Pro Arg Val Lys Ala Val Lys Ser
                80                  85                  90

Ser Glu His Ile Asn Glu Gly Glu Thr Ala Met Leu Val Cys Lys Ser
            95                  100                 105

Glu Ser Val Pro Pro Val Thr Asp Trp Ala Trp Tyr Lys Ile Thr Asp
```

```
        110                 115                 120

Ser Glu Asp Lys Ala Leu Met Asn Gly Ser Glu Ser Arg Phe Phe Val
    125                 130                 135

Ser Ser Ser Gln Gly Leu Ser Glu Leu His Ile Glu Asn Leu Asn Met
140                 145                 150                 155

Glu Ala Asp Pro Gly Gln Tyr Arg Cys Asn Gly Thr Ser Ser Lys Gly
                160                 165                 170

Ser Asp Gln Ala Ile Ile Thr Leu Arg Val Arg Ser His Leu Ala Ala
            175                 180                 185

Leu Trp Pro Phe Leu Gly Ile Val Ala Glu Val Leu Val Leu Val Thr
        190                 195                 200

Ile Ile Phe Ile Tyr Glu Lys Arg Arg Lys Pro Glu Asp Val Leu Asp
    205                 210                 215

Asp Asp Asp Ala Gly Ser Ala Pro Leu Lys Ser Ser Gly Gln His Gln
220                 225                 230                 235

Asn Asp Lys Gly Lys Asn Val Arg Gln Arg Asn Ser Ser
                240                 245


<210> SEQ ID NO 79
<211> LENGTH: 1466
<212> TYPE: DNA
<213> ORGANISM: Homo sapiens
<220> FEATURE:
<221> NAME/KEY: 5'UTR
<222> LOCATION: 1..343
<220> FEATURE:
<221> NAME/KEY: CDS
<222> LOCATION: 344..1144
<220> FEATURE:
<221> NAME/KEY: 3'UTR
<222> LOCATION: 1145..1466

<400> SEQUENCE: 79

attgtgactt tgggccaggc tgggggaaat gacccgggag ggtcccatgc ggctacataa     60

aattggcagc cttagaacta gtgggaaggc gggtgcgcga agtcgagggg cggagagagg    120

gggccggagg agctgctttc tgaatccaag ttcgtgggct ctctcagaag tcctcaggac    180

ggagcagagg tggccggcgg gcccggctga ctgcgcctyt gctttctttc cataaccttt    240

tctttcggac tcgaatcacg gctgctgcga agggtctagt tccggacact agggtgcccg    300

aacgcgctga tgccccgagt gctcgcaggg cttcccgcta acc atg ctg ccg ccg      355
                                                Met Leu Pro Pro

ccg cgg ccc gca gct gcc ttg gcg ctg cct gtg ctc ctg cta ctg ctg      403
Pro Arg Pro Ala Ala Ala Leu Ala Leu Pro Val Leu Leu Leu Leu Leu
-25                 -20                 -15                 -10

gtg gtg ctg acg ccg ccc ccg acc ggc gca agg cca tcc cca ggc cca      451
Val Val Leu Thr Pro Pro Pro Thr Gly Ala Arg Pro Ser Pro Gly Pro
                -5                  1               5

gat tac ctg cgg cgc ggc tgg atg cgg ctg cta gcg gag ggc gag ggc      499
Asp Tyr Leu Arg Arg Gly Trp Met Arg Leu Leu Ala Glu Gly Glu Gly
        10                  15                  20

tgc gct ccc tgc cgg cca gaa gag tgc gcc gcg ccg cgg ggc tgc ctg      547
Cys Ala Pro Cys Arg Pro Glu Glu Cys Ala Ala Pro Arg Gly Cys Leu
    25                  30                  35

gcg ggc agg gtg cgc gac gcg tgc ggc tgc tgc tgg gaa tgc gcc aac      595
Ala Gly Arg Val Arg Asp Ala Cys Gly Cys Cys Trp Glu Cys Ala Asn
40                  45                  50                  55

ctc gag ggc cag ctc tgc gac ctg gac ccc agt gct cac ttc tac ggg      643
Leu Glu Gly Gln Leu Cys Asp Leu Asp Pro Ser Ala His Phe Tyr Gly
                60                  65                  70
```

```
cac tgc ggc gag cag ctt gag tgc cgg ctg gac aca ggc ggc gac ctg      691
His Cys Gly Glu Gln Leu Glu Cys Arg Leu Asp Thr Gly Gly Asp Leu
            75                  80                  85

agc cgc gga gag gtg ccg gaa cct ctg tgt gcc tgt cgt tcg cag agt      739
Ser Arg Gly Glu Val Pro Glu Pro Leu Cys Ala Cys Arg Ser Gln Ser
        90                  95                  100

ccg ctc tgc ggg tcc gac ggt cac acc tac tcc cag atc tgc cgc ctg      787
Pro Leu Cys Gly Ser Asp Gly His Thr Tyr Ser Gln Ile Cys Arg Leu
    105                 110                 115

cag gag gcg gcc cgc gct cgg ccc gat gcc aac ctc act gtg gca cac      835
Gln Glu Ala Ala Arg Ala Arg Pro Asp Ala Asn Leu Thr Val Ala His
120                 125                 130                 135

ccg ggg ccc tgc gaa tcg ggg ccc cag atc gtg tca cat cca tat gac      883
Pro Gly Pro Cys Glu Ser Gly Pro Gln Ile Val Ser His Pro Tyr Asp
                140                 145                 150

act tgg aat gtg aca ggg cag gat gtg atc ttt ggc tgt gaa gtg ttt      931
Thr Trp Asn Val Thr Gly Gln Asp Val Ile Phe Gly Cys Glu Val Phe
            155                 160                 165

gcc tac ccc atg gcc tcc atc gag tgg agg aag gat ggc ttg gac atc      979
Ala Tyr Pro Met Ala Ser Ile Glu Trp Arg Lys Asp Gly Leu Asp Ile
        170                 175                 180

cag ctg cca ggg gat gac ccc cac atc tct gtg cag ttt agg ggt gga     1027
Gln Leu Pro Gly Asp Asp Pro His Ile Ser Val Gln Phe Arg Gly Gly
    185                 190                 195

ccc cag agg ttt gag gtg act ggc tgg ctg cag atc cag gct gtg cgt     1075
Pro Gln Arg Phe Glu Val Thr Gly Trp Leu Gln Ile Gln Ala Val Arg
200                 205                 210                 215

ccc agt gat gag ggc act tac cgc tgc ctt ggc cca atg ccc tgg gtc     1123
Pro Ser Asp Glu Gly Thr Tyr Arg Cys Leu Gly Pro Met Pro Trp Val
                220                 225                 230

aag tgg agg ccc ctg cta gct tgacagtgct cacacctgac cagctgaact        1174
Lys Trp Arg Pro Leu Leu Ala
            235

ctacaggcat cccccagctg cgatcactaa acctggttcc tgaggaggag gctgagagtg   1234

aagagaatga cgattactac taggtccaga gctctggccc atgggggtgg gtgagcggct   1294

atagtgttca tccctgctct tgaaaagacc tggaaagggg agcagggtcc cttcatcgac   1354

tgctttcatg ctgtcagtag ggatgatcat gggaggccta tttgactcca aggtagcagt   1414

gtggtaggat agagacaaaa gctggaggag ggtagggaga gaagctgaga cc           1466


<210> SEQ ID NO 80
<211> LENGTH: 267
<212> TYPE: PRT
<213> ORGANISM: Homo sapiens
<220> FEATURE:
<221> NAME/KEY: SIGNAL
<222> LOCATION: 1..30

<400> SEQUENCE: 80

Met Leu Pro Pro Pro Arg Pro Ala Ala Ala Leu Ala Leu Pro Val Leu
-30                 -25                 -20                 -15

Leu Leu Leu Leu Val Val Leu Thr Pro Pro Pro Thr Gly Ala Arg Pro
                -10                 -5                  1

Ser Pro Gly Pro Asp Tyr Leu Arg Arg Gly Trp Met Arg Leu Leu Ala
        5                   10                  15

Glu Gly Glu Gly Cys Ala Pro Cys Arg Pro Glu Glu Cys Ala Ala Pro
    20                  25                  30

Arg Gly Cys Leu Ala Gly Arg Val Arg Asp Ala Cys Gly Cys Cys Trp
```

-continued

```
35                  40                  45                  50

Glu Cys Ala Asn Leu Glu Gly Gln Leu Cys Asp Leu Asp Pro Ser Ala
                55                  60                  65

His Phe Tyr Gly His Cys Gly Glu Gln Leu Glu Cys Arg Leu Asp Thr
            70                  75                  80

Gly Gly Asp Leu Ser Arg Gly Glu Val Pro Glu Pro Leu Cys Ala Cys
        85                  90                  95

Arg Ser Gln Ser Pro Leu Cys Gly Ser Asp Gly His Thr Tyr Ser Gln
    100                 105                 110

Ile Cys Arg Leu Gln Glu Ala Ala Arg Ala Arg Pro Asp Ala Asn Leu
115                 120                 125                 130

Thr Val Ala His Pro Gly Pro Cys Glu Ser Gly Pro Gln Ile Val Ser
                135                 140                 145

His Pro Tyr Asp Thr Trp Asn Val Thr Gly Gln Asp Val Ile Phe Gly
            150                 155                 160

Cys Glu Val Phe Ala Tyr Pro Met Ala Ser Ile Glu Trp Arg Lys Asp
        165                 170                 175

Gly Leu Asp Ile Gln Leu Pro Gly Asp Asp Pro His Ile Ser Val Gln
    180                 185                 190

Phe Arg Gly Gly Pro Gln Arg Phe Glu Val Thr Gly Trp Leu Gln Ile
195                 200                 205                 210

Gln Ala Val Arg Pro Ser Asp Glu Gly Thr Tyr Arg Cys Leu Gly Pro
                215                 220                 225

Met Pro Trp Val Lys Trp Arg Pro Leu Leu Ala
            230                 235


<210> SEQ ID NO 81
<211> LENGTH: 1406
<212> TYPE: DNA
<213> ORGANISM: Homo sapiens
<220> FEATURE:
<221> NAME/KEY: 5'UTR
<222> LOCATION: 1..26
<220> FEATURE:
<221> NAME/KEY: CDS
<222> LOCATION: 27..689
<220> FEATURE:
<221> NAME/KEY: 3'UTR
<222> LOCATION: 690..1406
<220> FEATURE:
<221> NAME/KEY: polyA_signal
<222> LOCATION: 1302..1307
<220> FEATURE:
<221> NAME/KEY: polyA_site
<222> LOCATION: 1325..1406

<400> SEQUENCE: 81

cccggaagtg cgcaggcgct ggcaag atg gcg gga ggg gtg cgc ccg ctg cgg      53
                             Met Ala Gly Gly Val Arg Pro Leu Arg
                                 -30                 -25

ggc ctc cgc gcc ttg tgt cgc gtg ctg ctc ttc ctt tcg cag ttc tgc      101
Gly Leu Arg Ala Leu Cys Arg Val Leu Leu Phe Leu Ser Gln Phe Cys
        -20                 -15                 -10

att ctg tcg ggc ggt gaa agt act gaa atc cca cct tat gtg atg aag      149
Ile Leu Ser Gly Gly Glu Ser Thr Glu Ile Pro Pro Tyr Val Met Lys
    -5                  1               5                   10

tgt ccg agc aat ggt ttg tgt agc agg ctt cct gca gac tgt ata gac      197
Cys Pro Ser Asn Gly Leu Cys Ser Arg Leu Pro Ala Asp Cys Ile Asp
                15                  20                  25

tgc aca aca aat ttc tcc tgt acc tat ggg aag cct gtc act ttt gac      245
Cys Thr Thr Asn Phe Ser Cys Thr Tyr Gly Lys Pro Val Thr Phe Asp
```

-continued

```
          30                  35                  40

tgt gca gtg aaa cca tct gtt acc tgt gtt gat caa gac ttc aaa tcc      293
Cys Ala Val Lys Pro Ser Val Thr Cys Val Asp Gln Asp Phe Lys Ser
        45                  50                  55

caa aag aac ttc atc att aac atg act tgc aga ttt tgc tgg cag ctt      341
Gln Lys Asn Phe Ile Ile Asn Met Thr Cys Arg Phe Cys Trp Gln Leu
    60                  65                  70

cct gaa aca gat tac gag tgt acc aac tcc acc agc tgc atg acg gtg      389
Pro Glu Thr Asp Tyr Glu Cys Thr Asn Ser Thr Ser Cys Met Thr Val
75                  80                  85                  90

tcc tgt cct cgg cag cgc tac cct gcc aac tgc acg gtg cgg gac cac      437
Ser Cys Pro Arg Gln Arg Tyr Pro Ala Asn Cys Thr Val Arg Asp His
            95                  100                 105

gtc cac tgc ttg ggt aac cgt act ttt ccc aaa atg cta tat tgc aat      485
Val His Cys Leu Gly Asn Arg Thr Phe Pro Lys Met Leu Tyr Cys Asn
            110                 115                 120

tgg act gga ggc tat aag tgg tct acg gct ctg gct cta agc atc acc      533
Trp Thr Gly Gly Tyr Lys Trp Ser Thr Ala Leu Ala Leu Ser Ile Thr
        125                 130                 135

ctc ggt ggg ttt gga gca gac cgt ttc tac ctg ggc cag tgg cgg gaa      581
Leu Gly Gly Phe Gly Ala Asp Arg Phe Tyr Leu Gly Gln Trp Arg Glu
    140                 145                 150

ggc ctc ggc aag ctc ttc agc ttc ggt ggc ctg gga ata tgg acg ctg      629
Gly Leu Gly Lys Leu Phe Ser Phe Gly Gly Leu Gly Ile Trp Thr Leu
155                 160                 165                 170

ata gac gtc ctg ctc att gga gtt ggc tat gtt gga cca gca gat ggc      677
Ile Asp Val Leu Leu Ile Gly Val Gly Tyr Val Gly Pro Ala Asp Gly
            175                 180                 185

tct ttg tac att tagctgtggt gtgtgcttca gaaaggagca gggcttagaa          729
Ser Leu Tyr Ile
            190

aaagcccttt tgtccgtagg agttgatgtg gtgtgagtga tatatttcta tgtttttaat    789

gtacagcatc tgtactttgt ttgccttgat aaaggtaaga taaatgaaac gctgaactat    849

gctaatctgg aatttgtttt tatttgcctg aaatatattt ttttctgtga aaaaattaaa    909

acgtacttaa gccaggagaa tgaattatac agtgattgaa aatccattta attcctatga    969

cttttgtttt gtattgccca agtcaaacta catcacttgt atctccagcc caaatgtagt   1029

ctgccttgaa aagtctttca gctgtgactg caggaagtgg gagtgttttt attgttagct   1089

aattgctgtg actgcaggaa gtgggagtgt ttctgttgtt ggctaattga agttattagg   1149

ctcagcttca gtcatgtgta agttttgcag tgtaatacat atgtagtctg gtctgtatat   1209

atgaaaattt gaattaaact gcagaatgtt tatgtctagt tatggtttaa attttcttag   1269

tagtatataa aaggtaagag tactgaaaaa ttaataaaat tgcaagttaa gaaataaaaa   1329

aaaaaaaaaa aaaaaaaaaa aaaaaaaaaa aaaaaaaaaa aaaaaaaaaa aaaaaaaaaa   1389

taaaaaaaaa aaaaaat                                                  1406

<210> SEQ ID NO 82
<211> LENGTH: 221
<212> TYPE: PRT
<213> ORGANISM: Homo sapiens
<220> FEATURE:
<221> NAME/KEY: SIGNAL
<222> LOCATION: 1..32

<400> SEQUENCE: 82

Met Ala Gly Gly Val Arg Pro Leu Arg Gly Leu Arg Ala Leu Cys Arg
        -30                 -25                 -20
```

```
Val Leu Leu Phe Leu Ser Gln Phe Cys Ile Leu Ser Gly Gly Glu Ser
    -15                 -10                 -5

Thr Glu Ile Pro Pro Tyr Val Met Lys Cys Pro Ser Asn Gly Leu Cys
1               5                   10                  15

Ser Arg Leu Pro Ala Asp Cys Ile Asp Cys Thr Thr Asn Phe Ser Cys
            20                  25                  30

Thr Tyr Gly Lys Pro Val Thr Phe Asp Cys Ala Val Lys Pro Ser Val
        35                  40                  45

Thr Cys Val Asp Gln Asp Phe Lys Ser Gln Lys Asn Phe Ile Ile Asn
    50                  55                  60

Met Thr Cys Arg Phe Cys Trp Gln Leu Pro Glu Thr Asp Tyr Glu Cys
65                  70                  75                  80

Thr Asn Ser Thr Ser Cys Met Thr Val Ser Cys Pro Arg Gln Arg Tyr
                85                  90                  95

Pro Ala Asn Cys Thr Val Arg Asp His Val His Cys Leu Gly Asn Arg
            100                 105                 110

Thr Phe Pro Lys Met Leu Tyr Cys Asn Trp Thr Gly Gly Tyr Lys Trp
        115                 120                 125

Ser Thr Ala Leu Ala Leu Ser Ile Thr Leu Gly Gly Phe Gly Ala Asp
    130                 135                 140

Arg Phe Tyr Leu Gly Gln Trp Arg Glu Gly Leu Gly Lys Leu Phe Ser
145                 150                 155                 160

Phe Gly Gly Leu Gly Ile Trp Thr Leu Ile Asp Val Leu Leu Ile Gly
                165                 170                 175

Val Gly Tyr Val Gly Pro Ala Asp Gly Ser Leu Tyr Ile
            180                 185
```

<210> SEQ ID NO 83
<211> LENGTH: 1754
<212> TYPE: DNA
<213> ORGANISM: Homo sapiens
<220> FEATURE:
<221> NAME/KEY: 5'UTR
<222> LOCATION: 1..117
<220> FEATURE:
<221> NAME/KEY: CDS
<222> LOCATION: 118..510
<220> FEATURE:
<221> NAME/KEY: 3'UTR
<222> LOCATION: 511..1754
<220> FEATURE:
<221> NAME/KEY: polyA_signal
<222> LOCATION: 1718..1723
<220> FEATURE:
<221> NAME/KEY: polyA_site
<222> LOCATION: 1739..1754

<400> SEQUENCE: 83

```
tccccggccg ccgccgttgc gctcgccgcg ctcgcactga agcccgggcc ctcgcgcgcc      60

gcggttcgcc ccgcagcctc gccccctgcc cacccgggcg gccgtagggc ggtcacg        117

atg ctg ccg ccc tta ccc tcc cgc ctc ggg ctg ctg ctg ctg ctg ctc       165
Met Leu Pro Pro Leu Pro Ser Arg Leu Gly Leu Leu Leu Leu Leu Leu
            -20                 -15                 -10

ctg tgc ccg gcg cac gtc ggc gga ctg tgg tgg gct gtg ggc agc ccc       213
Leu Cys Pro Ala His Val Gly Gly Leu Trp Trp Ala Val Gly Ser Pro
        -5                  1               5

ttg gtt atg gac cct acc agc atc tgc agg aag gca cgg cgg ctg gcc       261
Leu Val Met Asp Pro Thr Ser Ile Cys Arg Lys Ala Arg Arg Leu Ala
10                  15                  20                  25
```

-continued

```
ggg cgg cag gcc gag ttg tgc cag gct gag ccg gaa gtg gtg gca gag      309
Gly Arg Gln Ala Glu Leu Cys Gln Ala Glu Pro Glu Val Val Ala Glu
                30                  35                  40

ctg gct cgg ggc gcc cgg ctc ggg gtg cga gag tgc cag ttc cag ttc      357
Leu Ala Arg Gly Ala Arg Leu Gly Val Arg Glu Cys Gln Phe Gln Phe
            45                  50                  55

cgc ttc cgc cgc tgg aat tgc tcc agc cac agc aag gcc ttt gga cgc      405
Arg Phe Arg Arg Trp Asn Cys Ser Ser His Ser Lys Ala Phe Gly Arg
        60                  65                  70

atc ctg caa cag ggt cag tgt ggg gag ggg cac cct gca agg acc ctg      453
Ile Leu Gln Gln Gly Gln Cys Gly Glu Gly His Pro Ala Arg Thr Leu
    75                  80                  85

cct ccc agg ccc ctg ggg cag ccc tcc cgc cgc agg ttt cag gtc cca      501
Pro Pro Arg Pro Leu Gly Gln Pro Ser Arg Arg Arg Phe Gln Val Pro
90                  95                  100                 105

ggc ccc agc tgaccgcccc agcccgcgct gattgcacct gtctgcattc              550
Gly Pro Ser

acagacattc gggagacggc cttcgtgttc gccatcactg cggccggcgc cagccacgcc    610

gtcacgcagg cctgttctat gggcgagctg ctgcagtgcg gctgccaggc gccccgcggg    670

cgggccccctc cccggccctc cggcctgccc ggcacccccg gacccctgg ccccgcgggc    730

tccccggaag gcagcgccgc ctgggagtgg ggaggctgcg gcgacgacgt ggacttcggg    790

gacgagaagt cgaggctctt tatgsacgcg cggcacaagc ggggacgcgg agacatccgc    850

gcgttggtgc aactgcacaa caacgaggcg ggcaggctgg ccgtgcggag ccacacgcgc    910

accgagtgca aatgccacgg gctgtcggga tcatgcgcgc tgcgcacctg ctggcagaag    970

ctgcctccat ttcgcgaggt gggcgcgcgg ctgctggagc gcttccacgg cgcctcacgc   1030

gtcatgggca ccaacgacgg caaggccctg ctgcccgccg tccgcacgct caagccgccg   1090

ggccgagcgg acctcctcta cgccgccgat tcgcccgact tctgcgcccc caaccgacgc   1150

accggctccc ccggcacgcg cggtcgcgcc tgcaatagca gcgccccgga cctcagcggc   1210

tgcgacctgc tgtgctgcgg ccgcgggcac cgccaggaga gcgtgcagct cgaagagaac   1270

tgcctgtgcc gcttccactg gtgctgcgta gtacagtgcc accgctgccg tgtgcgcaag   1330

gagctcagcc tctgcctgtg acccgccgcc cggccgctag actgacttcg cgcagcggtg   1390

gctcgcacct gtgggacctc agggcaccgg caccgggcgc ctctcgccgc tcgagcccag   1450

cctctccctg ccaaagccca actcccaggg ctctggaaat ggtgaggcga ggggcttgag   1510

aggaacgccc acccacgaag gcccagggcg ccagacggcc ccgaaaaggc gctcggggag   1570

cgtttaaagg acactgtaca ggccctccct ccccttggcc tctaggagga aacagttttt   1630

tagactggaa aaaagccagt ctaaaggcct ctggatactg ggctccccag aactgctggc   1690

cacaggatgg tgggtgaggt tagtatcaat aaagatattt aaaccaccaa aaaaaaaaaa   1750

aaaa                                                                  1754
```

<210> SEQ ID NO 84
<211> LENGTH: 131
<212> TYPE: PRT
<213> ORGANISM: Homo sapiens
<220> FEATURE:
<221> NAME/KEY: SIGNAL
<222> LOCATION: 1..24

<400> SEQUENCE: 84

```
Met Leu Pro Pro Leu Pro Ser Arg Leu Gly Leu Leu Leu Leu Leu
                -20                 -15                 -10
```

-continued

```
Leu Cys Pro Ala His Val Gly Gly Leu Trp Trp Ala Val Gly Ser Pro
            -5                  1               5

Leu Val Met Asp Pro Thr Ser Ile Cys Arg Lys Ala Arg Arg Leu Ala
    10                  15                  20

Gly Arg Gln Ala Glu Leu Cys Gln Ala Glu Pro Glu Val Val Ala Glu
25                  30                  35                  40

Leu Ala Arg Gly Ala Arg Leu Gly Val Arg Glu Cys Gln Phe Gln Phe
                45                  50                  55

Arg Phe Arg Arg Trp Asn Cys Ser Ser His Ser Lys Ala Phe Gly Arg
            60                  65                  70

Ile Leu Gln Gln Gly Gln Cys Gly Glu Gly His Pro Ala Arg Thr Leu
        75                  80                  85

Pro Pro Arg Pro Leu Gly Gln Pro Ser Arg Arg Arg Phe Gln Val Pro
    90                  95                  100

Gly Pro Ser
105
```

<210> SEQ ID NO 85
<211> LENGTH: 1754
<212> TYPE: DNA
<213> ORGANISM: Homo sapiens
<220> FEATURE:
<221> NAME/KEY: 5'UTR
<222> LOCATION: 1..117
<220> FEATURE:
<221> NAME/KEY: CDS
<222> LOCATION: 118..510
<220> FEATURE:
<221> NAME/KEY: 3'UTR
<222> LOCATION: 511..1754
<220> FEATURE:
<221> NAME/KEY: polyA_signal
<222> LOCATION: 1718..1723
<220> FEATURE:
<221> NAME/KEY: polyA_site
<222> LOCATION: 1739..1754

<400> SEQUENCE: 85

```
tccccggccg ccgccgttgc gctcgccgcg ctcgcactga agcccgggcc ctcgcgcgcc      60

gcggttcgcc ccgcagcctc gccccctgcc cacccgggcg gccgtagggc ggtcacg        117

atg ctg ccg ccc tta ccc tcc cgc ctc ggg ctg ctg ctg ctg ctc          165
Met Leu Pro Pro Leu Pro Ser Arg Leu Gly Leu Leu Leu Leu Leu
            -20                 -15                 -10

ctg tgc ccg gcg cac gtc ggc gga ctg tgg tgg gct gtg ggc agc ccc      213
Leu Cys Pro Ala His Val Gly Gly Leu Trp Trp Ala Val Gly Ser Pro
        -5                  1               5

ttg gtt atg gac cct acc agc atc tgc agg aag gca cgg cgg ctg gcc      261
Leu Val Met Asp Pro Thr Ser Ile Cys Arg Lys Ala Arg Arg Leu Ala
10                  15                  20                  25

ggg cgg cag gcc gag ttg tgc cag gct gag ccg gaa gtg gtg gca gag      309
Gly Arg Gln Ala Glu Leu Cys Gln Ala Glu Pro Glu Val Val Ala Glu
                30                  35                  40

ctg gct cgg ggc gcc cgg ctc ggg gtg cga gag tgc cag ttc cag ttc      357
Leu Ala Arg Gly Ala Arg Leu Gly Val Arg Glu Cys Gln Phe Gln Phe
            45                  50                  55

cgc ttc cgc cgc tgg aat tgc tcc agc cac agc aag gcc ttt gga cgc      405
Arg Phe Arg Arg Trp Asn Cys Ser Ser His Ser Lys Ala Phe Gly Arg
        60                  65                  70

atc ctg caa cag ggt cag tgt ggg gag ggg cac cct gca agg acc ctg      453
Ile Leu Gln Gln Gly Gln Cys Gly Glu Gly His Pro Ala Arg Thr Leu
    75                  80                  85
```

-continued

```
cct ccc agg ccc ctg ggg cag ccc tcc cgc cgc agg ttt cag gtc cca      501
Pro Pro Arg Pro Leu Gly Gln Pro Ser Arg Arg Arg Phe Gln Val Pro
90                  95                  100                 105

ggc ccc agc tgaccgcccc agcccgcgct gattgcacct gtctgcattc             550
Gly Pro Ser

acagacattc gggagacggc cttcgtgttc gccatcactg cggccggcgc cagccacgcc    610

gtcacgcagg cctgttctat gggcgagctg ctgcagtgcg gctgccaggc gccccgcggg    670

cgggcccctc cccggccctc cggcctgccc ggcacccccg gacccccctgg ccccgcgggc    730

tccccggaag gcagcgccgc ctgggagtgg ggaggctgcg gcgacgacgt ggacttcggg    790

gacgagaagt cgaggctctt tatggacgcg cggcacaagc ggggacgcgg agacatccgc    850

gcgttggtgc aactgcacaa caacgaggcg ggcaggctgg ccgtgcggag ccacacgcgc    910

accgagtgca aatgccacgg gctgtcggga tcatgcgcgc tgcgcacctg ctggcagaag    970

ctgcctccat ttcgcgaggt gggcgcgcgg ctgctggagc gcttycacgg cgcctcacgc   1030

gtcatgggca ccaacgacgg caaggccctg ctgcccgccg tccgcacgct caagccgccg   1090

ggccgagcgg acctcctcta cgccgccgat tcgcccgact tctgcgcccc caaccgacgc   1150

accggctccc ccggcacgcg cggtcgcgcc tgcaatagca gcgccccgga cctcagcggc   1210

tgcgacctgc tgtgctgcgg ccgcgggcac cgccaggaga gcgtgcagct cgaagagaac   1270

tgcctgtgcc gcttccactg gtgctgcgta gtacagtgcc accgctgccg tgtgcgcaag   1330

gagctcagcc tctgcctgtg acccgccgcc cggccgctag actgacttcg cgcagcggtg   1390

gctcgcacct gtgggacctc agggcaccgg caccgggcgc ctctcgccgc tcgagcccag   1450

cctctccctg ccaaagccca actcccaggg ctctggaaat ggtgaggcga ggggcttgag   1510

aggaacgccc acccacgaag gcccagggcg ccagacggcc ccgaaaaggc gctcggggag   1570

cgtttaaagg acactgtaca ggccctccct ccccttggcc tctaggagga aacagttttt   1630

tagactggaa aaaagccagt ctaaaggcct ctggatactg ggctccccag aactgctggc   1690

cacaggatgg tgggtgaggt tagtatcaat aaagatattt aaaccaccaa aaaaaaaaaa   1750

aaaa                                                                1754


<210> SEQ ID NO 86
<211> LENGTH: 131
<212> TYPE: PRT
<213> ORGANISM: Homo sapiens
<220> FEATURE:
<221> NAME/KEY: SIGNAL
<222> LOCATION: 1..24

<400> SEQUENCE: 86

Met Leu Pro Pro Leu Pro Ser Arg Leu Gly Leu Leu Leu Leu Leu Leu
                -20                 -15                 -10

Leu Cys Pro Ala His Val Gly Gly Leu Trp Trp Ala Val Gly Ser Pro
            -5                  1               5

Leu Val Met Asp Pro Thr Ser Ile Cys Arg Lys Ala Arg Arg Leu Ala
    10                  15                  20

Gly Arg Gln Ala Glu Leu Cys Gln Ala Glu Pro Glu Val Val Ala Glu
25                  30                  35                  40

Leu Ala Arg Gly Ala Arg Leu Gly Val Arg Glu Cys Gln Phe Gln Phe
                45                  50                  55

Arg Phe Arg Arg Trp Asn Cys Ser Ser His Ser Lys Ala Phe Gly Arg
            60                  65                  70

Ile Leu Gln Gln Gly Gln Cys Gly Glu Gly His Pro Ala Arg Thr Leu
```

```
        75                  80                  85

Pro Pro Arg Pro Leu Gly Gln Pro Ser Arg Arg Arg Phe Gln Val Pro
    90                  95                  100

Gly Pro Ser
105


<210> SEQ ID NO 87
<211> LENGTH: 1431
<212> TYPE: DNA
<213> ORGANISM: Homo sapiens
<220> FEATURE:
<221> NAME/KEY: 5'UTR
<222> LOCATION: 1..151
<220> FEATURE:
<221> NAME/KEY: CDS
<222> LOCATION: 152..655
<220> FEATURE:
<221> NAME/KEY: 3'UTR
<222> LOCATION: 656..1431
<220> FEATURE:
<221> NAME/KEY: polyA_signal
<222> LOCATION: 1399..1404
<220> FEATURE:
<221> NAME/KEY: polyA_site
<222> LOCATION: 1416..1431

<400> SEQUENCE: 87

aatttttctt cacaaggact gggtgaagag ttctgcagcc ttacagagac tggaaaagaa      60

gcccaaacca aggcccccag agaggtcccc caggcccctt tgggtccctg agcctcagct     120

ggagatccgg cgcaggagac caacgcctgc c atg ctg ttc cgg ctc tca gag       172
                                   Met Leu Phe Arg Leu Ser Glu
                                   1               5

cac tcc tca cca gag gag gaa gcc tcc ccc cac cag aga gcc tca gga      220
His Ser Ser Pro Glu Glu Glu Ala Ser Pro His Gln Arg Ala Ser Gly
        10                  15                  20

gag ggg cac cat ctc aag tcg aag aga ccc aac ccc tgt gcc tac aca      268
Glu Gly His His Leu Lys Ser Lys Arg Pro Asn Pro Cys Ala Tyr Thr
    25                  30                  35

cca cct tcg ctg aaa gct gtg cag cgc att gct gag tct cac ctg cag      316
Pro Pro Ser Leu Lys Ala Val Gln Arg Ile Ala Glu Ser His Leu Gln
40                  45                  50                  55

tct atc agc aat ttg aat gag aac cag gcc tca gag gag gag gat gag      364
Ser Ile Ser Asn Leu Asn Glu Asn Gln Ala Ser Glu Glu Glu Asp Glu
                60                  65                  70

ctg ggg gag ctt cgg gag ctg ggt tat cca aga gag gaa gat gag gag      412
Leu Gly Glu Leu Arg Glu Leu Gly Tyr Pro Arg Glu Glu Asp Glu Glu
            75                  80                  85

gaa gag gag gat gat gaa gaa gag gaa gaa gaa gag gac agc cag gct      460
Glu Glu Glu Asp Asp Glu Glu Glu Glu Glu Glu Glu Asp Ser Gln Ala
        90                  95                  100

gaa gtc ctg aag gtc atc agg cag tct gct ggg caa aag aca acc tgt      508
Glu Val Leu Lys Val Ile Arg Gln Ser Ala Gly Gln Lys Thr Thr Cys
    105                 110                 115

ggc cag ggt ctg gaa ggg ccc tgg gag cgc cca ccc cct ctg gat gag      556
Gly Gln Gly Leu Glu Gly Pro Trp Glu Arg Pro Pro Pro Leu Asp Glu
120                 125                 130                 135

tcc gag aga gat gga ggc tct gag gac caa gtg gaa gac cca gca cta      604
Ser Glu Arg Asp Gly Gly Ser Glu Asp Gln Val Glu Asp Pro Ala Leu
                140                 145                 150

agt gag cct ggg gag gaa cct cag cgc cct tcc ccc tct gag cct ggc      652
Ser Glu Pro Gly Glu Glu Pro Gln Arg Pro Ser Pro Ser Glu Pro Gly
            155                 160                 165
```

```
aca taggcaccca gcctgcatct cccaggagga agtggagggg acatcgctgt          705
Thr

tccccagaaa cccactctat cctcaccctg ttttgtgctc ttcccctcgc ctgctagggc    765

tgcggcttct gacttctaga agactaaggc tggtctgtgt ttgcttgttt gcccaccttt    825

ggctgatacc cagagaacct gggcacttgc tgcctgatgc ccacccctgc cagtcattcc    885

tccattcacc cagcgggagg tgggatgtga gacagcccac attggaaaat ccagaaaacc    945

gggaacaggg atttgccctt cacaattcta ctccccagat cctctcccct ggacacagga   1005

gacccacagg gcaggaccct aagatctggg gaaaggaggt cctgagaacc ttgaggtacc   1065

cttagatcct tttctaccca ctttcctatg gaggattcca agtcaccact tctctcaccg   1125

gcttctacca gggtccagga ctaaggcgtt tttctccata gcctcaacat tttgggaatc   1185

ttcccttaat cacccttgct cctcctgggt gcctggaaga tggactggca gagacctctt   1245

tgttgcgttt tgtgctttga tgccaggaat gccgcctagt ttatgtcccc ggtggggcac   1305

acagcggggg gcgccaggtt ttccttgtcc cccagctgct ctgccccttt ccccttcttc   1365

cctgactcca ggcctgaacc cctcccgtgc tgtaataaat ctttgtaaag aaaaaaaaaa   1425

aaaaaa                                                              1431


<210> SEQ ID NO 88
<211> LENGTH: 168
<212> TYPE: PRT
<213> ORGANISM: Homo sapiens

<400> SEQUENCE: 88

Met Leu Phe Arg Leu Ser Glu His Ser Ser Pro Glu Glu Glu Ala Ser
1               5                   10                  15

Pro His Gln Arg Ala Ser Gly Glu Gly His His Leu Lys Ser Lys Arg
            20                  25                  30

Pro Asn Pro Cys Ala Tyr Thr Pro Pro Ser Leu Lys Ala Val Gln Arg
        35                  40                  45

Ile Ala Glu Ser His Leu Gln Ser Ile Ser Asn Leu Asn Glu Asn Gln
    50                  55                  60

Ala Ser Glu Glu Glu Asp Glu Leu Gly Glu Leu Arg Glu Leu Gly Tyr
65                  70                  75                  80

Pro Arg Glu Glu Asp Glu Glu Glu Glu Asp Asp Glu Glu Glu Glu
                85                  90                  95

Glu Glu Glu Asp Ser Gln Ala Glu Val Leu Lys Val Ile Arg Gln Ser
            100                 105                 110

Ala Gly Gln Lys Thr Thr Cys Gly Gln Gly Leu Glu Gly Pro Trp Glu
        115                 120                 125

Arg Pro Pro Pro Leu Asp Glu Ser Glu Arg Asp Gly Gly Ser Glu Asp
    130                 135                 140

Gln Val Glu Asp Pro Ala Leu Ser Glu Pro Gly Glu Glu Pro Gln Arg
145                 150                 155                 160

Pro Ser Pro Ser Glu Pro Gly Thr
                165


<210> SEQ ID NO 89
<211> LENGTH: 1431
<212> TYPE: DNA
<213> ORGANISM: Homo sapiens
<220> FEATURE:
<221> NAME/KEY: 5'UTR
<222> LOCATION: 1..151
<220> FEATURE:
```

-continued

```
<221> NAME/KEY: CDS
<222> LOCATION: 152..655
<220> FEATURE:
<221> NAME/KEY: 3'UTR
<222> LOCATION: 656..1431
<220> FEATURE:
<221> NAME/KEY: polyA_signal
<222> LOCATION: 1399..1404
<220> FEATURE:
<221> NAME/KEY: polyA_site
<222> LOCATION: 1416..1431

<400> SEQUENCE: 89

aatttttct cacaaggact gggtgaagag ttctgcagcc ttacagagac tggaaaagaa     60

gcccaaacca aggcccccag agaggtcccc caggcccctt tgggtccctg agcctcagct    120

ggagatccgg cgcaggagac caacgcctgc c atg ctg ttc cgg ctc tca gag      172
                                   Met Leu Phe Arg Leu Ser Glu
                                   1               5

cac tcc tca cca gag gag gaa gcc tcc ccc cac cag aga gcc tca gga      220
His Ser Ser Pro Glu Glu Glu Ala Ser Pro His Gln Arg Ala Ser Gly
        10                  15                  20

gag ggg cac cat ctc aag tcg aag aga ccc aac ccc tgt gcc tac aca      268
Glu Gly His His Leu Lys Ser Lys Arg Pro Asn Pro Cys Ala Tyr Thr
    25                  30                  35

cca cct tcg ctg aaa gct gtg cag cgc att gct gag tct cac ctg cag      316
Pro Pro Ser Leu Lys Ala Val Gln Arg Ile Ala Glu Ser His Leu Gln
40                  45                  50                  55

tct atc agc aat ttg aat gag aac cag gcc tca gag gag gag gat gag      364
Ser Ile Ser Asn Leu Asn Glu Asn Gln Ala Ser Glu Glu Glu Asp Glu
                60                  65                  70

ctg ggg gag ctt cgg gag ctg ggt tat cca aga gag gaa gat gag gag      412
Leu Gly Glu Leu Arg Glu Leu Gly Tyr Pro Arg Glu Glu Asp Glu Glu
            75                  80                  85

gaa gag gag gat gat gaa gaa gag gaa gaa gaa gag gac agc cag gct      460
Glu Glu Glu Asp Asp Glu Glu Glu Glu Glu Glu Glu Asp Ser Gln Ala
        90                  95                  100

gaa gtc ctg aag gtc atc agg cag tct gct ggg caa aag aca acc tgt      508
Glu Val Leu Lys Val Ile Arg Gln Ser Ala Gly Gln Lys Thr Thr Cys
    105                 110                 115

ggc cag ggt ctg gaa ggg ccc tgg gag cgc cca ccc cct ctg gat gag      556
Gly Gln Gly Leu Glu Gly Pro Trp Glu Arg Pro Pro Pro Leu Asp Glu
120                 125                 130                 135

tcc gag aga gat gga ggc tct gag gac caa gtg gaa gac cca gca cta      604
Ser Glu Arg Asp Gly Gly Ser Glu Asp Gln Val Glu Asp Pro Ala Leu
                140                 145                 150

agt gag cct ggg gag gaa cct cag cgc cct tcc ccc tct gag cct ggc      652
Ser Glu Pro Gly Glu Glu Pro Gln Arg Pro Ser Pro Ser Glu Pro Gly
            155                 160                 165

aca taggcaccca gcctgcatct cccaggagga agtggagggg acatcgctgt           705
Thr

tccccagaaa cccactctat cctcaccctg ttttgtgctc ttcccctcgc ctgctagggc    765

tgcggcttct gacttctaga agactaaggc tggtctgtgt ttgcttgttt gcccaccttt    825

ggctgatacc cagagaacct gggcacttgc tgcctgatgc ccacccctgc cagtcattcc    885

tccattcacc cagcgggagg tgggatgtga gacagcccac attggaaaat ccagaaaacc    945

gggaacaggg atttgccctt cacaattcta ctccccagat cctctcccct ggacacagga   1005

gacccacagg gcaggaccct aagatctggg gaaaggaggt cctgagaacc ttgaggtacc   1065

cttagatcct tttctaccca ctttcctatg gaggattcca agtcaccact tctctcaccg   1125
```

-continued

```
gcttctacca gggtccagga ctaaggcgtt tttctccata gcctcaacat tttgggaatc   1185

ttcccttaat cacccttgct cctcctgggt gcctggaaga tggactggca gagacctctt   1245

tgttgcgttt tgtgctttga tgccaggaat gccgcctagt ttatgtcccc ggtggggcac   1305

acagcggggg gcgccaggtt ttccttgtcc cccagctgct ctgccccttt ccccttcttc   1365

cctgactcca ggcctgaacc cctcccgtgc tgtaataaat ctttgtaaag aaaaaaaaaa   1425

aaaaaa                                                              1431


<210> SEQ ID NO 90
<211> LENGTH: 168
<212> TYPE: PRT
<213> ORGANISM: Homo sapiens

<400> SEQUENCE: 90

Met Leu Phe Arg Leu Ser Glu His Ser Ser Pro Glu Glu Glu Ala Ser
1               5                   10                  15

Pro His Gln Arg Ala Ser Gly Glu Gly His His Leu Lys Ser Lys Arg
            20                  25                  30

Pro Asn Pro Cys Ala Tyr Thr Pro Pro Ser Leu Lys Ala Val Gln Arg
        35                  40                  45

Ile Ala Glu Ser His Leu Gln Ser Ile Ser Asn Leu Asn Glu Asn Gln
    50                  55                  60

Ala Ser Glu Glu Glu Asp Glu Leu Gly Glu Leu Arg Glu Leu Gly Tyr
65                  70                  75                  80

Pro Arg Glu Glu Asp Glu Glu Glu Glu Glu Asp Asp Glu Glu Glu Glu
                85                  90                  95

Glu Glu Glu Asp Ser Gln Ala Glu Val Leu Lys Val Ile Arg Gln Ser
            100                 105                 110

Ala Gly Gln Lys Thr Thr Cys Gly Gln Gly Leu Glu Gly Pro Trp Glu
        115                 120                 125

Arg Pro Pro Pro Leu Asp Glu Ser Glu Arg Asp Gly Gly Ser Glu Asp
    130                 135                 140

Gln Val Glu Asp Pro Ala Leu Ser Glu Pro Gly Glu Glu Pro Gln Arg
145                 150                 155                 160

Pro Ser Pro Ser Glu Pro Gly Thr
                165


<210> SEQ ID NO 91
<211> LENGTH: 1417
<212> TYPE: DNA
<213> ORGANISM: Homo sapiens
<220> FEATURE:
<221> NAME/KEY: 5'UTR
<222> LOCATION: 1..47
<220> FEATURE:
<221> NAME/KEY: CDS
<222> LOCATION: 48..1301
<220> FEATURE:
<221> NAME/KEY: 3'UTR
<222> LOCATION: 1302..1417
<220> FEATURE:
<221> NAME/KEY: polyA_signal
<222> LOCATION: 1360..1365
<220> FEATURE:
<221> NAME/KEY: polyA_site
<222> LOCATION: 1402..1417

<400> SEQUENCE: 91

ctcctcagct tcaggcacca ccactgacct gggacagtga atcgaca atg ccg tct       56
                                                    Met Pro Ser
```

-continued

```
tct gtc tcg tgg ggc atc ctc ctg ctg gca ggc ctg tgc tgc ctg gtc       104
Ser Val Ser Trp Gly Ile Leu Leu Leu Ala Gly Leu Cys Cys Leu Val
-20                 -15                 -10                 -5

cct gtc tcc ctg gct gag gat ccc cag gga gat gct gcc cag aag aca       152
Pro Val Ser Leu Ala Glu Asp Pro Gln Gly Asp Ala Ala Gln Lys Thr
                1               5                   10

gat aca tcc cac cat gat cag gat cac cca acc ttc aac aag atc acc       200
Asp Thr Ser His His Asp Gln Asp His Pro Thr Phe Asn Lys Ile Thr
        15                  20                  25

ccc aac ctg gct gag ttc gcc ttc agc cta tac cgc cag ctg gca cac       248
Pro Asn Leu Ala Glu Phe Ala Phe Ser Leu Tyr Arg Gln Leu Ala His
    30                  35                  40

cag tcc aac agc acc aat atc ttc ttc tcc cca gtg agc atc gct aca       296
Gln Ser Asn Ser Thr Asn Ile Phe Phe Ser Pro Val Ser Ile Ala Thr
45                  50                  55                  60

gcc ttt gca atg ctc tcc ctg ggg acc aag gct gac act cac gat gaa       344
Ala Phe Ala Met Leu Ser Leu Gly Thr Lys Ala Asp Thr His Asp Glu
                65                  70                  75

atc ctg gag agc ctg aat ttc aac ctc acg gag att ccg gag gct cag       392
Ile Leu Glu Ser Leu Asn Phe Asn Leu Thr Glu Ile Pro Glu Ala Gln
            80                  85                  90

atc cat gaa ggc ttc cag gaa ctc ctc cgt acc ctc aac cag cca gac       440
Ile His Glu Gly Phe Gln Glu Leu Leu Arg Thr Leu Asn Gln Pro Asp
        95                  100                 105

agc cag ctc cag ctg acc acc ggc aat ggc ctg ttc ctc agc gag ggc       488
Ser Gln Leu Gln Leu Thr Thr Gly Asn Gly Leu Phe Leu Ser Glu Gly
    110                 115                 120

ctg aag cta gtg gat aag ttt ttg gag gat gtt aaa aag ttg tac cac       536
Leu Lys Leu Val Asp Lys Phe Leu Glu Asp Val Lys Lys Leu Tyr His
125                 130                 135                 140

tca gaa gcc ttc act gtc aac ttc ggg gac acc gaa gag gcc aag aaa       584
Ser Glu Ala Phe Thr Val Asn Phe Gly Asp Thr Glu Glu Ala Lys Lys
                145                 150                 155

cag atc aac gat tac gtg gag aag ggt act caa ggg aaa att gtg gat       632
Gln Ile Asn Asp Tyr Val Glu Lys Gly Thr Gln Gly Lys Ile Val Asp
            160                 165                 170

ttg gtc aag gag ctt gac aga gac aca gtt ttt gct ctg gtg aat tac       680
Leu Val Lys Glu Leu Asp Arg Asp Thr Val Phe Ala Leu Val Asn Tyr
        175                 180                 185

atc ttc ttt aaa ggc aaa tgg gag aga ccc ttt gaa gtc aag gac acc       728
Ile Phe Phe Lys Gly Lys Trp Glu Arg Pro Phe Glu Val Lys Asp Thr
    190                 195                 200

gag gaa gag gac ttc cac gtg gac cag gcg acc acc gtg aag gtg cct       776
Glu Glu Glu Asp Phe His Val Asp Gln Ala Thr Thr Val Lys Val Pro
205                 210                 215                 220

atg atg aag cgt tta ggc atg ttt aac atc cag cac tgt aag aag ctg       824
Met Met Lys Arg Leu Gly Met Phe Asn Ile Gln His Cys Lys Lys Leu
                225                 230                 235

tcc agc tgg gtg ctg ctg atg aaa tac ctg ggc aat gcc acc gcc atc       872
Ser Ser Trp Val Leu Leu Met Lys Tyr Leu Gly Asn Ala Thr Ala Ile
            240                 245                 250

ttc ttc ctg cct gat gag ggg aaa cta cag cac ctg gaa aat gaa ctc       920
Phe Phe Leu Pro Asp Glu Gly Lys Leu Gln His Leu Glu Asn Glu Leu
        255                 260                 265

acc cac gat atc atc acc aag ttc ctg gaa aat gaa gac aga agg tct       968
Thr His Asp Ile Ile Thr Lys Phe Leu Glu Asn Glu Asp Arg Arg Ser
    270                 275                 280

gcc agc tta cat tta ccc aaa ctg tcc att act gga acc tat gat ctg      1016
Ala Ser Leu His Leu Pro Lys Leu Ser Ile Thr Gly Thr Tyr Asp Leu
285                 290                 295                 300
```

-continued

```
aag agc gtc ctg ggt caa ctg ggc atc act aag gtc ttc agc aat ggg     1064
Lys Ser Val Leu Gly Gln Leu Gly Ile Thr Lys Val Phe Ser Asn Gly
                305                 310                 315

gct gac ctc tcc ggg gtc aca gag gag gca ccc ctg aag ctc tcc aag     1112
Ala Asp Leu Ser Gly Val Thr Glu Glu Ala Pro Leu Lys Leu Ser Lys
            320                 325                 330

gcc gtg cat aag gct gtg ctg acc atc gac gag aaa ggg act gaa gct     1160
Ala Val His Lys Ala Val Leu Thr Ile Asp Glu Lys Gly Thr Glu Ala
        335                 340                 345

gct ggg gcc atg ttt tta gag gcc ata ccc atg tct atc ccc ccc gag     1208
Ala Gly Ala Met Phe Leu Glu Ala Ile Pro Met Ser Ile Pro Pro Glu
    350                 355                 360

gtc aag ttc aac aaa ccc ttt gtc ttc tta atg att gaa caa aat acc     1256
Val Lys Phe Asn Lys Pro Phe Val Phe Leu Met Ile Glu Gln Asn Thr
365                 370                 375                 380

aag tct ccc ctc ttc atg gga aaa gtg gtg aat ccc acc caa aaa         1301
Lys Ser Pro Leu Phe Met Gly Lys Val Val Asn Pro Thr Gln Lys
                385                 390                 395

taactgcctc tcgctcctca acccctcccc tccatccctg gccccctccc tggatgacat   1361

taaagaaggg ttgagctggt ccctgcctgc atgtgactgc aaaaaaaaaa aaaaaa       1417


<210> SEQ ID NO 92
<211> LENGTH: 418
<212> TYPE: PRT
<213> ORGANISM: Homo sapiens
<220> FEATURE:
<221> NAME/KEY: SIGNAL
<222> LOCATION: 1..24

<400> SEQUENCE: 92

Met Pro Ser Ser Val Ser Trp Gly Ile Leu Leu Leu Ala Gly Leu Cys
                -20                 -15                 -10

Cys Leu Val Pro Val Ser Leu Ala Glu Asp Pro Gln Gly Asp Ala Ala
            -5                  1               5

Gln Lys Thr Asp Thr Ser His His Asp Gln Asp His Pro Thr Phe Asn
    10                  15                  20

Lys Ile Thr Pro Asn Leu Ala Glu Phe Ala Phe Ser Leu Tyr Arg Gln
25                  30                  35                  40

Leu Ala His Gln Ser Asn Ser Thr Asn Ile Phe Phe Ser Pro Val Ser
                45                  50                  55

Ile Ala Thr Ala Phe Ala Met Leu Ser Leu Gly Thr Lys Ala Asp Thr
            60                  65                  70

His Asp Glu Ile Leu Glu Ser Leu Asn Phe Asn Leu Thr Glu Ile Pro
        75                  80                  85

Glu Ala Gln Ile His Glu Gly Phe Gln Glu Leu Leu Arg Thr Leu Asn
    90                  95                  100

Gln Pro Asp Ser Gln Leu Gln Leu Thr Thr Gly Asn Gly Leu Phe Leu
105                 110                 115                 120

Ser Glu Gly Leu Lys Leu Val Asp Lys Phe Leu Glu Asp Val Lys Lys
                125                 130                 135

Leu Tyr His Ser Glu Ala Phe Thr Val Asn Phe Gly Asp Thr Glu Glu
            140                 145                 150

Ala Lys Lys Gln Ile Asn Asp Tyr Val Glu Lys Gly Thr Gln Gly Lys
        155                 160                 165

Ile Val Asp Leu Val Lys Glu Leu Asp Arg Asp Thr Val Phe Ala Leu
    170                 175                 180
```

-continued

```
Val Asn Tyr Ile Phe Phe Lys Gly Lys Trp Glu Arg Pro Phe Glu Val
185                 190                 195                 200

Lys Asp Thr Glu Glu Glu Asp Phe His Val Asp Gln Ala Thr Thr Val
                205                 210                 215

Lys Val Pro Met Met Lys Arg Leu Gly Met Phe Asn Ile Gln His Cys
            220                 225                 230

Lys Lys Leu Ser Ser Trp Val Leu Leu Met Lys Tyr Leu Gly Asn Ala
        235                 240                 245

Thr Ala Ile Phe Phe Leu Pro Asp Glu Gly Lys Leu Gln His Leu Glu
    250                 255                 260

Asn Glu Leu Thr His Asp Ile Ile Thr Lys Phe Leu Glu Asn Glu Asp
265                 270                 275                 280

Arg Arg Ser Ala Ser Leu His Leu Pro Lys Leu Ser Ile Thr Gly Thr
                285                 290                 295

Tyr Asp Leu Lys Ser Val Leu Gly Gln Leu Gly Ile Thr Lys Val Phe
            300                 305                 310

Ser Asn Gly Ala Asp Leu Ser Gly Val Thr Glu Glu Ala Pro Leu Lys
        315                 320                 325

Leu Ser Lys Ala Val His Lys Ala Val Leu Thr Ile Asp Glu Lys Gly
    330                 335                 340

Thr Glu Ala Ala Gly Ala Met Phe Leu Glu Ala Ile Pro Met Ser Ile
345                 350                 355                 360

Pro Pro Glu Val Lys Phe Asn Lys Pro Phe Val Phe Leu Met Ile Glu
                365                 370                 375

Gln Asn Thr Lys Ser Pro Leu Phe Met Gly Lys Val Val Asn Pro Thr
            380                 385                 390

Gln Lys


<210> SEQ ID NO 93
<211> LENGTH: 1115
<212> TYPE: DNA
<213> ORGANISM: Homo sapiens
<220> FEATURE:
<221> NAME/KEY: 5'UTR
<222> LOCATION: 1..277
<220> FEATURE:
<221> NAME/KEY: CDS
<222> LOCATION: 278..733
<220> FEATURE:
<221> NAME/KEY: 3'UTR
<222> LOCATION: 734..1115
<220> FEATURE:
<221> NAME/KEY: polyA_signal
<222> LOCATION: 1072..1077
<220> FEATURE:
<221> NAME/KEY: polyA_site
<222> LOCATION: 1101..1115

<400> SEQUENCE: 93

ctctttgctc taacagacag cagcgacttt aggctggata atagtcaaat tcttacctcg      60

ctctttcact gctagtaaga tcagattgcg tttctttcag ttactcttca atcgccagtt     120

tcttgatctg cttctaaaag aagaagtaga gaagataaat cctgtcttca atacctggaa     180

ggaaaaacaa aataacctca actccgtttt gaaaaaaaca ttccaagaac tttcatcaga     240

gattttactt agatgattta cacaatgaag aaagtac atg cac ttt ggg ctt ctg      295
                                         Met His Phe Gly Leu Leu
                                                         -15

tcc ctg ctg ctt aat ctt gcc cct gcc cct ctt aat gct gat tct gag      343
Ser Leu Leu Leu Asn Leu Ala Pro Ala Pro Leu Asn Ala Asp Ser Glu
        -10                 -5                  1
```

```
gaa gat gaa gaa cac aca att atc aca gat acg gag ttg cca cca ctg      391
Glu Asp Glu Glu His Thr Ile Ile Thr Asp Thr Glu Leu Pro Pro Leu
5                   10                  15                  20

aaa ctt atg cat tca ttt tgt gca ttc aag gcg gat gat agc cca tgt      439
Lys Leu Met His Ser Phe Cys Ala Phe Lys Ala Asp Asp Ser Pro Cys
                25                  30                  35

aaa gca atc atg aaa aga ttt ttc ttc aat att ttc act cga cag tgc      487
Lys Ala Ile Met Lys Arg Phe Phe Phe Asn Ile Phe Thr Arg Gln Cys
            40                  45                  50

gaa gaa ttt ata tat ggg gga tgt gaa gga aat cag aat cga ttt gaa      535
Glu Glu Phe Ile Tyr Gly Gly Cys Glu Gly Asn Gln Asn Arg Phe Glu
        55                  60                  65

agt ctg gaa gag tgc aaa aaa atg tgt aca aga gat aat gca aac agg      583
Ser Leu Glu Glu Cys Lys Lys Met Cys Thr Arg Asp Asn Ala Asn Arg
    70                  75                  80

att ata aag aca aca ttg caa caa gaa aag cca gat ttc tgc ttt ttg      631
Ile Ile Lys Thr Thr Leu Gln Gln Glu Lys Pro Asp Phe Cys Phe Leu
85                  90                  95                  100

gaa gaa gat cct gga ata tgt cga ggt tat att acc agg tat ttt tat      679
Glu Glu Asp Pro Gly Ile Cys Arg Gly Tyr Ile Thr Arg Tyr Phe Tyr
                105                 110                 115

aac aat cag aca aaa cat gtg aac gtt tca agt atg gtg gat gcc tgg      727
Asn Asn Gln Thr Lys His Val Asn Val Ser Ser Met Val Asp Ala Trp
            120                 125                 130

gca ata tgaacaattt tgagacactg gaagaatgca agaacatttg tgaagatggt      783
Ala Ile

ccgaatggtt tccaggtgga taattatgga acccagctca atgctgtgaa taactccctg    843

actccgcaat caaccaaggt tcccagcctt tttgttacaa aagaaggaac aaatgatggt    903

tggaagaatg cggctcatat ttaccaagtc tttctgaacg ccttctgcat tcatgcatcc    963

atgttctttc taggattgga tagcatttca tgcctatgtt aatatttgtg cttttggcat   1023

ttccttaata tttatatgta tacgtgatgc ctttgatagc atactgctaa taaagtttta   1083

atatttacat gcataggaaa aaaaaaaaaa aa                                 1115


<210> SEQ ID NO 94
<211> LENGTH: 152
<212> TYPE: PRT
<213> ORGANISM: Homo sapiens
<220> FEATURE:
<221> NAME/KEY: SIGNAL
<222> LOCATION: 1..19

<400> SEQUENCE: 94

Met His Phe Gly Leu Leu Ser Leu Leu Leu Asn Leu Ala Pro Ala Pro
                -15                 -10                 -5

Leu Asn Ala Asp Ser Glu Glu Asp Glu Glu His Thr Ile Ile Thr Asp
            1                   5                   10

Thr Glu Leu Pro Pro Leu Lys Leu Met His Ser Phe Cys Ala Phe Lys
    15                  20                  25

Ala Asp Asp Ser Pro Cys Lys Ala Ile Met Lys Arg Phe Phe Phe Asn
30                  35                  40                  45

Ile Phe Thr Arg Gln Cys Glu Glu Phe Ile Tyr Gly Gly Cys Glu Gly
                50                  55                  60

Asn Gln Asn Arg Phe Glu Ser Leu Glu Glu Cys Lys Lys Met Cys Thr
            65                  70                  75

Arg Asp Asn Ala Asn Arg Ile Ile Lys Thr Thr Leu Gln Gln Glu Lys
        80                  85                  90
```

```
Pro Asp Phe Cys Phe Leu Glu Glu Asp Pro Gly Ile Cys Arg Gly Tyr
    95                  100                 105

Ile Thr Arg Tyr Phe Tyr Asn Asn Gln Thr Lys His Val Asn Val Ser
110                 115                 120                 125

Ser Met Val Asp Ala Trp Ala Ile
                130


<210> SEQ ID NO 95
<211> LENGTH: 1307
<212> TYPE: DNA
<213> ORGANISM: Homo sapiens
<220> FEATURE:
<221> NAME/KEY: 5'UTR
<222> LOCATION: 1..252
<220> FEATURE:
<221> NAME/KEY: CDS
<222> LOCATION: 253..744
<220> FEATURE:
<221> NAME/KEY: 3'UTR
<222> LOCATION: 745..1307
<220> FEATURE:
<221> NAME/KEY: polyA_signal
<222> LOCATION: 1269..1274
<220> FEATURE:
<221> NAME/KEY: polyA_site
<222> LOCATION: 1292..1307

<400> SEQUENCE: 95

ctctttgctc taacagacag cagcgacttt aggctggata atagtcaaat tcttacctcg     60

ctctttcact gctagtaaga tcagattgcg tttctttcag ttactcttca atcgccagtt    120

tcttgatctg cttctaaaag aagaagtaga gaagataaat cctgtcttca atacctggaa    180

ggaaaaacag aataacctca actccgtttt gaaaaaaaca ttccaagaac tttcatcaga    240

gattttactt ag atg att tac aca atg aag aaa gta cat gca ctt tgg gct    291
              Met Ile Tyr Thr Met Lys Lys Val His Ala Leu Trp Ala
                      -25                 -20                 -15

tct gta tgc ctg ctg ctt aat ctt gcc cct gcc cct ctt aat gct gat      339
Ser Val Cys Leu Leu Leu Asn Leu Ala Pro Ala Pro Leu Asn Ala Asp
                -10                 -5                  1

tct gag gaa gat gaa gaa cac aca att atc aca gat acg gag ttg cca      387
Ser Glu Glu Asp Glu Glu His Thr Ile Ile Thr Asp Thr Glu Leu Pro
        5                   10                  15

cca ctg aaa ctt atg cat tca ttt tgt gca ttc aag gcg gat gat ggc      435
Pro Leu Lys Leu Met His Ser Phe Cys Ala Phe Lys Ala Asp Asp Gly
    20                  25                  30

cca tgt aaa gca atc atg aaa aga ttt ttc ttc aat att ttc act cga      483
Pro Cys Lys Ala Ile Met Lys Arg Phe Phe Phe Asn Ile Phe Thr Arg
35                  40                  45                  50

cag tgc gaa gaa ttt ata tat ggg gga tgt gaa gga aat cag aat cga      531
Gln Cys Glu Glu Phe Ile Tyr Gly Gly Cys Glu Gly Asn Gln Asn Arg
                55                  60                  65

ttt gaa agt ctg gaa gag tgc aaa aaa atg tgt aca aga gat aat gca      579
Phe Glu Ser Leu Glu Glu Cys Lys Lys Met Cys Thr Arg Asp Asn Ala
            70                  75                  80

aac agg att ata aag aca aca ttg caa caa gaa aag cca gat ttc tgc      627
Asn Arg Ile Ile Lys Thr Thr Leu Gln Gln Glu Lys Pro Asp Phe Cys
        85                  90                  95

ttt ttg gaa gaa gat cct gga ata tgt cga ggt tat att acc agg tat      675
Phe Leu Glu Glu Asp Pro Gly Ile Cys Arg Gly Tyr Ile Thr Arg Tyr
    100                 105                 110

ttt tat aac aat cag aca aaa cag tgt gaa cgt ttc aag tat ggt gga      723
Phe Tyr Asn Asn Gln Thr Lys Gln Cys Glu Arg Phe Lys Tyr Gly Gly
```

-continued

```
115                 120                 125                 130

tgc ctg ggc aat caa caa ttt tgagacactg gaacaatgca agaacatttg         774
Cys Leu Gly Asn Gln Gln Phe
                135

tgaagatggt ccgaatggtt tccaggtgga taattatgga acccagctca atgctgtgaa    834

taactccctg actccgcaat caaccaaggt tcccagcctt tttgaatttc acggtccctc    894

atggtgtctc actccagcag acagaggatt gtgtcgtgcc aatgagaaca gattctacta    954

caattcagtc attgggaaat gccgcccatt taagtacagt ggatgtgggg gaaatgaaaa   1014

caattttact tccaaacaag aatgtctgag ggcatgtaaa aaaggtttca tccaaagaat   1074

atcaaaagga ggcctaatta aaaccaaaag aaaaagaaag aagcagagag tgaaaatagc   1134

atatgaagaa atttttgtta aaaatatgtg aatttgttat agcaatgtaa cattaattct   1194

actaaatatt ttatatgaaa tgtttcacta tgattttcta tttttcttct aaaatgcttt   1254

taattaatat gttcattaaa ttttctatgc ttattgcaaa aaaaaaaaaa aaa          1307


<210> SEQ ID NO 96
<211> LENGTH: 164
<212> TYPE: PRT
<213> ORGANISM: Homo sapiens
<220> FEATURE:
<221> NAME/KEY: SIGNAL
<222> LOCATION: 1..28

<400> SEQUENCE: 96

Met Ile Tyr Thr Met Lys Lys Val His Ala Leu Trp Ala Ser Val Cys
            -25                 -20                 -15

Leu Leu Leu Asn Leu Ala Pro Ala Pro Leu Asn Ala Asp Ser Glu Glu
        -10                 -5                  1

Asp Glu Glu His Thr Ile Ile Thr Asp Thr Glu Leu Pro Pro Leu Lys
5                   10                  15                  20

Leu Met His Ser Phe Cys Ala Phe Lys Ala Asp Asp Gly Pro Cys Lys
                25                  30                  35

Ala Ile Met Lys Arg Phe Phe Phe Asn Ile Phe Thr Arg Gln Cys Glu
            40                  45                  50

Glu Phe Ile Tyr Gly Gly Cys Glu Gly Asn Gln Asn Arg Phe Glu Ser
        55                  60                  65

Leu Glu Glu Cys Lys Lys Met Cys Thr Arg Asp Asn Ala Asn Arg Ile
    70                  75                  80

Ile Lys Thr Thr Leu Gln Gln Glu Lys Pro Asp Phe Cys Phe Leu Glu
85                  90                  95                  100

Glu Asp Pro Gly Ile Cys Arg Gly Tyr Ile Thr Arg Tyr Phe Tyr Asn
                105                 110                 115

Asn Gln Thr Lys Gln Cys Glu Arg Phe Lys Tyr Gly Gly Cys Leu Gly
            120                 125                 130

Asn Gln Gln Phe
        135


<210> SEQ ID NO 97
<211> LENGTH: 1855
<212> TYPE: DNA
<213> ORGANISM: Homo sapiens
<220> FEATURE:
<221> NAME/KEY: 5'UTR
<222> LOCATION: 1..117
<220> FEATURE:
<221> NAME/KEY: CDS
<222> LOCATION: 118..504
```

```
<220> FEATURE:
<221> NAME/KEY: 3'UTR
<222> LOCATION: 505..1855
<220> FEATURE:
<221> NAME/KEY: polyA_signal
<222> LOCATION: 1819..1824
<220> FEATURE:
<221> NAME/KEY: polyA_site
<222> LOCATION: 1840..1855

<400> SEQUENCE: 97

tccccggccg ccgccgttgc gctcgccgcg ctcgcactga agcccgggcc ctcgcgcgcc      60

gcggttcgcc ccgcagcctc gccccctgcc cacccgggcg gccgtagggc ggtcacg        117

atg ctg ccg ccc tta ccc tcc cgc ctc ggg ctg ctg ctg ctg ctg ctc       165
Met Leu Pro Pro Leu Pro Ser Arg Leu Gly Leu Leu Leu Leu Leu Leu
            -20                 -15                 -10

ctg tgc ccg gcg cac gtc ggc gga ctg tgg tgg gct gtg ggc agc ccc       213
Leu Cys Pro Ala His Val Gly Gly Leu Trp Trp Ala Val Gly Ser Pro
        -5                  1               5

ttg gtt atg gac cct acc agc atc tgc agg aag gca cgg cgg ctg gcc       261
Leu Val Met Asp Pro Thr Ser Ile Cys Arg Lys Ala Arg Arg Leu Ala
10                  15                  20                  25

ggg cgg cag gcc gag ttg tgc cag gct gag ccg gaa gtg gtg gca gag       309
Gly Arg Gln Ala Glu Leu Cys Gln Ala Glu Pro Glu Val Val Ala Glu
                30                  35                  40

ctg gct cgg ggc gcc cgg ctc ggg gtg cga gag tgc cag ttc cag ttc       357
Leu Ala Arg Gly Ala Arg Leu Gly Val Arg Glu Cys Gln Phe Gln Phe
            45                  50                  55

cgc ttc cgc cgc tgg aat tgc tcc agc cac agc aag gcc ttt gga cgc       405
Arg Phe Arg Arg Trp Asn Cys Ser Ser His Ser Lys Ala Phe Gly Arg
        60                  65                  70

atc ctg caa cag ggt cag tgt ggg gag ggg gcg gaa gtg ggg ctg ctt       453
Ile Leu Gln Gln Gly Gln Cys Gly Glu Gly Ala Glu Val Gly Leu Leu
    75                  80                  85

tct ccc tgc tgt ggg acc cga gga gag gag aac tgg ttc gct gaa gtt       501
Ser Pro Cys Cys Gly Thr Arg Gly Glu Glu Asn Trp Phe Ala Glu Val
90                  95                  100                 105

gcc tgagccccac ttccccctca catgtgtctg ggcaccctgc aaggaccctg            554
Ala

cctcccaggc ccctggggca gccctcccgc cgcaggtttc aggtcccagg ccccagctga     614

ccgccccagc ccgcgctgat tgcacctgtc tgcattcaca gacattcggg agacggcctt     674

cgtgttcgcc atcactgcgg ccggcgccag ccacgccgtc acgcaggcct gttctatggg     734

cgagctgctg cagtgcggct gccaggcgcc ccgcgggcgg gcccctcccc ggccctccgg     794

cctgcccggc acccccggac cccctggccc cgcgggctcc ccggaaggca gcgccgcctg     854

ggagtgggga ggctgcggcg acgacgtgga cttcggggac gagaagtcga ggctctttat     914

ggacgcgcgg cacaagcggg gacgcggaga catccgcgcg ttggtgcaac tgcacaacaa     974

cgaggcgggc aggctggccg tgcggagcca cacgcgcacc gagtgcaaat gccacgggct    1034

gtcgggatca tgcgcgctgc gcacctgctg gcagaagctg cctccatttc gcgaggtggg    1094

cgcgcggctg ctggagcgct tccacggcgc ctcacgcgtc atgggcacca acgacggcaa    1154

ggccctgctg cccgccgtcc gcacgctcaa gccgccgggc cgagcggacc tcctctacgc    1214

cgccgattcg cccgacttct gcgcccccaa ccgacgcacc ggctcccccg gcacgcgcgg    1274

tcgcgcctgc aatagcagcg ccccggacct cagcggctgc gacctgctgt gctgcggccg    1334

cgggcaccgc caggagagcg tgcagctcga agagaactgc ctgtgccgct tccactggtg    1394
```

-continued

```
ctgcgtagta cagtgccacc gctgccgtgt gcgcaaggag ctcagcctct gcctgtgacc   1454

cgccgcccgg ccgctagact gacttcgcgc agcggtggct cgcacctgtg ggacctcagg   1514

gcaccggcac cgggcgcctc tcgccgctcg agcccagcct ctccctgcca aagcccaact   1574

cccagggctc tggaaatggt gaggcgaggg gcttgagagg aacgcccacc cacgaaggcc   1634

cagggcgcca gacggccccg aaaaggcgct cggggagcgt ttaaaggaca ctgtacaggc   1694

cctccctccc cttggcctct aggaggaaac agttttttag actggaaaaa agccagtcta   1754

aaggcctctg gatactgggc tccccagaac tgctggccac aggatggtgg gtgaggttag   1814

tatcaataaa gatatttaaa ccaccaaaaa aaaaaaaaaa a                       1855
```

```
<210> SEQ ID NO 98
<211> LENGTH: 129
<212> TYPE: PRT
<213> ORGANISM: Homo sapiens
<220> FEATURE:
<221> NAME/KEY: SIGNAL
<222> LOCATION: 1..24

<400> SEQUENCE: 98

Met Leu Pro Pro Leu Pro Ser Arg Leu Gly Leu Leu Leu Leu Leu Leu
                -20                 -15                 -10

Leu Cys Pro Ala His Val Gly Gly Leu Trp Trp Ala Val Gly Ser Pro
            -5                  1               5

Leu Val Met Asp Pro Thr Ser Ile Cys Arg Lys Ala Arg Arg Leu Ala
    10                  15                  20

Gly Arg Gln Ala Glu Leu Cys Gln Ala Glu Pro Glu Val Val Ala Glu
25                  30                  35                  40

Leu Ala Arg Gly Ala Arg Leu Gly Val Arg Glu Cys Gln Phe Gln Phe
                45                  50                  55

Arg Phe Arg Arg Trp Asn Cys Ser Ser His Ser Lys Ala Phe Gly Arg
            60                  65                  70

Ile Leu Gln Gln Gly Gln Cys Gly Glu Gly Ala Glu Val Gly Leu Leu
        75                  80                  85

Ser Pro Cys Cys Gly Thr Arg Gly Glu Glu Asn Trp Phe Ala Glu Val
    90                  95                  100

Ala
105
```

```
<210> SEQ ID NO 99
<211> LENGTH: 667
<212> TYPE: DNA
<213> ORGANISM: Homo sapiens
<220> FEATURE:
<221> NAME/KEY: 5'UTR
<222> LOCATION: 1..94
<220> FEATURE:
<221> NAME/KEY: CDS
<222> LOCATION: 95..613
<220> FEATURE:
<221> NAME/KEY: 3'UTR
<222> LOCATION: 614..667
<220> FEATURE:
<221> NAME/KEY: polyA_signal
<222> LOCATION: 636..641
<220> FEATURE:
<221> NAME/KEY: polyA_site
<222> LOCATION: 652..667

<400> SEQUENCE: 99

ctctgcaaat ccaggacaca cattgtgctc cgcgctccac taaaggcttg agtgggcact     60
```

-continued

```
gttccatctc aacagcccct gttttggaaa ggac atg att gtc aag ggg gtg gcc     115
                                      Met Ile Val Lys Gly Val Ala
                                      1               5

tcc aga act gtg gtt tcc aga ccg ttc ccc ggt aac tgg ctt ttc tct       163
Ser Arg Thr Val Val Ser Arg Pro Phe Pro Gly Asn Trp Leu Phe Ser
        10                  15                  20

tcc atc cag ctg act gat gat cag ggc ccc gtc ctg atg acc act gta       211
Ser Ile Gln Leu Thr Asp Asp Gln Gly Pro Val Leu Met Thr Thr Val
    25                  30                  35

gcc atg cct gtg ttt agt aag cag aac gaa acc aga tcg aag ggc att       259
Ala Met Pro Val Phe Ser Lys Gln Asn Glu Thr Arg Ser Lys Gly Ile
40                  45                  50                  55

ctt ctg gga gtg gtt ggc aca gat gtc cca gtg aaa gaa ctt ctg aag       307
Leu Leu Gly Val Val Gly Thr Asp Val Pro Val Lys Glu Leu Leu Lys
                60                  65                  70

acc atc ccc aaa tac aag tta ggg att cac ggt tat gcc ttt gca atc       355
Thr Ile Pro Lys Tyr Lys Leu Gly Ile His Gly Tyr Ala Phe Ala Ile
            75                  80                  85

aca aat aat gga tat atc ctg acg cat ccg gaa ctc agg ctg ctg tac       403
Thr Asn Asn Gly Tyr Ile Leu Thr His Pro Glu Leu Arg Leu Leu Tyr
        90                  95                  100

gaa gaa gga aaa aag cga agg aaa cct aac tat agt agc gtt gac ctc       451
Glu Glu Gly Lys Lys Arg Arg Lys Pro Asn Tyr Ser Ser Val Asp Leu
    105                 110                 115

tct gag gtg gag tgg gaa gac cga gat gac gtg ttg aga aat gct atg       499
Ser Glu Val Glu Trp Glu Asp Arg Asp Asp Val Leu Arg Asn Ala Met
120                 125                 130                 135

gtg aat cga aag acg ggg aag ttt tcc atg gag gtg aag aag aca gtg       547
Val Asn Arg Lys Thr Gly Lys Phe Ser Met Glu Val Lys Lys Thr Val
                140                 145                 150

gac aaa ggg gta cat ttt tct caa aca ttt ttg ctg ctt aat tta aaa       595
Asp Lys Gly Val His Phe Ser Gln Thr Phe Leu Leu Leu Asn Leu Lys
            155                 160                 165

caa acc act gtg aaa aat tagctttgaa agctatatct ggaataaata              643
Gln Thr Thr Val Lys Asn
        170

tctttcgcaa aaaaaaaaaa aaaa                                            667


<210> SEQ ID NO 100
<211> LENGTH: 173
<212> TYPE: PRT
<213> ORGANISM: Homo sapiens

<400> SEQUENCE: 100

Met Ile Val Lys Gly Val Ala Ser Arg Thr Val Val Ser Arg Pro Phe
1               5                   10                  15

Pro Gly Asn Trp Leu Phe Ser Ser Ile Gln Leu Thr Asp Asp Gln Gly
            20                  25                  30

Pro Val Leu Met Thr Thr Val Ala Met Pro Val Phe Ser Lys Gln Asn
        35                  40                  45

Glu Thr Arg Ser Lys Gly Ile Leu Leu Gly Val Val Gly Thr Asp Val
    50                  55                  60

Pro Val Lys Glu Leu Leu Lys Thr Ile Pro Lys Tyr Lys Leu Gly Ile
65                  70                  75                  80

His Gly Tyr Ala Phe Ala Ile Thr Asn Asn Gly Tyr Ile Leu Thr His
                85                  90                  95

Pro Glu Leu Arg Leu Leu Tyr Glu Glu Gly Lys Lys Arg Arg Lys Pro
            100                 105                 110
```

-continued

```
Asn Tyr Ser Ser Val Asp Leu Ser Glu Val Glu Trp Glu Asp Arg Asp
        115                 120                 125

Asp Val Leu Arg Asn Ala Met Val Asn Arg Lys Thr Gly Lys Phe Ser
    130                 135                 140

Met Glu Val Lys Lys Thr Val Asp Lys Gly Val His Phe Ser Gln Thr
145                 150                 155                 160

Phe Leu Leu Leu Asn Leu Lys Gln Thr Thr Val Lys Asn
                165                 170


<210> SEQ ID NO 101
<211> LENGTH: 1062
<212> TYPE: DNA
<213> ORGANISM: Homo sapiens
<220> FEATURE:
<221> NAME/KEY: 5'UTR
<222> LOCATION: 1..153
<220> FEATURE:
<221> NAME/KEY: CDS
<222> LOCATION: 154..639
<220> FEATURE:
<221> NAME/KEY: 3'UTR
<222> LOCATION: 640..1062
<220> FEATURE:
<221> NAME/KEY: polyA_signal
<222> LOCATION: 1023..1028
<220> FEATURE:
<221> NAME/KEY: polyA_site
<222> LOCATION: 1047..1062

<400> SEQUENCE: 101

attggtgtat ggctttgcag caataactga tggctgtttc cctcctgct ttatctttca      60

gttaatgacc agccacggcg tccctgctgt gagctctggc cgctgccttc cagggctccc     120

gagccacacg ctgggggtgc tggctgaggg aac atg gct tgt tgg cct cag ctg      174
                                     Met Ala Cys Trp Pro Gln Leu
                                     1               5

agg ttg ctg ctg tgg aag aac ctc act ttc aga aga aga caa aca tgt      222
Arg Leu Leu Leu Trp Lys Asn Leu Thr Phe Arg Arg Arg Gln Thr Cys
        10                  15                  20

cag ctg ctg ctg gaa gtg gcc tgg cct cta ttt atc ttc ctg atc ctg      270
Gln Leu Leu Leu Glu Val Ala Trp Pro Leu Phe Ile Phe Leu Ile Leu
    25                  30                  35

atc tct gtt cgg ctg agc tac cca ccc tat gaa caa cat gaa tgc cat      318
Ile Ser Val Arg Leu Ser Tyr Pro Pro Tyr Glu Gln His Glu Cys His
40                  45                  50                  55

ttt cca aat aaa gcc atg ccc tct gca gga aca ctt cct tgg gtt cag      366
Phe Pro Asn Lys Ala Met Pro Ser Ala Gly Thr Leu Pro Trp Val Gln
                60                  65                  70

ggg att atc tgt aat gcc aac aac ccc tgt ttc cgt tac ccg act cct      414
Gly Ile Ile Cys Asn Ala Asn Asn Pro Cys Phe Arg Tyr Pro Thr Pro
            75                  80                  85
ggg gag gct ccc gga gtt gtt gga aac ttt aac aaa tcc att gtg gct      462
Gly Glu Ala Pro Gly Val Val Gly Asn Phe Asn Lys Ser Ile Val Ala
        90                  95                  100

cgc ctg ttc tca gat gct cgg agg ctt ctt tta tac agc cag aaa gac      510
Arg Leu Phe Ser Asp Ala Arg Arg Leu Leu Leu Tyr Ser Gln Lys Asp
    105                 110                 115
acc agc atg aag gac atg cgc aaa gtt ctg aga aca tta cag cag atc      558
Thr Ser Met Lys Asp Met Arg Lys Val Leu Arg Thr Leu Gln Gln Ile
120                 125                 130                 135

aag aaa tcc agc tca aga ggg gac aaa cgc cat ttc ctc aac tgg cag      606
Lys Lys Ser Ser Ser Arg Gly Asp Lys Arg His Phe Leu Asn Trp Gln
                140                 145                 150

aag gga ctg aag cct ctc cct caa gcc ctt tta taggggtcct cattgtcagg    659
Lys Gly Leu Lys Pro Leu Pro Gln Ala Leu Leu
```

```
        155                 160

cctctaagcc caagccaagc catcgcatcc cctgtgactt gcacatatac gcccagatgg    719

cctgaagtaa ctgaagaatc acaaaagaag tgaaaaggcc ctgcctcgcc ttaactgatg    779

acgttccacc attgtgattt gttcctgccc caccttaact gagtgattaa ccctgtgaat    839

ttccttctcc tggctcagaa gctcccccac tgagcacctt gtgacccct gcccctgccc    899

accagagaac aaccccctttt gactgtaatt ttccattacc ttcccaaatc ctataaaacg    959

gccccacccc tatctccctt tgctgactct cttttcggac tcagcccacc tgcagccagg   1019

tgaaaaaaac agctttattg ctcacacaaa aaaaaaaaaa aaa                     1062
```

<210> SEQ ID NO 102
<211> LENGTH: 162
<212> TYPE: PRT
<213> ORGANISM: Homo sapiens

<400> SEQUENCE: 102

```
Met Ala Cys Trp Pro Gln Leu Arg Leu Leu Leu Trp Lys Asn Leu Thr
1               5                   10                  15

Phe Arg Arg Arg Gln Thr Cys Gln Leu Leu Leu Glu Val Ala Trp Pro
            20                  25                  30

Leu Phe Ile Phe Leu Ile Leu Ile Ser Val Arg Leu Ser Tyr Pro Pro
        35                  40                  45

Tyr Glu Gln His Glu Cys His Phe Pro Asn Lys Ala Met Pro Ser Ala
    50                  55                  60

Gly Thr Leu Pro Trp Val Gln Gly Ile Ile Cys Asn Ala Asn Asn Pro
65                  70                  75                  80

Cys Phe Arg Tyr Pro Thr Pro Gly Glu Ala Pro Gly Val Val Gly Asn
                85                  90                  95

Phe Asn Lys Ser Ile Val Ala Arg Leu Phe Ser Asp Ala Arg Arg Leu
            100                 105                 110

Leu Leu Tyr Ser Gln Lys Asp Thr Ser Met Lys Asp Met Arg Lys Val
        115                 120                 125

Leu Arg Thr Leu Gln Gln Ile Lys Lys Ser Ser Ser Arg Gly Asp Lys
    130                 135                 140

Arg His Phe Leu Asn Trp Gln Lys Gly Leu Lys Pro Leu Pro Gln Ala
145                 150                 155                 160

Leu Leu
```

<210> SEQ ID NO 103
<211> LENGTH: 933
<212> TYPE: DNA
<213> ORGANISM: Homo sapiens
<220> FEATURE:
<221> NAME/KEY: 5'UTR
<222> LOCATION: 1..149
<220> FEATURE:
<221> NAME/KEY: CDS
<222> LOCATION: 150..392
<220> FEATURE:
<221> NAME/KEY: 3'UTR
<222> LOCATION: 393..933
<220> FEATURE:
<221> NAME/KEY: polyA_site
<222> LOCATION: 63..933

<400> SEQUENCE: 103

```
aaaccctcag ggacctggta tagacgcaga atctgtttca cacaacaact gctatttgaa     60

ggaaaaaaaa aaaaagaagc aaatgatacc aagacaagct cataacagag atccaatcag    120
```

```
cagatgtgta cggatgaaaa tacagtgag atg agt cag aaa ccg gcc aag gag      173
                                Met Ser Gln Lys Pro Ala Lys Glu
                                1               5

ggt ccc aga ctc tcc aaa aac cag aag tac tcc gaa cac ttc agc ata      221
Gly Pro Arg Leu Ser Lys Asn Gln Lys Tyr Ser Glu His Phe Ser Ile
    10                  15                  20

cac tgc tgc ccg ccg ttc acc ttc ctc aat tcc aag aag gag ata gtg      269
His Cys Cys Pro Pro Phe Thr Phe Leu Asn Ser Lys Lys Glu Ile Val
25                  30                  35                  40

gat cgg aaa tac agc atc tgt aag agc ggc tgc ttc tac cag aag aaa      317
Asp Arg Lys Tyr Ser Ile Cys Lys Ser Gly Cys Phe Tyr Gln Lys Lys
                45                  50                  55

gag gag gac tgg atc tgc tgc gcc tgc cag aag acc aga ttg aaa agg      365
Glu Glu Asp Trp Ile Cys Cys Ala Cys Gln Lys Thr Arg Leu Lys Arg
            60                  65                  70

aag atc agg cca acc cca aag aag aag tgaccaagga ggagtttaaa            412
Lys Ile Arg Pro Thr Pro Lys Lys Lys
        75                  80

ytgaatgaac aacctcggct cctggactca ttgcttcaca acccatctac ccctggatga    472

agttatctgg cttcaaatat tatgcagggg caaacacctg ctgatgtggc aactgctgat    532

gctcatggtc cccatggcat gggggcctca gggcagcctg cctggagtac tttgaagatg    592

tcatcccatt gtcttctgac ctctataatt gccactgaga gatctgctgt cagtctgctt    652

atccttccac ggactcaagt ttcttcaatc tgaagataca tgtctttctc caaggacatg    712

tggaaaaaaa aaagatgtta tacaaccatc aaagtggcaa aaataaaaaa aattggctgg    772

gcgtggtggc gggcgcctgt ggtcccagct actcgggagg ctgaggcagg agaatggcgt    832

gaacctggga ggcggagctt gcagtgagcc gagatcgcac cactgcactc cagcctgggc    892

gacagagcga gactctgtct caaacaaaaa aaaaaaaaaa a                        933


<210> SEQ ID NO 104
<211> LENGTH: 81
<212> TYPE: PRT
<213> ORGANISM: Homo sapiens

<400> SEQUENCE: 104

Met Ser Gln Lys Pro Ala Lys Glu Gly Pro Arg Leu Ser Lys Asn Gln
1               5                   10                  15

Lys Tyr Ser Glu His Phe Ser Ile His Cys Cys Pro Pro Phe Thr Phe
            20                  25                  30

Leu Asn Ser Lys Lys Glu Ile Val Asp Arg Lys Tyr Ser Ile Cys Lys
        35                  40                  45

Ser Gly Cys Phe Tyr Gln Lys Lys Glu Glu Asp Trp Ile Cys Cys Ala
    50                  55                  60

Cys Gln Lys Thr Arg Leu Lys Arg Lys Ile Arg Pro Thr Pro Lys Lys
65                  70                  75                  80

Lys


<210> SEQ ID NO 105
<211> LENGTH: 1187
<212> TYPE: DNA
<213> ORGANISM: Homo sapiens
<220> FEATURE:
<221> NAME/KEY: 5'UTR
<222> LOCATION: 1..34
<220> FEATURE:
<221> NAME/KEY: CDS
<222> LOCATION: 35..1069
```

```
<220> FEATURE:
<221> NAME/KEY: 3'UTR
<222> LOCATION: 1070..1187
<220> FEATURE:
<221> NAME/KEY: polyA_signal
<222> LOCATION: 1146..1151
<220> FEATURE:
<221> NAME/KEY: polyA_site
<222> LOCATION: 1172..1187

<400> SEQUENCE: 105

accactttgg tagtgccagt gtgactcatc caca atg att tct cca gtg ctc atc      55
                                      Met Ile Ser Pro Val Leu Ile
                                                      -15

ttg ttc tcg agt ttt ctc tgc cat gtt gct att gca gga cgg acc tgt       103
Leu Phe Ser Ser Phe Leu Cys His Val Ala Ile Ala Gly Arg Thr Cys
    -10                 -5                  1               5

ccc aag cca gat gat tta cca ttt tcc aca gtg gtc ccg tta aaa aca       151
Pro Lys Pro Asp Asp Leu Pro Phe Ser Thr Val Val Pro Leu Lys Thr
                10                  15                  20

ttc tat gag cca gga gaa gag att acg tat tcc tgc aag ccg ggc tat       199
Phe Tyr Glu Pro Gly Glu Glu Ile Thr Tyr Ser Cys Lys Pro Gly Tyr
            25                  30                  35

gtg tcc cga gga ggg atg aga aag ttt atc tgc cct ctc aca gga ctg       247
Val Ser Arg Gly Gly Met Arg Lys Phe Ile Cys Pro Leu Thr Gly Leu
        40                  45                  50

tgg ctc atc aac act ctg aaa tgt aca ccc aga gta tgt cct ttt gct       295
Trp Leu Ile Asn Thr Leu Lys Cys Thr Pro Arg Val Cys Pro Phe Ala
    55                  60                  65

gga atc tta gaa aat gga gcc gta cgc tat acg act ttt gaa tat ccc       343
Gly Ile Leu Glu Asn Gly Ala Val Arg Tyr Thr Thr Phe Glu Tyr Pro
70                  75                  80                  85

aac acg atc agt ttt tct tgt aac act ggg ttt tat ctg aat ggc gct       391
Asn Thr Ile Ser Phe Ser Cys Asn Thr Gly Phe Tyr Leu Asn Gly Ala
                90                  95                  100

gat tct gcc aag tgc act gag gaa gga aaa tgg agc ccg gag ctt cct       439
Asp Ser Ala Lys Cys Thr Glu Glu Gly Lys Trp Ser Pro Glu Leu Pro
            105                 110                 115

gtc tgt gct ccc atc atc tgc cct cca cca tcc ata cct acg ttt gca       487
Val Cys Ala Pro Ile Ile Cys Pro Pro Pro Ser Ile Pro Thr Phe Ala
        120                 125                 130

aca ctt cgt gtt tat aag cca tca gct gga aac aat tcc ctc tat cgg       535
Thr Leu Arg Val Tyr Lys Pro Ser Ala Gly Asn Asn Ser Leu Tyr Arg
    135                 140                 145

gac aca gca gtt ttt gaa tgt ttg cca caa cat gcg atg ttt gga aat       583
Asp Thr Ala Val Phe Glu Cys Leu Pro Gln His Ala Met Phe Gly Asn
150                 155                 160                 165

gat aca att acc tgc acg aca cat gga aat tgg act aaa tta cca gaa       631
Asp Thr Ile Thr Cys Thr Thr His Gly Asn Trp Thr Lys Leu Pro Glu
                170                 175                 180

tgc agg gaa gta aaa tgc cca ttc cca tca aga cca gac aat gga ttt       679
Cys Arg Glu Val Lys Cys Pro Phe Pro Ser Arg Pro Asp Asn Gly Phe
            185                 190                 195

gtg aac tat cct gca aaa cca aca ctt tat tac aag gat aaa gcc aca       727
Val Asn Tyr Pro Ala Lys Pro Thr Leu Tyr Tyr Lys Asp Lys Ala Thr
        200                 205                 210

ttt ggc tgc cat gat gga tat tct ctg gat ggc ccg gaa gaa ata gaa       775
Phe Gly Cys His Asp Gly Tyr Ser Leu Asp Gly Pro Glu Glu Ile Glu
    215                 220                 225

tgt acc aaa ctg gga aac tgg tct gcc atg cca agt tgt aaa gca tct       823
Cys Thr Lys Leu Gly Asn Trp Ser Ala Met Pro Ser Cys Lys Ala Ser
230                 235                 240                 245
```

```
tgt aaa gta cct gtg aaa aaa gcc act gtg gtg tac caa gga gag aga      871
Cys Lys Val Pro Val Lys Lys Ala Thr Val Val Tyr Gln Gly Glu Arg
                250                 255                 260

gta aag att cag gaa aaa ttt aag aat gga atg cta cat ggt gat aaa      919
Val Lys Ile Gln Glu Lys Phe Lys Asn Gly Met Leu His Gly Asp Lys
            265                 270                 275

gtt tct ttc ttc tgc aaa aat aag gaa aag aag tgt agc tat aca gag      967
Val Ser Phe Phe Cys Lys Asn Lys Glu Lys Lys Cys Ser Tyr Thr Glu
        280                 285                 290

gat gct cag tgt ata gat ggc act atc gaa gtc ccc aaa tgc ttc aag     1015
Asp Ala Gln Cys Ile Asp Gly Thr Ile Glu Val Pro Lys Cys Phe Lys
    295                 300                 305

gaa cac agt tct ctg gct ttt tgg aaa act gat gca tcc gat gta aag     1063
Glu His Ser Ser Leu Ala Phe Trp Lys Thr Asp Ala Ser Asp Val Lys
310                 315                 320                 325

cca tgc taaggtggtt ttcagattcc acataaaatg tcacacttgt ttcttgttca      1119
Pro Cys

tccaaggaac ctaattgaaa tttaaaaata aagctactga atttattgcc gcaaaaaaaa   1179

aaaaaaaa                                                             1187


<210> SEQ ID NO 106
<211> LENGTH: 345
<212> TYPE: PRT
<213> ORGANISM: Homo sapiens
<220> FEATURE:
<221> NAME/KEY: SIGNAL
<222> LOCATION: 1..19

<400> SEQUENCE: 106

Met Ile Ser Pro Val Leu Ile Leu Phe Ser Ser Phe Leu Cys His Val
                -15                 -10                 -5

Ala Ile Ala Gly Arg Thr Cys Pro Lys Pro Asp Asp Leu Pro Phe Ser
            1               5                   10

Thr Val Val Pro Leu Lys Thr Phe Tyr Glu Pro Gly Glu Glu Ile Thr
    15                  20                  25

Tyr Ser Cys Lys Pro Gly Tyr Val Ser Arg Gly Gly Met Arg Lys Phe
30                  35                  40                  45

Ile Cys Pro Leu Thr Gly Leu Trp Leu Ile Asn Thr Leu Lys Cys Thr
                50                  55                  60

Pro Arg Val Cys Pro Phe Ala Gly Ile Leu Glu Asn Gly Ala Val Arg
            65                  70                  75

Tyr Thr Thr Phe Glu Tyr Pro Asn Thr Ile Ser Phe Ser Cys Asn Thr
        80                  85                  90

Gly Phe Tyr Leu Asn Gly Ala Asp Ser Ala Lys Cys Thr Glu Glu Gly
    95                  100                 105

Lys Trp Ser Pro Glu Leu Pro Val Cys Ala Pro Ile Ile Cys Pro Pro
110                 115                 120                 125

Pro Ser Ile Pro Thr Phe Ala Thr Leu Arg Val Tyr Lys Pro Ser Ala
                130                 135                 140

Gly Asn Asn Ser Leu Tyr Arg Asp Thr Ala Val Phe Glu Cys Leu Pro
            145                 150                 155

Gln His Ala Met Phe Gly Asn Asp Thr Ile Thr Cys Thr Thr His Gly
        160                 165                 170

Asn Trp Thr Lys Leu Pro Glu Cys Arg Glu Val Lys Cys Pro Phe Pro
    175                 180                 185

Ser Arg Pro Asp Asn Gly Phe Val Asn Tyr Pro Ala Lys Pro Thr Leu
```

-continued

```
190                 195                 200                 205

Tyr Tyr Lys Asp Lys Ala Thr Phe Gly Cys His Asp Gly Tyr Ser Leu
                210                 215                 220

Asp Gly Pro Glu Glu Ile Glu Cys Thr Lys Leu Gly Asn Trp Ser Ala
            225                 230                 235

Met Pro Ser Cys Lys Ala Ser Cys Lys Val Pro Val Lys Lys Ala Thr
        240                 245                 250

Val Val Tyr Gln Gly Glu Arg Val Lys Ile Gln Glu Lys Phe Lys Asn
    255                 260                 265

Gly Met Leu His Gly Asp Lys Val Ser Phe Phe Cys Lys Asn Lys Glu
270                 275                 280                 285

Lys Lys Cys Ser Tyr Thr Glu Asp Ala Gln Cys Ile Asp Gly Thr Ile
                290                 295                 300

Glu Val Pro Lys Cys Phe Lys Glu His Ser Ser Leu Ala Phe Trp Lys
            305                 310                 315

Thr Asp Ala Ser Asp Val Lys Pro Cys
        320                 325


<210> SEQ ID NO 107
<211> LENGTH: 1520
<212> TYPE: DNA
<213> ORGANISM: Homo sapiens
<220> FEATURE:
<221> NAME/KEY: 5'UTR
<222> LOCATION: 1..15
<220> FEATURE:
<221> NAME/KEY: CDS
<222> LOCATION: 16..1449
<220> FEATURE:
<221> NAME/KEY: 3'UTR
<222> LOCATION: 1450..1520
<220> FEATURE:
<221> NAME/KEY: polyA_signal
<222> LOCATION: 1483..1488
<220> FEATURE:
<221> NAME/KEY: polyA_site
<222> LOCATION: 1505..1520

<400> SEQUENCE: 107

cttttttttg acaag atg gcg gca gga ggc agt ggc gtt ggt ggg aag cgc      51
                 Met Ala Ala Gly Gly Ser Gly Val Gly Gly Lys Arg
                 1               5                   10

agc tcg aaa agc gat gcc gat tct ggt ttc ctg ggg ctg cgg ccc act       99
Ser Ser Lys Ser Asp Ala Asp Ser Gly Phe Leu Gly Leu Arg Pro Thr
        15                  20                  25

tcg gtg gac cca gcg ctg agg cgg cgg cgg cga ggc cca aga aat aag      147
Ser Val Asp Pro Ala Leu Arg Arg Arg Arg Arg Gly Pro Arg Asn Lys
    30                  35                  40

aag cgg ggc tgg cgg cgg ctt gct cag gag ccg ctg ggg ctg gag gtt      195
Lys Arg Gly Trp Arg Arg Leu Ala Gln Glu Pro Leu Gly Leu Glu Val
45                  50                  55                  60

gac cag ttc ctg gaa gac gtg cgg cta cag gag cgc acg agc ggt ggc      243
Asp Gln Phe Leu Glu Asp Val Arg Leu Gln Glu Arg Thr Ser Gly Gly
                65                  70                  75

ttg ttg tca gag gcc cca aat gaa aaa ctc ttc ttc gtg gac act ggc      291
Leu Leu Ser Glu Ala Pro Asn Glu Lys Leu Phe Phe Val Asp Thr Gly
            80                  85                  90

tcc aag gaa aaa ggg ctg aca aag aag aga acc aaa gtc cag aag aag      339
Ser Lys Glu Lys Gly Leu Thr Lys Lys Arg Thr Lys Val Gln Lys Lys
        95                  100                 105

tca ctg ctt ctc aag aaa ccc ctt cgg gtt gac ctc atc ctg gag aac      387
Ser Leu Leu Leu Lys Lys Pro Leu Arg Val Asp Leu Ile Leu Glu Asn
```

-continued

```
    110                 115                 120

aca tcc aaa gtc cct gcc ccc aaa gac gtc ctc gcc cac cag gtc ccc      435
Thr Ser Lys Val Pro Ala Pro Lys Asp Val Leu Ala His Gln Val Pro
125                 130                 135                 140

aac gcc aag aag ctc agg cgg aag gag cag cta tgg gag aag ctg gcc      483
Asn Ala Lys Lys Leu Arg Arg Lys Glu Gln Leu Trp Glu Lys Leu Ala
                145                 150                 155

aag cag ggc gag ctg ccc cgg gag gtg cgc agg gcc cag gcc cgg ctc      531
Lys Gln Gly Glu Leu Pro Arg Glu Val Arg Arg Ala Gln Ala Arg Leu
            160                 165                 170

ctc aac cct tct gca aca agg gcc aag ccc ggg ccc cag gac acc gta      579
Leu Asn Pro Ser Ala Thr Arg Ala Lys Pro Gly Pro Gln Asp Thr Val
        175                 180                 185

gag cgg ccc ttc tac gac ctc tgg gcc tca gac aac ccc ctg gac agg      627
Glu Arg Pro Phe Tyr Asp Leu Trp Ala Ser Asp Asn Pro Leu Asp Arg
    190                 195                 200

ccg ttg gtt ggc cag gat gag ttt ttc ctg gag cag acc aag aag aaa      675
Pro Leu Val Gly Gln Asp Glu Phe Phe Leu Glu Gln Thr Lys Lys Lys
205                 210                 215                 220

gga gtg aag cgg cca gca cgc ctg cac acc aag ccg tcc cag gca ccc      723
Gly Val Lys Arg Pro Ala Arg Leu His Thr Lys Pro Ser Gln Ala Pro
                225                 230                 235

gcc gtg gag gtg gcg cct gcc gga gct tcc tac aat cca tcc ttt gaa      771
Ala Val Glu Val Ala Pro Ala Gly Ala Ser Tyr Asn Pro Ser Phe Glu
            240                 245                 250

gac cac cag acc ctg ctc tca gcg gcc cac gag gtg gag ttg cag cgg      819
Asp His Gln Thr Leu Leu Ser Ala Ala His Glu Val Glu Leu Gln Arg
        255                 260                 265

cag aag gag gcg gag aag ctg gag cgg cag ctg gcc ctg ccc gcc acg      867
Gln Lys Glu Ala Glu Lys Leu Glu Arg Gln Leu Ala Leu Pro Ala Thr
    270                 275                 280

gag cag gcc gcc acc cag gag tcc aca ttc cag gag ctg tgc gag ggg      915
Glu Gln Ala Ala Thr Gln Glu Ser Thr Phe Gln Glu Leu Cys Glu Gly
285                 290                 295                 300

ctg ctg gag gag tcg gat ggt gag ggg gag cca ggc cag ggc gag ggg      963
Leu Leu Glu Glu Ser Asp Gly Glu Gly Glu Pro Gly Gln Gly Glu Gly
                305                 310                 315

ccg gag gct ggg gat gcc gag gtc tgt ccc acg ccc gcc cgc ctg gcc     1011
Pro Glu Ala Gly Asp Ala Glu Val Cys Pro Thr Pro Ala Arg Leu Ala
            320                 325                 330

acc aca gag aag aag acg gag cag cag cgg cgg cgg gag aag gct gtg     1059
Thr Thr Glu Lys Lys Thr Glu Gln Gln Arg Arg Arg Glu Lys Ala Val
        335                 340                 345

cac agg ctg cgg gta cag cag gcc gcg ttg cgg gcc gcc cgg ctc cgg     1107
His Arg Leu Arg Val Gln Gln Ala Ala Leu Arg Ala Ala Arg Leu Arg
    350                 355                 360

cac cag gag ctg ttc cgg ctg cgc ggg atc aag gcc cag gtg gcc ctg     1155
His Gln Glu Leu Phe Arg Leu Arg Gly Ile Lys Ala Gln Val Ala Leu
365                 370                 375                 380

agg ctg gcg gag ctg gcg cgg cgg cag agg cgg cgg cag gcg cgg cgg     1203
Arg Leu Ala Glu Leu Ala Arg Arg Gln Arg Arg Arg Gln Ala Arg Arg
                385                 390                 395

gag gct gag gct gac aag ccc cga agg ctg ggg cgg ctc aag tac cag     1251
Glu Ala Glu Ala Asp Lys Pro Arg Arg Leu Gly Arg Leu Lys Tyr Gln
            400                 405                 410

gca cct gac atc gac gtg cag ctg agc tcg gag ctg aca gac tcg ctc     1299
Ala Pro Asp Ile Asp Val Gln Leu Ser Ser Glu Leu Thr Asp Ser Leu
        415                 420                 425

agg acc ctg aag ccc gag ggc aac atc ctt cga gac cgg ttc aag agc     1347
```

-continued

```
Arg Thr Leu Lys Pro Glu Gly Asn Ile Leu Arg Asp Arg Phe Lys Ser
    430                 435                 440

ttc cag agg agg aat atg atc gag cct cga gag aga gcc aag ttc aaa      1395
Phe Gln Arg Arg Asn Met Ile Glu Pro Arg Glu Arg Ala Lys Phe Lys
445                 450                 455                 460

cgc aag tac aag gtg aag ctg gtg gag aag cgg gcg ttc cgt gag atc      1443
Arg Lys Tyr Lys Val Lys Leu Val Glu Lys Arg Ala Phe Arg Glu Ile
                465                 470                 475

cag ttg tagctgccat cagatgccgg agactcgccc ttcaataaaa aatctcttct      1499
Gln Leu

agctcaaaaa aaaaaaaaaa a                                              1520


<210> SEQ ID NO 108
<211> LENGTH: 478
<212> TYPE: PRT
<213> ORGANISM: Homo sapiens

<400> SEQUENCE: 108

Met Ala Ala Gly Gly Ser Gly Val Gly Gly Lys Arg Ser Ser Lys Ser
1               5                   10                  15

Asp Ala Asp Ser Gly Phe Leu Gly Leu Arg Pro Thr Ser Val Asp Pro
            20                  25                  30

Ala Leu Arg Arg Arg Arg Arg Gly Pro Arg Asn Lys Lys Arg Gly Trp
        35                  40                  45

Arg Arg Leu Ala Gln Glu Pro Leu Gly Leu Glu Val Asp Gln Phe Leu
    50                  55                  60

Glu Asp Val Arg Leu Gln Glu Arg Thr Ser Gly Gly Leu Leu Ser Glu
65                  70                  75                  80

Ala Pro Asn Glu Lys Leu Phe Phe Val Asp Thr Gly Ser Lys Glu Lys
                85                  90                  95

Gly Leu Thr Lys Lys Arg Thr Lys Val Gln Lys Lys Ser Leu Leu Leu
            100                 105                 110

Lys Lys Pro Leu Arg Val Asp Leu Ile Leu Glu Asn Thr Ser Lys Val
        115                 120                 125

Pro Ala Pro Lys Asp Val Leu Ala His Gln Val Pro Asn Ala Lys Lys
    130                 135                 140

Leu Arg Arg Lys Glu Gln Leu Trp Glu Lys Leu Ala Lys Gln Gly Glu
145                 150                 155                 160

Leu Pro Arg Glu Val Arg Arg Ala Gln Ala Arg Leu Leu Asn Pro Ser
                165                 170                 175

Ala Thr Arg Ala Lys Pro Gly Pro Gln Asp Thr Val Glu Arg Pro Phe
            180                 185                 190

Tyr Asp Leu Trp Ala Ser Asp Asn Pro Leu Asp Arg Pro Leu Val Gly
        195                 200                 205

Gln Asp Glu Phe Phe Leu Glu Gln Thr Lys Lys Lys Gly Val Lys Arg
    210                 215                 220

Pro Ala Arg Leu His Thr Lys Pro Ser Gln Ala Pro Ala Val Glu Val
225                 230                 235                 240

Ala Pro Ala Gly Ala Ser Tyr Asn Pro Ser Phe Glu Asp His Gln Thr
                245                 250                 255

Leu Leu Ser Ala Ala His Glu Val Glu Leu Gln Arg Gln Lys Glu Ala
            260                 265                 270

Glu Lys Leu Glu Arg Gln Leu Ala Leu Pro Ala Thr Glu Gln Ala Ala
        275                 280                 285

Thr Gln Glu Ser Thr Phe Gln Glu Leu Cys Glu Gly Leu Leu Glu Glu
```

-continued

```
290                 295                 300

Ser Asp Gly Glu Gly Glu Pro Gly Gln Gly Glu Gly Pro Glu Ala Gly
305                 310                 315                 320

Asp Ala Glu Val Cys Pro Thr Pro Ala Arg Leu Ala Thr Thr Glu Lys
                325                 330                 335

Lys Thr Glu Gln Gln Arg Arg Arg Glu Lys Ala Val His Arg Leu Arg
            340                 345                 350

Val Gln Gln Ala Ala Leu Arg Ala Ala Arg Leu Arg His Gln Glu Leu
        355                 360                 365

Phe Arg Leu Arg Gly Ile Lys Ala Gln Val Ala Leu Arg Leu Ala Glu
    370                 375                 380

Leu Ala Arg Arg Gln Arg Arg Arg Gln Ala Arg Arg Glu Ala Glu Ala
385                 390                 395                 400

Asp Lys Pro Arg Arg Leu Gly Arg Leu Lys Tyr Gln Ala Pro Asp Ile
                405                 410                 415

Asp Val Gln Leu Ser Ser Glu Leu Thr Asp Ser Leu Arg Thr Leu Lys
            420                 425                 430

Pro Glu Gly Asn Ile Leu Arg Asp Arg Phe Lys Ser Phe Gln Arg Arg
        435                 440                 445

Asn Met Ile Glu Pro Arg Glu Arg Ala Lys Phe Lys Arg Lys Tyr Lys
    450                 455                 460

Val Lys Leu Val Glu Lys Arg Ala Phe Arg Glu Ile Gln Leu
465                 470                 475


<210> SEQ ID NO 109
<211> LENGTH: 1789
<212> TYPE: DNA
<213> ORGANISM: Homo sapiens
<220> FEATURE:
<221> NAME/KEY: 5'UTR
<222> LOCATION: 1..94
<220> FEATURE:
<221> NAME/KEY: CDS
<222> LOCATION: 95..1252
<220> FEATURE:
<221> NAME/KEY: 3'UTR
<222> LOCATION: 1253..1789
<220> FEATURE:
<221> NAME/KEY: polyA_signal
<222> LOCATION: 1751..1756
<220> FEATURE:
<221> NAME/KEY: polyA_site
<222> LOCATION: 1774..1789

<400> SEQUENCE: 109

ggtcttgcaa tatttattct gctttcgggt agatgggagg cccggggacc tggctgggtt      60

tctgccaagc ttctccgata cccaggtttc ataa atg tgt ttg ttg ctt tcc tgc     115
                                      Met Cys Leu Leu Leu Ser Cys
                                                      -10

cct tgc cac ccc tct gcc cac gga cag tcc atg tgg att gag aga acc       163
Pro Cys His Pro Ser Ala His Gly Gln Ser Met Trp Ile Glu Arg Thr
        -5                  1               5

tcc ttc gtg act gca tac aag ctg ccg ggg atc ctg cgc tgg ttt gag       211
Ser Phe Val Thr Ala Tyr Lys Leu Pro Gly Ile Leu Arg Trp Phe Glu
10                  15                  20                  25

gtg gtg cac atg tcg cag acc aca att agt cct ctg gag aat gcc ata       259
Val Val His Met Ser Gln Thr Thr Ile Ser Pro Leu Glu Asn Ala Ile
                30                  35                  40

gaa acc atg tcc acg gcc aat gag aag atc ctg atg atg ata aac cag       307
Glu Thr Met Ser Thr Ala Asn Glu Lys Ile Leu Met Met Ile Asn Gln
            45                  50                  55
```

-continued

```
tac cag agt gat gag acc ctc ccc atc aac cca ctc tcc atg ctc ctg      355
Tyr Gln Ser Asp Glu Thr Leu Pro Ile Asn Pro Leu Ser Met Leu Leu
        60                  65                  70

aac ggg att gtg gac cct gct gtc atg gga ggc ttc gcc aag tat gag      403
Asn Gly Ile Val Asp Pro Ala Val Met Gly Gly Phe Ala Lys Tyr Glu
    75                  80                  85

aag gcc ttc ttc act gaa gag tat gtc agg gac cac cct gag gac cag      451
Lys Ala Phe Phe Thr Glu Glu Tyr Val Arg Asp His Pro Glu Asp Gln
90                  95                  100                 105

gac aag ctg acc cac ctc aag gac ctg att gca tgg cag atc ccc ttc      499
Asp Lys Leu Thr His Leu Lys Asp Leu Ile Ala Trp Gln Ile Pro Phe
                110                 115                 120

ttg gga gct ggg att aag atc cat gag aaa agg gtg tca gat aac ttg      547
Leu Gly Ala Gly Ile Lys Ile His Glu Lys Arg Val Ser Asp Asn Leu
            125                 130                 135

cga ccc ttc cat gac cgg atg gag gaa tgt ttc aag aac ctg aaa atg      595
Arg Pro Phe His Asp Arg Met Glu Glu Cys Phe Lys Asn Leu Lys Met
        140                 145                 150

aag gtg gag aag gag tac ggt gtc cga gag atg cct gac ttt gac gac      643
Lys Val Glu Lys Glu Tyr Gly Val Arg Glu Met Pro Asp Phe Asp Asp
    155                 160                 165

agg aga gtg ggc cgt ccc agg tct atg ctg cgc tca tac aga cag atg      691
Arg Arg Val Gly Arg Pro Arg Ser Met Leu Arg Ser Tyr Arg Gln Met
170                 175                 180                 185

tcc atc atc tct ctg gct tcc atg aat tct gac tgc agc acc ccc agc      739
Ser Ile Ile Ser Leu Ala Ser Met Asn Ser Asp Cys Ser Thr Pro Ser
                190                 195                 200

aag cct acc tca gag agc ttt gac ctg gaa tta gca tca ccc aag acg      787
Lys Pro Thr Ser Glu Ser Phe Asp Leu Glu Leu Ala Ser Pro Lys Thr
            205                 210                 215

ccg aga gtg gag cag gag gaa ccg atc tcc ccg ggg agc acc ctg cct      835
Pro Arg Val Glu Gln Glu Glu Pro Ile Ser Pro Gly Ser Thr Leu Pro
        220                 225                 230

gag gtc aag ctg cgg agg tcc aag aag agg aca aag aga agc agc gta      883
Glu Val Lys Leu Arg Arg Ser Lys Lys Arg Thr Lys Arg Ser Ser Val
    235                 240                 245

gtt ttt gcg gat gag aaa gca gct gca gag tcg gac ctg aag cgg ctt      931
Val Phe Ala Asp Glu Lys Ala Ala Ala Glu Ser Asp Leu Lys Arg Leu
250                 255                 260                 265

tcc agg aag cat gag ttc atg agt gac acc aac ctc tcg gag cat gcg      979
Ser Arg Lys His Glu Phe Met Ser Asp Thr Asn Leu Ser Glu His Ala
                270                 275                 280

gcc atc ccc ctc aag gcg tct gtc ctc tct caa atg agc ttt gcc agc     1027
Ala Ile Pro Leu Lys Ala Ser Val Leu Ser Gln Met Ser Phe Ala Ser
            285                 290                 295

cag tcc atg cct acc atc cca gcc ctg gcg ctc tca gtg gca ggc atc     1075
Gln Ser Met Pro Thr Ile Pro Ala Leu Ala Leu Ser Val Ala Gly Ile
        300                 305                 310

cct ggg ttg gat gag gcc aac aca tct ccc cgc ctc agc cag acc ttc     1123
Pro Gly Leu Asp Glu Ala Asn Thr Ser Pro Arg Leu Ser Gln Thr Phe
    315                 320                 325

ctc caa ctc tca gat ggt gac aag aag aca ctc aca cgg aag aag gtc     1171
Leu Gln Leu Ser Asp Gly Asp Lys Lys Thr Leu Thr Arg Lys Lys Val
330                 335                 340                 345

aat cag ttc ttc aag aca atg ctg gcc agc aaa tcg gct gaa gaa ggc     1219
Asn Gln Phe Phe Lys Thr Met Leu Ala Ser Lys Ser Ala Glu Glu Gly
                350                 355                 360

aaa cag atc cca gac tcg ctg tcc acg gac ctg tgagctgctg ctgactaggg   1272
Lys Gln Ile Pro Asp Ser Leu Ser Thr Asp Leu
```

-continued

```
            365                 370

ctgcatggga gagccaggga ggggagtttc tggaagagga aagccatgcg tggaacatcg   1332

aagcctcaga gagtgggaga ctgtccccat cagttgtcct tacttagagg agacagagag   1392

gccaatcagg tcccagagct tgaatgctaa caagcccagc atcccctggg gctgtgatca   1452

tggtggatga ggaagcctca acgtagattc ctgaactcaa ggtaccagca agaatgcctt   1512

ctcccagtgt gctctcccca acatcctagg cacagctttc ataacccagt ttcttaggtg   1572

taagaaactg tttttatctc atttattaag tctcagaact taacagaaaa ggaagccttt   1632

taaatattct ttttaatttt attttagatt aacagttttg tactttacat ttttttatac   1692

aaccaaccag tttcttttct agccaatcat ctctgaagag ttgctgtttc ttactgacaa   1752

taaaaaatgt tctcttggtt caaaaaaaaa aaaaaaa                            1789


<210> SEQ ID NO 110
<211> LENGTH: 386
<212> TYPE: PRT
<213> ORGANISM: Homo sapiens
<220> FEATURE:
<221> NAME/KEY: SIGNAL
<222> LOCATION: 1..15

<400> SEQUENCE: 110

Met Cys Leu Leu Leu Ser Cys Pro Cys His Pro Ser Ala His Gly Gln
-15                 -10                 -5                  1

Ser Met Trp Ile Glu Arg Thr Ser Phe Val Thr Ala Tyr Lys Leu Pro
            5                   10                  15

Gly Ile Leu Arg Trp Phe Glu Val Val His Met Ser Gln Thr Thr Ile
        20                  25                  30

Ser Pro Leu Glu Asn Ala Ile Glu Thr Met Ser Thr Ala Asn Glu Lys
    35                  40                  45

Ile Leu Met Met Ile Asn Gln Tyr Gln Ser Asp Glu Thr Leu Pro Ile
50                  55                  60                  65

Asn Pro Leu Ser Met Leu Leu Asn Gly Ile Val Asp Pro Ala Val Met
                70                  75                  80

Gly Gly Phe Ala Lys Tyr Glu Lys Ala Phe Phe Thr Glu Glu Tyr Val
            85                  90                  95

Arg Asp His Pro Glu Asp Gln Asp Lys Leu Thr His Leu Lys Asp Leu
        100                 105                 110

Ile Ala Trp Gln Ile Pro Phe Leu Gly Ala Gly Ile Lys Ile His Glu
    115                 120                 125

Lys Arg Val Ser Asp Asn Leu Arg Pro Phe His Asp Arg Met Glu Glu
130                 135                 140                 145

Cys Phe Lys Asn Leu Lys Met Lys Val Glu Lys Glu Tyr Gly Val Arg
                150                 155                 160

Glu Met Pro Asp Phe Asp Asp Arg Arg Val Gly Arg Pro Arg Ser Met
            165                 170                 175

Leu Arg Ser Tyr Arg Gln Met Ser Ile Ile Ser Leu Ala Ser Met Asn
        180                 185                 190

Ser Asp Cys Ser Thr Pro Ser Lys Pro Thr Ser Glu Ser Phe Asp Leu
    195                 200                 205

Glu Leu Ala Ser Pro Lys Thr Pro Arg Val Glu Gln Glu Glu Pro Ile
210                 215                 220                 225

Ser Pro Gly Ser Thr Leu Pro Glu Val Lys Leu Arg Arg Ser Lys Lys
                230                 235                 240
```

-continued

```
Arg Thr Lys Arg Ser Ser Val Val Phe Ala Asp Glu Lys Ala Ala Ala
            245                 250                 255

Glu Ser Asp Leu Lys Arg Leu Ser Arg Lys His Glu Phe Met Ser Asp
        260                 265                 270

Thr Asn Leu Ser Glu His Ala Ala Ile Pro Leu Lys Ala Ser Val Leu
    275                 280                 285

Ser Gln Met Ser Phe Ala Ser Gln Ser Met Pro Thr Ile Pro Ala Leu
290                 295                 300                 305

Ala Leu Ser Val Ala Gly Ile Pro Gly Leu Asp Glu Ala Asn Thr Ser
                310                 315                 320

Pro Arg Leu Ser Gln Thr Phe Leu Gln Leu Ser Asp Gly Asp Lys Lys
            325                 330                 335

Thr Leu Thr Arg Lys Lys Val Asn Gln Phe Phe Lys Thr Met Leu Ala
        340                 345                 350

Ser Lys Ser Ala Glu Glu Gly Lys Gln Ile Pro Asp Ser Leu Ser Thr
    355                 360                 365

Asp Leu
370


<210> SEQ ID NO 111
<211> LENGTH: 1408
<212> TYPE: DNA
<213> ORGANISM: Homo sapiens
<220> FEATURE:
<221> NAME/KEY: 5'UTR
<222> LOCATION: 1..102
<220> FEATURE:
<221> NAME/KEY: CDS
<222> LOCATION: 103..1263
<220> FEATURE:
<221> NAME/KEY: 3'UTR
<222> LOCATION: 1264..1408
<220> FEATURE:
<221> NAME/KEY: polyA_signal
<222> LOCATION: 1341..1346
<220> FEATURE:
<221> NAME/KEY: polyA_site
<222> LOCATION: 1365..1408

<400> SEQUENCE: 111

cttcttgact ctctgttcac agaactcagg ctgcctccag ccagcctttg cccgctagac      60

tcactggccc tgatcacttg aaggtgcagc aagtcactga ga atg agc act ttc        114
                                               Met Ser Thr Phe
                                               1

ttc tcg gac aca gca tgg atc tgc ctg gct gtc ccc aca gta cta tgt      162
Phe Ser Asp Thr Ala Trp Ile Cys Leu Ala Val Pro Thr Val Leu Cys
5                   10                  15                  20

ggg aca gta ttt tgc aaa tac aag aag agc tca ggg cag ctg tgg agc      210
Gly Thr Val Phe Cys Lys Tyr Lys Lys Ser Ser Gly Gln Leu Trp Ser
                25                  30                  35

tgg atg gtc tgc ctg gca ggc ctc tgt gca gtc tgc ctg ctc atc ctg      258
Trp Met Val Cys Leu Ala Gly Leu Cys Ala Val Cys Leu Leu Ile Leu
            40                  45                  50

tcc cct ttt tgg ggc ttg atc ctc ttc tcg gtg tca tgc ttc ctc atg      306
Ser Pro Phe Trp Gly Leu Ile Leu Phe Ser Val Ser Cys Phe Leu Met
        55                  60                  65

tat act tac tta tct ggc caa gaa ttg tta cct gtg gat cag aag gca      354
Tyr Thr Tyr Leu Ser Gly Gln Glu Leu Leu Pro Val Asp Gln Lys Ala
    70                  75                  80

gtc ctg gtg aca ggt ggt gat tgc ggg ctt ggc cat gct ttg tgc aag      402
Val Leu Val Thr Gly Gly Asp Cys Gly Leu Gly His Ala Leu Cys Lys
85                  90                  95                  100
```

-continued

```
tat ctg gat gag ctg ggc ttc acg gta ttt gcc gga gtt ttg aat gaa      450
Tyr Leu Asp Glu Leu Gly Phe Thr Val Phe Ala Gly Val Leu Asn Glu
                105                 110                 115

aat ggc cca gga gct gag gaa ttg cga aga acc tgc tct ccg cgc ctc      498
Asn Gly Pro Gly Ala Glu Glu Leu Arg Arg Thr Cys Ser Pro Arg Leu
            120                 125                 130

tcg gtg ctc caa atg gac atc acg aag cca gtg cag ata aaa gat gct      546
Ser Val Leu Gln Met Asp Ile Thr Lys Pro Val Gln Ile Lys Asp Ala
        135                 140                 145

tac agc aag gtt gca gca atg ctg cag gac aga gga ctg tgg gct gtg      594
Tyr Ser Lys Val Ala Ala Met Leu Gln Asp Arg Gly Leu Trp Ala Val
    150                 155                 160

atc aac aat gct ggg gtg ctt ggc ttt cca act gat ggg gag ctt ctt      642
Ile Asn Asn Ala Gly Val Leu Gly Phe Pro Thr Asp Gly Glu Leu Leu
165                 170                 175                 180

ctt atg act gac tac aaa caa tgc atg gcc gtg aac ttc ttt gga act      690
Leu Met Thr Asp Tyr Lys Gln Cys Met Ala Val Asn Phe Phe Gly Thr
                185                 190                 195

gtg gag gtc aca aag acg ttt ttg cct ctt ctt aga aaa tcc aaa ggg      738
Val Glu Val Thr Lys Thr Phe Leu Pro Leu Leu Arg Lys Ser Lys Gly
            200                 205                 210

agg ctg gtg aat gtc agc agc atg gga gga ggg gcc cca gtg gaa agg      786
Arg Leu Val Asn Val Ser Ser Met Gly Gly Gly Ala Pro Val Glu Arg
        215                 220                 225

ctg gca tct tat ggc tca tca aag gcg gct gtg acc atg ttc tca tca      834
Leu Ala Ser Tyr Gly Ser Ser Lys Ala Ala Val Thr Met Phe Ser Ser
    230                 235                 240

gtt atg aga ctg gag ctt tcc aag tgg gga att aaa gtt gct tcc atc      882
Val Met Arg Leu Glu Leu Ser Lys Trp Gly Ile Lys Val Ala Ser Ile
245                 250                 255                 260

caa cct gga ggc ttc cta aca aat atc gca ggc acc agt gac aag tgg      930
Gln Pro Gly Gly Phe Leu Thr Asn Ile Ala Gly Thr Ser Asp Lys Trp
                265                 270                 275

gaa aag ctg gag aag gac att ctg gac cac ctc ccc gct gag gta cag      978
Glu Lys Leu Glu Lys Asp Ile Leu Asp His Leu Pro Ala Glu Val Gln
            280                 285                 290

gaa gac tac tgc cag gac tac atc tta gca cag cgg aat ttc ctc cta     1026
Glu Asp Tyr Cys Gln Asp Tyr Ile Leu Ala Gln Arg Asn Phe Leu Leu
        295                 300                 305

ttg atc aac tcg tta gcc agc aag gac ttc tct ccg gtg ctg cgg gac     1074
Leu Ile Asn Ser Leu Ala Ser Lys Asp Phe Ser Pro Val Leu Arg Asp
    310                 315                 320

atc cag cat gct atc ttg gcg aag agc cct ttt gcc tat tac acg cca     1122
Ile Gln His Ala Ile Leu Ala Lys Ser Pro Phe Ala Tyr Tyr Thr Pro
325                 330                 335                 340

ggg aaa ggc gct tac ttg tgg atc tgc ctt gct cac tat ttg cct att     1170
Gly Lys Gly Ala Tyr Leu Trp Ile Cys Leu Ala His Tyr Leu Pro Ile
                345                 350                 355

ggc ata tat gat tac ttt gct aaa aga cat ttt ggc caa gac aag ccc     1218
Gly Ile Tyr Asp Tyr Phe Ala Lys Arg His Phe Gly Gln Asp Lys Pro
            360                 365                 370

atg ccc aga gct tta aga atg cct aac tac aag aaa aag gcc ccc         1263
Met Pro Arg Ala Leu Arg Met Pro Asn Tyr Lys Lys Lys Ala Pro
        375                 380                 385

taggcaatgg aagccctcaa agaagtcgga atgtcatagt cttgaaatga aagggaaact   1323

gggaaattgg gtttctcatt aaagttgttt cccactctgt waaaaaaaaa aaaaaaaaaa   1383

aaaaaaaaga aaaaaaaaaa aaaaa                                         1408
```

<210> SEQ ID NO 112
<211> LENGTH: 387
<212> TYPE: PRT
<213> ORGANISM: Homo sapiens

<400> SEQUENCE: 112

```
Met Ser Thr Phe Phe Ser Asp Thr Ala Trp Ile Cys Leu Ala Val Pro
1               5                   10                  15

Thr Val Leu Cys Gly Thr Val Phe Cys Lys Tyr Lys Lys Ser Ser Gly
            20                  25                  30

Gln Leu Trp Ser Trp Met Val Cys Leu Ala Gly Leu Cys Ala Val Cys
        35                  40                  45

Leu Leu Ile Leu Ser Pro Phe Trp Gly Leu Ile Leu Phe Ser Val Ser
    50                  55                  60

Cys Phe Leu Met Tyr Thr Tyr Leu Ser Gly Gln Glu Leu Leu Pro Val
65                  70                  75                  80

Asp Gln Lys Ala Val Leu Val Thr Gly Gly Asp Cys Gly Leu Gly His
                85                  90                  95

Ala Leu Cys Lys Tyr Leu Asp Glu Leu Gly Phe Thr Val Phe Ala Gly
            100                 105                 110

Val Leu Asn Glu Asn Gly Pro Gly Ala Glu Glu Leu Arg Arg Thr Cys
        115                 120                 125

Ser Pro Arg Leu Ser Val Leu Gln Met Asp Ile Thr Lys Pro Val Gln
    130                 135                 140

Ile Lys Asp Ala Tyr Ser Lys Val Ala Ala Met Leu Gln Asp Arg Gly
145                 150                 155                 160

Leu Trp Ala Val Ile Asn Asn Ala Gly Val Leu Gly Phe Pro Thr Asp
                165                 170                 175

Gly Glu Leu Leu Leu Met Thr Asp Tyr Lys Gln Cys Met Ala Val Asn
            180                 185                 190

Phe Phe Gly Thr Val Glu Val Thr Lys Thr Phe Leu Pro Leu Leu Arg
        195                 200                 205

Lys Ser Lys Gly Arg Leu Val Asn Val Ser Ser Met Gly Gly Gly Ala
    210                 215                 220

Pro Val Glu Arg Leu Ala Ser Tyr Gly Ser Ser Lys Ala Ala Val Thr
225                 230                 235                 240

Met Phe Ser Ser Val Met Arg Leu Glu Leu Ser Lys Trp Gly Ile Lys
                245                 250                 255

Val Ala Ser Ile Gln Pro Gly Gly Phe Leu Thr Asn Ile Ala Gly Thr
            260                 265                 270

Ser Asp Lys Trp Glu Lys Leu Glu Lys Asp Ile Leu Asp His Leu Pro
        275                 280                 285

Ala Glu Val Gln Glu Asp Tyr Cys Gln Asp Tyr Ile Leu Ala Gln Arg
    290                 295                 300

Asn Phe Leu Leu Leu Ile Asn Ser Leu Ala Ser Lys Asp Phe Ser Pro
305                 310                 315                 320

Val Leu Arg Asp Ile Gln His Ala Ile Leu Ala Lys Ser Pro Phe Ala
                325                 330                 335

Tyr Tyr Thr Pro Gly Lys Gly Ala Tyr Leu Trp Ile Cys Leu Ala His
            340                 345                 350
```

-continued

```
Tyr Leu Pro Ile Gly Ile Tyr Asp Tyr Phe Ala Lys Arg His Phe Gly
        355                 360                 365

Gln Asp Lys Pro Met Pro Arg Ala Leu Arg Met Pro Asn Tyr Lys Lys
    370                 375                 380

Lys Ala Pro
385
```